United States Patent
Yasukawa et al.

(10) Patent No.: US 11,482,681 B2
(45) Date of Patent: Oct. 25, 2022

(54) COMPOUND, MATERIAL FOR ORGANIC ELECTROLUMINESCENCE ELEMENT, ORGANIC ELECTROLUMINESCENCE ELEMENT, AND ELECTRONIC DEVICE

(71) Applicant: IDEMITSU KOSAN CO., LTD., Chiyoda-ku (JP)

(72) Inventors: Keiichi Yasukawa, Sodegaura (JP); Shota Sawano, Sodegaura (JP); Keiji Okinaka, Sodegaura (JP); Toshinari Ogiwara, Sodegaura (JP); Takushi Shiomi, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 74 days.

(21) Appl. No.: 16/765,681

(22) PCT Filed: Jul. 24, 2019

(86) PCT No.: PCT/JP2019/029013
§ 371 (c)(1),
(2) Date: May 20, 2020

(87) PCT Pub. No.: WO2020/022378
PCT Pub. Date: Jan. 30, 2020

(65) Prior Publication Data
US 2021/0143341 A1    May 13, 2021

(30) Foreign Application Priority Data

Jul. 27, 2018   (JP) .............................. JP2018-141897
Nov. 6, 2018    (JP) .............................. JP2018-209147
Mar. 28, 2019   (JP) .............................. JP2019-064509

(51) Int. Cl.
*C07D 209/94* (2006.01)
*C07D 491/04* (2006.01)
(Continued)

(52) U.S. Cl.
CPC ........ *H01L 51/0072* (2013.01); *C07D 209/94* (2013.01); *C07D 491/048* (2013.01);
(Continued)

(58) Field of Classification Search
CPC . C07D 209/94; C07D 491/048; C07D 495/04
See application file for complete search history.

(56) References Cited

U.S. PATENT DOCUMENTS

2009/0026936 A1   1/2009   Satou et al.
2009/0072727 A1   3/2009   Takeda
(Continued)

FOREIGN PATENT DOCUMENTS

CN   104788355 A   7/2015
CN   106977514 A   7/2017
(Continued)

OTHER PUBLICATIONS

International Search Report dated Oct. 15, 2019 in PCT/JP2019/029013 filed on Jul. 24, 2019, 2 pages.
(Continued)

*Primary Examiner* — Shawquia Jackson
(74) *Attorney, Agent, or Firm* — Oblon, McClelland, Maier & Neustadt, L.L.P.

(57) ABSTRACT

A compound is represented by one of formulae (11) to (13). $R_1$ to $R_4$ each independently represent a group represented by a formula (1-1) or the like, or a group represented by a formula (2-1), a group represented by a formula (2-2) or the like. At least one of $R_1$ to $R_4$ is the group represented by the formula (1-1) or the like. At least one of $R_1$ to $R_4$ is the group represented by the formula (2-1), (2-2) or the like. For instance, $X_1$ represents an oxygen atom, a sulfur atom, or $CR_{151}R_{152}$, $R_{101}$ to $R_{110}$ and $R_{151}$ and $R_{152}$ each independently representing a hydrogen atom or a substituent. For instance, $R_{161}$ to $R_{168}$ and $R_{171}$ and $R_{180}$ each independently represent a hydrogen atom or a substituent. * each independently represents a bonding position to a carbon atom in a benzene ring in each of formulae (11) to (13):

(11)

(12)

(13)

(Continued)

-continued

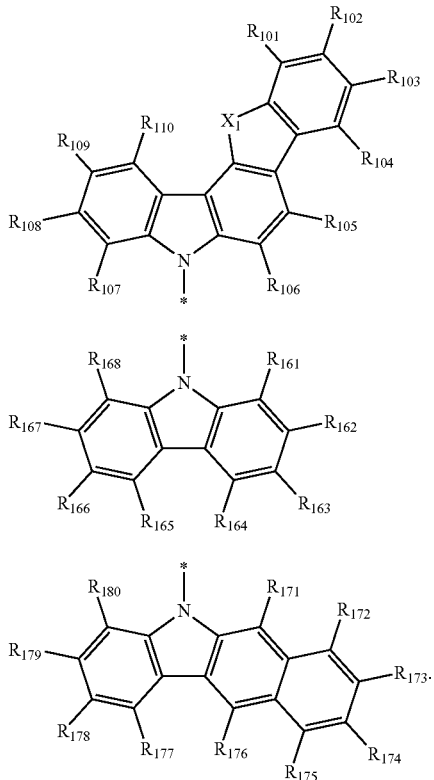

(1-1)

(2-1)

(2-2)

36 Claims, 6 Drawing Sheets

(51) Int. Cl.
  *C07D 495/04* (2006.01)
  *H01L 51/00* (2006.01)
  *C07D 491/048* (2006.01)
  *C09K 11/02* (2006.01)
  *C09K 11/06* (2006.01)
  *H01L 51/50* (2006.01)

(52) U.S. Cl.
  CPC ............ *C07D 495/04* (2013.01); *C09K 11/02* (2013.01); *C09K 11/06* (2013.01); *H01L 51/008* (2013.01); *H01L 51/0071* (2013.01); *C07B 2200/05* (2013.01); *C09K 2211/1007* (2013.01); *C09K 2211/1018* (2013.01); *H01L 51/5016* (2013.01); *H01L 51/5028* (2013.01); *H01L 2251/5384* (2013.01)

(56) References Cited

U.S. PATENT DOCUMENTS

| | | |
|---|---|---|
| 2009/0218938 A1 | 9/2009 | Takeda et al. |
| 2012/0080670 A1 | 4/2012 | Park et al. |
| 2013/0313536 A1 | 11/2013 | Nishimura et al. |
| 2013/0328027 A1 | 12/2013 | Sotoyama et al. |
| 2014/0042411 A1 | 2/2014 | Fukuzaki |
| 2014/0175419 A1 | 6/2014 | Nakano et al. |
| 2014/0183486 A1 | 7/2014 | Nakano et al. |
| 2014/0225046 A1 | 8/2014 | Jatsch et al. |
| 2014/0371461 A1 | 12/2014 | Nakayama et al. |
| 2014/0374711 A1 | 12/2014 | Cho et al. |
| 2015/0053960 A1 | 2/2015 | Park et al. |
| 2015/0060796 A1 | 3/2015 | Kim et al. |
| 2015/0105564 A1 | 4/2015 | Adachi et al. |
| 2015/0129861 A1 | 5/2015 | Hamano et al. |
| 2015/0236262 A1 | 8/2015 | Cho et al. |
| 2015/0318488 A1 | 11/2015 | Ito et al. |
| 2015/0325798 A1 | 11/2015 | Cho et al. |
| 2015/0325801 A1 | 11/2015 | Ito et al. |
| 2015/0380662 A1 | 12/2015 | Kim et al. |
| 2016/0005979 A1 | 1/2016 | Kim et al. |
| 2016/0028025 A1 | 1/2016 | Ogiwara et al. |
| 2016/0035992 A1 | 2/2016 | Stoessel et al. |
| 2016/0072076 A1 | 3/2016 | Stoessel et al. |
| 2016/0087224 A1 | 3/2016 | Kim et al. |
| 2016/0087227 A1 | 3/2016 | Kim et al. |
| 2016/0093812 A1 | 3/2016 | Stoessel et al. |
| 2016/0093813 A1 | 3/2016 | Stoessel et al. |
| 2016/0126478 A1 | 5/2016 | Zheng et al. |
| 2016/0130225 A1 | 5/2016 | Tasaki et al. |
| 2016/0133844 A1 | 5/2016 | Kim et al. |
| 2016/0149139 A1 | 5/2016 | Xia et al. |
| 2016/0163999 A1 | 6/2016 | Kim et al. |
| 2016/0164020 A1 | 6/2016 | Kim et al. |
| 2016/0181545 A1 | 6/2016 | Stoessel et al. |
| 2016/0211466 A1 | 7/2016 | Ogiwara et al. |
| 2016/0226001 A1 | 8/2016 | Parham et al. |
| 2016/0260905 A1 | 9/2016 | Lee et al. |
| 2016/0268516 A1 | 9/2016 | Tanaka et al. |
| 2016/0301012 A1 | 10/2016 | Han et al. |
| 2016/0301016 A1 | 10/2016 | Stoessel et al. |
| 2016/0315268 A1 | 10/2016 | Stoessel et al. |
| 2016/0322582 A1 | 11/2016 | Qui et al. |
| 2016/0329512 A1 | 11/2016 | Nishide et al. |
| 2016/0351822 A1 | 12/2016 | Lee et al. |
| 2016/0372688 A1 | 12/2016 | Seo et al. |
| 2017/0025630 A1 | 1/2017 | Seo et al. |
| 2017/0047527 A1 | 2/2017 | Lee et al. |
| 2017/0047529 A1 | 2/2017 | Min et al. |
| 2017/0062731 A1 | 3/2017 | Ogiwara et al. |
| 2017/0077418 A1 | 3/2017 | Stoessel et al. |
| 2017/0077421 A1 | 3/2017 | Ihn et al. |
| 2017/0084844 A1 | 3/2017 | Parham et al. |
| 2017/0092875 A1 | 3/2017 | Parham et al. |
| 2017/0117486 A1 | 4/2017 | Cho et al. |
| 2017/0117488 A1 | 4/2017 | Ahn et al. |
| 2017/0125697 A1 | 5/2017 | Cho et al. |
| 2017/0125699 A1 | 5/2017 | Ahn et al. |
| 2017/0170408 A1 | 6/2017 | Park et al. |
| 2017/0186964 A1 | 6/2017 | Cho et al. |
| 2017/0186978 A1 | 6/2017 | Kim et al. |
| 2017/0194569 A1 | 7/2017 | Kim et al. |
| 2017/0194585 A1 | 7/2017 | Yan et al. |
| 2017/0207396 A1 | 7/2017 | Park et al. |
| 2017/0213968 A1 | 7/2017 | Park et al. |
| 2017/0250351 A1 | 8/2017 | Takagi |
| 2017/0256733 A1 | 9/2017 | Tsukamoto et al. |
| 2017/0271610 A1 | 9/2017 | Takahashi |
| 2017/0288147 A1 | 10/2017 | Fujita et al. |
| 2017/0294613 A1 | 10/2017 | Cho et al. |
| 2017/0309841 A1 | 10/2017 | Kim et al. |
| 2017/0338436 A1 | 11/2017 | Mitsumuri et al. |
| 2017/0342057 A1 | 11/2017 | Shim et al. |
| 2017/0346029 A1 | 11/2017 | Kim et al. |
| 2017/0352813 A1 | 12/2017 | Duan et al. |
| 2017/0352816 A1 | 12/2017 | Jeon et al. |
| 2017/0352818 A1 | 12/2017 | Zysman-Colman et al. |
| 2018/0010040 A1 | 1/2018 | Pan et al. |
| 2018/0013073 A1 | 1/2018 | Duan et al. |
| 2018/0016493 A1 | 1/2018 | Lygaitis et al. |
| 2018/0040833 A1 | 2/2018 | Ahn et al. |
| 2018/0053907 A1 | 2/2018 | He et al. |
| 2018/0086763 A1 | 3/2018 | Raimann et al. |
| 2018/0114918 A1 | 4/2018 | Han et al. |
| 2018/0123052 A1 | 5/2018 | Zysman-Colman et al. |
| 2018/0138436 A1 | 5/2018 | Takagi |
| 2018/0138437 A1 | 5/2018 | Takagi |
| 2018/0166645 A1 | 6/2018 | Tang |
| 2018/0175294 A1 | 6/2018 | Duan et al. |
| 2018/0190924 A1 | 7/2018 | Tsang et al. |

(56) References Cited

U.S. PATENT DOCUMENTS

| | | |
|---|---|---|
| 2018/0233678 A1 | 8/2018 | Ihn et al. |
| 2018/0240981 A1 | 8/2018 | Cho et al. |
| 2018/0248145 A1 | 8/2018 | Ihn et al. |
| 2018/0269406 A1 | 9/2018 | Stoessel et al. |
| 2018/0294420 A1 | 10/2018 | Feldman et al. |
| 2018/0358414 A1 | 12/2018 | Song et al. |
| 2018/0366677 A1 | 12/2018 | Tsang et al. |
| 2019/0044084 A1 | 2/2019 | O'Carroll |
| 2019/0058130 A1 | 2/2019 | Aguilera-Iparraguirre et al. |
| 2019/0157570 A1 | 5/2019 | Sim et al. |
| 2019/0181353 A1 | 6/2019 | Ihn et al. |
| 2019/0214569 A1 | 7/2019 | Sasada et al. |
| 2019/0214579 A1 | 7/2019 | Seda et al. |
| 2019/0229276 A1 | 7/2019 | Kwon et al. |
| 2019/0245152 A1 | 8/2019 | Saito et al. |
| 2019/0259959 A1 | 8/2019 | Duan et al. |
| 2019/0267554 A1 | 8/2019 | Yang et al. |
| 2019/0288221 A1 | 9/2019 | Yoshizaki et al. |
| 2019/0319194 A1 | 10/2019 | Xia et al. |
| 2019/0337872 A1 | 11/2019 | Saito et al. |
| 2019/0348625 A1 | 11/2019 | Mitsumori et al. |
| 2019/0393424 A1 | 12/2019 | Ihn et al. |
| 2019/0393425 A1 | 12/2019 | Ihn et al. |
| 2020/0028094 A1 | 1/2020 | Sim et al. |
| 2020/0058878 A1 | 2/2020 | Cho et al. |
| 2020/0079735 A1 | 3/2020 | Ma et al. |
| 2020/0091439 A1 | 3/2020 | Ihn et al. |
| 2020/0119286 A1 | 4/2020 | Liaptsis et al. |
| 2020/0119299 A1 | 4/2020 | Hong et al. |
| 2020/0127214 A1 | 4/2020 | Choi et al. |
| 2020/0136059 A1 | 4/2020 | Hong et al. |
| 2020/0161564 A1 | 5/2020 | Kim et al. |
| 2020/0185633 A1 | 6/2020 | Hong et al. |
| 2020/0203621 A1 | 6/2020 | Kim et al. |
| 2021/0020846 A1 | 1/2021 | Yoshizaki et al. |
| 2021/0043840 A1 | 2/2021 | Seo et al. |

FOREIGN PATENT DOCUMENTS

| | | |
|---|---|---|
| CN | 108264478 A | 7/2018 |
| CN | 108658841 A | 10/2018 |
| CN | 110066227 A | 7/2019 |
| CN | 110183426 A | 8/2019 |
| CN | 110642841 A | 1/2020 |
| DE | 10 2016 113 277 A1 | 1/2018 |
| DE | 10 2016 123 105 A1 | 3/2018 |
| DE | 20 2019 005 189 U1 | 3/2020 |
| EP | 3 072 943 A1 | 9/2016 |
| EP | 3 587 423 A1 | 1/2020 |
| EP | 3 651 225 A1 | 5/2020 |
| EP | 3 696 187 A1 | 8/2020 |
| JP | 2014-45101 A | 3/2014 |
| JP | 2014-96572 A | 5/2014 |
| JP | 2015-53476 A | 3/2015 |
| JP | 2015-72889 A | 4/2015 |
| JP | 2015-106659 A | 6/2015 |
| JP | 2015-109428 A | 6/2015 |
| JP | 2016-36022 A | 3/2016 |
| JP | 2016-92280 A | 5/2016 |
| JP | 2016-115734 A | 6/2016 |
| JP | 2016-516085 A | 6/2016 |
| JP | 2017-126598 A | 7/2017 |
| JP | 2017-162872 A | 9/2017 |
| JP | 2018-14404 A | 1/2018 |
| JP | 2018-61028 A | 4/2018 |
| JP | 2018-61030 A | 4/2018 |
| JP | 2018-200995 A | 12/2018 |
| JP | 2019-68068 A | 4/2019 |
| JP | 2019-112572 A | 7/2019 |
| JP | 2019-165102 A | 9/2019 |
| JP | 2020-26426 A | 2/2020 |
| KR | 10-2015-059324 A | 6/2015 |
| KR | 10-2015-0085661 A | 7/2015 |
| KR | 10-2015-0094217 A | 8/2015 |
| KR | 10-2018-0028183 A | 3/2018 |
| KR | 10-2018-0080970 A | 7/2018 |
| KR | 10-2019-0027343 A | 3/2019 |
| KR | 10-2019-0049525 A | 5/2019 |
| KR | 10-2019-0137436 A | 12/2019 |
| KR | 10-2020-3021881 A | 3/2020 |
| KR | 10-2020-0071002 A | 6/2020 |
| WO | WO 2012/002221 A1 | 1/2012 |
| WO | WO 2012/153780 A1 | 11/2012 |
| WO | WO 2013/038650 A1 | 3/2013 |
| WO | WO 2013/179845 A1 | 12/2013 |
| WO | WO 2014/128945 A1 | 8/2014 |
| WO | WO 2014/146752 A1 | 9/2014 |
| WO | WO 2014/208698 A1 | 12/2014 |
| WO | WO 2019/076198 A1 | 4/2015 |
| WO | WO 2016/086887 A1 | 6/2016 |
| WO | WO 2016/138077 A1 | 9/2016 |
| WO | WO 2017/194435 A1 | 11/2017 |
| WO | WO 2017216557 A1 | 11/2017 |
| WO | WO 2018/030446 A1 | 2/2018 |
| WO | WO 2018/181188 A1 | 4/2018 |
| WO | WO 2018/139662 A1 | 8/2018 |
| WO | WO 2018/155642 A1 | 8/2018 |
| WO | WO 2018/173593 A1 | 9/2018 |
| WO | WO 2018/186462 A1 | 10/2018 |
| WO | WO 2018/207776 A1 | 11/2018 |
| WO | WO 2018/237389 A1 | 12/2018 |
| WO | WO 2019/009307 A1 | 1/2019 |
| WO | WO 2019/031524 A1 | 2/2019 |
| WO | WO 2019/039414 A1 | 2/2019 |
| WO | WO 2019/062686 A1 | 4/2019 |
| WO | WO 2019/066054 A1 | 4/2019 |
| WO | WO 2019/120125 A1 | 6/2019 |
| WO | WO 2019/128104 A1 | 7/2019 |
| WO | WO 2019/132399 A1 | 7/2019 |
| WO | WO 2019/146396 A1 | 8/2019 |
| WO | WO 2019/181858 A1 | 9/2019 |
| WO | WO 2019/230708 A1 | 12/2019 |
| WO | WO 2020/012304 A1 | 1/2020 |
| WO | WO 2020/039708 A1 | 2/2020 |
| WO | WO 2020/042608 A1 | 3/2020 |
| WO | WO 2020/042626 A1 | 3/2020 |
| WO | WO 2020/059862 A1 | 3/2020 |
| WO | WO 2020/080108 A1 | 4/2020 |
| WO | WO 2020/085446 A1 | 4/2020 |
| WO | WO 2020/085765 A1 | 4/2020 |
| WO | WO 2020/101001 A1 | 5/2020 |
| WO | WO 2020/111205 A1 | 6/2020 |
| WO | WO 2020/111277 A1 | 6/2020 |

OTHER PUBLICATIONS

Adachi, "Yuki Hando-tai no Debaisu Bussei (Device Physics of Organic Semiconductors)" Kodansha, 2012, 19 total pages (with English translation).

Uoyama et al., "Highly efficient organic light-emitting diodes from delayed fluorescence", Nature, 2012, vol. 492, 7 total pages.

International Preliminary Report on Patentability and Written Opinion dated Feb. 2, 2021 in PCT/JP2019/029013 (submitting English translation only), 5 pages.

COMPOUND, MATERIAL FOR ORGANIC ELECTROLUMINESCENCE ELEMENT, ORGANIC ELECTROLUMINESCENCE ELEMENT, AND ELECTRONIC DEVICE

TECHNICAL FIELD

The present invention relates to a compound, a material for an organic electroluminescence device, an organic electroluminescence device, and an electronic device.

BACKGROUND ART

When a voltage is applied to an organic electroluminescence device (hereinafter, sometimes referred to as an "organic EL device"), holes are injected from an anode and electrons are injected from a cathode into an emitting layer. The injected electrons and holes are recombined in the emitting layer to form excitons. Specifically, according to the electron spin statistics theory, singlet excitons and triplet excitons are generated at a ratio of 25%:75%.

A fluorescent organic EL device using light emission from singlet excitons has been applied to a full-color display such as a mobile phone and a television set, but an internal quantum efficiency is said to be at a limit of 25%. Accordingly, studies has been made to improve a performance of the organic EL device.

Moreover, it is expected to further efficiently emit the organic EL device using triplet excitons in addition to singlet excitons. In view of the above, a highly efficient fluorescent organic EL device using thermally activated delayed fluorescence (hereinafter, sometimes simply referred to as "delayed fluorescence") has been proposed and studied.

For instance, a TADF (Thermally Activated Delayed Fluorescence) mechanism has been studied. The TADF mechanism uses such a phenomenon that inverse intersystem crossing from triplet excitons to singlet excitons thermally occurs when a material having a small energy difference ($\Delta ST$) between singlet energy level and triplet energy level is used. Delayed fluorescence (thermally activated delayed fluorescence) is explained in "Yuki Hando-tai no Debaisu Bussei (Device Physics of Organic Semiconductors)" (edited by ADACHI, Chihaya, published by Kodansha, issued on Apr. 1, 2012, on pages 261-268).

As a compound exhibiting TADF properties (hereinafter also referred to as a TADF compound), for example, a compound in which a donor moiety and an acceptor moiety are bonded in a molecule is known.

For instance, Patent Literatures 1 and 2 disclose a compound in which a fused carbazole group and a cyano group are bonded to a benzene ring.

CITATION LIST

Patent Literature(s)

Patent Literature 1: International Publication No. WO2014/146752
Patent Literature 2: International Publication No. WO2014/208698

SUMMARY OF THE INVENTION

Problems to be Solved by the Invention

In a compound, such as those disclosed in Patent Literatures 1 and 2, in which a plurality of cyano groups having a relatively high acceptor properties and a fused plurality of carbazole groups having a relatively high donor properties are simply bonded to a benzene, a sublimation temperature of the compound tends to be increased when the compound is sublimated and purified. When the sublimation temperature of the compound is increased, a purification time is prolonged to reduce a purification efficiency. In recent years, the sublimation temperature is required to be further decreased in terms of the purification efficiency.

In the meantime, it is crucial that TADF properties of the TADF compound are kept favorable.

An object of the invention is to provide a compound capable of decreasing a sublimation temperature when being sublimated and purified while maintaining TADF properties, an organic-EL-device material containing the compound, an organic EL device containing the compound, and an electronic device provided with the organic EL device.

Another object of the invention is to provide the organic EL device and the electronic device each having an excellent performance by using the compound and the organic-EL-device material containing the compound, to provide a compound capable of achieving the organic EL device and the electronic device each having an excellent performance, and to provide the organic-EL-device material containing the compound.

Means for Solving the Problems

According to an aspect of the invention, a compound represented by one of formulae (11) to (13) below is provided.

[Formula 1]

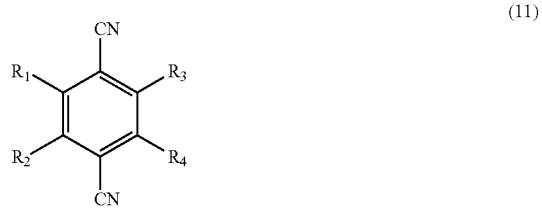

(11)

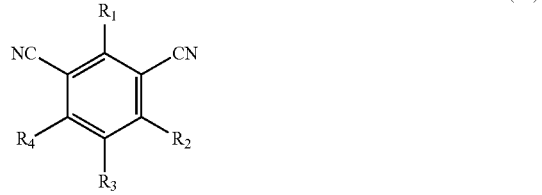

(12)

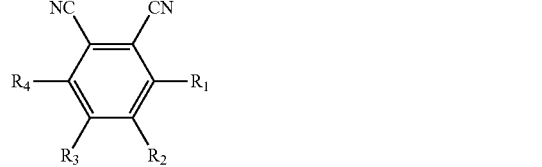

(13)

In the formulae (11) to (13), $R_1$ to $R_4$ are each independently a group represented by one of formulae (1-1) to (1-6) or a group represented by one of formulae (2-1) to (2-4). However, at least one of $R_1$ to $R_4$ is the group represented by one of formulae (1-1) to (1-6) while at least one of $R_1$ to $R_4$ is the group represented by one of formulae (2-1) to (2-4).

[Formula 2]

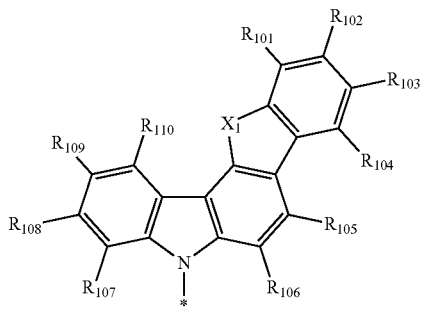

(1-1)

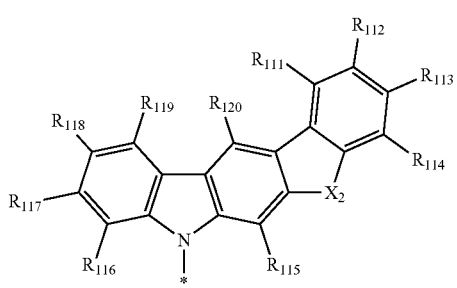

(1-2)

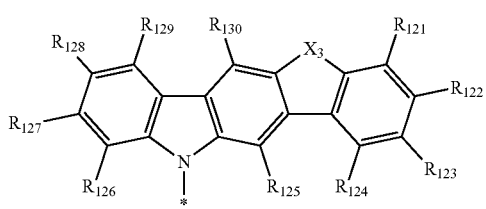

(1-3)

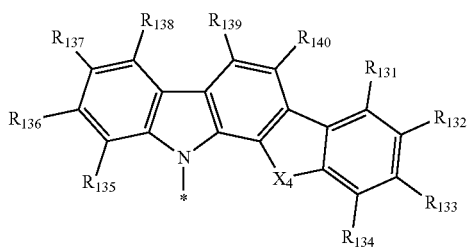

(1-4)

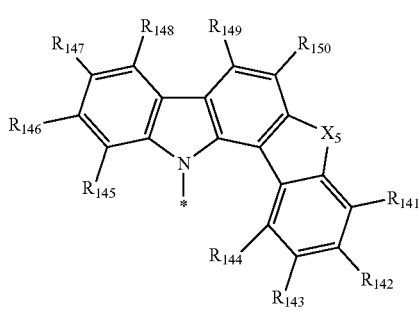

(1-5)

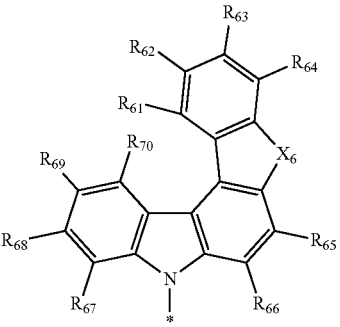

(1-6)

In the formula (1-1): $X_1$ is an oxygen atom, a sulfur atom, or $CR_{151}R_{152}$; $R_{101}$ to $R_{110}$ are each independently a hydrogen atom or a substituent; $R_{151}$ and $R_{152}$ are each independently a hydrogen atom or a substituent, or $R_{151}$ and $R_{152}$ are mutually bonded to form a ring.

$R_{101}$ to $R_{110}$, $R_{151}$ and $R_{152}$ as the substituent each independently represent a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkysilyl group having 3 to 6 carbon atoms, a substituted or unsubstituted alkoxy group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

In the formula (1-2), $X_2$ and $R_{111}$ to $R_{120}$ respectively represent the same as $X_1$ and $R_{101}$ to $R_{110}$ in the formula (1-1).

In the formula (1-3), $X_3$ and $R_{121}$ to $R_{130}$ respectively represent the same as $X_1$ and $R_{101}$ to $R_{110}$ in the formula (1-1).

In the formula (1-4), $X_4$ and $R_{131}$ to $R_{140}$ respectively represent the same as $X_1$ and $R_{101}$ to $R_{110}$ in the formula (1-1).

In the formula (1-5), $X_5$ and $R_{141}$ to $R_{150}$ respectively represent the same as $X_1$ and $R_{101}$ to $R_{110}$ in the formula (1-1).

In the formula (1-6), $X_6$ and $R_{61}$ to $R_{70}$ respectively represent the same as $X_1$ and $R_{101}$ to $R_{110}$ in the formula (1-1). * each independently represents a bonding position to a carbon atom in a benzene ring in each of the formulae (11) to (13).

[Formula 3]

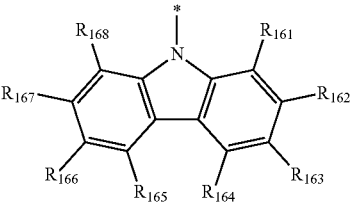

(2-1)

-continued

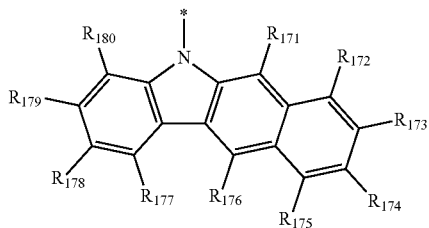

(2-2)

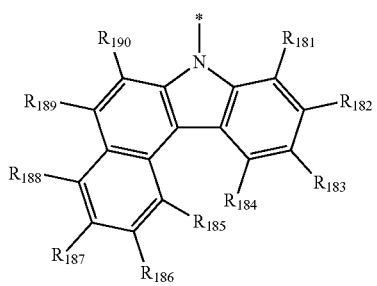

(2-3)

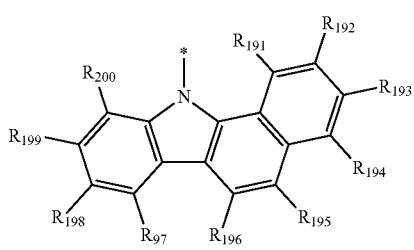

(2-4)

In the formula (2-1), $R_{161}$ to $R_{168}$ each independently represent a hydrogen atom or a substituent.

$R_{161}$ to $R_{168}$ as the substituent each independently represent a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 30 carbon atoms, a substituted or unsubstituted alkysilyl group having 3 to 6 carbon atoms, a substituted or unsubstituted alkoxy group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

In the formula (2-2), $R_{171}$ to $R_{180}$ each independently represent a hydrogen atom or a substituent. $R_{171}$ to $R_{180}$ as the substituent each independently represent the same examples of the substituent for $R_{161}$ to $R_{168}$ in the formula (2-1).

In the formula (2-3), $R_{181}$ to $R_{190}$ each independently represent a hydrogen atom or a substituent. $R_{181}$ to $R_{190}$ as the substituent each independently represent the same examples of the substituent for $R_{161}$ to $R_{168}$ in the formula (2-1).

In the formula (2-4), $R_{191}$ to $R_{200}$ each independently represent a hydrogen atom or a substituent. $R_{191}$ to $R_{200}$ as the substituent each independently represent the same examples of the substituent for $R_{161}$ to $R_{168}$ in the formula (2-1). * each independently represents a bonding position to a carbon atom in a benzene ring in each of the formulae (11) to (13).

According to another aspect of the invention, an organic-electroluminescence-device material containing the compound according to the above aspect of the invention is provided.

According to still another aspect of the invention, an organic electroluminescence device: including an anode; a cathode; and a first organic layer provided between the anode and the cathode, in which the first organic layer contains a first compound, and the first compound is the compound according to the above aspect of the invention is provided.

According to a further aspect of the invention, an electronic device provided with the organic electroluminescence device according to the above aspect of the invention is provided.

According to the above aspects of the invention, a compound capable of decreasing a sublimation temperature when being sublimated and purified while maintaining TADF properties, an organic-EL-device material containing the compound, an organic EL device containing the compound, and an electronic device provided with the organic EL device can be provided.

BRIEF EXPLANATION OF DRAWING(S)

FIG. 1 is a figure schematically illustrating an arrangement of an organic electroluminescence device according to a third exemplary embodiment of the invention.

FIG. 2 schematically shows a device of measuring transient PL.

MEANS FOR SOLVING THE PROBLEMS

First Exemplary Embodiment

Compound

Figure 1:
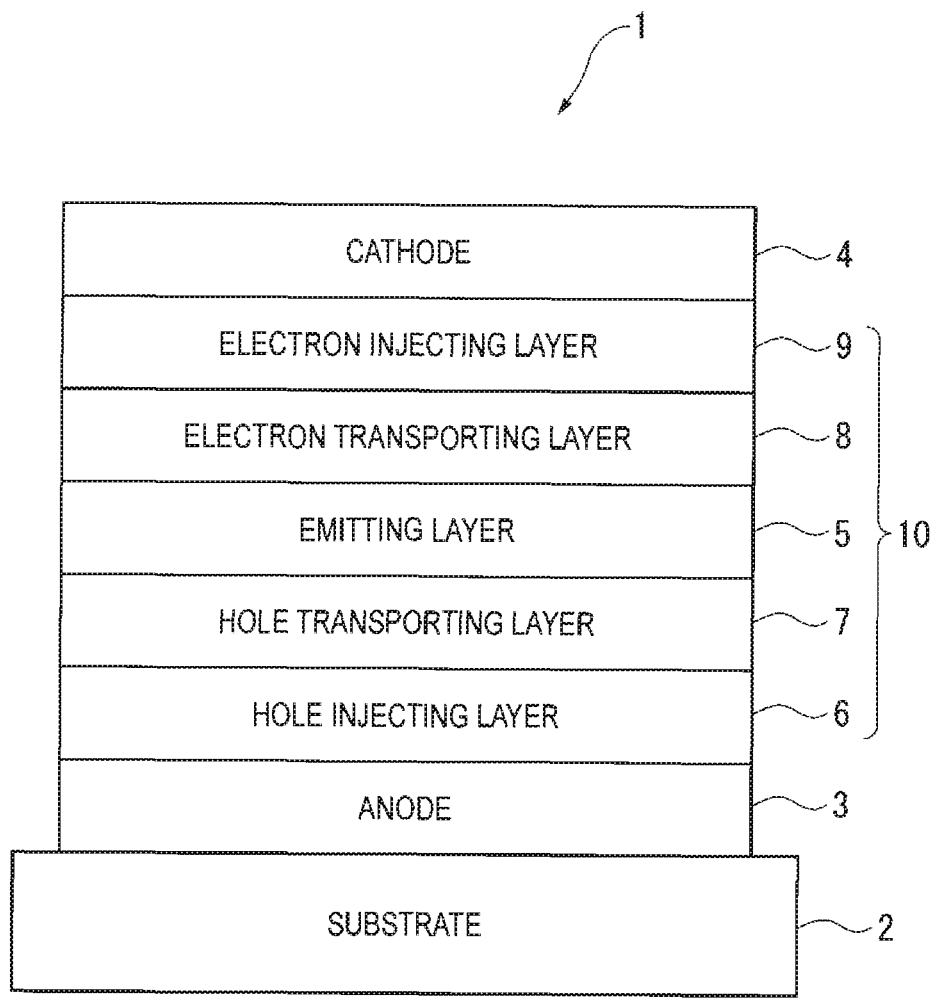

A compound according to a first exemplary embodiment is represented by one of formulae (11) to (13) below.

[Formula 4]

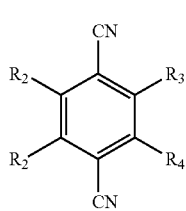

(11)

-continued

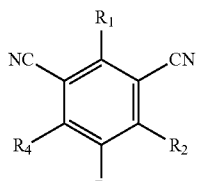
(12)

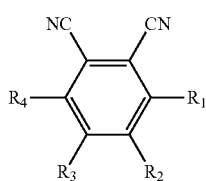
(13)

In the formulae (11) to (13), $R_1$ to $R_4$ are each independently a group represented by one of formulae (1-1) to (1-6) or a group represented by one of formulae (2-1) to (2-4). However, at least one of $R_1$ to $R_4$ is the group represented by one of formulae (1-1) to (1-6) while at least one of $R_1$ to $R_4$ is the group represented by one of formulae (2-1) to (2-4).

[Formula 5]

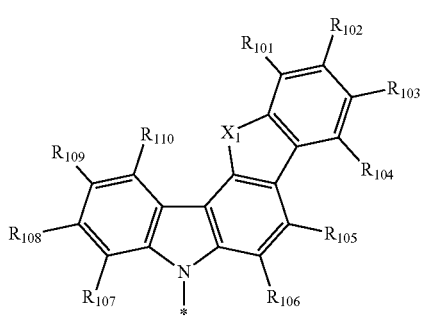
(1-1)

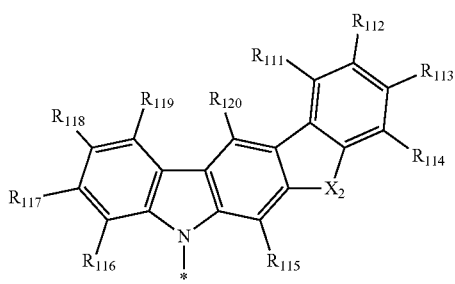
(1-2)

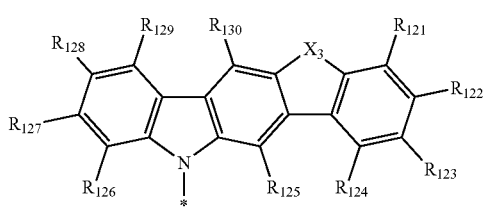
(1-3)

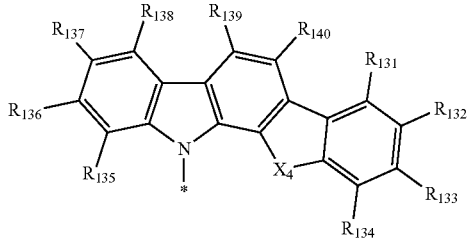
(1-4)

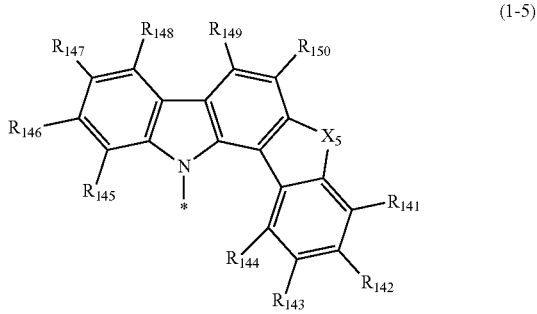
(1-5)

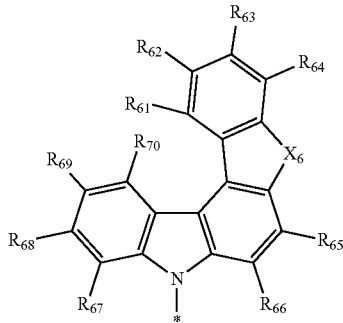
(1-6)

In the formula (1-1): $X_1$ is an oxygen atom, a sulfur atom, or $CR_{151}R_{152}$; $R_{101}$ to $R_{110}$ are each independently a hydrogen atom or a substituent; and $R_{151}$ and $R_{152}$ are each independently a hydrogen atom or a substituent, or $R_{151}$ and $R_{152}$ are mutually bonded to form a ring.

$R_{101}$ to $R_{110}$, $R_{151}$ and $R_{152}$ as the substituent each independently represent a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkysilyl group having 3 to 6 carbon atoms, a substituted or unsubstituted alkoxy group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

In the formula (1-2), $X_2$ and $R_{111}$ to $R_{120}$ respectively represent the same as $X_1$ and $R_{101}$ to $R_{110}$ in the formula (1-1).

In the formula (1-3), $X_3$ and $R_{121}$ to $R_{130}$ respectively represent the same as $X_1$ and $R_{101}$ to $R_{110}$ in the formula (1-1).

In the formula (1-4), $X_4$ and $R_{131}$ to $R_{140}$ respectively represent the same as $X_1$ and $R_{101}$ to $R_{110}$ in the formula (1-1).

In the formula (1-5), $X_5$ and $R_{141}$ to $R_{150}$ respectively represent the same as $X_1$ and $R_{101}$ to $R_{110}$ in the formula (1-1).

In the formula (1-6), $X_6$ and $R_{61}$ to $R_{70}$ respectively represent the same as $X_1$ and $R_{101}$ to $R_{110}$ in the formula (1-1). * each independently represents a bonding position to a carbon atom in a benzene ring in each of the formulae (11) to (13).

In the formulae (1-1) to (1-6), when one or more of $R_{101}$ to $R_{110}$, $R_{111}$ to $R_{120}$, $R_{121}$ to $R_{130}$, $R_{131}$ to $R_{140}$, $R_{141}$ to $R_{150}$, $R_{61}$ to $R_{70}$, $R_{151}$ and $R_{152}$ are hydrogen atom(s), it is preferable that all of the hydrogen atom(s) are protium, one or more of the hydrogen atom(s) are deuterium, or all of the hydrogen atom(s) are deuterium.

In the formulae (1-1) to (1-6), when one or more of $R_{101}$ to $R_{110}$, $R_{111}$ to $R_{120}$, $R_{121}$ to $R_{130}$, $R_{131}$ to $R_{140}$, $R_{141}$ to $R_{150}$, $R_{61}$ to $R_{70}$, $R_{151}$ and $R_{152}$ are substituent(s) and the substituent(s) have one or more hydrogen atom(s), it is preferable that all of the hydrogen atom(s) are protium, one or more of the hydrogen atom(s) are deuterium, or all of the hydrogen atom(s) are deuterium.

[Formula 6]

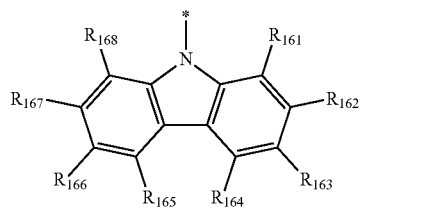

(2-1)

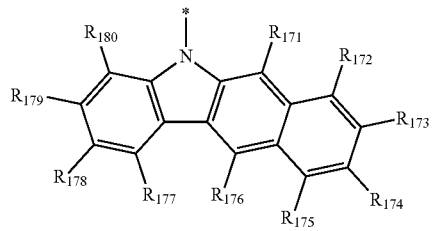

(2-2)

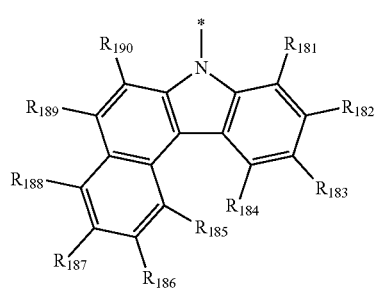

(2-3)

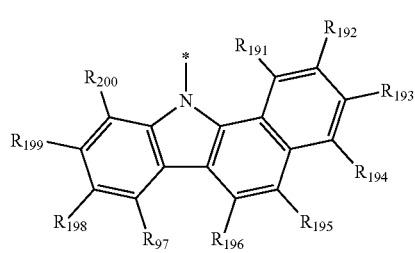

(2-4)

In the formula (2-1), $R_{161}$ to $R_{168}$ each independently represent a hydrogen atom or a substituent.

$R_{161}$ to $R_{168}$ as the substituent each independently represent a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 30 carbon atoms, a substituted or unsubstituted alkysilyl group having 3 to 6 carbon atoms, a substituted or unsubstituted alkoxy group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

In the formula (2-2), $R_{171}$ to $R_{180}$ each independently represent a hydrogen atom or a substituent. $R_{171}$ to $R_{180}$ as the substituent each independently represent the same examples of the substituent for $R_{161}$ to $R_{168}$ in the formula (2-1).

In the formula (2-3), $R_{181}$ to $R_{190}$ each independently represent a hydrogen atom or a substituent. $R_{181}$ to $R_{190}$ as the substituent each independently represent the same examples of the substituent for $R_{161}$ to $R_{168}$ in the formula (2-1).

In the formula (2-4), $R_{191}$ to $R_{200}$ each independently represent a hydrogen atom or a substituent. $R_{191}$ to $R_{200}$ as the substituent each independently represent the same examples of the substituent for $R_{161}$ to $R_{168}$ in the formula (2-1). * each independently represents a bonding position to a carbon atom in a benzene ring in each of the formulae (11) to (13).

In the formulae (2-1) to (2-4), when one or more of $R_{161}$ to $R_{168}$, $R_{171}$ to $R_{180}$, $R_{181}$ to $R_{190}$ and $R_{191}$ to $R_{200}$ are hydrogen atom(s), it is preferable that all of the hydrogen atom(s) are protium, one or more of the hydrogen atom(s) are deuterium, or all of the hydrogen atom(s) are deuterium.

In the formulae (2-1) to (2-4), when one or more of $R_{161}$ to $R_{168}$, $R_{171}$ to $R_{180}$, $R_{181}$ to $R_{190}$ and $R_{191}$ to $R_{200}$ are substituent(s) and the substituent(s) have one or more hydrogen atom(s), it is preferable that all of the hydrogen atom(s) are protium, one or more of the hydrogen atom(s) are deuterium, or all of the hydrogen atom(s) are deuterium.

A group formed by bonding a five-membered ring (in which a hetero atom is not a nitrogen atom) and a benzene ring to a carbazole group is specifically a group represented by one of formulae (1-1) to (1-6) (hereinafter, also referred to as a "five-ring carbazole group"). It is inferred that a compound formed by bonding the five-ring carbazole group to dicyanobenzene works well for properties of the organic EL device.

It is believed that this is because a conjugation length of the five-ring carbazole group extends longer than that of, for instance, each of groups represented by formulae (2-1) to (2-4). It is also believed that a skeleton specific to the five-ring carbazole group is contributable. For this reason, an ionization potential tends to become low (an absolute value tends to become small). As a result, when the compound having the five-ring carbazole group is contained, for instance, in the emitting layer, it is inferred that hole injection properties from the hole transporting layer to the emitting layer are improved while charge transport properties in the emitting layer are improved.

In contrast, with respect to a compound formed by bonding four five-ring carbazole groups having the above charge transport properties to, for instance, dicyanobenzene, a sublimation temperature is easily increased when the compound is sublimated and purified. When the sublimation temperature of the compound is increased, a purifying time is prolonged to reduce a purification efficiency.

The inventors have found a compound capable of decreasing the sublimation temperature while keeping TADF properties, the compound formed by bonding four groups in total of (i) the five-ring carbazole group (i.e., groups represented by the formulae (1-1) to (1-6)) and (ii) the three-ring or four-ring carbazole group (groups represented by the formulae (2-1) to (2-4)) to dicyanobenzene.

In other words, with respect to the compound of the exemplary embodiment, it is expected that the five-ring carbazole group and the three-ring or four-ring carbazole group contained in a single compound contributes to decrease in the sublimation temperature.

In addition, since the three-ring or four-ring carbazole group has a skeleton having a higher triplet energy than the five-ring carbazole group, it is expected that, for instance, presence of the three-ring or four-ring carbazole group in the emitting layer can express the function of inhibiting energy deactivation from the triplet state.

Thus, according to the exemplary embodiment, it is expected that the combined use of the "five-ring carbazole group" having excellent charge transport properties and the "three-ring or four-ring carbazole group" can keep a balance between the decrease in the sublimation temperature and the maintenance of the TADF properties. As a result, it is expected that the compound capable of decreasing the sublimation temperature when the compound is sublimated and purified, while maintaining the TADF properties, can be obtained.

Maintaining of the TADF properties herein means, for instance, specifically the "value of $X_D/X_P$", which is measured in Examples, is 0.05 or more.

The amount of Prompt emission is denoted by $X_P$ and the amount of Delay emission is denoted by $X_D$. Details of the measurement method is described in the description about Examples.

In the compound of the exemplary embodiment, when a plurality of groups represented by the formula (1-1) are present as groups for $R_1$ to $R_4$, the plurality of groups represented by the formula (1-1) are preferably the same group having the same substituent.

When a plurality of groups represented by the formula (1-2) are present as the groups for $R_1$ to $R_4$, the plurality of groups represented by the formula (1-2) are preferably the same group having the same substituent.

When a plurality of groups represented by the formula (1-3) are present as groups for $R_1$ to $R_4$, the plurality of groups represented by the formula (1-3) are preferably the same group having the same substituent.

When a plurality of groups represented by the formula (1-4) are present as groups for $R_1$ to $R_4$, the plurality of groups represented by the formula (1-4) are preferably the same group having the same substituent.

When a plurality of groups represented by the formula (1-5) are present as groups for $R_1$ to $R_4$, the plurality of groups represented by the formula (1-5) are preferably the same group having the same substituent.

When a plurality of groups represented by the formula (1-6) are present as groups for $R_1$ to $R_4$, the plurality of groups represented by the formula (1-6) are preferably the same group having the same substituent.

Specifically, for instance, when two groups represented by the formula (1-1) are selected as the groups for $R_1$ and $R_2$, one group represented by the formula (1-2) is selected as the group for $R_3$, and one group represented by the formula (2-1) is selected as the group for $R_4$, the two groups represented by the formula (1-1) are preferably the same group having the same substituent.

Moreover, for instance, when three groups represented by the formula (1-1) are selected as the groups for $R_1$ to $R_3$, the three groups represented by the formula (1-1) (the groups for $R_1$ to $R_3$) are preferably the same group having the same substituent.

In the compound of the exemplary embodiment, when two groups for $R_1$ to $R_4$ are selected from the groups represented by the formulae (1-1) to (1-6) and the remaining two groups for $R_1$ to $R_4$ are selected from the groups represented by the formulae (2-1) to (2-4), it is preferable that the two groups represented by the formulae (1-1) to (1-6) are represented by one of the formulae (1-1) to (1-6) and are the same group having the same substituent.

When three groups for $R_1$ to $R_4$ are selected from the groups represented by the formulae (1-1) to (1-6) and the remaining one group for $R_1$ to $R_4$ is selected from the groups represented by the formulae (2-1) to (2-4), it is preferable that the three groups represented by the formulae (1-1) to (1-6) are represented by one of the formulae (1-1) to (1-6) and are the same group having the same substituent.

For instance, when three groups each represented by the formula (1-1) are selected as the groups for $R_1$ to $R_4$, it is preferable that the three groups are represented by the formula (1-1) and are the same group having the same substituent.

In the compound of the exemplary embodiment, when a plurality of groups each represented by the formula (2-1) are present as groups for $R_1$ to $R_4$, the plurality of groups represented by the formula (2-1) are preferably the same group having the same substituent.

When a plurality of groups each represented by the formula (2-2) are present as groups for $R_1$ to $R_4$, the plurality of groups represented by the formula (2-2) are preferably the same group having the same substituent.

When a plurality of groups each represented by the formula (2-3) are present as groups for $R_1$ to $R_4$, the plurality of groups represented by the formula (2-3) are preferably the same group having the same substituent.

When a plurality of groups each represented by the formula (2-4) are present as groups for $R_1$ to $R_4$, the plurality of groups represented by the formula (2-4) are preferably the same group having the same substituent.

Specifically, for instance, when two groups represented by the formula (2-1) are selected as the groups for $R_1$ and $R_2$, one group represented by the formula (2-2) is selected as the group for $R_3$, and one group represented by the formula (1-1) is selected as the group for $R_4$, the two groups represented by the formula (2-1) (the groups for $R_1$ and $R_2$) are preferably the same group having the same substituent.

Moreover, for instance, when three groups represented by the formula (2-1) are selected as the groups for $R_1$ to $R_3$, the three groups represented by the formula (2-1) (the groups for $R_1$ to $R_3$) are preferably the same group having the same substituent.

In the compound of the exemplary embodiment, when two groups for $R_1$ to $R_4$ are selected from the groups represented by the formulae (2-1) to (2-4) and the remaining two groups for $R_1$ to $R_4$ are selected from the groups represented by the formulae (1-1) to (1-6), it is preferable that the two groups represented by the formulae (2-1) to (2-4) are represented by one of the formulae (2-1) to (2-4) and are the same group having the same substituent.

When three groups for $R_1$ to $R_4$ are selected from the groups represented by the formulae (2-1) to (2-4) and the remaining one group for $R_1$ to $R_4$ is selected from the groups represented by the formulae (1-1) to (1-6), it is preferable that the three groups represented by the formulae (2-1) to (2-4) are represented by one of the formulae (2-1) to (2-4) and are the same group having the same substituent.

For instance, when three groups each represented by the formula (2-1) are selected as the groups for $R_1$ to $R_4$, it is preferable that the three groups are represented by the formula (2-1) and are the same group having the same substituent.

The compound in the exemplary embodiment is preferably a compound represented by one of formulae (101) to (123).

[Formula 7]

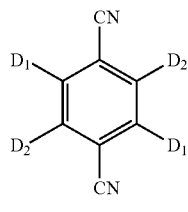
(101)

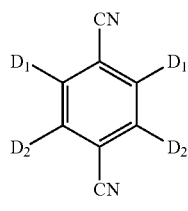
(102)

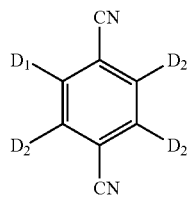
(103)

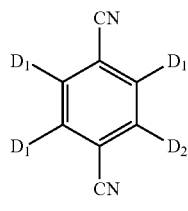
(104)

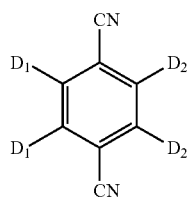
(105)

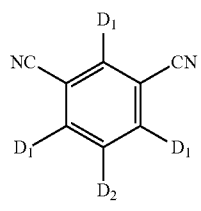
(106)

[Formula 8]

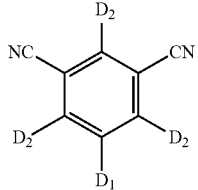
(107)

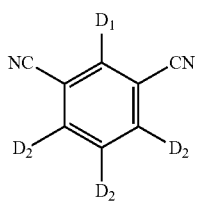
(108)

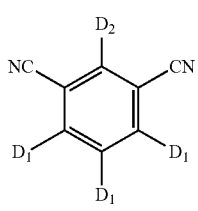
(109)

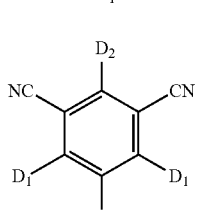
(110)

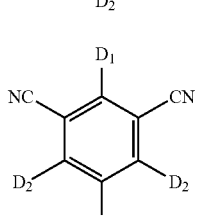
(111)

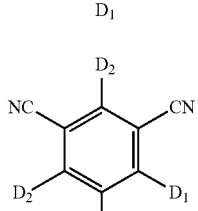
(112)

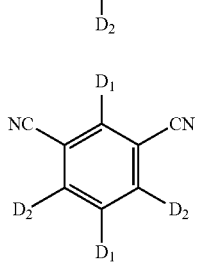
(113)

-continued (114) 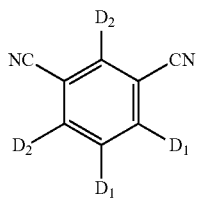

(115) 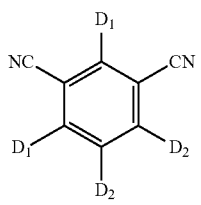

(116) 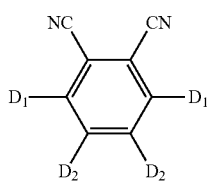

(117) 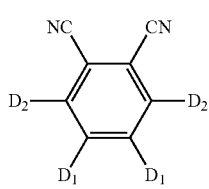

(118) 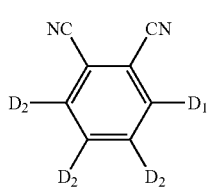

(119) 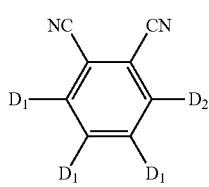

(120) 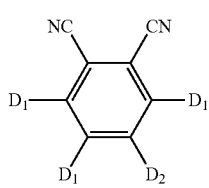

(121) 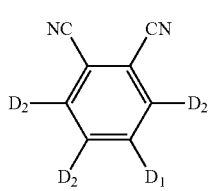

-continued (122) 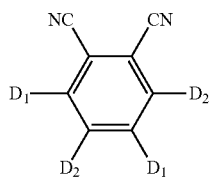

(123) 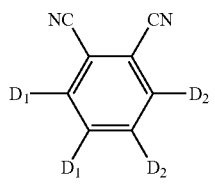

In the formulae (101) to (123), $D_1$ each independently represents one of the groups represented by the formulae (1-1) to (1-6), $D_2$ each independently represents one of the groups represented by the formulae (2-1) to (2-4). A plurality of $D_1$ are mutually the same or different. A plurality of $D_2$ are mutually the same or different.

In the compound of the exemplary embodiment, $D_1$ in the formulae (101) to (123) are preferably mutually the same group.

In the compound of the exemplary embodiment, $D_2$ in the formulae (101) to (123) are preferably mutually the same group.

In other words, it is more preferable that $D_1$ are mutually the same group and $D_2$ are mutually the same group in the formulae (101) to (123) in the compound of the exemplary embodiment.

The compound in the exemplary embodiment is preferably one of the compounds respectively represented by one of the formulae (101), (106), (107), (110), (111) and (116) to (119).

In the formulae (1-1) to (1-6), $X_1$ to $X_6$ are preferably oxygen atoms.

In the formulae (1-1) to (1-6), $X_1$ to $X_6$ are also preferably sulfur atoms.

In the formulae (1-1) to (1-6), $X_1$ to $X_6$ are also preferably $CR_{151}R_{152}$.

In the compound of the exemplary embodiment, each of the groups represented by the formulae (1-1) to (1-6) is preferably the group represented by the formula (1-1), the group represented by the formula (1-2), or the group represented by the formula (1-4).

In the compound of the exemplary embodiment, each of the groups represented by the formulae (2-1) to (2-4) is preferably one of groups represented by formulae (2-5) to (2-17).

[Formula 10]

(2-5) 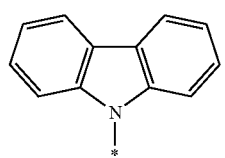

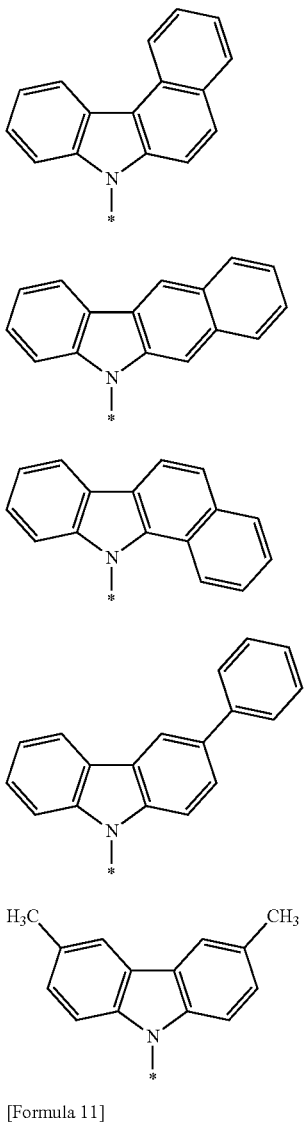

In the formulae (2-5) to (2-17), * each independently represents a bonding position to a carbon atom in a benzene ring in each of the formulae (11) to (13). D represents deuterium.

In the compound of the exemplary embodiment, each of the groups represented by the formulae (2-1) to (2-4) is preferably the group represented by the formula (2-2), the group represented by the formula (2-3), or the group represented by the formula (2-4).

In the compound of the exemplary embodiment, each of the groups represented by the formulae (2-1) to (2-4) is also preferably the group represented by the formula (2-1).

In the compound of the exemplary embodiment, the group represented by the formula (2-1) is also preferably the group represented by the formula (2-5) or the group represented by the formula (2-15).

When the compound in the exemplary embodiment has the group represented by the formula (2-1), $R_{161}$ to $R_{168}$ each independently preferably represent a hydrogen atom, a substituted or unsubstituted aryl group having 6 to 14 ring carbon atoms, or a substituted or unsubstituted alkyl group having 1 to 6 carbon atoms.

When the compound in the exemplary embodiment has a group represented by the formula (2-1), it is also preferable that at least one of $R_{161}$, $R_{163}$, $R_{166}$ and $R_{168}$ is a substituent, the substituent each independently is a substituted or unsubstituted aryl group having 6 to 14 ring carbon atoms, or a substituted or unsubstituted alkyl group having 1 to 6 carbon atoms, and $R_{162}$, $R_{164}$, $R_{165}$ and $R_{167}$ are hydrogen atoms.

It is more preferable that the compound in the exemplary embodiment is one of compounds respectively represented by the formulae (101), (106), (107), (110), (111), and (116) to (119), where $D_1$ is each independently the group represented by the formula (1-1), the group represented by the formula (1-2) or the group represented by the formula (1-4), and $D_2$ is each independently the group represented by one of the formulae (2-5) to (2-14).

A plurality of $D_1$ are mutually the same or different. A plurality of $D_2$ are mutually the same or different.

The compound in the exemplary embodiment is preferably the compound represented by the formula (11).

The compound in the exemplary embodiment is also preferably the compound represented by the formula (12).

The compound in the exemplary embodiment is also preferably the compound represented by the formula (13).

In the formulae (1-1) to (1-6) and (2-1) to (2-4), $R_{101}$ to $R_{150}$, $R_{151}$, $R_{152}$, $R_{161}$ to $R_{168}$, $R_{171}$ to $R_{200}$, $R_{171}$ to $R_{180}$ and $R_{61}$ to $R_{70}$ as the substituent each independently preferably a halogen atom, an unsubstituted aryl group having 6 to 14 ring carbon atoms, an unsubstituted heterocyclic group having 5 to 14 ring atoms, an unsubstituted alkyl group having 1 to 6 carbon atoms, an unsubstituted alkyl halide group having 1 to 6 carbon atoms, an unsubstituted alkylsilyl group having 3 to 6 carbon atoms, an unsubstituted alkoxy group having 1 to 6 carbon atoms, an unsubstituted aryloxy group having 6 to 14 ring carbon atoms, an unsubstituted alkylamino group having 2 to 12 carbon atoms, an unsubstituted alkylthio group having 1 to 6 carbon atoms, or an unsubstituted arylthio group having 6 to 14 ring carbon atoms.

It is preferable that, in the formulae (1-1) to (1-6) and (2-1) to (2-4), $R_{101}$ to $R_{150}$, $R_{151}$, $R_{152}$, $R_{161}$ to $R_{168}$, $R_{171}$ to $R_{200}$ and $R_{61}$ to $R_{70}$ are each independently an unsubstituted aryl group having 6 to 14 ring carbon atoms or an unsubstituted alkyl group having 1 to 6 carbon atoms.

It is also preferable that, in the formulae (1-1) to (1-6), $R_{101}$ to $R_{150}$ and $R_{61}$ to $R_{70}$ are each a hydrogen atom, and $R_{151}$ and $R_{152}$ are each an unsubstituted aryl group having 6 to 14 ring carbon atoms or an unsubstituted alkyl group having 1 to 6 carbon atoms, and in the formulae (2-1) to (2-4), $R_{161}$ to $R_{168}$ and $R_{171}$ to $R_{200}$ are each a hydrogen atom.

When a sum of atomic weight of atoms forming each of $R_1$ to $R_4$ in the compound of the exemplary embodiment is calculated, it is preferable that a minimum sum M1 (min) among the sums of the groups corresponding to the groups represented by the formulae (1-1) to (1-6) and a maximum sum M2 (max) among the sums of the groups corresponding to the groups represented by the formulae (2-1) to (2-4) satisfies a relationship represented by a numerical formula (Numerical Formula 1) below.

Moreover, it is further preferable that the minimum sum M1 (min) among the sums and the maximum sum M2 (max) among the sums of the groups corresponding to the groups represented by the formulae (2-1) to (2-10) satisfy a relationship represented by a numerical formula (Numerical Formula 1X) below.

Moreover, it is particularly preferable that the minimum sum M1 (min) among the sums and the maximum sum M2 (max) among the sums of the groups corresponding to the groups represented by the formulae (2-1) to (2-10) satisfy a relationship represented by a numerical formula (Numerical Formula 1Y) below.

By satisfying the relationship represented by the numerical formula (Numerical Formula 1), (Numerical Formula 1X) or (Numerical Formula 1Y), the TADF properties are kept favorable and the sublimation temperature when the compound is sublimated and purified is easily lowered.

$$M1(\text{min}) > M2(\text{max}) \quad \text{(Numerical Formula 1)}$$

$$140 > M1(\text{min}) - M2(\text{max}) \quad \text{(Numerical Formula 1X)}$$

$$110 > M1(\text{min}) - M2(\text{max}) \quad \text{(Numerical Formula 1Y)}$$

A numerical formula (Numerical Formula 1) will be described.

The compound in the exemplary embodiment will be described with an exemplary compound represented by the formula (11) in which $R_1$ is an unsubstituted 5H-benzofuro[3,2-c]carbazole group ($C_{18}H_{10}ON$), $R_4$ is a 5H-benzofuro[3,2-c]carbazole group ($C_{19}H_{12}ON$) substituted by a single methyl group, $R_2$ is an unsubstituted carbazole group ($C_{12}H_8N$), and $R_3$ is a carbazole group ($C_{13}H_{10}N$) substituted by a single methyl group.

The compound represented by the formula (11) having the above groups for $R_1$ to $R_4$ is defined as a compound A below.

At this time, a sum of atomic weights of atoms forming $R_1$ ($C_{18}H_{10}ON$) (hereinafter, also referred to as a "sum $M_{R1}$") is calculated as $12/18+10+16+14=256$.

A sum of atomic weights of atoms forming $R_4$ ($C_{19}H_{120}N$) (hereinafter, also referred to as a "sum $M_{R4}$") is calculated as $12 \times 19+12+16+14=270$.

A sum of atomic weights of atoms forming $R_2$ ($C_{12}H_8N$) (hereinafter, also referred to as a "sum $M_{R2}$") is calculated as $12 \times 12+8+14=166$.

A sum of atomic weights of atoms forming $R_3$ ($C_{13}H_{10}ON$) (hereinafter, also referred to as a "sum $M_{R3}$") is calculated as $12 \times 13+10+14=180$.

$R_1$ and $R_4$ are groups corresponding to the groups represented by the formulae (1-1) to (1-6).

In a comparison between $R_1$ and $R_4$ in terms of the sum of the atomic weights, the sum $M_{R4}$>the sum $M_{R1}$ in which the minimum sum M1 (min) is equal to the sum Mn.

$R_2$ and $R_3$ are groups corresponding to the groups represented by the formulae (2-1) to (2-4).

In a comparison between $R_2$ and $R_3$ in terms of the sum of the atomic weights, the sum $M_{R3}$>the sum $M_{R2}$ in which the maximum sum M2 (max) is equal to the sum $M_{R3}$.

Accordingly, since the compound A satisfies "the sum $M_{R1}$>the sum $M_{R3}$", the compound A is a compound satisfying a relationship represented by the numerical formula (Numerical Formula 1).

[Formula 13]

Compound A

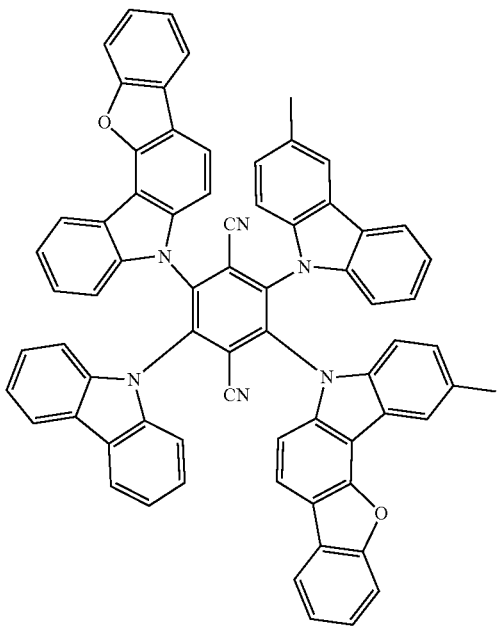

Manufacturing Method of Compound According to Exemplary Embodiment

The compound according to the exemplary embodiment can be manufactured through, for instance, a process described later in Examples. The compound according to the exemplary embodiment can be manufactured, for instance, by application of known substitution reactions and/or materials depending on a target compound according to reactions described later in Examples.

Examples of the compound according to the exemplary embodiment include compounds represented by formulae (11-1), (12-1) to (12-2) and (13-1) to (13-2).

[Formula 14]

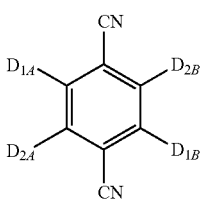

(11-1)

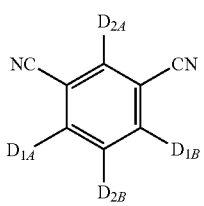

(12-1)

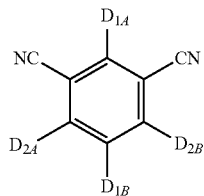

(12-2)

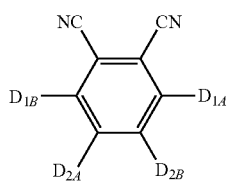

(13-1)

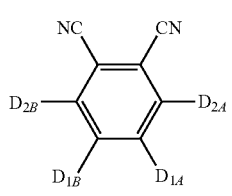

(13-2)

In the formula (11-1), $D_{1A}$, $D_{2A}$, $D_{1B}$, and $D_{2B}$ respectively represent groups corresponding to numbers given to columns of $D_{1A}$, $D_{2A}$, $D_{1B}$, and $D_{2B}$ in Tables 3 to 20 below.

In the formula (12-1), $D_{1A}$, $D_{2A}$, $D_{1B}$, and $D_{2B}$ respectively represent groups corresponding to numbers given to columns of $D_{1A}$, $D_{2A}$, $D_{1B}$, and $D_{2B}$ in Tables 3 to 20 below.

In the formula (12-2), $D_{1A}$, $D_{2A}$, $D_{1B}$, and $D_{2B}$ respectively represent groups corresponding to numbers given to columns of $D_{1A}$, $D_{2A}$, $D_{1B}$, and $D_{2B}$ in Tables 3 to 20 below.

In the formula (13-1), $D_{1A}$, $D_{2A}$, $D_{1B}$, and $D_{2B}$ respectively represent groups corresponding to numbers given to columns of $D_{1A}$, $D_{2A}$, $D_{1B}$, and $D_{2B}$ in Tables 3 to 20 below.

In the formula (13-2), $D_{1A}$, $D_{2A}$, $D_{1B}$, and $D_{2B}$ respectively represent groups corresponding to numbers given to columns of $D_{1A}$, $D_{2A}$, $D_{1B}$, and $D_{2B}$ in Tables 3 to 20 below.

In Tables 3 to 20 below, the numbers given to columns of $D_{1A}$, $D_{1A}$, $D_{1B}$, and $D_{2B}$ correspond to numbers of later-described groups 1 to 36 and groups 1' to 18'.

The groups 1 to 36 and groups 1' to 18' are shown below, * each independently represents a bonding position to a carbon atom of a benzene ring in each of the formulae (11-1), (12-1) to (12-2) and (13-1) to (13-2) and later-described formulae (11-2), (12-3) to (12-6) and (13-3) to (13-4). Me represents a methyl group. D represents deuterium.

[Formula 15]

1

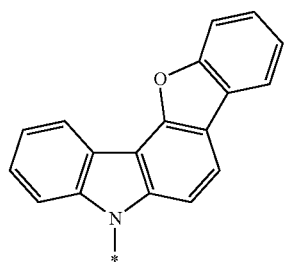

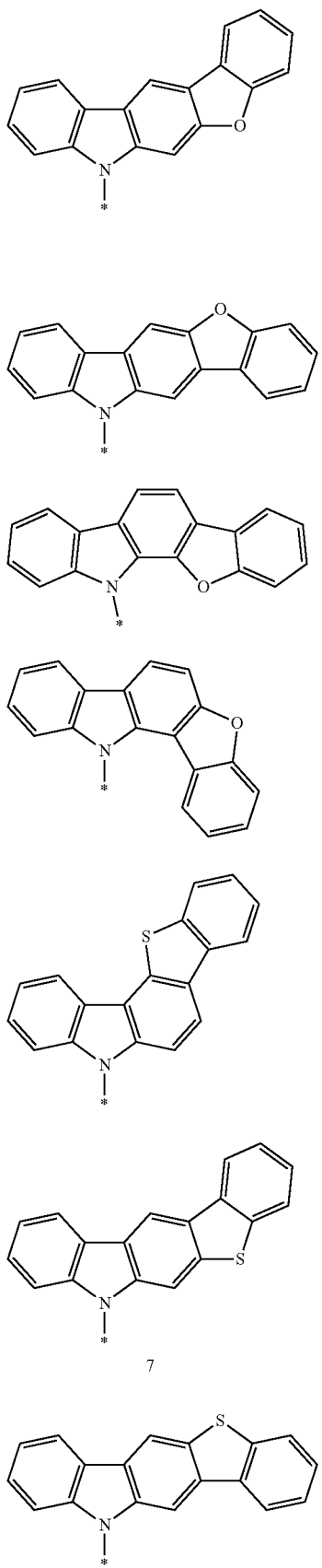
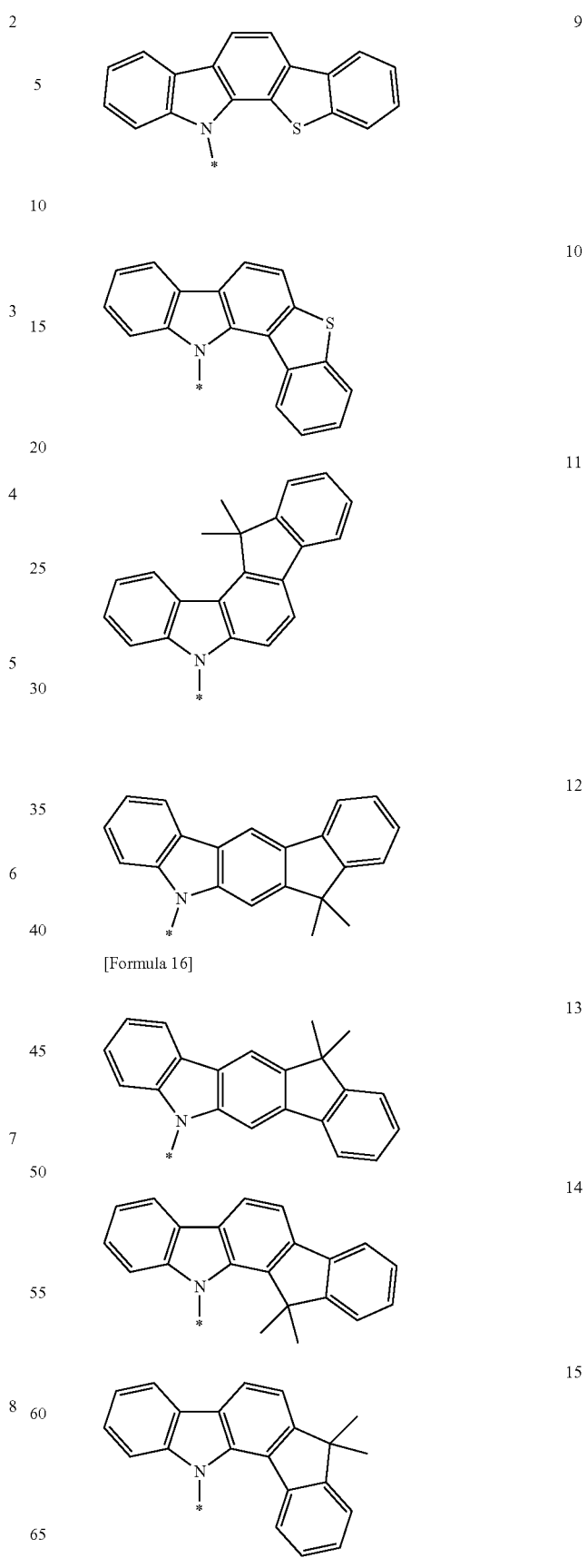
[Formula 16]

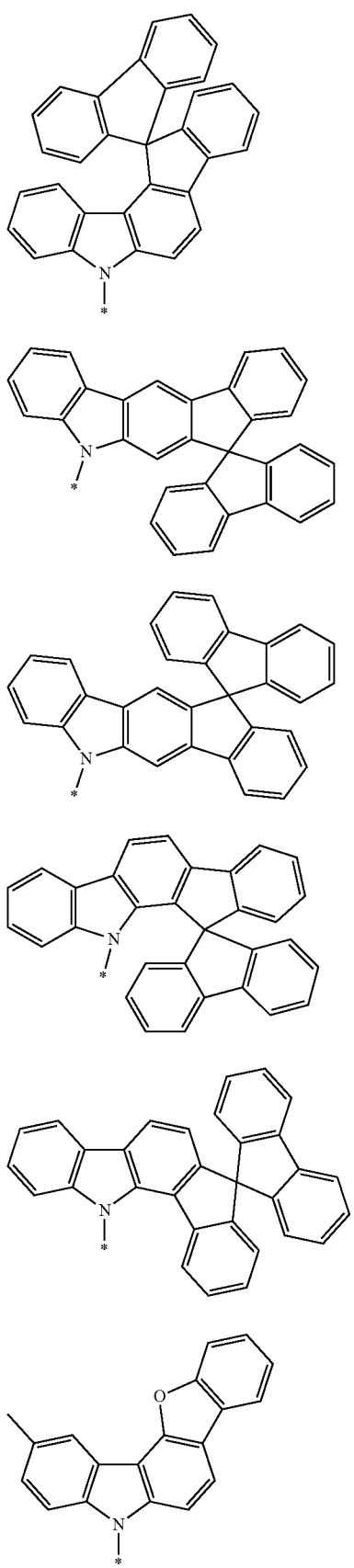
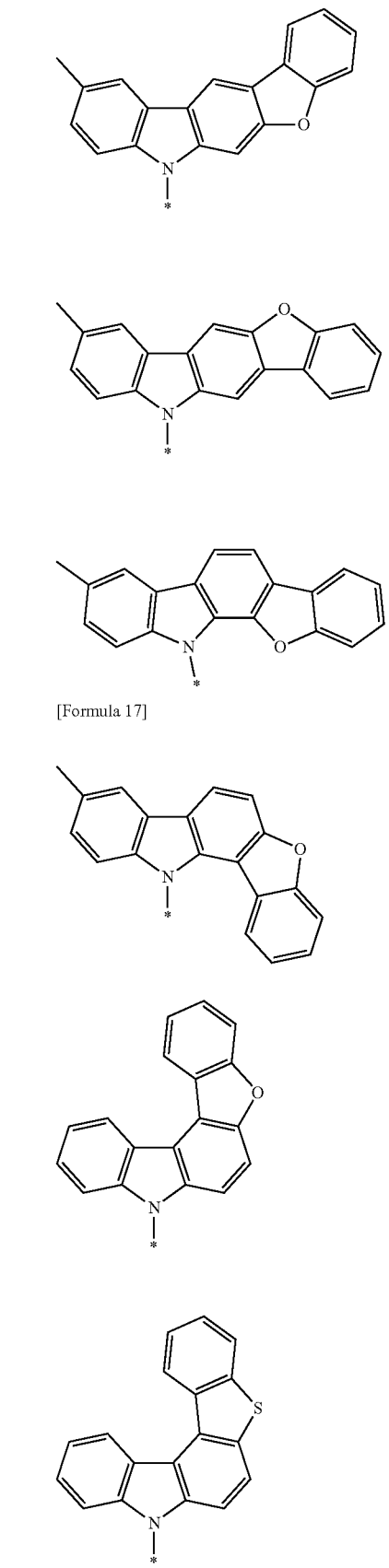
[Formula 17]

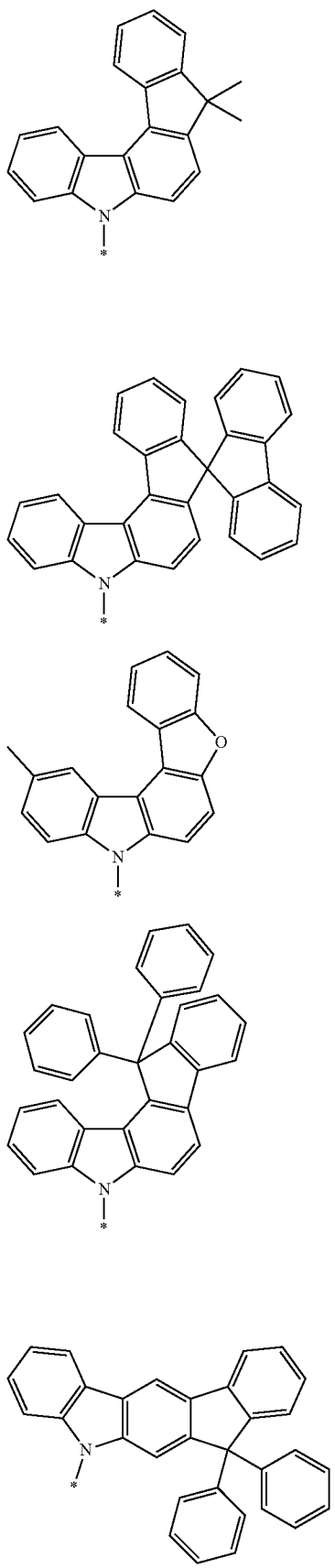
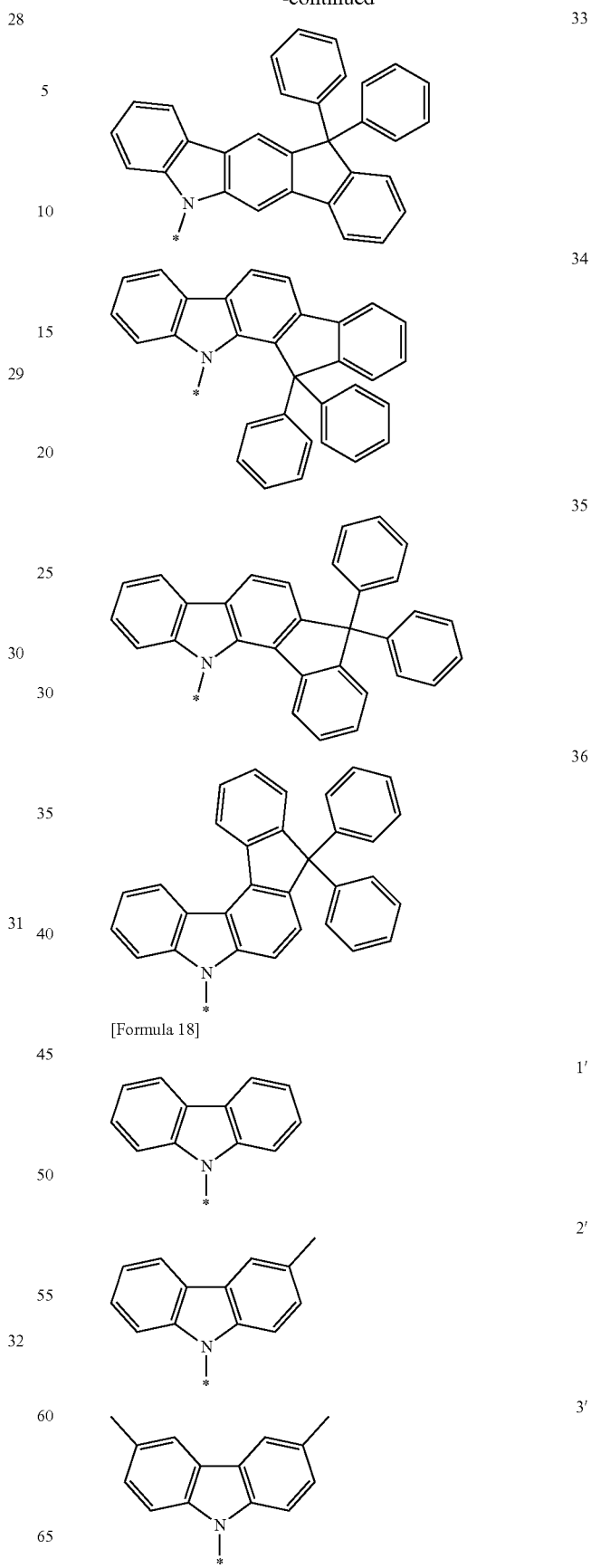
[Formula 18]

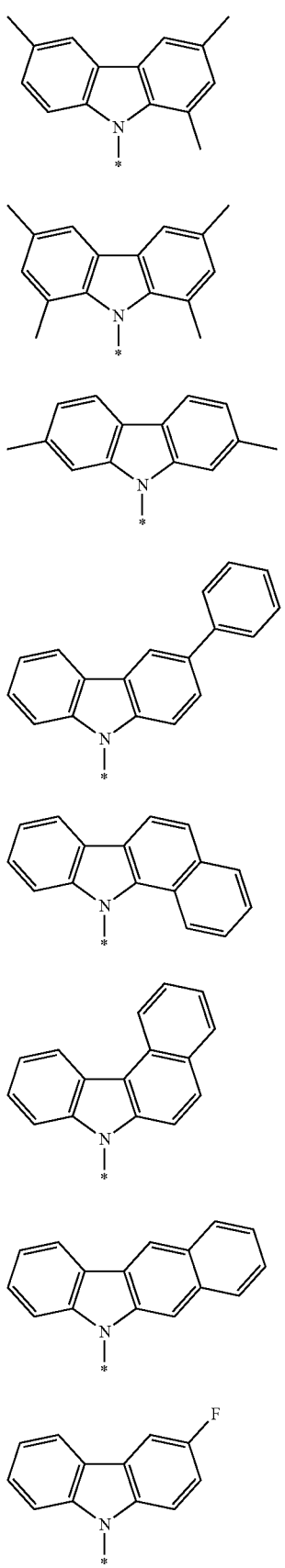
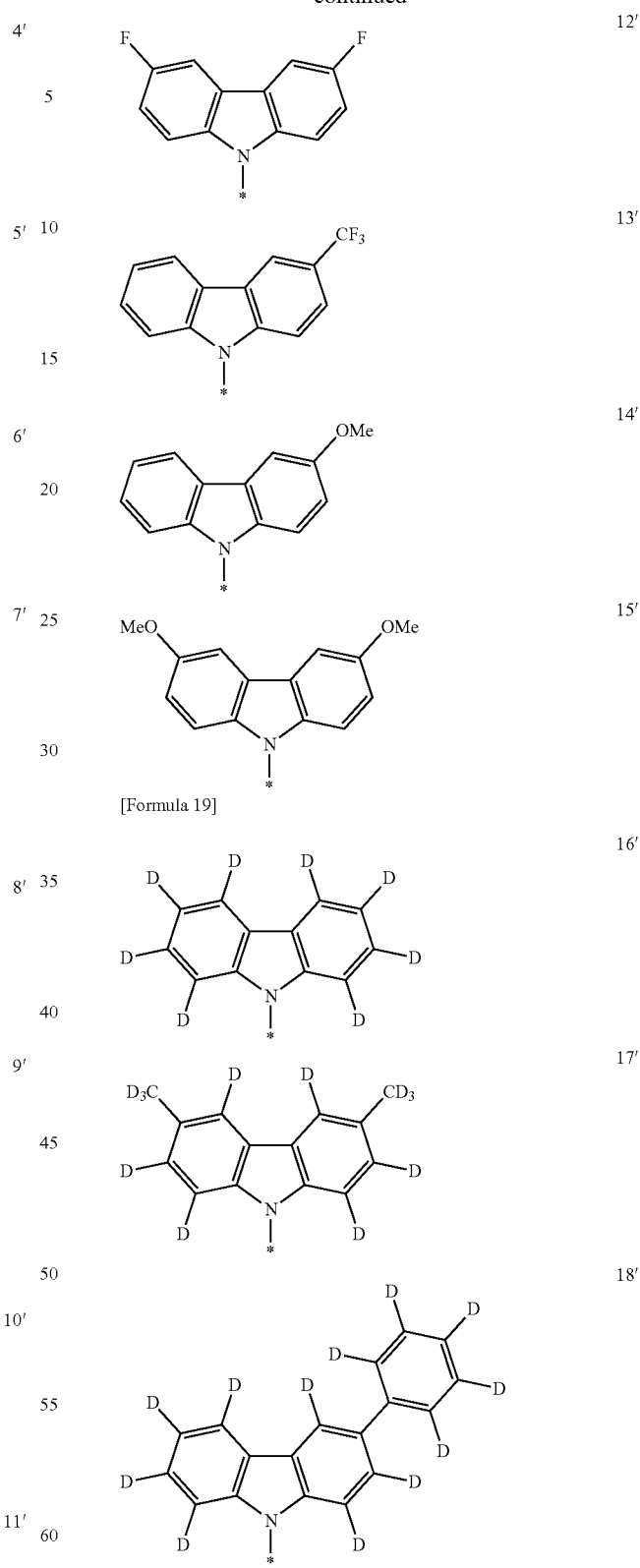
For instance, in Table 3, a compound 1 represents a compound 1a represented by the formula (11-1) in which $D_{1A}$ and $D_{1B}$ are groups 1 and $D_{2A}$ and $D_{2B}$ are groups 1', a compound 1b represented by the formula (12-1) in which $D_{1A}$ and $D_{1B}$ are groups 1 and $D_{2A}$ and $D_{2B}$ are groups 1', a compound 1c represented by the formula (12-2) in which $D_{1A}$ and $D_{1B}$ are groups 1 and $D_{2A}$ and $D_{2B}$ are groups 1', a compound 1 d represented by the formula (13-1) in which $D_{1A}$ and $D_{1B}$ are groups 1 and $D_{2A}$ and $D_{2B}$ are groups 1', and a compound 1e represented by the formula (13-2) in which $D_{1A}$ and 013 are groups 1 and $D_{2A}$ and $D_{2B}$ are groups 1'.

In other words, the compound 1 is any one of the compounds 1a to 1e.

[Formula 20]

Compound 1a

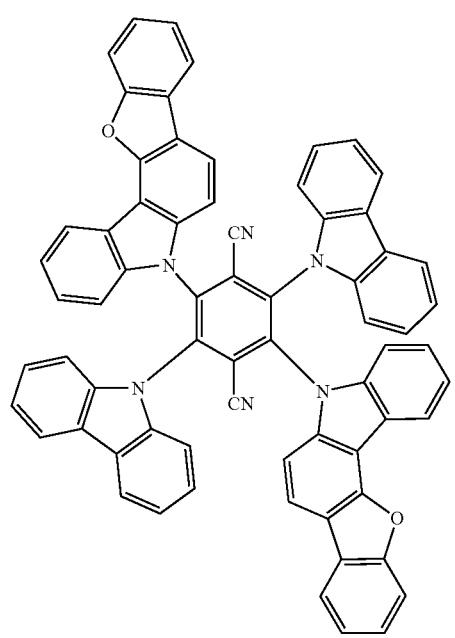

Compound 1b

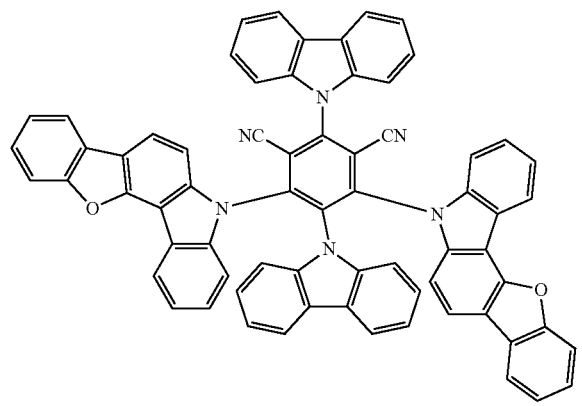

Compound 1c

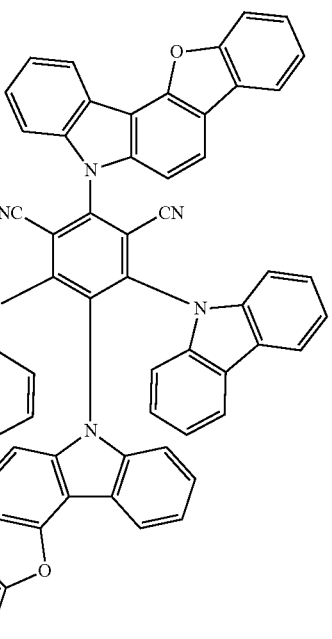

Compound 1d

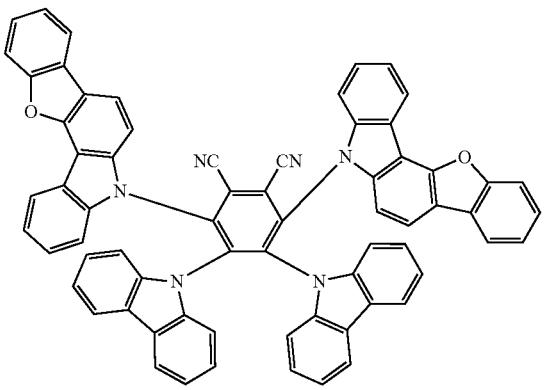

Compound 1e

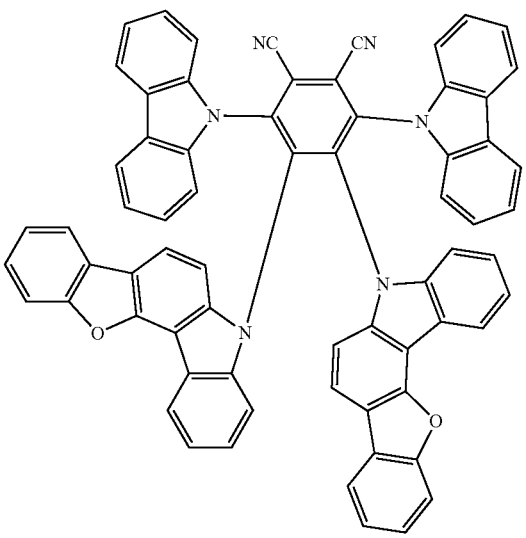

A relationship between the compound 1 and the compounds 1a to 1e is shown in Table 1 below.

Herein, the compounds 1 to 540 and 1621 to 1728 are also referred to as a compound X. X is an integer from 1 to 540 and from 1621 to 1728. Specifically, the compound X represents compounds Xa to Xe.

A relationship between the compound X and the compounds Xa to Xe is shown in Table 2 below.

TABLE 1

| Compound No. | Type | Formula No. | $D_{1A}$ | $D_{1B}$ | $D_{2A}$ | $D_{2B}$ |
|---|---|---|---|---|---|---|
| Compound 1 | Compound 1a | (11-1) | 1 | 1 | 1' | 1' |
|  | Compound 1b | (12-1) | 1 | 1 | 1' | 1' |
|  | Compound 1c | (12-2) | 1 | 1 | 1' | 1' |
|  | Compound 1d | (13-1) | 1 | 1 | 1' | 1' |
|  | Compound 1e | (13-2) | 1 | 1 | 1' | 1' |

TABLE 2

| Compound No. | Type | Formula No. |
|---|---|---|
| Compound X | Compound Xa | (11-1) |
|  | Compound Xb | (12-1) |
|  | Compound Xc | (12-2) |
|  | Compound Xd | (13-1) |
|  | Compound Xe | (13-2) |

TABLE 3

| Compound No | $D_{1A}$ | $D_{1B}$ | $D_{2A}$ | $D_{2B}$ |
|---|---|---|---|---|
| Compound 1 | 1 | 1 | 1' | 1' |
| Compound 2 | 2 | 2 | 1' | 1' |
| Compound 3 | 3 | 3 | 1' | 1' |
| Compound 4 | 4 | 4 | 1' | 1' |
| Compound 5 | 5 | 5 | 1' | 1' |
| Compound 6 | 6 | 6 | 1' | 1' |
| Compound 7 | 7 | 7 | 1' | 1' |
| Compound 8 | 8 | 8 | 1' | 1' |
| Compound 9 | 9 | 9 | 1' | 1' |
| Compound 10 | 10 | 10 | 1' | 1' |
| Compound 11 | 11 | 11 | 1' | 1' |
| Compound 12 | 12 | 12 | 1' | 1' |
| Compound 13 | 13 | 13 | 1' | 1' |
| Compound 14 | 14 | 14 | 1' | 1' |
| Compound 15 | 15 | 15 | 1' | 1' |
| Compound 16 | 16 | 16 | 1' | 1' |
| Compound 17 | 17 | 17 | 1' | 1' |
| Compound 18 | 18 | 18 | 1' | 1' |
| Compound 19 | 19 | 19 | 1' | 1' |
| Compound 20 | 20 | 20 | 1' | 1' |
| Compound 21 | 21 | 21 | 1' | 1' |
| Compound 22 | 22 | 22 | 1' | 1' |
| Compound 23 | 23 | 23 | 1' | 1' |
| Compound 24 | 24 | 24 | 1' | 1' |
| Compound 25 | 25 | 25 | 1' | 1' |
| Compound 26 | 26 | 26 | 1' | 1' |
| Compound 27 | 27 | 27 | 1' | 1' |
| Compound 28 | 28 | 28 | 1' | 1' |
| Compound 29 | 29 | 29 | 1' | 1' |
| Compound 30 | 30 | 30 | 1' | 1' |
| Compound 31 | 31 | 31 | 1' | 1' |
| Compound 32 | 32 | 32 | 1' | 1' |
| Compound 33 | 33 | 33 | 1' | 1' |
| Compound 34 | 34 | 34 | 1' | 1' |
| Compound 35 | 35 | 35 | 1' | 1' |
| Compound 36 | 36 | 36 | 1' | 1' |

TABLE 4

| Compound No. | $D_{1A}$ | $D_{1B}$ | $D_{2A}$ | $D_{2B}$ |
|---|---|---|---|---|
| Compound 37 | 1 | 1 | 2' | 2' |
| Compound 38 | 2 | 2 | 2' | 2' |
| Compound 39 | 3 | 3 | 2' | 2' |
| Compound 40 | 4 | 4 | 2' | 2' |
| Compound 41 | 5 | 5 | 2' | 2' |
| Compound 42 | 6 | 6 | 2' | 2' |
| Compound 43 | 7 | 7 | 2' | 2' |
| Compound 44 | 8 | 8 | 2' | 2' |
| Compound 45 | 9 | 9 | 2' | 2' |
| Compound 46 | 10 | 10 | 2' | 2' |
| Compound 47 | 11 | 11 | 2' | 2' |
| Compound 48 | 12 | 12 | 2' | 2' |
| Compound 49 | 13 | 13 | 2' | 2' |
| Compound 50 | 14 | 14 | 2' | 2' |
| Compound 51 | 15 | 15 | 2' | 2' |
| Compound 52 | 16 | 16 | 2' | 2' |
| Compound 53 | 17 | 17 | 2' | 2' |
| Compound 54 | 18 | 18 | 2' | 2' |
| Compound 55 | 19 | 19 | 2' | 2' |
| Compound 56 | 20 | 20 | 2' | 2' |
| Compound 57 | 21 | 21 | 2' | 2' |
| Compound 58 | 22 | 22 | 2' | 2' |
| Compound 59 | 23 | 23 | 2' | 2' |
| Compound 60 | 24 | 24 | 2' | 2' |
| Compound 61 | 25 | 25 | 2' | 2' |
| Compound 62 | 26 | 26 | 2' | 2' |
| Compound 63 | 27 | 27 | 2' | 2' |
| Compound 64 | 28 | 28 | 2' | 2' |
| Compound 65 | 29 | 29 | 2' | 2' |
| Compound 66 | 30 | 30 | 2' | 2' |
| Compound 67 | 31 | 31 | 2' | 2' |
| Compound 68 | 32 | 32 | 2' | 2' |
| Compound 69 | 33 | 33 | 2' | 2' |
| Compound 70 | 34 | 34 | 2' | 2' |
| Compound 71 | 35 | 35 | 2' | 2' |
| Compound 72 | 36 | 36 | 2' | 2' |

TABLE 5

| Compound No. | $D_{1A}$ | $D_{1B}$ | $D_{2A}$ | $D_{2B}$ |
|---|---|---|---|---|
| Compound 73 | 1 | 1 | 3' | 3' |
| Compound 74 | 2 | 2 | 3' | 3' |
| Compound 75 | 3 | 3 | 3' | 3' |
| Compound 76 | 4 | 4 | 3' | 3' |
| Compound 77 | 5 | 5 | 3' | 3' |
| Compound 78 | 6 | 6 | 3' | 3' |
| Compound 79 | 7 | 7 | 3' | 3' |
| Compound 80 | 8 | 8 | 3' | 3' |
| Compound 81 | 9 | 9 | 3' | 3' |
| Compound 82 | 10 | 10 | 3' | 3' |
| Compound 83 | 11 | 11 | 3' | 3' |
| Compound 84 | 12 | 12 | 3' | 3' |
| Compound 85 | 13 | 13 | 3' | 3' |
| Compound 86 | 14 | 14 | 3' | 3' |
| Compound 87 | 15 | 15 | 3' | 3' |
| Compound 88 | 16 | 16 | 3' | 3' |
| Compound 89 | 17 | 17 | 3' | 3' |
| Compound 90 | 18 | 18 | 3' | 3' |
| Compound 91 | 19 | 19 | 3' | 3' |
| Compound 92 | 20 | 20 | 3' | 3' |
| Compound 93 | 21 | 21 | 3' | 3' |
| Compound 94 | 22 | 22 | 3' | 3' |
| Compound 95 | 23 | 23 | 3' | 3' |
| Compound 96 | 24 | 24 | 3' | 3' |
| Compound 97 | 25 | 25 | 3' | 3' |
| Compound 98 | 26 | 26 | 3' | 3' |
| Compound 99 | 27 | 27 | 3' | 3' |
| Compound 100 | 28 | 28 | 3' | 3' |
| Compound 101 | 29 | 29 | 3' | 3' |
| Compound 102 | 30 | 30 | 3' | 3' |
| Compound 103 | 31 | 31 | 3' | 3' |
| Compound 104 | 32 | 32 | 3' | 3' |
| Compound 105 | 33 | 33 | 3' | 3' |
| Compound 106 | 34 | 34 | 3' | 3' |

TABLE 5-continued

| Compound No. | $D_{1A}$ | $D_{1B}$ | $D_{2A}$ | $D_{2B}$ |
|---|---|---|---|---|
| Compound 107 | 35 | 35 | 3' | 3' |
| Compound 108 | 36 | 36 | 3' | 3' |

TABLE 6

| Compound No. | $D_{1A}$ | $D_{1B}$ | $D_{2A}$ | $D_{2B}$ |
|---|---|---|---|---|
| Compound 109 | 1 | 1 | 4' | 4' |
| Compound 110 | 2 | 2 | 4' | 4' |
| Compound 111 | 3 | 3 | 4' | 4' |
| Compound 112 | 4 | 4 | 4' | 4' |
| Compound 113 | 5 | 5 | 4' | 4' |
| Compound 114 | 6 | 6 | 4' | 4' |
| Compound 115 | 7 | 7 | 4' | 4' |
| Compound 116 | 8 | 8 | 4' | 4' |
| Compound 117 | 9 | 9 | 4' | 4' |
| Compound 118 | 10 | 10 | 4' | 4' |
| Compound 119 | 11 | 11 | 4' | 4' |
| Compound 120 | 12 | 12 | 4' | 4' |
| Compound 121 | 13 | 13 | 4' | 4' |
| Compound 122 | 14 | 14 | 4' | 4' |
| Compound 123 | 15 | 15 | 4' | 4' |
| Compound 124 | 16 | 16 | 4' | 4' |
| Compound 125 | 17 | 17 | 4' | 4' |
| Compound 126 | 18 | 18 | 4' | 4' |
| Compound 127 | 19 | 19 | 4' | 4' |
| Compound 128 | 20 | 20 | 4' | 4' |
| Compound 129 | 21 | 21 | 4' | 4' |
| Compound 130 | 22 | 22 | 4' | 4' |
| Compound 131 | 23 | 23 | 4' | 4' |
| Compound 132 | 24 | 24 | 4' | 4' |
| Compound 133 | 25 | 25 | 4' | 4' |
| Compound 134 | 26 | 26 | 4' | 4' |
| Compound 135 | 27 | 27 | 4' | 4' |
| Compound 136 | 28 | 28 | 4' | 4' |
| Compound 137 | 29 | 29 | 4' | 4' |
| Compound 138 | 30 | 30 | 4' | 4' |
| Compound 139 | 31 | 31 | 4' | 4' |
| Compound 140 | 32 | 32 | 4' | 4' |
| Compound 141 | 33 | 33 | 4' | 4' |
| Compound 142 | 34 | 34 | 4' | 4' |
| Compound 143 | 35 | 35 | 4' | 4' |
| Compound 144 | 36 | 36 | 4' | 4' |

TABLE 7

| Compound No. | $D_{1A}$ | $D_{1B}$ | $D_{2A}$ | $D_{2B}$ |
|---|---|---|---|---|
| Compound 145 | 1 | 1 | 5' | 5' |
| Compound 146 | 2 | 2 | 5' | 5' |
| Compound 147 | 3 | 3 | 5' | 5' |
| Compound 148 | 4 | 4 | 5' | 5' |
| Compound 149 | 5 | 5 | 5' | 5' |
| Compound 150 | 6 | 6 | 5' | 5' |
| Compound 151 | 7 | 7 | 5' | 5' |
| Compound 152 | 8 | 8 | 5' | 5' |
| Compound 153 | 9 | 9 | 5' | 5' |
| Compound 154 | 10 | 10 | 5' | 5' |
| Compound 155 | 11 | 11 | 5' | 5' |
| Compound 156 | 12 | 12 | 5' | 5' |
| Compound 157 | 13 | 13 | 5' | 5' |
| Compound 158 | 14 | 14 | 5' | 5' |
| Compound 159 | 15 | 15 | 5' | 5' |
| Compound 160 | 16 | 16 | 5' | 5' |
| Compound 161 | 17 | 17 | 5' | 5' |
| Compound 162 | 18 | 18 | 5' | 5' |
| Compound 163 | 19 | 19 | 5' | 5' |
| Compound 164 | 20 | 20 | 5' | 5' |
| Compound 165 | 21 | 21 | 5' | 5' |
| Compound 166 | 22 | 22 | 5' | 5' |
| Compound 167 | 23 | 23 | 5' | 5' |
| Compound 168 | 24 | 24 | 5' | 5' |
| Compound 169 | 25 | 25 | 5' | 5' |

TABLE 7-continued

| Compound No. | $D_{1A}$ | $D_{1B}$ | $D_{2A}$ | $D_{2B}$ |
|---|---|---|---|---|
| Compound 170 | 26 | 26 | 5' | 5' |
| Compound 171 | 27 | 27 | 5' | 5' |
| Compound 172 | 28 | 28 | 5' | 5' |
| Compound 173 | 29 | 29 | 5' | 5' |
| Compound 174 | 30 | 30 | 5' | 5' |
| Compound 175 | 31 | 31 | 5' | 5' |
| Compound 176 | 32 | 32 | 5' | 5' |
| Compound 177 | 33 | 33 | 5' | 5' |
| Compound 178 | 34 | 34 | 5' | 5' |
| Compound 179 | 35 | 35 | 5' | 5' |
| Compound 180 | 36 | 36 | 5' | 5' |

TABLE 8

| Compound No. | $D_{1A}$ | $D_{1B}$ | $D_{2A}$ | $D_{2B}$ |
|---|---|---|---|---|
| Compound 181 | 1 | 1 | 6' | 6' |
| Compound 182 | 2 | 2 | 6' | 6' |
| Compound 183 | 3 | 3 | 6' | 6' |
| Compound 184 | 4 | 4 | 6' | 6' |
| Compound 185 | 5 | 5 | 6' | 6' |
| Compound 186 | 6 | 6 | 6' | 6' |
| Compound 187 | 7 | 7 | 6' | 6' |
| Compound 188 | 8 | 8 | 6' | 6' |
| Compound 189 | 9 | 9 | 6' | 6' |
| Compound 190 | 10 | 10 | 6' | 6' |
| Compound 191 | 11 | 11 | 6' | 6' |
| Compound 192 | 12 | 12 | 6' | 6' |
| Compound 193 | 13 | 13 | 6' | 6' |
| Compound 194 | 14 | 14 | 6' | 6' |
| Compound 195 | 15 | 15 | 6' | 6' |
| Compound 196 | 16 | 16 | 6' | 6' |
| Compound 197 | 17 | 17 | 6' | 6' |
| Compound 198 | 18 | 18 | 6' | 6' |
| Compound 199 | 19 | 19 | 6' | 6' |
| Compound 200 | 20 | 20 | 6' | 6' |
| Compound 201 | 21 | 21 | 6' | 6' |
| Compound 202 | 22 | 22 | 6' | 6' |
| Compound 203 | 23 | 23 | 6' | 6' |
| Compound 204 | 24 | 24 | 6' | 6' |
| Compound 205 | 25 | 25 | 6' | 6' |
| Compound 206 | 26 | 26 | 6' | 6' |
| Compound 207 | 27 | 27 | 6' | 6' |
| Compound 208 | 28 | 28 | 6' | 6' |
| Compound 209 | 29 | 29 | 6' | 6' |
| Compound 210 | 30 | 30 | 6' | 6' |
| Compound 211 | 31 | 31 | 6' | 6' |
| Compound 212 | 32 | 32 | 6' | 6' |
| Compound 213 | 33 | 33 | 6' | 6' |
| Compound 214 | 34 | 34 | 6' | 6' |
| Compound 215 | 35 | 35 | 6' | 6' |
| Compound 216 | 36 | 36 | 6' | 6' |

TABLE 9

| Compound No. | $D_{1A}$ | $D_{1B}$ | $D_{2A}$ | $D_{2B}$ |
|---|---|---|---|---|
| Compound 217 | 1 | 1 | 7' | 7' |
| Compound 218 | 2 | 2 | 7' | 7' |
| Compound 219 | 3 | 3 | 7' | 7' |
| Compound 220 | 4 | 4 | 7' | 7' |
| Compound 221 | 5 | 5 | 7' | 7' |
| Compound 222 | 6 | 6 | 7' | 7' |
| Compound 223 | 7 | 7 | 7' | 7' |
| Compound 224 | 8 | 8 | 7' | 7 |
| Compound 225 | 9 | 9 | 7' | 7' |
| Compound 226 | 10 | 10 | 7' | 7' |
| Compound 227 | 11 | 11 | 7' | 7' |
| Compound 228 | 12 | 12 | 7' | 7' |
| Compound 229 | 13 | 13 | 7' | 7' |
| Compound 230 | 14 | 14 | 7' | 7' |
| Compound 231 | 15 | 15 | 7' | 7' |
| Compound 232 | 16 | 16 | 7' | 7' |

TABLE 9-continued

| Compound No. | $D_{1A}$ | $D_{1B}$ | $D_{2A}$ | $D_{2B}$ |
|---|---|---|---|---|
| Compound 233 | 17 | 17 | 7' | 7' |
| Compound 234 | 18 | 18 | 7' | 7' |
| Compound 235 | 19 | 19 | 7' | 7' |
| Compound 236 | 20 | 20 | 7' | 7' |
| Compound 237 | 21 | 21 | 7' | 7' |
| Compound 238 | 22 | 22 | 7' | 7' |
| Compound 239 | 23 | 23 | 7' | 7' |
| Compound 240 | 24 | 24 | 7' | 7' |
| Compound 241 | 25 | 25 | 7' | 7' |
| Compound 242 | 26 | 26 | 7' | 7' |
| Compound 243 | 27 | 27 | 7' | 7' |
| Compound 244 | 28 | 28 | 7' | 7' |
| Compound 245 | 29 | 29 | 7' | 7' |
| Compound 246 | 30 | 30 | 7' | 7' |
| Compound 247 | 31 | 31 | 7' | 7' |
| Compound 248 | 32 | 32 | 7' | 7' |
| Compound 249 | 33 | 33 | 7' | 7' |
| Compound 250 | 34 | 34 | 7' | 7' |
| Compound 251 | 35 | 35 | 7' | 7' |
| Compound 252 | 36 | 36 | 7' | 7' |

TABLE 10

| Compound No. | $D_{1A}$ | $D_{1B}$ | $D_{2A}$ | $D_{2B}$ |
|---|---|---|---|---|
| Compound 253 | 1 | 1 | 8' | 8' |
| Compound 254 | 2 | 2 | 8' | 8' |
| Compound 255 | 3 | 3 | 8' | 8' |
| Compound 256 | 4 | 4 | 8' | 8' |
| Compound 257 | 5 | 5 | 8' | 8' |
| Compound 258 | 6 | 6 | 8' | 8' |
| Compound 259 | 7 | 7 | 8' | 8' |
| Compound 260 | 8 | 8 | 8' | 8' |
| Compound 261 | 9 | 9 | 8' | 8' |
| Compound 262 | 10 | 10 | 8' | 8' |
| Compound 263 | 11 | 11 | 8' | 8' |
| Compound 264 | 12 | 12 | 8' | 8' |
| Compound 265 | 13 | 13 | 8' | 8' |
| Compound 266 | 14 | 14 | 8' | 8' |
| Compound 267 | 15 | 15 | 8' | 8' |
| Compound 268 | 16 | 16 | 8' | 8' |
| Compound 269 | 17 | 17 | 8' | 8' |
| Compound 270 | 18 | 18 | 8' | 8' |
| Compound 271 | 19 | 19 | 8' | 8' |
| Compound 272 | 20 | 20 | 8' | 8' |
| Compound 273 | 21 | 21 | 8' | 8' |
| Compound 274 | 22 | 22 | 8' | 8' |
| Compound 275 | 23 | 23 | 8' | 8' |
| Compound 276 | 24 | 24 | 8' | 8' |
| Compound 277 | 25 | 25 | 8' | 8' |
| Compound 278 | 26 | 26 | 8' | 8' |
| Compound 279 | 27 | 27 | 8' | 8' |
| Compound 280 | 28 | 28 | 8' | 8' |
| Compound 281 | 29 | 29 | 8' | 8' |
| Compound 282 | 30 | 30 | 8' | 8' |
| Compound 283 | 31 | 31 | 8' | 8' |
| Compound 284 | 32 | 32 | 8' | 8' |
| Compound 285 | 33 | 33 | 8' | 8' |
| Compound 286 | 34 | 34 | 8' | 8' |
| Compound 287 | 35 | 35 | 8' | 8' |
| Compound 288 | 36 | 36 | 8' | 8' |

TABLE 11

| Compound No. | $D_{1A}$ | $D_{1B}$ | $D_{2A}$ | $D_{2B}$ |
|---|---|---|---|---|
| Compound 289 | 1 | 1 | 9' | 9' |
| Compound 290 | 2 | 2 | 9' | 9' |
| Compound 291 | 3 | 3 | 9' | 9' |
| Compound 292 | 4 | 4 | 9' | 9' |
| Compound 293 | 5 | 5 | 9' | 9' |
| Compound 294 | 6 | 6 | 9' | 9' |
| Compound 295 | 7 | 7 | 9' | 9' |
| Compound 296 | 8 | 8 | 9' | 9' |
| Compound 297 | 9 | 9 | 9' | 9' |
| Compound 298 | 10 | 10 | 9' | 9' |
| Compound 299 | 11 | 11 | 9' | 9' |
| Compound 300 | 12 | 12 | 9' | 9' |
| Compound 301 | 13 | 13 | 9' | 9' |
| Compound 302 | 14 | 14 | 9' | 9' |
| Compound 303 | 15 | 15 | 9' | 9' |
| Compound 304 | 16 | 16 | 9' | 9' |
| Compound 305 | 17 | 17 | 9' | 9' |
| Compound 306 | 18 | 18 | 9' | 9' |
| Compound 307 | 19 | 19 | 9' | 9' |
| Compound 308 | 20 | 20 | 9' | 9' |
| Compound 309 | 21 | 21 | 9' | 9' |
| Compound 310 | 22 | 22 | 9' | 9' |
| Compound 311 | 23 | 23 | 9' | 9' |
| Compound 312 | 24 | 24 | 9' | 9' |
| Compound 313 | 25 | 25 | 9' | 9' |
| Compound 314 | 26 | 26 | 9' | 9' |
| Compound 315 | 27 | 27 | 9' | 9' |
| Compound 316 | 28 | 28 | 9' | 9' |
| Compound 317 | 29 | 29 | 9' | 9' |
| Compound 318 | 30 | 30 | 9' | 9' |
| Compound 319 | 31 | 31 | 9' | 9' |
| Compound 320 | 32 | 32 | 9' | 9' |
| Compound 321 | 33 | 33 | 9' | 9' |
| Compound 322 | 34 | 34 | 9' | 9' |
| Compound 323 | 35 | 35 | 9' | 9' |
| Compound 324 | 36 | 36 | 9' | 9' |

TABLE 12

| Compound No. | $D_{1A}$ | $D_{1B}$ | $D_{2A}$ | $D_{2B}$ |
|---|---|---|---|---|
| Compound 325 | 1 | 1 | 10' | 10' |
| Compound 326 | 2 | 2 | 10' | 10' |
| Compound 327 | 3 | 3 | 10' | 10' |
| Compound 328 | 4 | 4 | 10' | 10' |
| Compound 329 | 5 | 5 | 10' | 10' |
| Compound 330 | 6 | 6 | 10' | 10' |
| Compound 331 | 7 | 7 | 10' | 10' |
| Compound 332 | 8 | 8 | 10' | 10' |
| Compound 333 | 9 | 9 | 10' | 10' |
| Compound 334 | 10 | 10 | 10' | 10' |
| Compound 335 | 11 | 11 | 10' | 10' |
| Compound 336 | 12 | 12 | 10' | 10' |
| Compound 337 | 13 | 13 | 10' | 10' |
| Compound 338 | 14 | 14 | 10' | 10' |
| Compound 339 | 15 | 15 | 10' | 10' |
| Compound 340 | 16 | 16 | 10' | 10' |
| Compound 341 | 17 | 17 | 10' | 10' |
| Compound 342 | 18 | 18 | 10' | 10' |
| Compound 343 | 19 | 19 | 10' | 10' |
| Compound 344 | 20 | 20 | 10' | 10' |
| Compound 345 | 21 | 21 | 10' | 10' |
| Compound 346 | 22 | 22 | 10' | 10' |
| Compound 347 | 23 | 23 | 10' | 10' |
| Compound 348 | 24 | 24 | 10' | 10' |
| Compound 349 | 25 | 25 | 10' | 10' |
| Compound 350 | 26 | 26 | 10' | 10' |
| Compound 351 | 27 | 27 | 10' | 10' |
| Compound 352 | 28 | 28 | 10' | 10' |
| Compound 353 | 29 | 29 | 10' | 10' |
| Compound 354 | 30 | 30 | 10' | 10' |
| Compound 355 | 31 | 31 | 10' | 10' |
| Compound 356 | 32 | 32 | 10' | 10' |
| Compound 357 | 33 | 33 | 10' | 10' |
| Compound 358 | 34 | 34 | 10' | 10' |
| Compound 359 | 35 | 35 | 10' | 10' |
| Compound 360 | 36 | 36 | 10' | 10' |

TABLE 13

| Compound No | $D_{1A}$ | $D_{1B}$ | $D_{2A}$ | $D_{2B}$ |
|---|---|---|---|---|
| Compound 361 | 1 | 1 | 11' | 11' |
| Compound 362 | 2 | 2 | 11' | 11' |
| Compound 363 | 3 | 3 | 11' | 11' |
| Compound 364 | 4 | 4 | 11' | 11' |
| Compound 365 | 5 | 5 | 11' | 11' |
| Compound 366 | 6 | 6 | 11' | 11' |
| Compound 367 | 7 | 7 | 11' | 11' |
| Compound 368 | 8 | 8 | 11' | 11' |
| Compound 369 | 9 | 9 | 11' | 11' |
| Compound 370 | 10 | 10 | 11' | 11' |
| Compound 371 | 11 | 11 | 11' | 11' |
| Compound 372 | 12 | 12 | 11' | 11' |
| Compound 373 | 13 | 13 | 11' | 11' |
| Compound 374 | 14 | 14 | 11' | 11' |
| Compound 375 | 15 | 15 | 11' | 11' |
| Compound 376 | 16 | 16 | 11' | 11' |
| Compound 377 | 17 | 17 | 11' | 11' |
| Compound 378 | 18 | 18 | 11' | 11' |
| Compound 379 | 19 | 19 | 11' | 11' |
| Compound 380 | 20 | 20 | 11' | 11' |
| Compound 381 | 21 | 21 | 11' | 11' |
| Compound 382 | 22 | 22 | 11' | 11' |
| Compound 383 | 23 | 23 | 11' | 11' |
| Compound 384 | 24 | 24 | 11' | 11' |
| Compound 385 | 25 | 25 | 11' | 11' |
| Compound 386 | 26 | 26 | 11' | 11' |
| Compound 387 | 27 | 27 | 11' | 11' |
| Compound 388 | 28 | 28 | 11' | 11' |
| Compound 389 | 29 | 29 | 11' | 11' |
| Compound 390 | 30 | 30 | 11' | 11' |
| Compound 391 | 31 | 31 | 11' | 11' |
| Compound 392 | 32 | 32 | 11' | 11' |
| Compound 393 | 33 | 33 | 11' | 11' |
| Compound 394 | 34 | 34 | 11' | 11' |
| Compound 395 | 35 | 35 | 11' | 11' |
| Compound 396 | 36 | 36 | 11' | 11' |

TABLE 14

| Compound No. | $D_{1A}$ | $D_{1B}$ | $D_{2A}$ | $D_{2B}$ |
|---|---|---|---|---|
| Compound 397 | 1 | 1 | 12' | 12' |
| Compound 398 | 2 | 2 | 12' | 12' |
| Compound 399 | 3 | 3 | 12' | 12' |
| Compound 400 | 4 | 4 | 12' | 12' |
| Compound 401 | 5 | 5 | 12' | 12' |
| Compound 402 | 6 | 6 | 12' | 12' |
| Compound 403 | 7 | 7 | 12' | 12' |
| Compound 404 | 8 | 8 | 12' | 12' |
| Compound 405 | 9 | 9 | 12' | 12' |
| Compound 406 | 10 | 10 | 12' | 12' |
| Compound 407 | 11 | 11 | 12' | 12' |
| Compound 408 | 12 | 12 | 12' | 12' |
| Compound 409 | 13 | 13 | 12' | 12' |
| Compound 410 | 14 | 14 | 12' | 12' |
| Compound 411 | 15 | 15 | 12' | 12' |
| Compound 412 | 16 | 16 | 12' | 12' |
| Compound 413 | 17 | 17 | 12' | 12' |
| Compound 414 | 18 | 18 | 12' | 12' |
| Compound 415 | 19 | 19 | 12' | 12' |
| Compound 416 | 20 | 20 | 12' | 12' |
| Compound 417 | 21 | 21 | 12' | 12' |
| Compound 418 | 22 | 22 | 12' | 12' |
| Compound 419 | 23 | 23 | 12' | 12' |
| Compound 420 | 24 | 24 | 12' | 12' |
| Compound 421 | 25 | 25 | 12' | 12' |
| Compound 422 | 26 | 26 | 12' | 12' |
| Compound 423 | 27 | 27 | 12' | 12' |
| Compound 424 | 28 | 28 | 12' | 12' |
| Compound 425 | 29 | 29 | 12' | 12' |
| Compound 426 | 30 | 30 | 12' | 12' |
| Compound 427 | 31 | 31 | 12' | 12' |
| Compound 428 | 32 | 32 | 12' | 12' |
| Compound 429 | 33 | 33 | 12' | 12' |
| Compound 430 | 34 | 34 | 12' | 12' |
| Compound 431 | 35 | 35 | 12' | 12' |
| Compound 432 | 36 | 36 | 12' | 12' |

TABLE 15

| Compound No | $D_{1A}$ | $D_{1B}$ | $D_{2A}$ | $D_{2B}$ |
|---|---|---|---|---|
| Compound 433 | 1 | 1 | 13' | 13' |
| Compound 434 | 2 | 2 | 13' | 13' |
| Compound 435 | 3 | 3 | 13' | 13' |
| Compound 436 | 4 | 4 | 13' | 13' |
| Compound 437 | 5 | 5 | 13' | 13' |
| Compound 438 | 6 | 6 | 13' | 13' |
| Compound 439 | 7 | 7 | 13' | 13' |
| Compound 440 | 8 | 8 | 13' | 13' |
| Compound 441 | 9 | 9 | 13' | 13' |
| Compound 442 | 10 | 10 | 13' | 13' |
| Compound 443 | 11 | 11 | 13' | 13' |
| Compound 444 | 12 | 12 | 13' | 13' |
| Compound 445 | 13 | 13 | 13' | 13' |
| Compound 446 | 14 | 14 | 13' | 13' |
| Compound 447 | 15 | 15 | 13' | 13' |
| Compound 448 | 16 | 16 | 13' | 13' |
| Compound 449 | 17 | 17 | 13' | 13' |
| Compound 450 | 18 | 18 | 13' | 13' |
| Compound 451 | 19 | 19 | 13' | 13' |
| Compound 452 | 20 | 20 | 13' | 13' |
| Compound 453 | 21 | 21 | 13' | 13' |
| Compound 454 | 22 | 22 | 13' | 13' |
| Compound 455 | 23 | 23 | 13' | 13' |
| Compound 456 | 24 | 24 | 13' | 13' |
| Compound 457 | 25 | 25 | 13' | 13' |
| Compound 458 | 26 | 26 | 13' | 13' |
| Compound 459 | 27 | 27 | 13' | 13' |
| Compound 460 | 28 | 28 | 13' | 13' |
| Compound 461 | 29 | 29 | 13' | 13' |
| Compound 462 | 30 | 30 | 13' | 13' |
| Compound 463 | 31 | 31 | 13' | 13' |
| Compound 464 | 32 | 32 | 13' | 13' |
| Compound 465 | 33 | 33 | 13' | 13' |
| Compound 466 | 34 | 34 | 13' | 13' |
| Compound 467 | 35 | 35 | 13' | 13' |
| Compound 468 | 36 | 36 | 13' | 13' |

TABLE 16

| Compound No. | $D_{1A}$ | $D_{1B}$ | $D_{2A}$ | $D_{2B}$ |
|---|---|---|---|---|
| Compound 469 | 1 | 1 | 14' | 14' |
| Compound 470 | 2 | 2 | 14' | 14' |
| Compound 471 | 3 | 3 | 14' | 14' |
| Compound 472 | 4 | 4 | 14' | 14' |
| Compound 473 | 5 | 5 | 14' | 14' |
| Compound 474 | 6 | 6 | 14' | 14' |
| Compound 475 | 7 | 7 | 14' | 14' |
| Compound 476 | 8 | 8 | 14' | 14' |
| Compound 477 | 9 | 9 | 14' | 14' |
| Compound 478 | 10 | 10 | 14' | 14' |
| Compound 479 | 11 | 11 | 14' | 14' |
| Compound 480 | 12 | 12 | 14' | 14' |
| Compound 481 | 13 | 13 | 14' | 14' |
| Compound 482 | 14 | 14 | 14' | 14' |
| Compound 483 | 15 | 15 | 14' | 14' |
| Compound 484 | 16 | 16 | 14' | 14' |
| Compound 485 | 17 | 17 | 14' | 14' |
| Compound 486 | 18 | 18 | 14' | 14' |
| Compound 487 | 19 | 19 | 14' | 14' |
| Compound 488 | 20 | 20 | 14' | 14' |
| Compound 489 | 21 | 21 | 14' | 14' |
| Compound 490 | 22 | 22 | 14' | 14' |
| Compound 491 | 23 | 23 | 14' | 14' |
| Compound 492 | 24 | 24 | 14' | 14' |
| Compound 493 | 25 | 25 | 14' | 14' |

TABLE 16-continued

| Compound No. | $D_{1A}$ | $D_{1B}$ | $D_{2A}$ | $D_{2B}$ |
|---|---|---|---|---|
| Compound 494 | 26 | 26 | 14' | 14' |
| Compound 495 | 27 | 27 | 14' | 14' |
| Compound 496 | 28 | 28 | 14' | 14' |
| Compound 497 | 29 | 29 | 14' | 14' |
| Compound 498 | 30 | 30 | 14' | 14' |
| Compound 499 | 31 | 31 | 14' | 14' |
| Compound 500 | 32 | 32 | 14' | 14' |
| Compound 501 | 33 | 33 | 14' | 14' |
| Compound 502 | 34 | 34 | 14' | 14' |
| Compound 503 | 35 | 35 | 14' | 14' |
| Compound 504 | 36 | 36 | 14' | 14' |

TABLE 17

| Compound No. | $D_{1A}$ | $D_{1B}$ | $D_{2A}$ | $D_{2B}$ |
|---|---|---|---|---|
| Compound 505 | 1 | 1 | 15' | 15' |
| Compound 506 | 2 | 2 | 15' | 15' |
| Compound 507 | 3 | 3 | 15' | 15' |
| Compound 508 | 4 | 4 | 15' | 15' |
| Compound 509 | 5 | 5 | 15' | 15' |
| Compound 510 | 6 | 6 | 15' | 15' |
| Compound 511 | 7 | 7 | 15' | 15' |
| Compound 512 | 8 | 8 | 15' | 15' |
| Compound 513 | 9 | 9 | 15' | 15' |
| Compound 514 | 10 | 10 | 15' | 15' |
| Compound 515 | 11 | 11 | 15' | 15' |
| Compound 516 | 12 | 12 | 15' | 15' |
| Compound 517 | 13 | 13 | 15' | 15' |
| Compound 518 | 14 | 14 | 15' | 15' |
| Compound 519 | 15 | 15 | 15' | 15' |
| Compound 520 | 16 | 16 | 15' | 15' |
| Compound 521 | 17 | 17 | 15' | 15' |
| Compound 522 | 18 | 18 | 15' | 15' |
| Compound 523 | 19 | 19 | 15' | 15' |
| Compound 524 | 20 | 20 | 15' | 15' |
| Compound 525 | 21 | 21 | 15' | 15' |
| Compound 526 | 22 | 22 | 15' | 15' |
| Compound 527 | 23 | 23 | 15' | 15' |
| Compound 528 | 24 | 24 | 15' | 15' |
| Compound 529 | 25 | 25 | 15' | 15' |
| Compound 530 | 26 | 26 | 15' | 15' |
| Compound 531 | 27 | 27 | 15' | 15' |
| Compound 532 | 28 | 28 | 15' | 15' |
| Compound 533 | 29 | 29 | 15' | 15' |
| Compound 534 | 30 | 30 | 15' | 15' |
| Compound 535 | 31 | 31 | 15' | 15' |
| Compound 536 | 32 | 32 | 15' | 15' |
| Compound 537 | 33 | 33 | 15' | 15' |
| Compound 538 | 34 | 34 | 15' | 15' |
| Compound 539 | 35 | 35 | 15' | 15' |
| Compound 540 | 36 | 36 | 15' | 15' |

TABLE 18

| Compound No. | $D_{1A}$ | $D_{1B}$ | $D_{2A}$ | $D_{2B}$ |
|---|---|---|---|---|
| Compound 1621 | 1 | 1 | 16' | 16' |
| Compound 1622 | 2 | 2 | 16' | 16' |
| Compound 1623 | 3 | 3 | 16' | 16' |
| Compound 1624 | 4 | 4 | 16' | 16' |
| Compound 1625 | 5 | 5 | 16' | 16' |
| Compound 1626 | 6 | 6 | 16' | 16' |
| Compound 1627 | 7 | 7 | 16' | 16' |
| Compound 1628 | 8 | 8 | 16' | 16' |
| Compound 1629 | 9 | 9 | 16' | 16' |
| Compound 1630 | 10 | 10 | 16' | 16' |
| Compound 1631 | 11 | 11 | 16' | 16' |
| Compound 1632 | 12 | 12 | 16' | 16' |
| Compound 1633 | 13 | 13 | 16' | 16' |
| Compound 1634 | 14 | 14 | 16' | 16' |
| Compound 1635 | 15 | 15 | 16' | 16' |
| Compound 1636 | 16 | 16 | 16' | 16' |

TABLE 18-continued

| Compound No. | $D_{1A}$ | $D_{1B}$ | $D_{2A}$ | $D_{2B}$ |
|---|---|---|---|---|
| Compound 1637 | 17 | 17 | 16' | 16' |
| Compound 1638 | 18 | 18 | 16' | 16' |
| Compound 1639 | 19 | 19 | 16' | 16' |
| Compound 1640 | 20 | 20 | 16' | 16' |
| Compound 1641 | 21 | 21 | 16' | 16' |
| Compound 1642 | 22 | 22 | 16' | 16' |
| Compound 1643 | 23 | 23 | 16' | 16' |
| Compound 1644 | 24 | 24 | 16' | 16' |
| Compound 1645 | 25 | 25 | 16' | 16' |
| Compound 1646 | 26 | 26 | 16' | 16' |
| Compound 1647 | 27 | 27 | 16' | 16' |
| Compound 1648 | 28 | 28 | 16' | 16' |
| Compound 1649 | 29 | 29 | 16' | 16' |
| Compound 1650 | 30 | 30 | 16' | 16' |
| Compound 1651 | 31 | 31 | 16' | 16' |
| Compound 1652 | 32 | 32 | 16' | 16' |
| Compound 1653 | 33 | 33 | 16' | 16' |
| Compound 1654 | 34 | 34 | 16' | 16' |
| Compound 1655 | 35 | 35 | 16' | 16' |
| Compound 1656 | 36 | 36 | 16' | 16' |

TABLE 19

| Compound No. | $D_{1A}$ | $D_{1B}$ | $D_{2A}$ | $D_{2B}$ |
|---|---|---|---|---|
| Compound 1657 | 1 | 1 | 17' | 17' |
| Compound 1658 | 2 | 2 | 17' | 17' |
| Compound 1659 | 3 | 3 | 17' | 17' |
| Compound 1660 | 4 | 4 | 17' | 17' |
| Compound 1661 | 5 | 5 | 17' | 17' |
| Compound 1662 | 6 | 6 | 17' | 17' |
| Compound 1663 | 7 | 7 | 17' | 17' |
| Compound 1664 | 8 | 8 | 17' | 17' |
| Compound 1665 | 9 | 9 | 17' | 17' |
| Compound 1666 | 10 | 10 | 17' | 17' |
| Compound 1667 | 11 | 11 | 17' | 17' |
| Compound 1668 | 12 | 12 | 17' | 17' |
| Compound 1669 | 13 | 13 | 17' | 17' |
| Compound 1670 | 14 | 14 | 17' | 17' |
| Compound 1671 | 15 | 15 | 17' | 17' |
| Compound 1672 | 16 | 16 | 17' | 17' |
| Compound 1673 | 17 | 17 | 17' | 17' |
| Compound 1674 | 18 | 18 | 17' | 17' |
| Compound 1675 | 19 | 19 | 17' | 17' |
| Compound 1676 | 20 | 20 | 17' | 17' |
| Compound 1677 | 21 | 21 | 17' | 17' |
| Compound 1678 | 22 | 22 | 17' | 17' |
| Compound 1679 | 23 | 23 | 17' | 17' |
| Compound 1680 | 24 | 24 | 17' | 17' |
| Compound 1681 | 25 | 25 | 17' | 17' |
| Compound 1682 | 26 | 26 | 17' | 17' |
| Compound 1683 | 27 | 27 | 17' | 17' |
| Compound 1684 | 28 | 28 | 17' | 17' |
| Compound 1685 | 29 | 29 | 17' | 17' |
| Compound 1686 | 30 | 30 | 17' | 17' |
| Compound 1687 | 31 | 31 | 17' | 17' |
| Compound 1688 | 32 | 32 | 17' | 17' |
| Compound 1689 | 33 | 33 | 17' | 17' |
| Compound 1690 | 34 | 34 | 17' | 17' |
| Compound 1691 | 35 | 35 | 17' | 17' |
| Compound 1692 | 36 | 36 | 17' | 17' |

TABLE 20

| Compound No. | $D_{1A}$ | $D_{1B}$ | $D_{2A}$ | $D_{2B}$ |
|---|---|---|---|---|
| Compound 1693 | 1 | 1 | 18' | 18' |
| Compound 1694 | 2 | 2 | 18' | 18' |
| Compound 1695 | 3 | 3 | 18' | 18' |
| Compound 1696 | 4 | 4 | 18' | 18' |
| Compound 1697 | 5 | 5 | 18' | 18' |
| Compound 1698 | 6 | 6 | 18' | 18' |
| Compound 1699 | 7 | 7 | 18' | 18' |

TABLE 20-continued

| Compound No. | $D_{1A}$ | $D_{1B}$ | $D_{2A}$ | $D_{2B}$ |
|---|---|---|---|---|
| Compound 1700 | 8 | 8 | 18' | 18' |
| Compound 1701 | 9 | 9 | 18' | 18' |
| Compound 1702 | 10 | 10 | 18' | 18' |
| Compound 1703 | 11 | 11 | 18' | 18' |
| Compound 1704 | 12 | 12 | 18' | 18' |
| Compound 1705 | 13 | 13 | 18' | 18' |
| Compound 1706 | 14 | 14 | 18' | 18' |
| Compound 1707 | 15 | 15 | 18' | 18' |
| Compound 1708 | 16 | 16 | 18' | 18' |
| Compound 1709 | 17 | 17 | 18' | 18' |
| Compound 1710 | 18 | 18 | 18' | 18' |
| Compound 1711 | 19 | 19 | 18' | 18' |
| Compound 1712 | 20 | 20 | 18' | 18' |
| Compound 1713 | 21 | 21 | 18' | 18' |
| Compound 1714 | 22 | 22 | 18' | 18' |
| Compound 1715 | 23 | 23 | 18' | 18' |
| Compound 1716 | 24 | 24 | 18' | 18' |
| Compound 1717 | 25 | 25 | 18' | 18' |
| Compound 1718 | 26 | 26 | 18' | 18' |
| Compound 1719 | 27 | 27 | 18' | 18' |
| Compound 1720 | 28 | 28 | 18' | 18' |
| Compound 1721 | 29 | 29 | 18' | 18' |
| Compound 1722 | 30 | 30 | 18' | 18' |
| Compound 1723 | 31 | 31 | 18' | 18' |
| Compound 1724 | 32 | 32 | 18' | 18' |
| Compound 1725 | 33 | 33 | 18' | 18' |
| Compound 1726 | 34 | 34 | 18' | 18' |
| Compound 1727 | 35 | 35 | 18' | 18' |
| Compound 1728 | 36 | 36 | 18' | 18' |

Examples of the compound according to the exemplary embodiment include compounds represented by the formulae (12-3) to (12-5), (13-3) and (11-2).

In the formula (12-3), $D_{1A}$, $D_{2A}$, $D_{2B}$, and $D_{2C}$ respectively represent the groups denoted by the numbers shown in Tables 22 to 39.

In the formula (13-3), $D_{1A}$, $D_{2A}$, $D_{2B}$, and $D_{2C}$ respectively represent the groups denoted by the numbers shown in Tables 22 to 39.

In the formula (12-4), $D_{1A}$, $D_{2A}$, $D_{2B}$, and $D_{2C}$ respectively represent the groups denoted by the numbers shown in Tables 22 to 39.

In the formula (12-5), $D_{1A}$, $D_{2A}$, $D_{2B}$, and $D_{2C}$ respectively represent the groups denoted by the numbers shown in Tables 22 to 39.

In the formula (11-2), $D_{1A}$, $D_{2A}$, $D_{2B}$, and $D_{2C}$ respectively represent the groups denoted by the numbers shown in Tables 22 to 39.

In Tables 22 to 39 below, the numbers given to columns of $D_{1A}$, $D_{2A}$, $D_{1B}$, and $D_{2B}$ correspond to numbers of the above-described groups 1 to 36 and groups 1' to 18'.

For instance, in Table 22, a compound 541 represents a compound 541a represented by the formula (12-3) in which $D_{1A}$ is the group 1 and $D_{2A}$, $D_{2B}$ and $D_{2C}$ are the groups 1', a compound 541b represented by the formula (13-3) in which $D_{1A}$ is the group 1 and $D_{2A}$, $D_{2B}$ and $D_{2C}$ are the groups 1', a compound 541c represented by the formula (12-4) in which $D_{1A}$ is the group 1 and $D_{2A}$, $D_{2B}$ and $D_{2C}$ are the groups 1', a compound 541d represented by the formula (12-5) in which $D_{1A}$ is the group 1 and $D_{2A}$, $D_{2B}$ and $D_{2C}$ are the groups 1', and a compound 541e represented by the formula (11-2) in which $D_{1A}$ is the group 1 and $D_{2A}$, $D_{2B}$ and $D_{2C}$ are the groups 1'.

In other words, the compound 541 is any one of the compounds 541a to 541e.

[Formula 21]

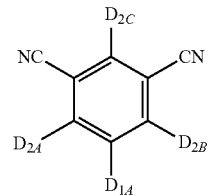
(12-3)

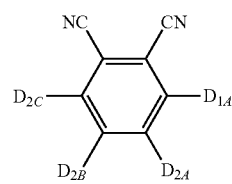
(13-3)

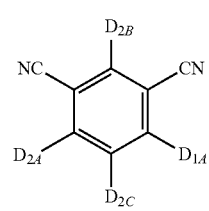
(12-4)

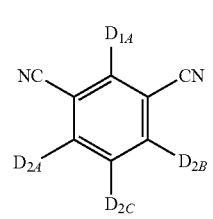
(12-5)

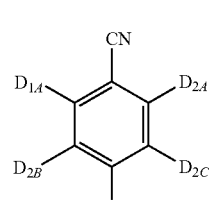
(11-2)

[Formula 22]

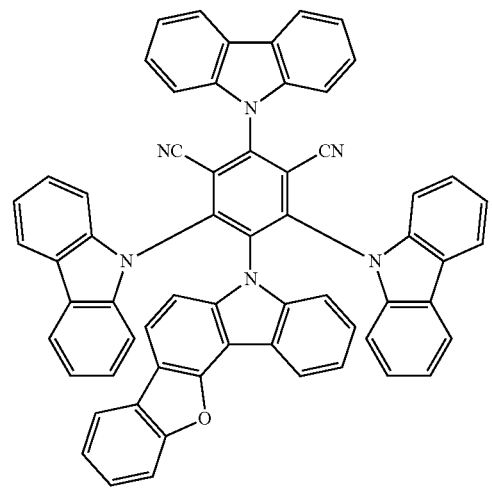

Compound 541a

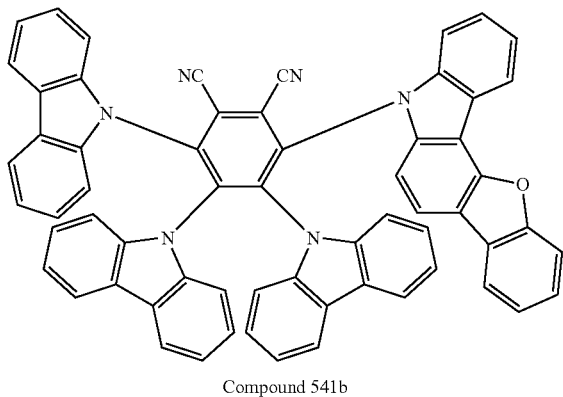

Compound 541b

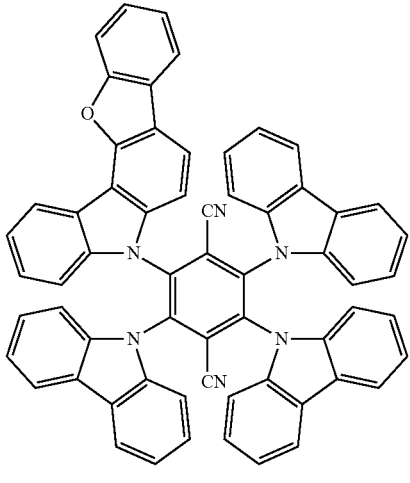

Compound 541e

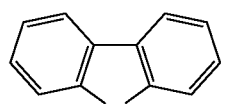

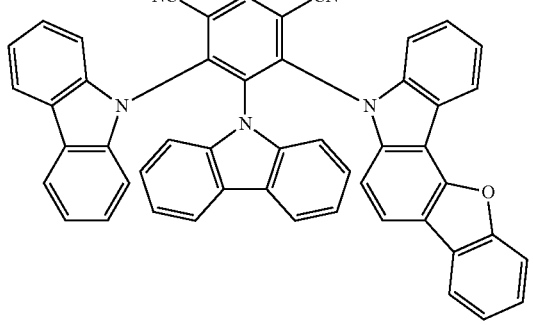

Compound 541c

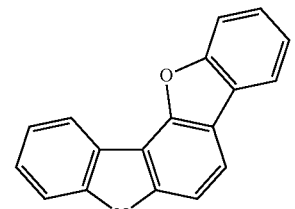

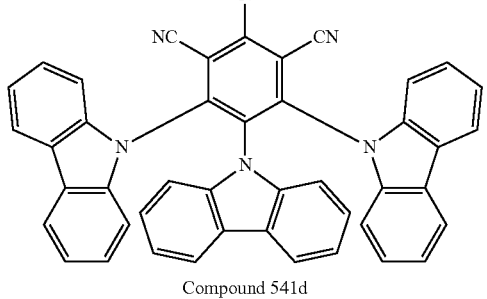

Compound 541d

Herein, the compounds 541 to 1080 and 1729 to 1836 are also referred to as a compound Y. Y is an integer from 541 to 1080 and from 1729 to 1836. Specifically, the compound Y represents a compound Ya, Yb, Yc, Yd or Ye.

A relationship between the compound Y and the compounds Ya to Ye is shown in Table 21 below.

TABLE 21

| Compound No. | Type | Formula No. |
|---|---|---|
| Compound Y | Compound Ya | (12-3) |
|  | Compound Yb | (13-3) |
|  | Compound Yc | (12-4) |
|  | Compound Yd | (12-5) |
|  | Compound Ye | (11-2) |

TABLE 22

| Compound No. | $D_{1A}$ | $D_{2A}$ | $D_{2B}$ | $D_{2C}$ |
|---|---|---|---|---|
| Compound 541 | 1 | 1' | 1' | 1' |
| Compound 542 | 2 | 1' | 1' | 1' |
| Compound 543 | 3 | 1' | 1' | 1' |
| Compound 544 | 4 | 1' | 1' | 1' |
| Compound 545 | 5 | 1' | 1' | 1' |
| Compound 546 | 6 | 1' | 1' | 1' |
| Compound 547 | 7 | 1' | 1' | 1' |
| Compound 548 | 8 | 1' | 1' | 1' |
| Compound 549 | 9 | 1' | 1' | 1' |
| Compound 550 | 10 | 1' | 1' | 1' |
| Compound 551 | 11 | 1' | 1' | 1' |
| Compound 552 | 12 | 1' | 1' | 1' |
| Compound 553 | 13 | 1' | 1' | 1' |
| Compound 554 | 14 | 1' | 1' | 1' |
| Compound 555 | 15 | 1' | 1' | 1' |
| Compound 556 | 16 | 1' | 1' | 1' |
| Compound 557 | 17 | 1' | 1' | 1' |
| Compound 558 | 18 | 1' | 1' | 1' |
| Compound 559 | 19 | 1' | 1' | 1' |
| Compound 560 | 20 | 1' | 1' | 1' |
| Compound 561 | 21 | 1' | 1' | 1' |
| Compound 562 | 22 | 1' | 1' | 1' |
| Compound 563 | 23 | 1' | 1' | 1' |
| Compound 564 | 24 | 1' | 1' | 1' |
| Compound 565 | 25 | 1' | 1' | 1' |
| Compound 566 | 26 | 1' | 1' | 1' |
| Compound 567 | 27 | 1' | 1' | 1' |
| Compound 568 | 28 | 1' | 1' | 1' |
| Compound 569 | 29 | 1' | 1' | 1' |
| Compound 570 | 30 | 1' | 1' | 1' |

TABLE 22-continued

| Compound No. | $D_{1A}$ | $D_{2A}$ | $D_{2B}$ | $D_{2C}$ |
|---|---|---|---|---|
| Compound 571 | 31 | 1' | 1' | 1' |
| Compound 572 | 32 | 1' | 1' | 1' |
| Compound 573 | 33 | 1' | 1' | 1' |
| Compound 574 | 34 | 1' | 1' | 1' |
| Compound 575 | 35 | 1' | 1' | 1' |
| Compound 576 | 36 | 1' | 1' | 1' |

TABLE 23

| Compound No. | $D_{1A}$ | $D_{2A}$ | $D_{2B}$ | $D_{2C}$ |
|---|---|---|---|---|
| Compound 577 | 1 | 2' | 2' | 2' |
| Compound 578 | 2 | 2' | 2' | 2' |
| Compound 579 | 3 | 2' | 2' | 2' |
| Compound 580 | 4 | 2' | 2' | 2' |
| Compound 581 | 5 | 2' | 2' | 2' |
| Compound 582 | 6 | 2' | 2' | 2' |
| Compound 583 | 7 | 2' | 2' | 2' |
| Compound 584 | 8 | 2' | 2' | 2' |
| Compound 585 | 9 | 2' | 2' | 2' |
| Compound 586 | 10 | 2' | 2' | 2' |
| Compound 587 | 11 | 2' | 2' | 2' |
| Compound 588 | 12 | 2' | 2' | 2' |
| Compound 589 | 13 | 2' | 2' | 2' |
| Compound 590 | 14 | 2' | 2' | 2' |
| Compound 591 | 15 | 2' | 2' | 2' |
| Compound 592 | 16 | 2' | 2' | 2' |
| Compound 593 | 17 | 2' | 2' | 2' |
| Compound 594 | 18 | 2' | 2' | 2' |
| Compound 595 | 19 | 2' | 2' | 2' |
| Compound 596 | 20 | 2' | 2' | 2' |
| Compound 597 | 21 | 2' | 2' | 2' |
| Compound 598 | 22 | 2' | 2' | 2' |
| Compound 599 | 23 | 2' | 2' | 2' |
| Compound 600 | 24 | 2' | 2' | 2' |
| Compound 601 | 25 | 2' | 2' | 2' |
| Compound 602 | 26 | 2' | 2' | 2' |
| Compound 603 | 27 | 2' | 2' | 2' |
| Compound 604 | 28 | 2' | 2' | 2' |
| Compound 605 | 29 | 2' | 2' | 2' |
| Compound 606 | 30 | 2' | 2' | 2' |
| Compound 607 | 31 | 2' | 2' | 2' |
| Compound 608 | 32 | 2' | 2' | 2' |
| Compound 609 | 33 | 2' | 2' | 2' |
| Compound 610 | 34 | 2' | 2' | 2' |
| Compound 611 | 35 | 2' | 2' | 2' |
| Compound 612 | 36 | 2' | 2' | 2' |

TABLE 24

| Compound No | $D_{1A}$ | $D_{2A}$ | $D_{2B}$ | $D_{2C}$ |
|---|---|---|---|---|
| Compound 613 | 1 | 3' | 3' | 3' |
| Compound 614 | 2 | 3' | 3' | 3' |
| Compound 615 | 3 | 3' | 3' | 3' |
| Compound 616 | 4 | 3' | 3' | 3' |
| Compound 617 | 5 | 3' | 3' | 3' |
| Compound 618 | 6 | 3' | 3' | 3' |
| Compound 619 | 7 | 3' | 3' | 3' |
| Compound 620 | 8 | 3' | 3' | 3' |
| Compound 621 | 9 | 3' | 3' | 3' |
| Compound 622 | 10 | 3' | 3' | 3' |
| Compound 623 | 11 | 3' | 3' | 3' |
| Compound 624 | 12 | 3' | 3' | 3' |
| Compound 625 | 13 | 3' | 3' | 3' |
| Compound 626 | 14 | 3' | 3' | 3' |
| Compound 627 | 15 | 3' | 3' | 3' |
| Compound 628 | 16 | 3' | 3' | 3' |
| Compound 629 | 17 | 3' | 3' | 3' |
| Compound 630 | 18 | 3' | 3' | 3' |
| Compound 631 | 19 | 3' | 3' | 3' |
| Compound 632 | 20 | 3' | 3' | 3' |
| Compound 633 | 21 | 3' | 3' | 3' |

TABLE 24-continued

| Compound No | $D_{1A}$ | $D_{2A}$ | $D_{2B}$ | $D_{2C}$ |
|---|---|---|---|---|
| Compound 634 | 22 | 3' | 3' | 3' |
| Compound 635 | 23 | 3' | 3' | 3' |
| Compound 636 | 24 | 3' | 3' | 3' |
| Compound 637 | 25 | 3' | 3' | 3' |
| Compound 638 | 26 | 3' | 3' | 3' |
| Compound 639 | 27 | 3' | 3' | 3' |
| Compound 640 | 28 | 3' | 3' | 3' |
| Compound 641 | 29 | 3' | 3' | 3' |
| Compound 642 | 30 | 3' | 3' | 3' |
| Compound 643 | 31 | 3' | 3' | 3' |
| Compound 644 | 32 | 3' | 3' | 3' |
| Compound 645 | 33 | 3' | 3' | 3' |
| Compound 646 | 34 | 3' | 3' | 3' |
| Compound 647 | 35 | 3' | 3' | 3' |
| Compound 648 | 36 | 3' | 3' | 3' |

TABLE 25

| Compound No. | $D_{1A}$ | $D_{2A}$ | $D_{2B}$ | $D_{2C}$ |
|---|---|---|---|---|
| Compound 649 | 1 | 4' | 4' | 4' |
| Compound 650 | 2 | 4' | 4' | 4' |
| Compound 651 | 3 | 4' | 4' | 4' |
| Compound 652 | 4 | 4' | 4' | 4' |
| Compound 653 | 5 | 4' | 4' | 4' |
| Compound 654 | 6 | 4' | 4' | 4' |
| Compound 655 | 7 | 4' | 4' | 4' |
| Compound 656 | 8 | 4' | 4' | 4' |
| Compound 657 | 9 | 4' | 4' | 4' |
| Compound 658 | 10 | 4' | 4' | 4' |
| Compound 659 | 11 | 4' | 4' | 4' |
| Compound 660 | 12 | 4' | 4' | 4' |
| Compound 661 | 13 | 4' | 4' | 4' |
| Compound 662 | 14 | 4' | 4' | 4' |
| Compound 663 | 15 | 4' | 4' | 4' |
| Compound 664 | 16 | 4' | 4' | 4' |
| Compound 665 | 17 | 4' | 4' | 4' |
| Compound 666 | 18 | 4' | 4' | 4' |
| Compound 667 | 19 | 4' | 4' | 4' |
| Compound 668 | 20 | 4' | 4' | 4' |
| Compound 669 | 21 | 4' | 4' | 4' |
| Compound 670 | 22 | 4' | 4' | 4' |
| Compound 671 | 23 | 4' | 4' | 4' |
| Compound 672 | 24 | 4' | 4' | 4' |
| Compound 673 | 25 | 4' | 4' | 4' |
| Compound 674 | 26 | 4' | 4' | 4' |
| Compound 675 | 27 | 4' | 4' | 4' |
| Compound 676 | 28 | 4' | 4' | 4' |
| Compound 677 | 29 | 4' | 4' | 4' |
| Compound 678 | 30 | 4' | 4' | 4' |
| Compound 679 | 31 | 4' | 4' | 4' |
| Compound 680 | 32 | 4' | 4' | 4' |
| Compound 681 | 33 | 4' | 4' | 4' |
| Compound 682 | 34 | 4' | 4' | 4' |
| Compound 683 | 35 | 4' | 4' | 4' |
| Compound 684 | 36 | 4' | 4' | 4' |

TABLE 26

| Compound No | $D_{1A}$ | $D_{2A}$ | $D_{2B}$ | $D_{2C}$ |
|---|---|---|---|---|
| Compound 685 | 1 | 5' | 5' | 5' |
| Compound 686 | 2 | 5' | 5' | 5' |
| Compound 687 | 3 | 5' | 5' | 5' |
| Compound 688 | 4 | 5' | 5' | 5' |
| Compound 689 | 5 | 5' | 5' | 5' |
| Compound 690 | 6 | 5' | 5' | 5' |
| Compound 691 | 7 | 5' | 5' | 5' |
| Compound 692 | 8 | 5' | 5' | 5' |
| Compound 693 | 9 | 5' | 5' | 5' |
| Compound 694 | 10 | 5' | 5' | 5' |
| Compound 695 | 11 | 5' | 5' | 5' |
| Compound 696 | 12 | 5' | 5' | 5' |

TABLE 26-continued

| Compound No | $D_{1A}$ | $D_{2A}$ | $D_{2B}$ | $D_{2C}$ |
|---|---|---|---|---|
| Compound 697 | 13 | 5' | 5' | 5' |
| Compound 698 | 14 | 5' | 5' | 5' |
| Compound 699 | 15 | 5' | 5' | 5' |
| Compound 700 | 16 | 5' | 5' | 5' |
| Compound 701 | 17 | 5' | 5' | 5' |
| Compound 702 | 18 | 5' | 5' | 5' |
| Compound 703 | 19 | 5' | 5' | 5' |
| Compound 704 | 20 | 5' | 5' | 5' |
| Compound 705 | 21 | 5' | 5' | 5' |
| Compound 706 | 22 | 5' | 5' | 5' |
| Compound 707 | 23 | 5' | 5' | 5' |
| Compound 708 | 24 | 5' | 5' | 5' |
| Compound 709 | 25 | 5' | 5' | 5' |
| Compound 710 | 26 | 5' | 5' | 5' |
| Compound 711 | 27 | 5' | 5' | 5' |
| Compound 712 | 28 | 5' | 5' | 5' |
| Compound 713 | 29 | 5' | 5' | 5' |
| Compound 714 | 30 | 5' | 5' | 5' |
| Compound 715 | 31 | 5' | 5' | 5' |
| Compound 716 | 32 | 5' | 5' | 5' |
| Compound 717 | 33 | 5' | 5' | 5' |
| Compound 718 | 34 | 5' | 5' | 5' |
| Compound 719 | 35 | 5' | 5' | 5' |
| Compound 720 | 36 | 5' | 5' | 5' |

TABLE 27

| Compound No. | $D_{1A}$ | $D_{2A}$ | $D_{2B}$ | $D_{2C}$ |
|---|---|---|---|---|
| Compound 721 | 1 | 6' | 6' | 6' |
| Compound 722 | 2 | 6' | 6' | 6' |
| Compound 723 | 3 | 6' | 6' | 6' |
| Compound 724 | 4 | 6' | 6' | 6' |
| Compound 725 | 5 | 6' | 6' | 6' |
| Compound 726 | 6 | 6' | 6' | 6' |
| Compound 727 | 7 | 6' | 6' | 6' |
| Compound 728 | 8 | 6' | 6' | 6' |
| Compound 729 | 9 | 6' | 6' | 6' |
| Compound 730 | 10 | 6' | 6' | 6' |
| Compound 731 | 11 | 6' | 6' | 6' |
| Compound 732 | 12 | 6' | 6' | 6' |
| Compound 733 | 13 | 6' | 6' | 6' |
| Compound 734 | 14 | 6' | 6' | 6' |
| Compound 735 | 15 | 6' | 6' | 6' |
| Compound 736 | 16 | 6' | 6' | 6' |
| Compound 737 | 17 | 6' | 6' | 6' |
| Compound 738 | 18 | 6' | 6' | 6' |
| Compound 739 | 19 | 6' | 6' | 6' |
| Compound 740 | 20 | 6' | 6' | 6' |
| Compound 741 | 21 | 6' | 6' | 6' |
| Compound 742 | 22 | 6' | 6' | 6' |
| Compound 743 | 23 | 6' | 6' | 6' |
| Compound 744 | 24 | 6' | 6' | 6' |
| Compound 745 | 25 | 6' | 6' | 6' |
| Compound 746 | 26 | 6' | 6' | 6' |
| Compound 747 | 27 | 6' | 6' | 6' |
| Compound 748 | 28 | 6' | 6' | 6' |
| Compound 749 | 29 | 6' | 6' | 6' |
| Compound 750 | 30 | 6' | 6' | 6' |
| Compound 751 | 31 | 6' | 6' | 6' |
| Compound 752 | 32 | 6' | 6' | 6' |
| Compound 753 | 33 | 6' | 6' | 6' |
| Compound 754 | 34 | 6' | 6' | 6' |
| Compound 755 | 35 | 6' | 6' | 6' |
| Compound 756 | 36 | 6' | 6' | 6' |

TABLE 28

| Compound No. | $D_{1A}$ | $D_{2A}$ | $D_{2B}$ | $D_{2C}$ |
|---|---|---|---|---|
| Compound 757 | 1 | 7' | 7' | 7' |
| Compound 758 | 2 | 7' | 7' | 7' |
| Compound 759 | 3 | 7' | 7' | 7' |
| Compound 760 | 4 | 7' | 7' | 7' |
| Compound 761 | 5 | 7' | 7' | 7' |
| Compound 762 | 6 | 7' | 7' | 7' |
| Compound 763 | 7 | 7' | 7' | 7' |
| Compound 764 | 8 | 7' | 7' | 7' |
| Compound 765 | 9 | 7' | 7' | 7' |
| Compound 766 | 10 | 7' | 7' | 7' |
| Compound 767 | 11 | 7' | 7' | 7' |
| Compound 768 | 12 | 7' | 7' | 7' |
| Compound 769 | 13 | 7' | 7' | 7' |
| Compound 770 | 14 | 7' | 7' | 7' |
| Compound 771 | 15 | 7' | 7' | 7' |
| Compound 772 | 16 | 7' | 7' | 7' |
| Compound 773 | 17 | 7' | 7' | 7' |
| Compound 774 | 18 | 7' | 7' | 7' |
| Compound 775 | 19 | 7' | 7' | 7' |
| Compound 776 | 20 | 7' | 7' | 7' |
| Compound 777 | 21 | 7' | 7' | 7' |
| Compound 778 | 22 | 7' | 7' | 7' |
| Compound 779 | 23 | 7' | 7' | 7' |
| Compound 780 | 24 | 7' | 7' | 7' |
| Compound 781 | 25 | 7' | 7' | 7' |
| Compound 782 | 26 | 7' | 7' | 7' |
| Compound 783 | 27 | 7' | 7' | 7' |
| Compound 784 | 28 | 7' | 7' | 7' |
| Compound 785 | 29 | 7' | 7' | 7' |
| Compound 786 | 30 | 7' | 7' | 7' |
| Compound 787 | 31 | 7' | 7' | 7' |
| Compound 788 | 32 | 7' | 7' | 7' |
| Compound 789 | 33 | 7' | 7' | 7' |
| Compound 790 | 34 | 7' | 7' | 7' |
| Compound 791 | 35 | 7' | 7' | 7' |
| Compound 792 | 36 | 7' | 7' | 7' |

TABLE 29

| Compound No. | $D_{1A}$ | $D_{2A}$ | $D_{2B}$ | $D_{2C}$ |
|---|---|---|---|---|
| Compound 793 | 1 | 8' | 8' | 8' |
| Compound 794 | 2 | 8' | 8' | 8' |
| Compound 795 | 3 | 8' | 8' | 8' |
| Compound 796 | 4 | 8' | 8' | 8' |
| Compound 797 | 5 | 8' | 8' | 8' |
| Compound 798 | 6 | 8' | 8' | 8' |
| Compound 799 | 7 | 8' | 8' | 8' |
| Compound 800 | 8 | 8' | 8' | 8' |
| Compound 801 | 9 | 8' | 8' | 8' |
| Compound 802 | 10 | 8' | 8' | 8' |
| Compound 803 | 11 | 8' | 8' | 8' |
| Compound 804 | 12 | 8' | 8' | 8' |
| Compound 805 | 13 | 8' | 8' | 8' |
| Compound 806 | 14 | 8' | 8' | 8' |
| Compound 807 | 15 | 8' | 8' | 8' |
| Compound 808 | 16 | 8' | 8' | 8' |
| Compound 809 | 17 | 8' | 8' | 8' |
| Compound 810 | 18 | 8' | 8' | 8' |
| Compound 811 | 19 | 8' | 8' | 8' |
| Compound 812 | 20 | 8' | 8' | 8' |
| Compound 813 | 21 | 8' | 8' | 8' |
| Compound 814 | 22 | 8' | 8' | 8' |
| Compound 815 | 23 | 8' | 8' | 8' |
| Compound 816 | 24 | 8' | 8' | 8' |
| Compound 817 | 25 | 8' | 8' | 8' |
| Compound 818 | 26 | 8' | 8' | 8' |
| Compound 819 | 27 | 8' | 8' | 8' |
| Compound 820 | 28 | 8' | 8' | 8' |
| Compound 821 | 29 | 8' | 8' | 8' |
| Compound 822 | 30 | 8' | 8' | 8' |
| Compound 823 | 31 | 8' | 8' | 8' |
| Compound 824 | 32 | 8' | 8' | 8' |
| Compound 825 | 33 | 8' | 8' | 8' |
| Compound 826 | 34 | 8' | 8' | 8' |
| Compound 827 | 35 | 8' | 8' | 8' |
| Compound 828 | 36 | 8' | 8' | 8' |

TABLE 30

| Compound No. | $D_{1A}$ | $D_{2A}$ | $D_{2B}$ | $D_{2C}$ |
|---|---|---|---|---|
| Compound 829 | 1 | 9' | 9' | 9' |
| Compound 830 | 2 | 9' | 9' | 9' |
| Compound 831 | 3 | 9' | 9' | 9' |
| Compound 832 | 4 | 9' | 9 | 9' |
| Compound 833 | 5 | 9' | 9' | 9' |
| Compound 834 | 6 | 9' | 9' | 9' |
| Compound 835 | 7 | 9' | 9' | 9' |
| Compound 836 | 8 | 9' | 9' | 9' |
| Compound 837 | 9 | 9' | 9' | 9' |
| Compound 838 | 10 | 9' | 9' | 9' |
| Compound 839 | 11 | 9' | 9' | 9' |
| Compound 840 | 12 | 9' | 9' | 9' |
| Compound 841 | 13 | 9' | 9' | 9' |
| Compound 842 | 14 | 9' | 9' | 9' |
| Compound 843 | 15 | 9' | 9' | 9' |
| Compound 844 | 16 | 9' | 9' | 9' |
| Compound 845 | 17 | 9' | 9' | 9' |
| Compound 846 | 18 | 9' | 9' | 9' |
| Compound 847 | 19 | 9' | 9' | 9' |
| Compound 848 | 20 | 9' | 9' | 9' |
| Compound 849 | 21 | 9' | 9' | 9' |
| Compound 850 | 22 | 9' | 9' | 9' |
| Compound 851 | 23 | 9' | 9' | 9' |
| Compound 852 | 24 | 9' | 9' | 9' |
| Compound 853 | 25 | 9' | 9' | 9' |
| Compound 854 | 26 | 9' | 9' | 9' |
| Compound 855 | 27 | 9' | 9' | 9' |
| Compound 856 | 28 | 9' | 9' | 9' |
| Compound 857 | 29 | 9' | 9' | 9' |
| Compound 858 | 30 | 9' | 9' | 9' |
| Compound 859 | 31 | 9' | 9' | 9' |
| Compound 860 | 32 | 9' | 9' | 9' |
| Compound 861 | 33 | 9' | 9' | 9' |
| Compound 862 | 34 | 9' | 9' | 9' |
| Compound 863 | 35 | 9' | 9' | 9' |
| Compound 864 | 36 | 9' | 9' | 9' |

TABLE 31

| Compound No. | $D_{1A}$ | $D_{2A}$ | $D_{2B}$ | $D_{2C}$ |
|---|---|---|---|---|
| Compound 865 | 1 | 10' | 10' | 10' |
| Compound 866 | 2 | 10' | 10' | 10' |
| Compound 867 | 3 | 10' | 10' | 10' |
| Compound 868 | 4 | 10' | 10' | 10' |
| Compound 869 | 5 | 10' | 10' | 10' |
| Compound 870 | 6 | 10' | 10' | 10' |
| Compound 871 | 7 | 10' | 10' | 10' |
| Compound 872 | 8 | 10' | 10' | 10' |
| Compound 873 | 9 | 10' | 10' | 10' |
| Compound 874 | 10 | 10' | 10' | 10' |
| Compound 875 | 11 | 10' | 10' | 10' |
| Compound 876 | 12 | 10' | 10' | 10' |
| Compound 877 | 13 | 10' | 10' | 10' |
| Compound 878 | 14 | 10' | 10' | 10' |
| Compound 879 | 15 | 10' | 10' | 10' |
| Compound 880 | 16 | 10' | 10' | 10' |
| Compound 881 | 17 | 10' | 10' | 10' |
| Compound 882 | 18 | 10' | 10' | 10' |
| Compound 883 | 19 | 10' | 10' | 10' |
| Compound 884 | 20 | 10' | 10' | 10' |
| Compound 885 | 21 | 10' | 10' | 10' |
| Compound 886 | 22 | 10' | 10' | 10' |
| Compound 887 | 23 | 10' | 10' | 10' |
| Compound 888 | 24 | 10' | 10' | 10' |
| Compound 889 | 25 | 10' | 10' | 10' |
| Compound 890 | 26 | 10' | 10' | 10' |
| Compound 891 | 27 | 10' | 10' | 10' |
| Compound 892 | 28 | 10' | 10' | 10' |
| Compound 893 | 29 | 10' | 10' | 10' |
| Compound 894 | 30 | 10' | 10' | 10' |
| Compound 895 | 31 | 10' | 10' | 10' |
| Compound 896 | 32 | 10' | 10' | 10' |
| Compound 897 | 33 | 10' | 10' | 10' |
| Compound 898 | 34 | 10' | 10' | 10' |
| Compound 899 | 35 | 10' | 10' | 10' |
| Compound 900 | 36 | 10' | 10' | 10' |

TABLE 32

| Compound No. | $D_{1A}$ | $D_{2A}$ | $D_{2B}$ | $D_{2C}$ |
|---|---|---|---|---|
| Compound 901 | 1 | 11' | 11' | 11' |
| Compound 902 | 2 | 11' | 11' | 11' |
| Compound 903 | 3 | 11' | 11' | 11' |
| Compound 904 | 4 | 11' | 11' | 11' |
| Compound 905 | 5 | 11' | 11' | 11' |
| Compound 906 | 6 | 11' | 11' | 11' |
| Compound 907 | 7 | 11' | 11' | 11' |
| Compound 908 | 8 | 11' | 11' | 11' |
| Compound 909 | 9 | 11' | 11' | 11' |
| Compound 910 | 10 | 11' | 11' | 11' |
| Compound 911 | 11 | 11' | 11' | 11' |
| Compound 912 | 12 | 11' | 11' | 11' |
| Compound 913 | 13 | 11' | 11' | 11' |
| Compound 914 | 14 | 11' | 11' | 11' |
| Compound 915 | 15 | 11' | 11' | 11' |
| Compound 916 | 16 | 11' | 11' | 11' |
| Compound 917 | 17 | 11' | 11' | 11' |
| Compound 918 | 18 | 11' | 11' | 11' |
| Compound 919 | 19 | 11' | 11' | 11' |
| Compound 920 | 20 | 11' | 11' | 11' |
| Compound 921 | 21 | 11' | 11' | 11' |
| Compound 922 | 22 | 11' | 11' | 11' |
| Compound 923 | 23 | 11' | 11' | 11' |
| Compound 924 | 24 | 11' | 11' | 11 |
| Compound 925 | 25 | 11' | 11' | 11' |
| Compound 926 | 26 | 11' | 11' | 11' |
| Compound 927 | 27 | 11' | 11' | 11' |
| Compound 928 | 28 | 11' | 11' | 11' |
| Compound 929 | 29 | 11' | 11' | 11' |
| Compound 930 | 30 | 11' | 11' | 11' |
| Compound 931 | 31 | 11' | 11' | 11' |
| Compound 932 | 32 | 11' | 11' | 11' |
| Compound 933 | 33 | 11' | 11' | 11' |
| Compound 934 | 34 | 11' | 11' | 11' |
| Compound 935 | 35 | 11' | 11' | 11' |
| Compound 936 | 36 | 11' | 11' | 11' |

TABLE 33

| Compound No. | $D_{1A}$ | $D_{2A}$ | $D_{2B}$ | $D_{2C}$ |
|---|---|---|---|---|
| Compound 937 | 1 | 12' | 12' | 12' |
| Compound 938 | 2 | 12' | 12' | 12' |
| Compound 939 | 3 | 12' | 12' | 12' |
| Compound 940 | 4 | 12' | 12' | 12' |
| Compound 941 | 5 | 12' | 12' | 12' |
| Compound 942 | 6 | 12' | 12' | 12' |
| Compound 943 | 7 | 12' | 12' | 12' |
| Compound 944 | 8 | 12' | 12' | 12' |
| Compound 945 | 9 | 12' | 12' | 12' |
| Compound 946 | 10 | 12' | 12' | 12' |
| Compound 947 | 11 | 12' | 12' | 12' |
| Compound 948 | 12 | 12' | 12' | 12' |
| Compound 949 | 13 | 12' | 12' | 12' |
| Compound 950 | 14 | 12' | 12' | 12' |
| Compound 951 | 15 | 12' | 12' | 12' |
| Compound 952 | 16 | 12' | 12' | 12' |
| Compound 953 | 17 | 12' | 12' | 12' |
| Compound 954 | 18 | 12' | 12' | 12' |
| Compound 955 | 19 | 12' | 12' | 12' |
| Compound 956 | 20 | 12' | 12' | 12' |
| Compound 957 | 21 | 12' | 12' | 12' |
| Compound 958 | 22 | 12' | 12' | 12' |
| Compound 959 | 23 | 12' | 12' | 12' |
| Compound 960 | 24 | 12' | 12' | 12' |
| Compound 961 | 25 | 12' | 12' | 12' |

TABLE 33-continued

| Compound No. | $D_{1A}$ | $D_{2A}$ | $D_{2B}$ | $D_{2C}$ |
| --- | --- | --- | --- | --- |
| Compound 962 | 26 | 12' | 12' | 12' |
| Compound 963 | 27 | 12' | 12' | 12' |
| Compound 964 | 28 | 12' | 12' | 12' |
| Compound 965 | 29 | 12' | 12' | 12' |
| Compound 966 | 30 | 12' | 12' | 12' |
| Compound 967 | 31 | 12' | 12' | 12' |
| Compound 968 | 32 | 12' | 12' | 12' |
| Compound 969 | 33 | 12' | 12' | 12' |
| Compound 970 | 34 | 12' | 12' | 12' |
| Compound 971 | 35 | 12' | 12' | 12' |
| Compound 972 | 36 | 12' | 12' | 12' |

TABLE 34

| Compound No. | $D_{1A}$ | $D_{2A}$ | $D_{2B}$ | $D_{2C}$ |
| --- | --- | --- | --- | --- |
| Compound 973 | 1 | 13' | 13' | 13' |
| Compound 974 | 2 | 13' | 13' | 13' |
| Compound 975 | 3 | 13' | 13' | 13' |
| Compound 976 | 4 | 13' | 13' | 13' |
| Compound 977 | 5 | 13' | 13' | 13' |
| Compound 978 | 6 | 13' | 13' | 13' |
| Compound 979 | 7 | 13' | 13' | 13' |
| Compound 980 | 8 | 13' | 13' | 13' |
| Compound 981 | 9 | 13' | 13' | 13' |
| Compound 982 | 10 | 13' | 13' | 13' |
| Compound 983 | 11 | 13' | 13' | 13' |
| Compound 984 | 12 | 13' | 13' | 13' |
| Compound 985 | 13 | 13' | 13' | 13' |
| Compound 986 | 14 | 13 | 13' | 13' |
| Compound 987 | 15 | 13' | 13' | 13' |
| Compound 988 | 16 | 13' | 13' | 13' |
| Compound 989 | 17 | 13' | 13' | 13' |
| Compound 990 | 18 | 13' | 13' | 13' |
| Compound 991 | 19 | 13' | 13' | 13' |
| Compound 992 | 20 | 13' | 13' | 13' |
| Compound 993 | 21 | 13' | 13' | 13' |
| Compound 994 | 22 | 13' | 13' | 13' |
| Compound 995 | 23 | 13' | 13' | 13' |
| Compound 996 | 24 | 13' | 13' | 13' |
| Compound 997 | 25 | 13' | 13' | 13' |
| Compound 998 | 26 | 13' | 13' | 13' |
| Compound 999 | 27 | 13' | 13' | 13' |
| Compound 1000 | 28 | 13' | 13' | 13' |
| Compound 1001 | 29 | 13' | 13' | 13' |
| Compound 1002 | 30 | 13' | 13' | 13' |
| Compound 1003 | 31 | 13' | 13' | 13' |
| Compound 1004 | 32 | 13' | 13' | 13' |
| Compound 1005 | 33 | 13' | 13' | 13' |
| Compound 1006 | 34 | 13' | 13' | 13' |
| Compound 1007 | 35 | 13' | 13' | 13' |
| Compound 1008 | 36 | 13' | 13' | 13' |

TABLE 35

| Compound No. | $D_{1A}$ | $D_{2A}$ | $D_{2B}$ | $D_{2C}$ |
| --- | --- | --- | --- | --- |
| Compound 1009 | 1 | 14' | 14' | 14' |
| Compound 1010 | 2 | 14' | 14' | 14' |
| Compound 1011 | 3 | 14' | 14' | 14' |
| Compound 1012 | 4 | 14' | 14' | 14' |
| Compound 1013 | 5 | 14' | 14' | 14' |
| Compound 1014 | 6 | 14' | 14' | 14' |
| Compound 1015 | 7 | 14' | 14' | 14' |
| Compound 1016 | 8 | 14' | 14' | 14' |
| Compound 1017 | 9 | 14' | 14' | 14' |
| Compound 1018 | 10 | 14' | 14' | 14' |
| Compound 1019 | 11 | 14' | 14' | 14' |
| Compound 1020 | 12 | 14' | 14' | 14' |
| Compound 1021 | 13 | 14' | 14' | 14' |
| Compound 1022 | 14 | 14' | 14' | 14' |
| Compound 1023 | 15 | 14' | 14' | 14' |
| Compound 1024 | 16 | 14' | 14' | 14' |

TABLE 35-continued

| Compound No. | $D_{1A}$ | $D_{2A}$ | $D_{2B}$ | $D_{2C}$ |
| --- | --- | --- | --- | --- |
| Compound 1025 | 17 | 14' | 14' | 14' |
| Compound 1026 | 18 | 14' | 14' | 14' |
| Compound 1027 | 19 | 14' | 14' | 14' |
| Compound 1028 | 20 | 14' | 14' | 14' |
| Compound 1029 | 21 | 14' | 14' | 14' |
| Compound 1030 | 22 | 14' | 14' | 14' |
| Compound 1031 | 23 | 14' | 14' | 14' |
| Compound 1032 | 24 | 14' | 14' | 14' |
| Compound 1033 | 25 | 14' | 14' | 14' |
| Compound 1034 | 26 | 14' | 14' | 14' |
| Compound 1035 | 27 | 14' | 14' | 14' |
| Compound 1036 | 28 | 14' | 14' | 14' |
| Compound 1037 | 29 | 14' | 14' | 14' |
| Compound 1038 | 30 | 14' | 14' | 14' |
| Compound 1039 | 31 | 14' | 14' | 14' |
| Compound 1040 | 32 | 14' | 14' | 14' |
| Compound 1041 | 33 | 14' | 14' | 14' |
| Compound 1042 | 34 | 14' | 14' | 14' |
| Compound 1043 | 35 | 14' | 14' | 14' |
| Compound 1044 | 36 | 14' | 14' | 14' |

TABLE 36

| Compound No. | $D_{1A}$ | $D_{2A}$ | $D_{2B}$ | $D_{2C}$ |
| --- | --- | --- | --- | --- |
| Compound 1045 | 1 | 15' | 15' | 15' |
| Compound 1046 | 2 | 15' | 15' | 15' |
| Compound 1047 | 3 | 15' | 15' | 15' |
| Compound 1048 | 4 | 15' | 15' | 15' |
| Compound 1049 | 5 | 15' | 15' | 15' |
| Compound 1050 | 6 | 15' | 15' | 15' |
| Compound 1051 | 7 | 15' | 15' | 15' |
| Compound 1052 | 8 | 15' | 15' | 15' |
| Compound 1053 | 9 | 15' | 15' | 15' |
| Compound 1054 | 10 | 15' | 15' | 15' |
| Compound 1055 | 11 | 15' | 15' | 15' |
| Compound 1056 | 12 | 15' | 15' | 15' |
| Compound 1057 | 13 | 15' | 15' | 15' |
| Compound 1058 | 14 | 15' | 15' | 15' |
| Compound 1059 | 15 | 15' | 15' | 15' |
| Compound 1060 | 16 | 15' | 15' | 15' |
| Compound 1061 | 17 | 15' | 15' | 15' |
| Compound 1062 | 18 | 15' | 15' | 15' |
| Compound 1063 | 19 | 15' | 15' | 15' |
| Compound 1064 | 20 | 15' | 15' | 15' |
| Compound 1065 | 21 | 15' | 15' | 15' |
| Compound 1066 | 22 | 15' | 15' | 15' |
| Compound 1067 | 23 | 15' | 15' | 15' |
| Compound 1068 | 24 | 15' | 15' | 15' |
| Compound 1069 | 25 | 15' | 15' | 15' |
| Compound 1070 | 26 | 15' | 15' | 15' |
| Compound 1071 | 27 | 15' | 15' | 15' |
| Compound 1072 | 28 | 15' | 15' | 15' |
| Compound 1073 | 29 | 15' | 15' | 15' |
| Compound 1074 | 30 | 15' | 15' | 15' |
| Compound 1075 | 31 | 15' | 15' | 15' |
| Compound 1076 | 32 | 15' | 15' | 15' |
| Compound 1077 | 33 | 15' | 15' | 15' |
| Compound 1078 | 34 | 15' | 15' | 15' |
| Compound 1079 | 35 | 15' | 15' | 15' |
| Compound 1080 | 36 | 15' | 15' | 15' |

TABLE 37

| Compound No. | $D_{1A}$ | $D_{2A}$ | $D_{2B}$ | $D_{2C}$ |
| --- | --- | --- | --- | --- |
| Compound 1729 | 1 | 16' | 16' | 16' |
| Compound 1730 | 2 | 16' | 16' | 16' |
| Compound 1731 | 3 | 16' | 16' | 16' |
| Compound 1732 | 4 | 16' | 16' | 16' |
| Compound 1733 | 5 | 16' | 16' | 16' |
| Compound 1734 | 6 | 16' | 16' | 16' |
| Compound 1735 | 7 | 16' | 16' | 16' |

TABLE 37-continued

| Compound No. | $D_{1A}$ | $D_{2A}$ | $D_{2B}$ | $D_{2C}$ |
|---|---|---|---|---|
| Compound 1736 | 8 | 16' | 16' | 16' |
| Compound 1737 | 9 | 16' | 16' | 16' |
| Compound 1738 | 10 | 16' | 16' | 16' |
| Compound 1739 | 11 | 16' | 16' | 16' |
| Compound 1740 | 12 | 16' | 16' | 16' |
| Compound 1741 | 13 | 16' | 16' | 16' |
| Compound 1742 | 14 | 16' | 16' | 16' |
| Compound 1743 | 15 | 16' | 16' | 16' |
| Compound 1744 | 16 | 16' | 16' | 16' |
| Compound 1745 | 17 | 16' | 16' | 16' |
| Compound 1746 | 18 | 16' | 16' | 16' |
| Compound 1747 | 19 | 16' | 16' | 16' |
| Compound 1748 | 20 | 16' | 16' | 16' |
| Compound 1749 | 21 | 16' | 16' | 16' |
| Compound 1750 | 22 | 16' | 16' | 16' |
| Compound 1751 | 23 | 16' | 16' | 16' |
| Compound 1752 | 24 | 16' | 16' | 16' |
| Compound 1753 | 25 | 16' | 16' | 16' |
| Compound 1754 | 26 | 16' | 16' | 16' |
| Compound 1755 | 27 | 16' | 16' | 16' |
| Compound 1756 | 28 | 16' | 16' | 16' |
| Compound 1757 | 29 | 16' | 16' | 16' |
| Compound 1758 | 30 | 16' | 16' | 16' |
| Compound 1759 | 31 | 16' | 16' | 16' |
| Compound 1760 | 32 | 16' | 16' | 16' |
| Compound 1761 | 33 | 16' | 16' | 16' |
| Compound 1762 | 34 | 16' | 16' | 16' |
| Compound 1763 | 35 | 16' | 16' | 16' |
| Compound 1764 | 36 | 16' | 16' | 16' |

TABLE 38

| Compound No | $D_{1A}$ | $D_{2A}$ | $D_{2B}$ | $D_{2C}$ |
|---|---|---|---|---|
| Compound 1765 | 1 | 17' | 17' | 17' |
| Compound 1766 | 2 | 17' | 17' | 17' |
| Compound 1767 | 3 | 17' | 17' | 17' |
| Compound 1768 | 4 | 17' | 17' | 17' |
| Compound 1769 | 5 | 17' | 17' | 17' |
| Compound 1770 | 6 | 17' | 17' | 17' |
| Compound 1771 | 7 | 17' | 17' | 17' |
| Compound 1772 | 8 | 17' | 17' | 17' |
| Compound 1773 | 9 | 17' | 17' | 17' |
| Compound 1774 | 10 | 17' | 17' | 17' |
| Compound 1775 | 11 | 17' | 17' | 17' |
| Compound 1776 | 12 | 17' | 17' | 17' |
| Compound 1777 | 13 | 17' | 17' | 17' |
| Compound 1778 | 14 | 17' | 17' | 17' |
| Compound 1779 | 15 | 17' | 17' | 17' |
| Compound 1780 | 16 | 17' | 17' | 17' |
| Compound 1781 | 17 | 17' | 17' | 17' |
| Compound 1782 | 18 | 17' | 17' | 17' |
| Compound 1783 | 19 | 17' | 17' | 17' |
| Compound 1784 | 20 | 17' | 17' | 17' |
| Compound 1785 | 21 | 17' | 17' | 17' |
| Compound 1786 | 22 | 17' | 17' | 17' |
| Compound 1787 | 23 | 17' | 17' | 17' |
| Compound 1788 | 24 | 17' | 17' | 17' |
| Compound 1789 | 25 | 17' | 17' | 17' |
| Compound 1790 | 26 | 17' | 17' | 17' |
| Compound 1791 | 27 | 17' | 17' | 17' |
| Compound 1792 | 28 | 17' | 17' | 17' |
| Compound 1793 | 29 | 17' | 17' | 17' |
| Compound 1794 | 30 | 17' | 17' | 17' |
| Compound 1795 | 31 | 17' | 17' | 17' |
| Compound 1796 | 32 | 17' | 17' | 17' |
| Compound 1797 | 33 | 17' | 17' | 17' |
| Compound 1798 | 34 | 17' | 17' | 17' |
| Compound 1799 | 35 | 17' | 17' | 17' |
| Compound 1800 | 36 | 17' | 17' | 17' |

TABLE 39

| Compound No. | $D_{1A}$ | $D_{2A}$ | $D_{2B}$ | $D_{2C}$ |
|---|---|---|---|---|
| Compound 1801 | 1 | 18' | 18' | 18' |
| Compound 1802 | 2 | 18' | 18' | 18' |
| Compound 1803 | 3 | 18' | 18' | 18' |
| Compound 1804 | 4 | 18' | 18' | 18' |
| Compound 1805 | 5 | 18' | 18' | 18' |
| Compound 1806 | 6 | 18' | 18' | 18' |
| Compound 1807 | 7 | 18' | 18' | 18' |
| Compound 1808 | 8 | 18' | 18' | 18' |
| Compound 1809 | 9 | 18' | 18' | 18' |
| Compound 1810 | 10 | 18' | 18' | 18' |
| Compound 1811 | 11 | 18' | 18' | 18' |
| Compound 1812 | 12 | 18' | 18' | 18' |
| Compound 1813 | 13 | 18' | 18' | 18' |
| Compound 1814 | 14 | 18' | 18' | 18' |
| Compound 1815 | 15 | 18' | 18' | 18' |
| Compound 1816 | 16 | 18' | 18' | 18' |
| Compound 1817 | 17 | 18' | 18' | 18' |
| Compound 1818 | 18 | 18' | 18' | 18' |
| Compound 1819 | 19 | 18' | 18' | 18' |
| Compound 1820 | 20 | 18' | 18' | 18' |
| Compound 1821 | 21 | 18' | 18' | 18' |
| Compound 1822 | 22 | 18' | 18' | 18' |
| Compound 1823 | 23 | 18' | 18' | 18' |
| Compound 1824 | 24 | 18' | 18' | 18' |
| Compound 1825 | 25 | 18' | 18' | 18' |
| Compound 1826 | 26 | 18' | 18' | 18' |
| Compound 1827 | 27 | 18' | 18' | 18' |
| Compound 1828 | 28 | 18' | 18' | 18' |
| Compound 1829 | 29 | 18' | 18' | 18' |
| Compound 1830 | 30 | 18' | 18' | 18' |
| Compound 1831 | 31 | 18' | 18' | 18' |
| Compound 1832 | 32 | 18' | 18' | 18' |
| Compound 1833 | 33 | 18' | 18' | 18' |
| Compound 1834 | 34 | 18' | 18' | 18' |
| Compound 1835 | 35 | 18' | 18' | 18' |
| Compound 1836 | 36 | 18' | 18' | 18' |

Examples of the compound according to the exemplary embodiment include compounds represented by the formulae (12-6) and (13-4).

In the formula (12-6), $D_{1A}$, $D_{1B}$, $D_{1C}$, and $D_{2A}$ respectively represent the groups denoted by the numbers shown in Tables 41 to 58.

In the formula (13-4), $D_{1A}$, $D_{1B}$, $D_{1C}$, and $D_{2A}$ respectively represent the groups denoted by the numbers shown in Tables 41 to 58.

In Tables 41 to 58 below, the numbers given to columns of $D_{1A}$, $D_{1B}$, $D_{1C}$, and $D_{2A}$, correspond to numbers of the above-described groups 1 to 36 and groups 1' to 18'.

For instance, in Table 41, a compound 1081 represents a compound 1081a represented by the formula (12-6) in which $D_{1A}$, $D_{1B}$ and $D_{1C}$ are the groups 1 and $D_{2A}$ is the group 1', or a compound 1081b represented by the formula (13-4) in which $D_{1A}$, $D_{1B}$ and $D_{1C}$ are the groups 1 and $D_{2A}$ is the group 1'.

In other words, the compound 1081 is the compound 1081a or 1081b.

[Formula 23]

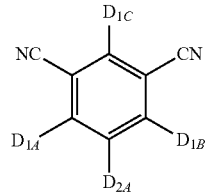

(12-6)

-continued

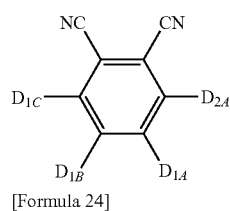

[Formula 24]

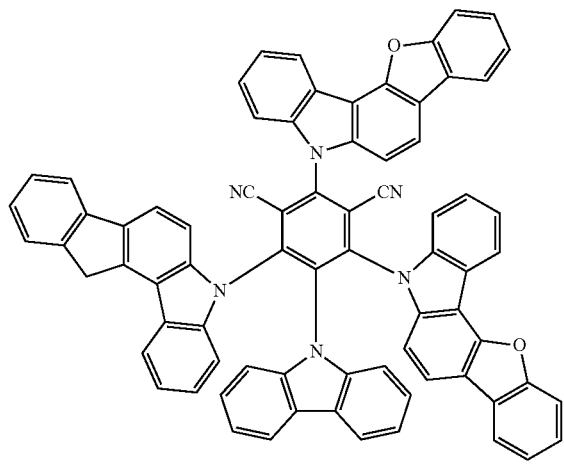

Compound 1081a

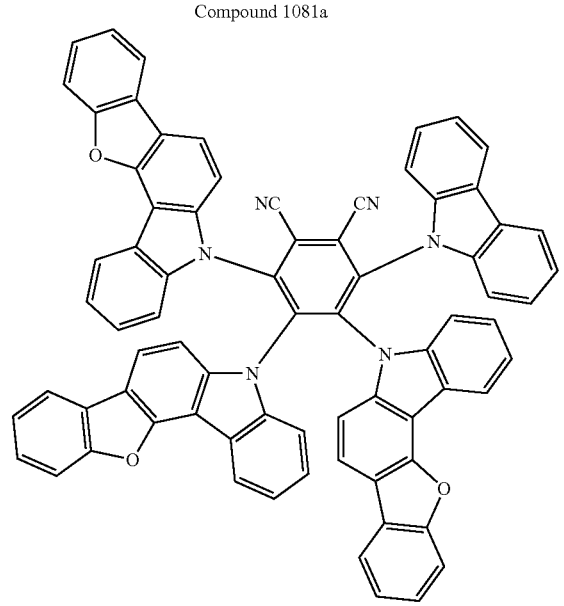

Compound 1081b

Herein, the compounds 1081 to 1620 and 1837 to 1944 are also referred to as a compound Z. Z is an integer from 1081 to 1620 and from 1837 to 1944. Specifically, the compound Z represents a compound Za or a compound Zb.

A relationship between the compound Z and the compounds Za and Zb is shown in Table 40 below.

TABLE 40

| Compound No. | Type | Formula No. |
|---|---|---|
| Compound Z | Compound Za | (12-6) |
|  | Compound Zb | (13-4) |

TABLE 41

| Compound No | $D_{1A}$ | $D_{1B}$ | $D_{1C}$ | $D_{2A}$ |
|---|---|---|---|---|
| Compound 1081 | 1 | 1 | 1 | 1' |
| Compound 1082 | 2 | 2 | 2 | 1' |
| Compound 1083 | 3 | 3 | 3 | 1' |
| Compound 1084 | 4 | 4 | 4 | 1' |
| Compound 1085 | 5 | 5 | 5 | 1' |
| Compound 1086 | 6 | 6 | 6 | 1' |
| Compound 1087 | 7 | 7 | 7 | 1' |
| Compound 1088 | 8 | 8 | 8 | 1' |
| Compound 1089 | 9 | 9 | 9 | 1' |
| Compound 1090 | 10 | 10 | 10 | 1' |
| Compound 1091 | 11 | 11 | 11 | 1' |
| Compound 1092 | 12 | 12 | 12 | 1' |
| Compound 1093 | 13 | 13 | 13 | 1' |
| Compound 1094 | 14 | 14 | 14 | 1' |
| Compound 1095 | 15 | 15 | 15 | 1' |
| Compound 1096 | 16 | 16 | 16 | 1' |
| Compound 1097 | 17 | 17 | 17 | 1' |
| Compound 1098 | 18 | 18 | 18 | 1' |
| Compound 1099 | 19 | 19 | 19 | 1' |
| Compound 1100 | 20 | 20 | 20 | 1' |
| Compound 1101 | 21 | 21 | 21 | 1' |
| Compound 1102 | 22 | 22 | 22 | 1' |
| Compound 1103 | 23 | 23 | 23 | 1' |
| Compound 1104 | 24 | 24 | 24 | 1' |
| Compound 1105 | 25 | 25 | 25 | 1' |
| Compound 1106 | 26 | 26 | 26 | 1' |
| Compound 1107 | 27 | 27 | 27 | 1' |
| Compound 1108 | 28 | 28 | 28 | 1' |
| Compound 1109 | 29 | 29 | 29 | 1' |
| Compound 1110 | 30 | 30 | 30 | 1' |
| Compound 1111 | 31 | 31 | 31 | 1' |
| Compound 1112 | 32 | 32 | 32 | 1' |
| Compound 1113 | 33 | 33 | 33 | 1' |
| Compound 1114 | 34 | 34 | 34 | 1' |
| Compound 1115 | 35 | 35 | 35 | 1' |
| Compound 1116 | 36 | 36 | 36 | 1' |

TABLE 42

| Compound No. | $D_{1A}$ | $D_{1B}$ | $D_{1C}$ | $D_{2A}$ |
|---|---|---|---|---|
| Compound 1117 | 1 | 1 | 1 | 2' |
| Compound 1118 | 2 | 2 | 2 | 2' |
| Compound 1119 | 3 | 3 | 3 | 2' |
| Compound 1120 | 4 | 4 | 4 | 2' |
| Compound 1121 | 5 | 5 | 5 | 2' |
| Compound 1122 | 6 | 6 | 6 | 2' |
| Compound 1123 | 7 | 7 | 7 | 2' |
| Compound 1124 | 8 | 8 | 8 | 2' |
| Compound 1125 | 9 | 9 | 9 | 2' |
| Compound 1126 | 10 | 10 | 10 | 2' |
| Compound 1127 | 11 | 11 | 11 | 2' |
| Compound 1128 | 12 | 12 | 12 | 2' |
| Compound 1129 | 13 | 13 | 13 | 2' |
| Compound 1130 | 14 | 14 | 14 | 2' |
| Compound 1131 | 15 | 15 | 15 | 2' |
| Compound 1132 | 16 | 16 | 16 | 2' |
| Compound 1133 | 17 | 17 | 17 | 2' |
| Compound 1134 | 18 | 18 | 18 | 2' |
| Compound 1135 | 19 | 19 | 19 | 2' |
| Compound 1136 | 20 | 20 | 20 | 2' |
| Compound 1137 | 21 | 21 | 21 | 2' |
| Compound 1138 | 22 | 22 | 22 | 2' |
| Compound 1139 | 23 | 23 | 23 | 2' |
| Compound 1140 | 24 | 24 | 24 | 2' |
| Compound 1141 | 25 | 25 | 25 | 2' |
| Compound 1142 | 26 | 26 | 26 | 2' |
| Compound 1143 | 27 | 27 | 27 | 2' |
| Compound 1144 | 28 | 28 | 28 | 2' |
| Compound 1145 | 29 | 29 | 29 | 2' |
| Compound 1146 | 30 | 30 | 30 | 2' |
| Compound 1147 | 31 | 31 | 31 | 2' |
| Compound 1148 | 32 | 32 | 32 | 2' |
| Compound 1149 | 33 | 33 | 33 | 2' |
| Compound 1150 | 34 | 34 | 34 | 2' |

TABLE 42-continued

| Compound No. | $D_{1A}$ | $D_{1B}$ | $D_{1C}$ | $D_{2A}$ |
| --- | --- | --- | --- | --- |
| Compound 1151 | 35 | 35 | 35 | 2' |
| Compound 1152 | 36 | 36 | 36 | 2' |

TABLE 43

| Compound No | $D_{1A}$ | $D_{1B}$ | $D_{1C}$ | $D_{2A}$ |
| --- | --- | --- | --- | --- |
| Compound 1153 | 1 | 1 | 1 | 3' |
| Compound 1154 | 2 | 2 | 2 | 3' |
| Compound 1155 | 3 | 3 | 3 | 3' |
| Compound 1156 | 4 | 4 | 4 | 3' |
| Compound 1157 | 5 | 5 | 5 | 3' |
| Compound 1158 | 6 | 6 | 6 | 3' |
| Compound 1159 | 7 | 7 | 7 | 3' |
| Compound 1160 | 8 | 8 | 8 | 3' |
| Compound 1161 | 9 | 9 | 9 | 3' |
| Compound 1162 | 10 | 10 | 10 | 3' |
| Compound 1163 | 11 | 11 | 11 | 3' |
| Compound 1164 | 12 | 12 | 12 | 3' |
| Compound 1165 | 13 | 13 | 13 | 3' |
| Compound 1166 | 14 | 14 | 14 | 3' |
| Compound 1167 | 15 | 15 | 15 | 3' |
| Compound 1168 | 16 | 16 | 16 | 3' |
| Compound 1169 | 17 | 17 | 17 | 3' |
| Compound 1170 | 18 | 18 | 18 | 3' |
| Compound 1171 | 19 | 19 | 19 | 3' |
| Compound 1172 | 20 | 20 | 20 | 3' |
| Compound 1173 | 21 | 21 | 21 | 3' |
| Compound 1174 | 22 | 22 | 22 | 3' |
| Compound 1175 | 23 | 23 | 23 | 3' |
| Compound 1176 | 24 | 24 | 24 | 3' |
| Compound 1177 | 25 | 25 | 25 | 3' |
| Compound 1178 | 26 | 26 | 26 | 3' |
| Compound 1179 | 27 | 27 | 27 | 3' |
| Compound 1180 | 28 | 28 | 28 | 3' |
| Compound 1181 | 29 | 29 | 29 | 3' |
| Compound 1182 | 30 | 30 | 30 | 3' |
| Compound 1183 | 31 | 31 | 31 | 3' |
| Compound 1184 | 32 | 32 | 32 | 3' |
| Compound 1185 | 33 | 33 | 33 | 3' |
| Compound 1186 | 34 | 34 | 34 | 3' |
| Compound 1187 | 35 | 35 | 35 | 3' |
| Compound 1188 | 36 | 36 | 36 | 3' |

TABLE 44

| Compound No. | $D_{1A}$ | $D_{1B}$ | $D_{1C}$ | $D_{2A}$ |
| --- | --- | --- | --- | --- |
| Compound 1189 | 1 | 1 | 1 | 4' |
| Compound 1190 | 2 | 2 | 2 | 4' |
| Compound 1191 | 3 | 3 | 3 | 4' |
| Compound 1192 | 4 | 4 | 4 | 4' |
| Compound 1193 | 5 | 5 | 5 | 4' |
| Compound 1194 | 6 | 6 | 6 | 4' |
| Compound 1195 | 7 | 7 | 7 | 4' |
| Compound 1196 | 8 | 8 | 8 | 4' |
| Compound 1197 | 9 | 9 | 9 | 4' |
| Compound 1198 | 10 | 10 | 10 | 4' |
| Compound 1199 | 11 | 11 | 11 | 4' |
| Compound 1200 | 12 | 12 | 12 | 4' |
| Compound 1201 | 13 | 13 | 13 | 4' |
| Compound 1202 | 14 | 14 | 14 | 4' |
| Compound 1203 | 15 | 15 | 15 | 4' |
| Compound 1204 | 16 | 16 | 16 | 4' |
| Compound 1205 | 17 | 17 | 17 | 4' |
| Compound 1206 | 18 | 18 | 18 | 4' |
| Compound 1207 | 19 | 19 | 19 | 4' |
| Compound 1208 | 20 | 20 | 20 | 4' |
| Compound 1209 | 21 | 21 | 21 | 4' |
| Compound 1210 | 22 | 22 | 22 | 4' |
| Compound 1211 | 23 | 23 | 23 | 4' |
| Compound 1212 | 24 | 24 | 24 | 4' |
| Compound 1213 | 25 | 25 | 25 | 4' |

TABLE 44-continued

| Compound No. | $D_{1A}$ | $D_{1B}$ | $D_{1C}$ | $D_{2A}$ |
| --- | --- | --- | --- | --- |
| Compound 1214 | 26 | 26 | 26 | 4' |
| Compound 1215 | 27 | 27 | 27 | 4' |
| Compound 1216 | 28 | 28 | 28 | 4' |
| Compound 1217 | 29 | 29 | 29 | 4' |
| Compound 1218 | 30 | 30 | 30 | 4' |
| Compound 1219 | 31 | 31 | 31 | 4' |
| Compound 1220 | 32 | 32 | 32 | 4' |
| Compound 1221 | 33 | 33 | 33 | 4' |
| Compound 1222 | 34 | 34 | 34 | 4' |
| Compound 1223 | 35 | 35 | 35 | 4' |
| Compound 1224 | 36 | 36 | 36 | 4' |

TABLE 45

| Compound No. | $D_{1A}$ | $D_{1B}$ | $D_{1C}$ | $D_{2A}$ |
| --- | --- | --- | --- | --- |
| Compound 1225 | 1 | 1 | 1 | 5' |
| Compound 1226 | 2 | 2 | 2 | 5' |
| Compound 1227 | 3 | 3 | 3 | 5' |
| Compound 1228 | 4 | 4 | 4 | 5' |
| Compound 1229 | 5 | 5 | 5 | 5' |
| Compound 1230 | 6 | 6 | 6 | 5' |
| Compound 1231 | 7 | 7 | 7 | 5' |
| Compound 1232 | 8 | 8 | 8 | 5' |
| Compound 1233 | 9 | 9 | 9 | 5' |
| Compound 1234 | 10 | 10 | 10 | 5' |
| Compound 1235 | 11 | 11 | 11 | 5' |
| Compound 1236 | 12 | 12 | 12 | 5' |
| Compound 1237 | 13 | 13 | 13 | 5' |
| Compound 1238 | 14 | 14 | 14 | 5' |
| Compound 1239 | 15 | 15 | 15 | 5' |
| Compound 1240 | 16 | 16 | 16 | 5' |
| Compound 1241 | 17 | 17 | 17 | 5' |
| Compound 1242 | 18 | 18 | 18 | 5' |
| Compound 1243 | 19 | 19 | 19 | 5' |
| Compound 1244 | 20 | 20 | 20 | 5' |
| Compound 1245 | 21 | 21 | 21 | 5' |
| Compound 1246 | 22 | 22 | 22 | 5' |
| Compound 1247 | 23 | 23 | 23 | 5' |
| Compound 1248 | 24 | 24 | 24 | 5' |
| Compound 1249 | 25 | 25 | 25 | 5' |
| Compound 1250 | 26 | 26 | 26 | 5' |
| Compound 1251 | 27 | 27 | 27 | 5' |
| Compound 1252 | 28 | 28 | 28 | 5' |
| Compound 1253 | 29 | 29 | 29 | 5' |
| Compound 1254 | 30 | 30 | 30 | 5' |
| Compound 1255 | 31 | 31 | 31 | 5' |
| Compound 1256 | 32 | 32 | 32 | 5' |
| Compound 1257 | 33 | 33 | 33 | 5' |
| Compound 1258 | 34 | 34 | 34 | 5' |
| Compound 1259 | 35 | 35 | 35 | 5' |
| Compound 1260 | 36 | 36 | 36 | 5' |

TABLE 46

| Compound No. | $D_{1A}$ | $D_{1B}$ | $D_{1C}$ | $D_{2A}$ |
| --- | --- | --- | --- | --- |
| Compound 1261 | 1 | 1 | 1 | 6' |
| Compound 1262 | 2 | 2 | 2 | 6' |
| Compound 1263 | 3 | 3 | 3 | 6' |
| Compound 1264 | 4 | 4 | 4 | 6' |
| Compound 1265 | 5 | 5 | 5 | 6' |
| Compound 1266 | 6 | 6 | 6 | 6' |
| Compound 1267 | 7 | 7 | 7 | 6' |
| Compound 1268 | 8 | 8 | 8 | 6' |
| Compound 1269 | 9 | 9 | 9 | 6' |
| Compound 1270 | 10 | 10 | 10 | 6' |
| Compound 1271 | 11 | 11 | 11 | 6' |
| Compound 1272 | 12 | 12 | 12 | 6' |
| Compound 1273 | 13 | 13 | 13 | 6' |
| Compound 1274 | 14 | 14 | 14 | 6' |
| Compound 1275 | 15 | 15 | 15 | 6' |
| Compound 1276 | 16 | 16 | 16 | 6' |

TABLE 46-continued

| Compound No. | $D_{1A}$ | $D_{1B}$ | $D_{1C}$ | $D_{2A}$ |
|---|---|---|---|---|
| Compound 1277 | 17 | 17 | 17 | 6' |
| Compound 1278 | 18 | 18 | 18 | 6' |
| Compound 1279 | 19 | 19 | 19 | 6' |
| Compound 1280 | 20 | 20 | 20 | 6' |
| Compound 1281 | 21 | 21 | 21 | 6' |
| Compound 1282 | 22 | 22 | 22 | 6' |
| Compound 1283 | 23 | 23 | 23 | 6' |
| Compound 1284 | 24 | 24 | 24 | 6' |
| Compound 1285 | 25 | 25 | 25 | 6' |
| Compound 1286 | 26 | 26 | 26 | 6' |
| Compound 1287 | 27 | 27 | 27 | 6' |
| Compound 1288 | 28 | 28 | 28 | 6' |
| Compound 1289 | 29 | 29 | 29 | 6' |
| Compound 1290 | 30 | 30 | 30 | 6' |
| Compound 1291 | 31 | 31 | 31 | 6' |
| Compound 1292 | 32 | 32 | 32 | 6' |
| Compound 1293 | 33 | 33 | 33 | 6' |
| Compound 1294 | 34 | 34 | 34 | 6' |
| Compound 1295 | 35 | 35 | 35 | 6' |
| Compound 1296 | 36 | 36 | 36 | 6' |

TABLE 47

| Compound No. | $D_{1A}$ | $D_{1B}$ | $D_{1C}$ | $D_{2A}$ |
|---|---|---|---|---|
| Compound 1297 | 1 | 1 | 1 | 7' |
| Compound 1298 | 2 | 2 | 2 | 7' |
| Compound 1299 | 3 | 3 | 3 | 7' |
| Compound 1300 | 4 | 4 | 4 | 7' |
| Compound 1301 | 5 | 5 | 5 | 7' |
| Compound 1302 | 6 | 6 | 6 | 7' |
| Compound 1303 | 7 | 7 | 7 | 7' |
| Compound 1304 | 8 | 8 | 8 | 7' |
| Compound 1305 | 9 | 9 | 9 | 7' |
| Compound 1306 | 10 | 10 | 10 | 7' |
| Compound 1307 | 11 | 11 | 11 | 7' |
| Compound 1308 | 12 | 12 | 12 | 7' |
| Compound 1309 | 13 | 13 | 13 | 7' |
| Compound 1310 | 14 | 14 | 14 | 7' |
| Compound 1311 | 15 | 15 | 15 | 7' |
| Compound 1312 | 16 | 16 | 16 | 7' |
| Compound 1313 | 17 | 17 | 17 | 7' |
| Compound 1314 | 18 | 18 | 18 | 7' |
| Compound 1315 | 19 | 19 | 19 | 7' |
| Compound 1316 | 20 | 20 | 20 | 7' |
| Compound 1317 | 21 | 21 | 21 | 7' |
| Compound 1318 | 22 | 22 | 22 | 7' |
| Compound 1319 | 23 | 23 | 23 | 7' |
| Compound 1320 | 24 | 24 | 24 | 7' |
| Compound 1321 | 25 | 25 | 25 | 7' |
| Compound 1322 | 26 | 26 | 26 | 7' |
| Compound 1323 | 27 | 27 | 27 | 7' |
| Compound 1324 | 28 | 28 | 28 | 7' |
| Compound 1325 | 29 | 29 | 29 | 7' |
| Compound 1326 | 30 | 30 | 30 | 7' |
| Compound 1327 | 31 | 31 | 31 | 7' |
| Compound 1328 | 32 | 32 | 32 | 7' |
| Compound 1329 | 33 | 33 | 33 | 7' |
| Compound 1330 | 34 | 34 | 34 | 7' |
| Compound 1331 | 35 | 35 | 35 | 7' |
| Compound 1332 | 36 | 36 | 36 | 7' |

TABLE 48

| Compound No. | $D_{1A}$ | $D_{1B}$ | $D_{1C}$ | $D_{2A}$ |
|---|---|---|---|---|
| Compound 1333 | 1 | 1 | 1 | 8' |
| Compound 1334 | 2 | 2 | 2 | 8' |
| Compound 1335 | 3 | 3 | 3 | 8' |
| Compound 1336 | 4 | 4 | 4 | 8' |
| Compound 1337 | 5 | 5 | 5 | 8' |
| Compound 1338 | 6 | 6 | 6 | 8' |
| Compound 1339 | 7 | 7 | 7 | 8' |
| Compound 1340 | 8 | 8 | 8 | 8' |
| Compound 1341 | 9 | 9 | 9 | 8' |
| Compound 1342 | 10 | 10 | 10 | 8' |
| Compound 1343 | 11 | 11 | 11 | 8' |
| Compound 1344 | 12 | 12 | 12 | 8' |
| Compound 1345 | 13 | 13 | 13 | 8' |
| Compound 1346 | 14 | 14 | 14 | 8' |
| Compound 1347 | 15 | 15 | 15 | 8' |
| Compound 1348 | 16 | 16 | 16 | 8' |
| Compound 1349 | 17 | 17 | 17 | 8' |
| Compound 1350 | 18 | 18 | 18 | 8' |
| Compound 1351 | 19 | 19 | 19 | 8' |
| Compound 1352 | 20 | 20 | 20 | 8' |
| Compound 1353 | 21 | 21 | 21 | 8' |
| Compound 1354 | 22 | 22 | 22 | 8' |
| Compound 1355 | 23 | 23 | 23 | 8' |
| Compound 1356 | 24 | 24 | 24 | 8' |
| Compound 1357 | 25 | 25 | 25 | 8' |
| Compound 1358 | 26 | 26 | 26 | 8' |
| Compound 1359 | 27 | 27 | 27 | 8' |
| Compound 1360 | 28 | 28 | 28 | 8' |
| Compound 1361 | 29 | 29 | 29 | 8' |
| Compound 1362 | 30 | 30 | 30 | 8' |
| Compound 1363 | 31 | 31 | 31 | 8' |
| Compound 1364 | 32 | 32 | 32 | 8' |
| Compound 1365 | 33 | 33 | 33 | 8' |
| Compound 1366 | 34 | 34 | 34 | 8' |
| Compound 1367 | 35 | 35 | 35 | 8' |
| Compound 1368 | 36 | 36 | 36 | 8' |

TABLE 49

| Compound No. | $D_{1A}$ | $D_{1B}$ | $D_{1C}$ | $D_{2A}$ |
|---|---|---|---|---|
| Compound 1369 | 1 | 1 | 1 | 9' |
| Compound 1370 | 2 | 2 | 2 | 9' |
| Compound 1371 | 3 | 3 | 3 | 9' |
| Compound 1372 | 4 | 4 | 4 | 9' |
| Compound 1373 | 5 | 5 | 5 | 9' |
| Compound 1374 | 6 | 6 | 6 | 9' |
| Compound 1375 | 7 | 7 | 7 | 9' |
| Compound 1376 | 8 | 8 | 8 | 9' |
| Compound 1377 | 9 | 9 | 9 | 9' |
| Compound 1378 | 10 | 10 | 10 | 9' |
| Compound 1379 | 11 | 11 | 11 | 9' |
| Compound 1380 | 12 | 12 | 12 | 9' |
| Compound 1381 | 13 | 13 | 13 | 9' |
| Compound 1382 | 14 | 14 | 14 | 9' |
| Compound 1383 | 15 | 15 | 15 | 9' |
| Compound 1384 | 16 | 16 | 16 | 9' |
| Compound 1385 | 17 | 17 | 17 | 9' |
| Compound 1386 | 18 | 18 | 18 | 9' |
| Compound 1387 | 19 | 19 | 19 | 9' |
| Compound 1388 | 20 | 20 | 20 | 9' |
| Compound 1389 | 21 | 21 | 21 | 9' |
| Compound 1390 | 22 | 22 | 22 | 9' |
| Compound 1391 | 23 | 23 | 23 | 9' |
| Compound 1392 | 24 | 24 | 24 | 9' |
| Compound 1393 | 25 | 25 | 25 | 9' |
| Compound 1394 | 26 | 26 | 26 | 9' |
| Compound 1395 | 27 | 27 | 27 | 9' |
| Compound 1396 | 28 | 28 | 28 | 9' |
| Compound 1397 | 29 | 29 | 29 | 9' |
| Compound 1398 | 30 | 30 | 30 | 9' |
| Compound 1399 | 31 | 31 | 31 | 9' |
| Compound 1400 | 32 | 32 | 32 | 9' |
| Compound 1401 | 33 | 33 | 33 | 9' |
| Compound 1402 | 34 | 34 | 34 | 9' |
| Compound 1403 | 35 | 35 | 35 | 9' |
| Compound 1404 | 36 | 36 | 36 | 9' |

TABLE 50

| Compound No | $D_{1A}$ | $D_{1B}$ | $D_{1C}$ | $D_{2A}$ |
|---|---|---|---|---|
| Compound 1405 | 1 | 1 | 1 | 10' |
| Compound 1406 | 2 | 2 | 2 | 10' |
| Compound 1407 | 3 | 3 | 3 | 10' |
| Compound 1408 | 4 | 4 | 4 | 10' |
| Compound 1409 | 5 | 5 | 5 | 10' |
| Compound 1410 | 6 | 6 | 6 | 10' |
| Compound 1411 | 7 | 7 | 7 | 10' |
| Compound 1412 | 8 | 8 | 8 | 10' |
| Compound 1413 | 9 | 9 | 9 | 10' |
| Compound 1414 | 10 | 10 | 10 | 10' |
| Compound 1415 | 11 | 11 | 11 | 10' |
| Compound 1416 | 12 | 12 | 12 | 10' |
| Compound 1417 | 13 | 13 | 13 | 10' |
| Compound 1418 | 14 | 14 | 14 | 10' |
| Compound 1419 | 15 | 15 | 15 | 10' |
| Compound 1420 | 16 | 16 | 16 | 10' |
| Compound 1421 | 17 | 17 | 17 | 10' |
| Compound 1422 | 18 | 18 | 18 | 10' |
| Compound 1423 | 19 | 19 | 19 | 10' |
| Compound 1424 | 20 | 20 | 20 | 10' |
| Compound 1425 | 21 | 21 | 21 | 10' |
| Compound 1426 | 22 | 22 | 22 | 10' |
| Compound 1427 | 23 | 23 | 23 | 10' |
| Compound 1428 | 24 | 24 | 24 | 10' |
| Compound 1429 | 25 | 25 | 25 | 10' |
| Compound 1430 | 26 | 26 | 26 | 10' |
| Compound 1431 | 27 | 27 | 27 | 10' |
| Compound 1432 | 28 | 28 | 28 | 10' |
| Compound 1433 | 29 | 29 | 29 | 10' |
| Compound 1434 | 30 | 30 | 30 | 10' |
| Compound 1435 | 31 | 31 | 31 | 10' |
| Compound 1436 | 32 | 32 | 32 | 10' |
| Compound 1437 | 33 | 33 | 33 | 10' |
| Compound 1438 | 34 | 34 | 34 | 10' |
| Compound 1439 | 35 | 35 | 35 | 10' |
| Compound 1440 | 36 | 36 | 36 | 10' |

TABLE 51

| Compound No. | $D_{1A}$ | $D_{1B}$ | $D_{1C}$ | $D_{2A}$ |
|---|---|---|---|---|
| Compound 1441 | 1 | 1 | 1 | 11' |
| Compound 1442 | 2 | 2 | 2 | 11' |
| Compound 1443 | 3 | 3 | 3 | 11' |
| Compound 1444 | 4 | 4 | 4 | 11' |
| Compound 1445 | 5 | 5 | 5 | 11' |
| Compound 1446 | 6 | 6 | 6 | 11' |
| Compound 1447 | 7 | 7 | 7 | 11' |
| Compound 1448 | 8 | 8 | 8 | 11' |
| Compound 1449 | 9 | 9 | 9 | 11' |
| Compound 1450 | 10 | 10 | 10 | 11' |
| Compound 1451 | 11 | 11 | 11 | 11' |
| Compound 1452 | 12 | 12 | 12 | 11' |
| Compound 1453 | 13 | 13 | 13 | 11' |
| Compound 1454 | 14 | 14 | 14 | 11' |
| Compound 1455 | 15 | 15 | 15 | 11' |
| Compound 1456 | 16 | 16 | 16 | 11' |
| Compound 1457 | 17 | 17 | 17 | 11' |
| Compound 1458 | 18 | 18 | 18 | 11' |
| Compound 1459 | 19 | 19 | 19 | 11' |
| Compound 1460 | 20 | 20 | 20 | 11' |
| Compound 1461 | 21 | 21 | 21 | 11' |
| Compound 1462 | 22 | 22 | 22 | 11' |
| Compound 1463 | 23 | 23 | 23 | 11' |
| Compound 1464 | 24 | 24 | 24 | 11' |
| Compound 1465 | 25 | 25 | 25 | 11' |
| Compound 1466 | 26 | 26 | 26 | 11' |
| Compound 1467 | 27 | 27 | 27 | 11' |
| Compound 1468 | 28 | 28 | 28 | 11' |
| Compound 1469 | 29 | 29 | 29 | 11' |
| Compound 1470 | 30 | 30 | 30 | 11' |
| Compound 1471 | 31 | 31 | 31 | 11' |
| Compound 1472 | 32 | 32 | 32 | 11' |
| Compound 1473 | 33 | 33 | 33 | 11' |
| Compound 1474 | 34 | 34 | 34 | 11' |
| Compound 1475 | 35 | 35 | 35 | 11' |
| Compound 1476 | 36 | 36 | 36 | 11' |

TABLE 52

| Compound No. | $D_{1A}$ | $D_{1B}$ | $D_{1C}$ | $D_{2A}$ |
|---|---|---|---|---|
| Compound 1477 | 1 | 1 | 1 | 12' |
| Compound 1478 | 2 | 2 | 2 | 12' |
| Compound 1479 | 3 | 3 | 3 | 12' |
| Compound 1480 | 4 | 4 | 4 | 12' |
| Compound 1481 | 5 | 5 | 5 | 12' |
| Compound 1482 | 6 | 6 | 6 | 12' |
| Compound 1483 | 7 | 7 | 7 | 12' |
| Compound 1484 | 8 | 8 | 8 | 12' |
| Compound 1485 | 9 | 9 | 9 | 12' |
| Compound 1486 | 10 | 10 | 10 | 12' |
| Compound 1487 | 11 | 11 | 11 | 12' |
| Compound 1488 | 12 | 12 | 12 | 12' |
| Compound 1489 | 13 | 13 | 13 | 12' |
| Compound 1490 | 14 | 14 | 14 | 12' |
| Compound 1491 | 15 | 15 | 15 | 12' |
| Compound 1492 | 16 | 16 | 16 | 12' |
| Compound 1493 | 17 | 17 | 17 | 12' |
| Compound 1494 | 18 | 18 | 18 | 12' |
| Compound 1495 | 19 | 19 | 19 | 12' |
| Compound 1496 | 20 | 20 | 20 | 12' |
| Compound 1497 | 21 | 21 | 21 | 12' |
| Compound 1498 | 22 | 22 | 22 | 12' |
| Compound 1499 | 23 | 23 | 23 | 12' |
| Compound 1500 | 24 | 24 | 24 | 12' |
| Compound 1501 | 25 | 25 | 25 | 12' |
| Compound 1502 | 26 | 26 | 26 | 12' |
| Compound 1503 | 27 | 27 | 27 | 12' |
| Compound 1504 | 28 | 28 | 28 | 12' |
| Compound 1505 | 29 | 29 | 29 | 12' |
| Compound 1506 | 30 | 30 | 30 | 12' |
| Compound 1507 | 31 | 31 | 31 | 12' |
| Compound 1508 | 32 | 32 | 32 | 12' |
| Compound 1509 | 33 | 33 | 33 | 12' |
| Compound 1510 | 34 | 34 | 34 | 12' |
| Compound 1511 | 35 | 35 | 35 | 12' |
| Compound 1512 | 36 | 36 | 36 | 12' |

TABLE 53

| Compound No. | $D_{1A}$ | $D_{1B}$ | $D_{1C}$ | $D_{2A}$ |
|---|---|---|---|---|
| Compound 1513 | 1 | 1 | 1 | 13' |
| Compound 1514 | 2 | 2 | 2 | 13' |
| Compound 1515 | 3 | 3 | 3 | 13' |
| Compound 1516 | 4 | 4 | 4 | 13' |
| Compound 1517 | 5 | 5 | 5 | 13' |
| Compound 1518 | 6 | 6 | 6 | 13' |
| Compound 1519 | 7 | 7 | 7 | 13' |
| Compound 1520 | 8 | 8 | 8 | 13' |
| Compound 1521 | 9 | 9 | 9 | 13' |
| Compound 1522 | 10 | 10 | 10 | 13' |
| Compound 1523 | 11 | 11 | 11 | 13' |
| Compound 1524 | 12 | 12 | 12 | 13' |
| Compound 1525 | 13 | 13 | 13 | 13' |
| Compound 1526 | 14 | 14 | 14 | 13' |
| Compound 1527 | 15 | 15 | 15 | 13' |
| Compound 1528 | 16 | 16 | 16 | 13' |
| Compound 1529 | 17 | 17 | 17 | 13' |
| Compound 1530 | 18 | 18 | 18 | 13' |
| Compound 1531 | 19 | 19 | 19 | 13' |
| Compound 1532 | 20 | 20 | 20 | 13' |
| Compound 1533 | 21 | 21 | 21 | 13' |
| Compound 1534 | 22 | 22 | 22 | 13' |
| Compound 1535 | 23 | 23 | 23 | 13' |
| Compound 1536 | 24 | 24 | 24 | 13' |
| Compound 1537 | 25 | 25 | 25 | 13' |

TABLE 53-continued

| Compound No. | $D_{1A}$ | $D_{1B}$ | $D_{1C}$ | $D_{2A}$ |
| --- | --- | --- | --- | --- |
| Compound 1538 | 26 | 26 | 26 | 13' |
| Compound 1539 | 27 | 27 | 27 | 13' |
| Compound 1540 | 28 | 28 | 28 | 13' |
| Compound 1541 | 29 | 29 | 29 | 13' |
| Compound 1542 | 30 | 30 | 30 | 13' |
| Compound 1543 | 31 | 31 | 31 | 13' |
| Compound 1544 | 32 | 32 | 32 | 13' |
| Compound 1545 | 33 | 33 | 33 | 13' |
| Compound 1546 | 34 | 34 | 34 | 13' |
| Compound 1547 | 35 | 35 | 35 | 13' |
| Compound 1548 | 36 | 36 | 36 | 13' |

TABLE 54

| Compound No. | $D_{1A}$ | $D_{1B}$ | $D_{1C}$ | $D_{2A}$ |
| --- | --- | --- | --- | --- |
| Compound 1549 | 1 | 1 | 1 | 14' |
| Compound 1550 | 2 | 2 | 2 | 14' |
| Compound 1551 | 3 | 3 | 3 | 14' |
| Compound 1552 | 4 | 4 | 4 | 14' |
| Compound 1553 | 5 | 5 | 5 | 14' |
| Compound 1554 | 6 | 6 | 6 | 14' |
| Compound 1555 | 7 | 7 | 7 | 14' |
| Compound 1556 | 8 | 8 | 8 | 14' |
| Compound 1557 | 9 | 9 | 9 | 14' |
| Compound 1558 | 10 | 10 | 10 | 14' |
| Compound 1559 | 11 | 11 | 11 | 14' |
| Compound 1560 | 12 | 12 | 12 | 14' |
| Compound 1561 | 13 | 13 | 13 | 14' |
| Compound 1562 | 14 | 14 | 14 | 14' |
| Compound 1563 | 15 | 15 | 15 | 14' |
| Compound 1564 | 16 | 16 | 16 | 14' |
| Compound 1565 | 17 | 17 | 17 | 14' |
| Compound 1566 | 18 | 18 | 18 | 14' |
| Compound 1567 | 19 | 19 | 19 | 14' |
| Compound 1568 | 20 | 20 | 20 | 14' |
| Compound 1569 | 21 | 21 | 21 | 14' |
| Compound 1570 | 22 | 22 | 22 | 14' |
| Compound 1571 | 23 | 23 | 23 | 14' |
| Compound 1572 | 24 | 24 | 24 | 14' |
| Compound 1573 | 25 | 25 | 25 | 14' |
| Compound 1574 | 26 | 26 | 26 | 14' |
| Compound 1575 | 27 | 27 | 27 | 14' |
| Compound 1576 | 28 | 28 | 28 | 14' |
| Compound 1577 | 29 | 29 | 29 | 14' |
| Compound 1578 | 30 | 30 | 30 | 14' |
| Compound 1579 | 31 | 31 | 31 | 14' |
| Compound 1580 | 32 | 32 | 32 | 14' |
| Compound 1581 | 33 | 33 | 33 | 14' |
| Compound 1582 | 34 | 34 | 34 | 14' |
| Compound 1583 | 35 | 35 | 35 | 14' |
| Compound 1584 | 36 | 36 | 36 | 14' |

TABLE 55

| Compound No. | $D_{1A}$ | $D_{1B}$ | $D_{1C}$ | $D_{2A}$ |
| --- | --- | --- | --- | --- |
| Compound 1585 | 1 | 1 | 1 | 15' |
| Compound 1586 | 2 | 2 | 2 | 15' |
| Compound 1587 | 3 | 3 | 3 | 15' |
| Compound 1588 | 4 | 4 | 4 | 15' |
| Compound 1589 | 5 | 5 | 5 | 15' |
| Compound 1590 | 6 | 6 | 6 | 15' |
| Compound 1591 | 7 | 7 | 7 | 15' |
| Compound 1592 | 8 | 8 | 8 | 15' |
| Compound 1593 | 9 | 9 | 9 | 15' |
| Compound 1594 | 10 | 10 | 10 | 15' |
| Compound 1595 | 11 | 11 | 11 | 15' |
| Compound 1596 | 12 | 12 | 12 | 15' |
| Compound 1597 | 13 | 13 | 13 | 15' |
| Compound 1598 | 14 | 14 | 14 | 15' |
| Compound 1599 | 15 | 15 | 15 | 15' |
| Compound 1600 | 16 | 16 | 16 | 15' |

TABLE 55-continued

| Compound No. | $D_{1A}$ | $D_{1B}$ | $D_{1C}$ | $D_{2A}$ |
| --- | --- | --- | --- | --- |
| Compound 1601 | 17 | 17 | 17 | 15' |
| Compound 1602 | 18 | 18 | 18 | 15' |
| Compound 1603 | 19 | 19 | 19 | 15' |
| Compound 1604 | 20 | 20 | 20 | 15' |
| Compound 1605 | 21 | 21 | 21 | 15' |
| Compound 1606 | 22 | 22 | 22 | 15' |
| Compound 1607 | 23 | 23 | 23 | 15' |
| Compound 1608 | 24 | 24 | 24 | 15' |
| Compound 1609 | 25 | 25 | 25 | 15' |
| Compound 1610 | 26 | 26 | 26 | 15' |
| Compound 1611 | 27 | 27 | 27 | 15' |
| Compound 1612 | 28 | 28 | 28 | 15' |
| Compound 1613 | 29 | 29 | 29 | 15' |
| Compound 1614 | 30 | 30 | 30 | 15' |
| Compound 1615 | 31 | 31 | 31 | 15' |
| Compound 1616 | 32 | 32 | 32 | 15' |
| Compound 1617 | 33 | 33 | 33 | 15' |
| Compound 1618 | 34 | 34 | 34 | 15' |
| Compound 1619 | 35 | 35 | 35 | 15' |
| Compound 1620 | 36 | 36 | 36 | 15' |

TABLE 56

| Compound No. | $D_{1A}$ | $D_{1B}$ | $D_{1C}$ | $D_{2A}$ |
| --- | --- | --- | --- | --- |
| Compound 1837 | 1 | 1 | 1 | 16' |
| Compound 1838 | 2 | 2 | 2 | 16' |
| Compound 1839 | 3 | 3 | 3 | 16' |
| Compound 1840 | 4 | 4 | 4 | 16' |
| Compound 1841 | 5 | 5 | 5 | 16' |
| Compound 1842 | 6 | 6 | 6 | 16' |
| Compound 1843 | 7 | 7 | 7 | 16' |
| Compound 1844 | 8 | 8 | 8 | 16' |
| Compound 1845 | 9 | 9 | 9 | 16' |
| Compound 1846 | 10 | 10 | 10 | 16' |
| Compound 1847 | 11 | 11 | 11 | 16' |
| Compound 1848 | 12 | 12 | 12 | 16' |
| Compound 1849 | 13 | 13 | 13 | 16' |
| Compound 1850 | 14 | 14 | 14 | 16' |
| Compound 1851 | 15 | 15 | 15 | 16' |
| Compound 1852 | 16 | 16 | 16 | 16' |
| Compound 1853 | 17 | 17 | 17 | 16' |
| Compound 1854 | 18 | 18 | 18 | 16' |
| Compound 1855 | 19 | 19 | 19 | 16' |
| Compound 1856 | 20 | 20 | 20 | 16' |
| Compound 1857 | 21 | 21 | 21 | 16' |
| Compound 1858 | 22 | 22 | 22 | 16' |
| Compound 1859 | 23 | 23 | 23 | 16' |
| Compound 1860 | 24 | 24 | 24 | 16' |
| Compound 1861 | 25 | 25 | 25 | 16' |
| Compound 1862 | 26 | 26 | 26 | 16' |
| Compound 1863 | 27 | 27 | 27 | 16' |
| Compound 1864 | 28 | 28 | 28 | 16' |
| Compound 1865 | 29 | 29 | 29 | 16' |
| Compound 1866 | 30 | 30 | 30 | 16' |
| Compound 1867 | 31 | 31 | 31 | 16' |
| Compound 1868 | 32 | 32 | 32 | 16' |
| Compound 1869 | 33 | 33 | 33 | 16' |
| Compound 1870 | 34 | 34 | 34 | 16' |
| Compound 1871 | 35 | 35 | 35 | 16' |
| Compound 1872 | 36 | 36 | 36 | 16' |

TABLE 57

| Compound No. | $D_{1A}$ | $D_{1B}$ | $D_{1C}$ | $D_{2A}$ |
| --- | --- | --- | --- | --- |
| Compound 1873 | 1 | 1 | 1 | 17' |
| Compound 1874 | 2 | 2 | 2 | 17' |
| Compound 1875 | 3 | 3 | 3 | 17' |
| Compound 1876 | 4 | 4 | 4 | 17' |
| Compound 1877 | 5 | 5 | 5 | 17' |
| Compound 1878 | 6 | 6 | 6 | 17' |
| Compound 1879 | 7 | 7 | 7 | 17' |

TABLE 57-continued

| Compound No. | $D_{1A}$ | $D_{1B}$ | $D_{1C}$ | $D_{2A}$ |
|---|---|---|---|---|
| Compound 1880 | 8  | 8  | 8  | 17' |
| Compound 1881 | 9  | 9  | 9  | 17' |
| Compound 1882 | 10 | 10 | 10 | 17' |
| Compound 1883 | 11 | 11 | 11 | 17' |
| Compound 1884 | 12 | 12 | 12 | 17' |
| Compound 1885 | 13 | 13 | 13 | 17' |
| Compound 1886 | 14 | 14 | 14 | 17' |
| Compound 1887 | 15 | 15 | 15 | 17' |
| Compound 1888 | 16 | 16 | 16 | 17' |
| Compound 1889 | 17 | 17 | 17 | 17' |
| Compound 1890 | 18 | 18 | 18 | 17' |
| Compound 1891 | 19 | 19 | 19 | 17' |
| Compound 1892 | 20 | 20 | 20 | 17' |
| Compound 1893 | 21 | 21 | 21 | 17' |
| Compound 1894 | 22 | 22 | 22 | 17' |
| Compound 1895 | 23 | 23 | 23 | 17' |
| Compound 1896 | 24 | 24 | 24 | 17' |
| Compound 1897 | 25 | 25 | 25 | 17' |
| Compound 1898 | 26 | 26 | 26 | 17' |
| Compound 1899 | 27 | 27 | 27 | 17' |
| Compound 1900 | 28 | 28 | 28 | 17' |
| Compound 1901 | 29 | 29 | 29 | 17' |
| Compound 1902 | 30 | 30 | 30 | 17' |
| Compound 1903 | 31 | 31 | 31 | 17' |
| Compound 1904 | 32 | 32 | 32 | 17' |
| Compound 1905 | 33 | 33 | 33 | 17' |
| Compound 1906 | 34 | 34 | 34 | 17' |
| Compound 1907 | 35 | 35 | 35 | 17' |
| Compound 1908 | 36 | 36 | 36 | 17' |

TABLE 58

| Compound No. | $D_{1A}$ | $D_{1B}$ | $D_{1C}$ | $D_{2A}$ |
|---|---|---|---|---|
| Compound 1909 | 1  | 1  | 1  | 18' |
| Compound 1910 | 2  | 2  | 2  | 18' |
| Compound 1911 | 3  | 3  | 3  | 18' |
| Compound 1912 | 4  | 4  | 4  | 18' |
| Compound 1913 | 5  | 5  | 5  | 18' |
| Compound 1914 | 6  | 6  | 6  | 18' |
| Compound 1915 | 7  | 7  | 7  | 18' |
| Compound 1916 | 8  | 8  | 8  | 18' |
| Compound 1917 | 9  | 9  | 9  | 18' |
| Compound 1918 | 10 | 10 | 10 | 18' |
| Compound 1919 | 11 | 11 | 11 | 18' |
| Compound 1920 | 12 | 12 | 12 | 18' |
| Compound 1921 | 13 | 13 | 13 | 18' |
| Compound 1922 | 14 | 14 | 14 | 18' |
| Compound 1923 | 15 | 15 | 15 | 18' |
| Compound 1924 | 16 | 16 | 16 | 18' |
| Compound 1925 | 17 | 17 | 17 | 18' |
| Compound 1926 | 18 | 18 | 18 | 18' |
| Compound 1927 | 19 | 19 | 19 | 18' |
| Compound 1928 | 20 | 20 | 20 | 18' |
| Compound 1929 | 21 | 21 | 21 | 18' |
| Compound 1930 | 22 | 22 | 22 | 18' |
| Compound 1931 | 23 | 23 | 23 | 18' |
| Compound 1932 | 24 | 24 | 24 | 18' |
| Compound 1933 | 25 | 25 | 25 | 18' |
| Compound 1934 | 26 | 26 | 26 | 18' |
| Compound 1935 | 27 | 27 | 27 | 18' |
| Compound 1936 | 28 | 28 | 28 | 18' |
| Compound 1937 | 29 | 29 | 29 | 18' |
| Compound 1938 | 30 | 30 | 30 | 18' |
| Compound 1939 | 31 | 31 | 31 | 18' |
| Compound 1940 | 32 | 32 | 32 | 18' |
| Compound 1941 | 33 | 33 | 33 | 18' |
| Compound 1942 | 34 | 34 | 34 | 18' |
| Compound 1943 | 35 | 35 | 35 | 18' |
| Compound 1944 | 36 | 36 | 36 | 18' |

The compound in the exemplary embodiment is preferably the compound represented by the formula (103), more preferably a compound represented by a formula (103A).

[Formula 25]

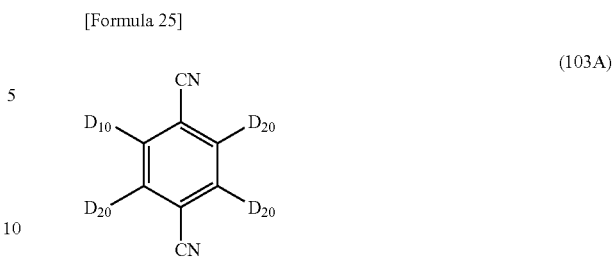

(103A)

In the formula (103A), $D_{1C}$ is a group represented by a formula (1-4A) below, $D_{20}$ is a group represented by a formula (2-1). A plurality of $D_{20}$ in the formula (103A) are mutually the same group.

That "a plurality of $D_{20}$ are mutually the same group" means that all variables represented by the same signs in the formula (2-1) are the same. The "variables in the formula (2-1)" refer to $R_{161}$ to $R_{168}$. Specifically, in the "groups represented by the formula (2-1)" representing the plurality of $D_{20}$ in the formula (103A), $R_{161}$ are the same, $R_{162}$ are the same, $R_{163}$ are the same, $R_{164}$ are the same, $R_{165}$ are the same, $R_{166}$ are the same, $R_{167}$ are the same, and $R_{168}$ are the same. In other words, three 020 in the formula (103A) are the same group having the same substituent.

[Formula 26]

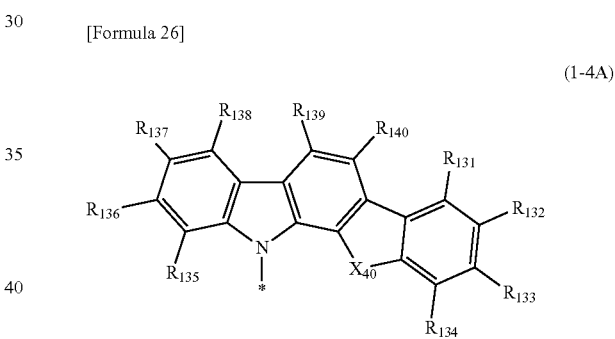

(1-4A)

In the formula (1-4A), $X_{40}$ represents an oxygen atom or a sulfur atom, $R_{131}$ to $R_{140}$ represent the same as $R_{131}$ to $R_{140}$ in the formula (1-4).

* represents a bonding position to a benzene ring in the formula (103A).

In the formula (1-4A), $X_{40}$ is preferably a sulfur atom.

In the formula (1-4A), $X_{40}$ is also preferably an oxygen atom.

In the compound represented by the formula (103A), the group represented by the formula (2-1) is preferably one of groups represented by formulae (2-5) and (2-9) to (2-17).

[Formula 27]

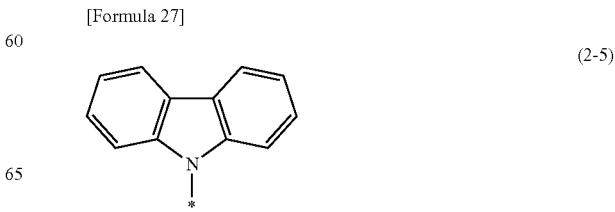

(2-5)

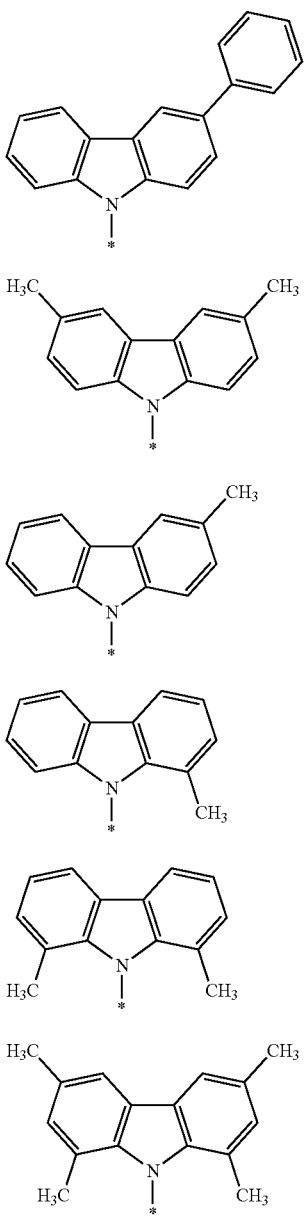

[Formula 28]

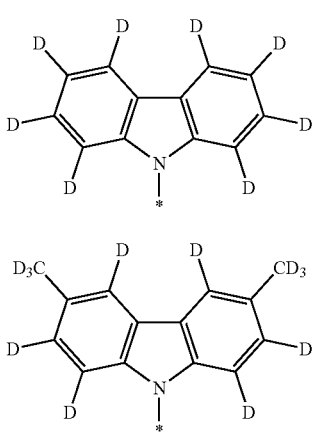

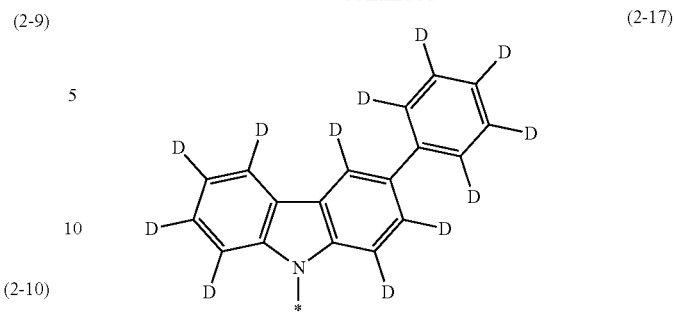

In the formulae (2-5) and (2-9) to (2-17), * each independently represents a bonding position to a benzene ring in the formula (103A), and D represents deuterium.

In the formulae (2-1), $R_{161}$ to $R_{168}$ are each independently preferably a hydrogen atom, a substituted or unsubstituted aryl group having 6 to 14 ring carbon atoms, or a substituted or unsubstituted alkyl group having 1 to 6 carbon atoms, more preferably a hydrogen atom or a substituted or unsubstituted alkyl group having 1 to 6 carbon atoms.

In the formula (2-1), it is also preferable that at least one of $R_{161}$, $R_{163}$, $R_{166}$ and $R_{168}$ has a substituent, the substituent is each independently a substituted or unsubstituted aryl group having 6 to 14 ring carbon atoms or a substituted or unsubstituted alkyl group having 1 to 6 carbon atoms, and $R_{162}$, $R_{164}$, $R_{165}$ and $R_{167}$ are each a hydrogen atom.

In the formula (2-1), when one or more of $R_{161}$ to $R_{168}$ are hydrogen atom(s), it is preferable that all of the hydrogen atom(s) are protium, one or more of the hydrogen atom(s) are deuterium, or all of the hydrogen atom(s) are deuterium.

In the formulae (1-4A) and (2-1), $R_{131}$ to $R_{140}$ and $R_{161}$ to $R_{168}$ as the substituent are each independently preferably a halogen atom, an unsubstituted aryl group having 6 to 14 ring carbon atoms, an unsubstituted heterocyclic group having 5 to 14 ring atoms, an unsubstituted alkyl group having 1 to 6 carbon atoms, an unsubstituted alkyl halide group having 1 to 6 carbon atoms, an unsubstituted alkylsilyl group having 3 to 6 carbon atoms, an unsubstituted alkoxy group having 1 to 6 carbon atoms, an unsubstituted aryloxy group having 6 to 14 ring carbon atoms, an unsubstituted alkylamino group having 2 to 12 carbon atoms, an unsubstituted alkylthio group having 1 to 6 carbon atoms, or an unsubstituted arylthio group having 6 to 14 ring carbon atoms.

In the formulae (1-4A) and (2-1), $R_{131}$ to $R_{140}$ and $R_{161}$ to $R_{168}$ are each independently preferably a hydrogen atom, a substituted or unsubstituted aryl group having 6 to 14 ring carbon atoms, substituted or unsubstituted heterocyclic group having 5 to 14 ring atoms, or substituted or unsubstituted alkyl group having 1 to 6 carbon atoms, more preferably a hydrogen atom, a substituted or unsubstituted aryl group having 6 to 14 ring carbon atoms, or substituted or unsubstituted alkyl group having 1 to 6 carbon atoms, further preferably a hydrogen atom or a substituted or unsubstituted alkyl group having 1 to 6 carbon atoms.

In the formulae (1-4A) and (2-1), $R_{131}$ to $R_{140}$ and $R_{161}$ to $R_{168}$ as the substituent are each independently more preferably an unsubstituted aryl group having 6 to 14 ring carbon atoms or an unsubstituted alkyl group having 1 to 6 carbon atoms.

In the formulae (1-4A) and (2-1), it is also preferable that $R_{137}$ is a substituent and $R_{137}$ as the substituent is a substituted or unsubstituted aryl group having 6 to 14 ring carbon atoms or a substituted or unsubstituted alkyl group having 1 to 6 carbon atoms, and $R_{131}$ to $R_{136}$ and $R_{138}$ to $R_{140}$ are each a hydrogen atom.

In the formulae (1-4A) and (2-1), it is also preferable that $R_{131}$ to $R_{140}$ and $R_{161}$ to $R_{168}$ are each a hydrogen atom.

Examples of the compound according to the exemplary embodiment are shown below. The compound of the invention is by no means limited to the Examples. Me represents a methyl group.

Examples of the compound according to the exemplary embodiment are shown below. The compound of the invention is by no means limited to the Examples.

[Formula 29]

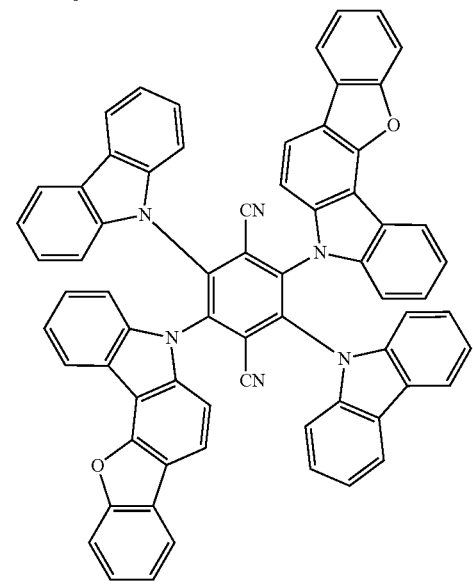

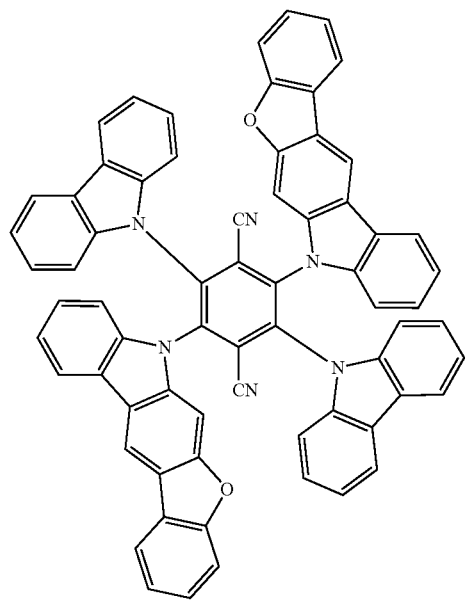

-continued

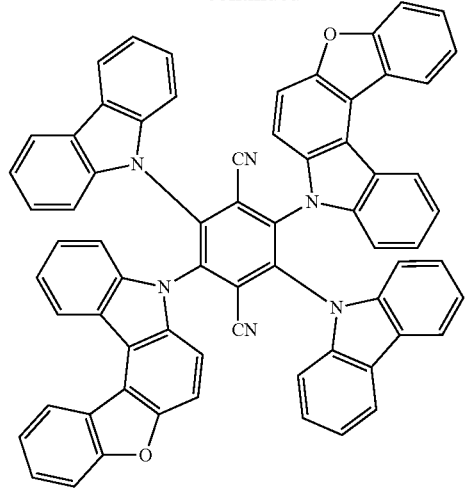

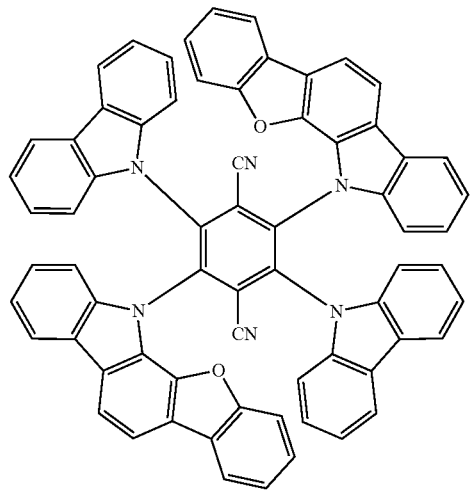

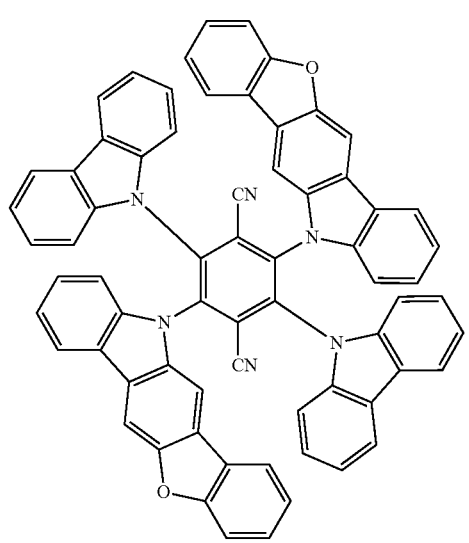

73
-continued
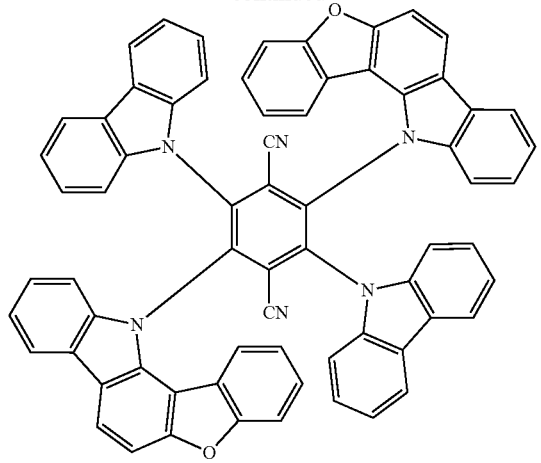
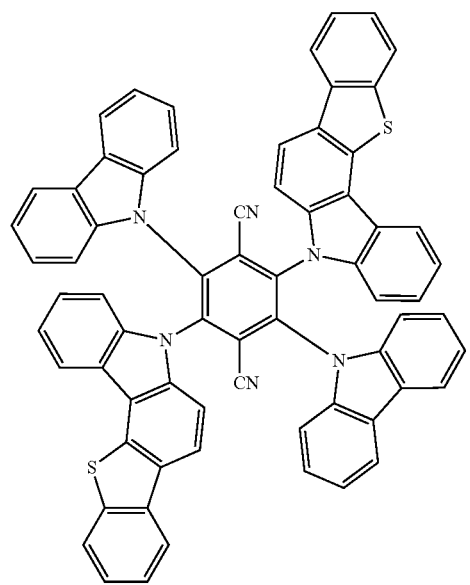
74
-continued
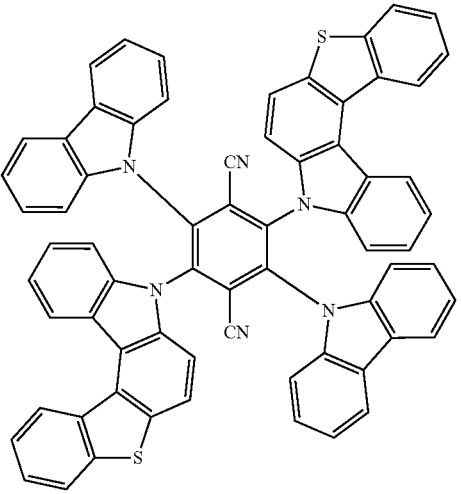
[Formula 30]
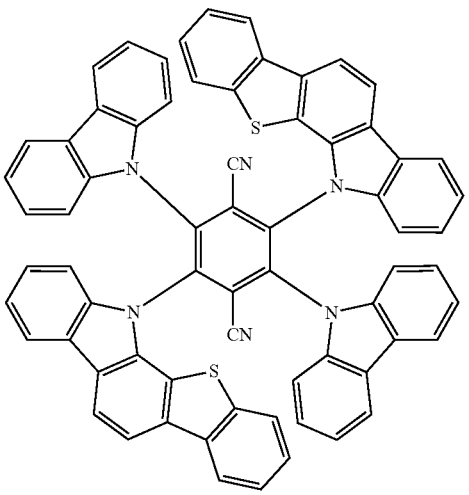
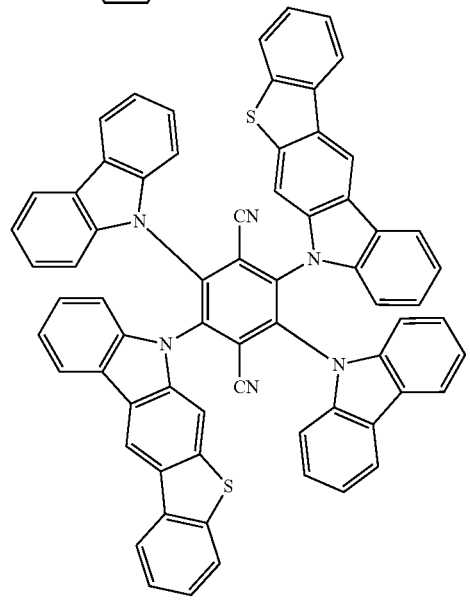
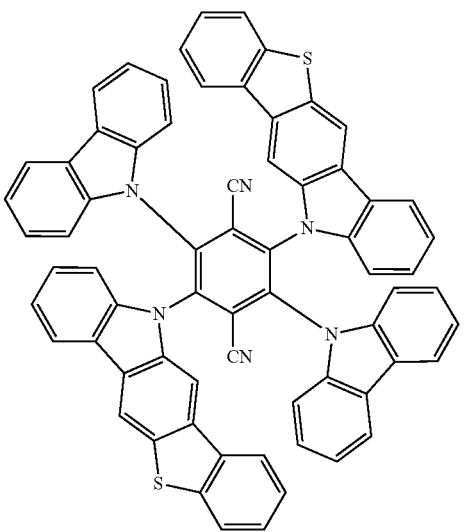

75
-continued
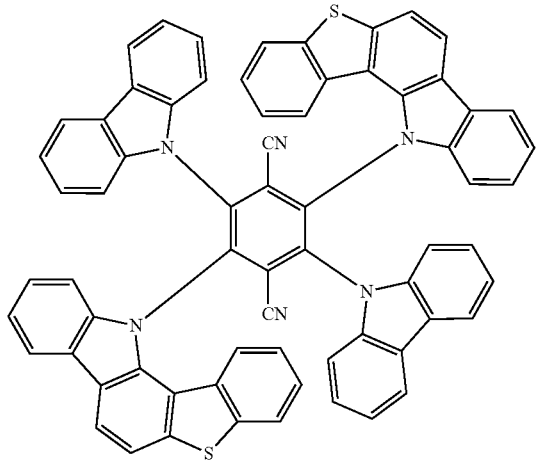
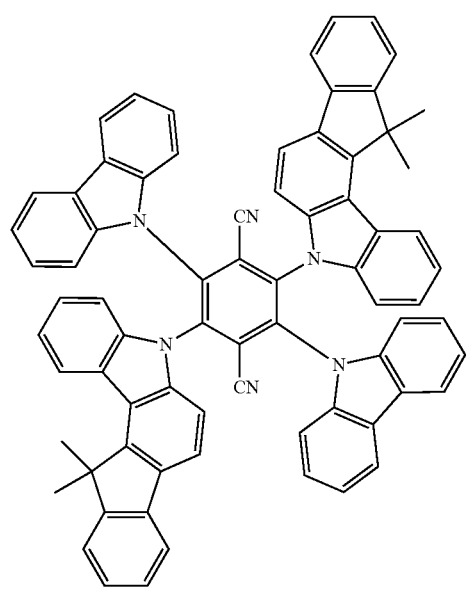
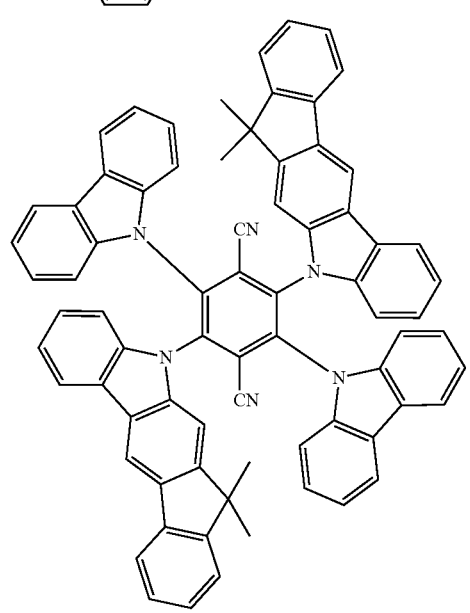
76
-continued
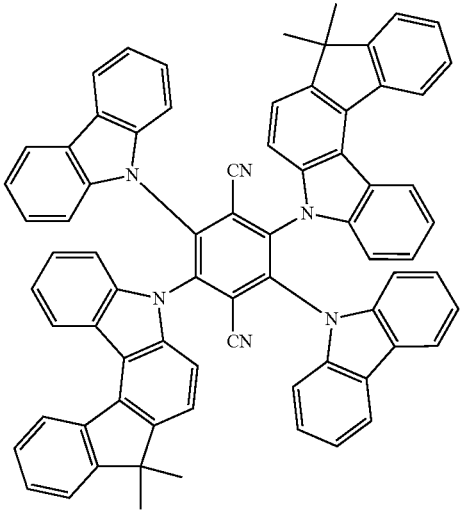
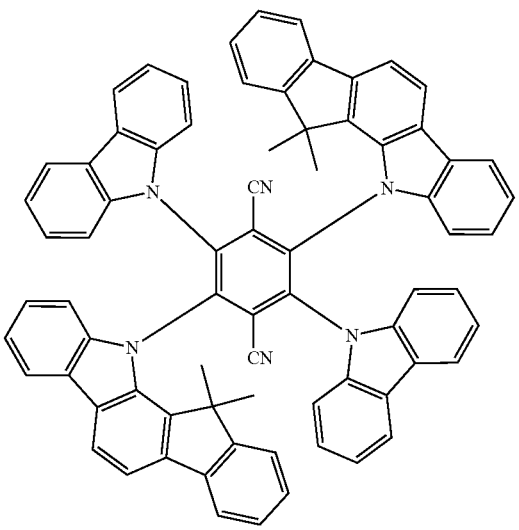
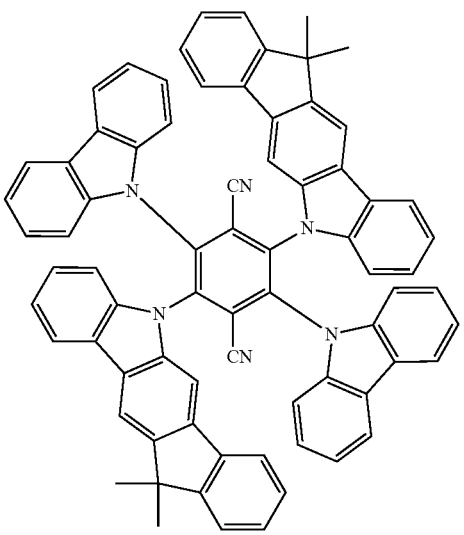

77
-continued
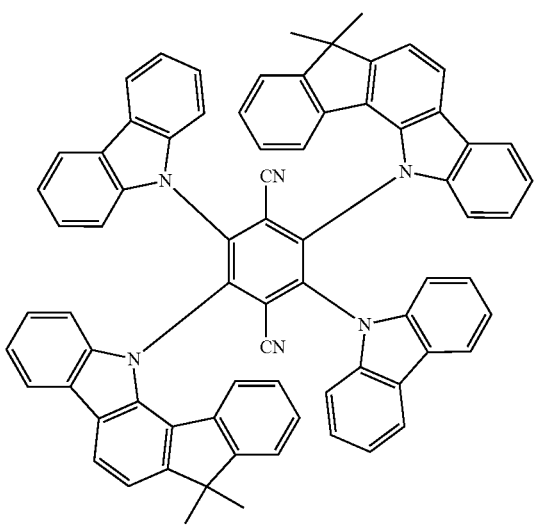
78
-continued
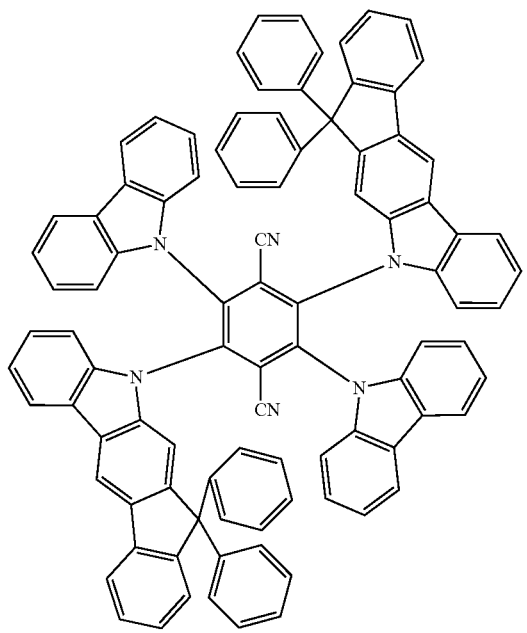
[Formula 31]
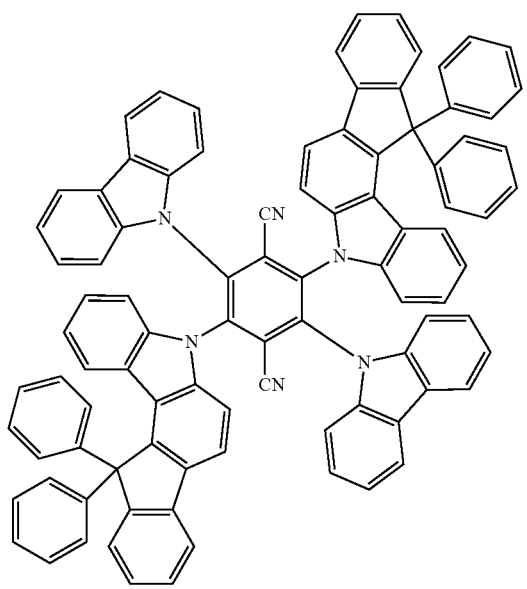
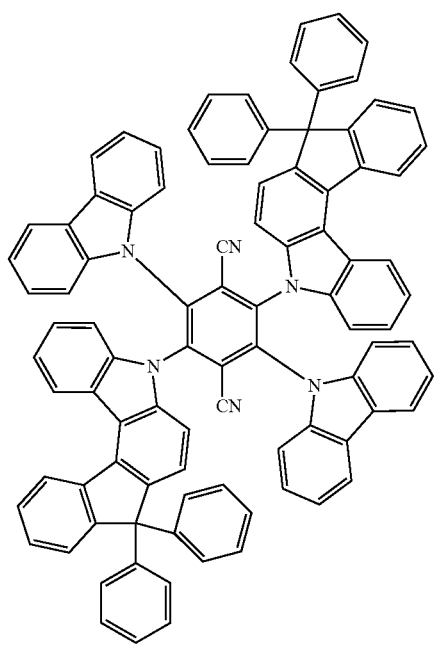

-continued
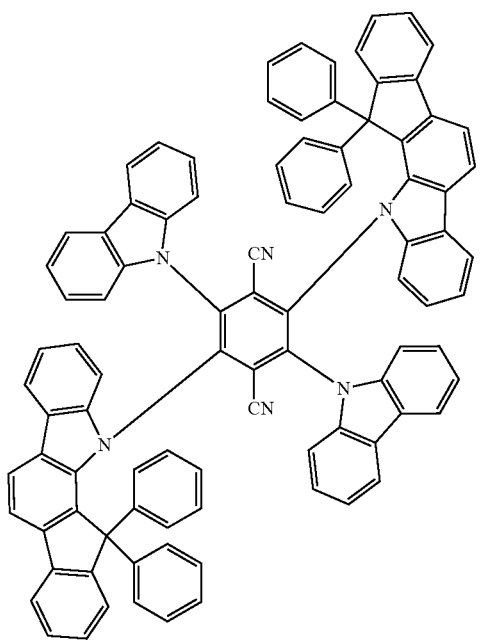
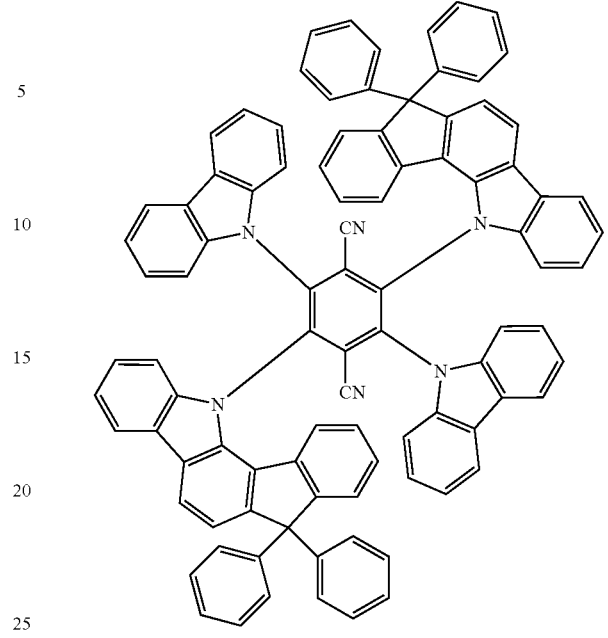
[Formula 32]
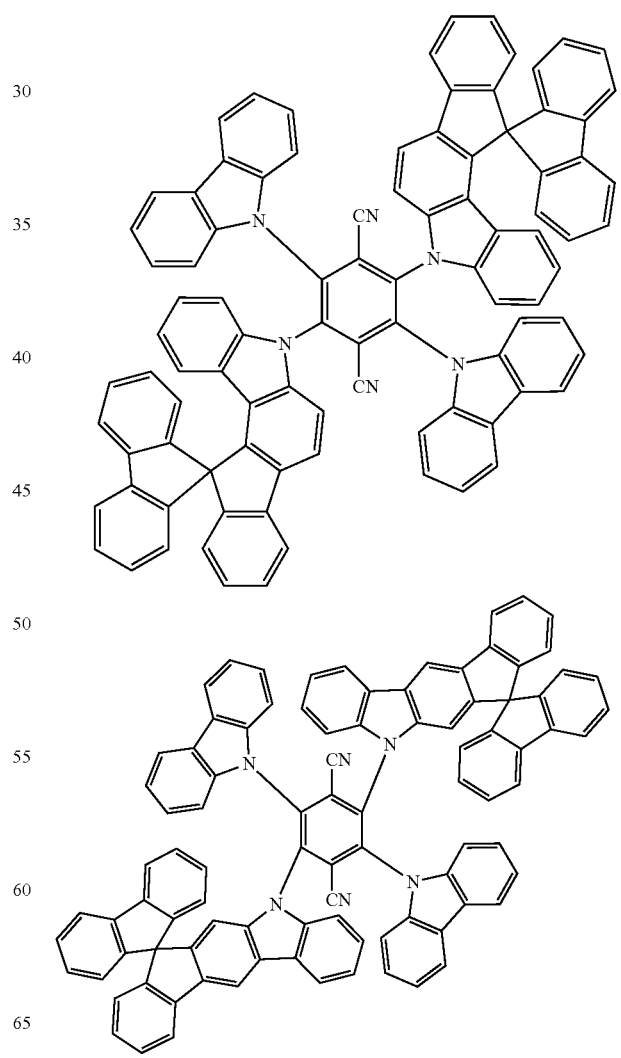
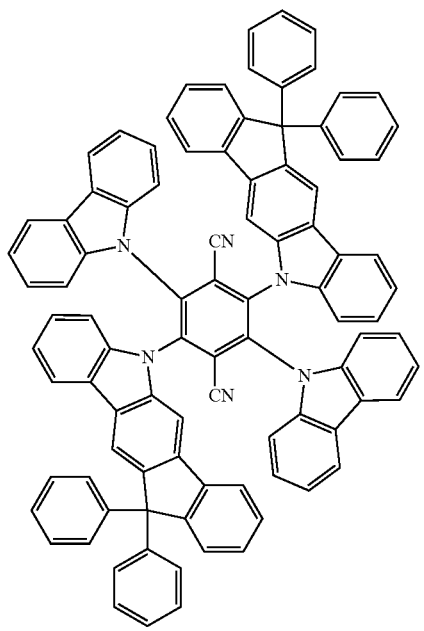

-continued
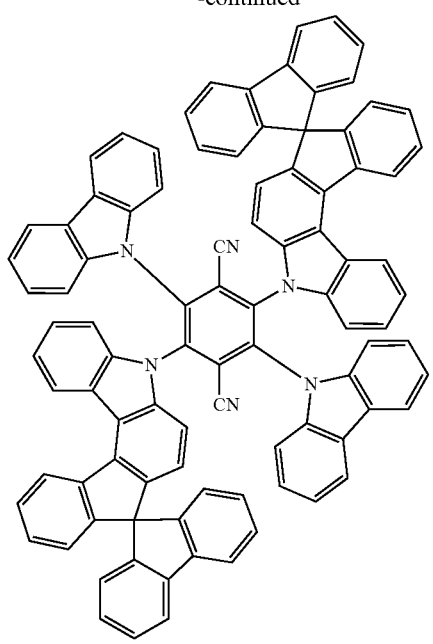
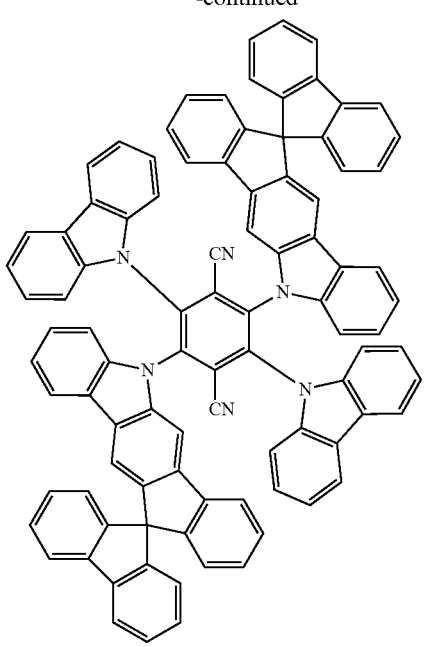
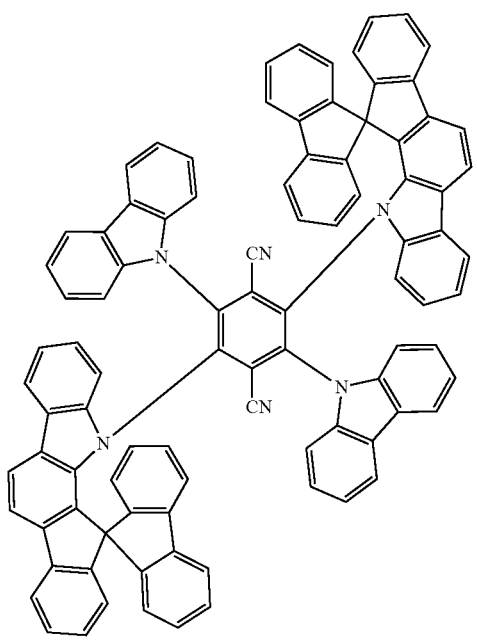
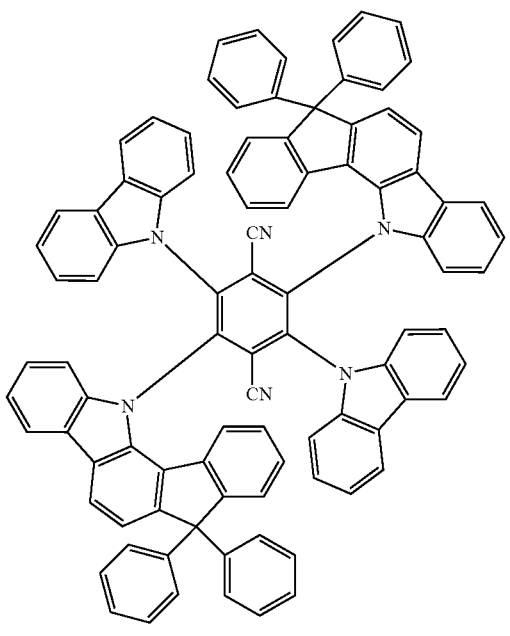

[Formula 33]
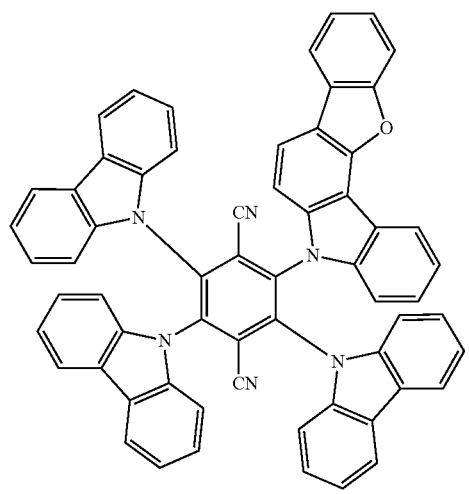
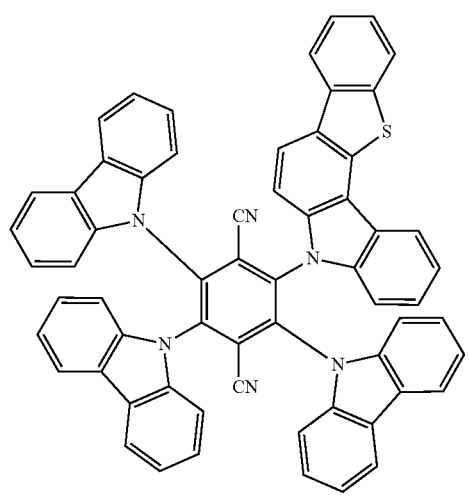
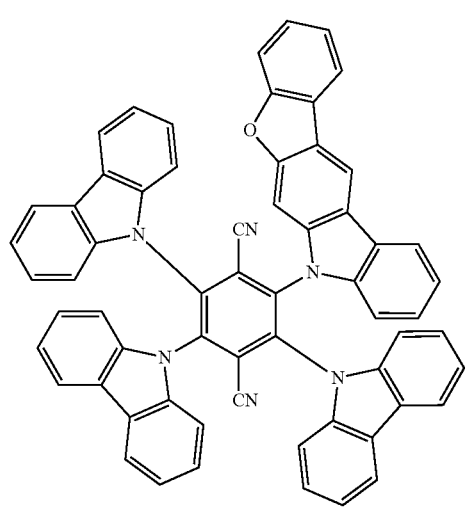
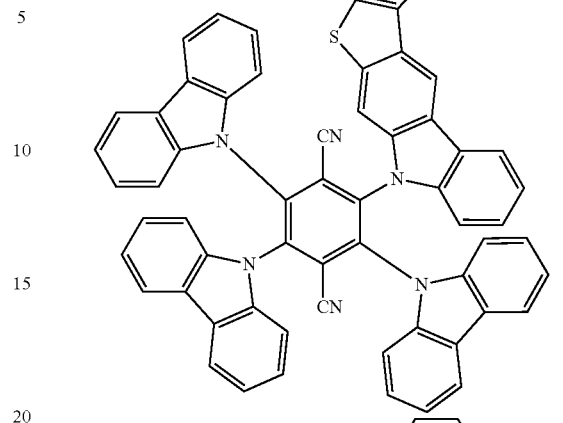
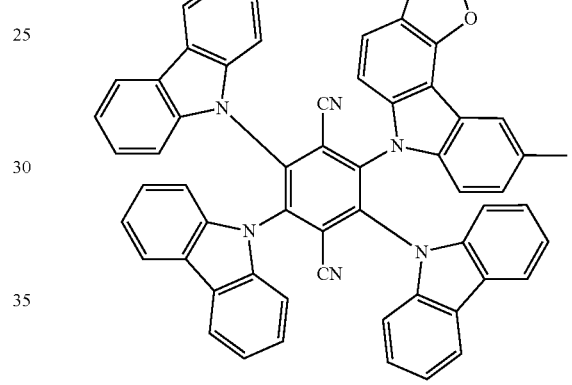
[Formula 34]
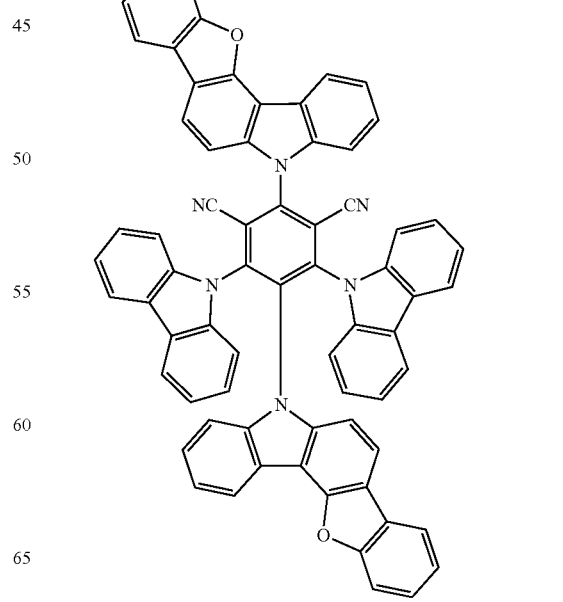

85
-continued
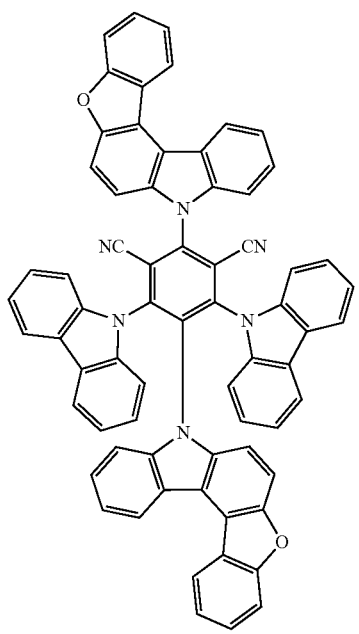
86
-continued
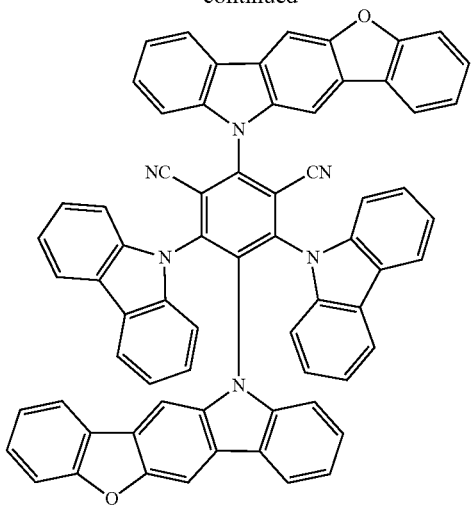
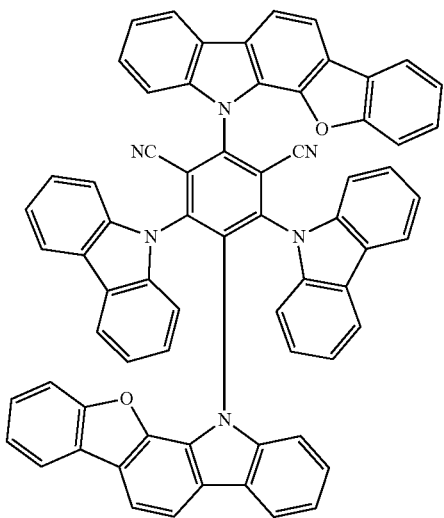
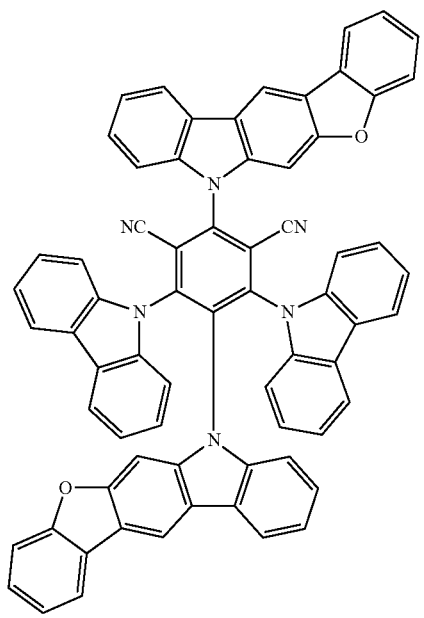

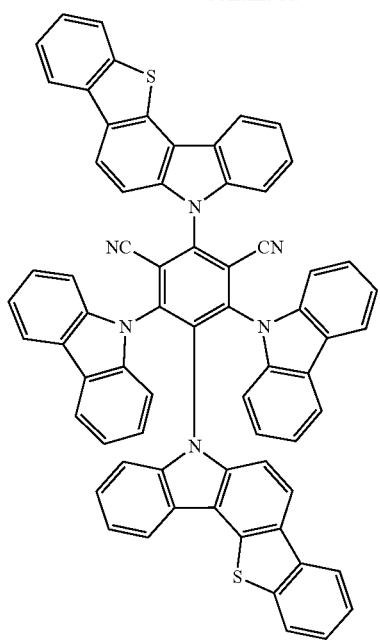
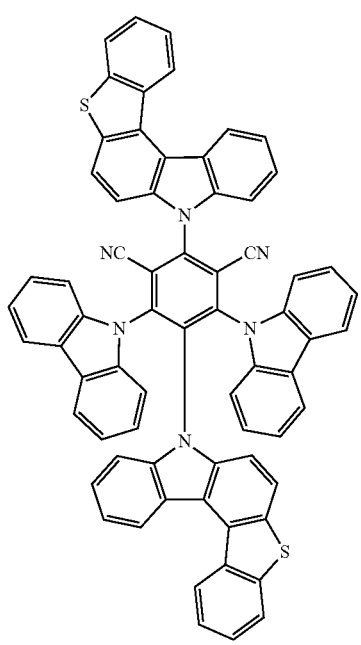
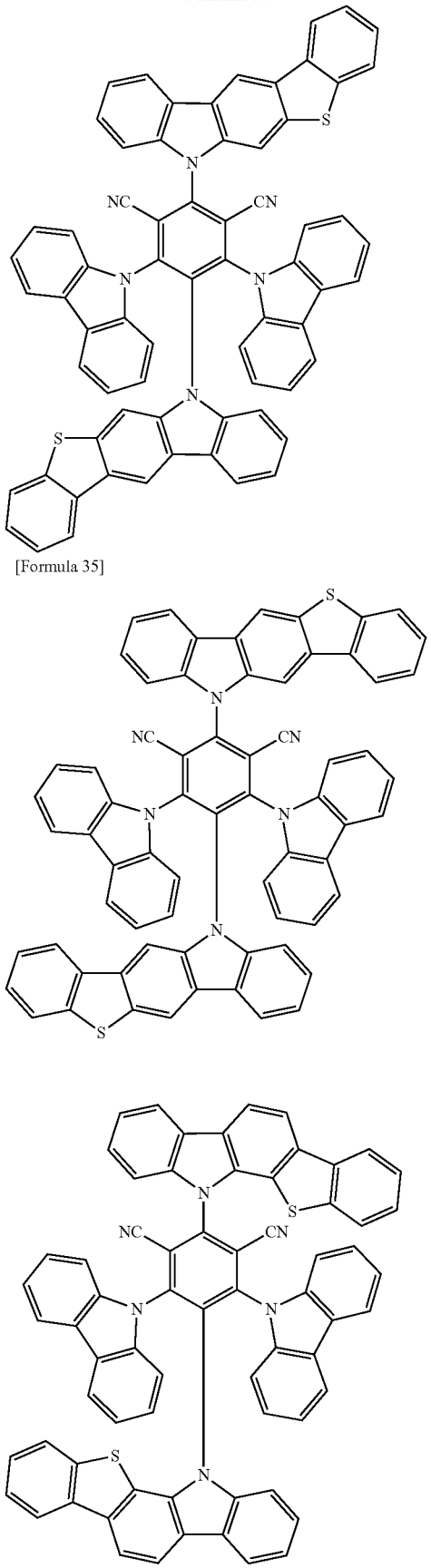
[Formula 35]

89
-continued
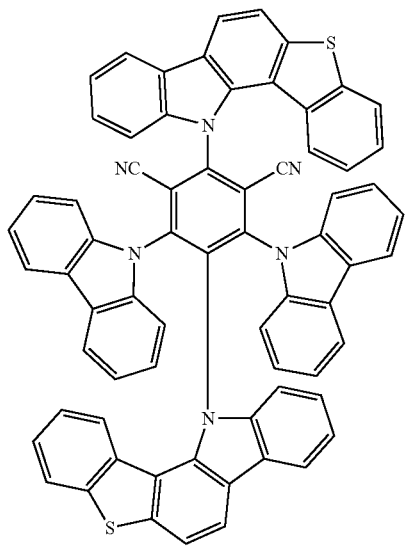
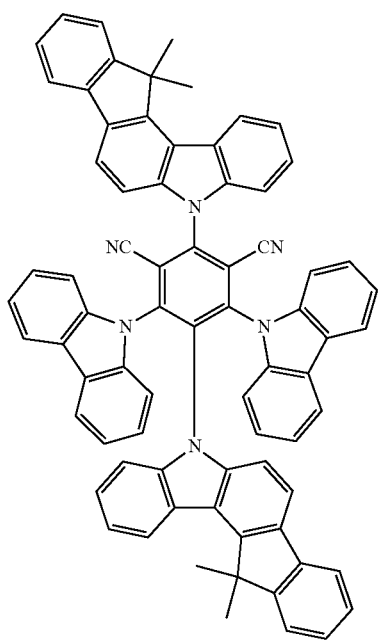
90
-continued
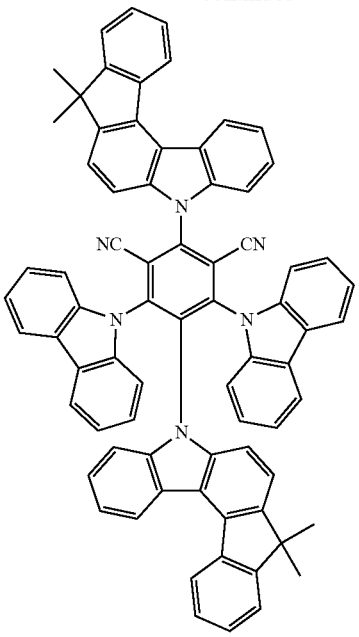
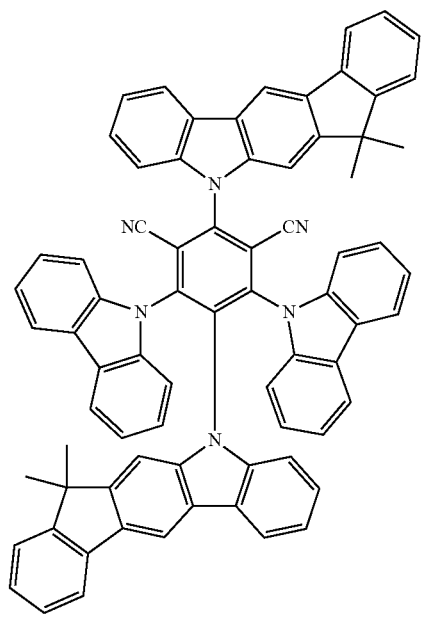

91
-continued
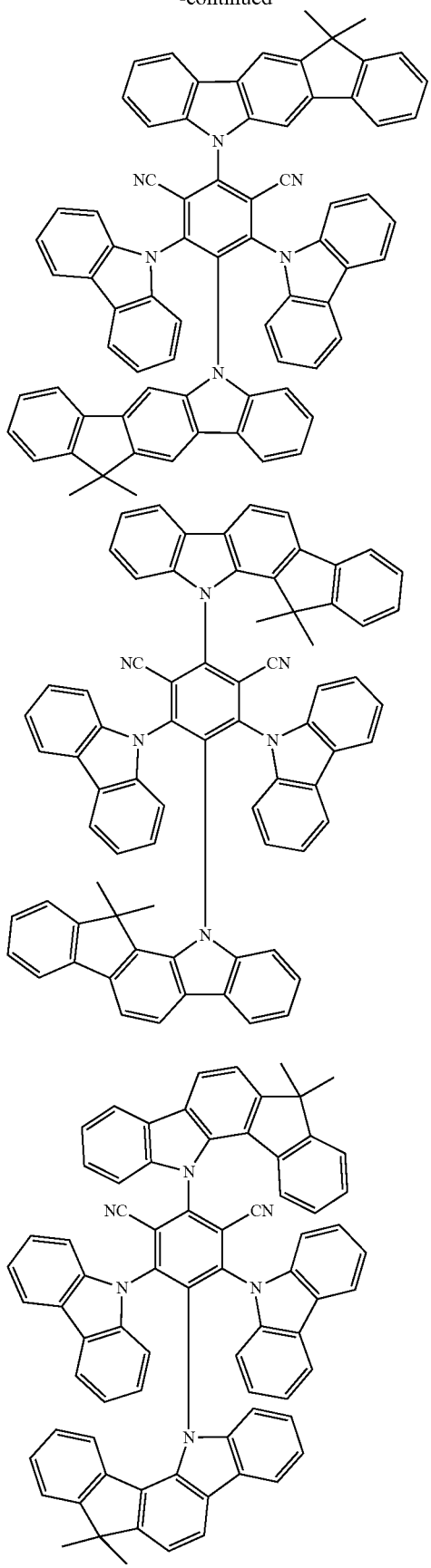
92
-continued
[Formula 36]
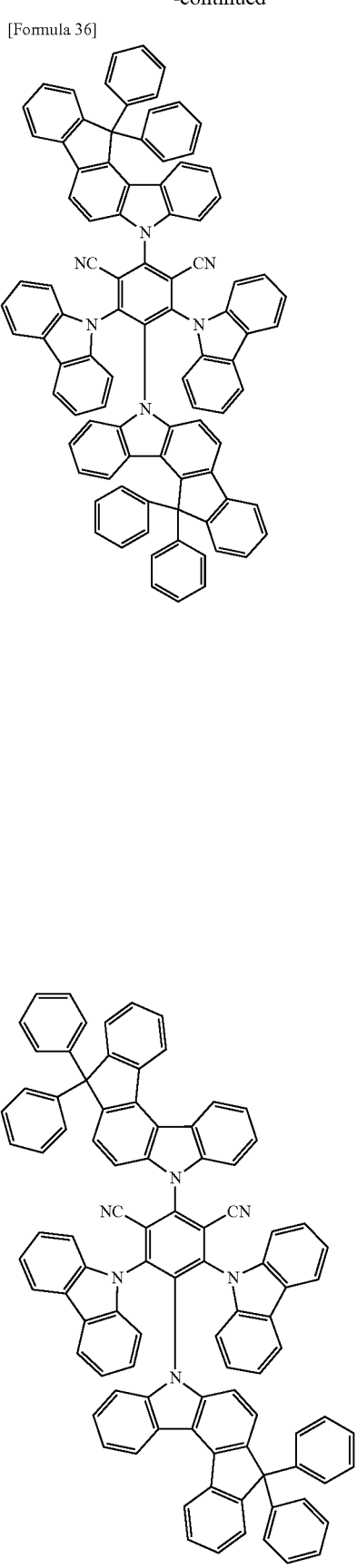

93
-continued
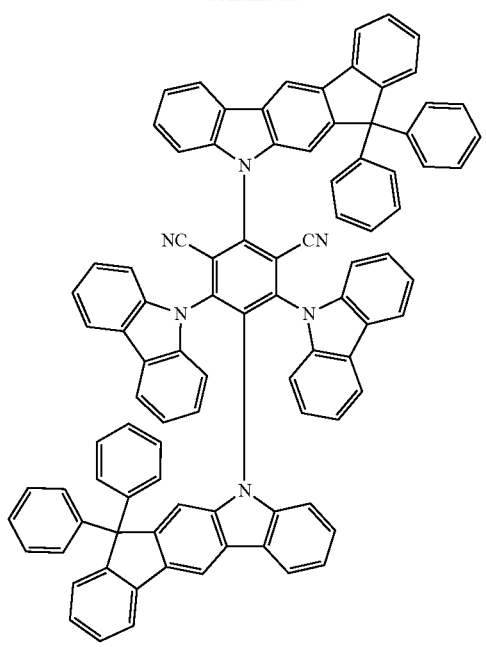
94
-continued
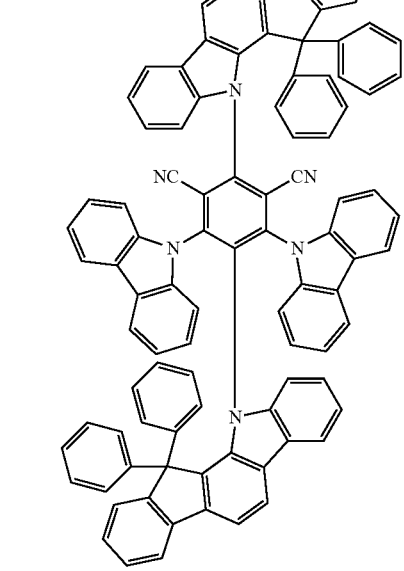
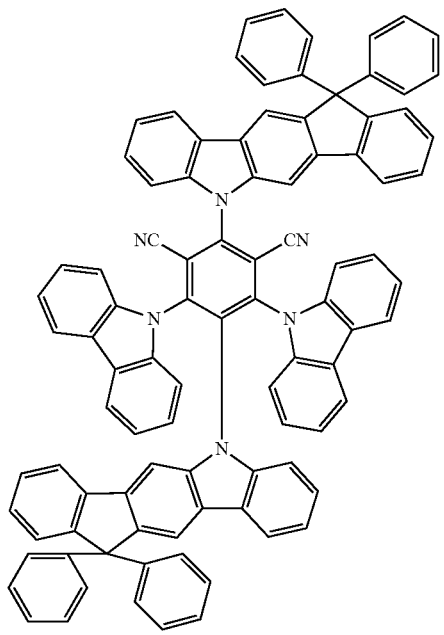
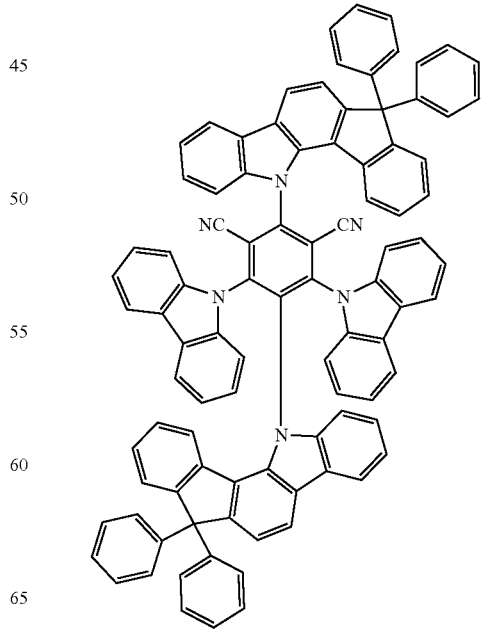

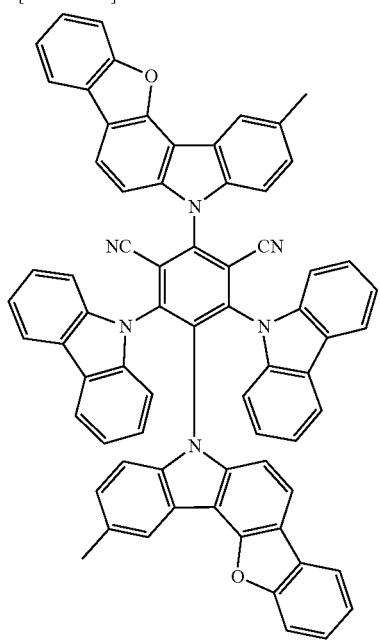
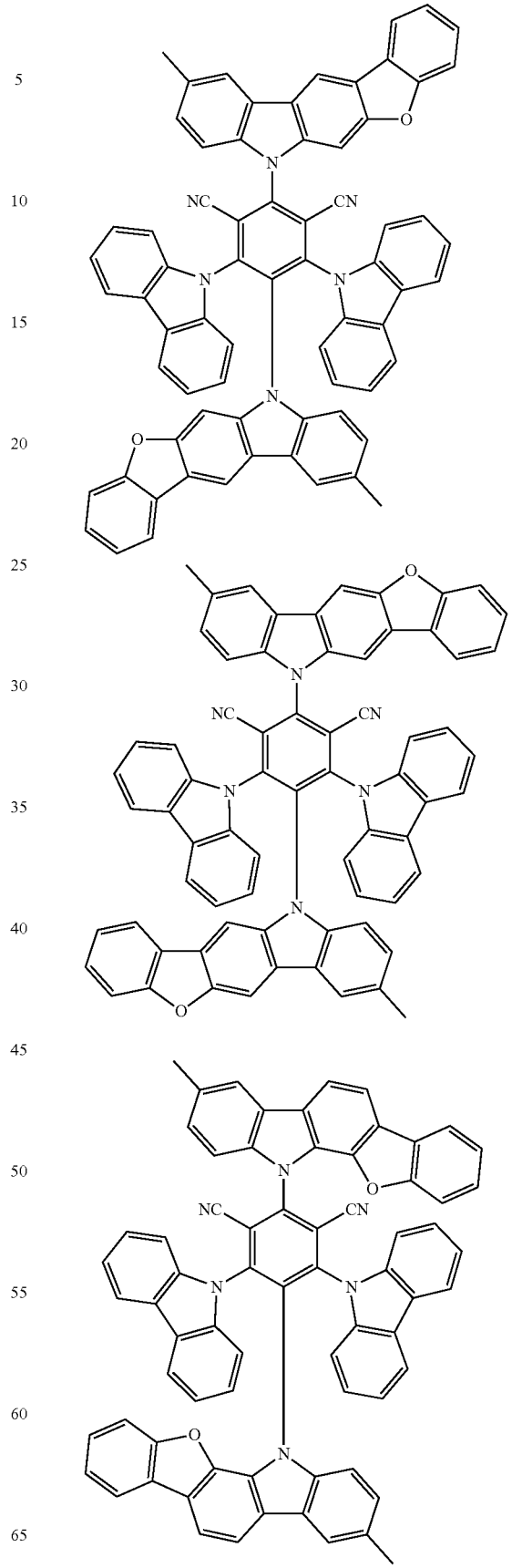
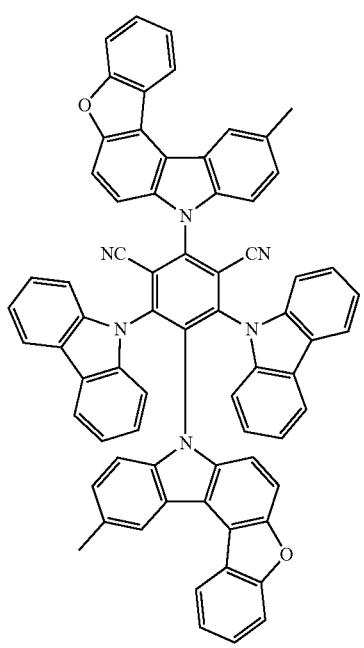

97
-continued
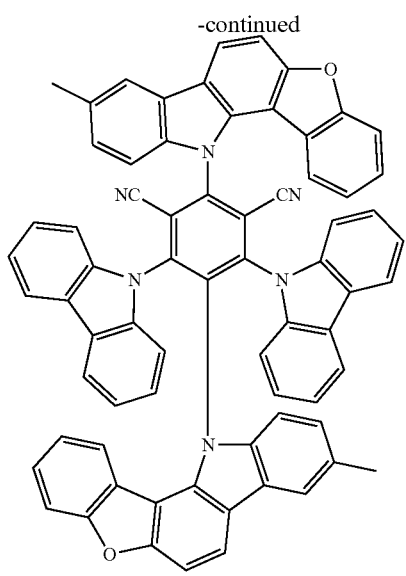
[Formula 38]
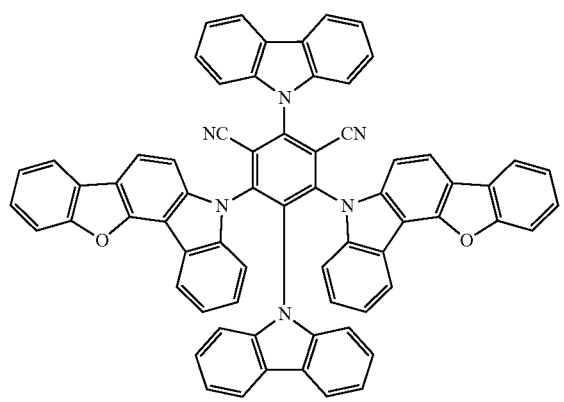
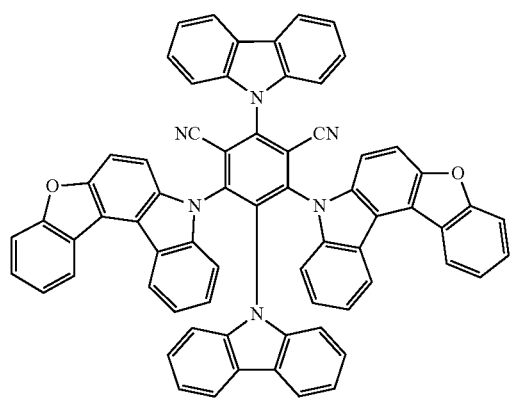
98
-continued
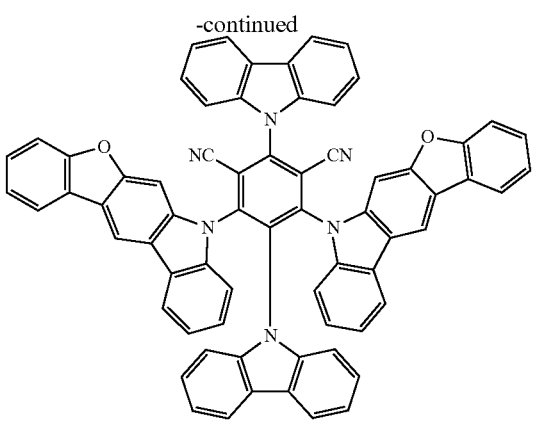
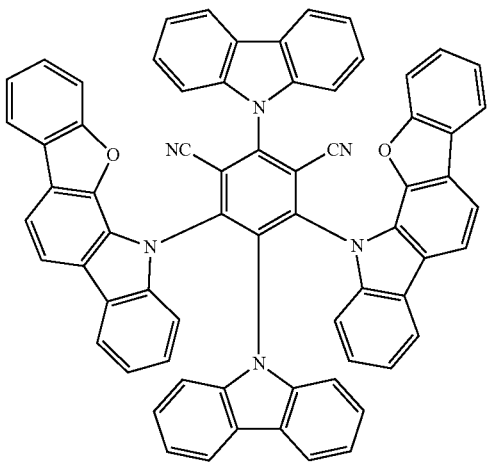

99
-continued
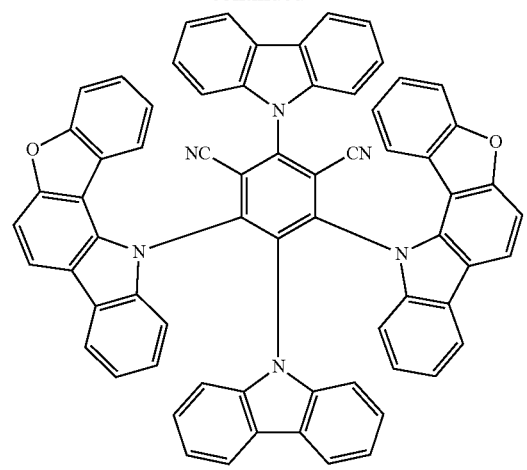
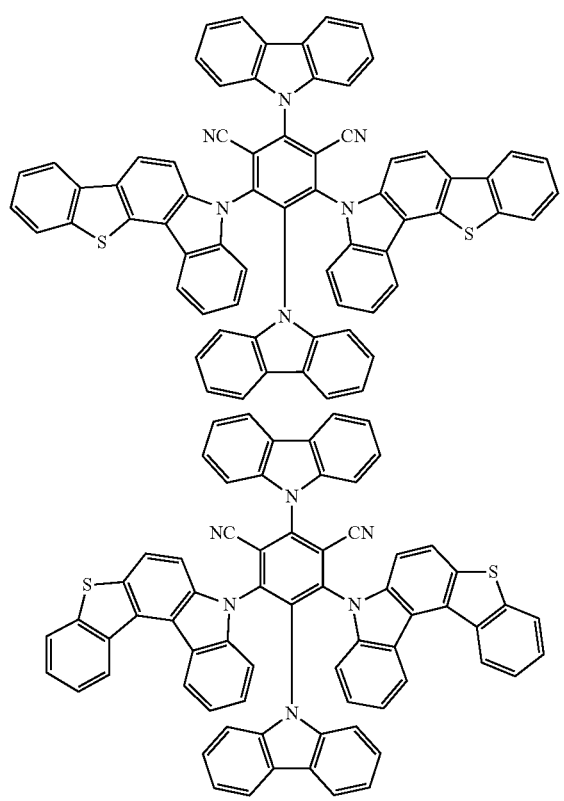
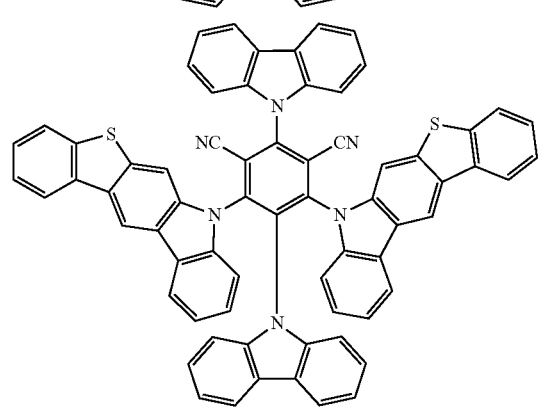
100
-continued
[Formula 39]
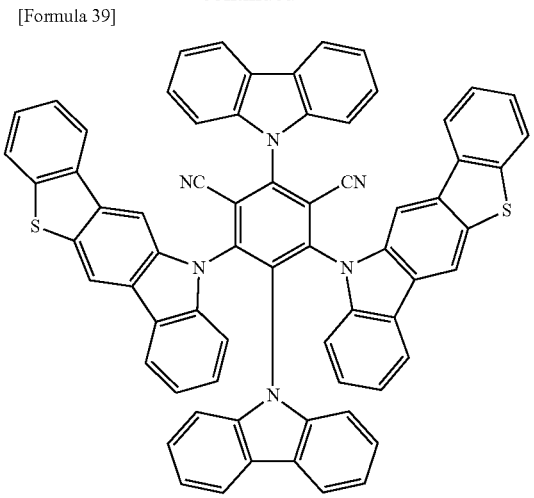
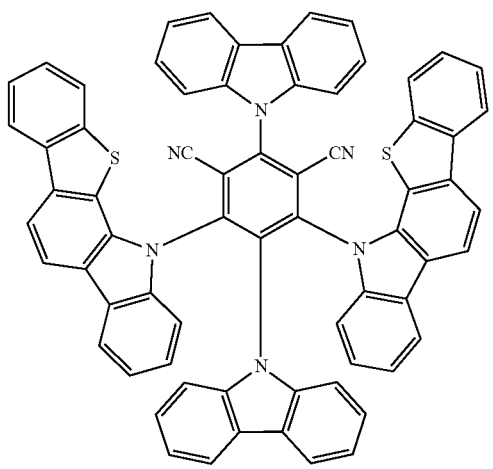
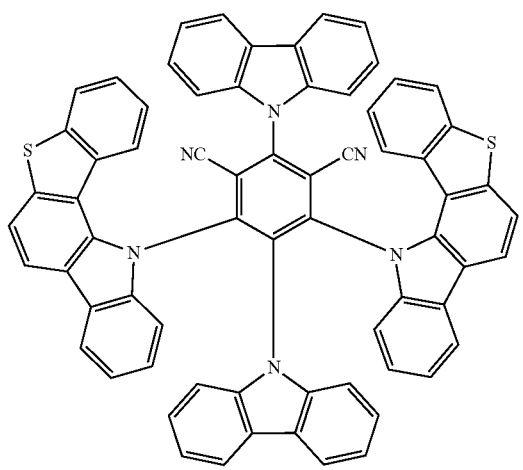

101
-continued
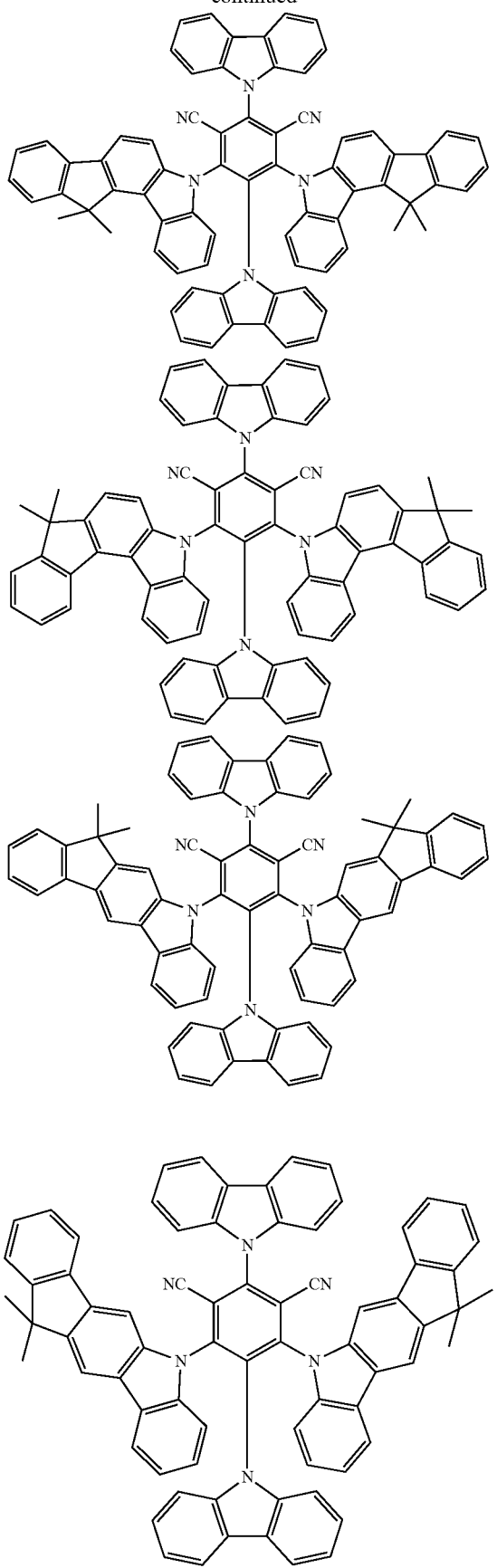
102
-continued
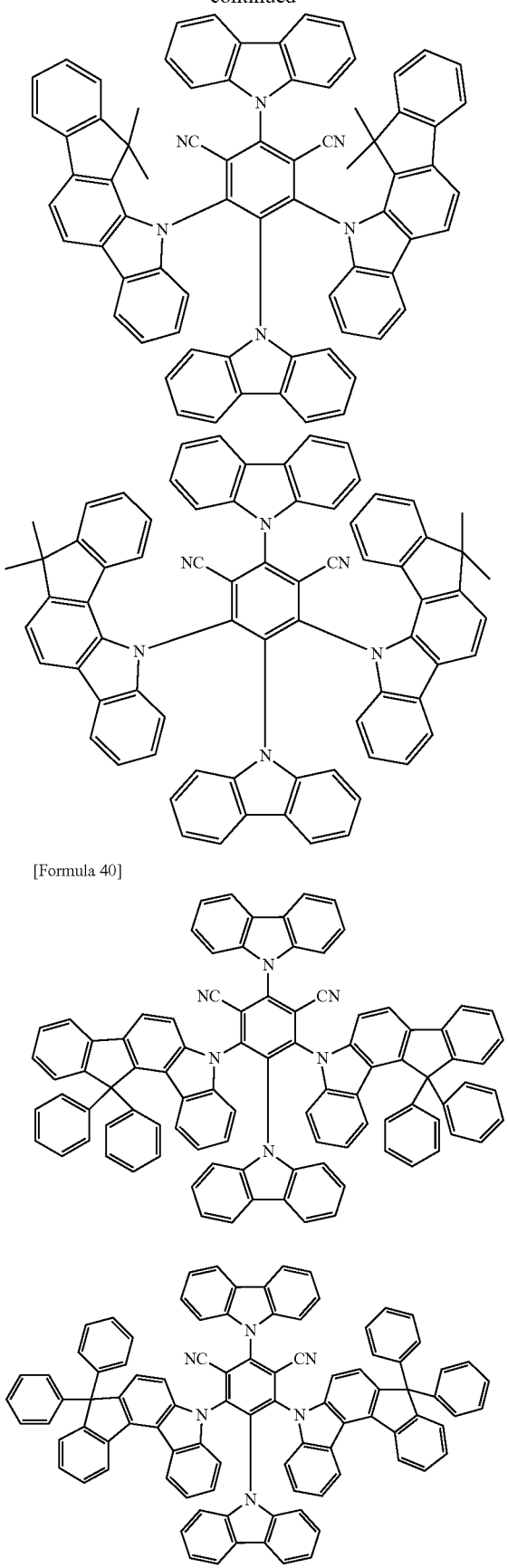
[Formula 40]

103
-continued
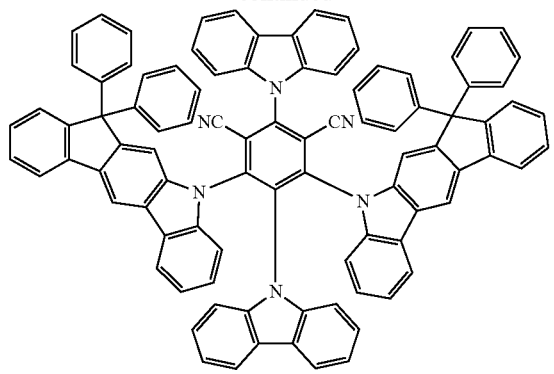
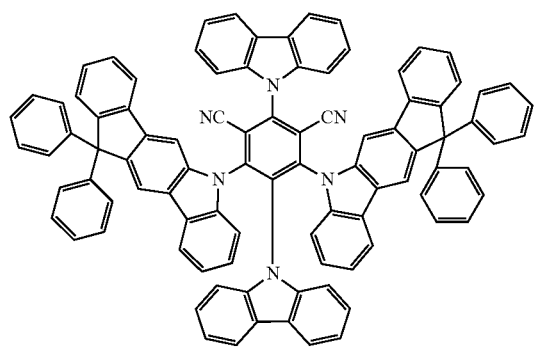
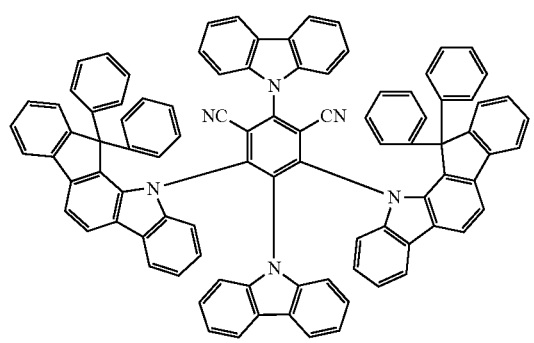
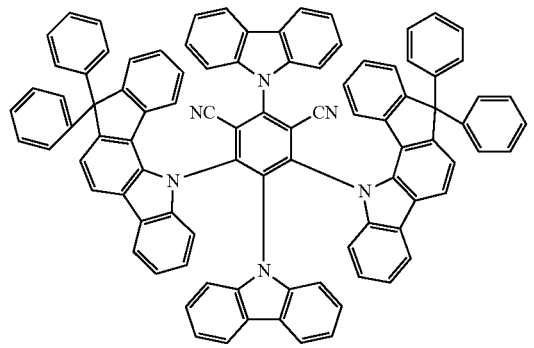
104
-continued
[Formula 41]
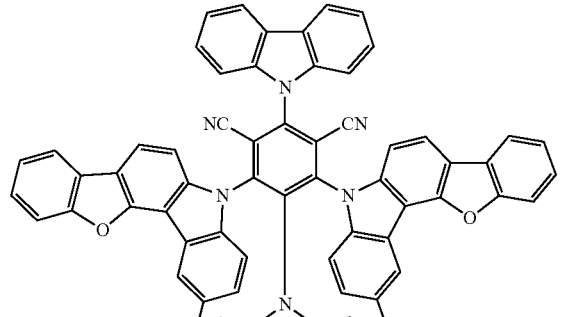
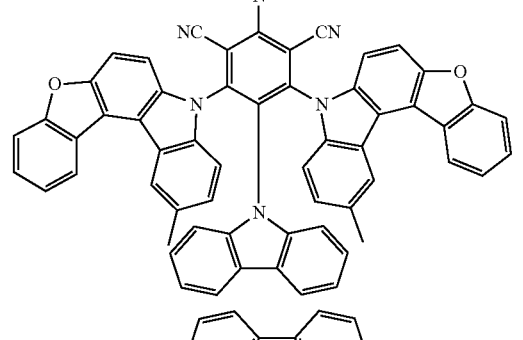
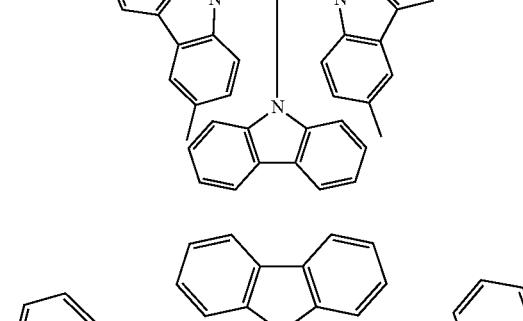
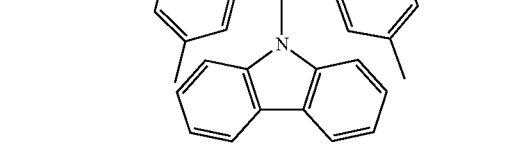

105
-continued
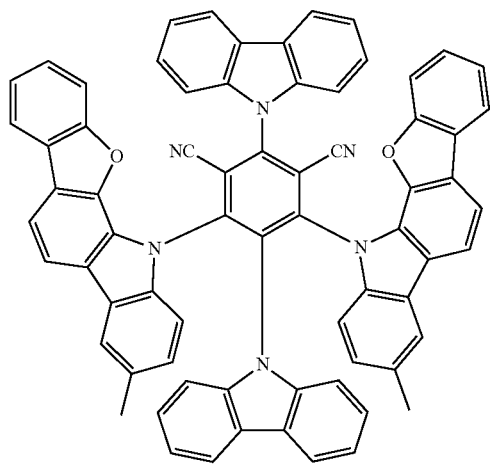
106
-continued
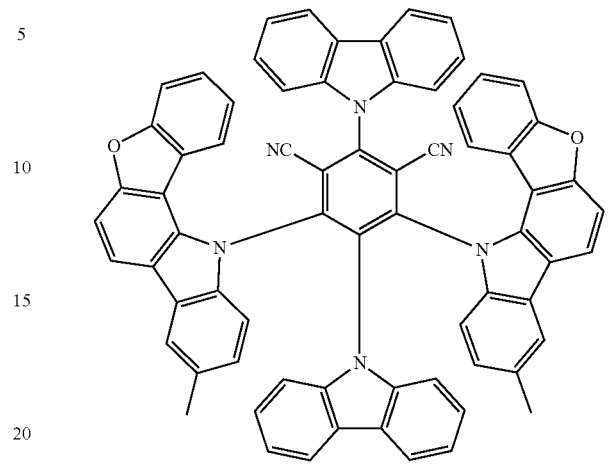
[Formula 42]
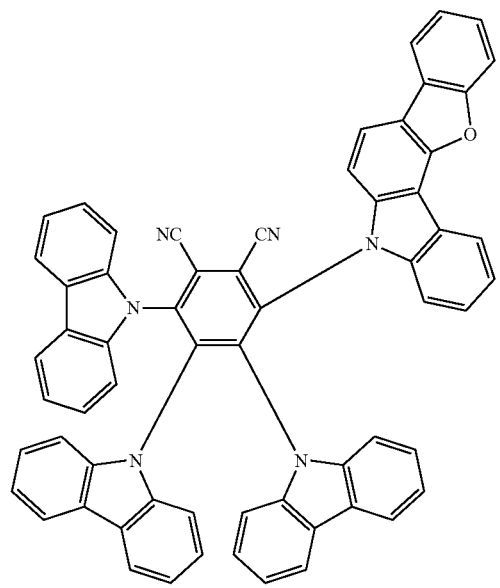
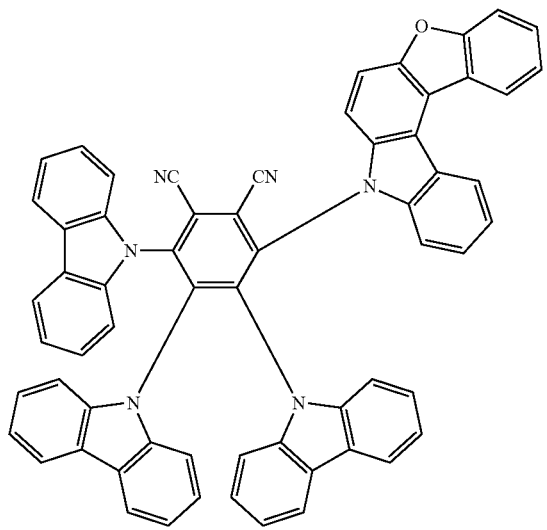

-continued
107
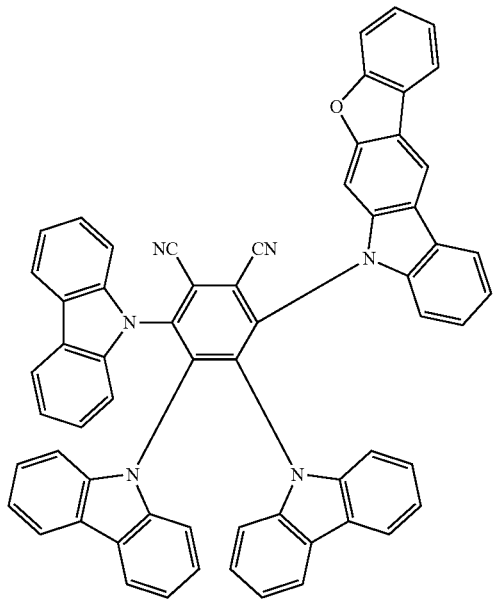
108
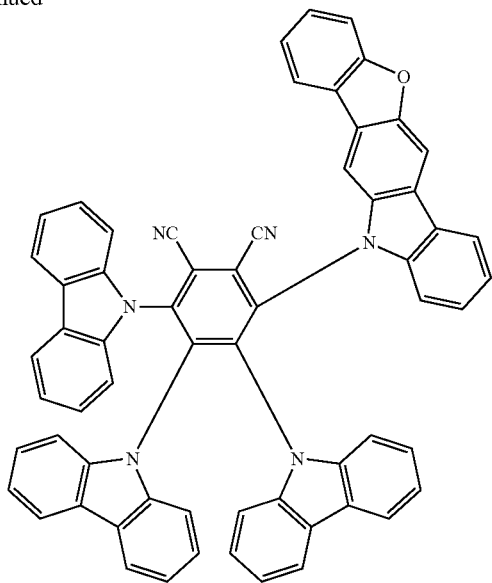
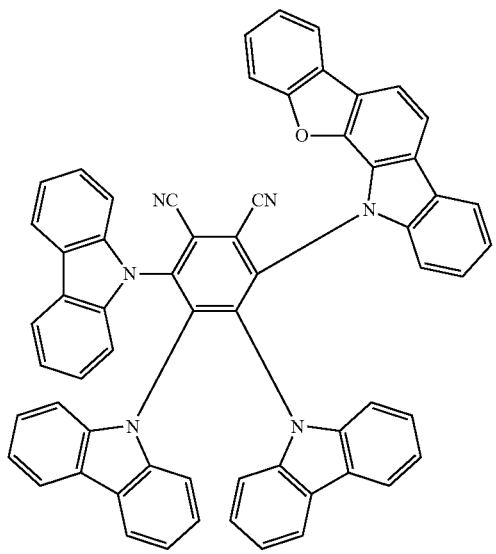
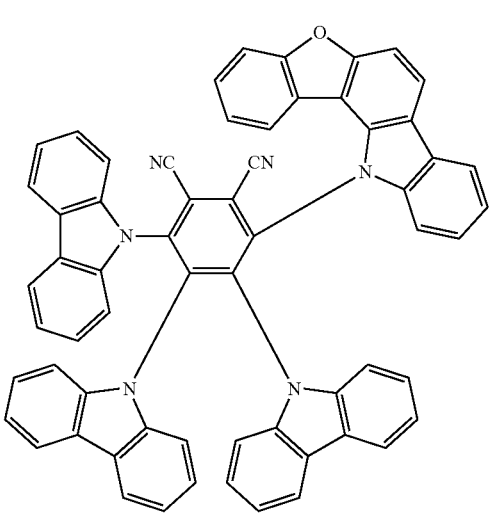

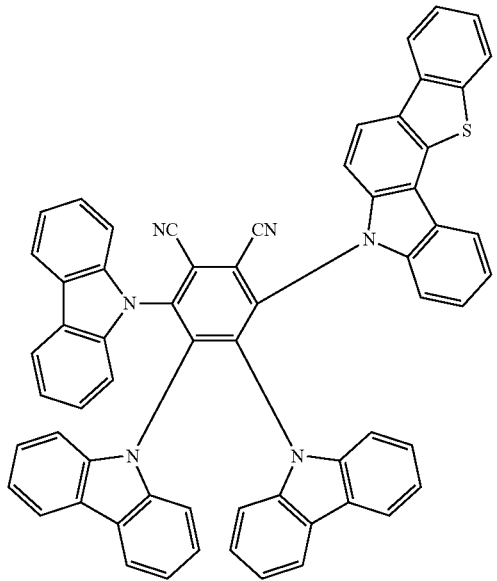
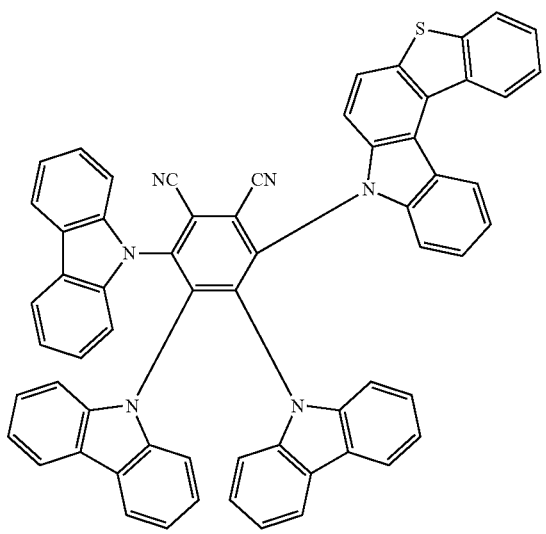
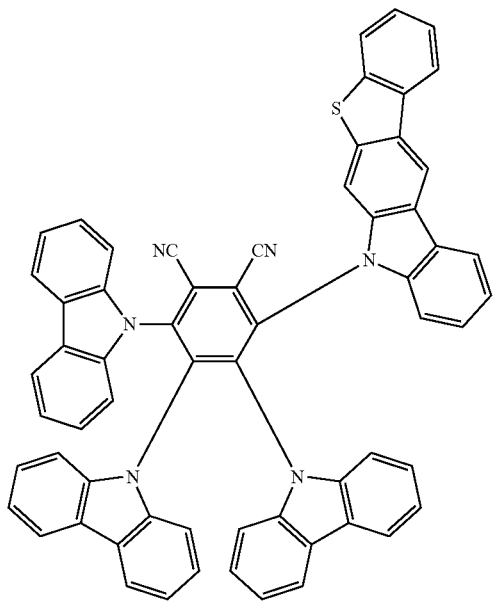

[Formula 43]
111
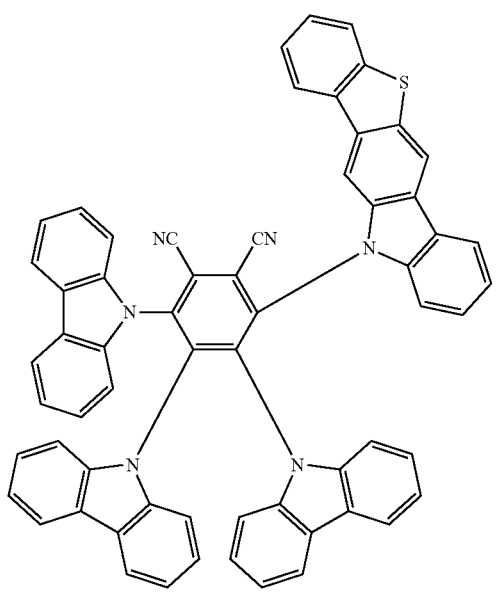
112
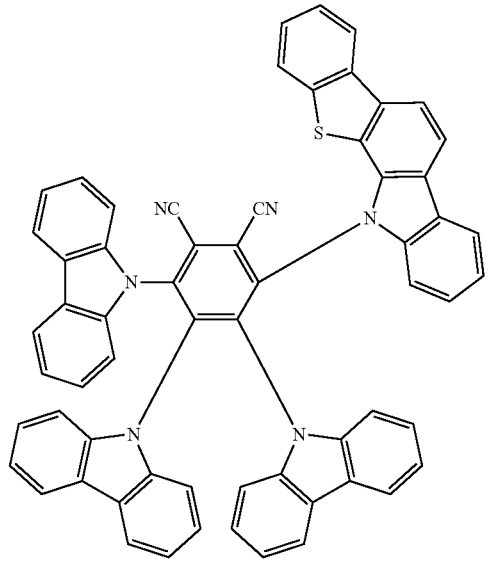
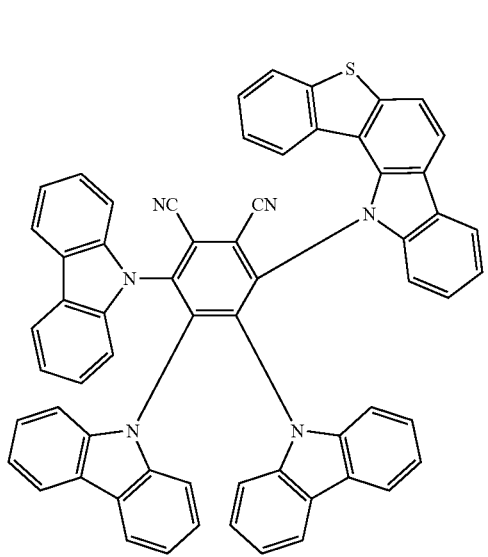
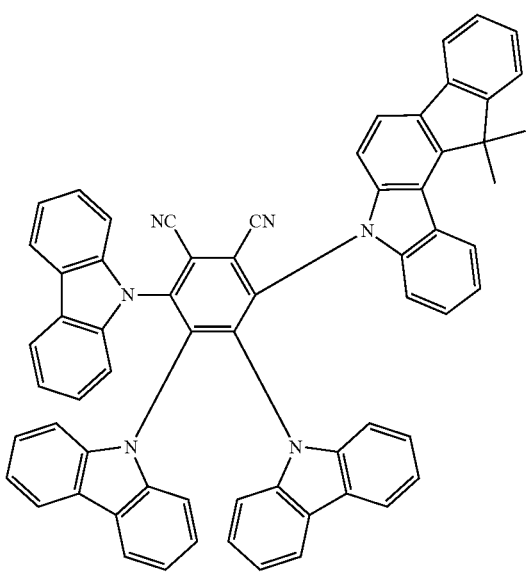

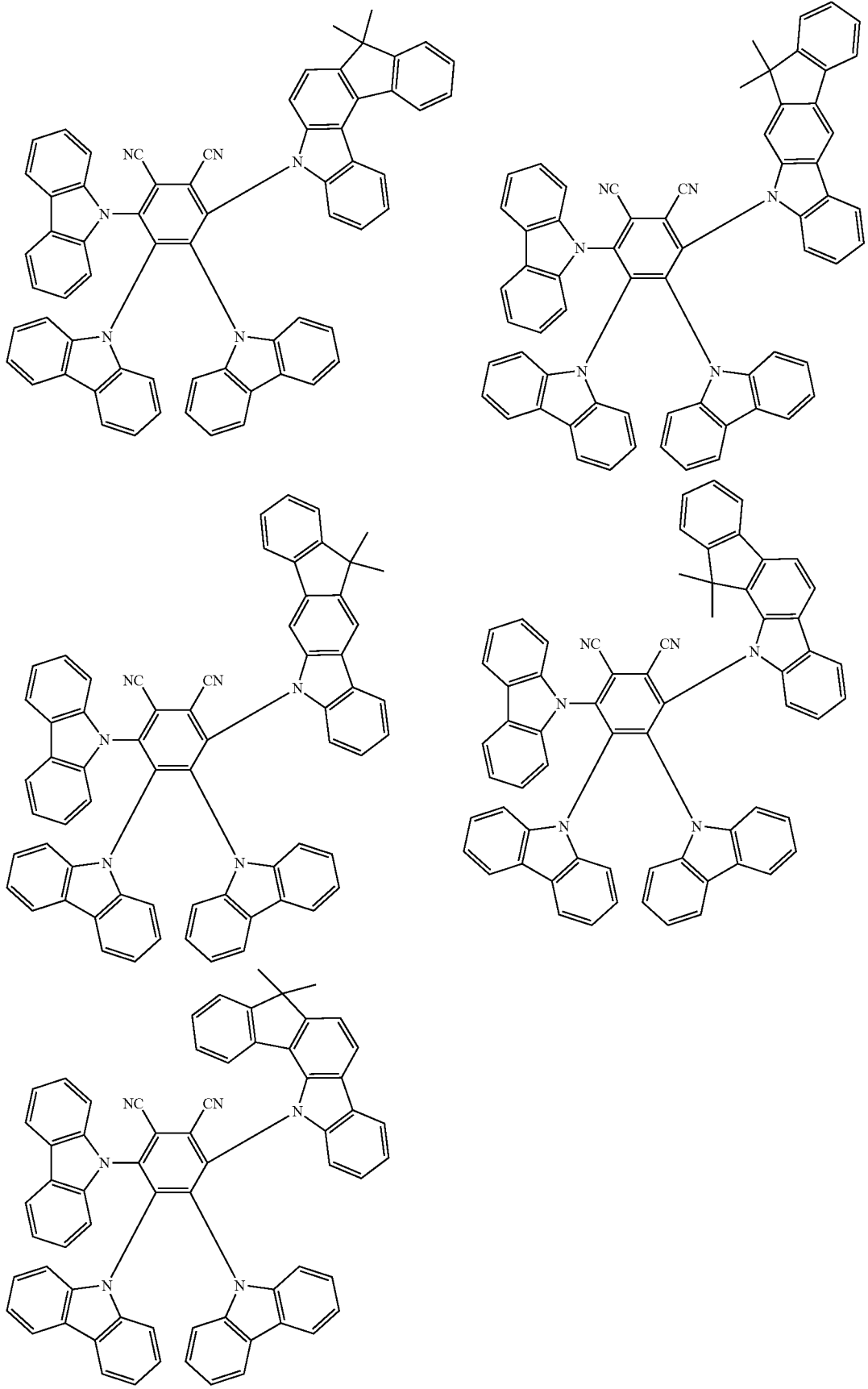

[Formula 44]
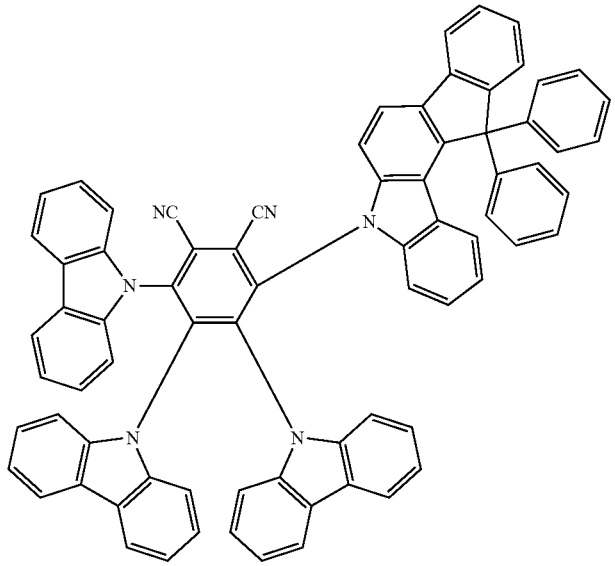
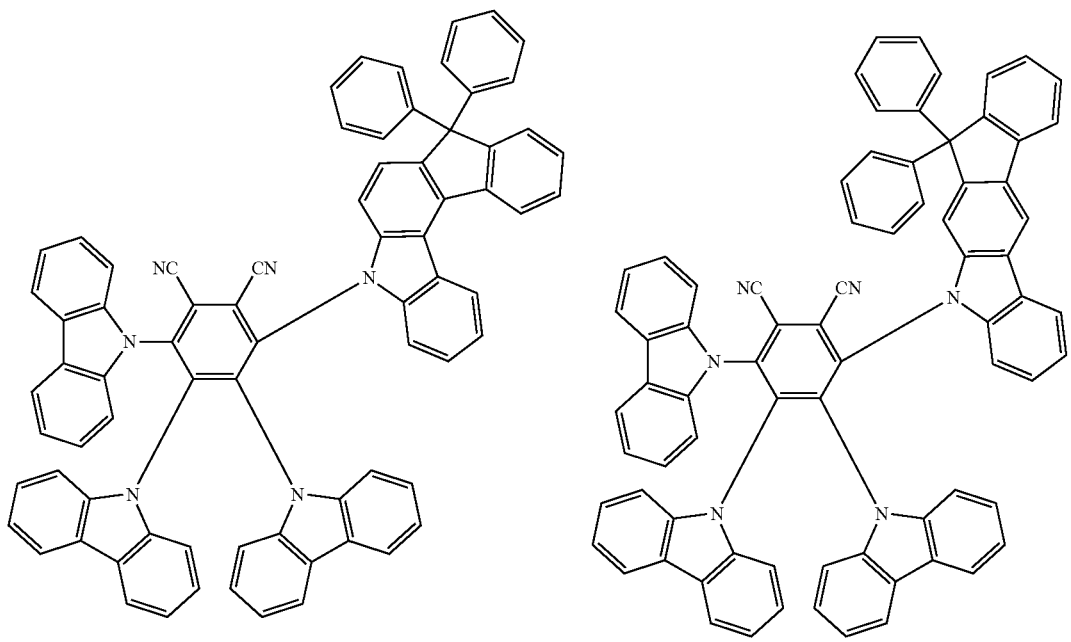

117 118
-continued
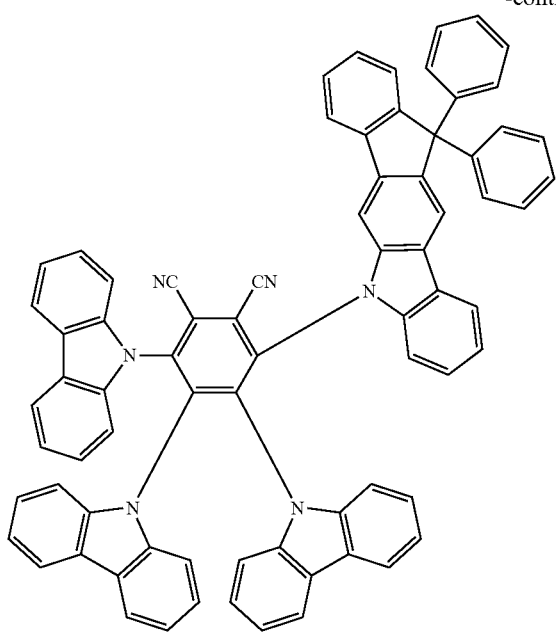
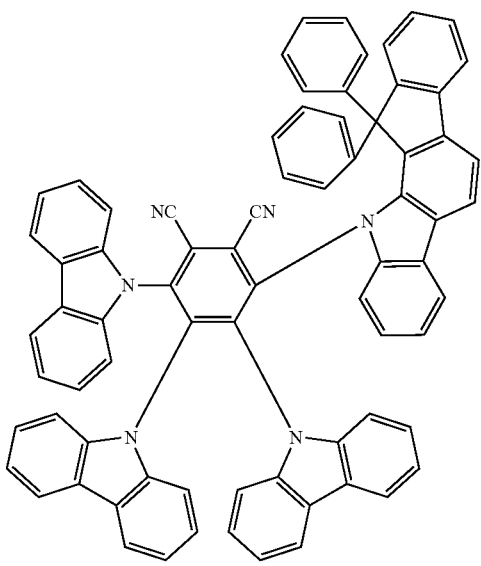
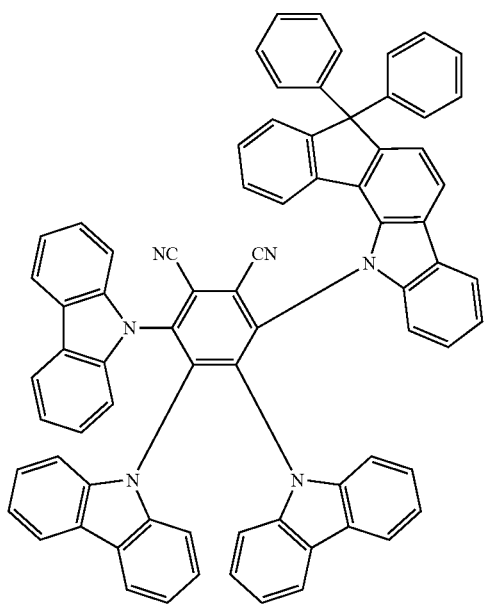

[Formula 45]
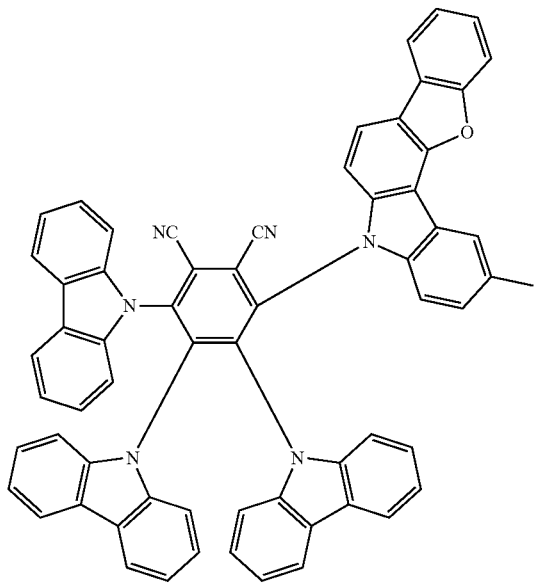
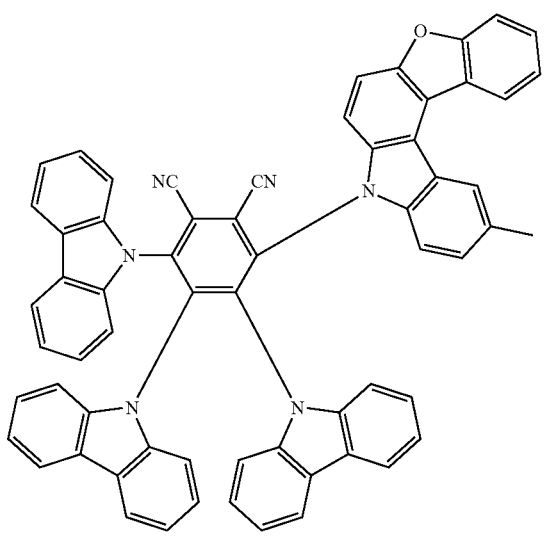
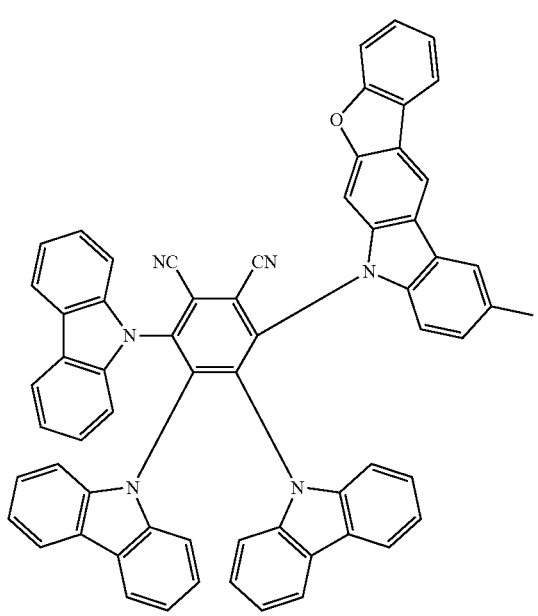
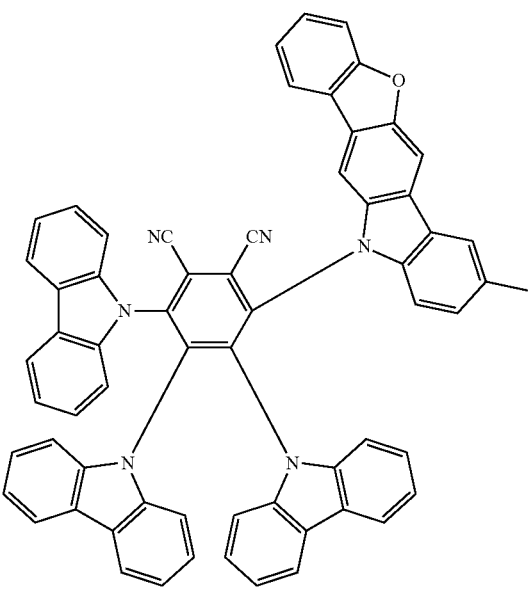

121 122
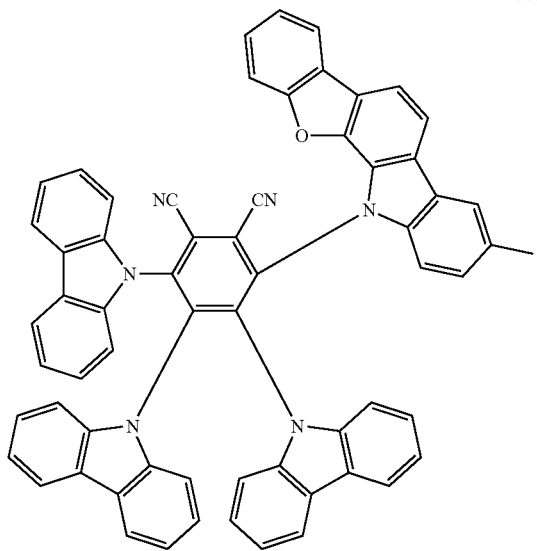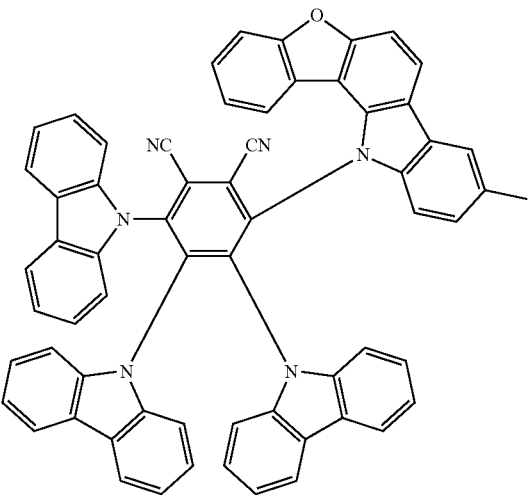
[Formula 46]
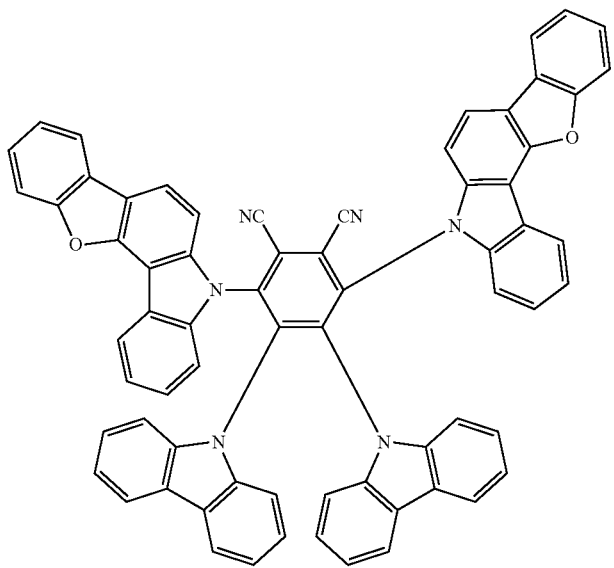
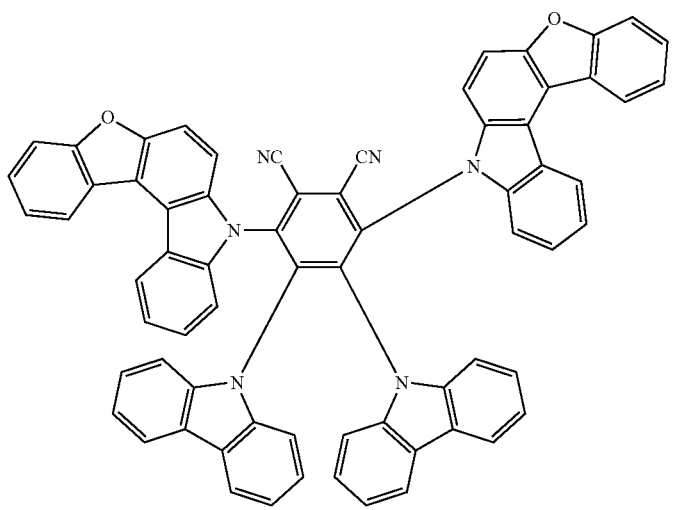

-continued
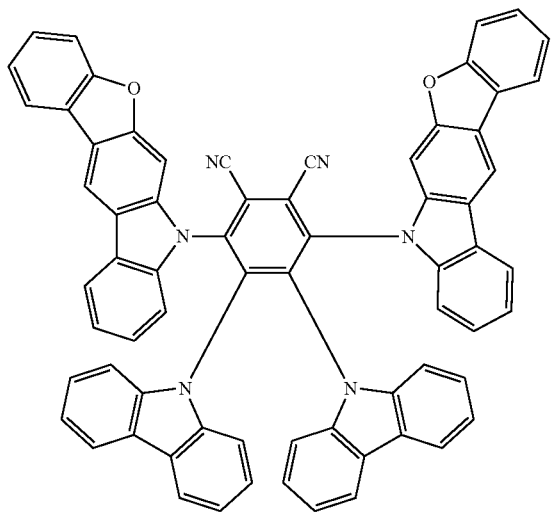
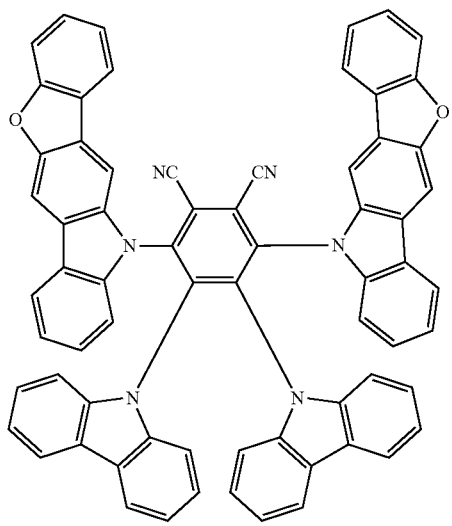
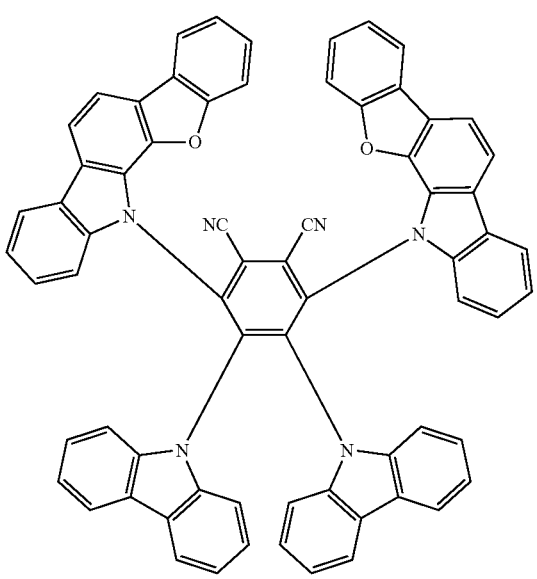
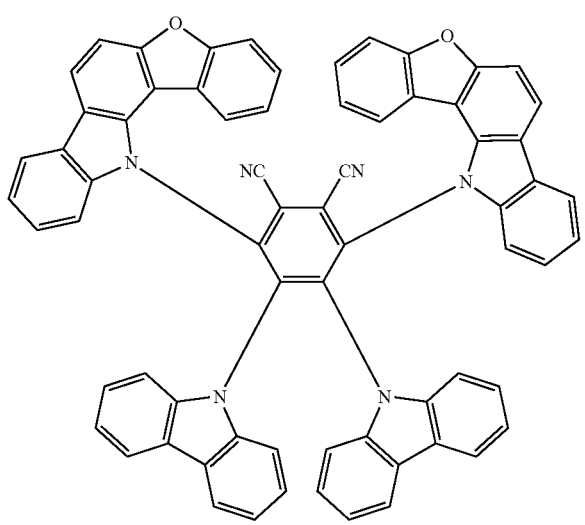

-continued
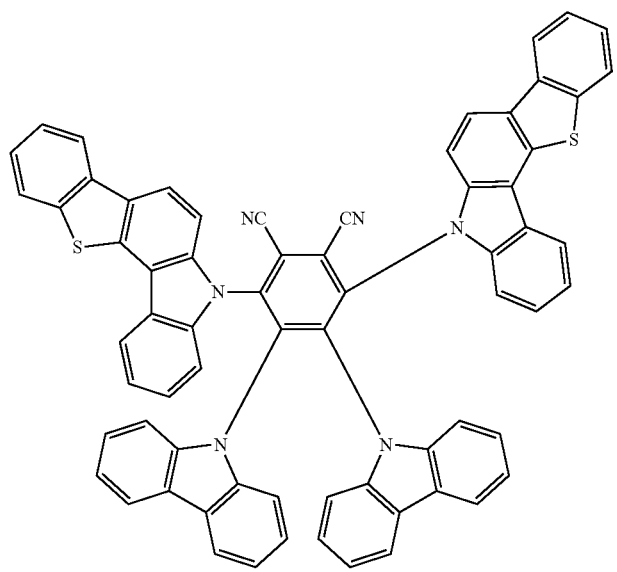
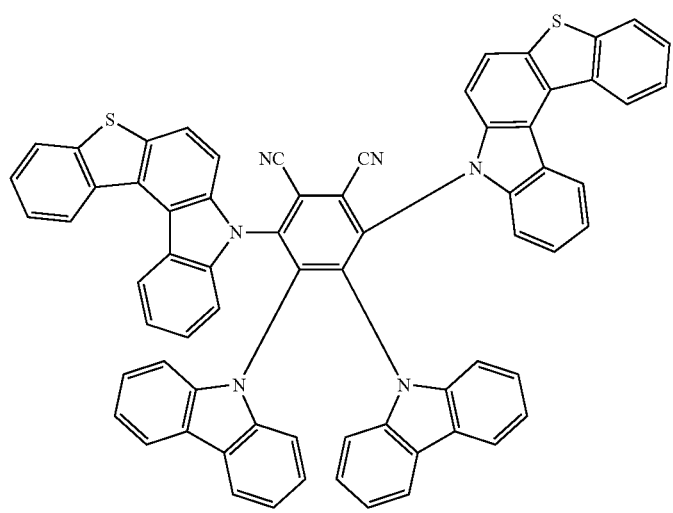
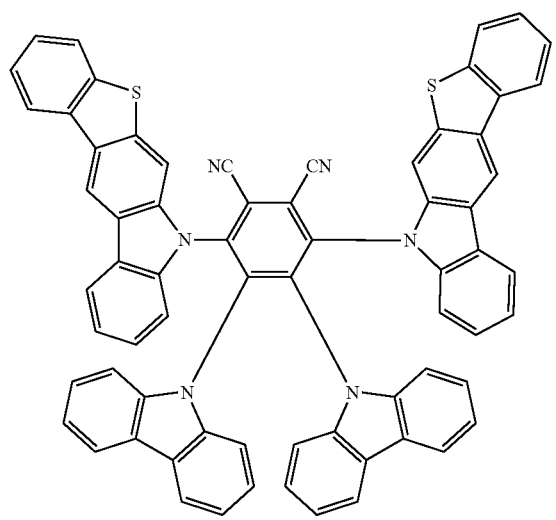

[Formula 47]
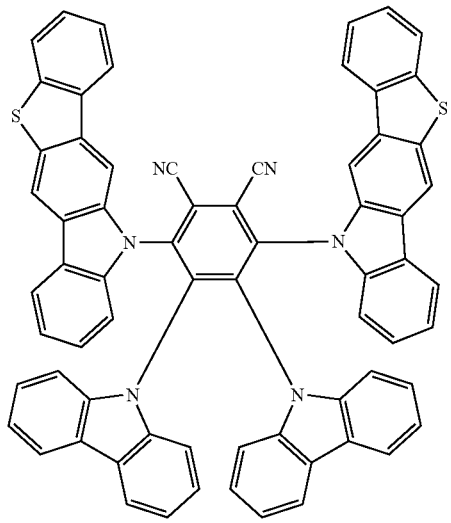
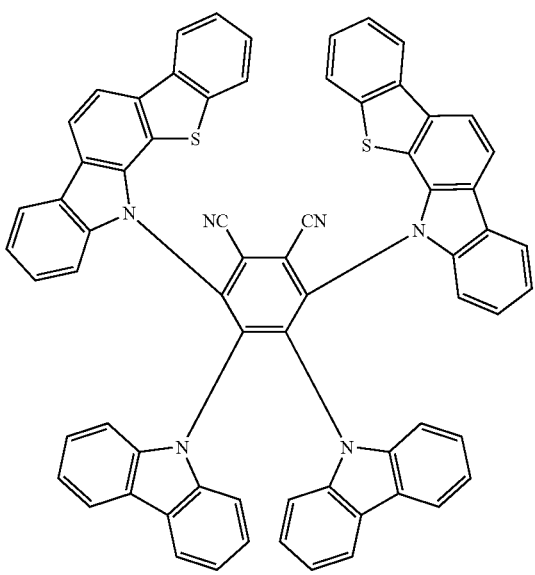
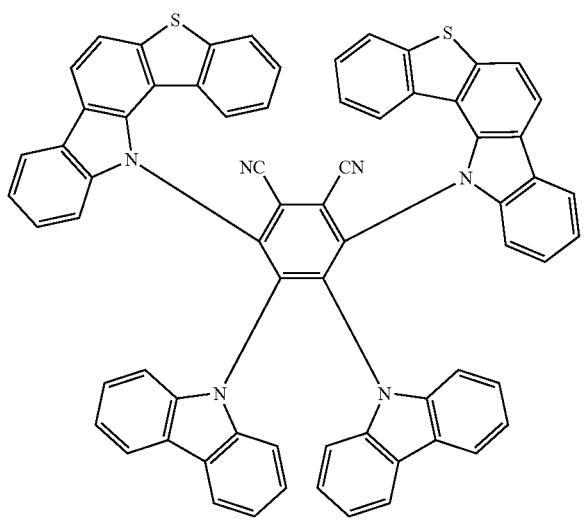
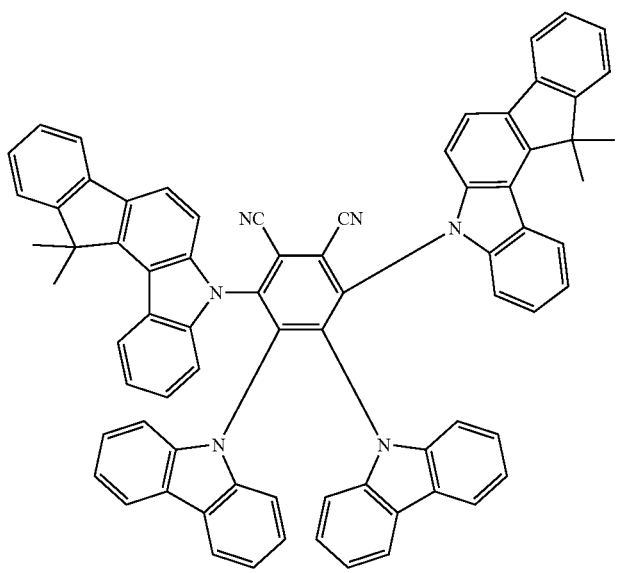

-continued
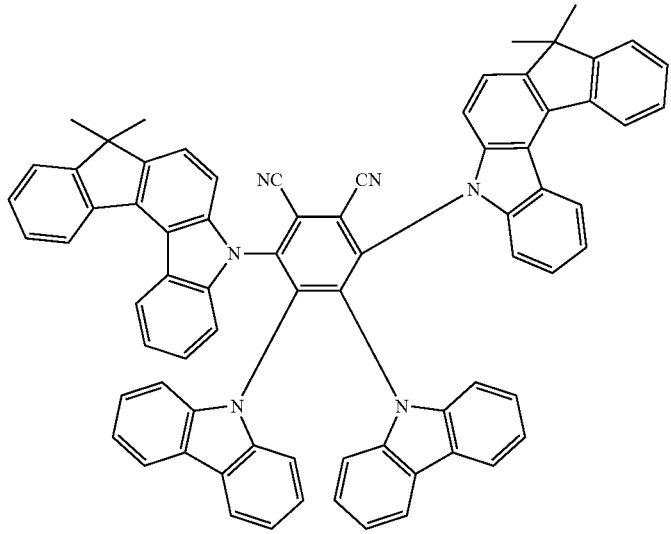
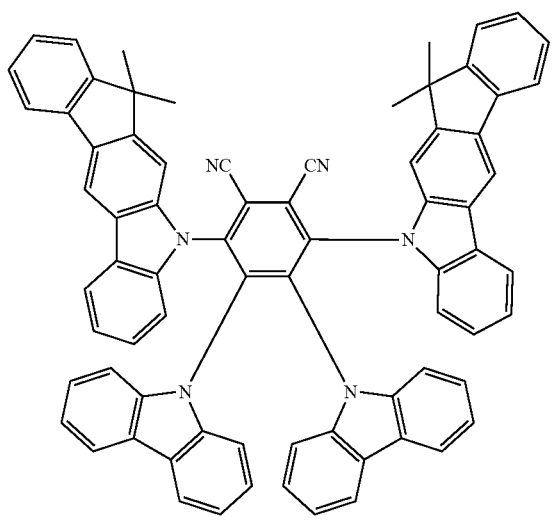
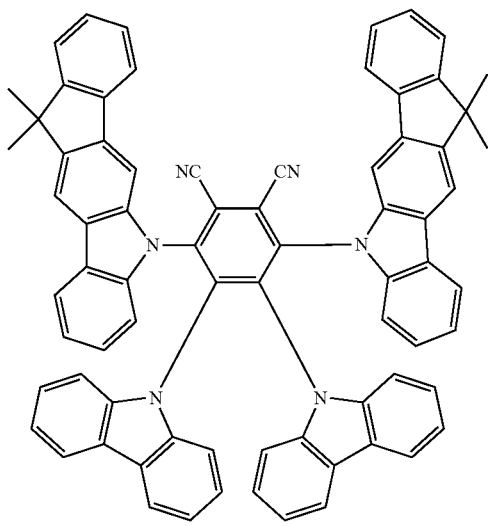
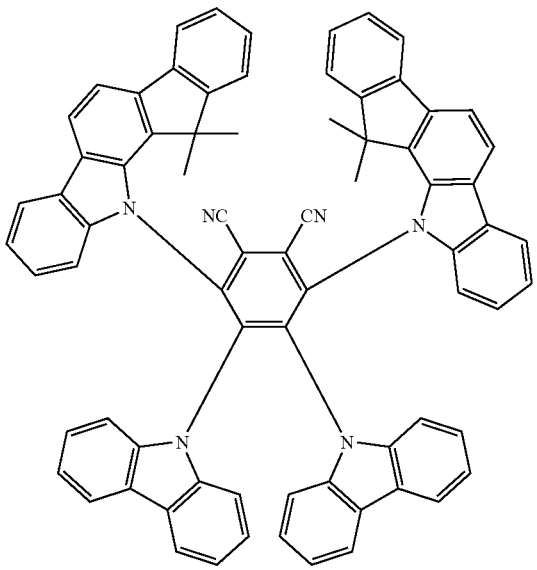

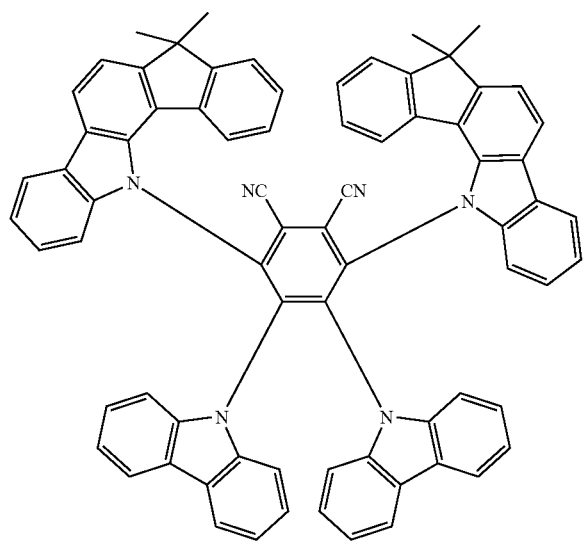
[Formula 48]
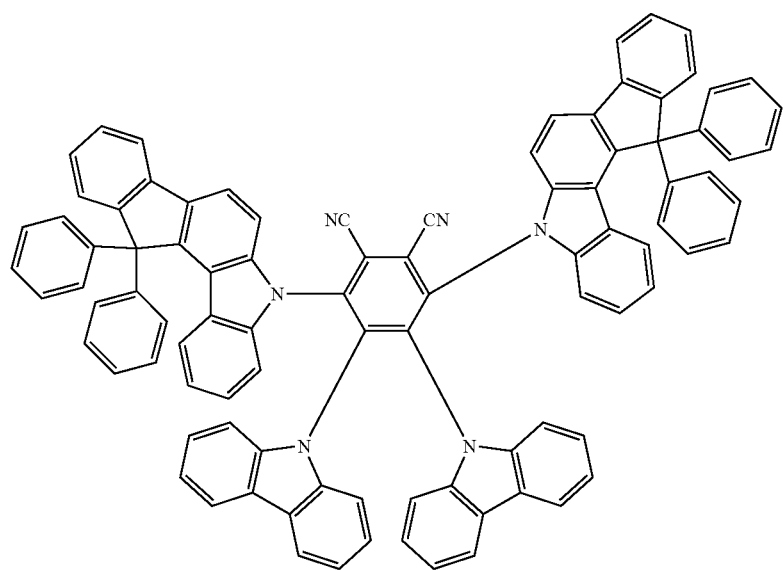

-continued
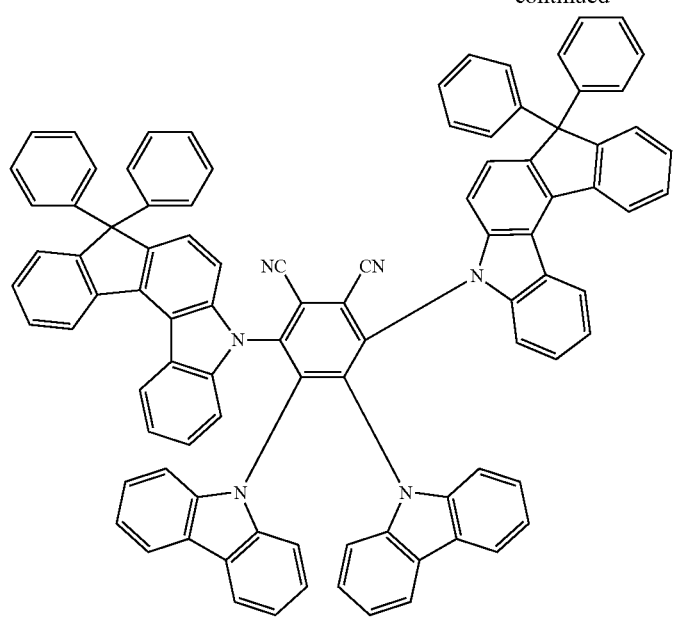
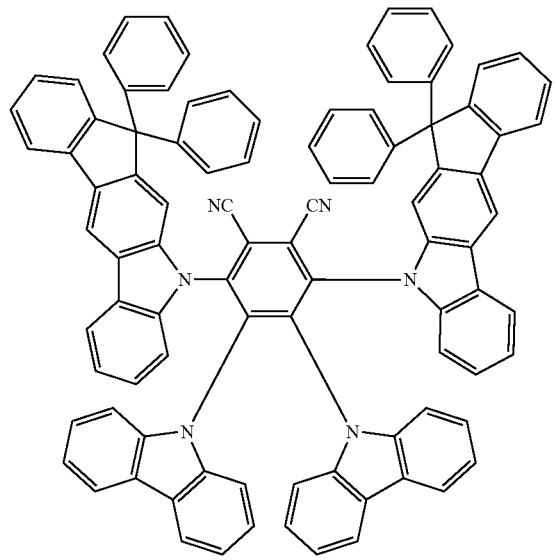
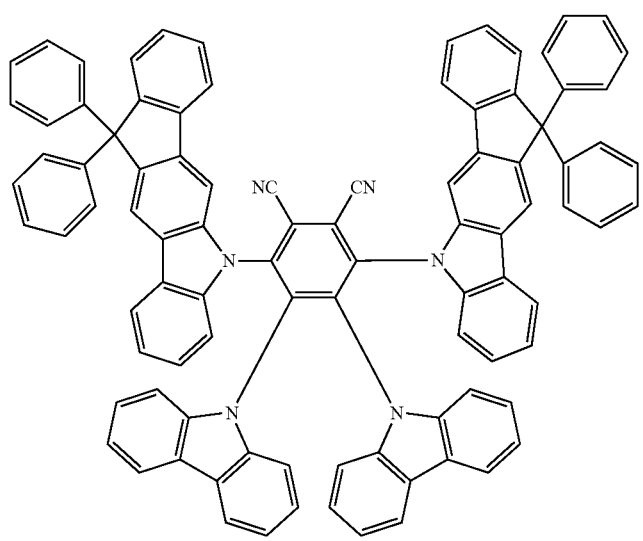

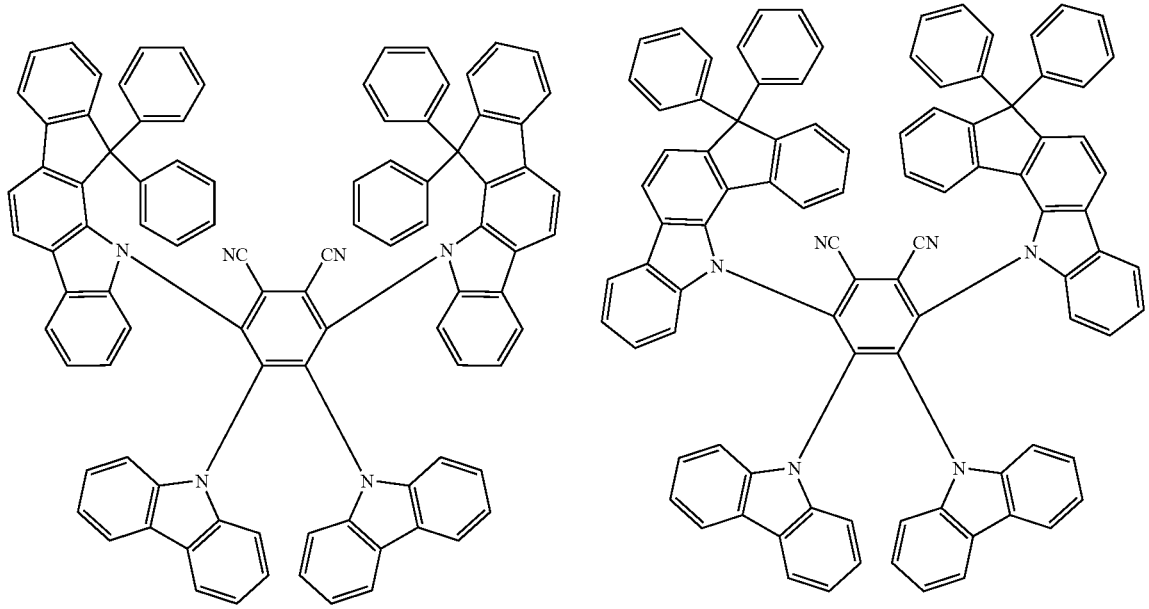
[Formula 49]
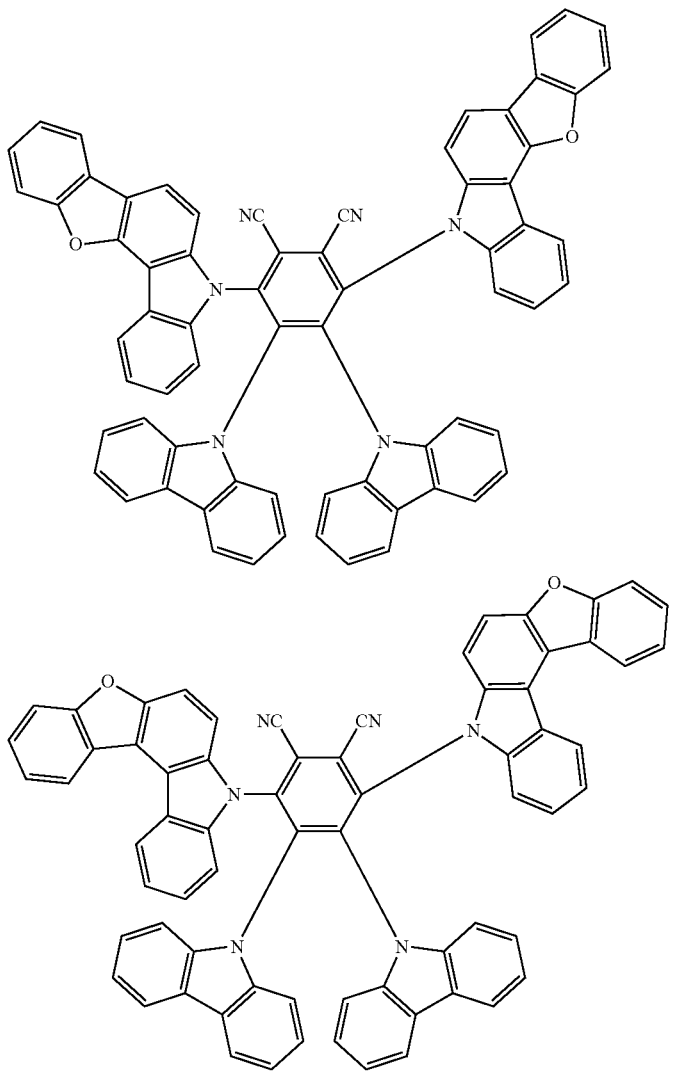

-continued
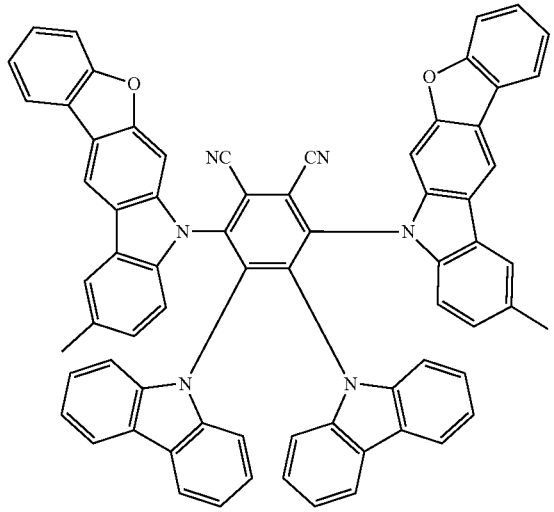
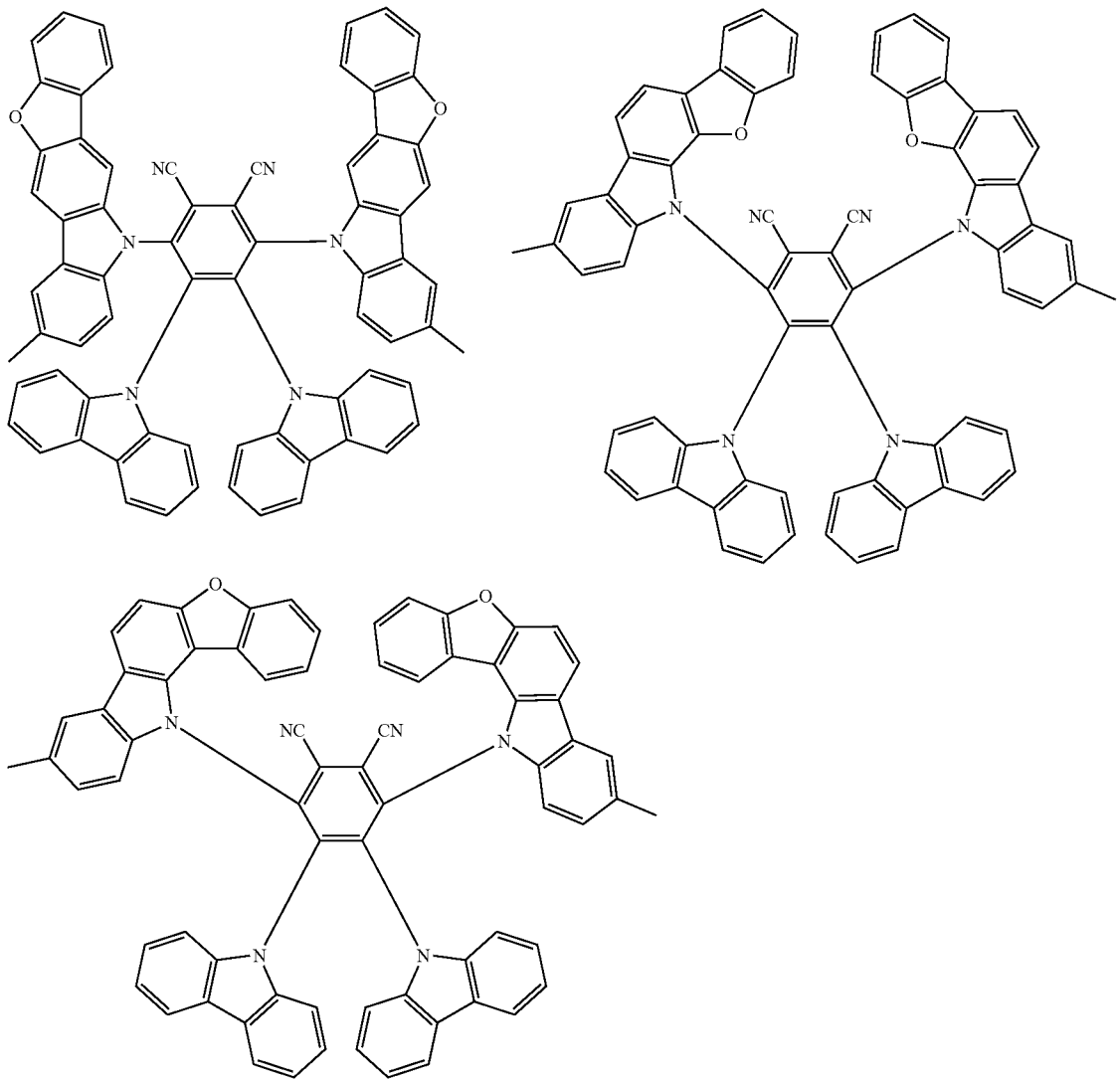

[Formula 50]
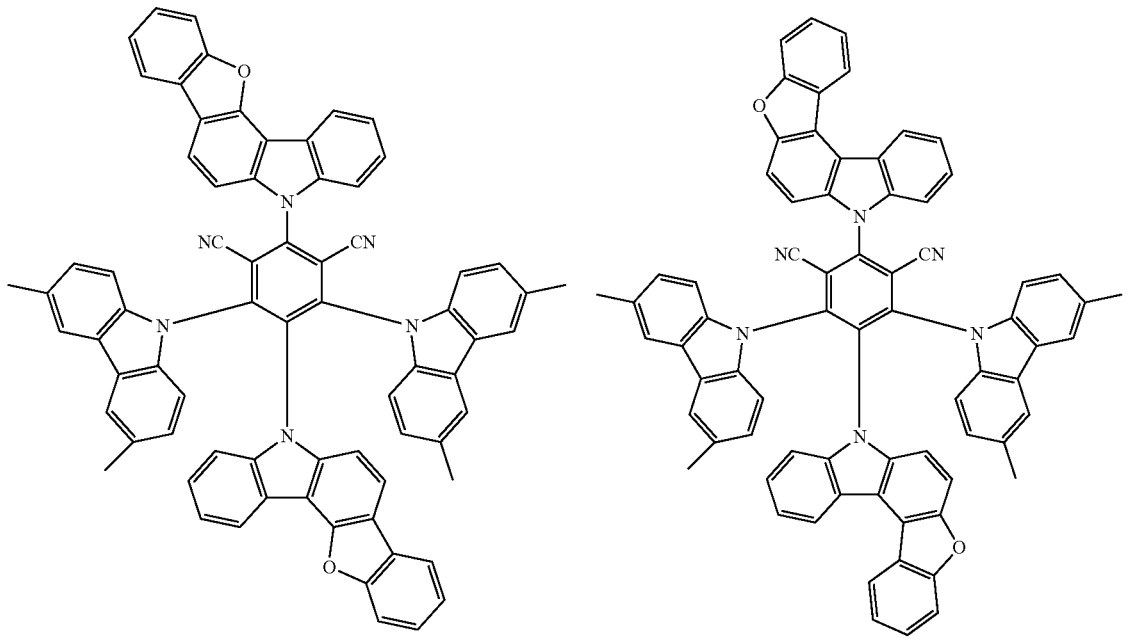
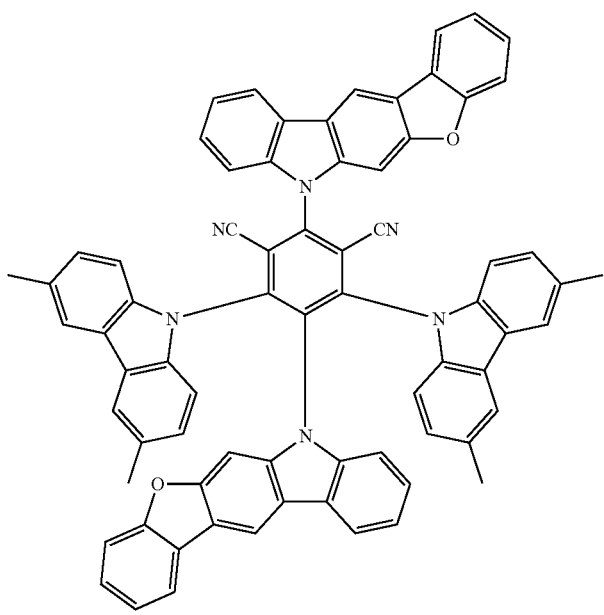

-continued
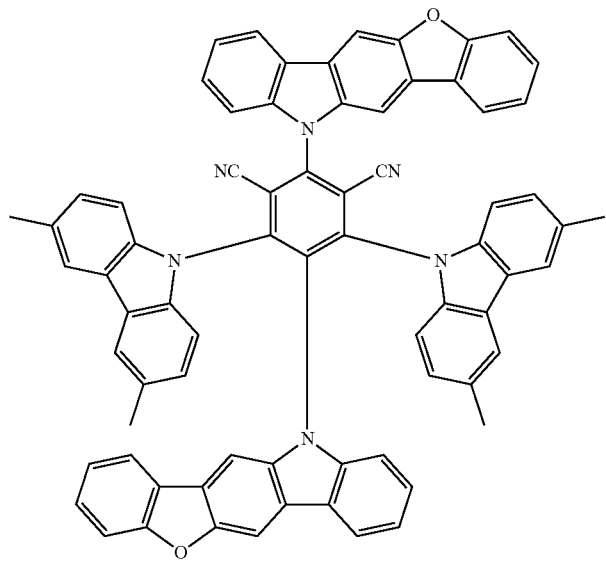
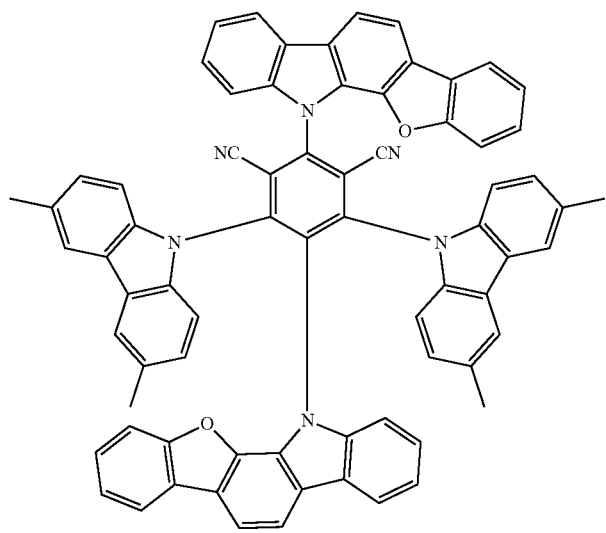
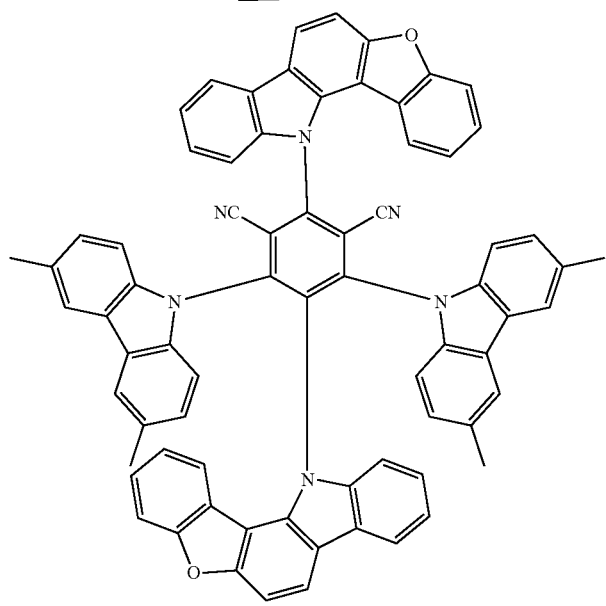

-continued
143
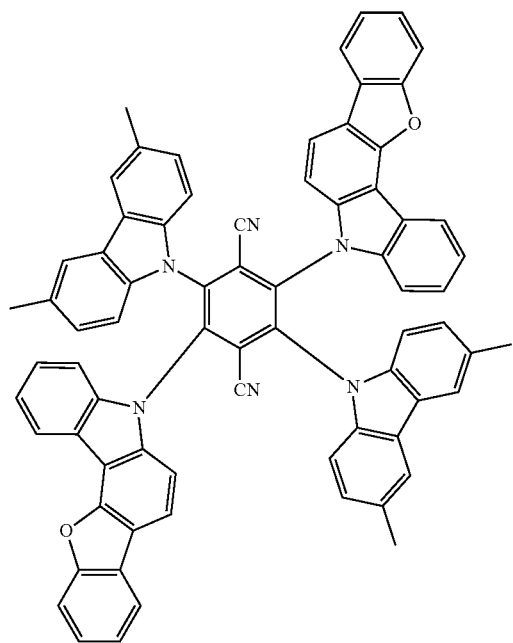
144
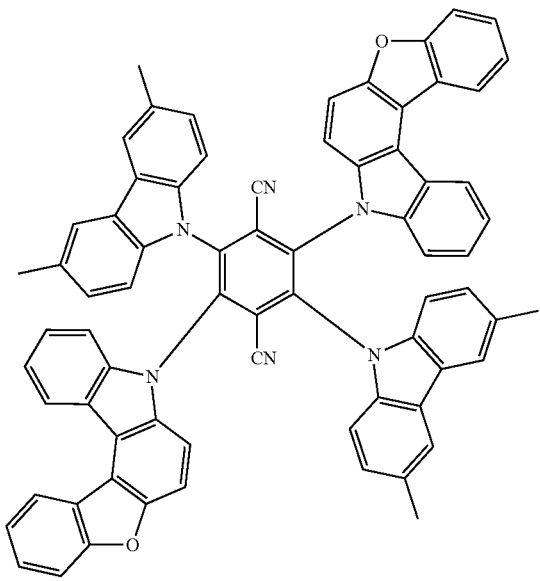
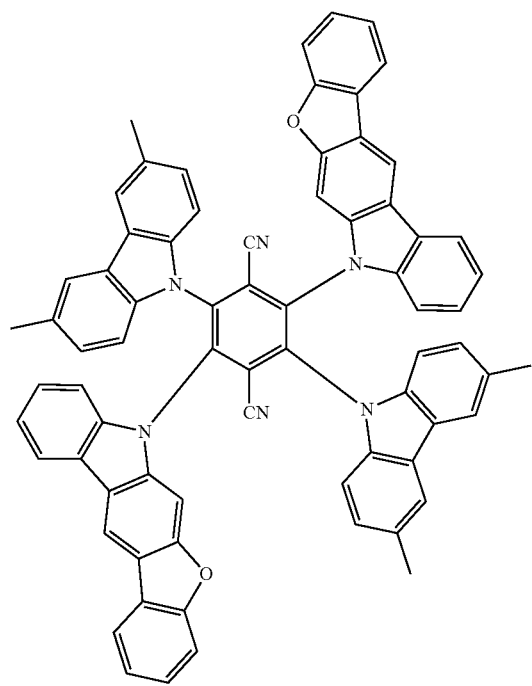

[Formula 51]
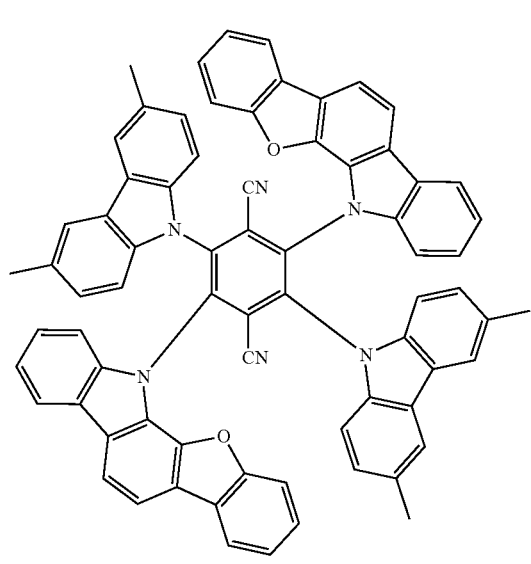
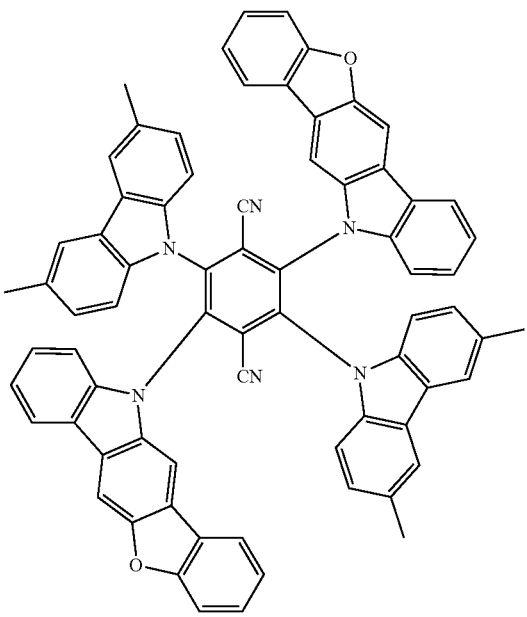
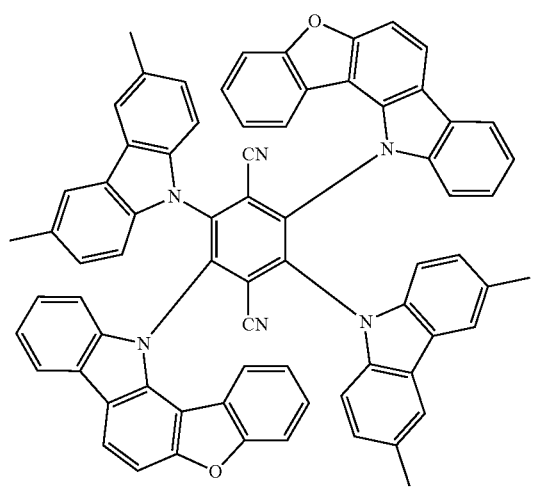
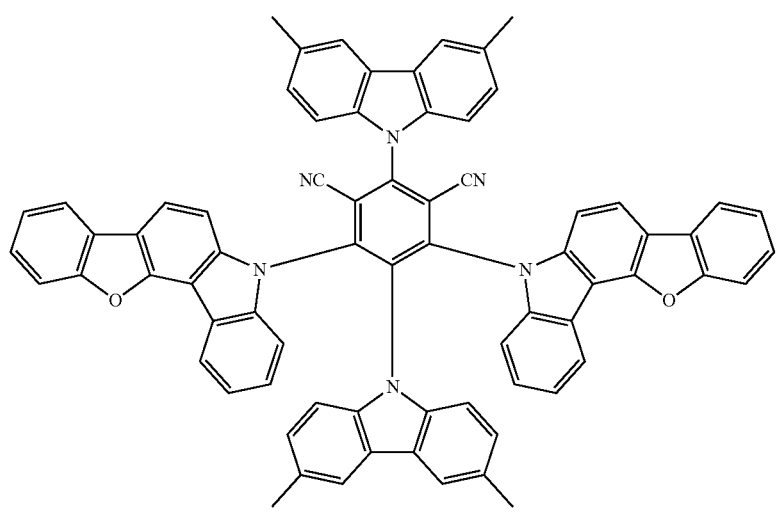

-continued
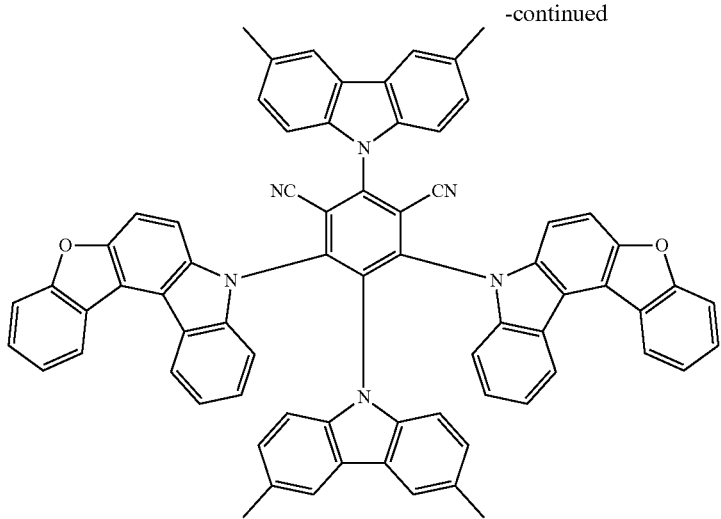
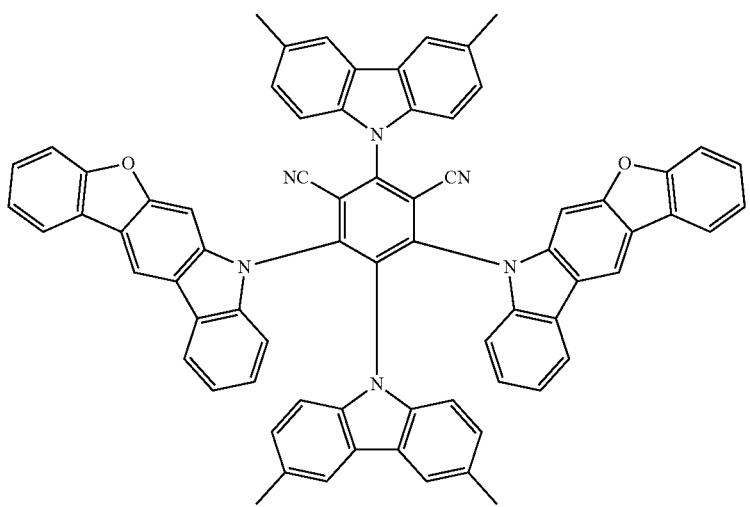
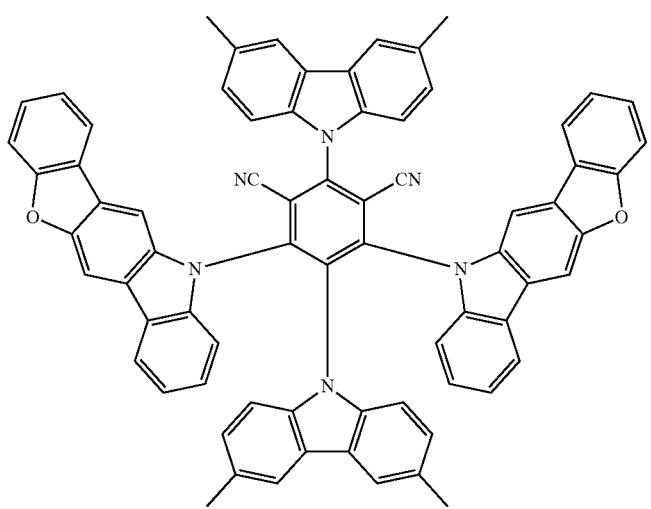

149
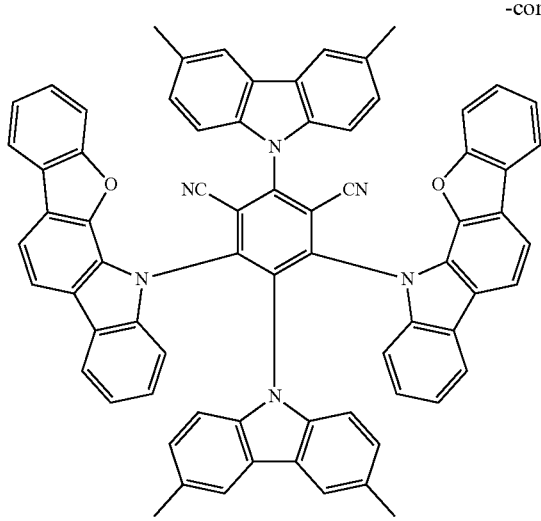
150
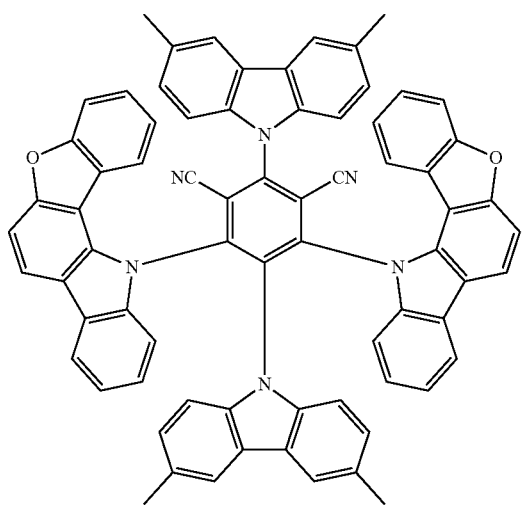
[Formula 52]
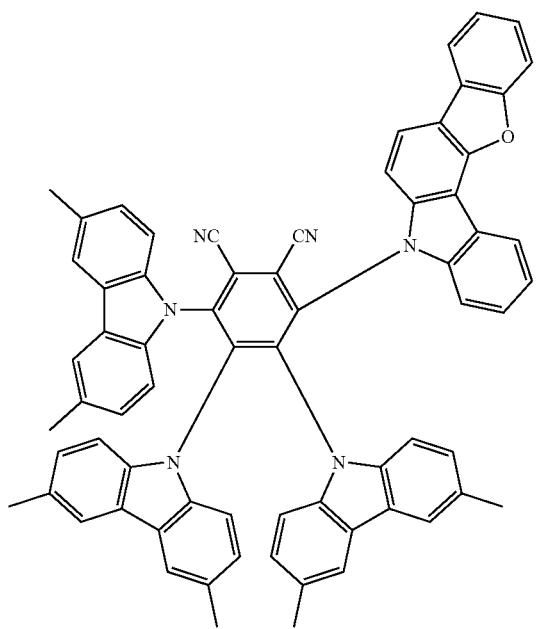
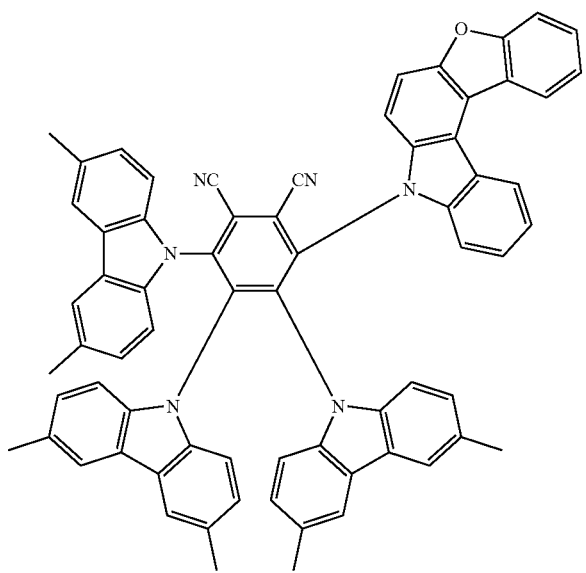

-continued
| 151 | 152 |
|---|---|
| 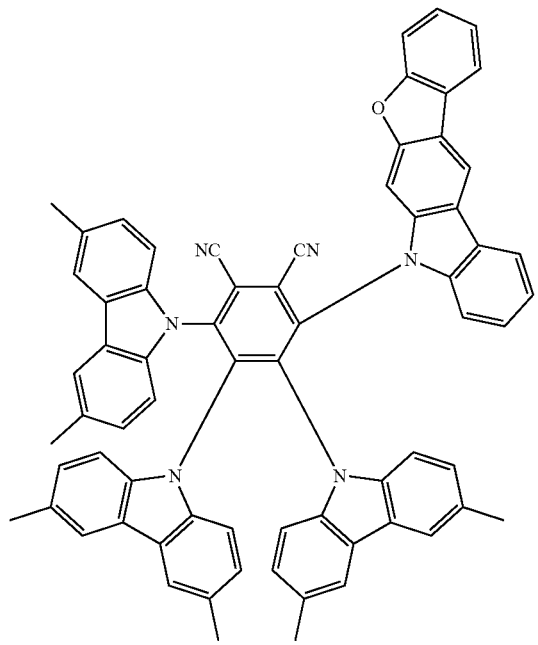 | 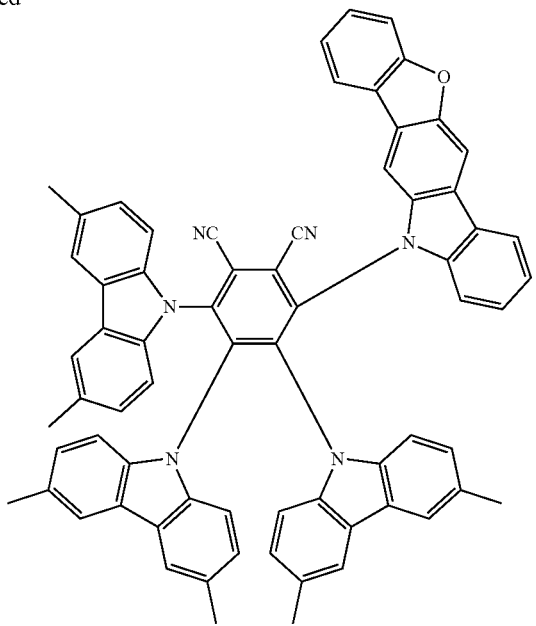 |
| 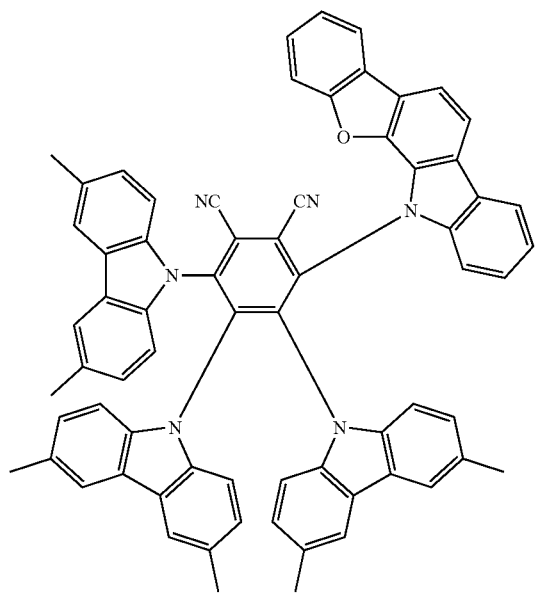 | 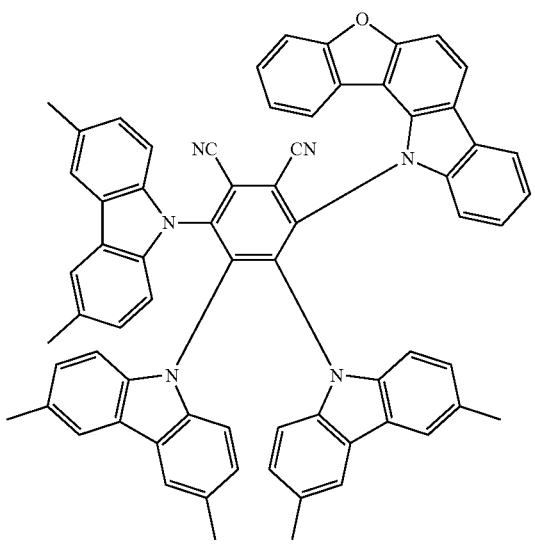 |

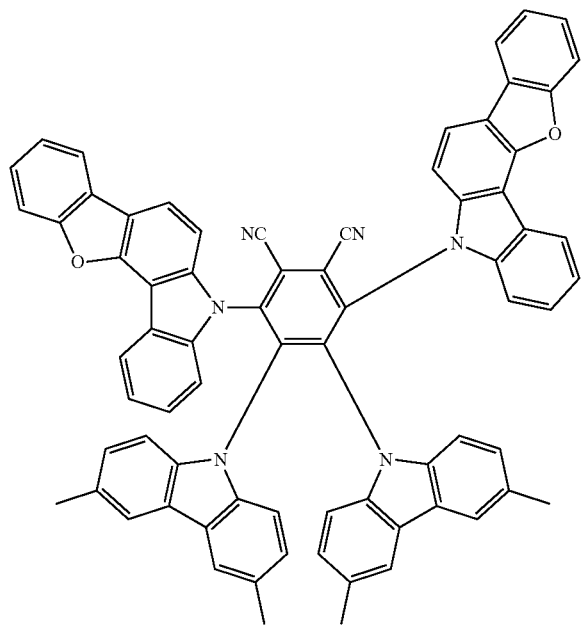
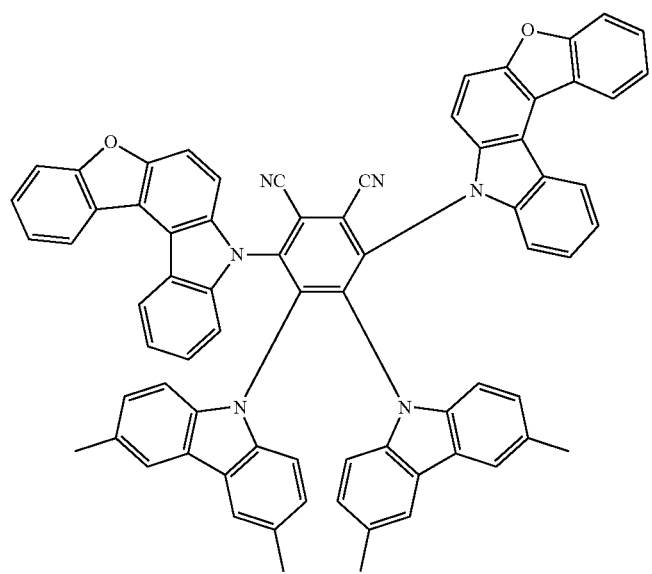

-continued
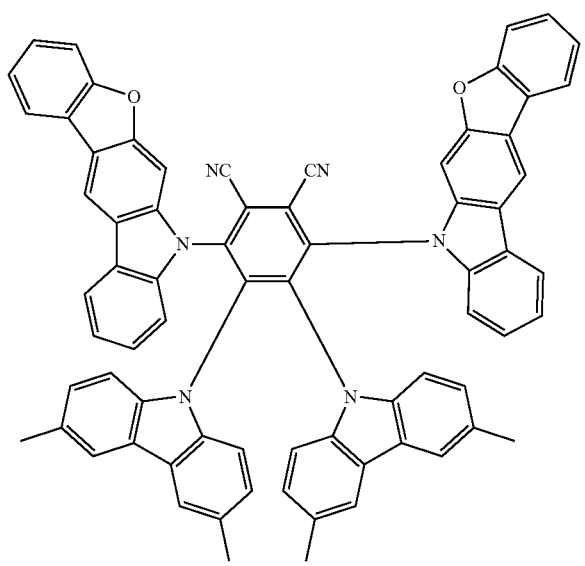
[Formula 53]
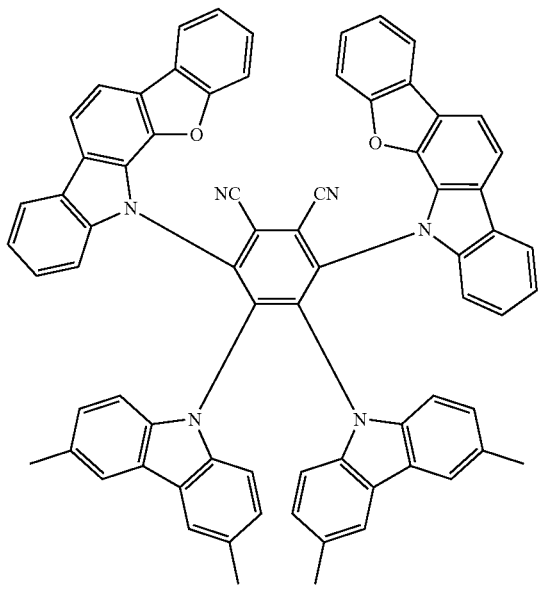

157
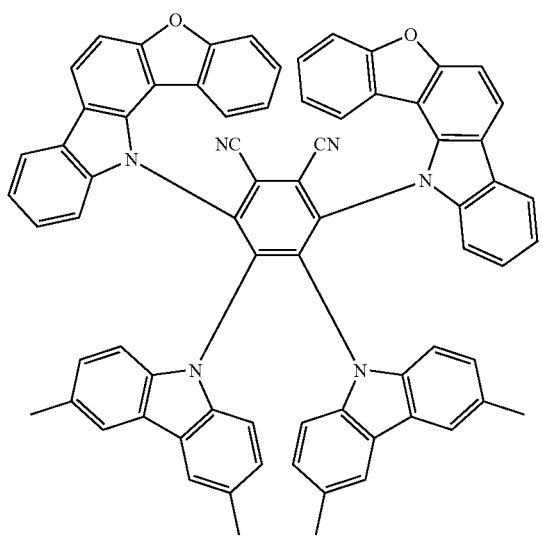
158
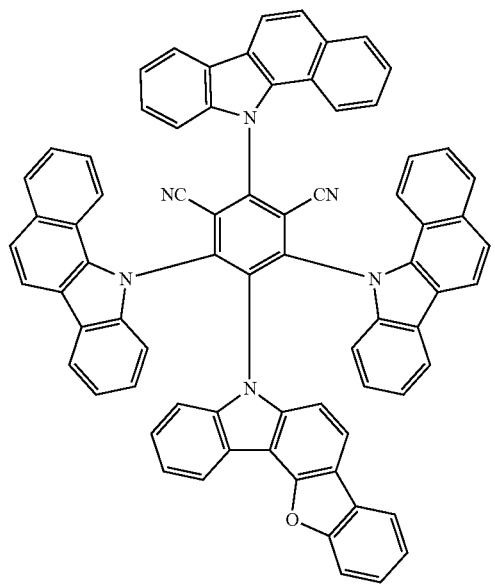
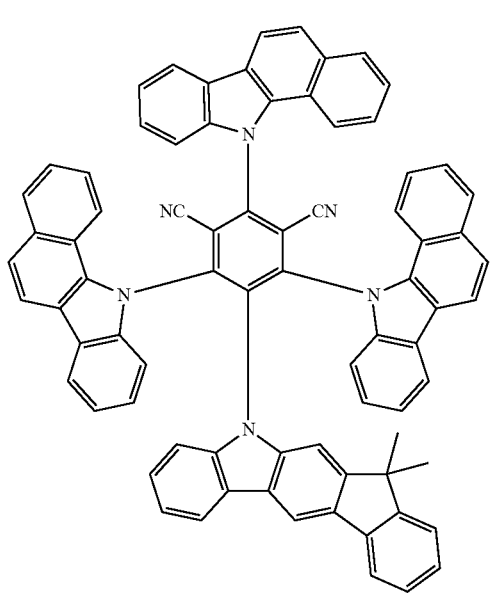
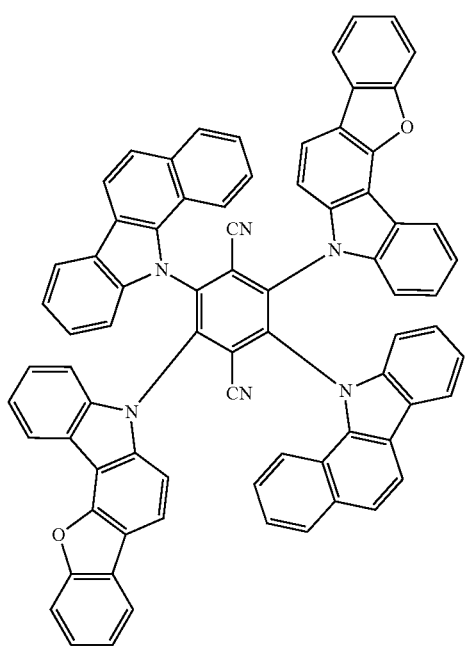

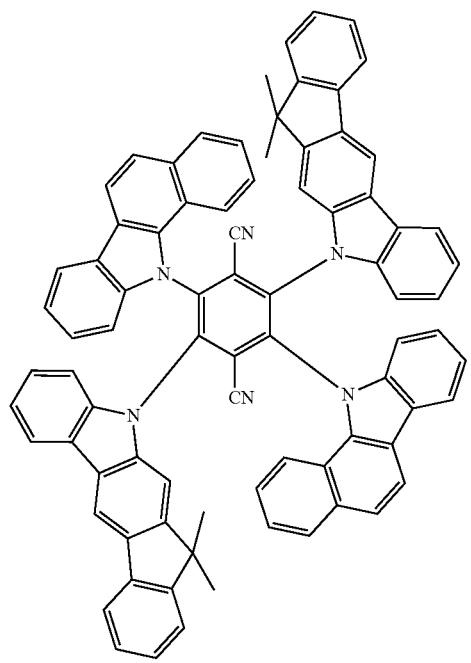
[Formula 54]
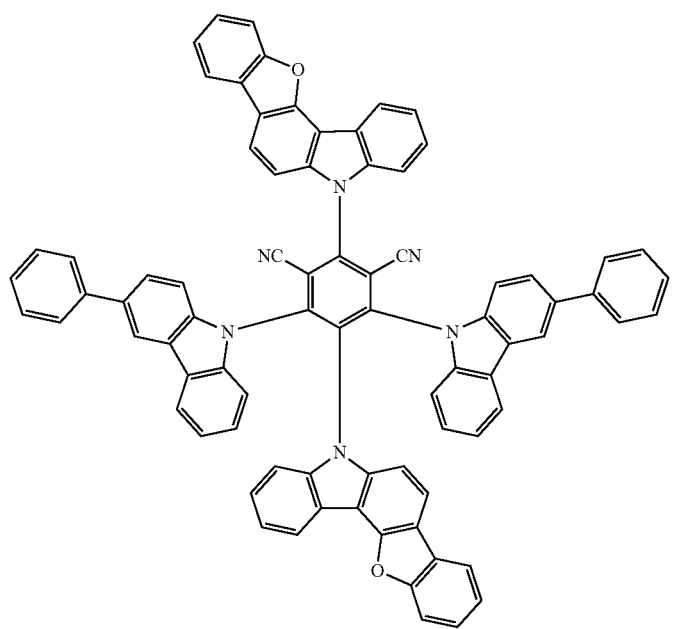

-continued
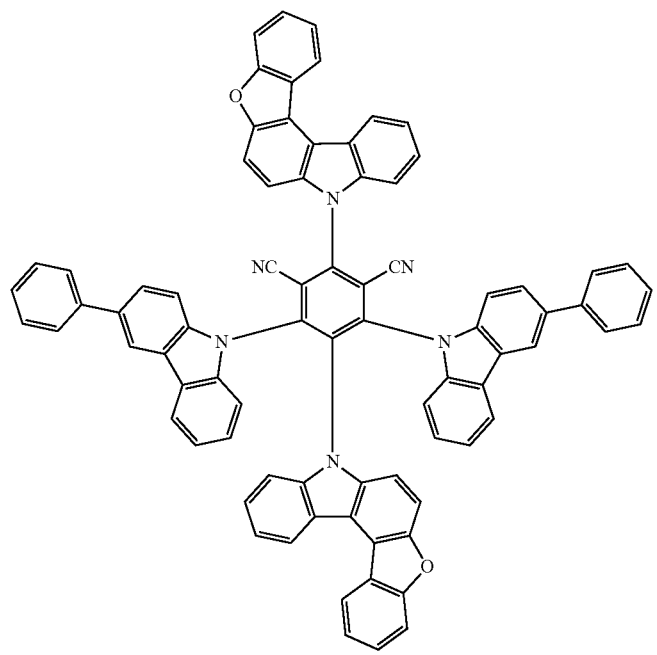
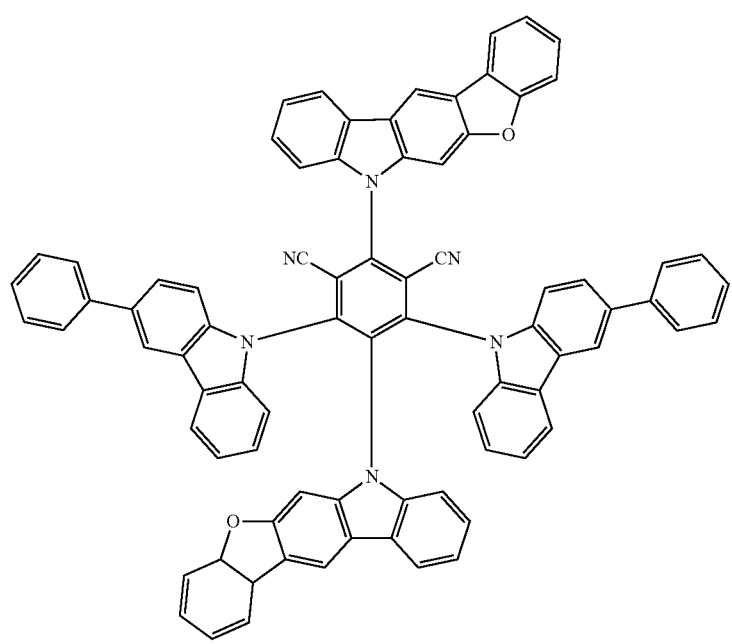

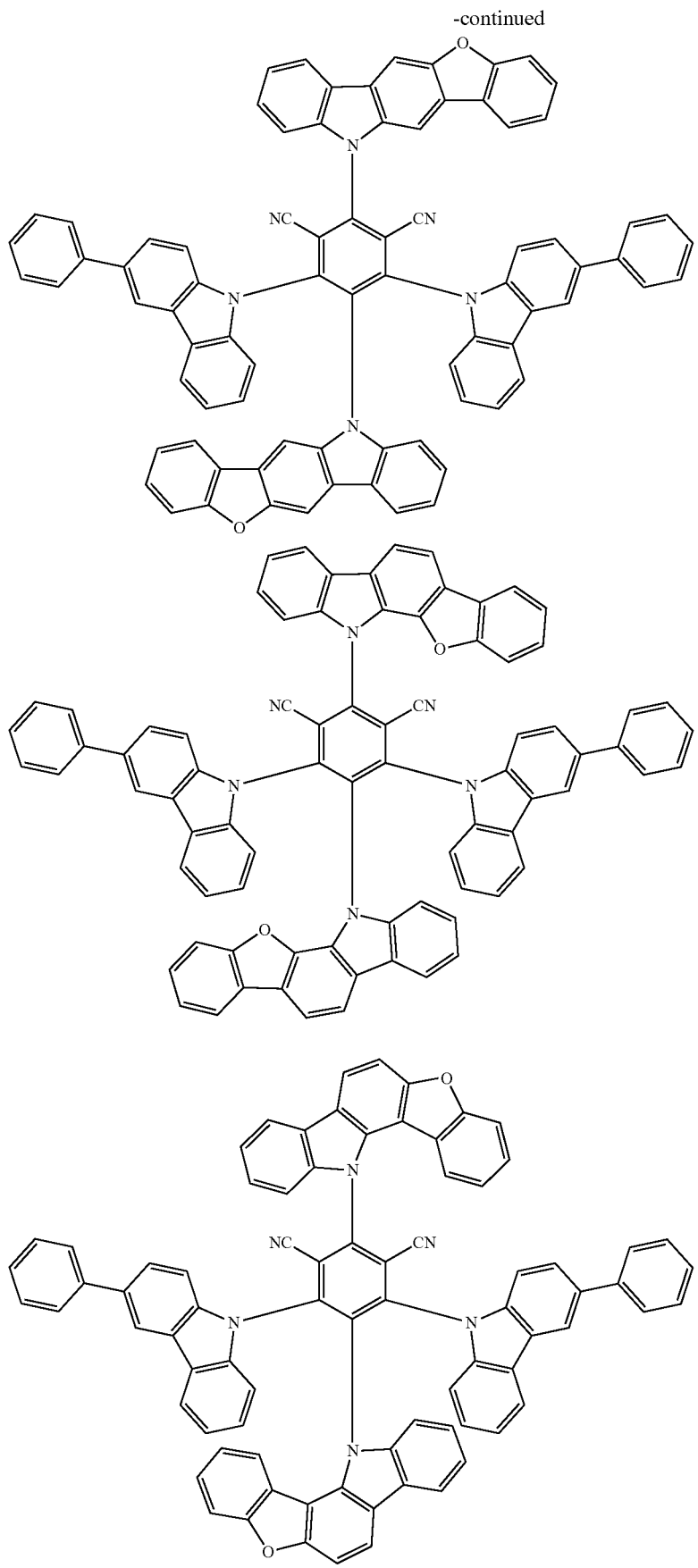

-continued
165
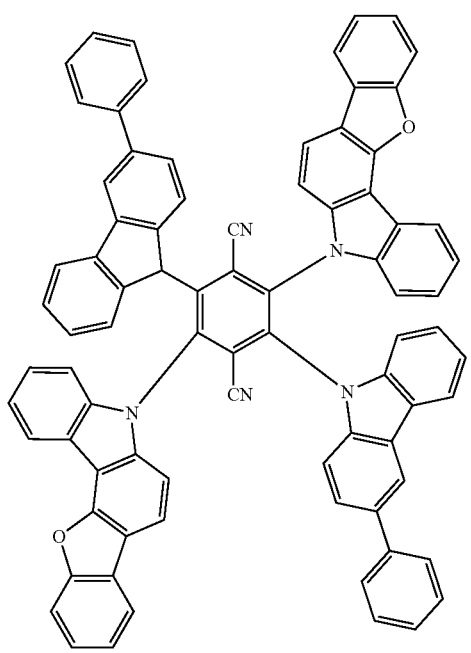
166
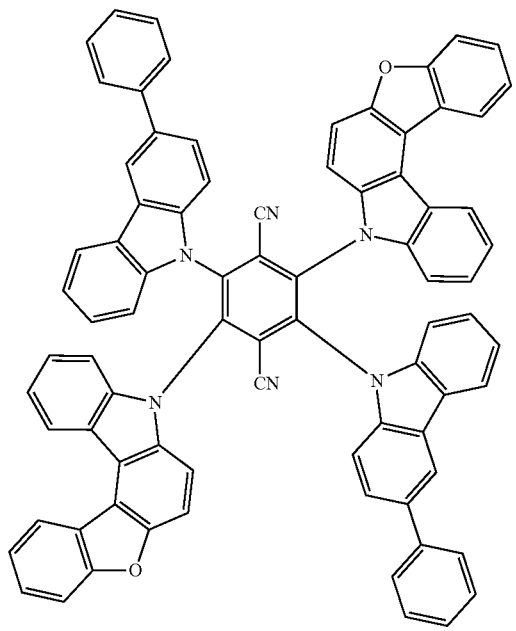
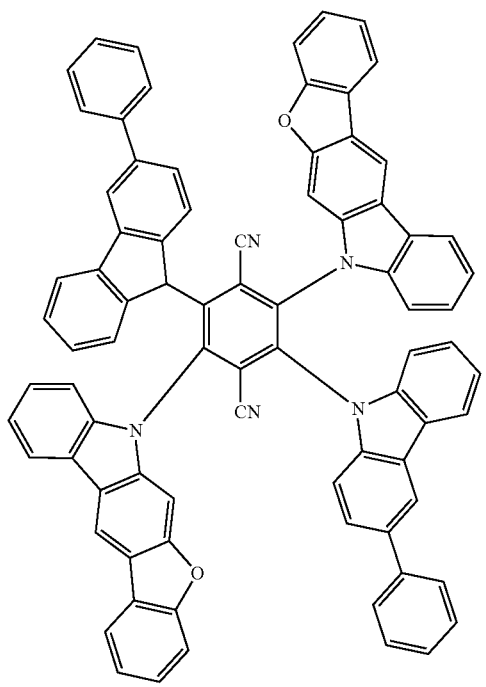

[Formula 55]
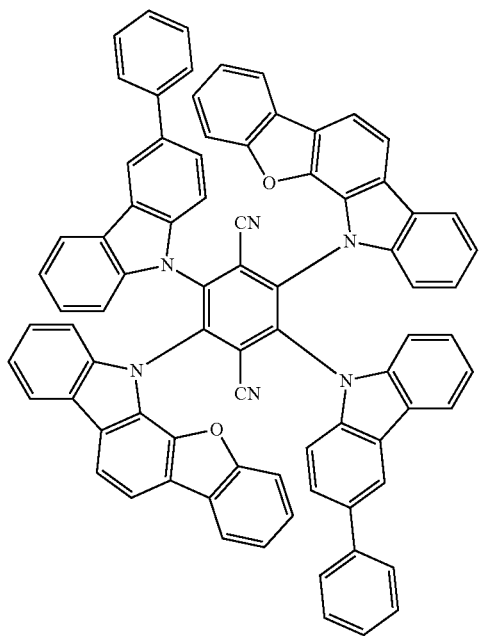
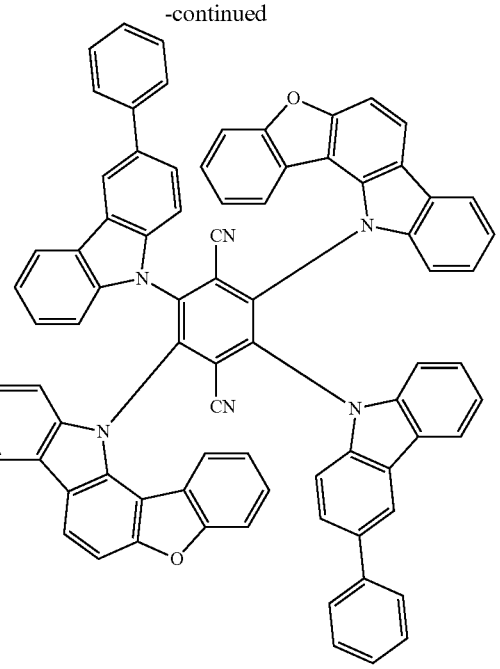
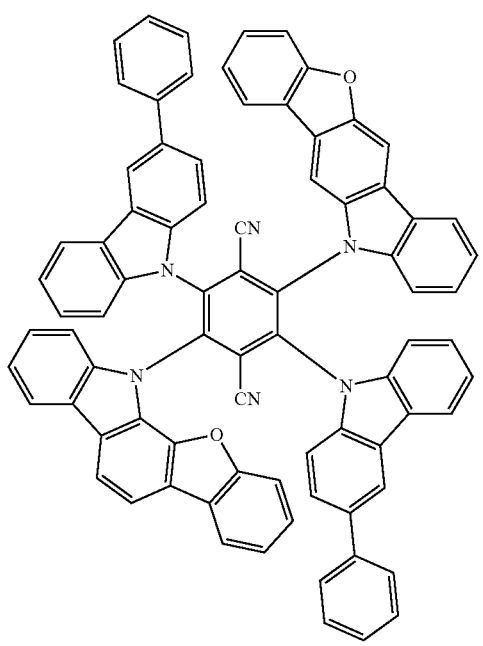
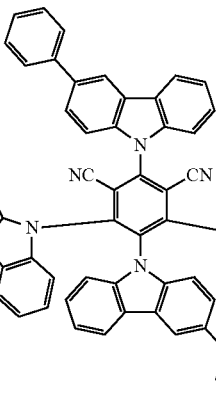
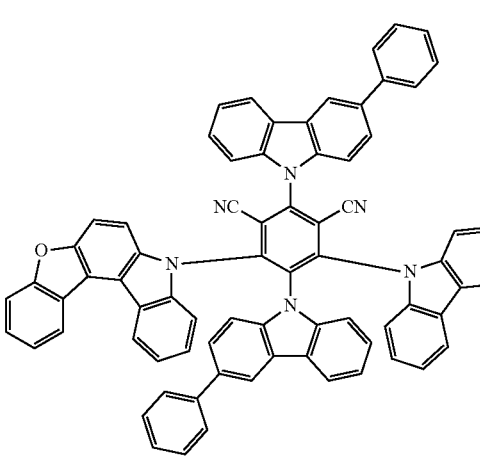

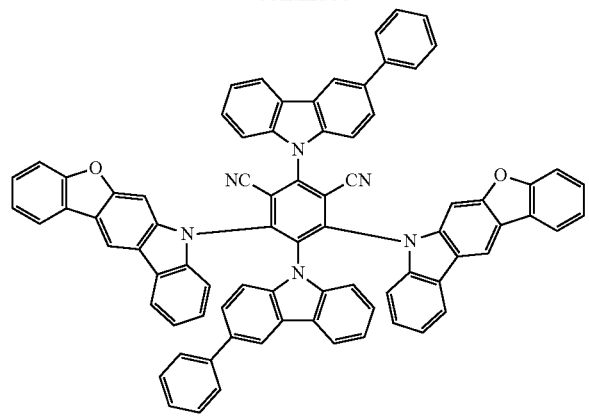
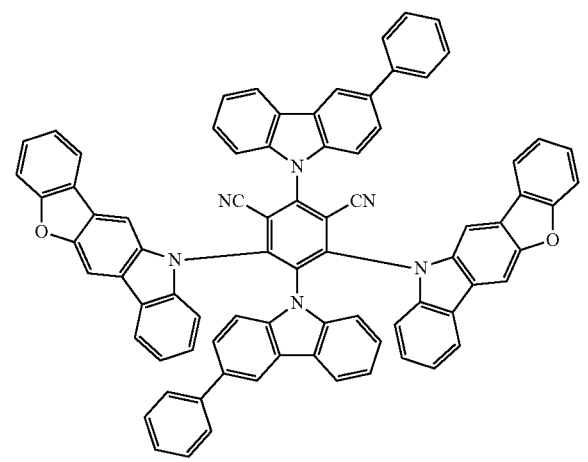
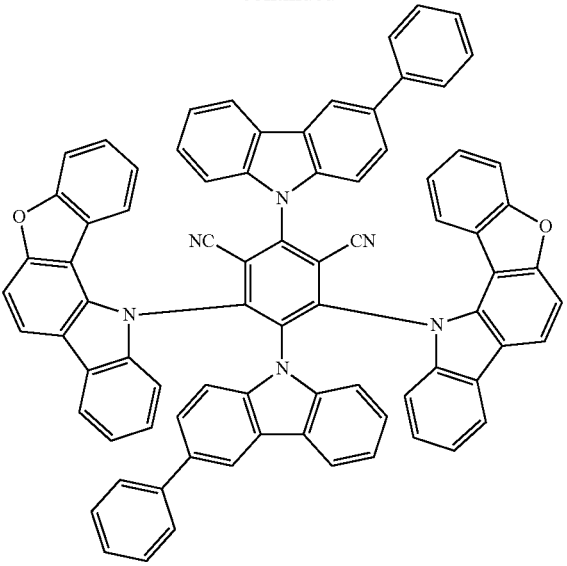
[Formula 56]
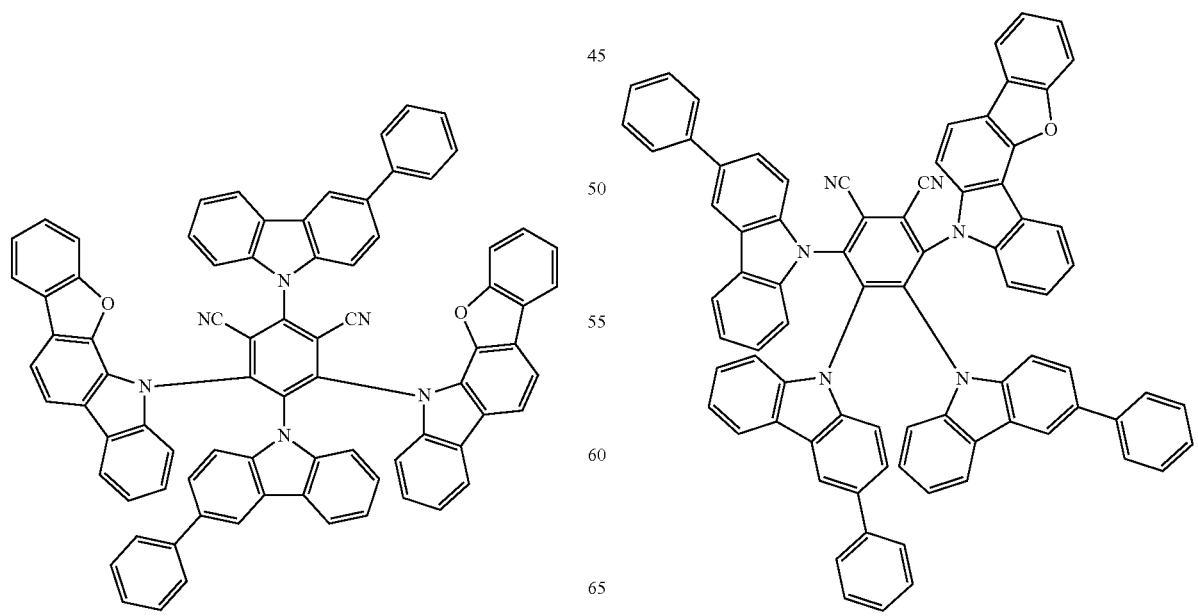

171
-continued
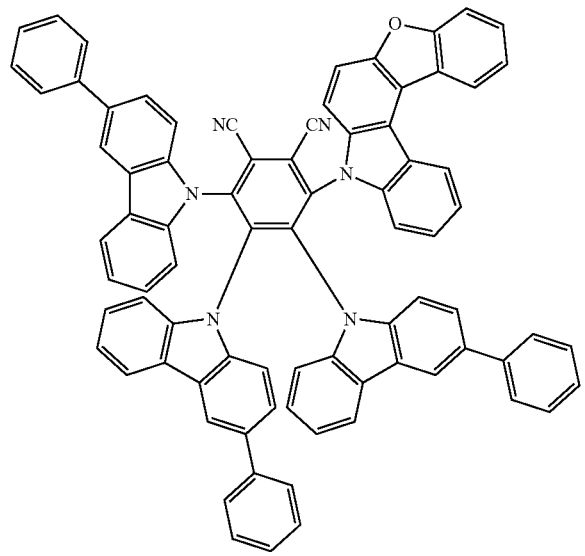
172
-continued
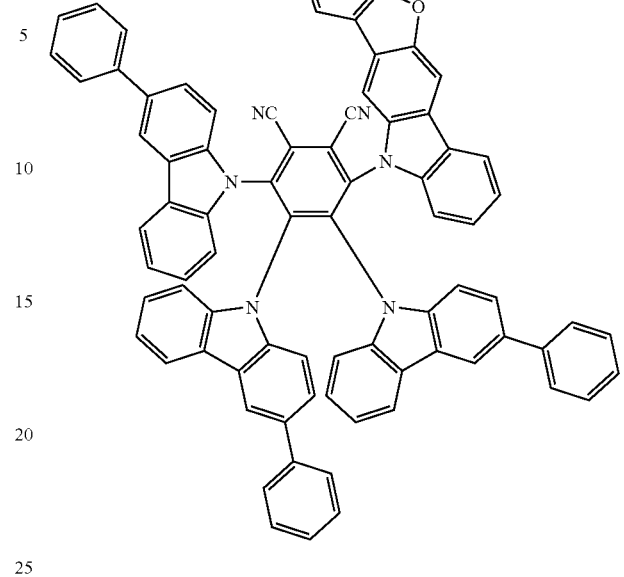
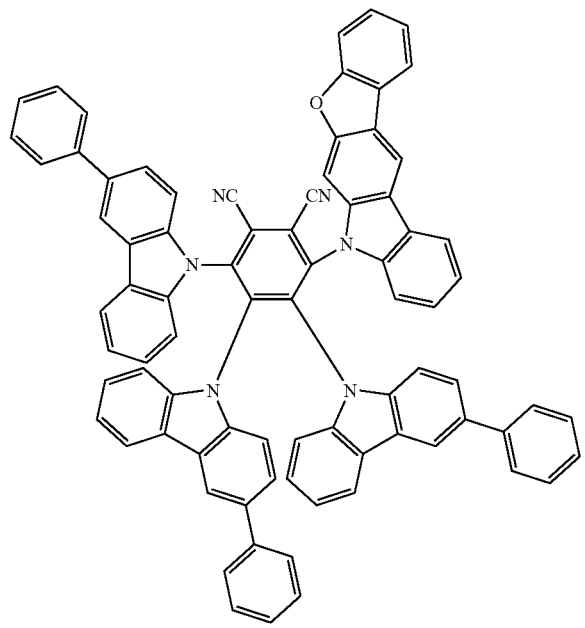
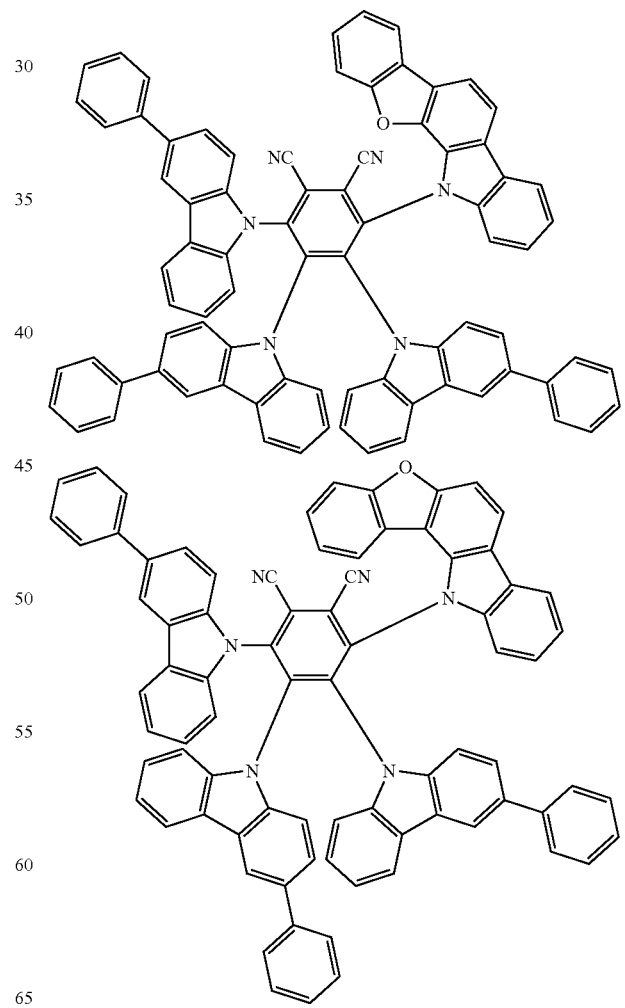

173
-continued
[Formula 57]
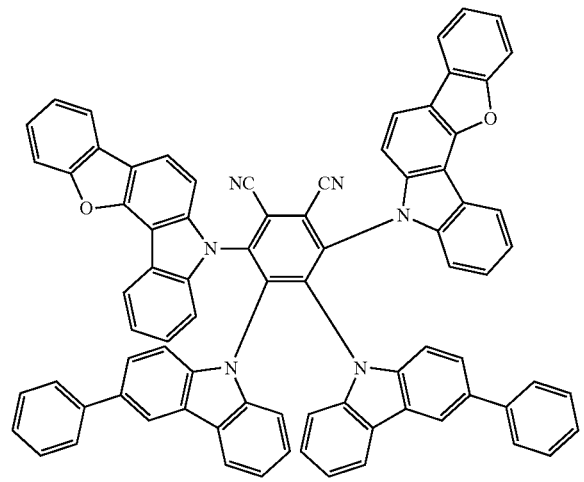
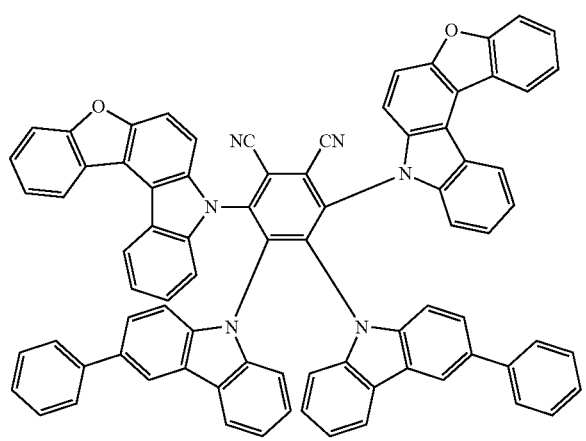
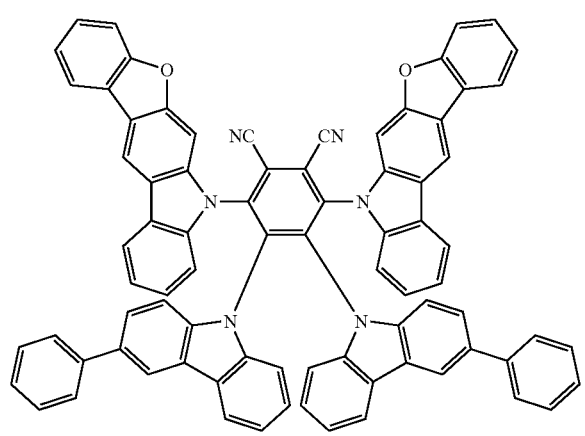
174
-continued
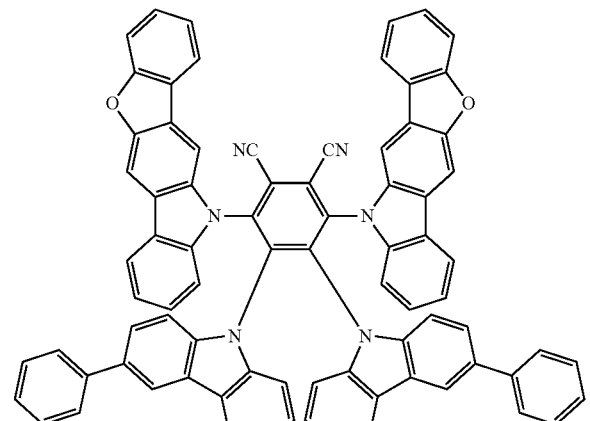
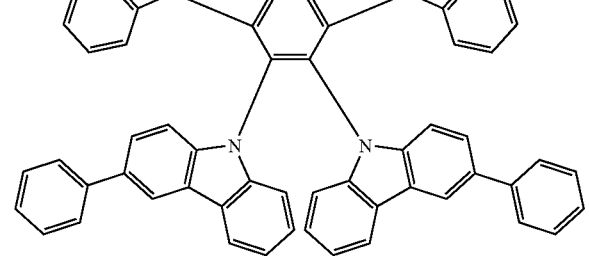
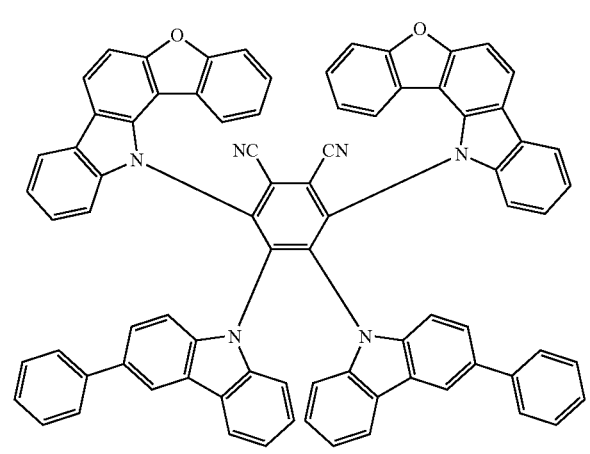

[Formula 58]
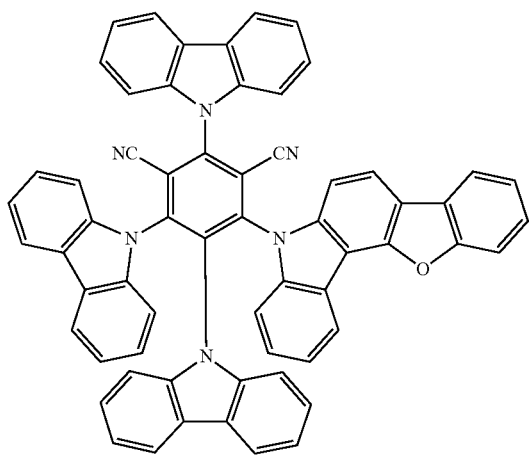
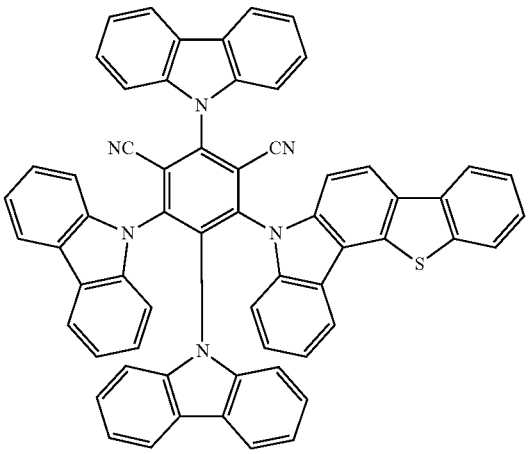
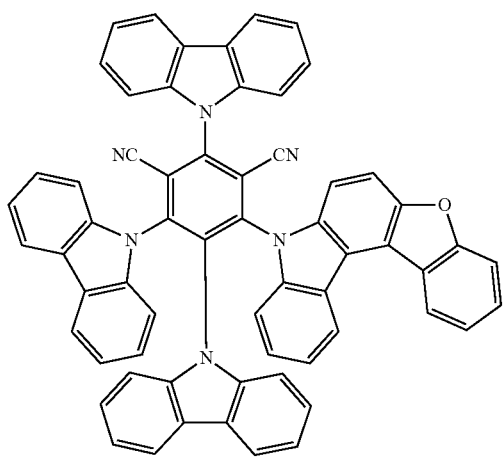
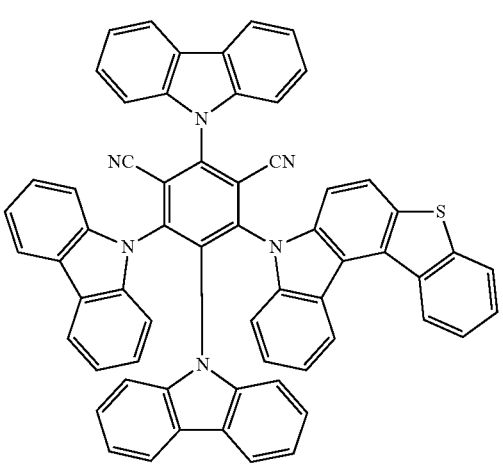
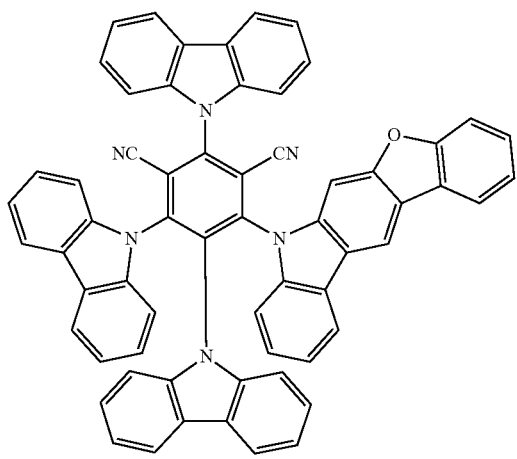
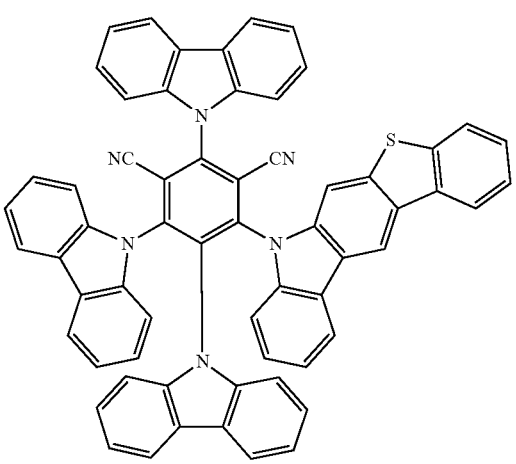

177
-continued
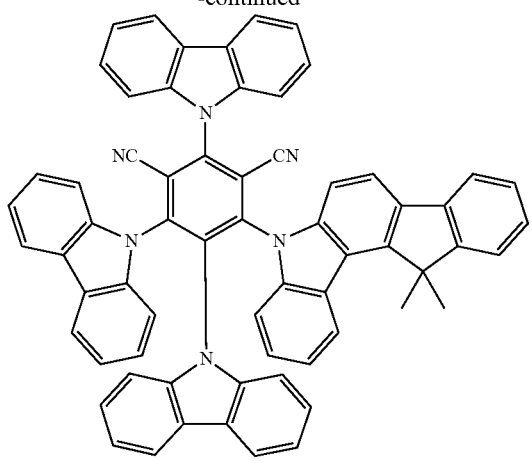
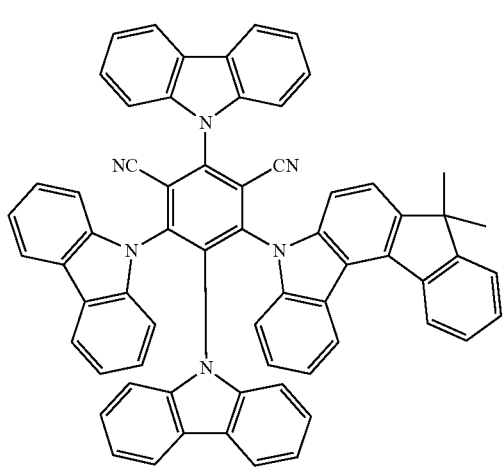
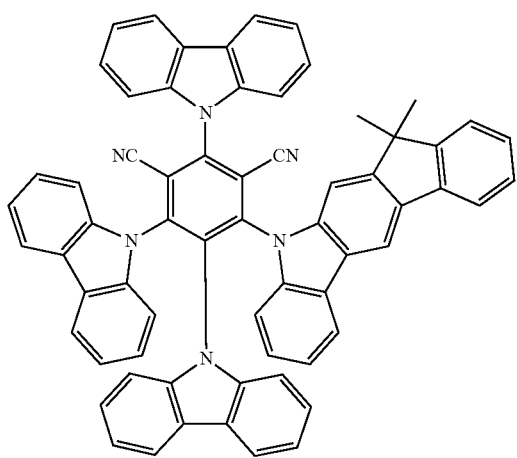
178
-continued
[Formula 59]
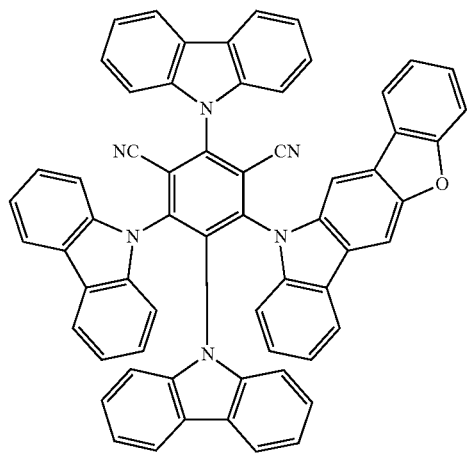
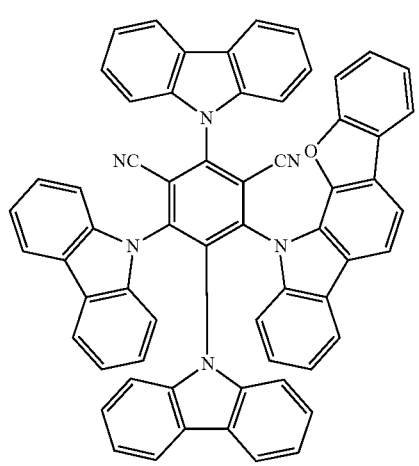
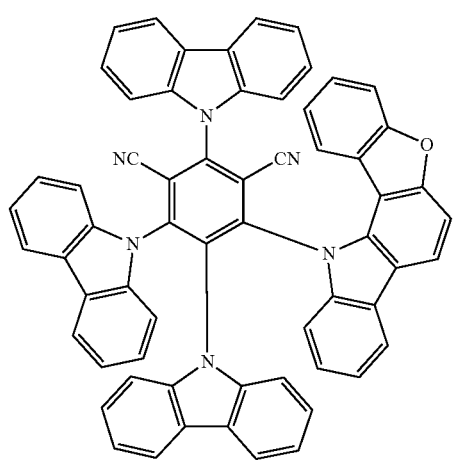

179
-continued
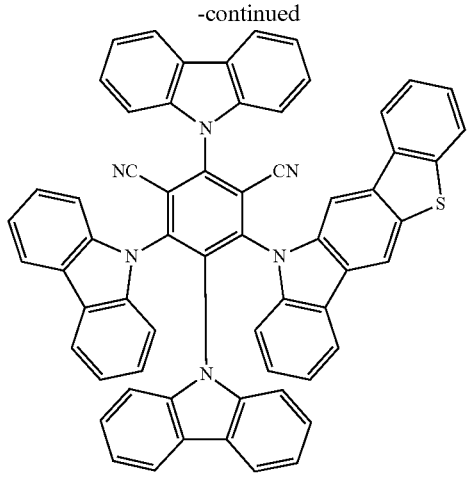
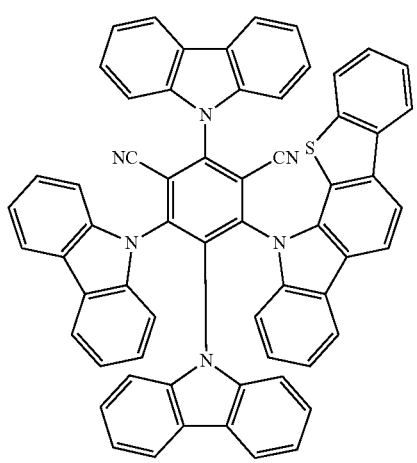
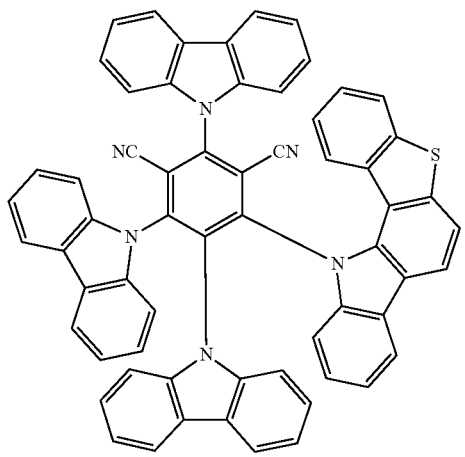
180
-continued
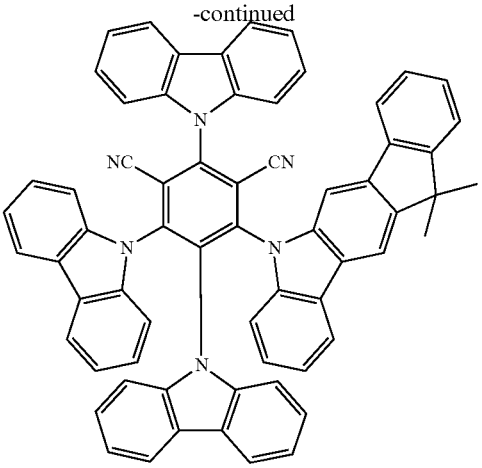
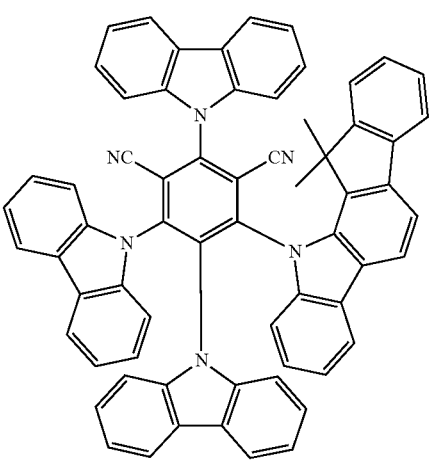
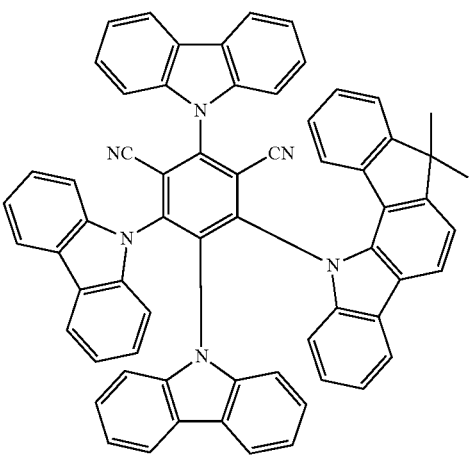

[Formula 60]
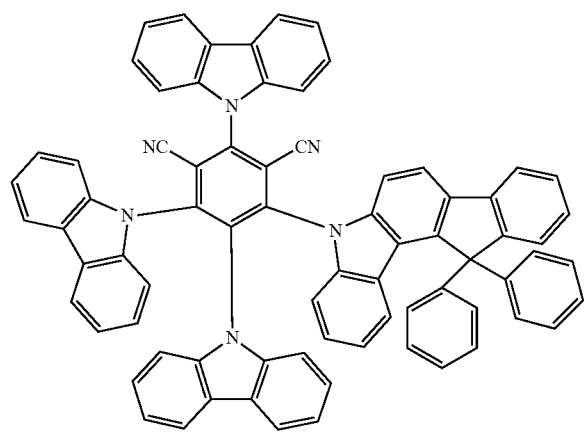
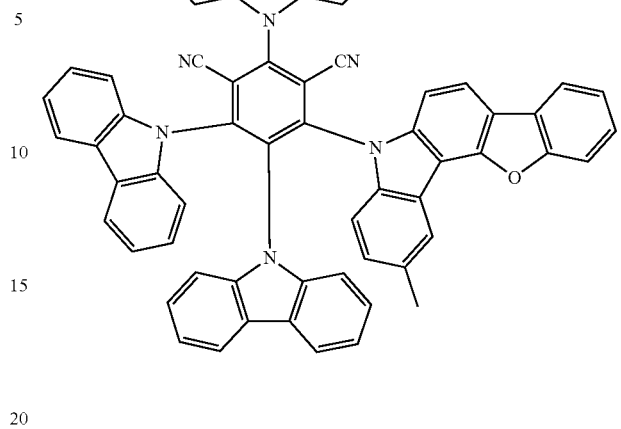
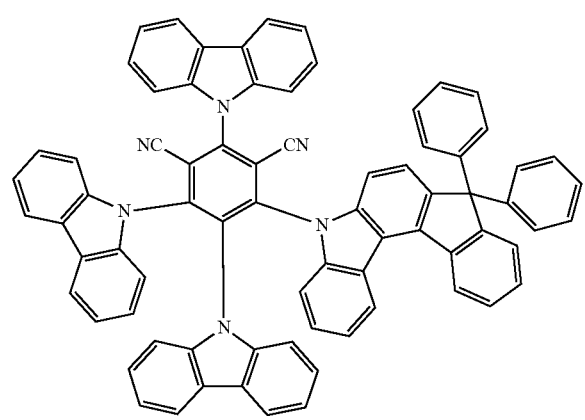
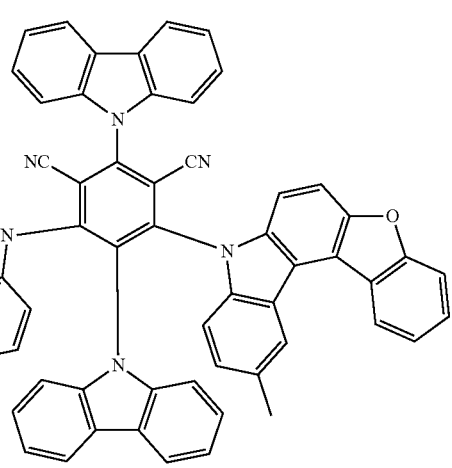
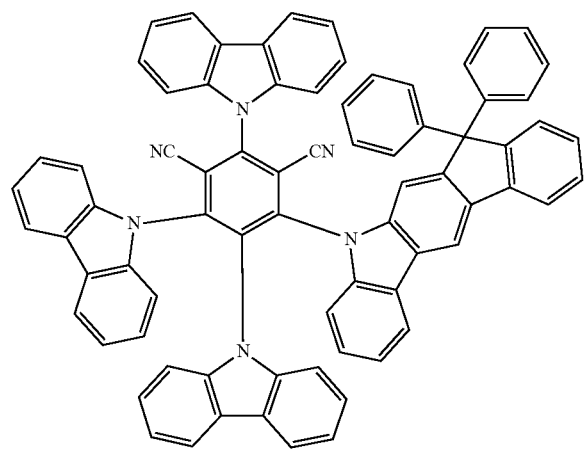
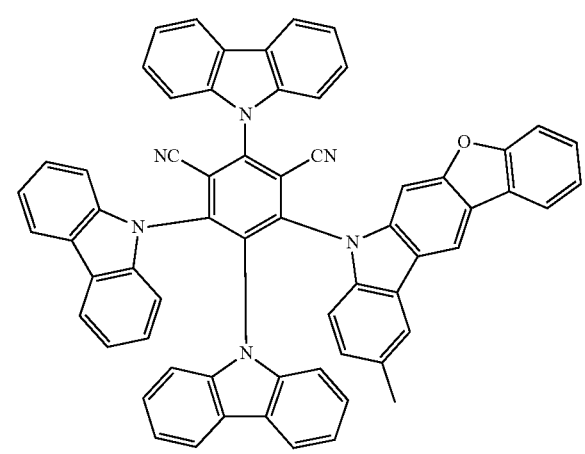

183
-continued
[Formula 61]
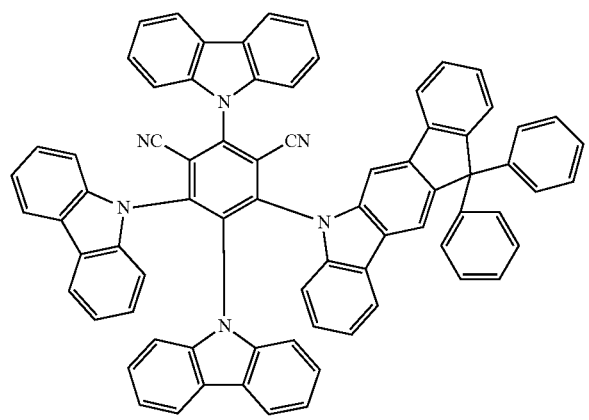
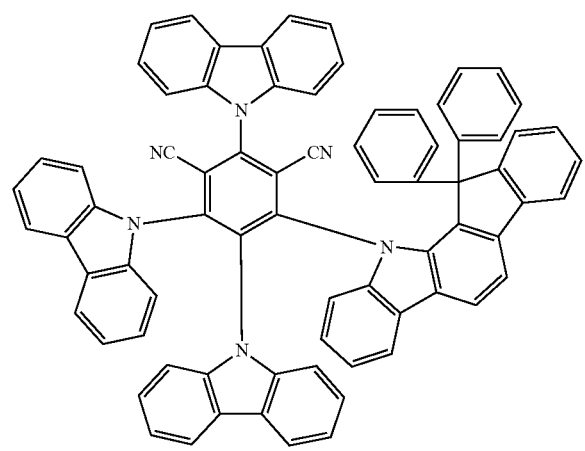
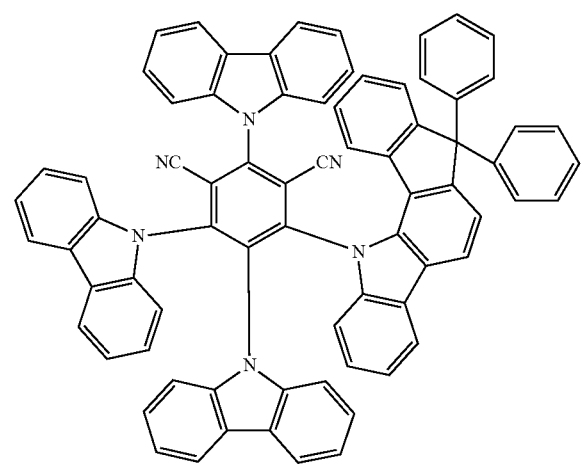
184
-continued
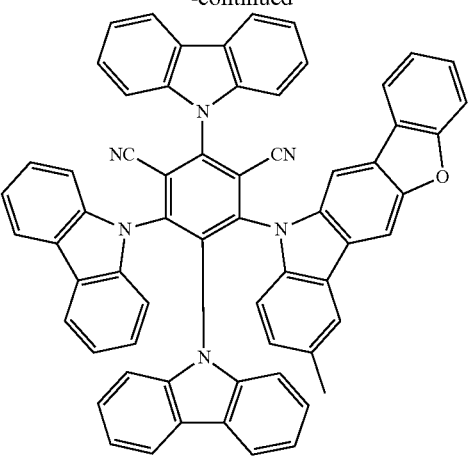
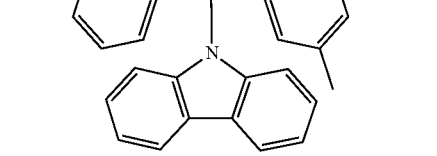
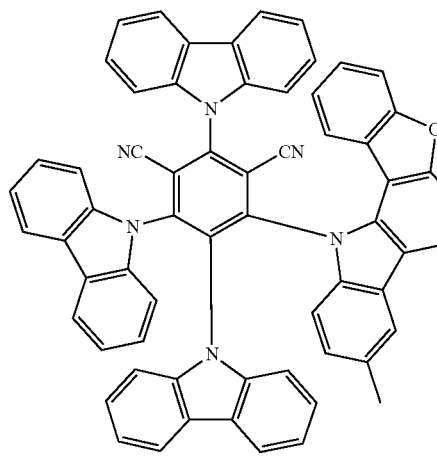

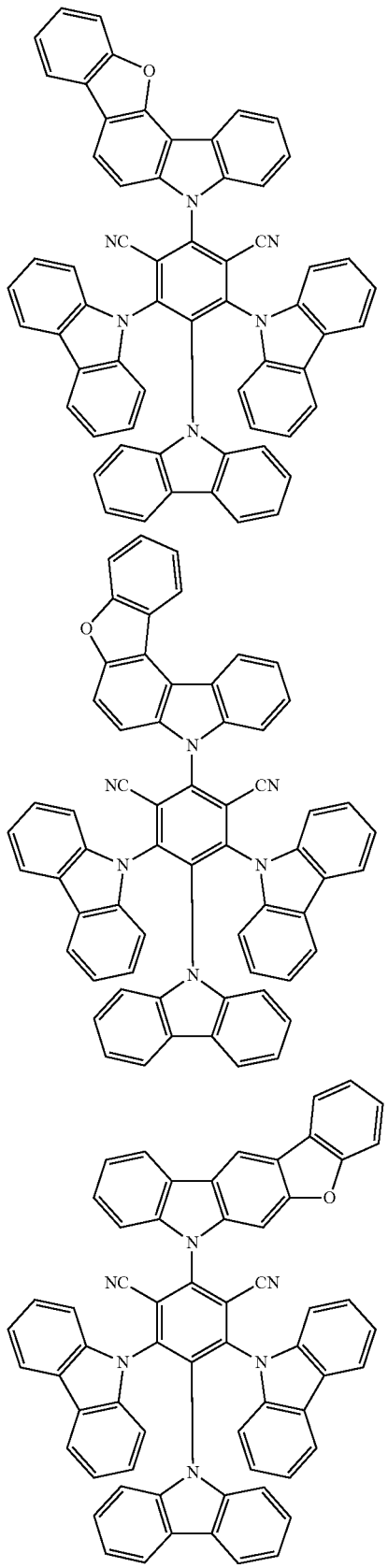
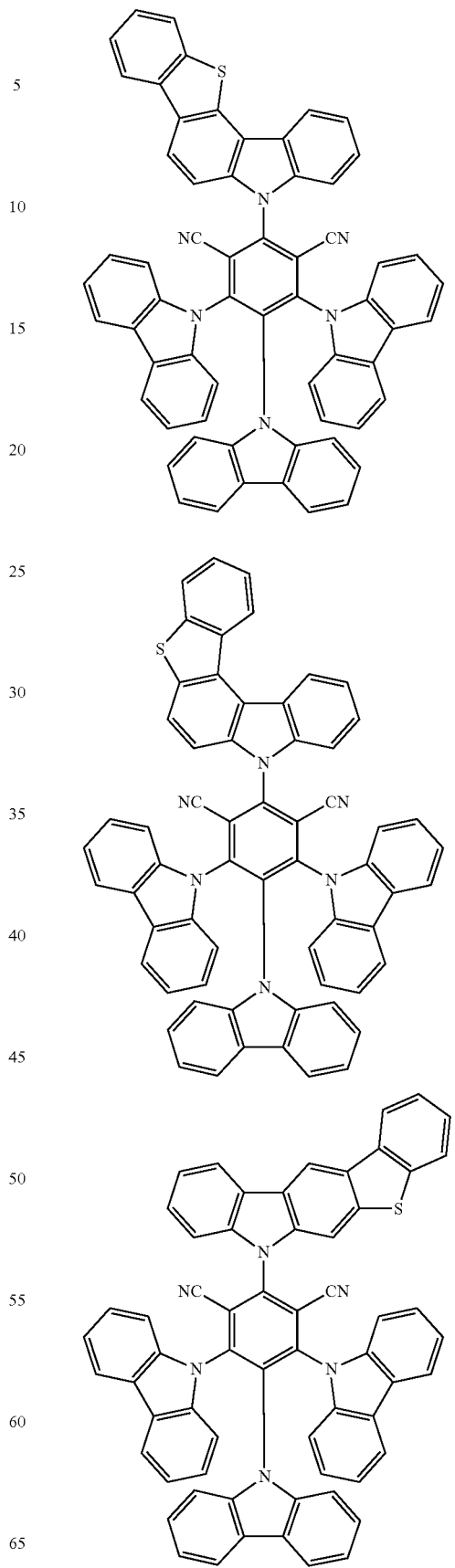

187
-continued
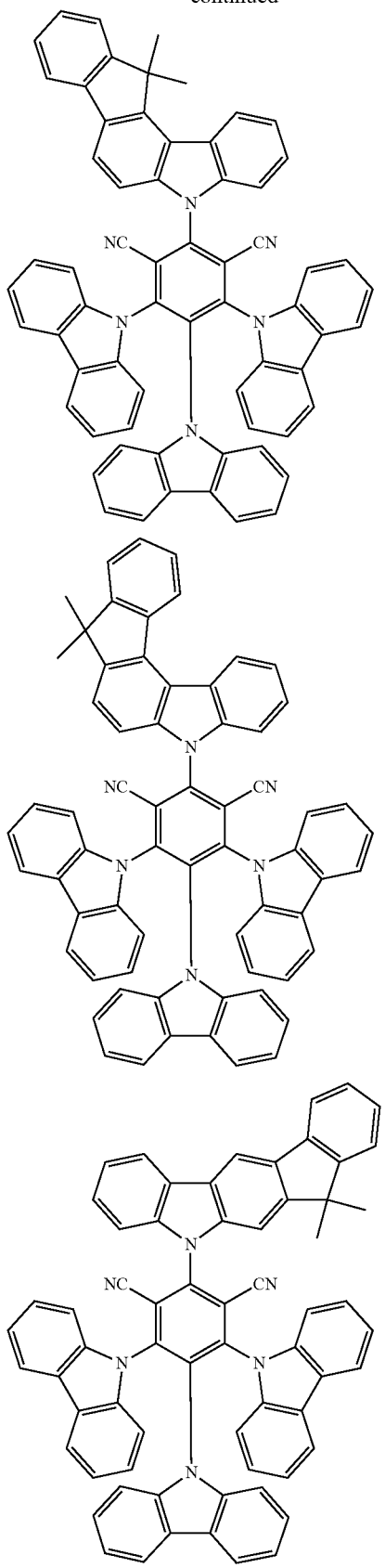
188
-continued
[Formula 63]
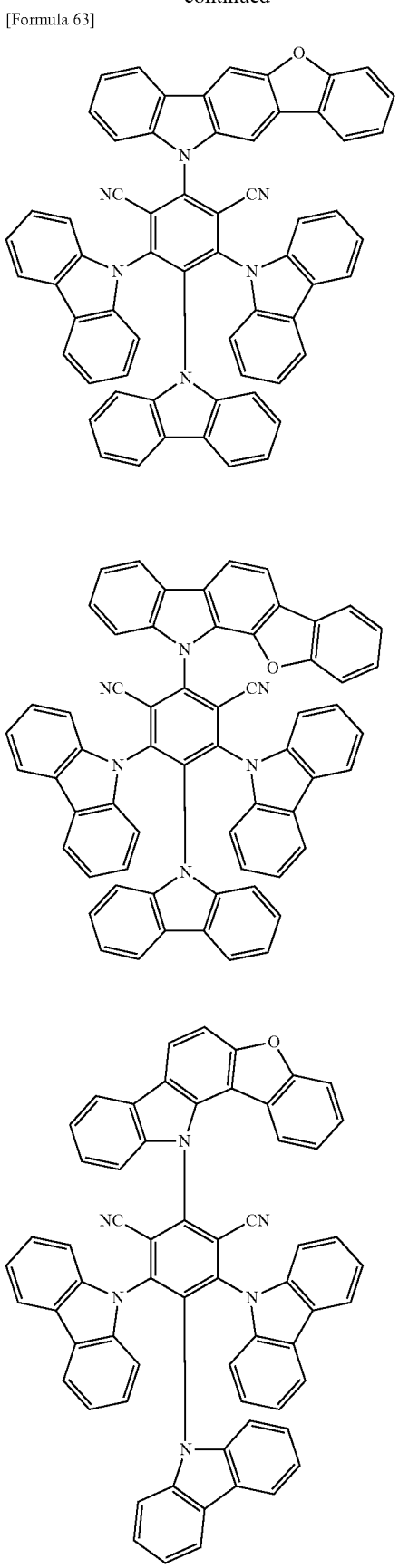

189
-continued
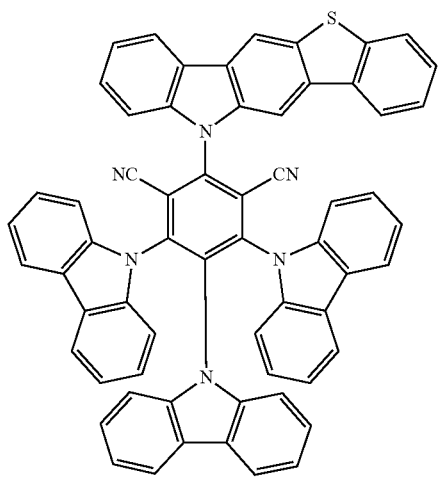
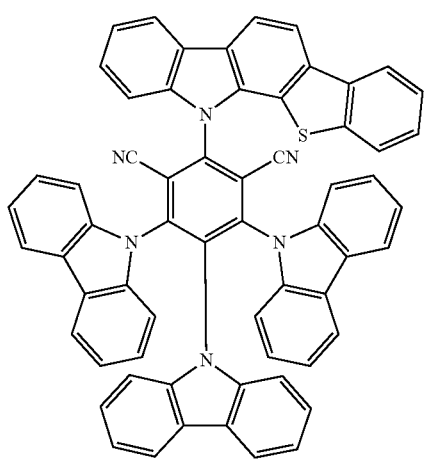
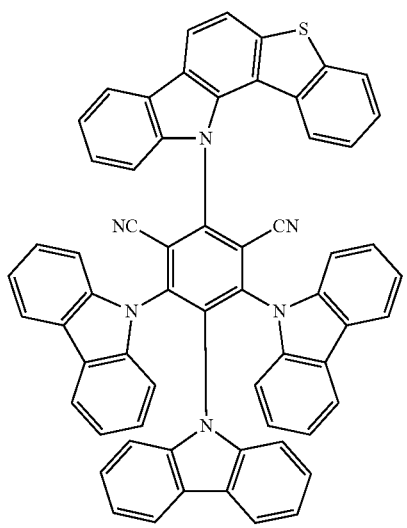
190
-continued
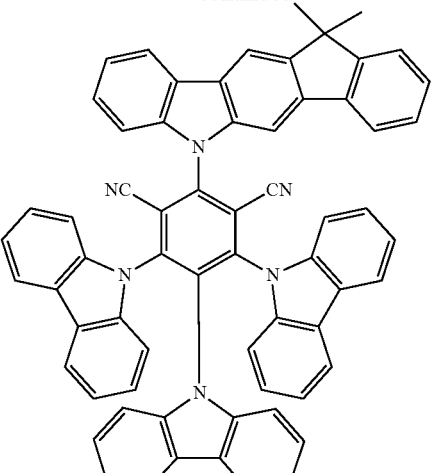
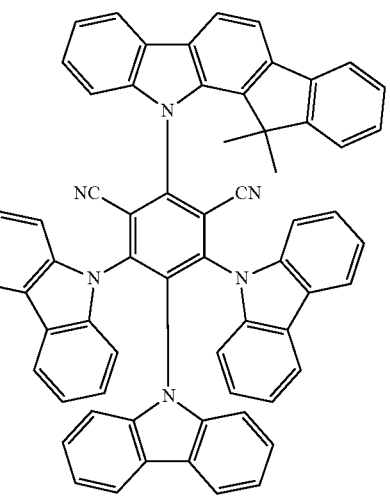
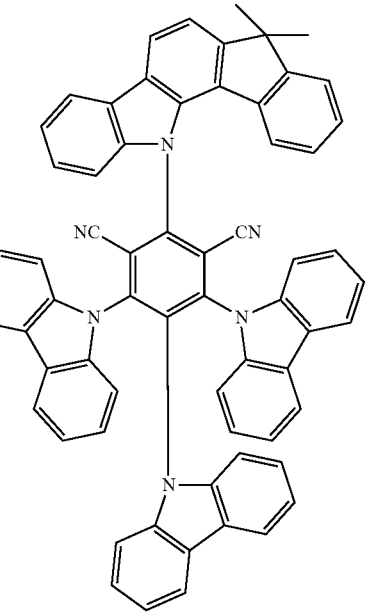

191
-continued
[Formula 64]
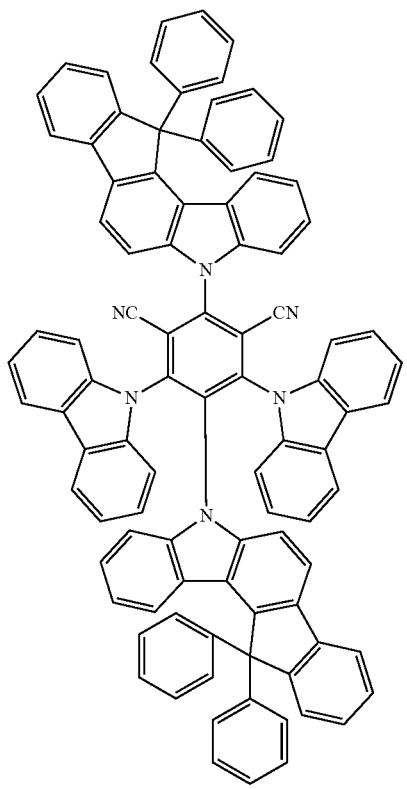
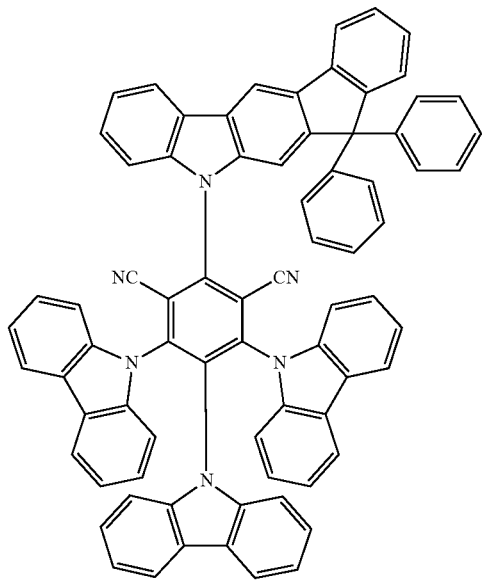
192
-continued
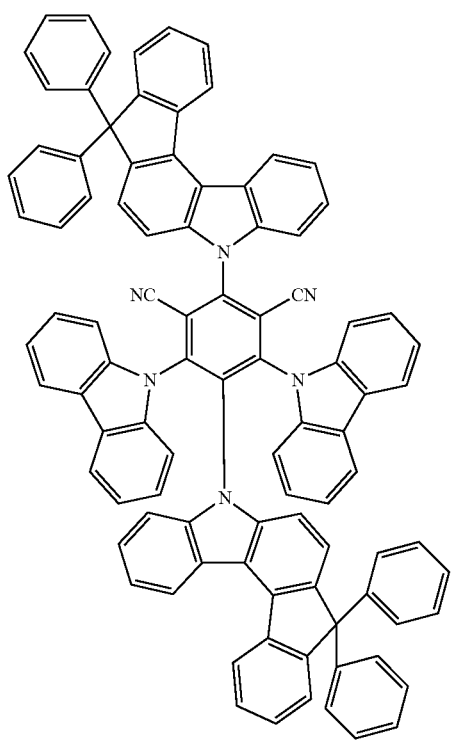
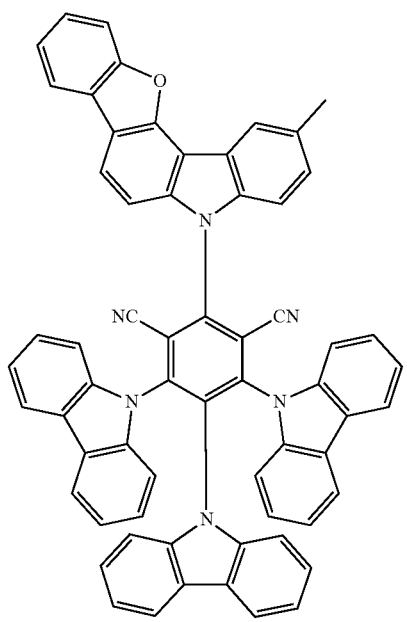

[Formula 65]
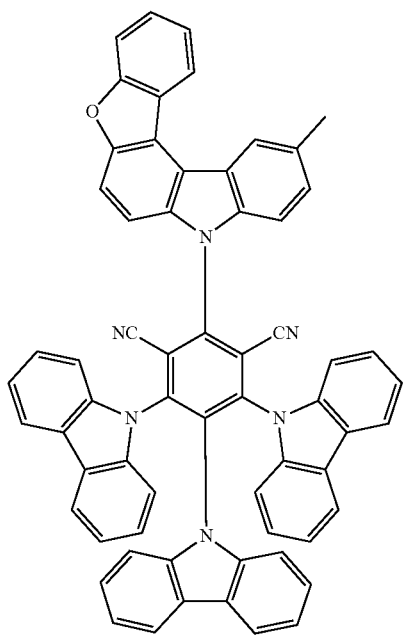
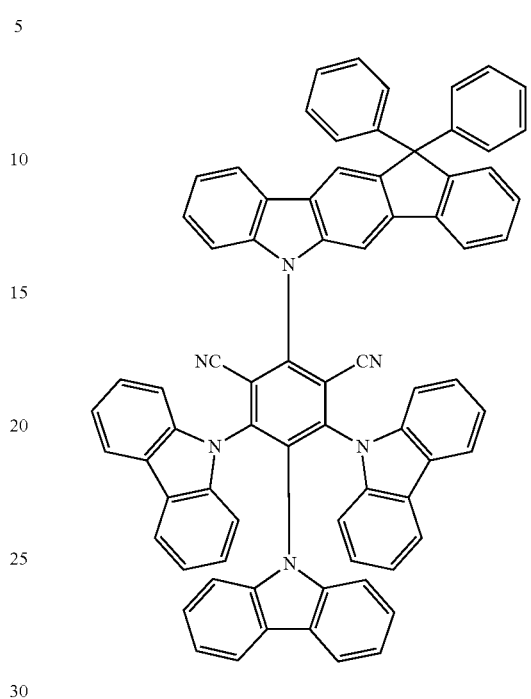
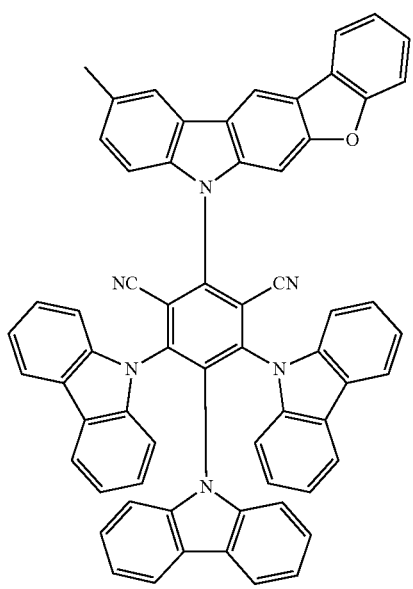
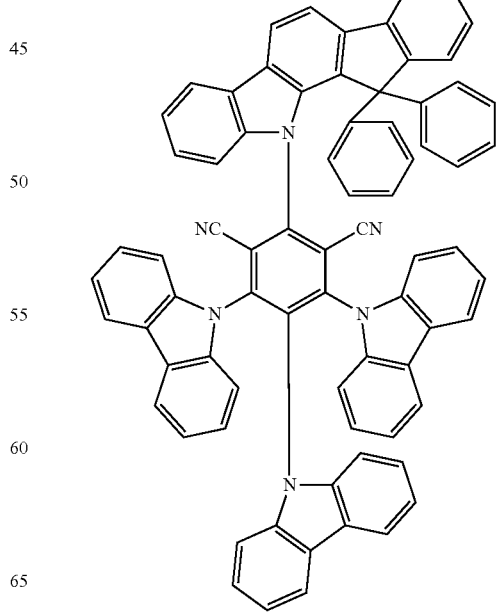

195
-continued
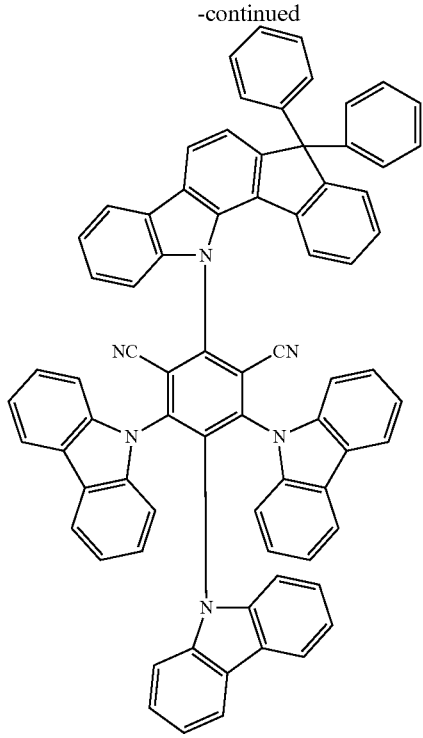
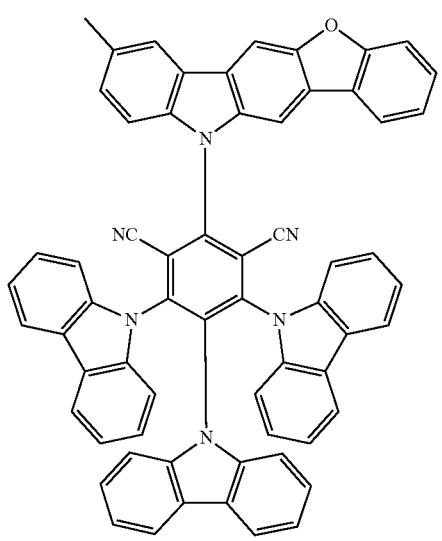
196
-continued
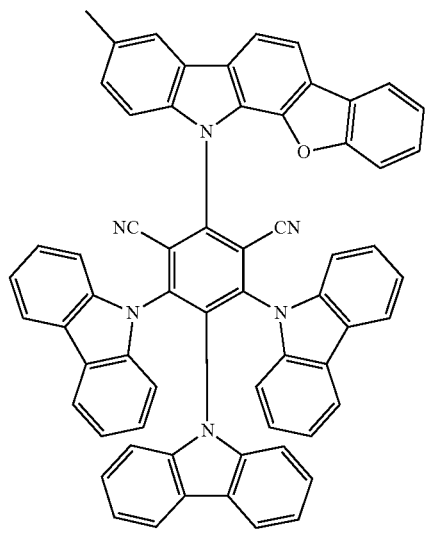
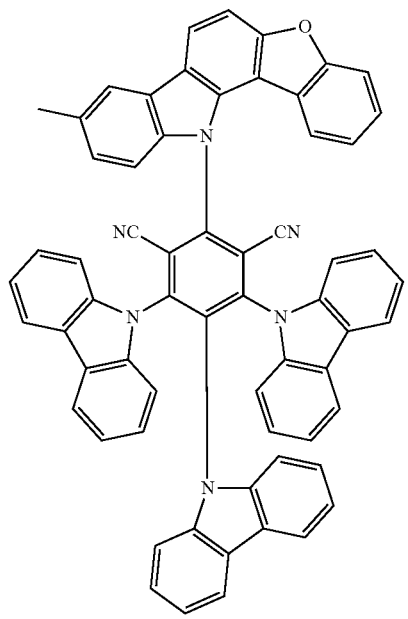

-continued
[Formula 66]
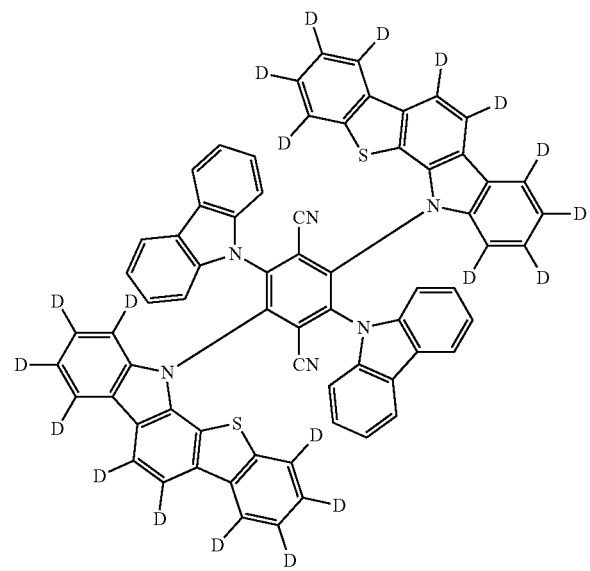
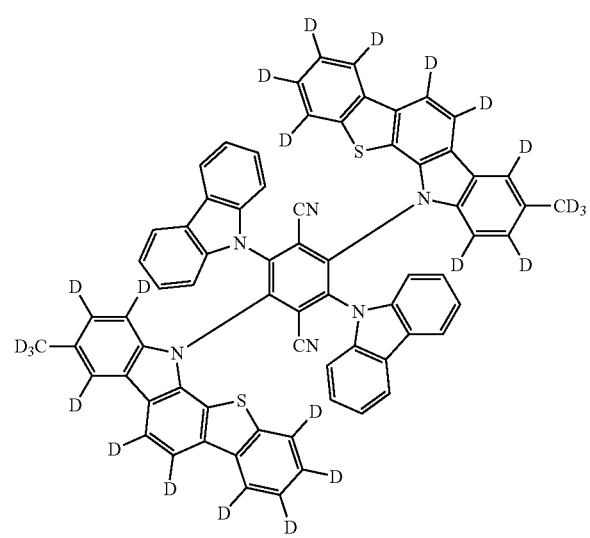
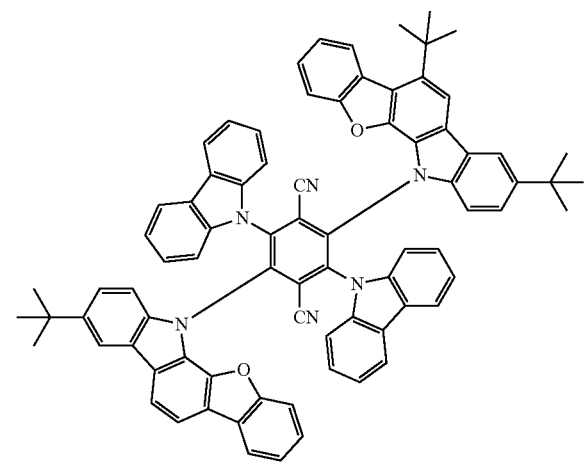
-continued
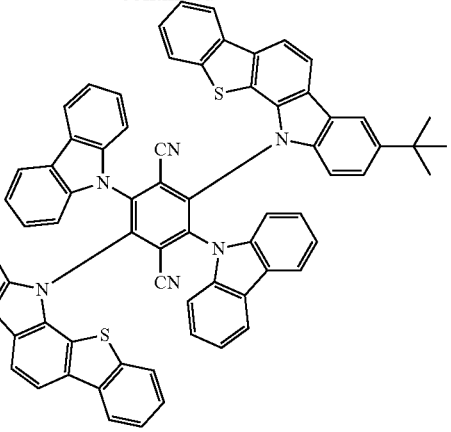
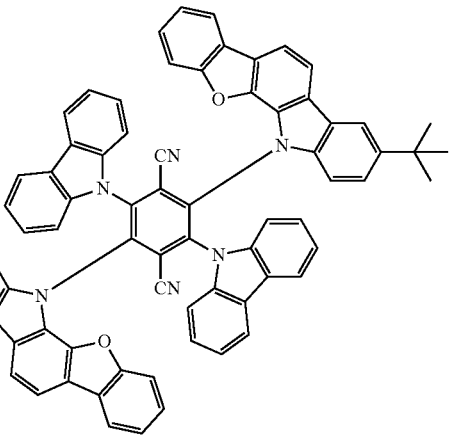
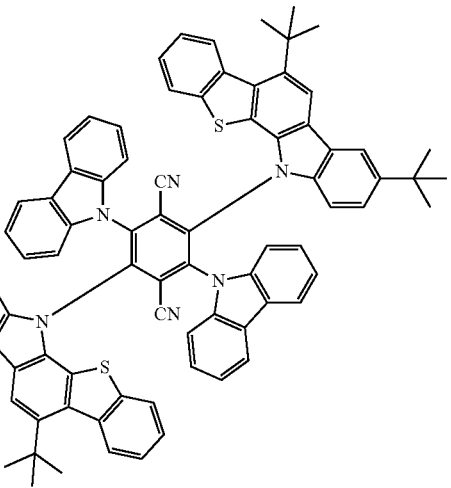

[Formula 67]
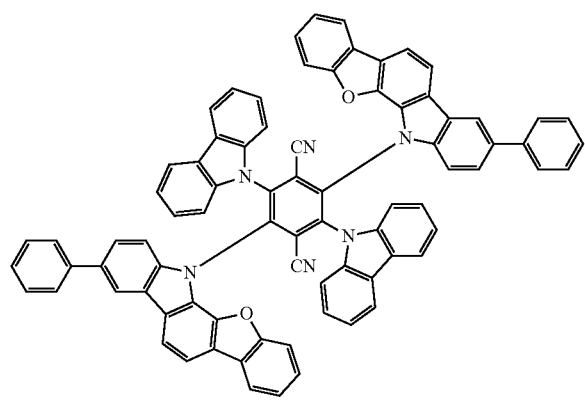
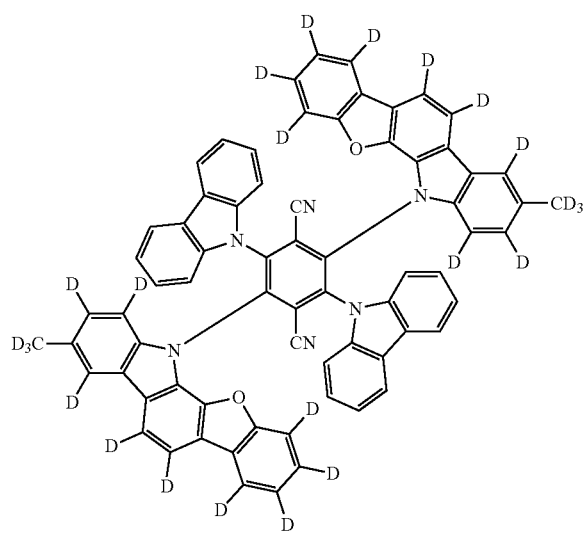
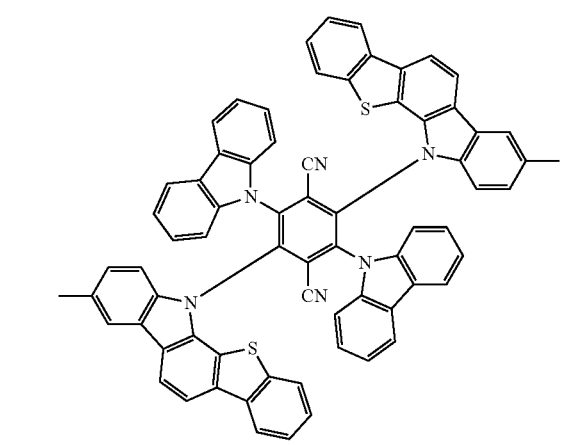
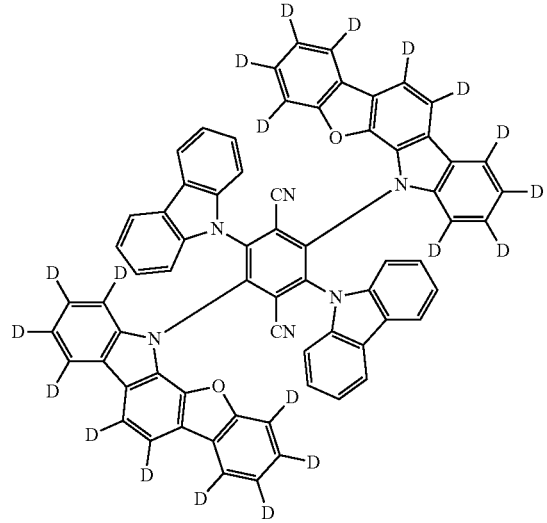
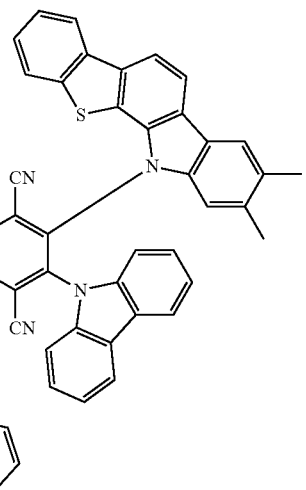

[Formula 68]
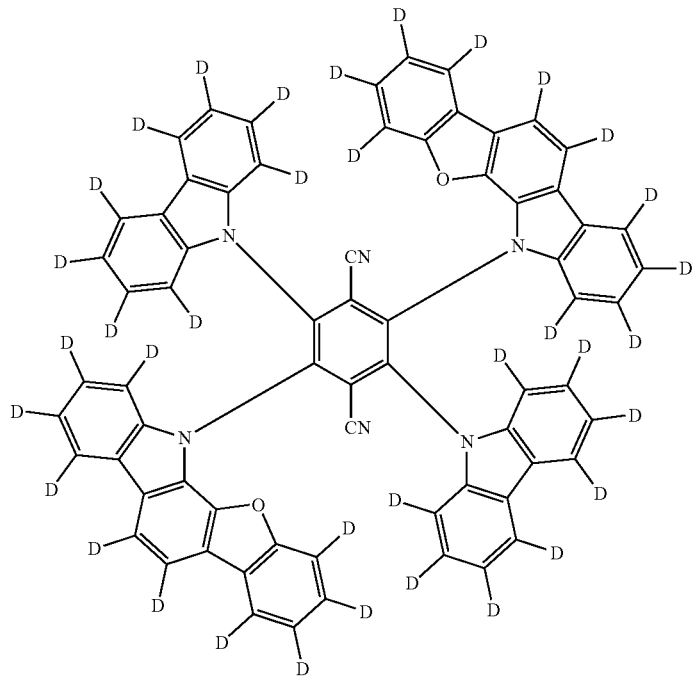
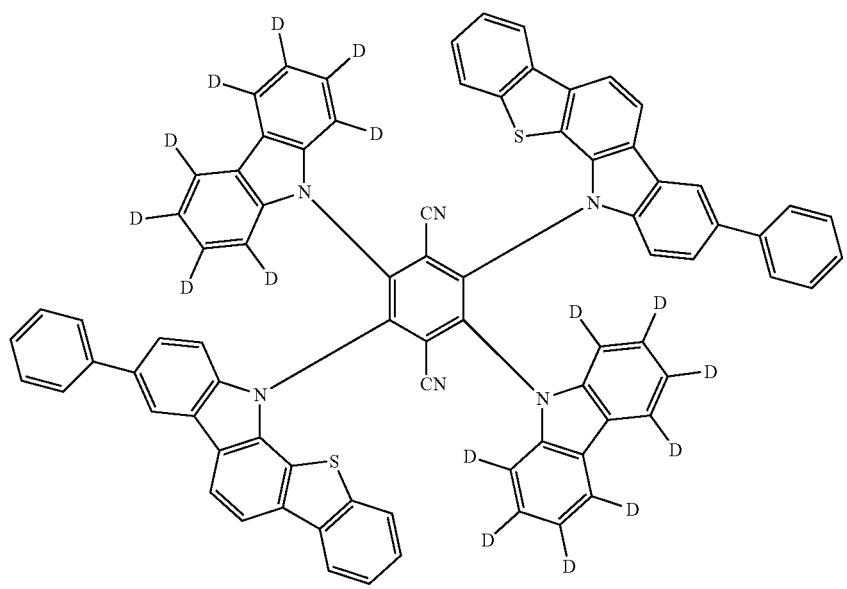

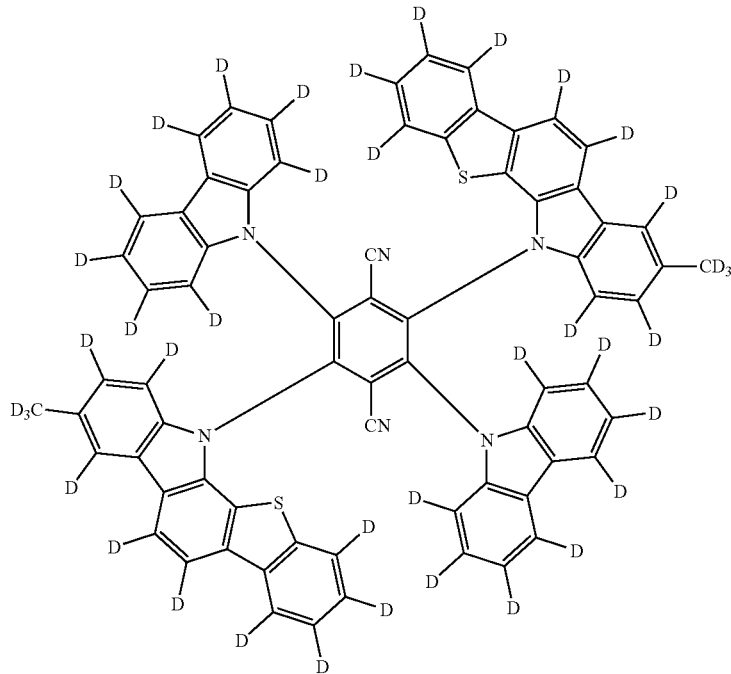
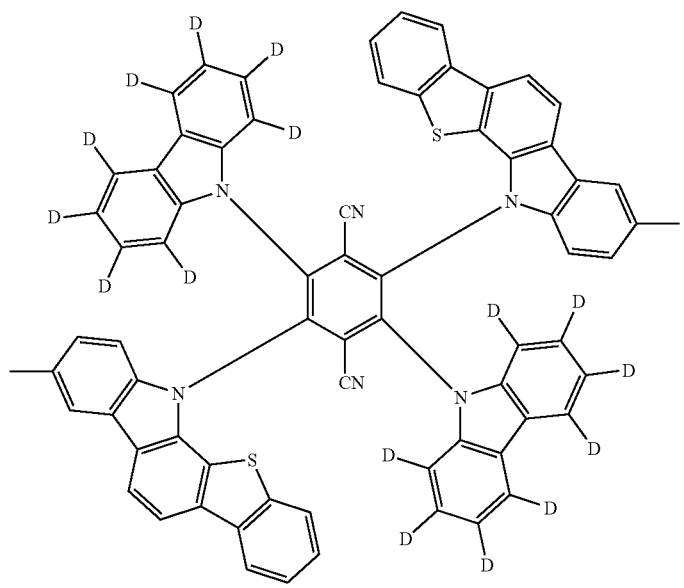

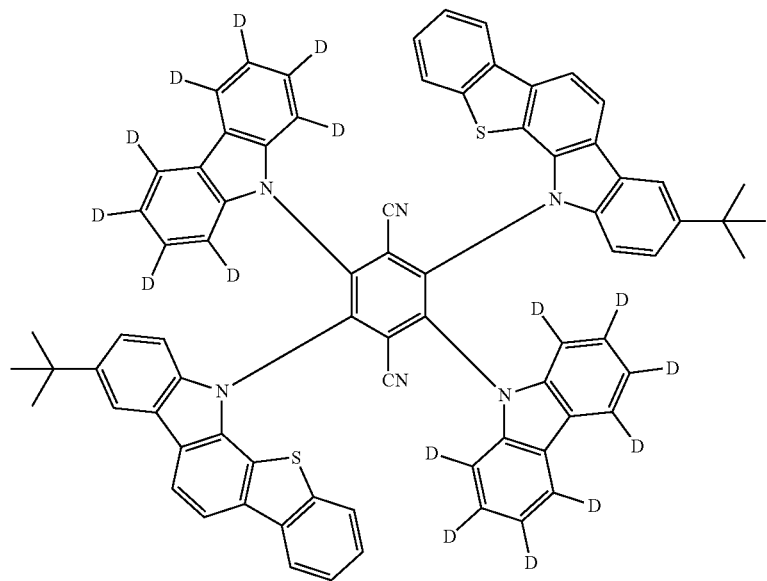
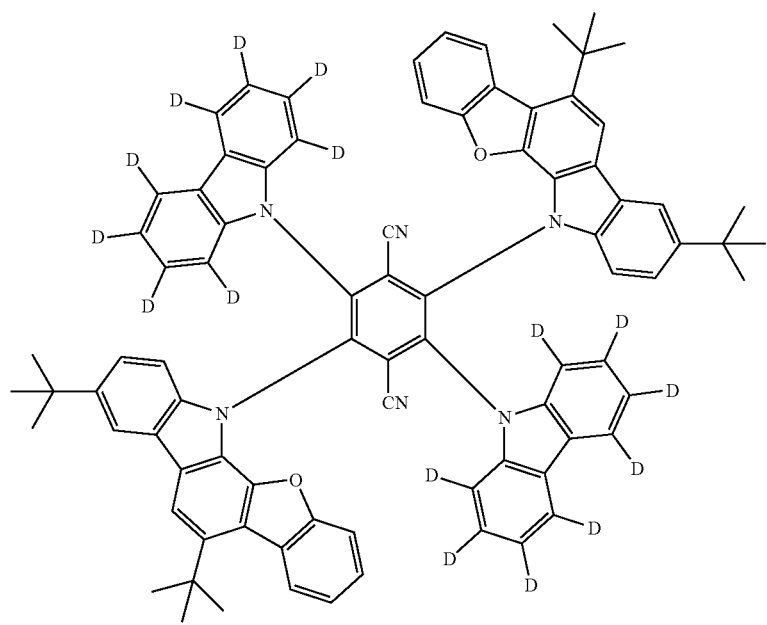

[Formula 69]
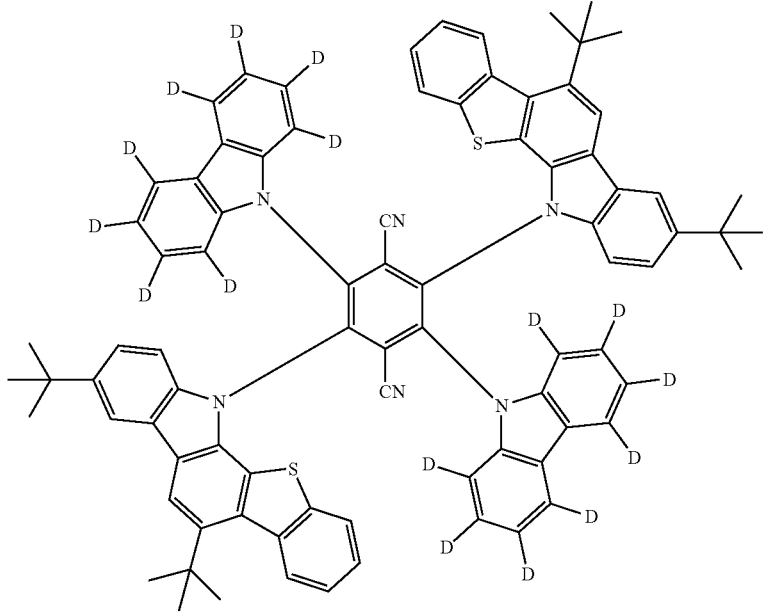
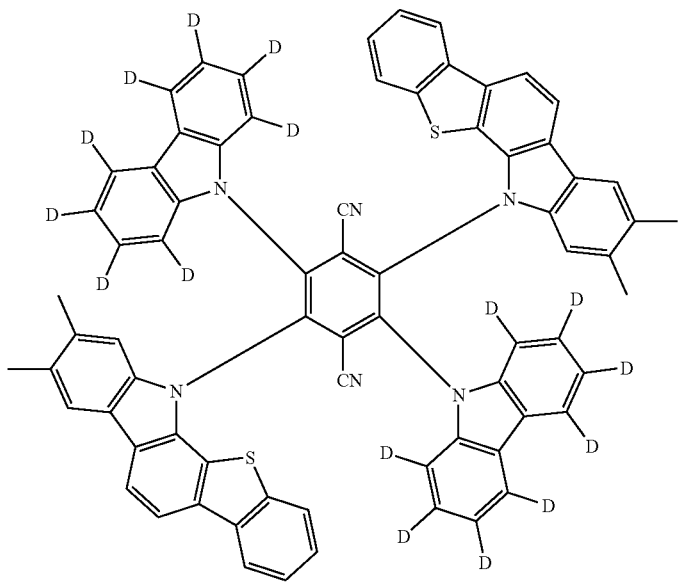

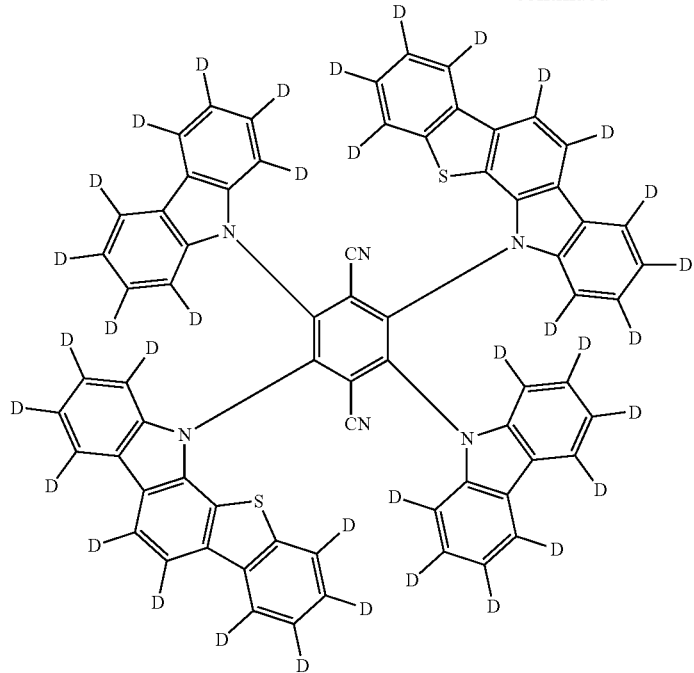
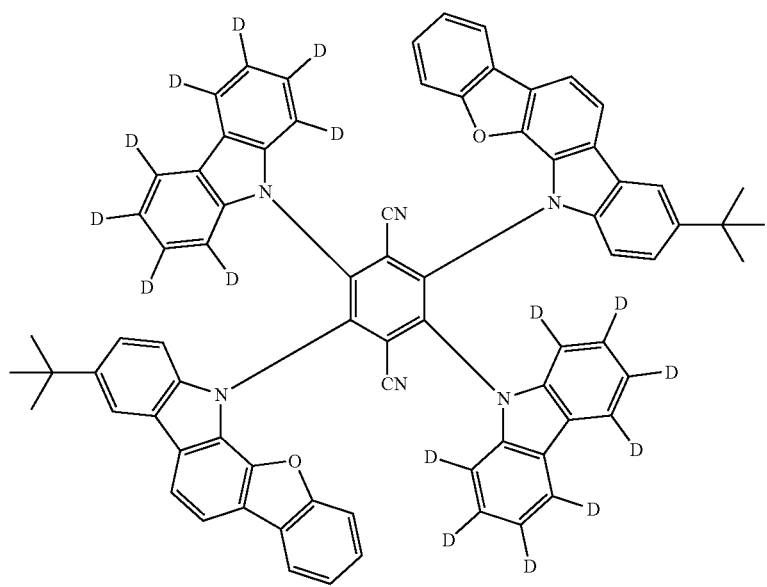

211 212
-continued
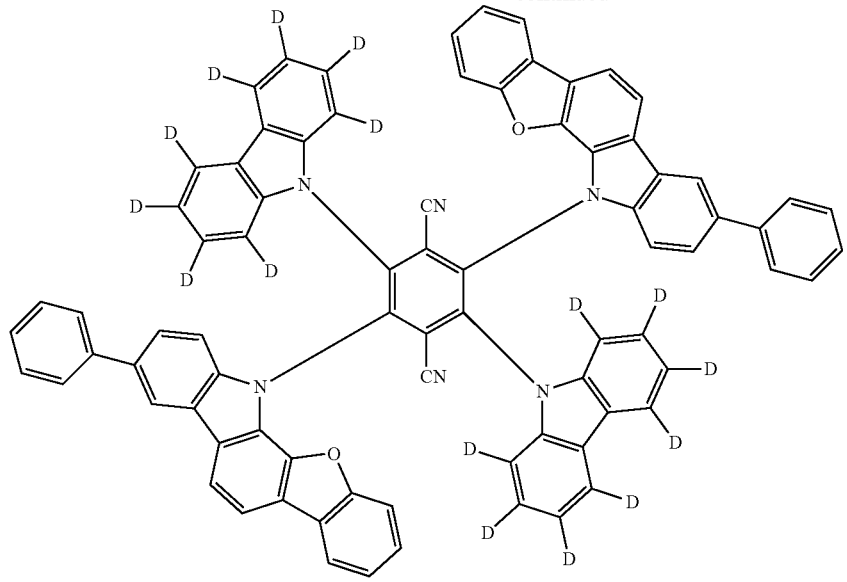
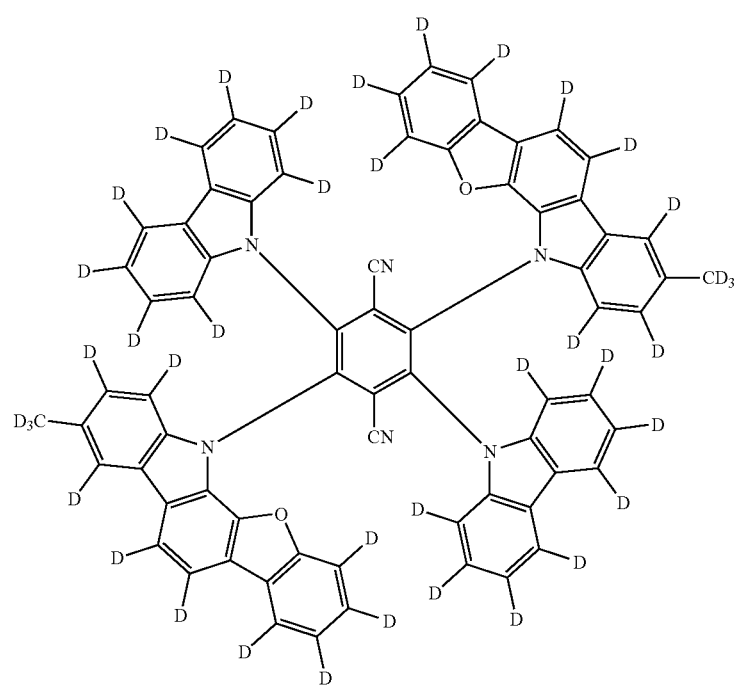

[Formula 70]
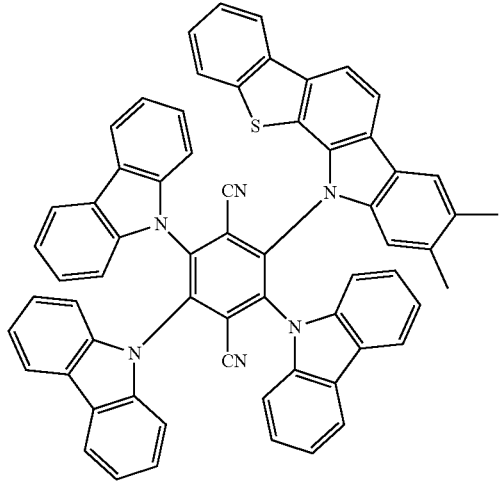
213
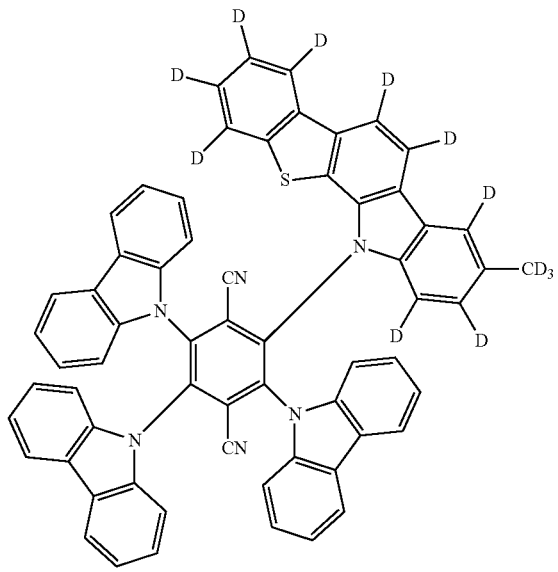
214
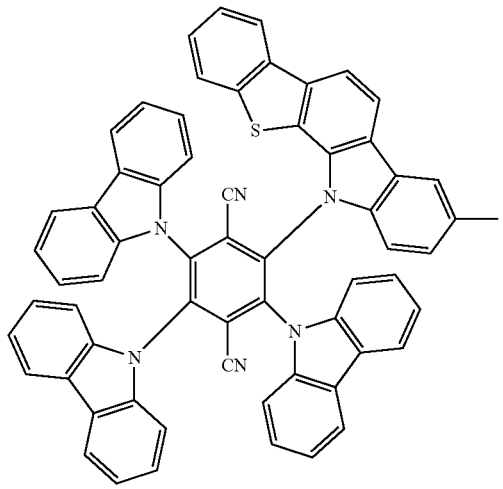
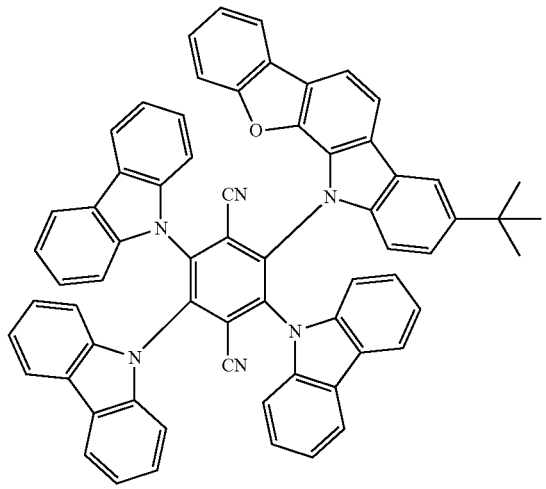
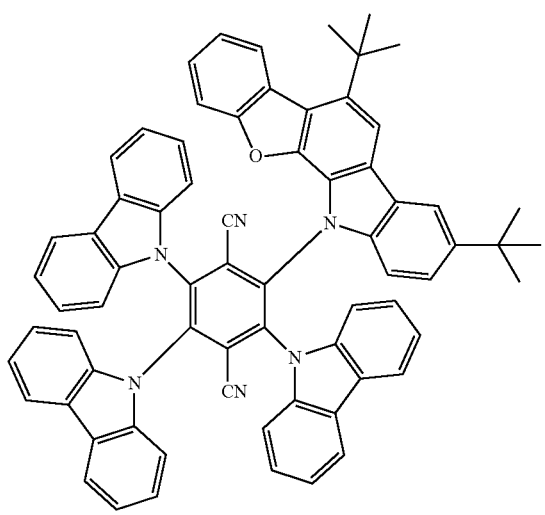
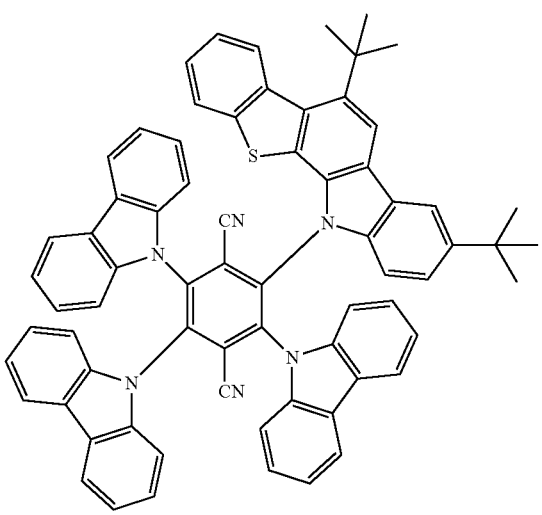

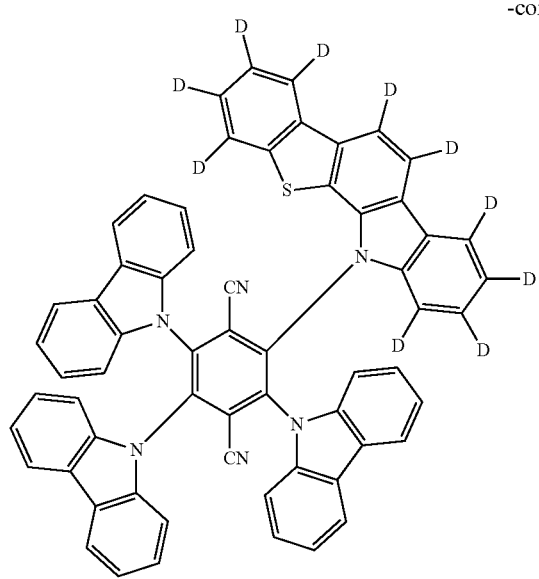
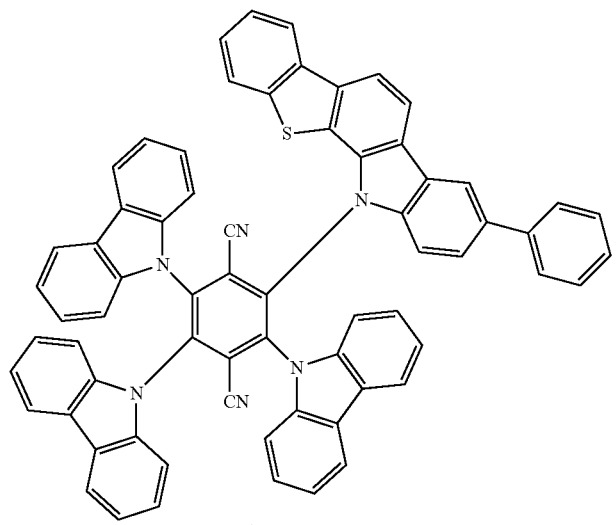
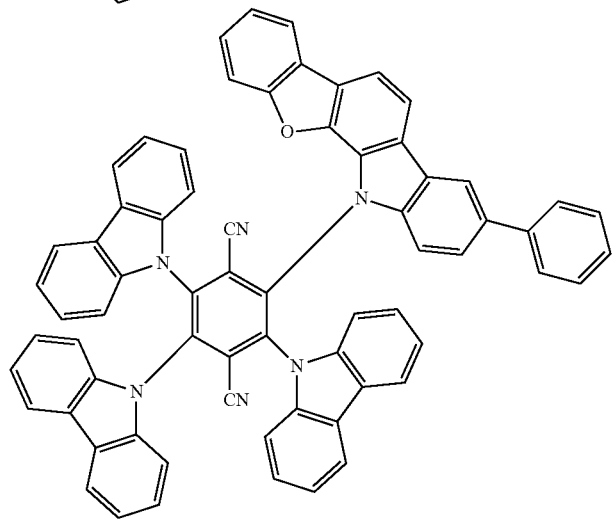

217 218
-continued
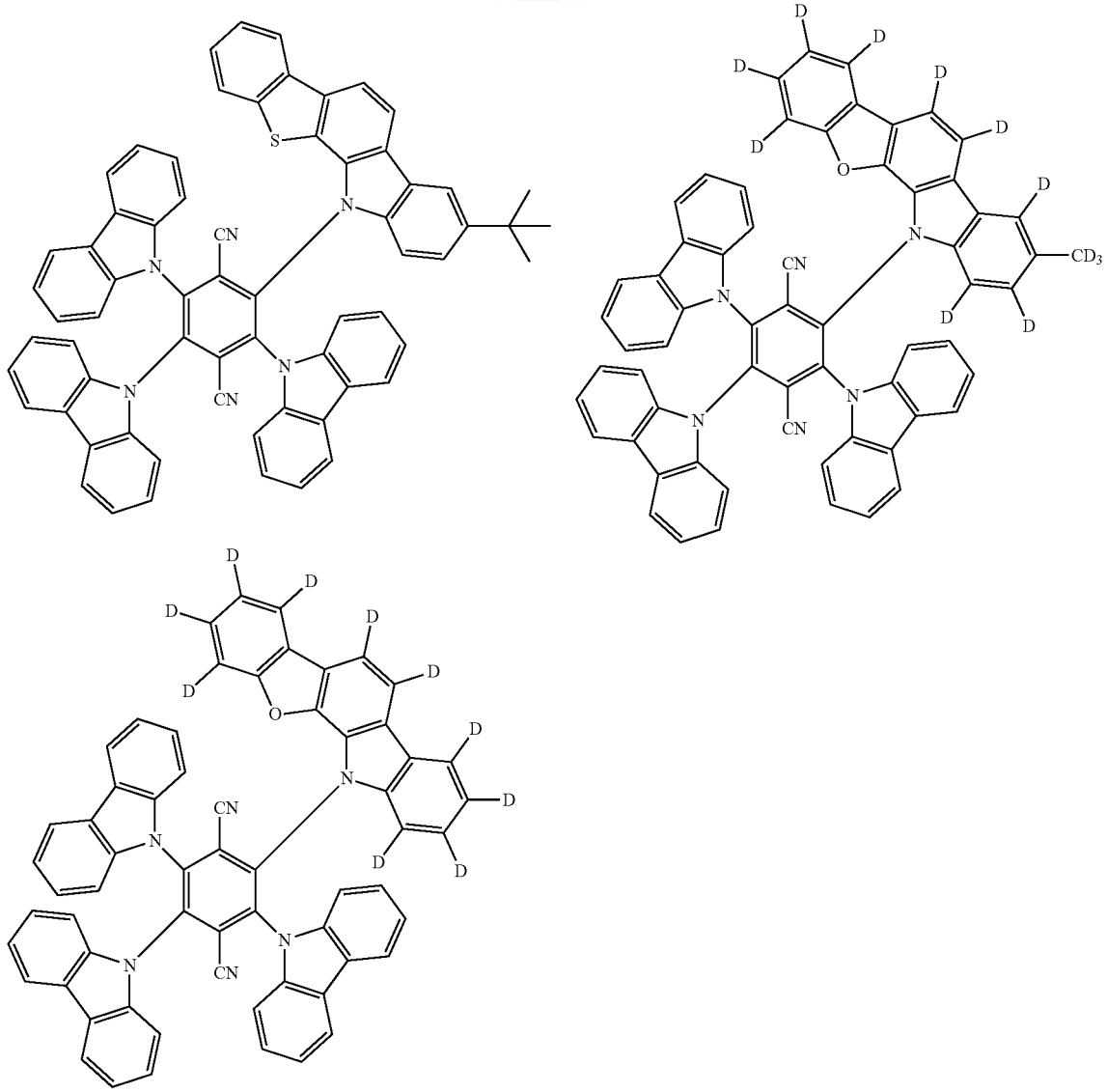
[Formula 71]
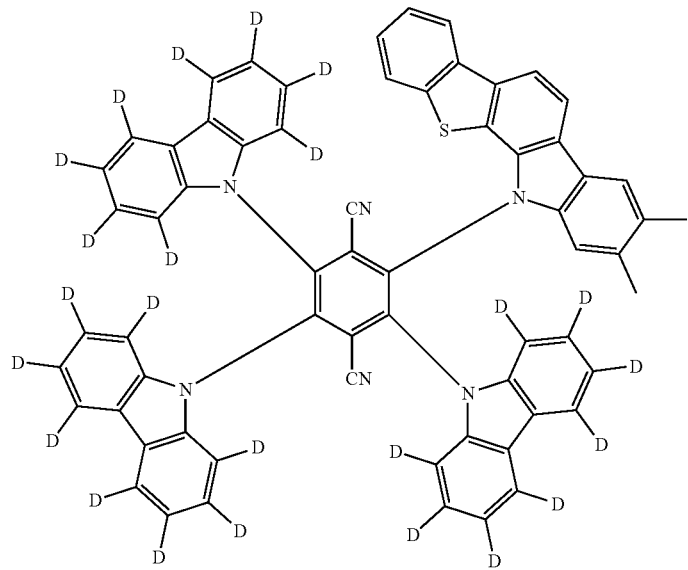

-continued
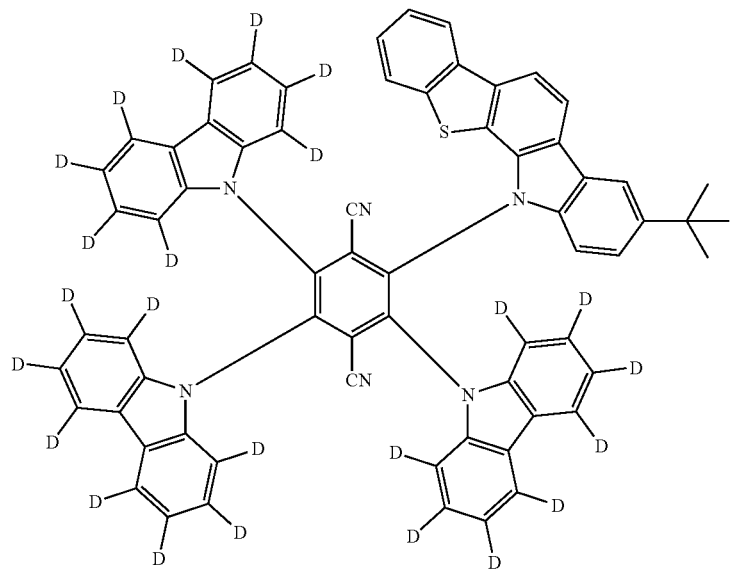
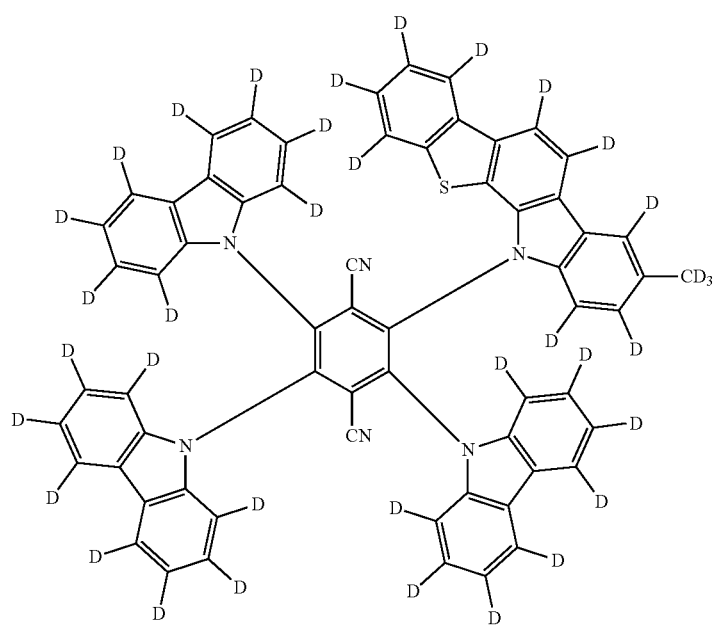

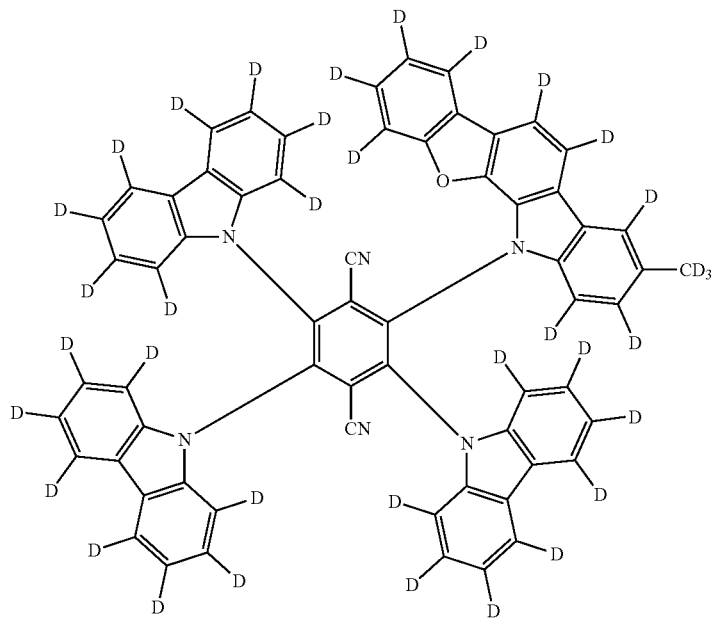
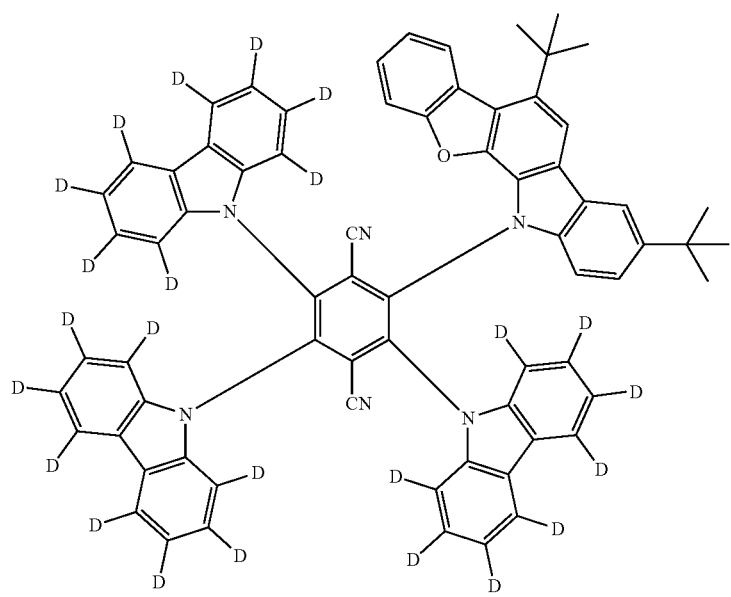

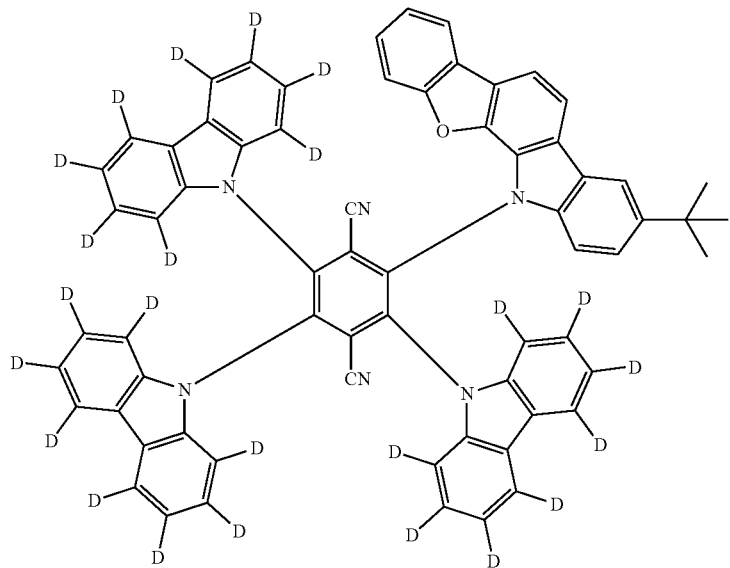
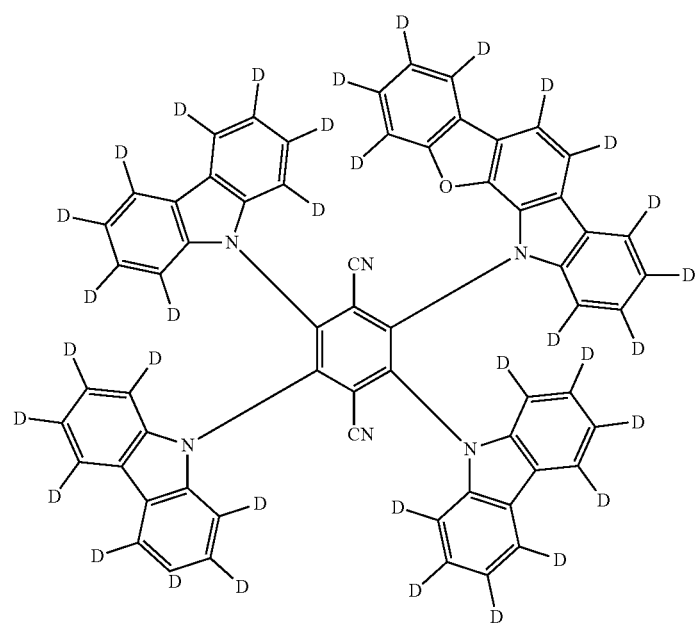

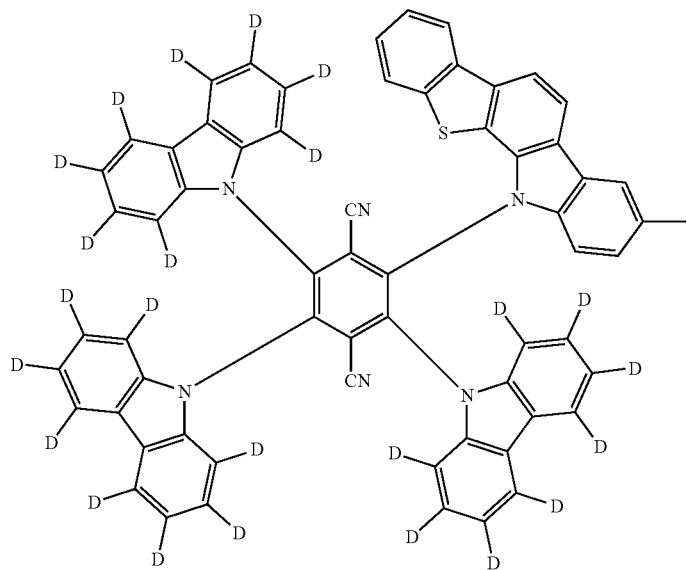
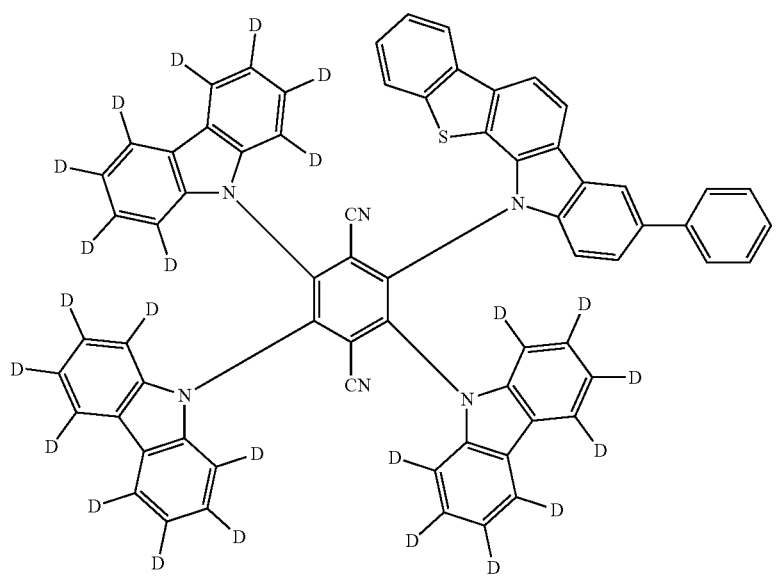

-continued
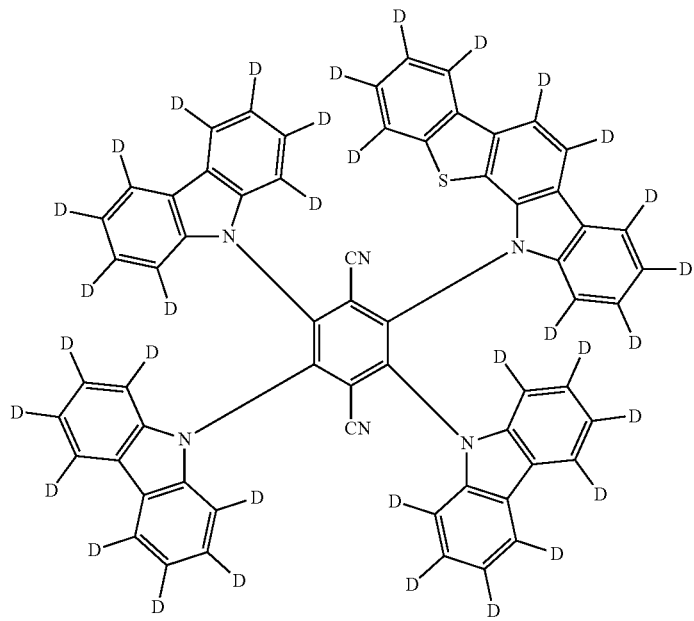
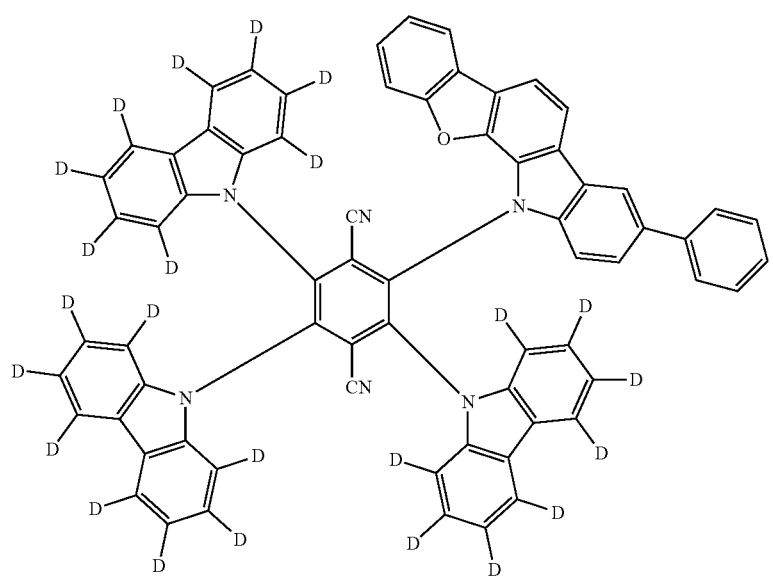

-continued
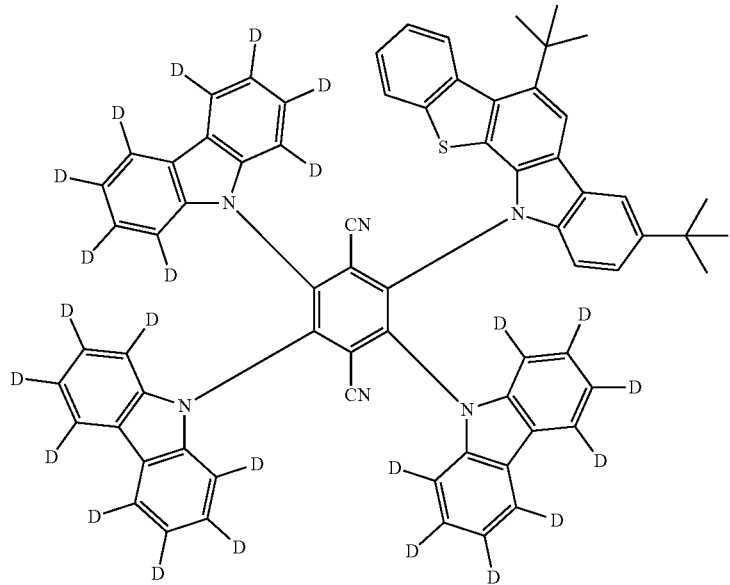
[Formula 72]
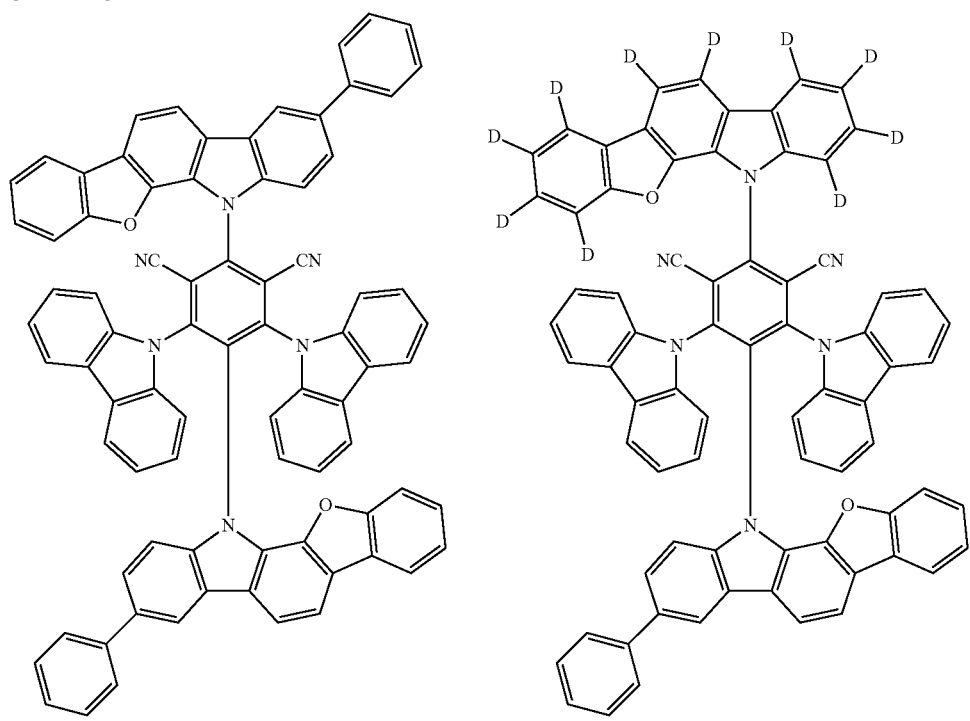

-continued
| 231 | 232 |
|---|---|
| 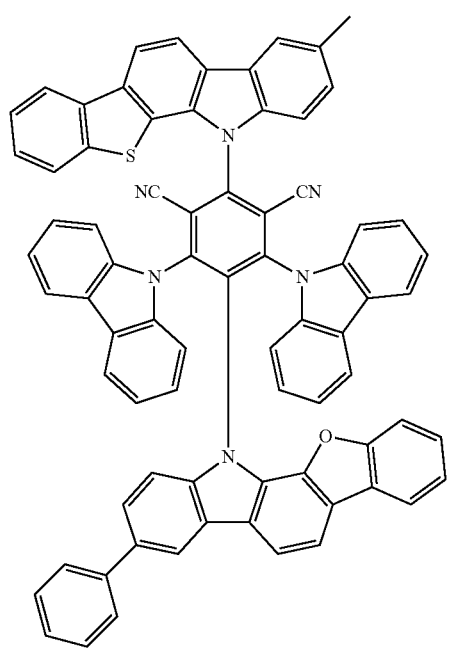 | 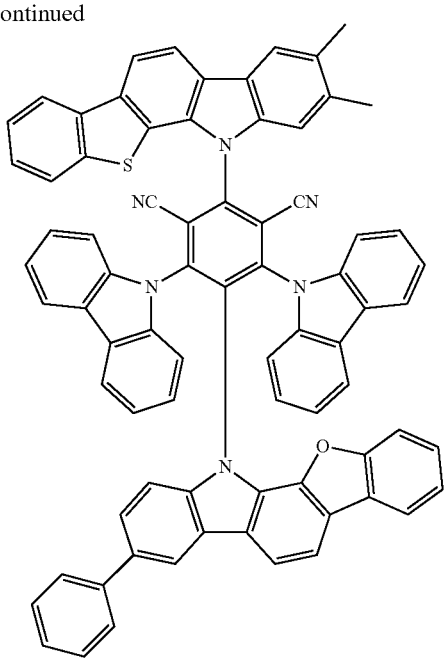 |
| 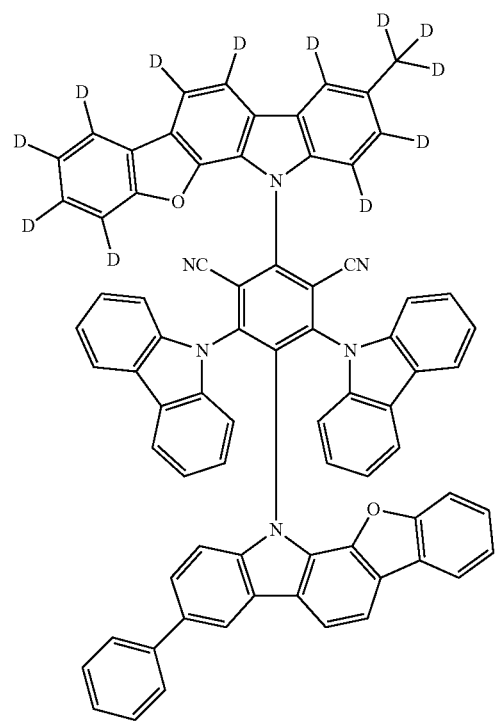 | 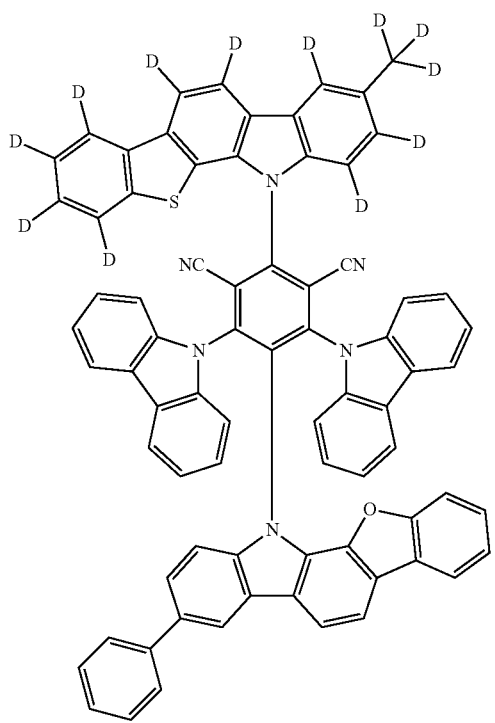 |

233
234
-continued
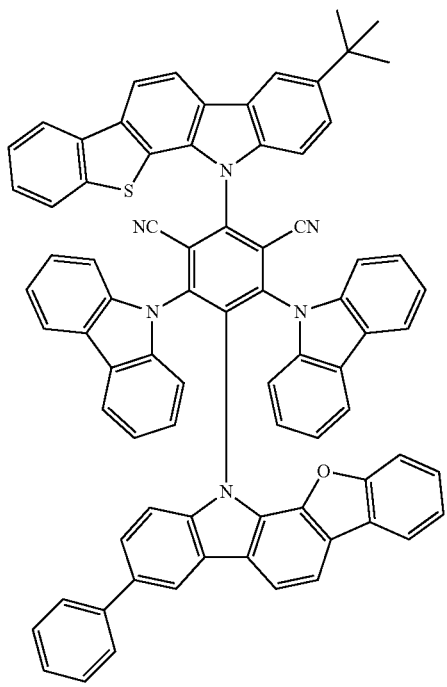
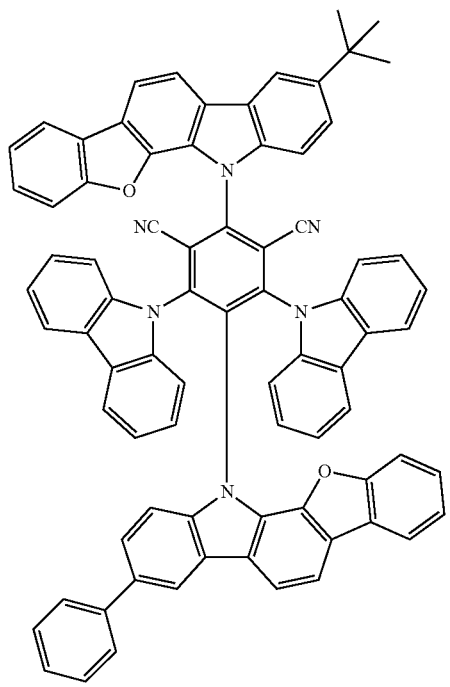
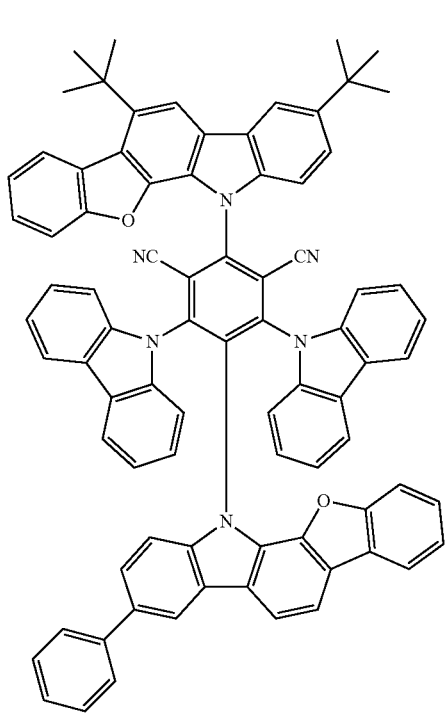
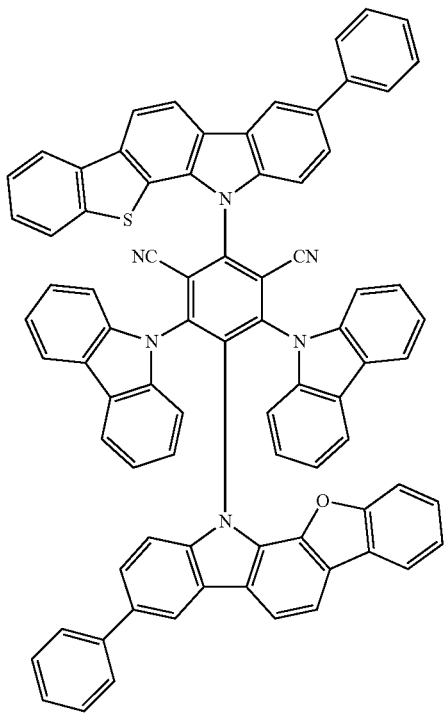

235
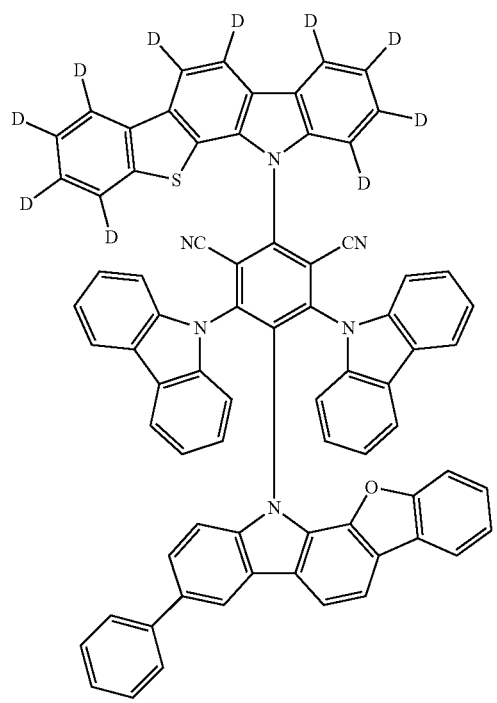
236
-continued
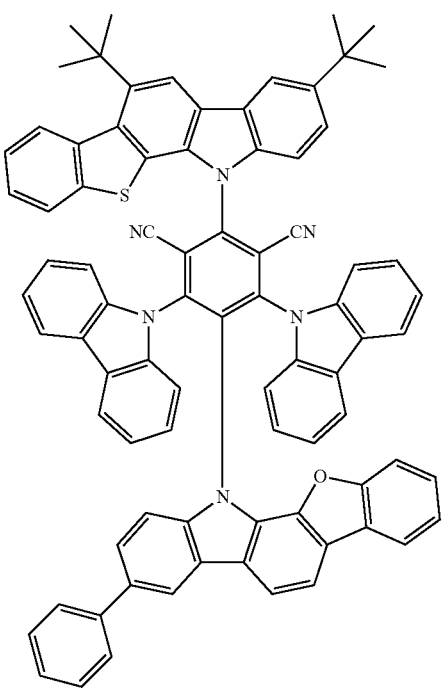
[Formula 73]
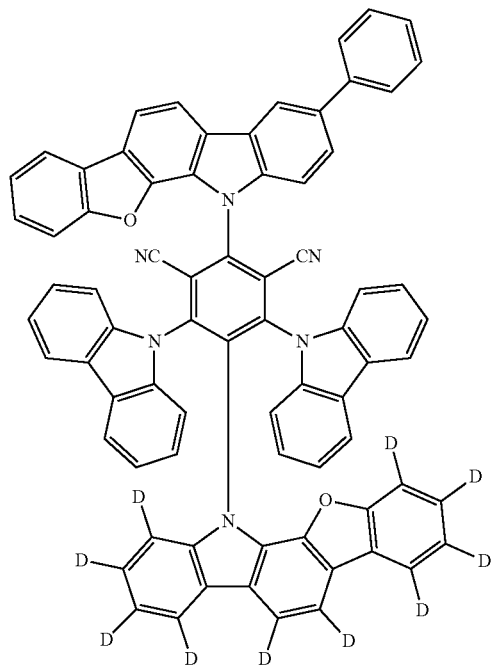
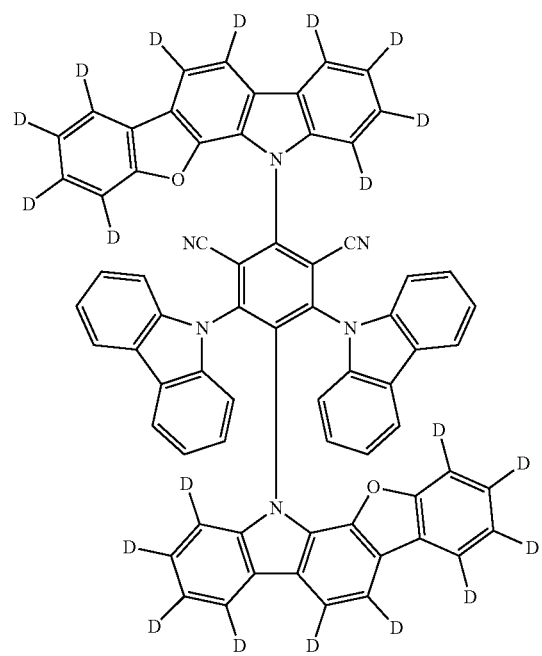

-continued
237
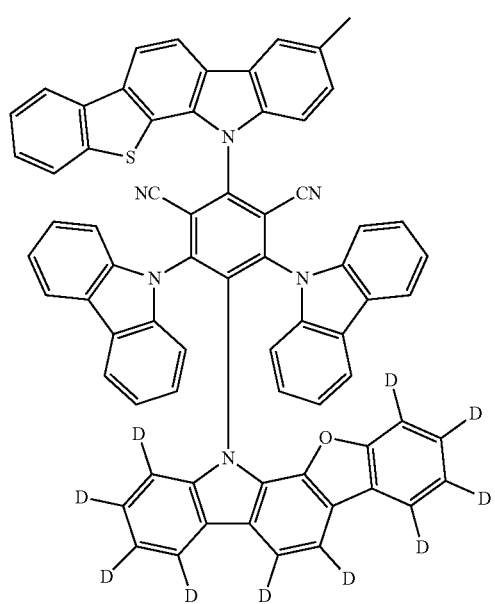
238
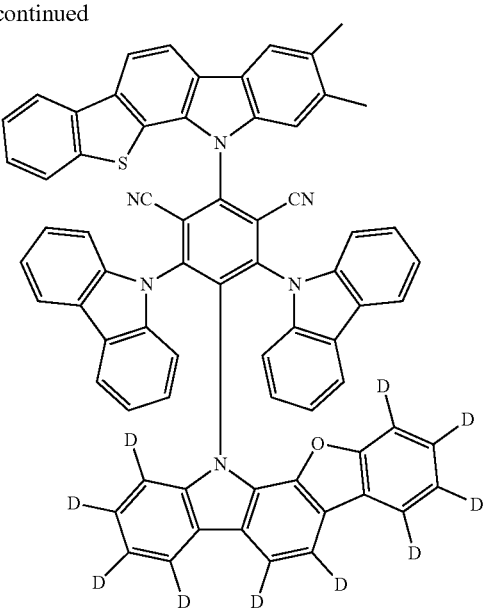
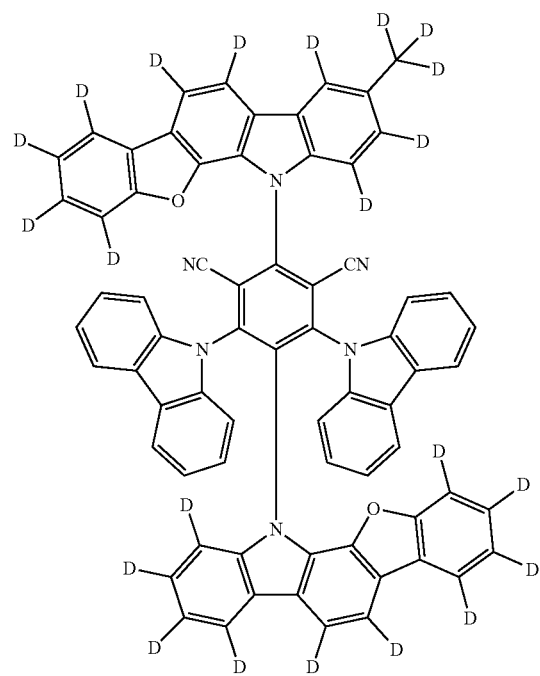
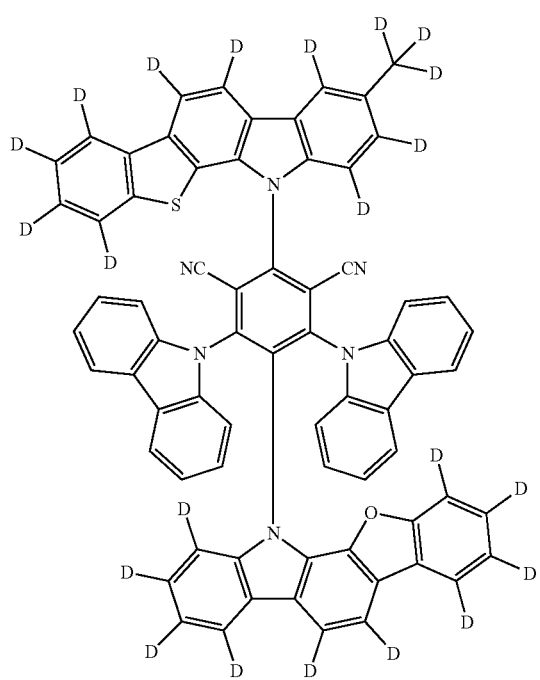

-continued
239
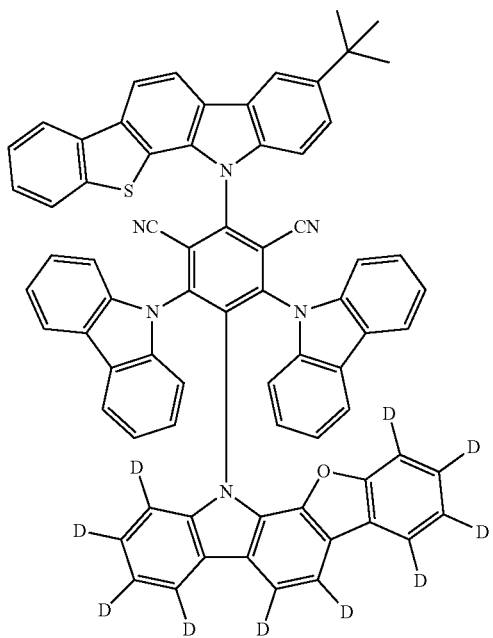
240
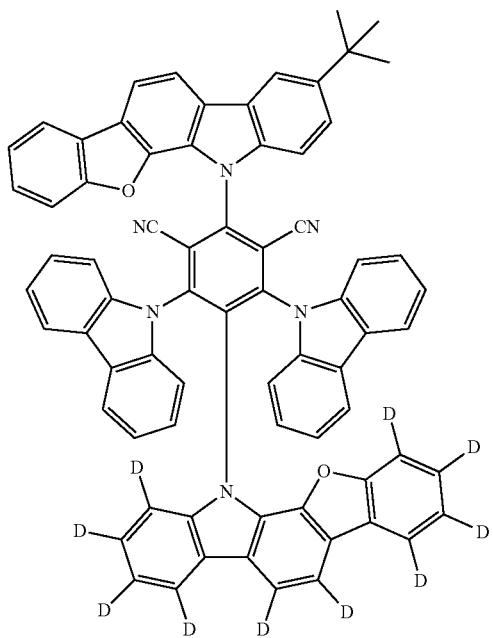
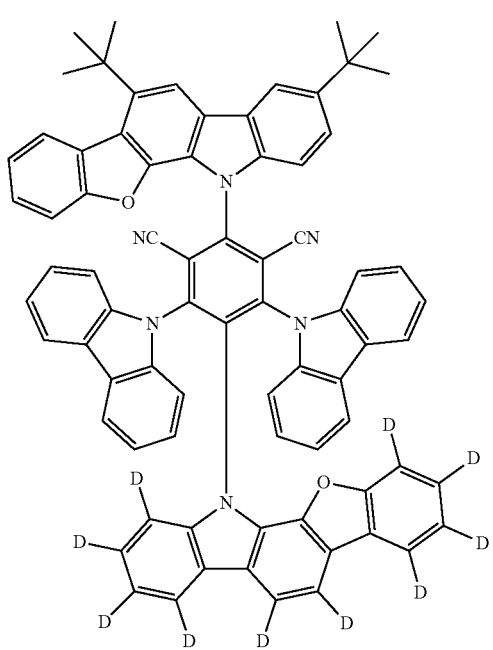
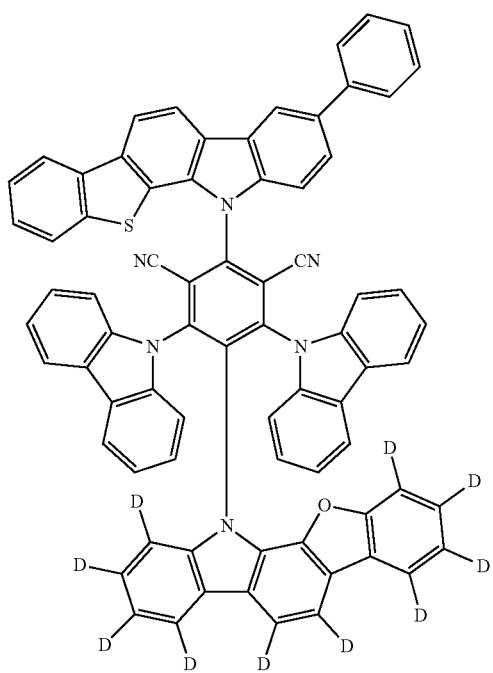

241
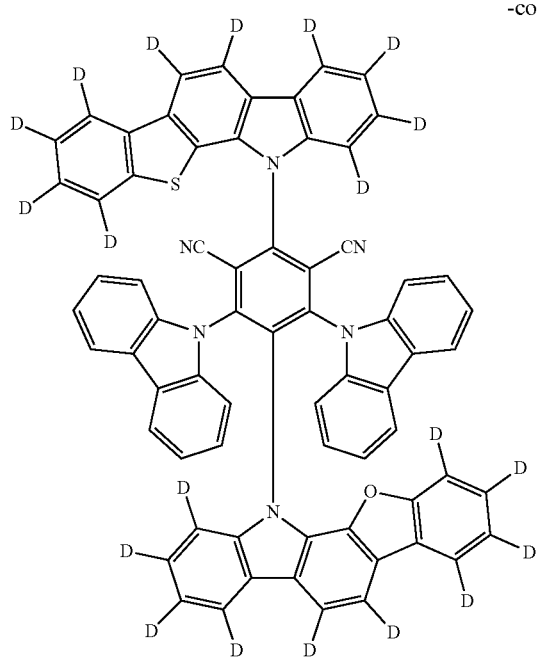
242
-continued
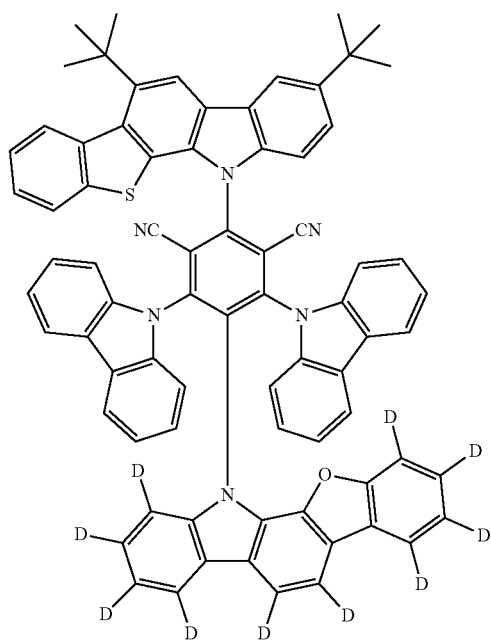
[Formula 74]
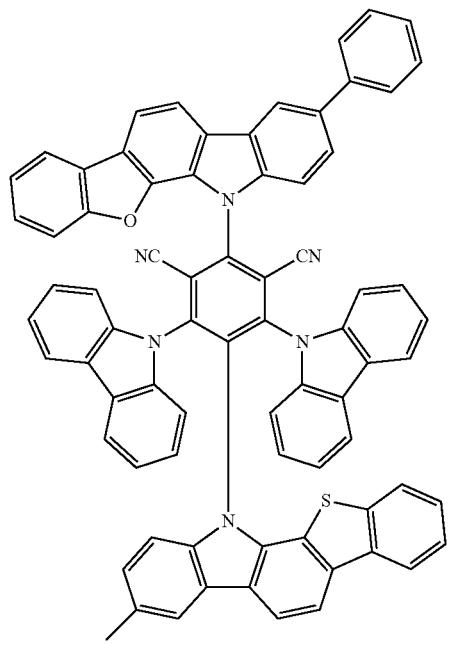
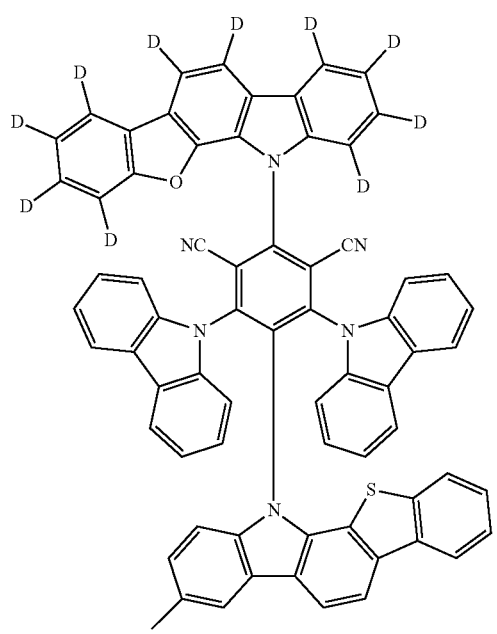

243
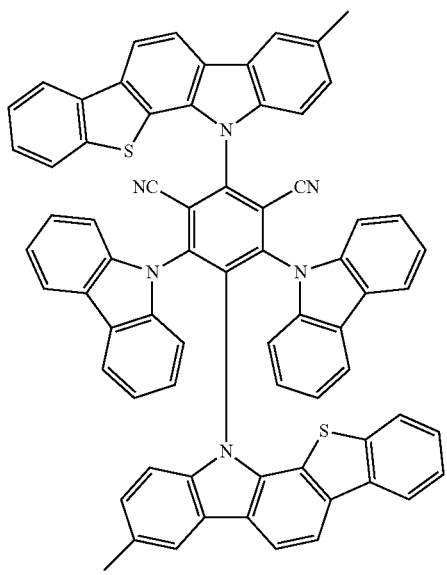
244
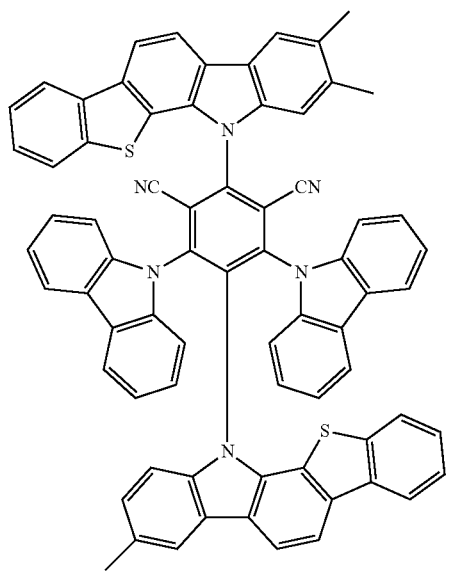
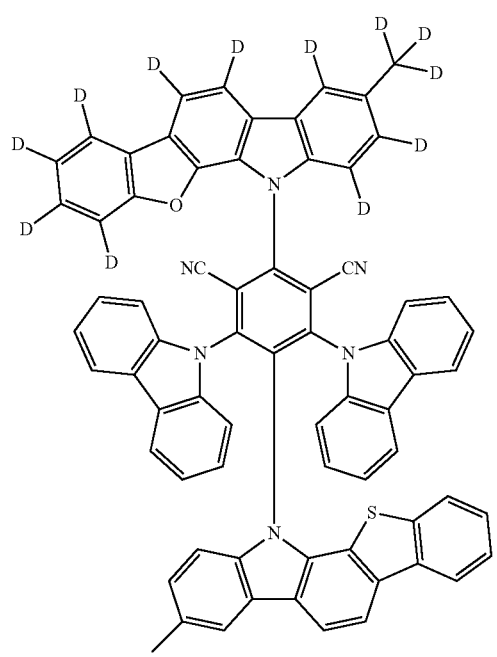
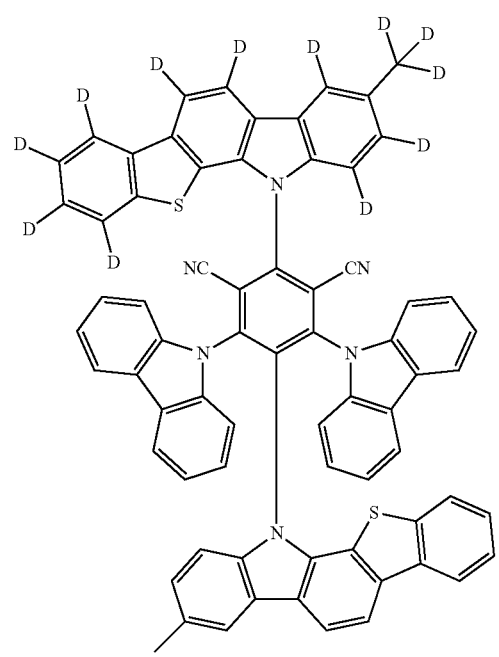

245
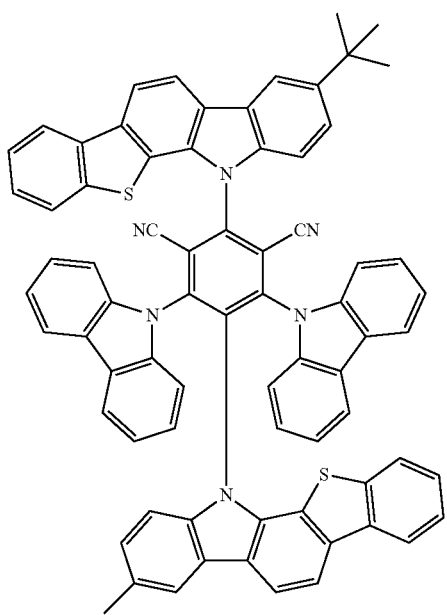
246
-continued
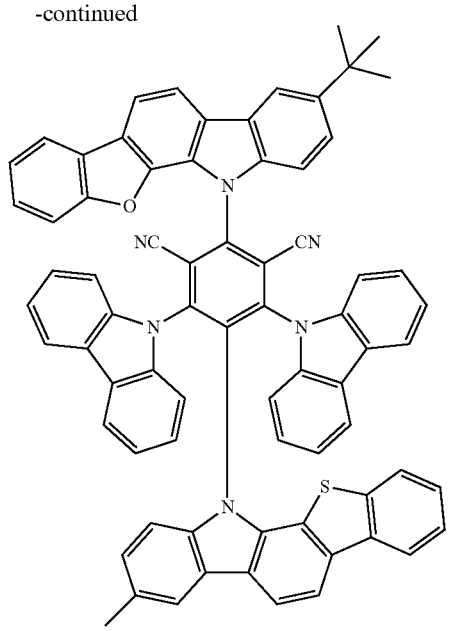
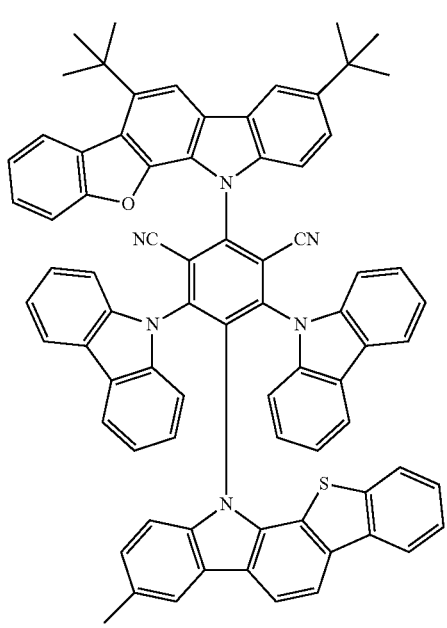
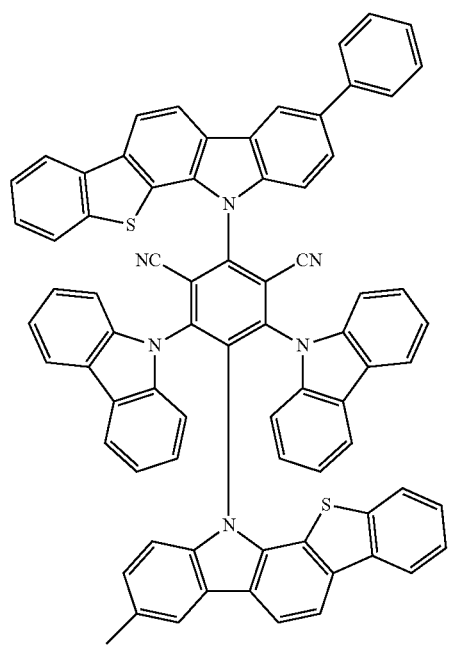

247
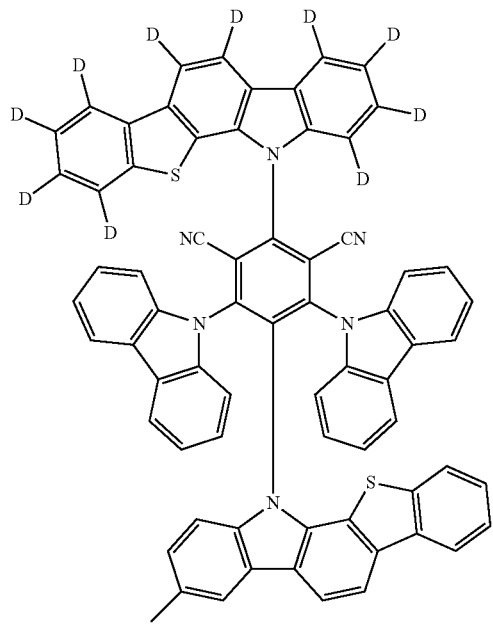
248
-continued
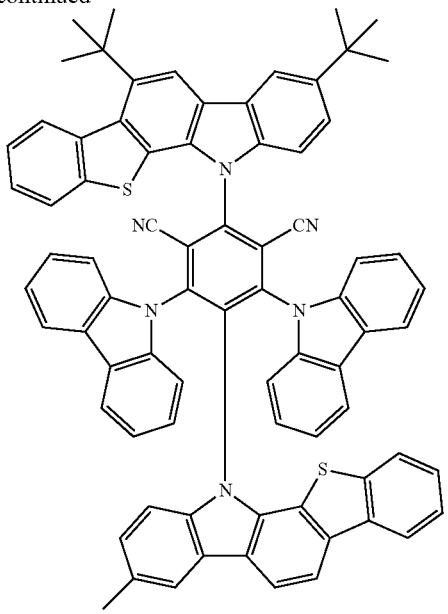
[Formula 75]
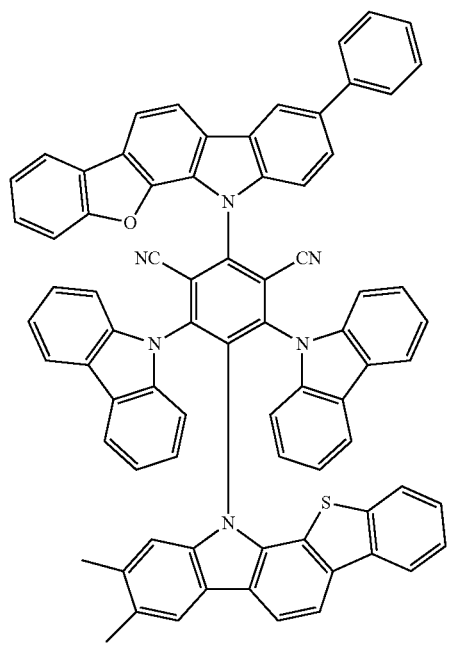
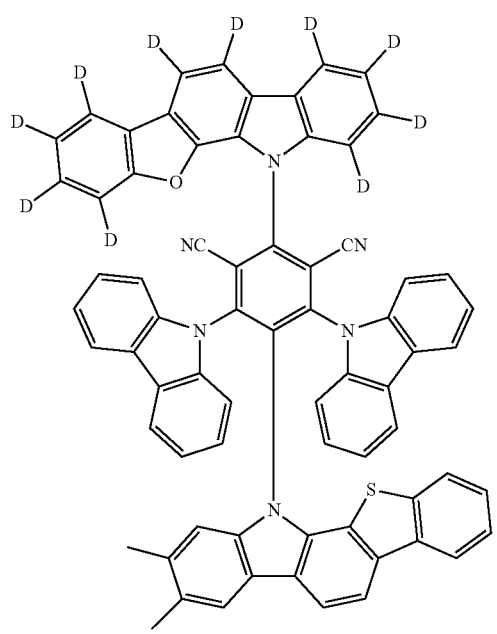

249 250
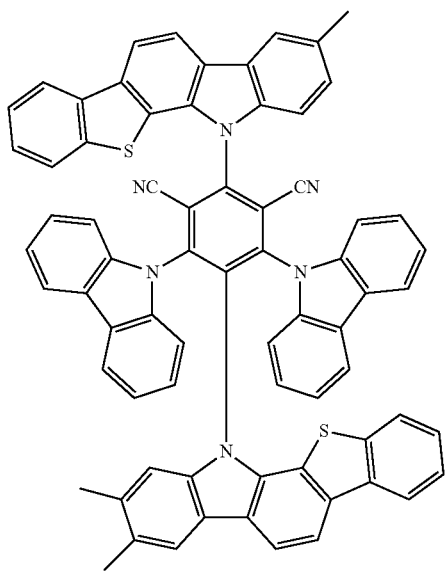
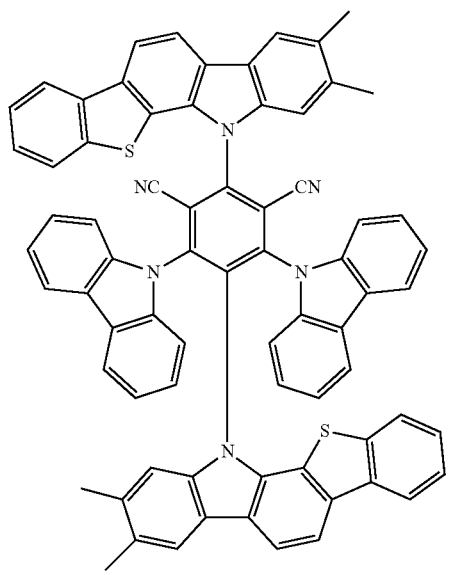
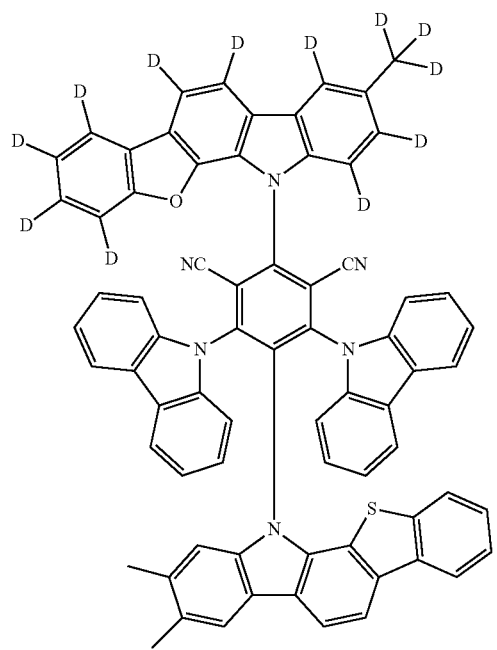
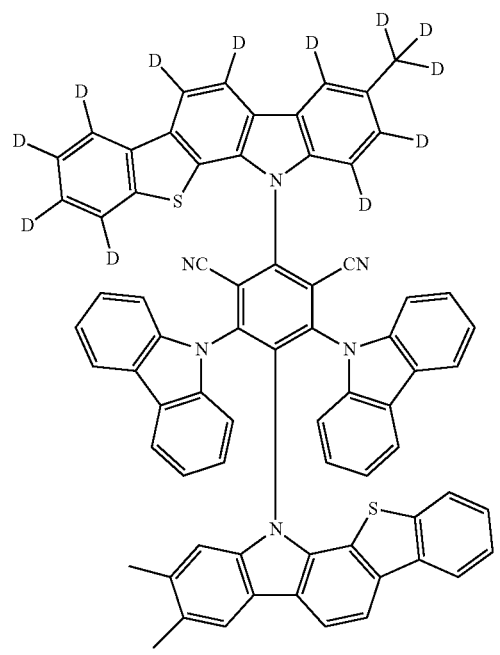

251
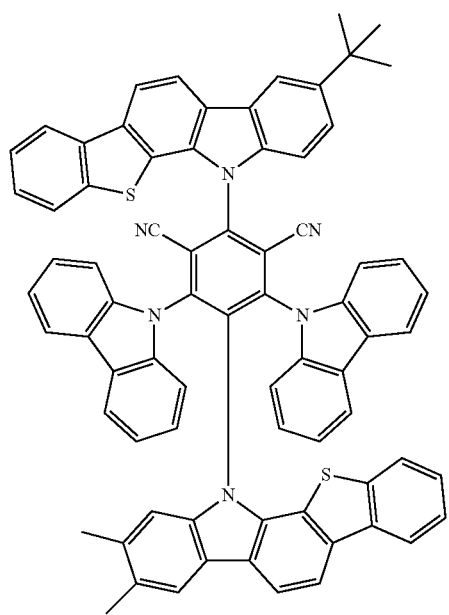
252
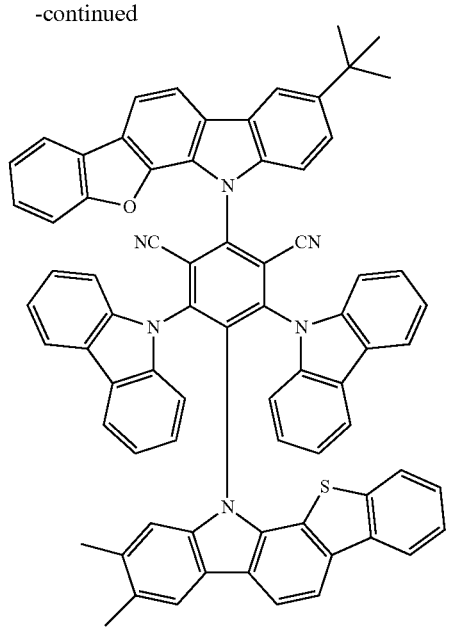
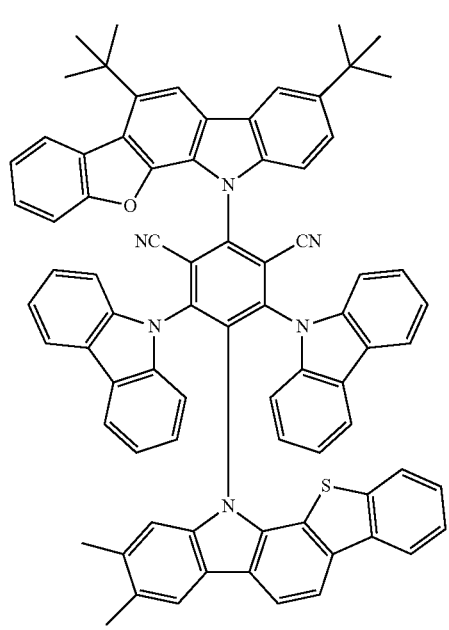
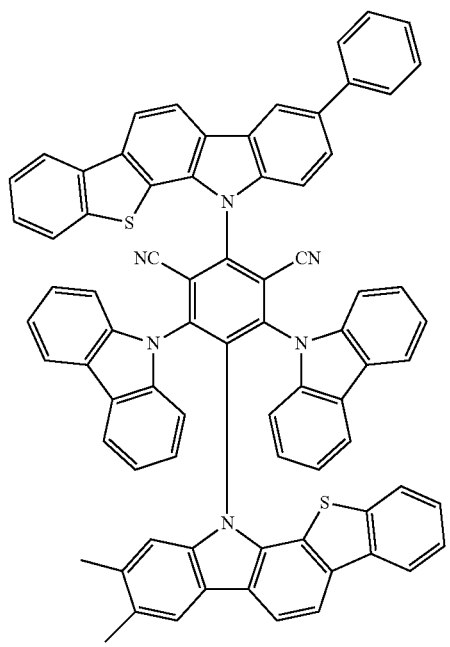

253
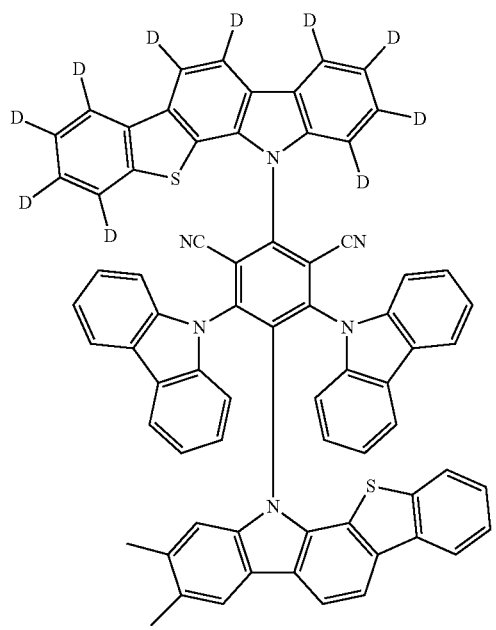
254
-continued
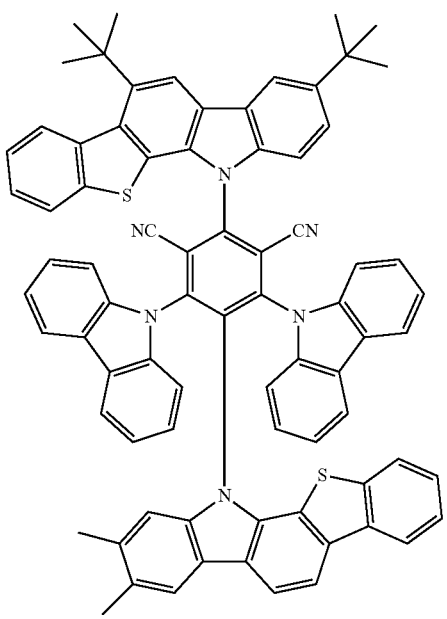
[Formula 76]
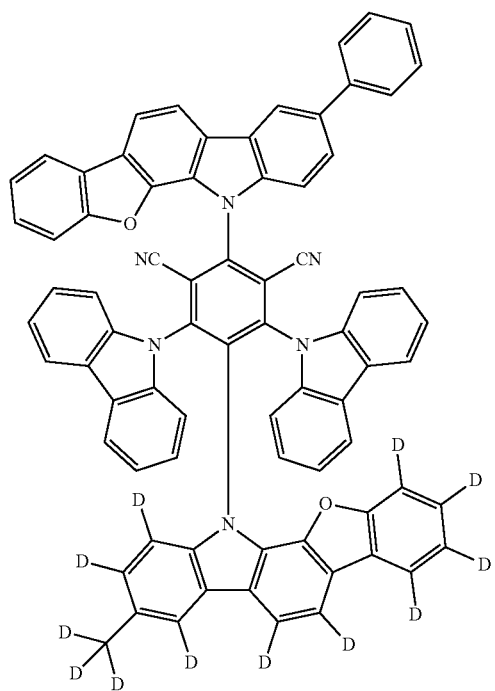
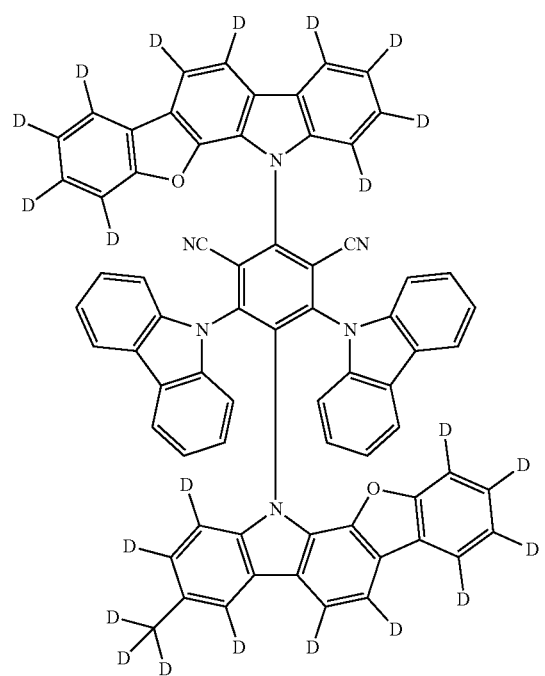

-continued
255 256
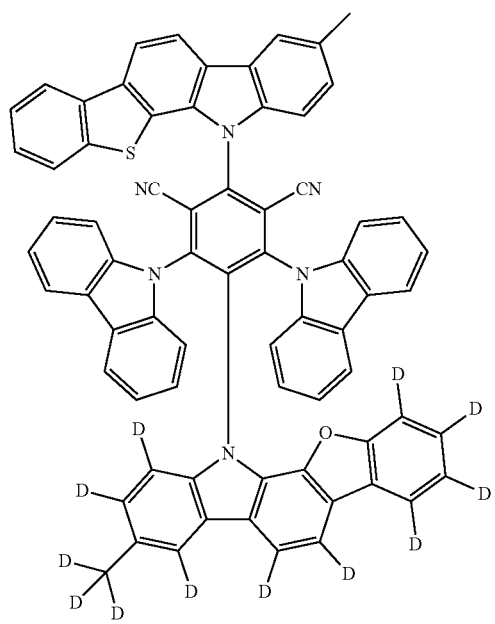 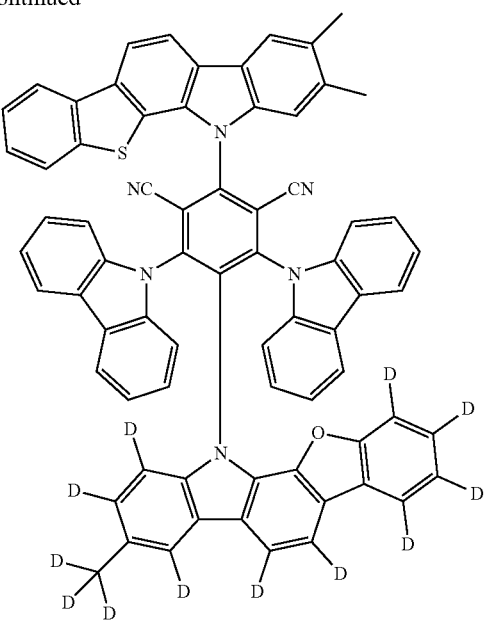
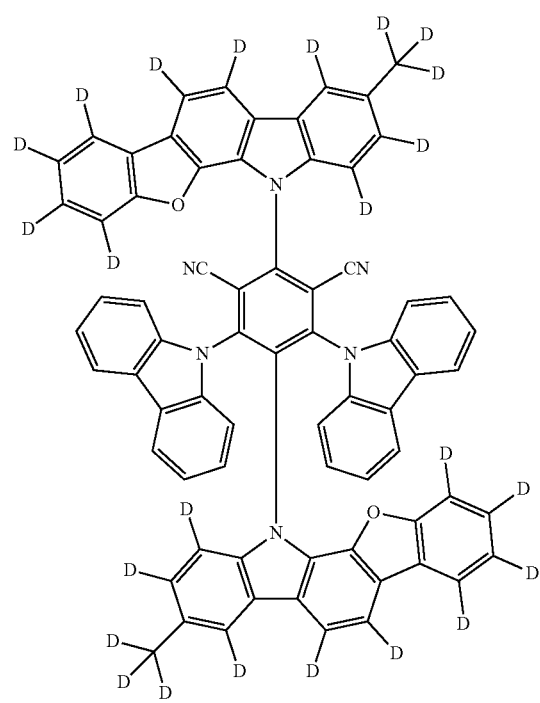 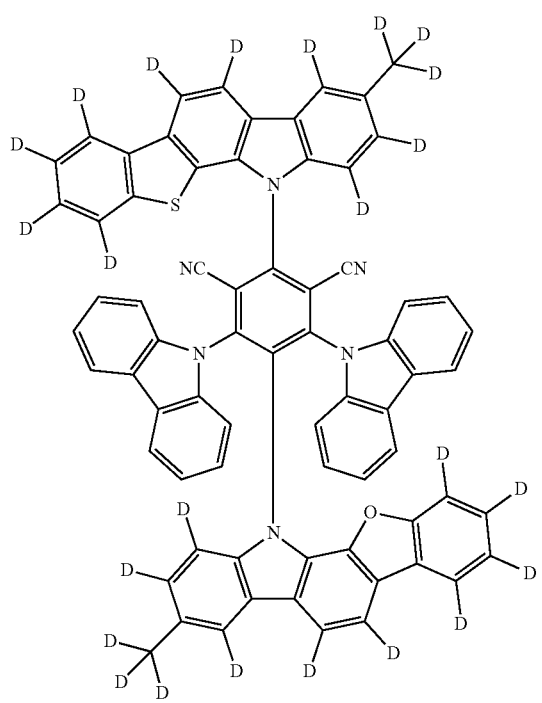

-continued
257
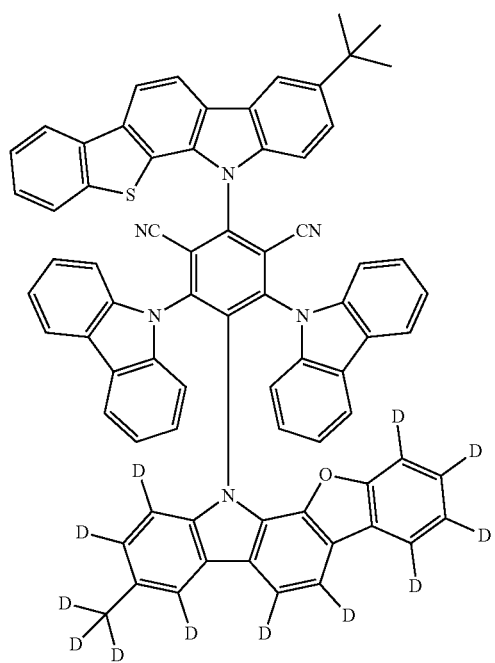
258
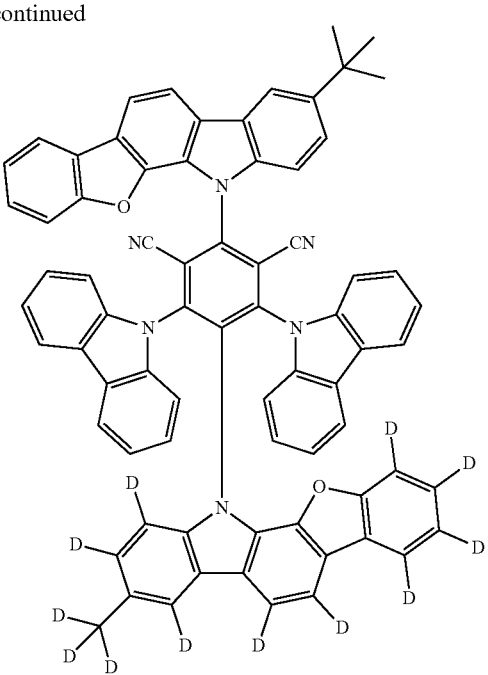
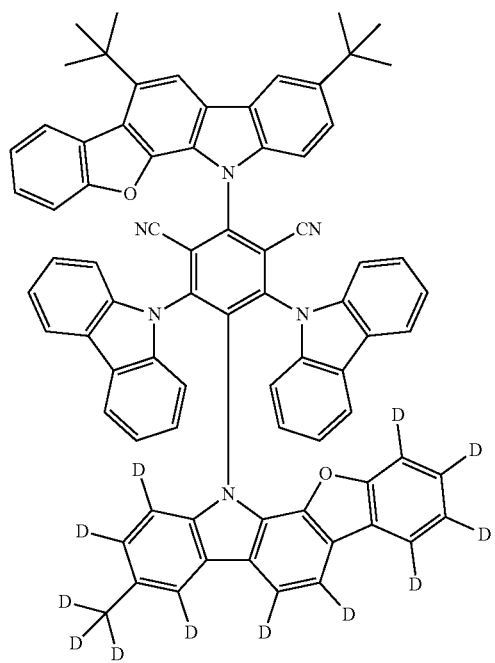
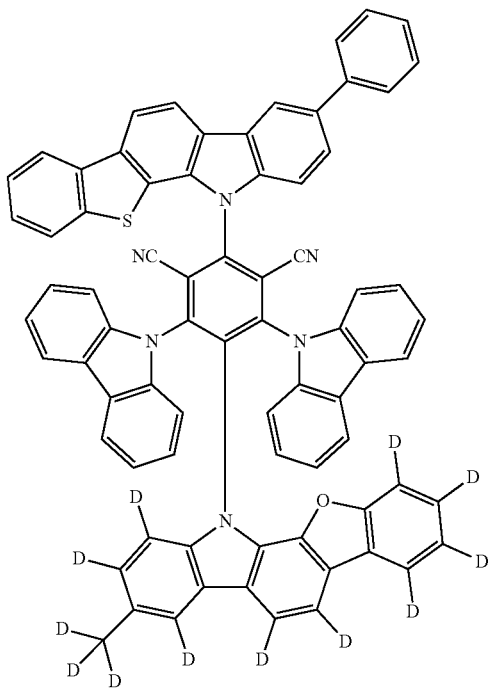

259
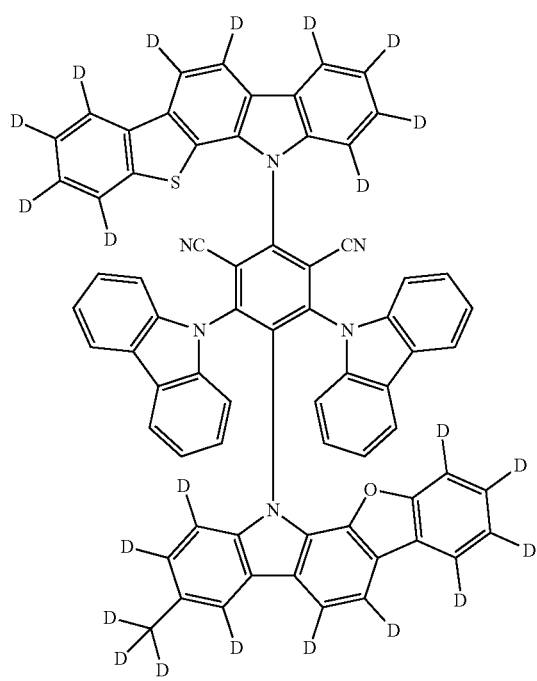
260
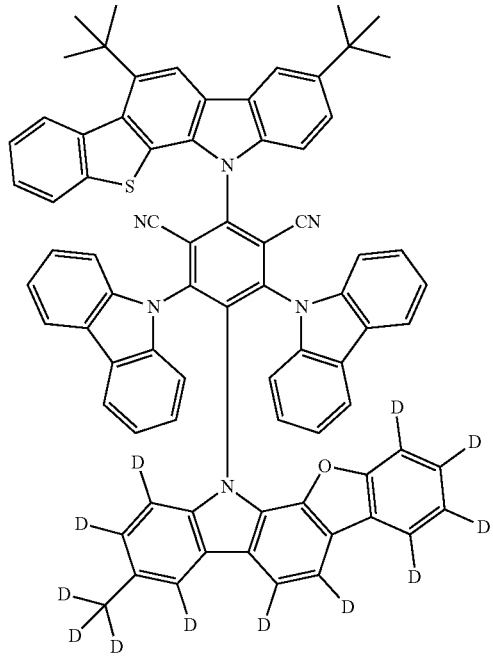
[Formula 77]
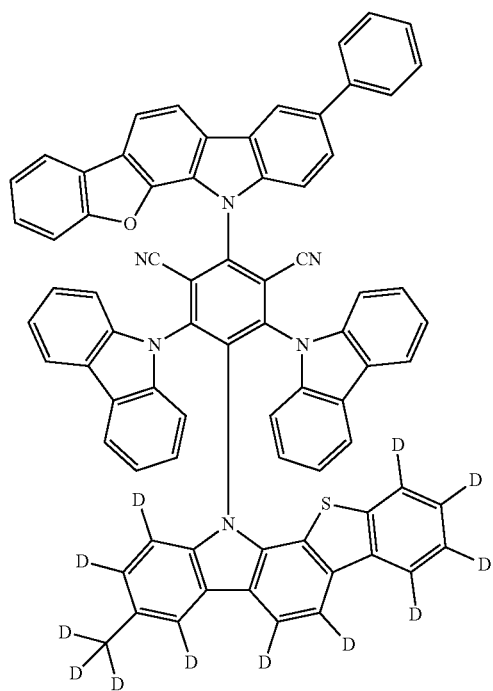
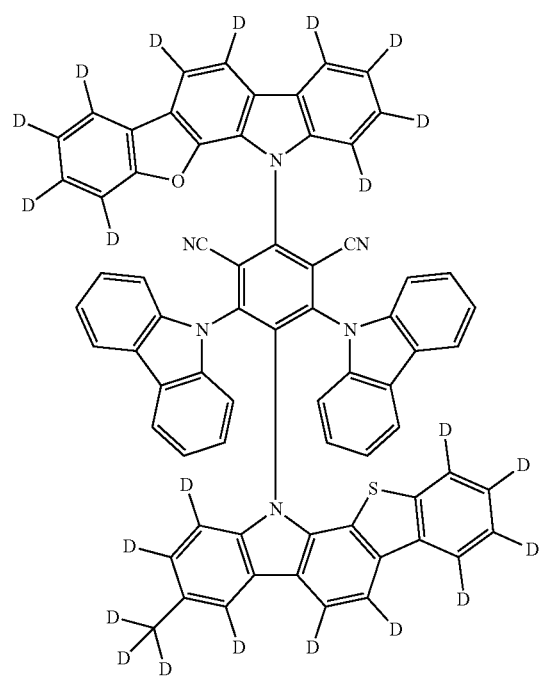

261
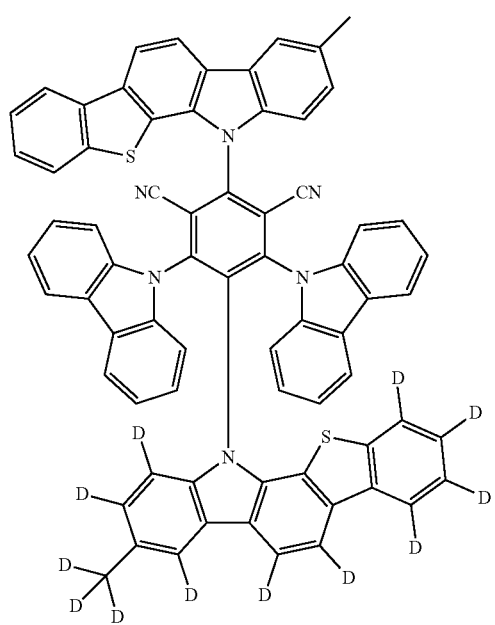
262
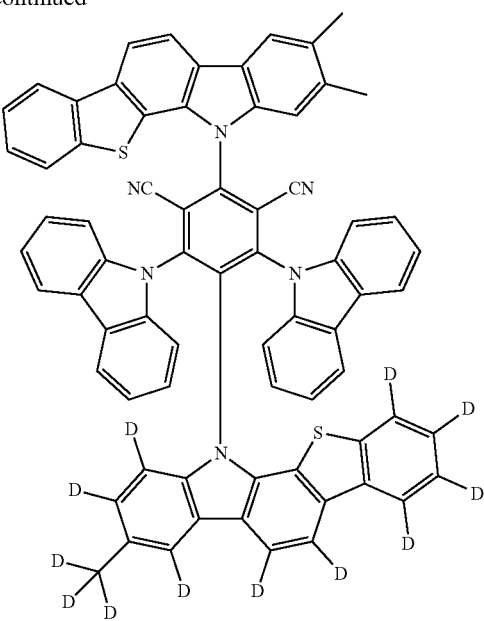
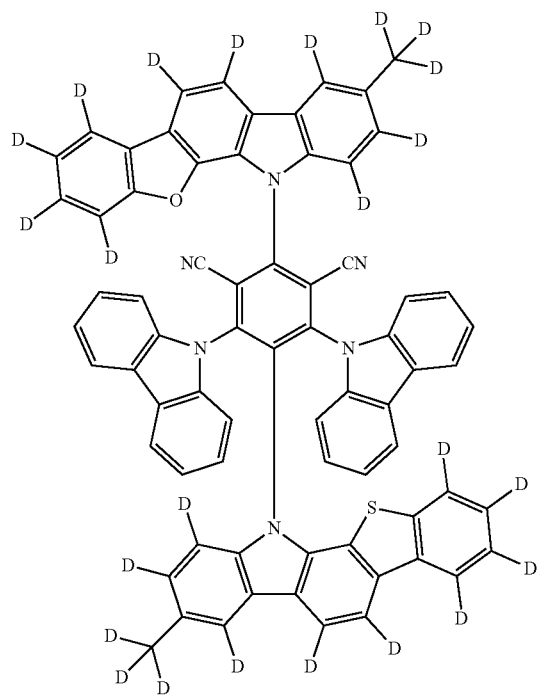
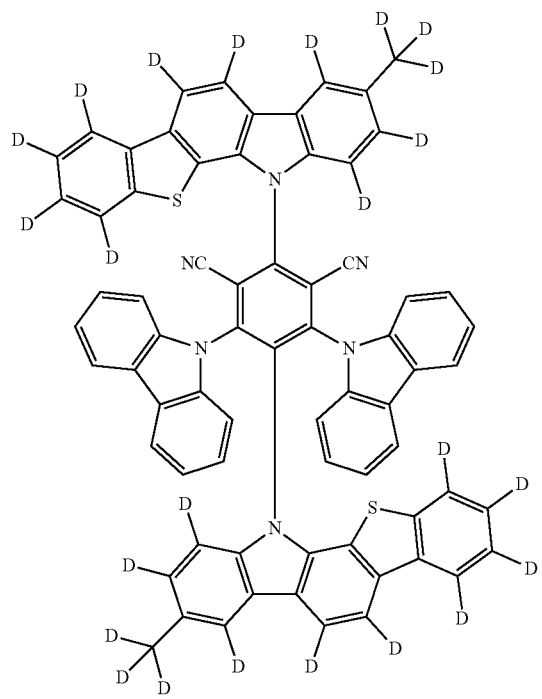

263
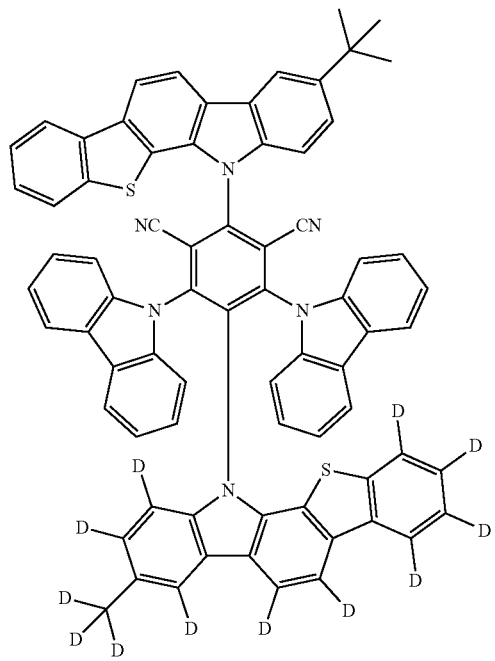
264
-continued
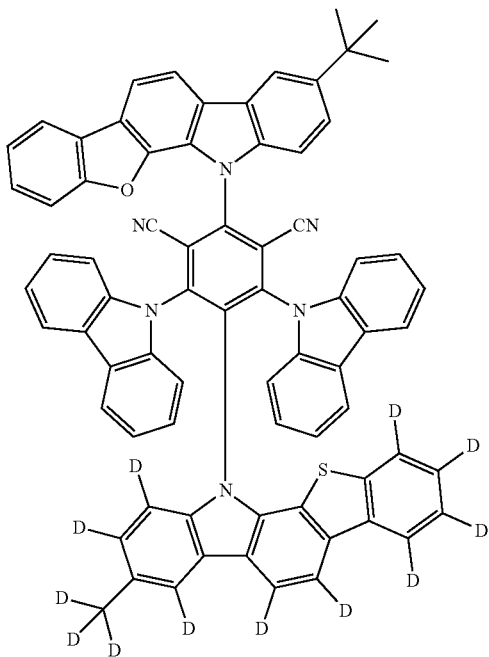
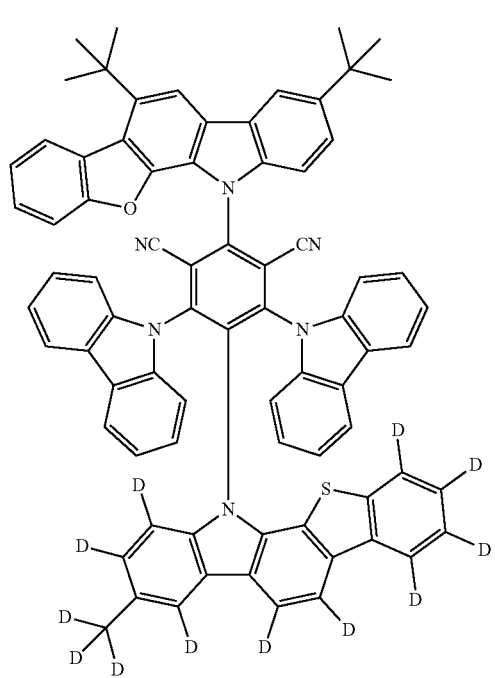
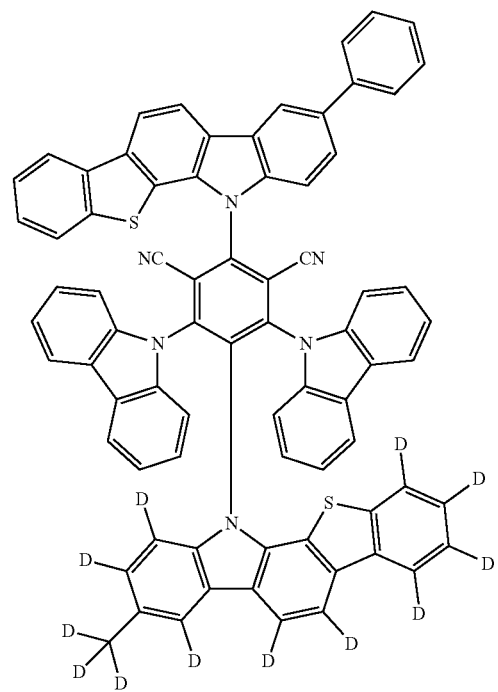

265
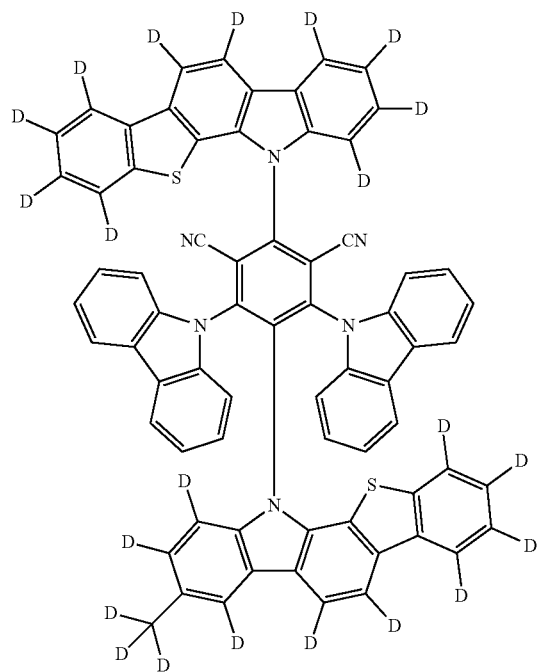
266
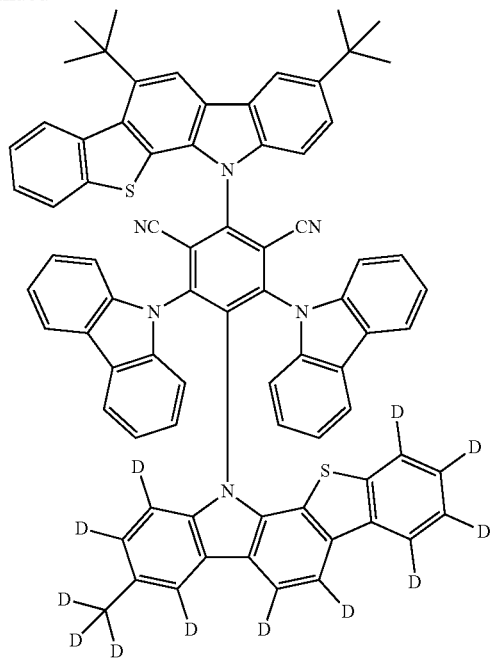
[Formula 78]
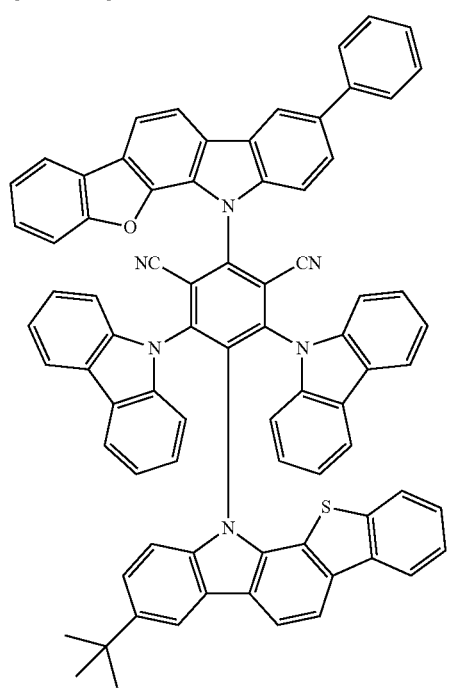
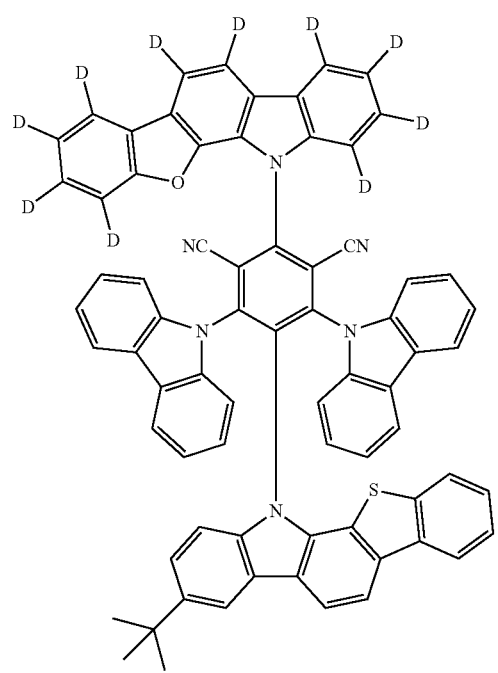

267 268
-continued
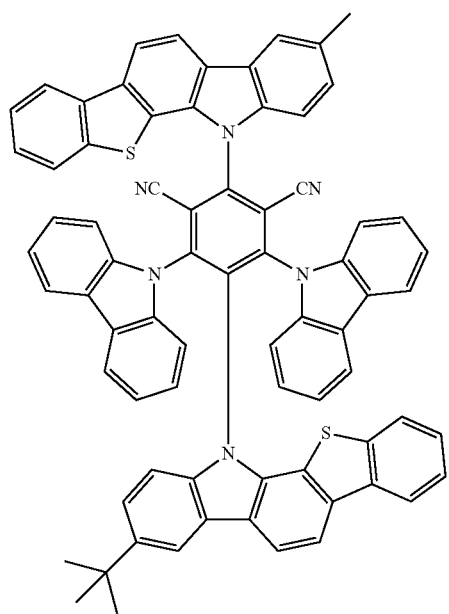
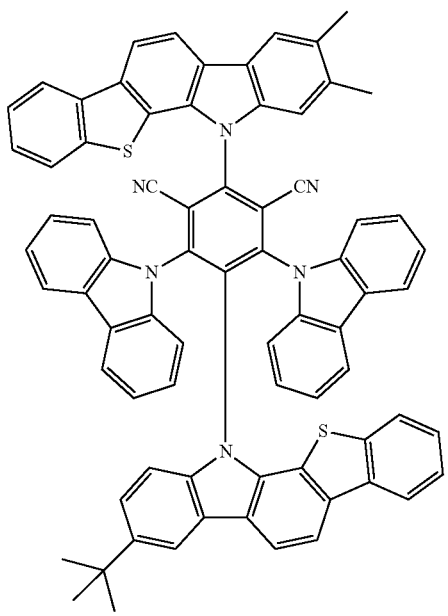
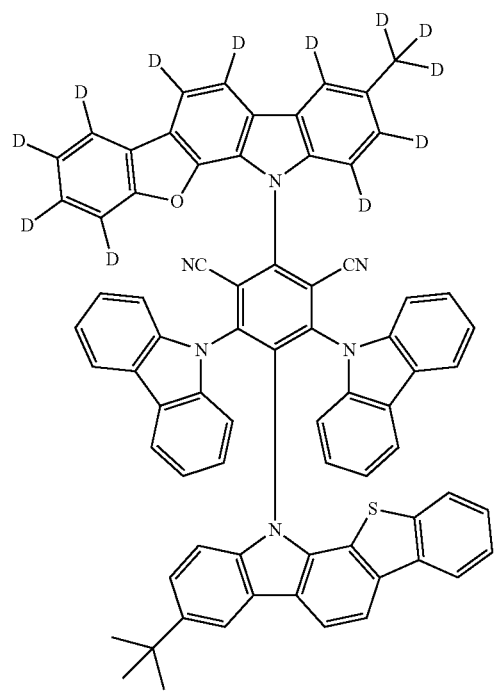
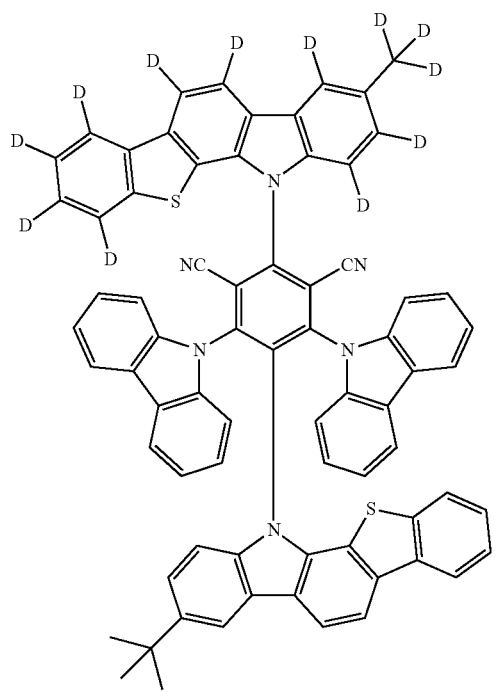

269 270
-continued
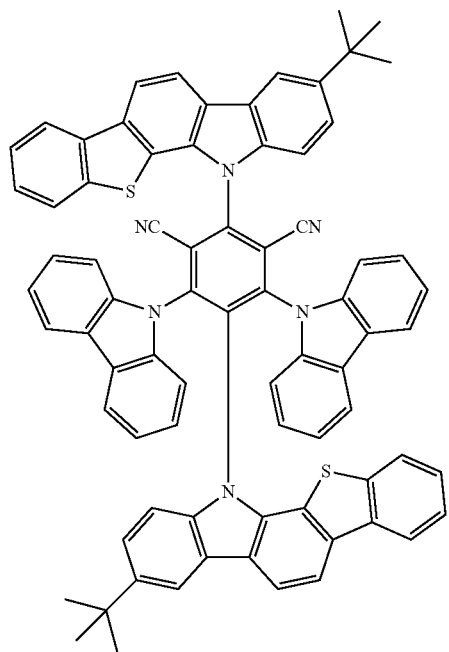
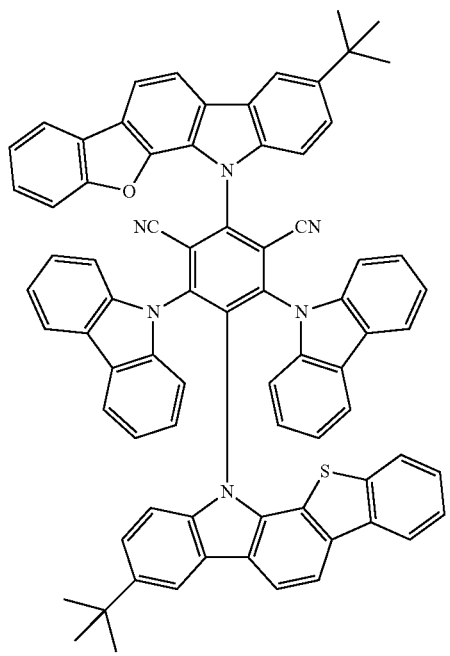
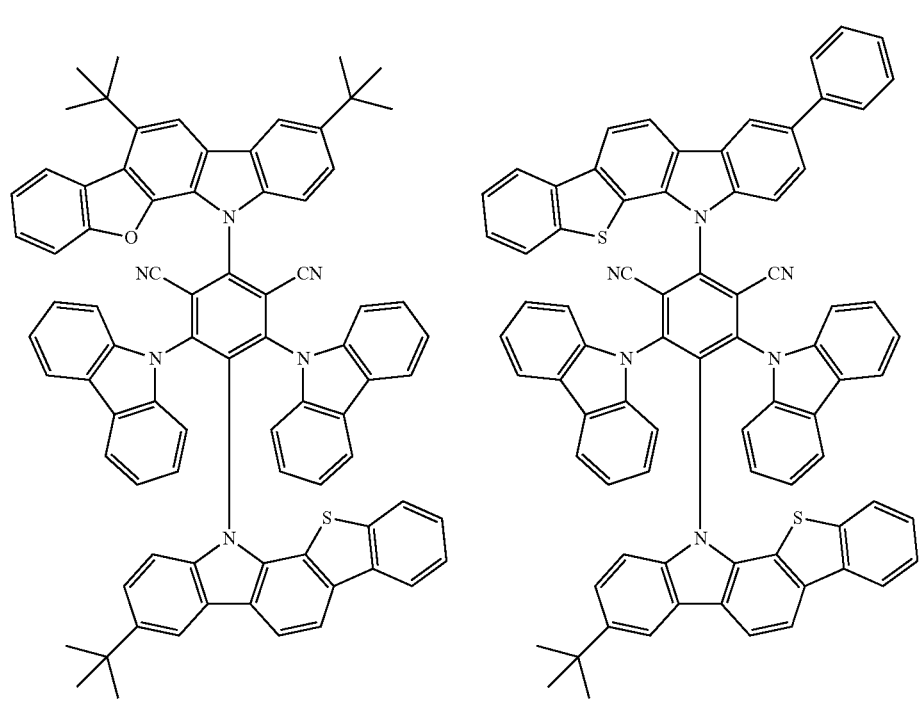

271
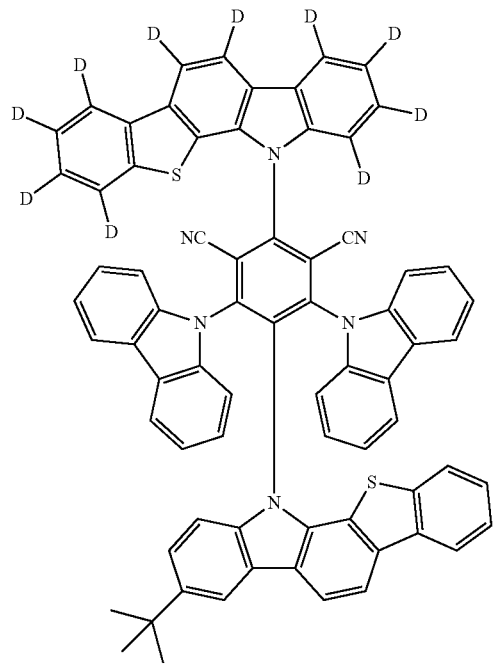
272
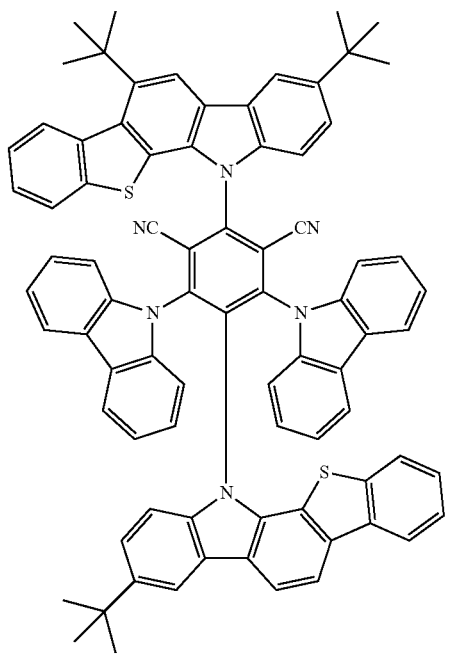
[Formula 79]
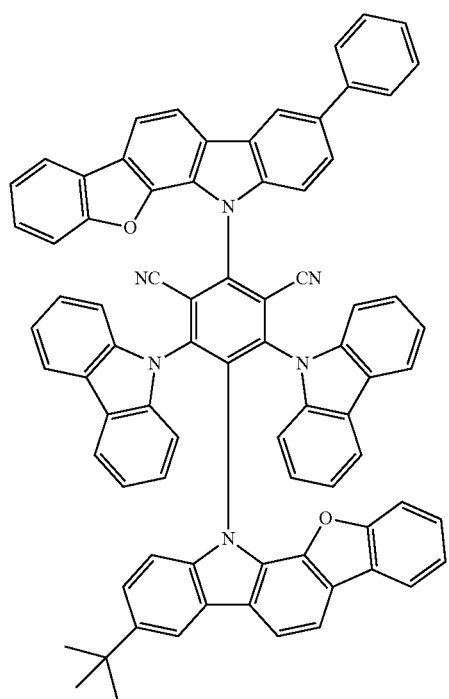
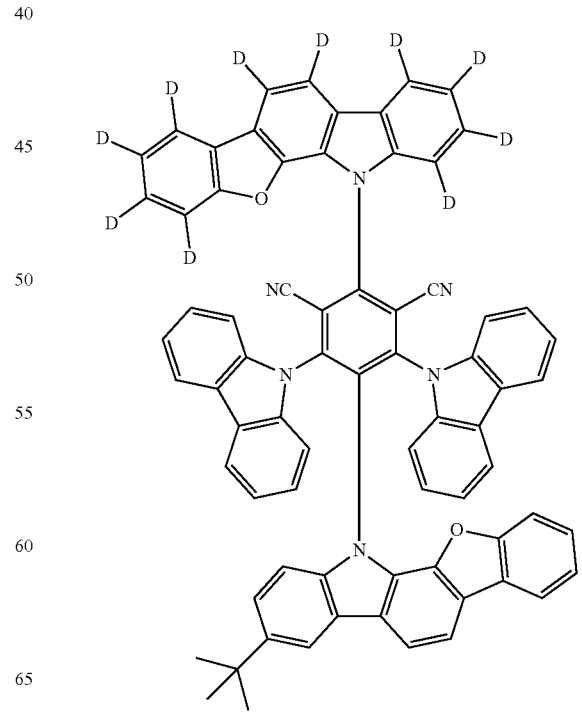

273
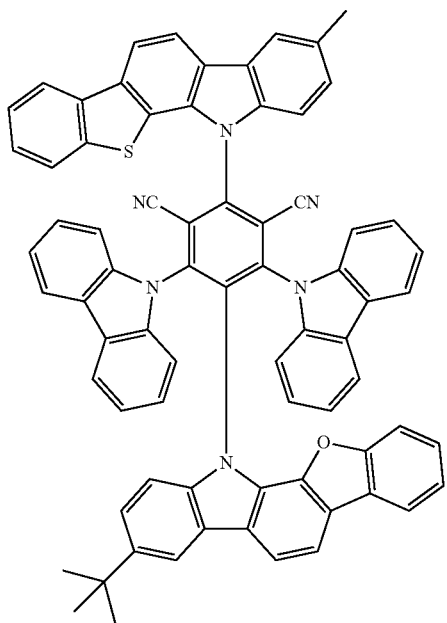
274
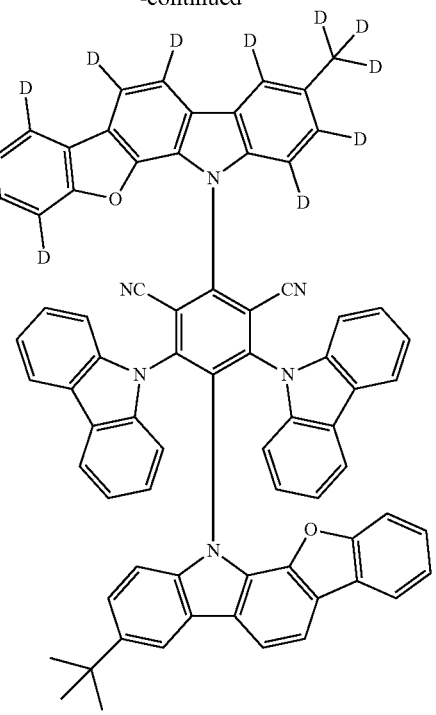
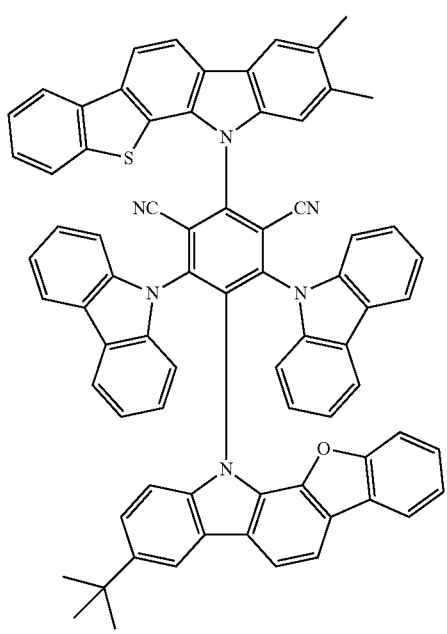
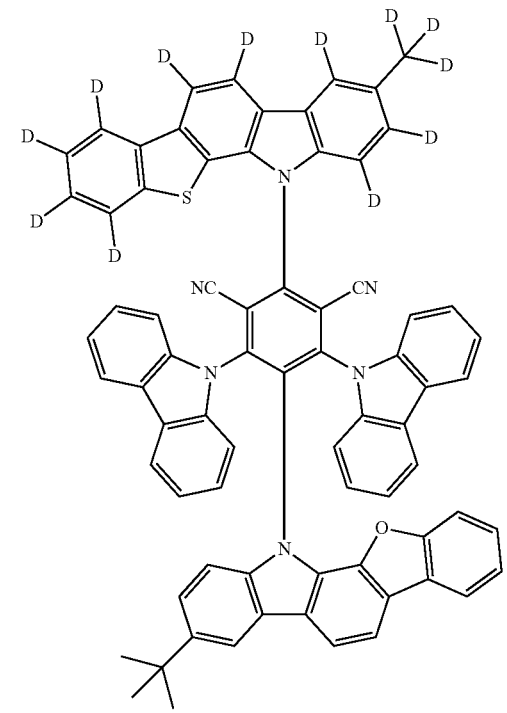

275
-continued
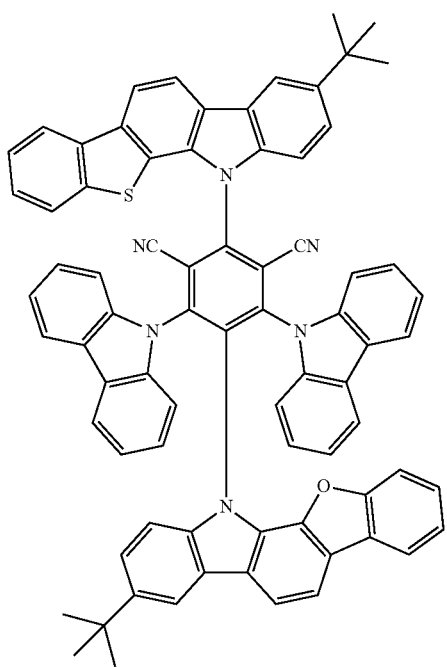
276
-continued
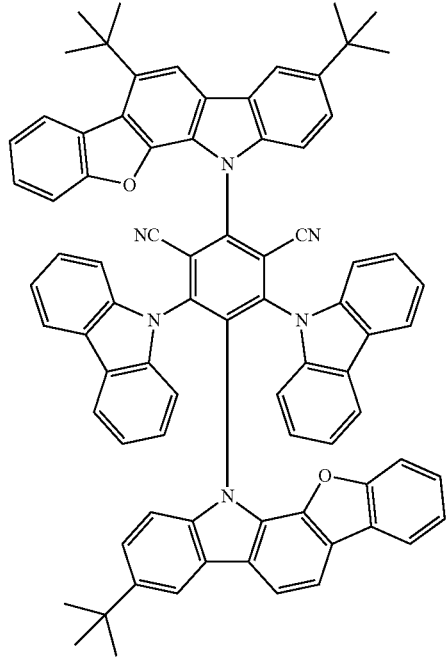
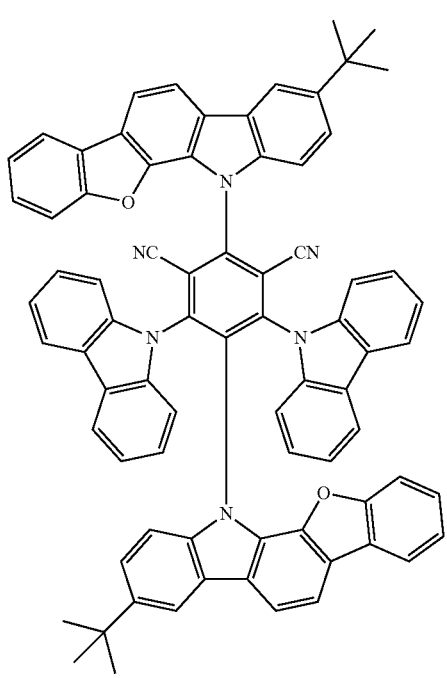
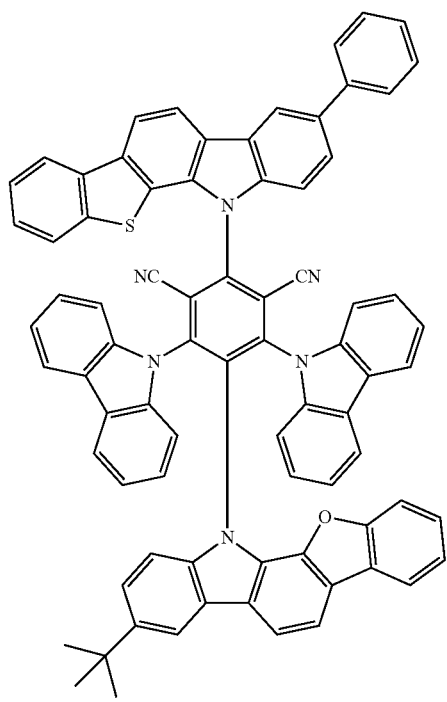

277
-continued
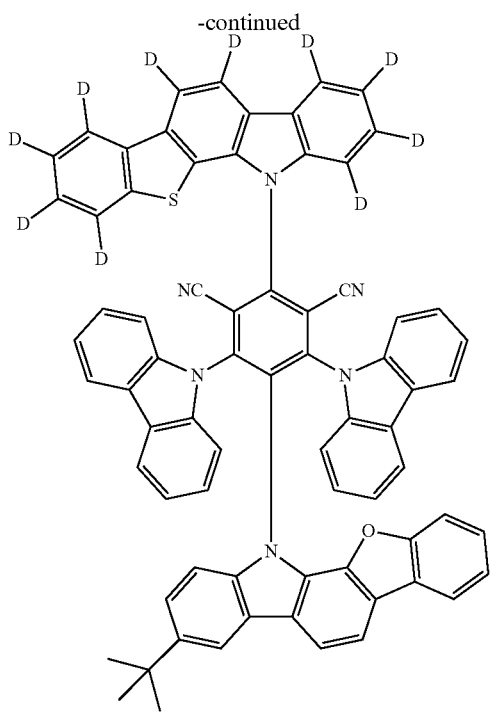
278
-continued
[Formula 80]
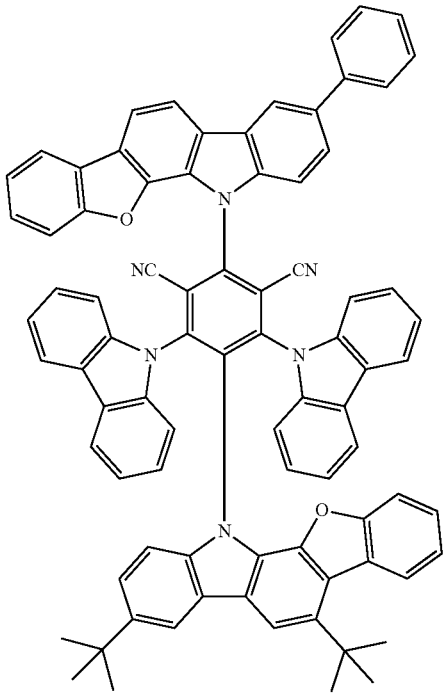
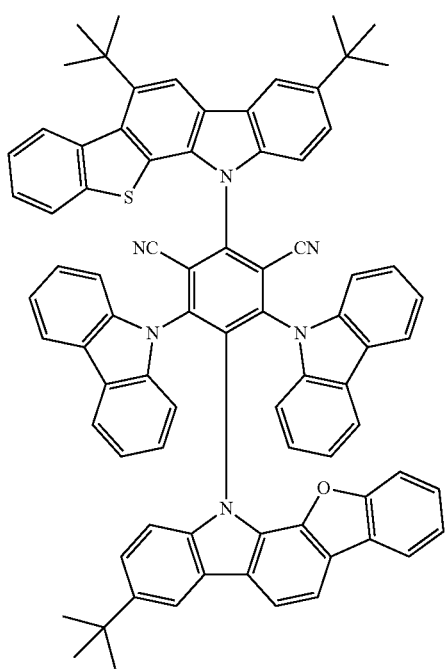
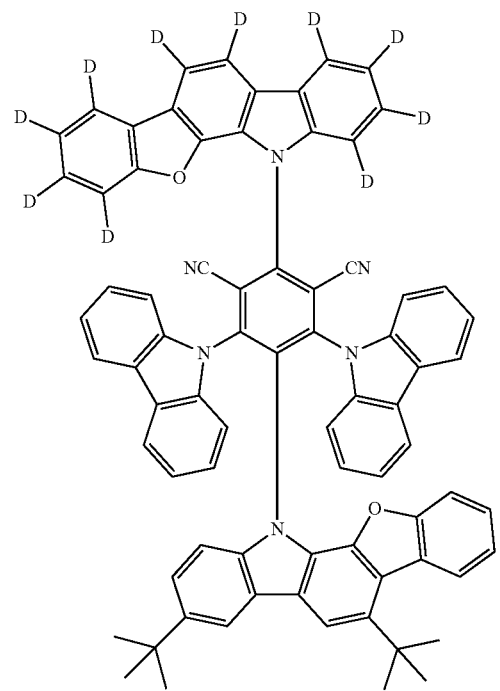

279
-continued
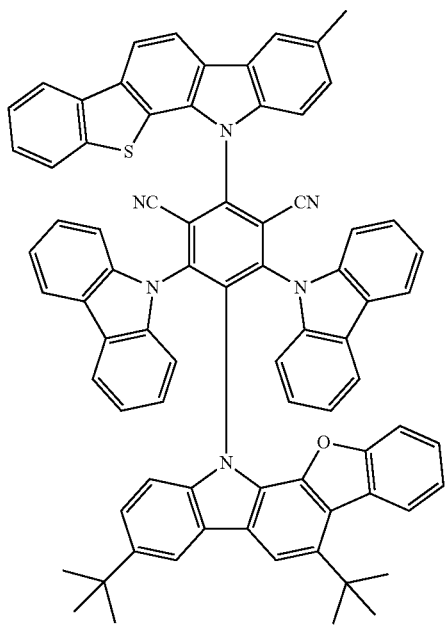
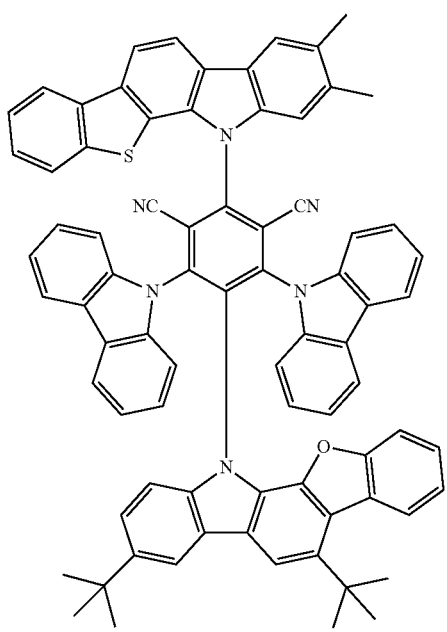
280
-continued
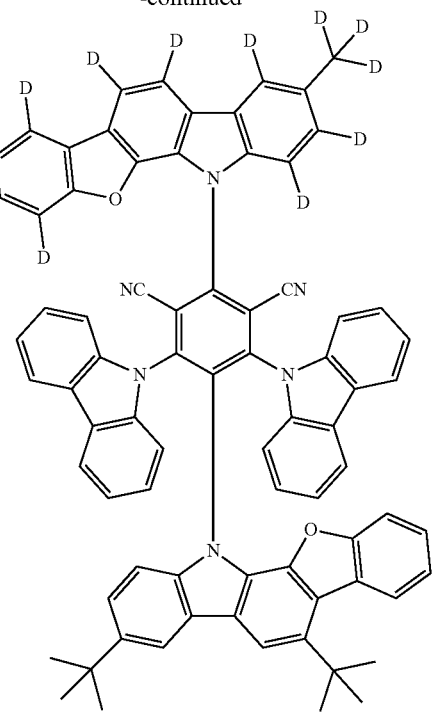
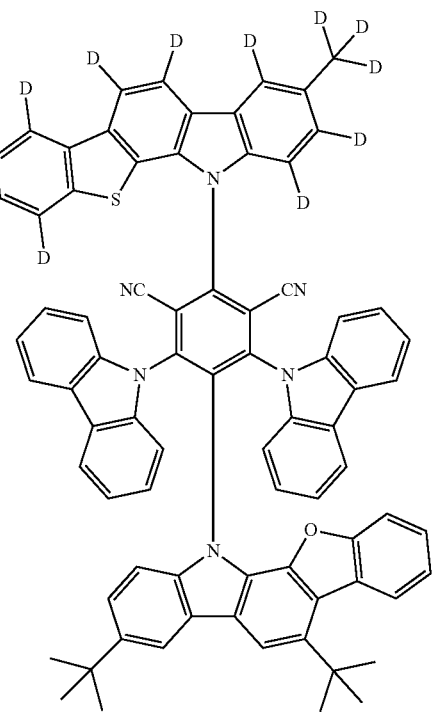

281
-continued
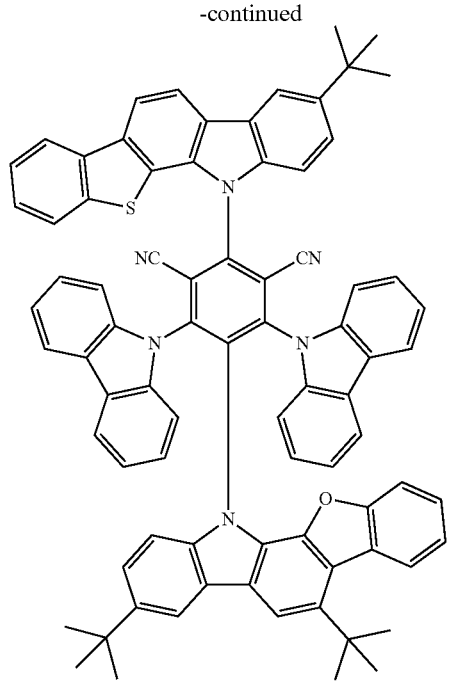
282
-continued
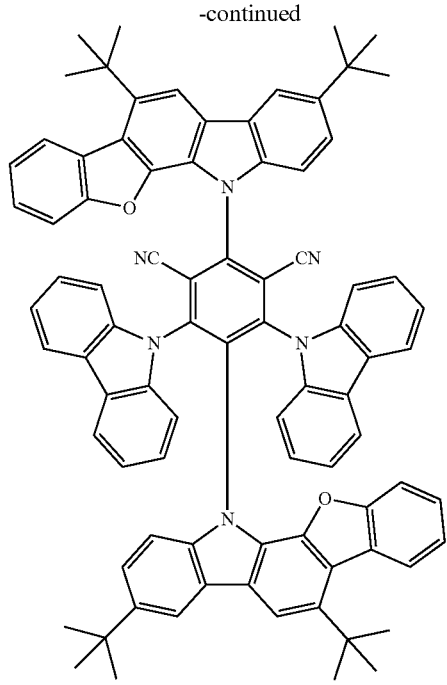
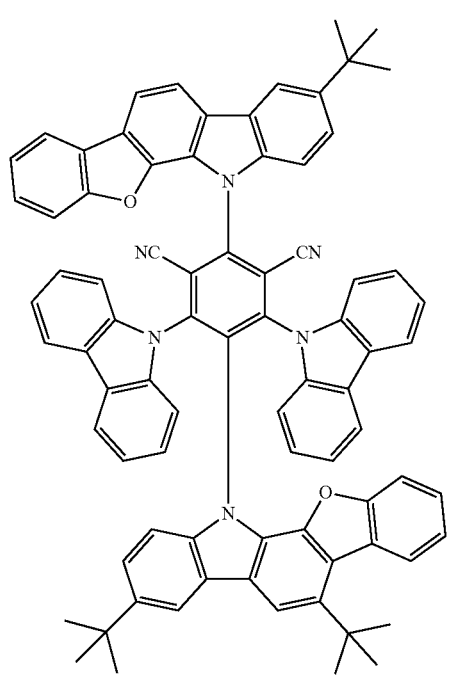
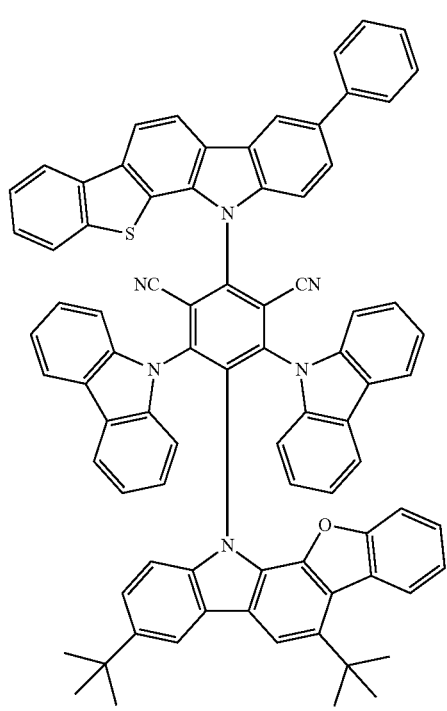

283
-continued
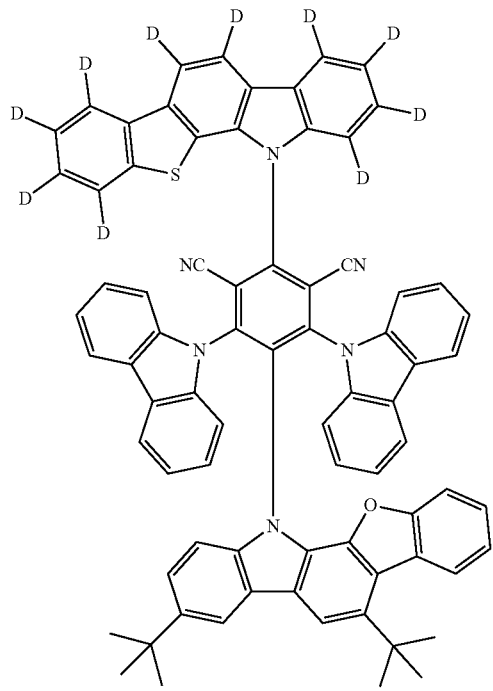
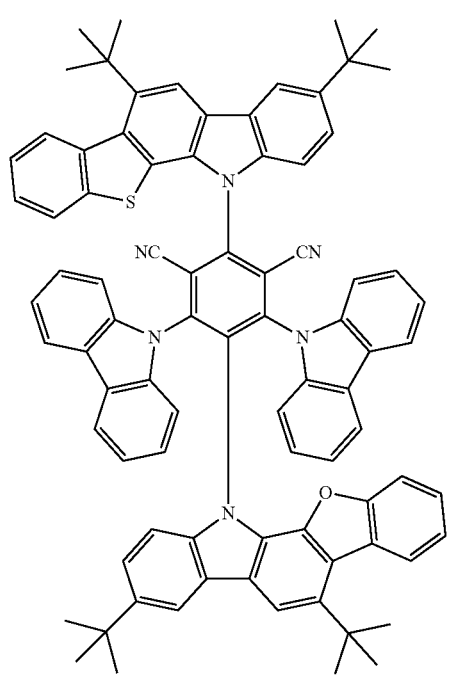
284
-continued
[Formula 81]
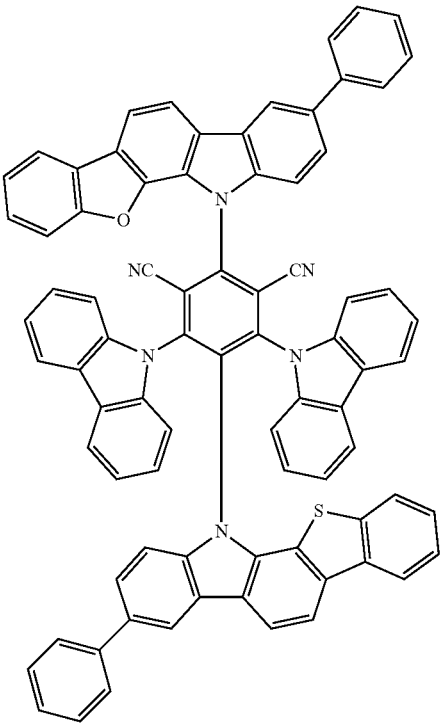
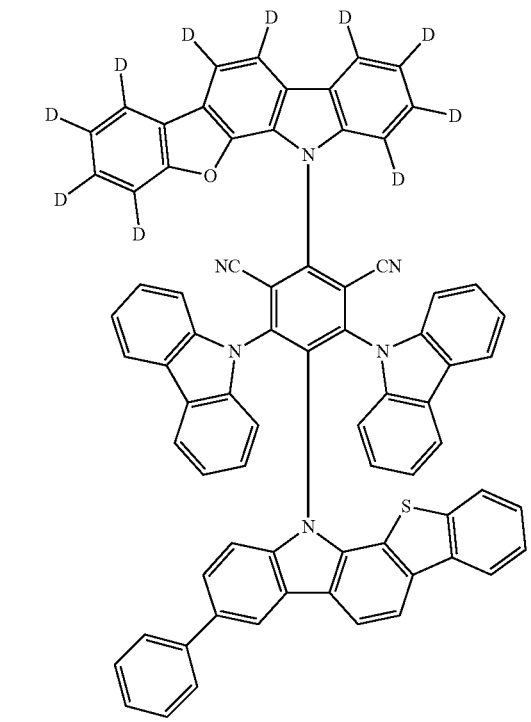

285
-continued
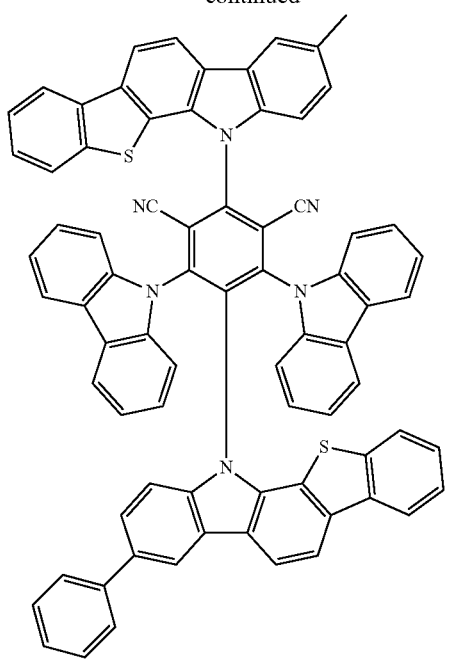
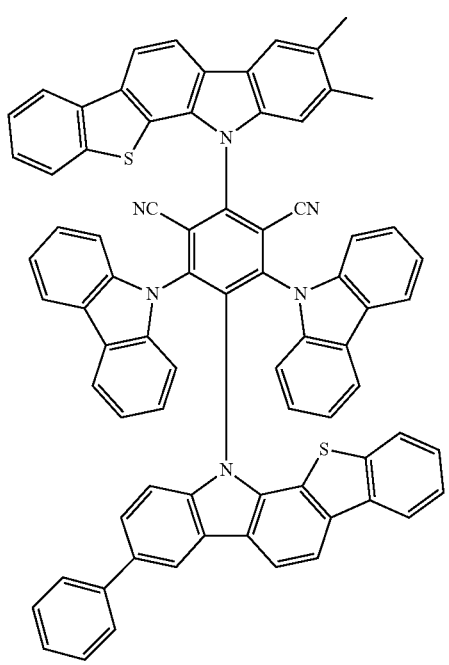
286
-continued
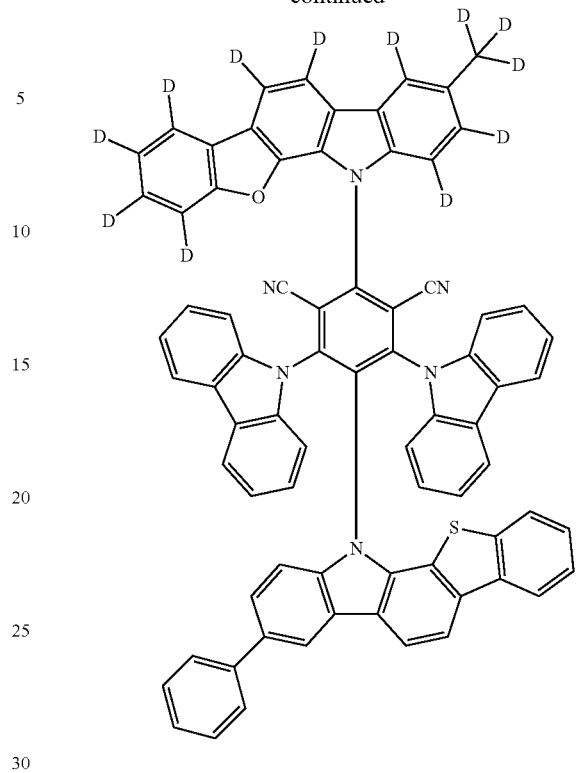
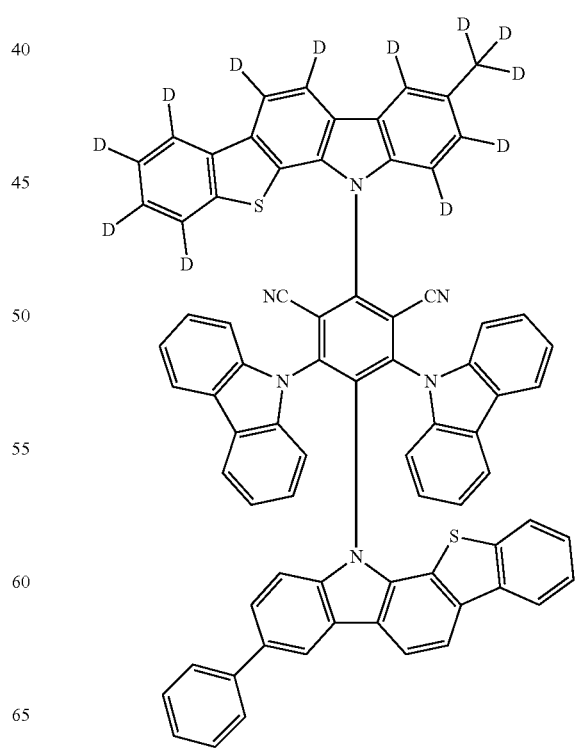

287
-continued
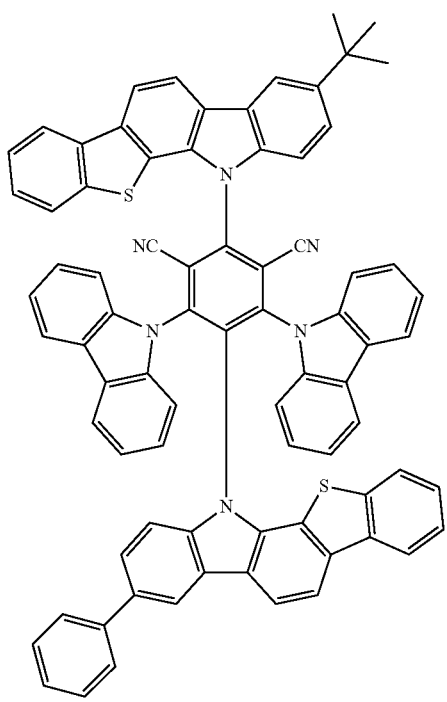
288
-continued
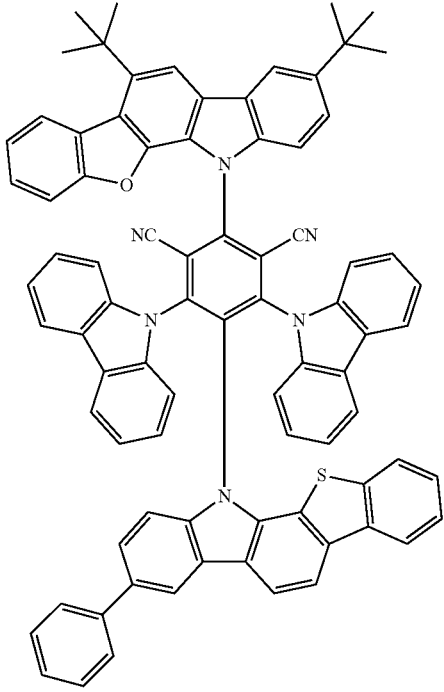
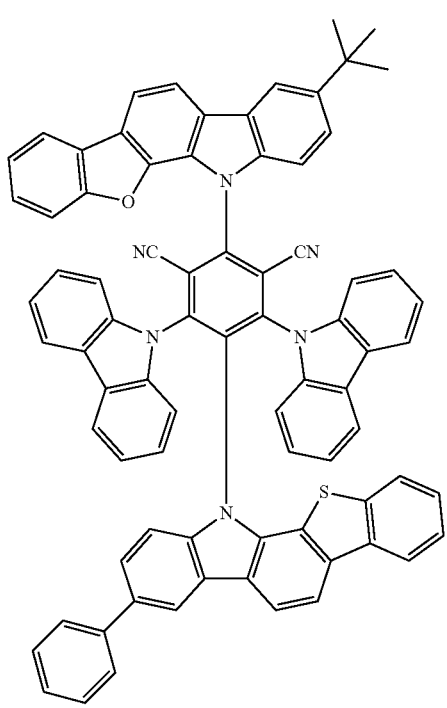
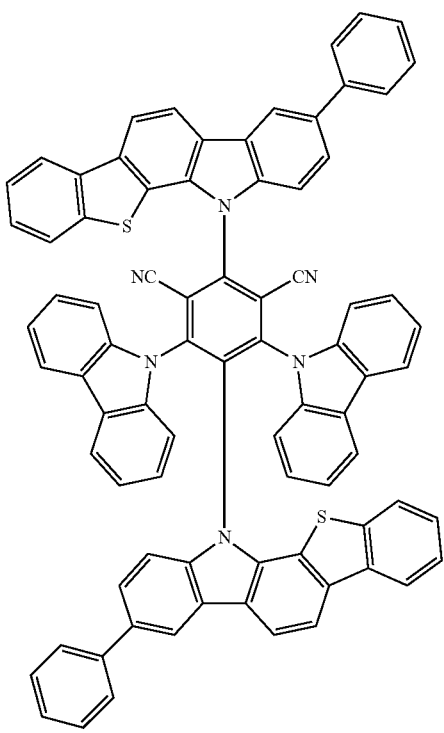

289
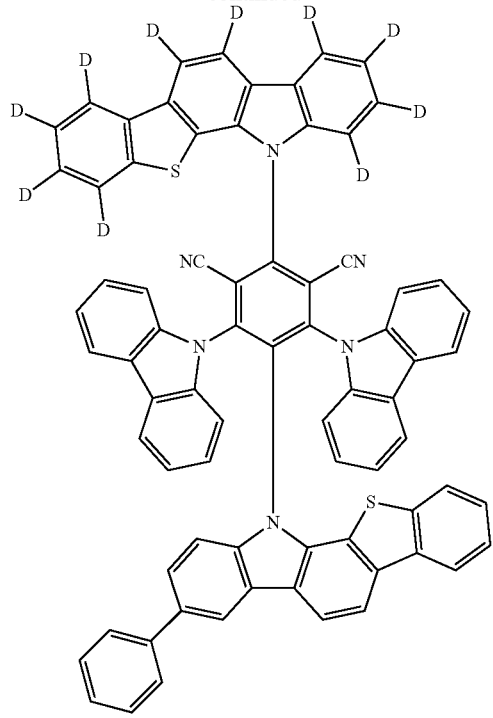
290
[Formula 82]
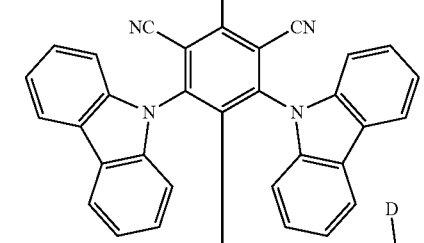
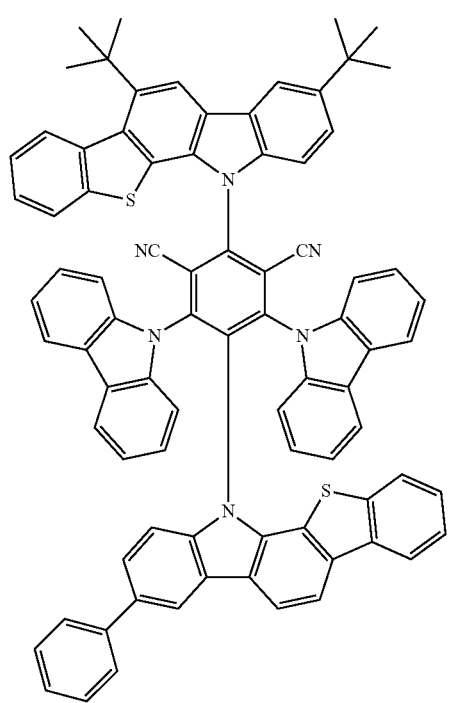
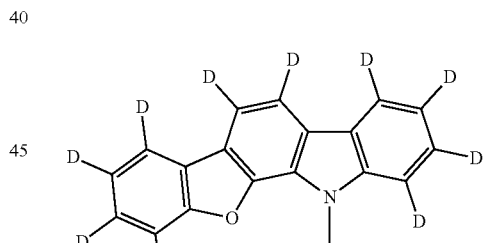
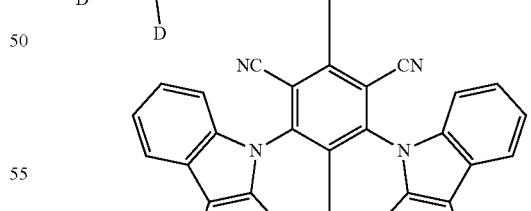
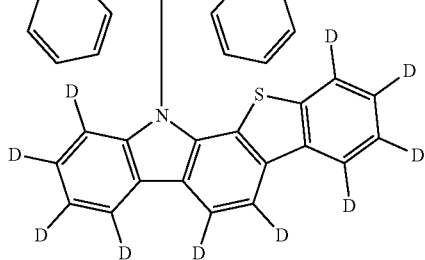

291
-continued
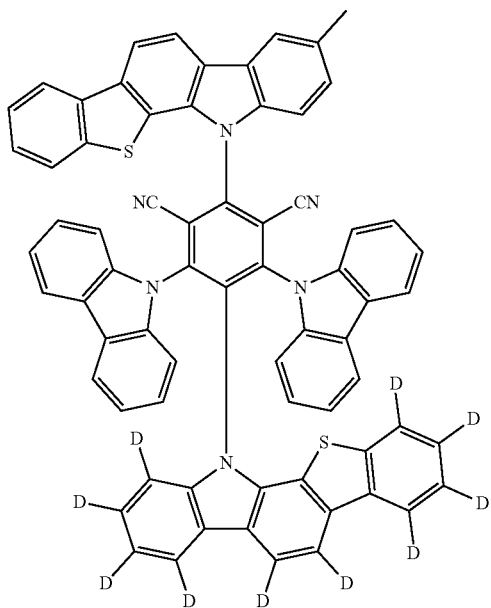
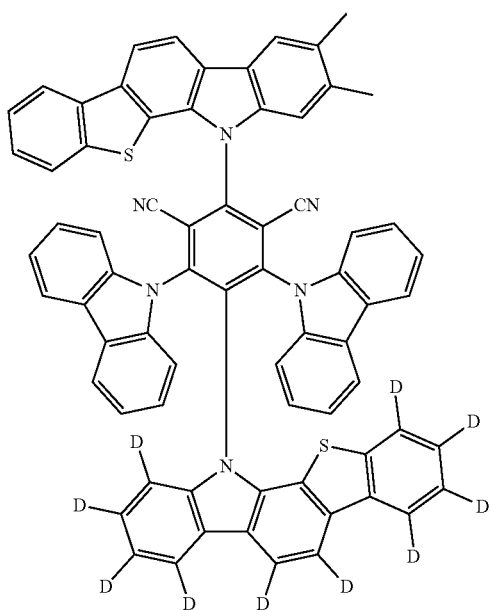
292
-continued
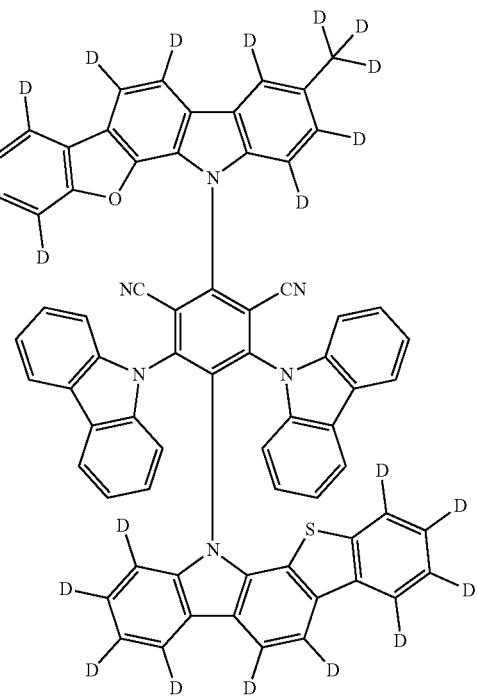
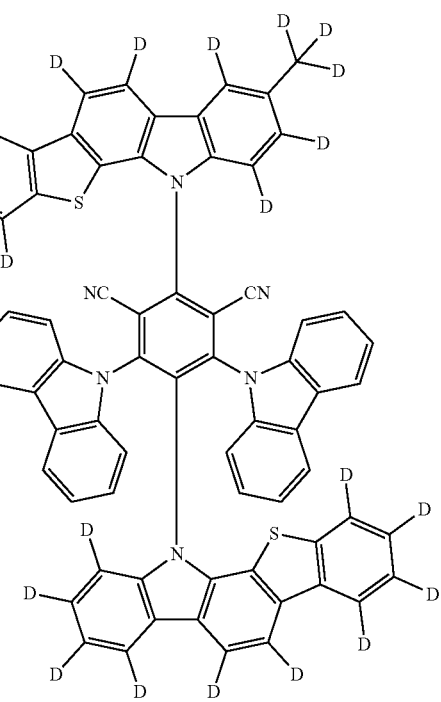

293
-continued
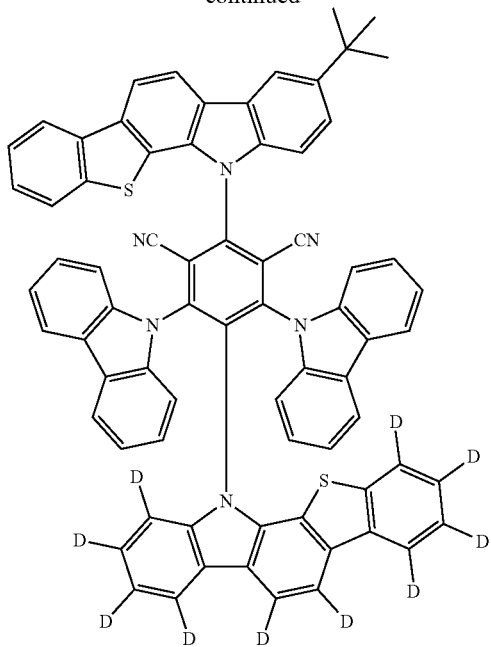
294
-continued
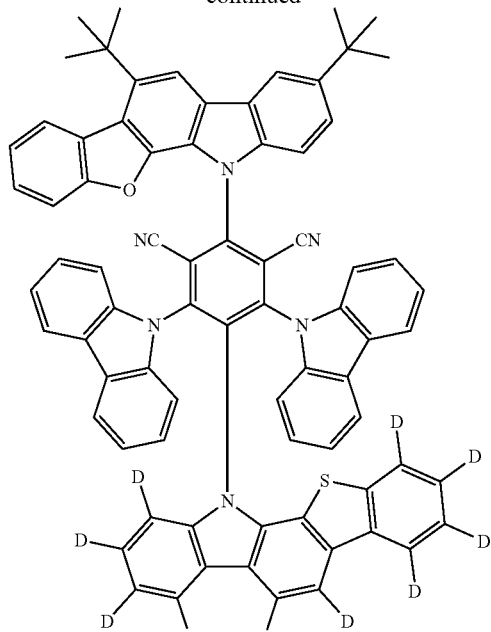
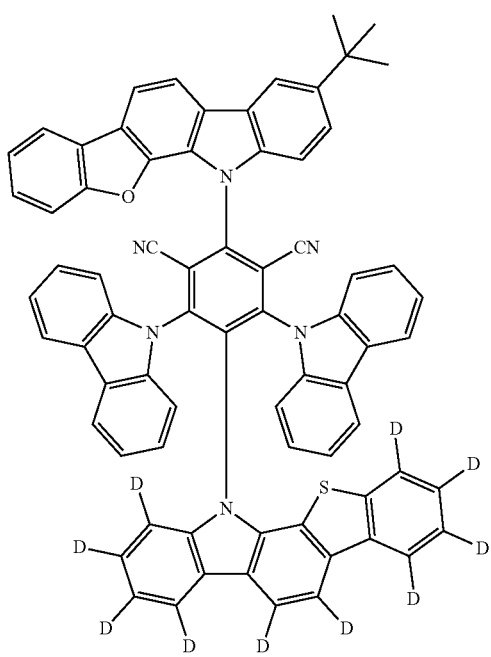
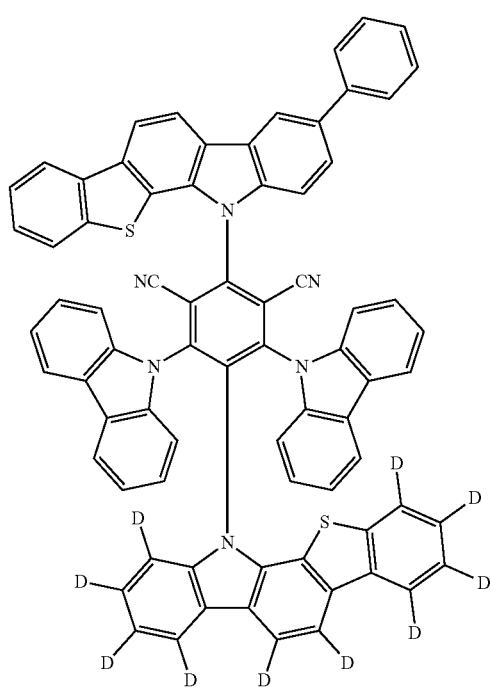

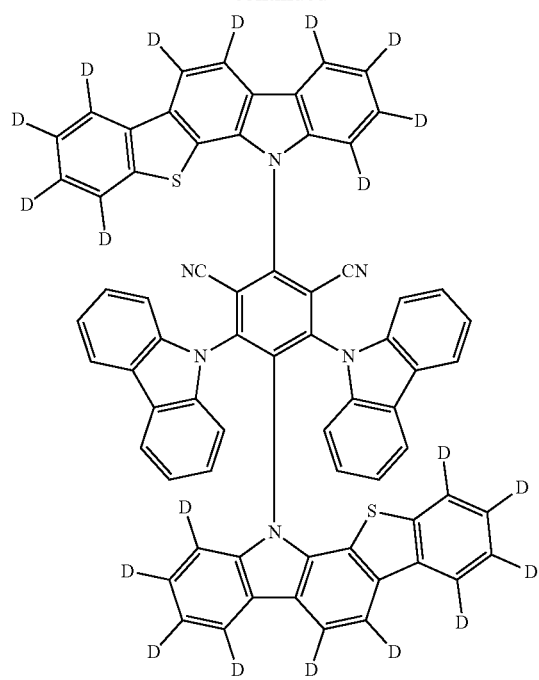
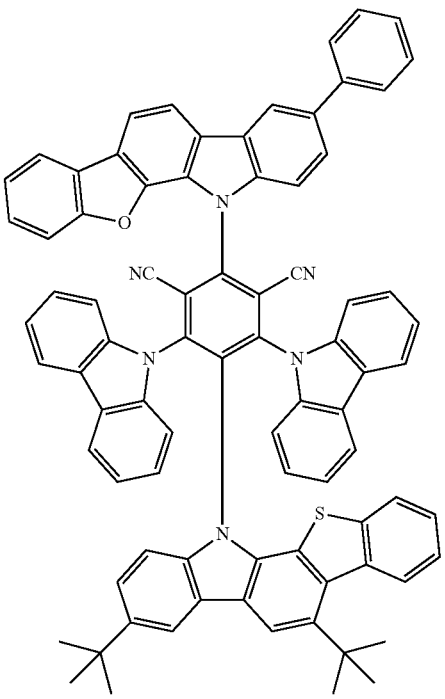
[Formula 83]
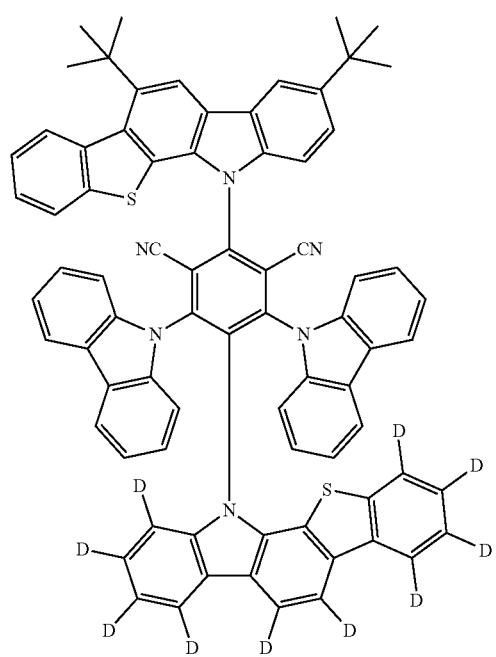
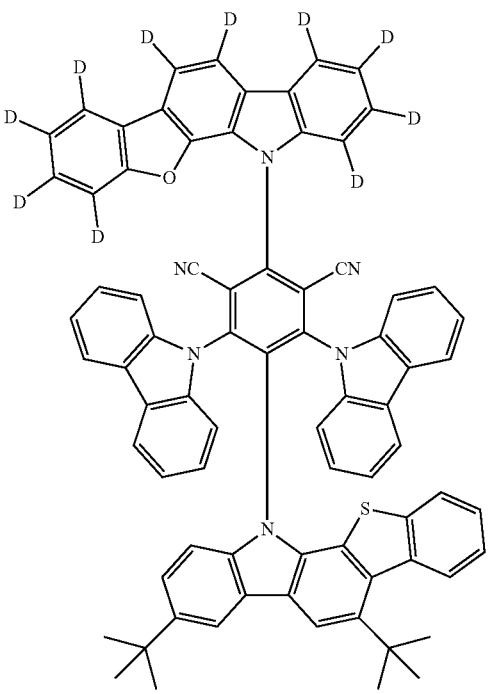

297
-continued
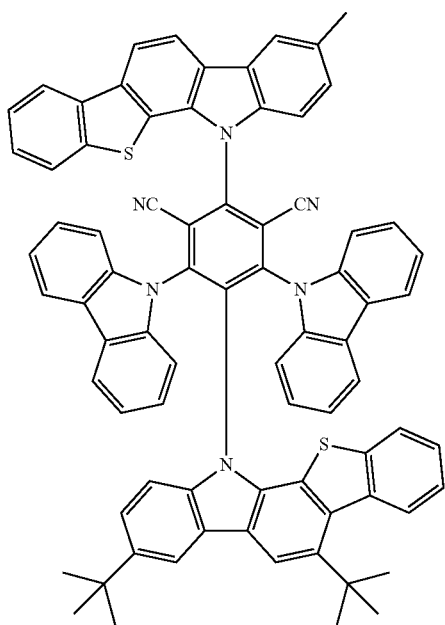
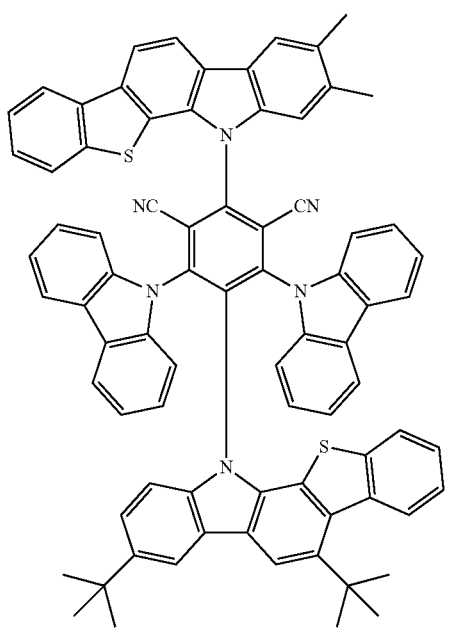
298
-continued
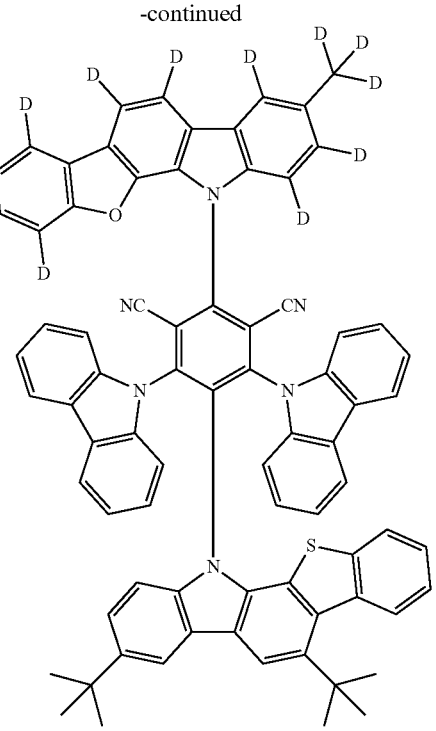
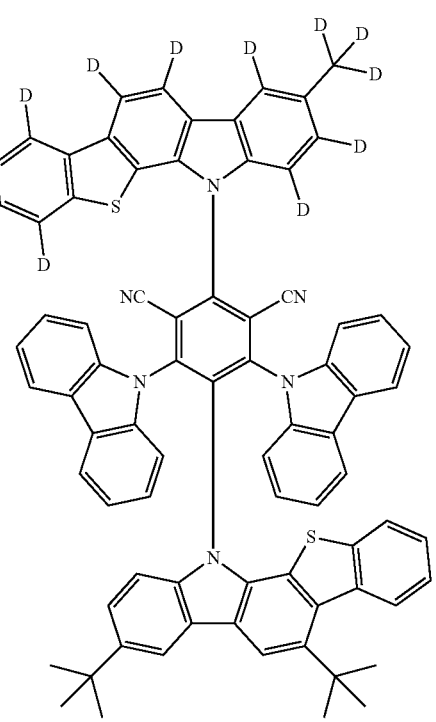

299
-continued
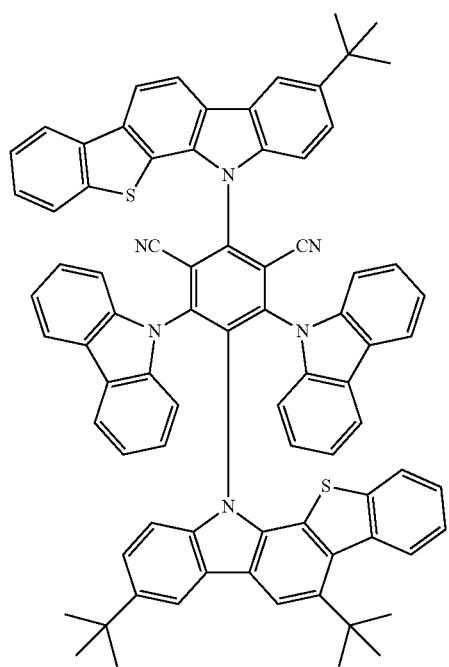
300
-continued
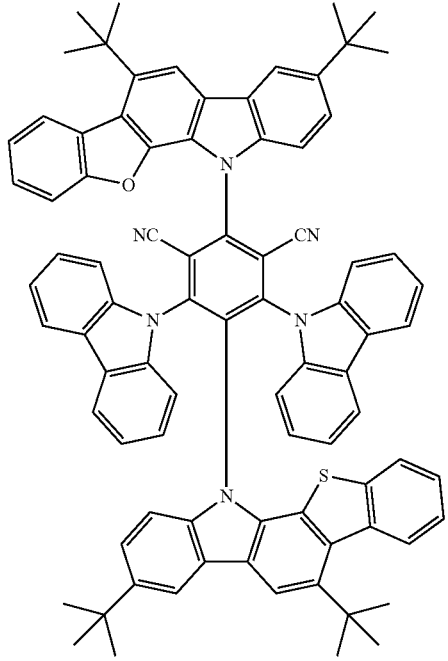
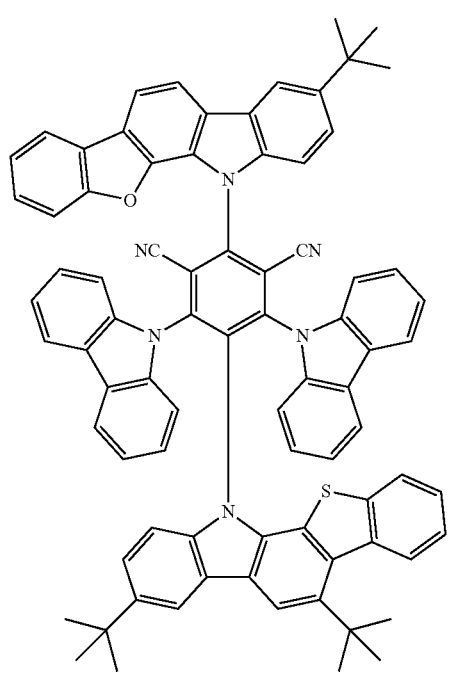
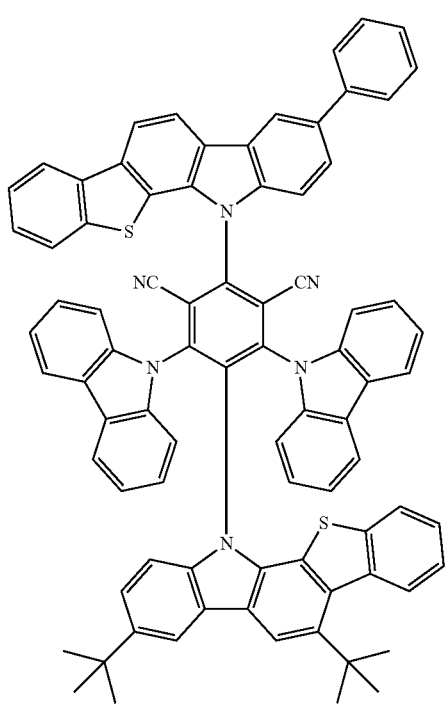

301
-continued
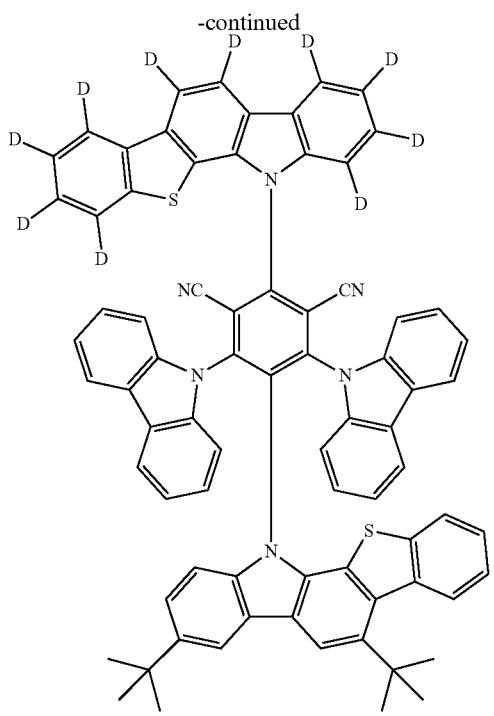
[Formula 84]
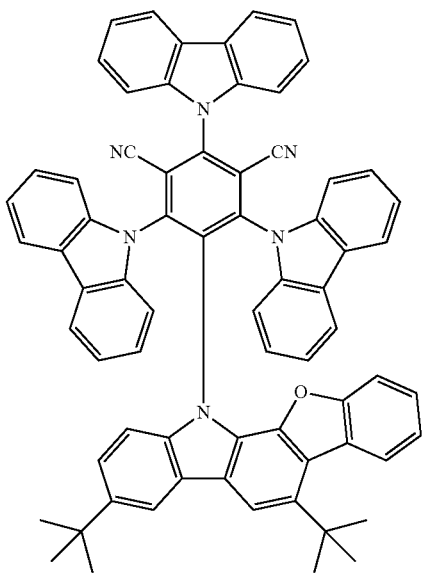
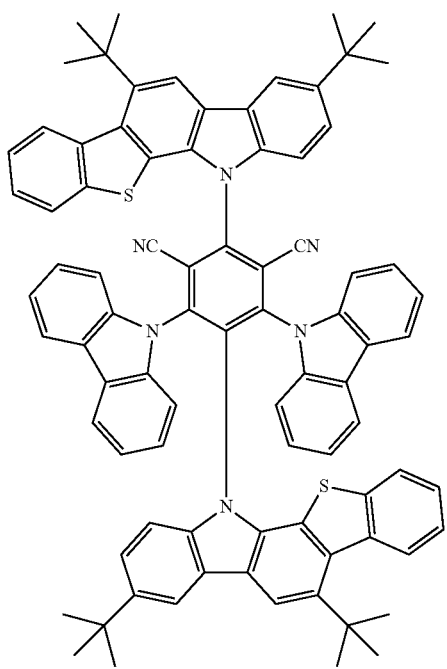
302
-continued
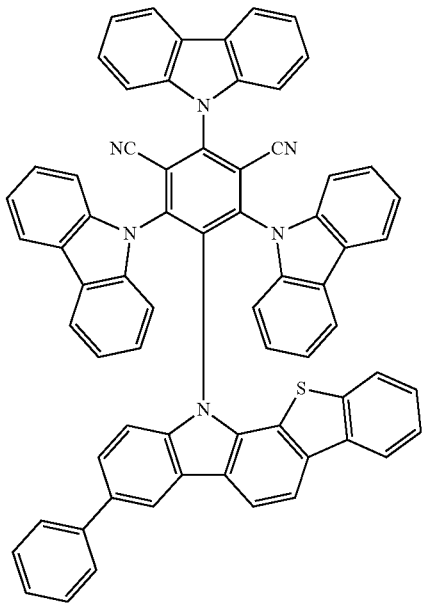

303
-continued
304
-continued
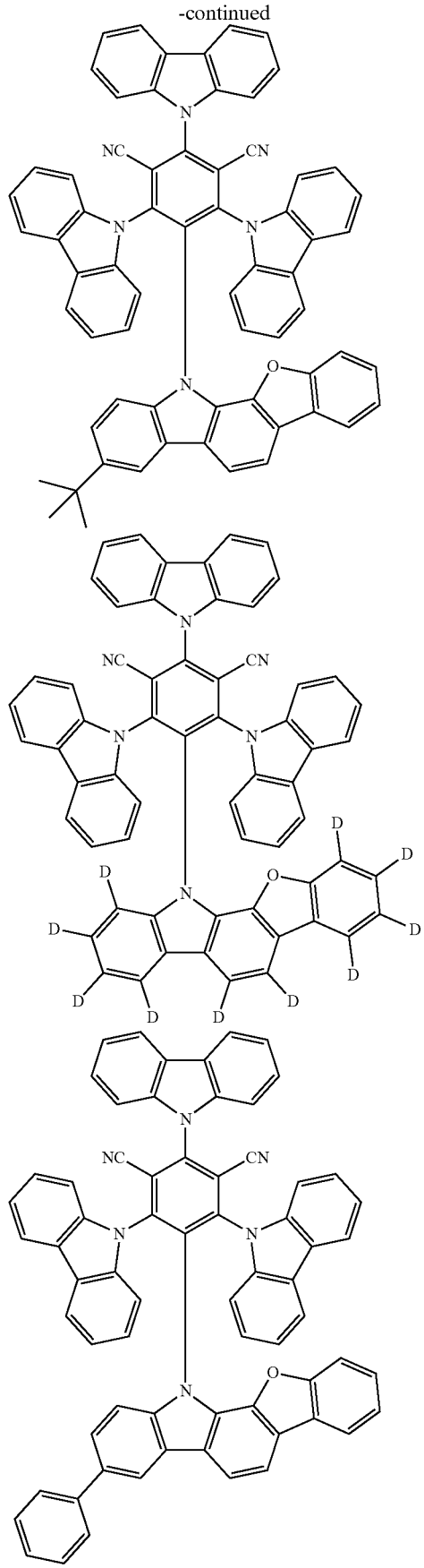
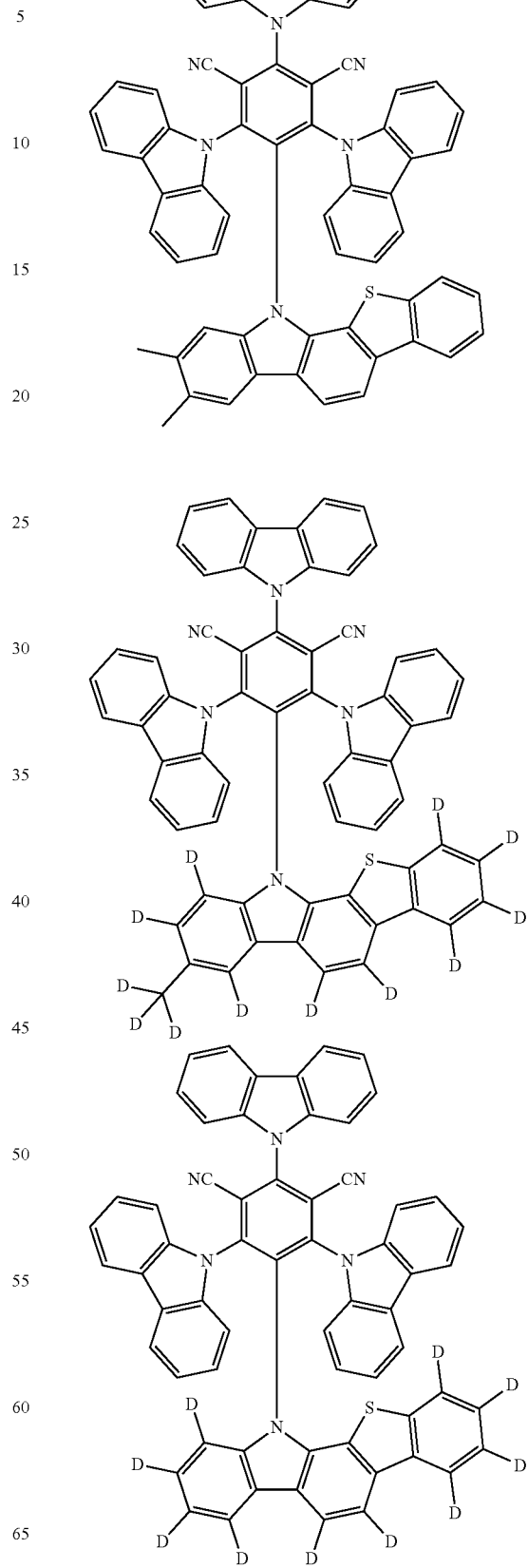

305
-continued
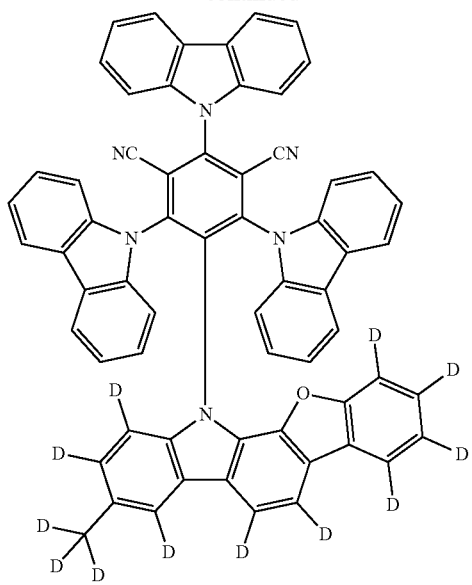
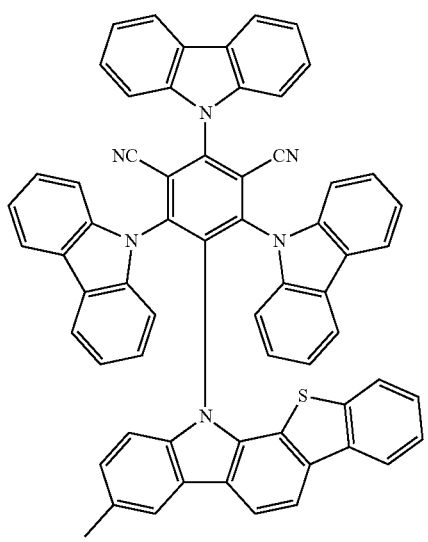
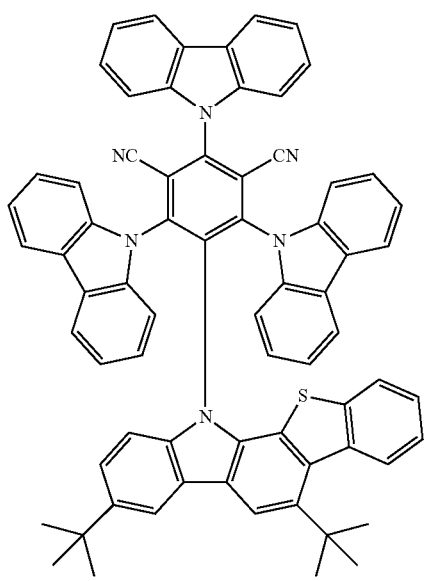
306
-continued
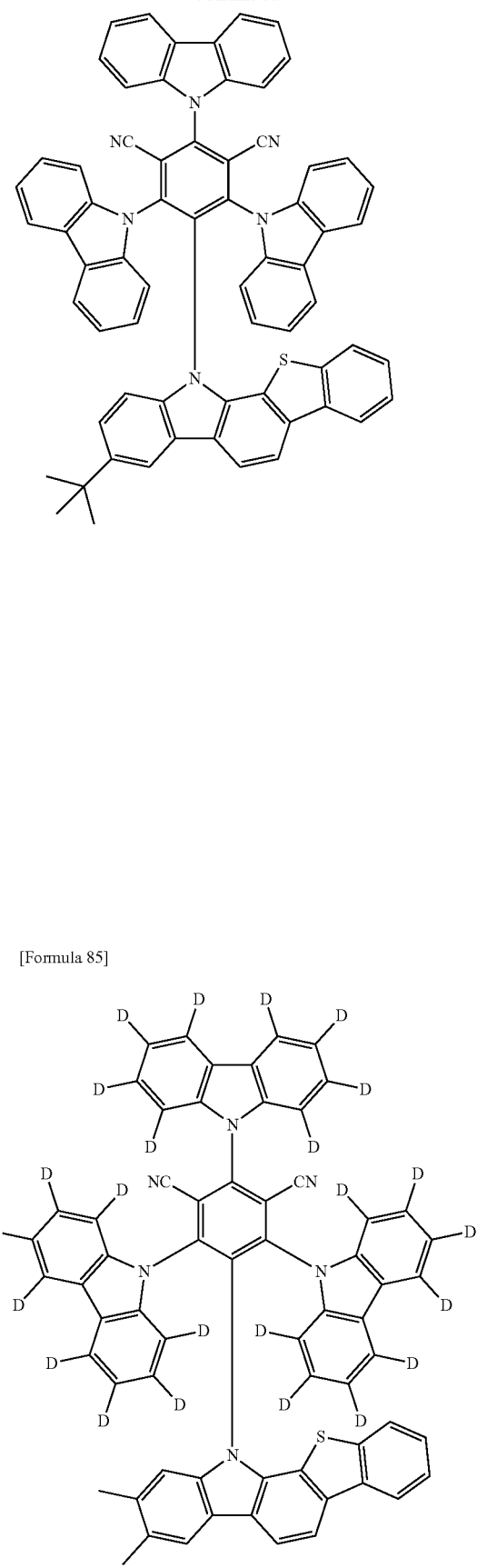
[Formula 85]

307
-continued
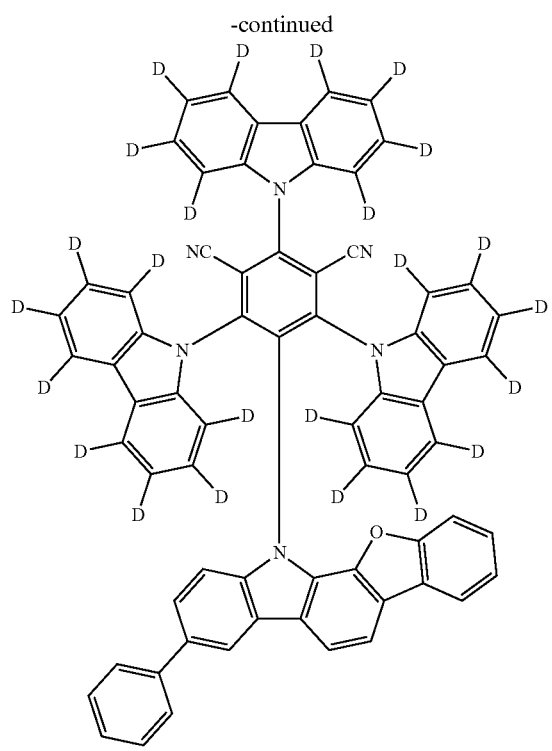
308
-continued
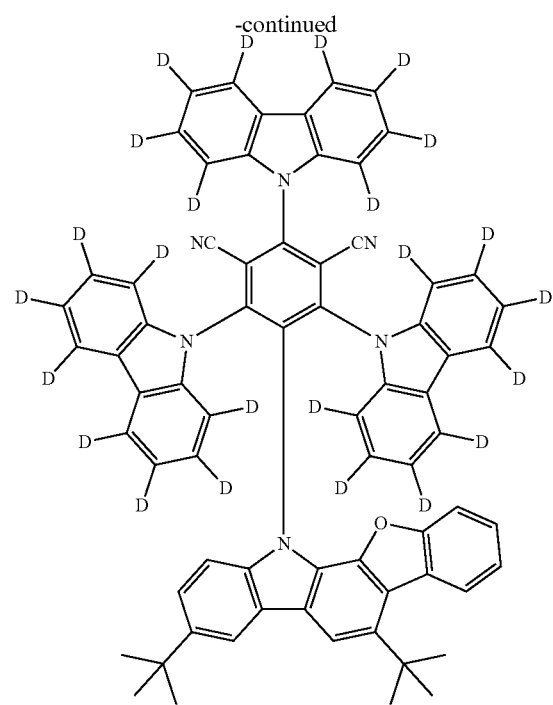
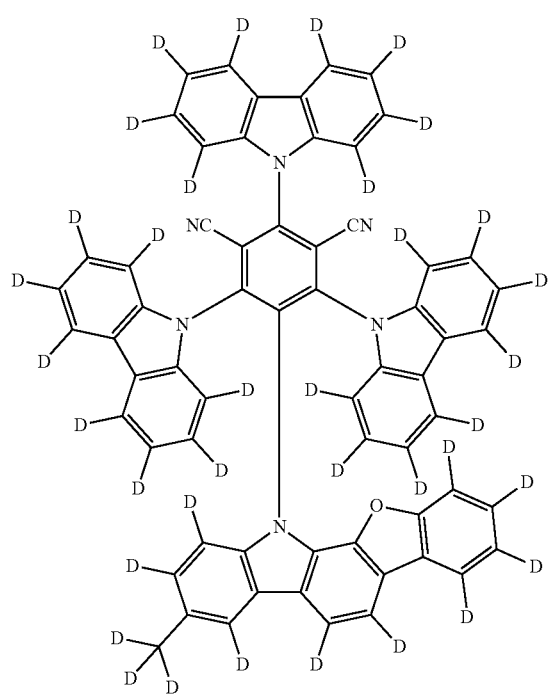
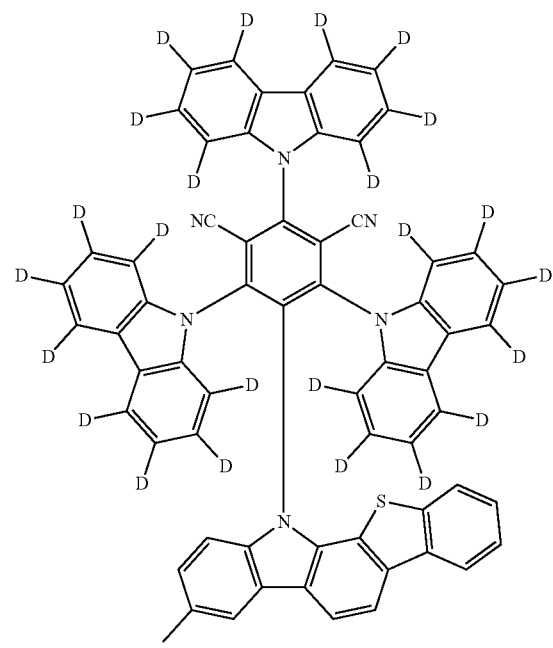

309
-continued
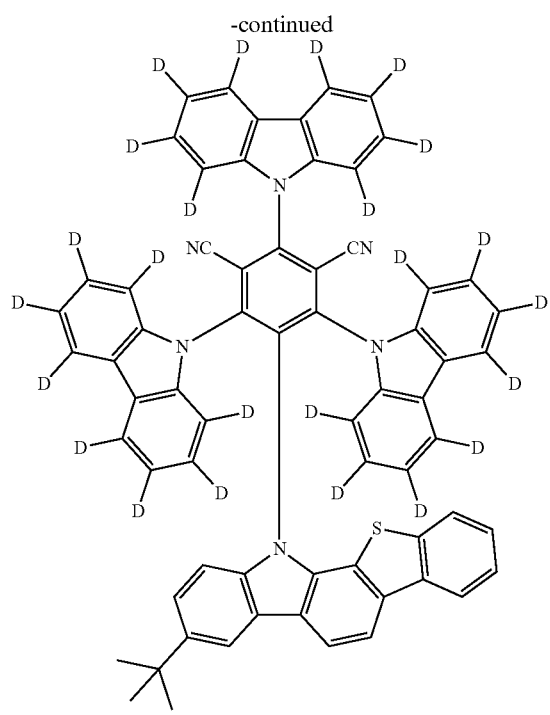
310
-continued
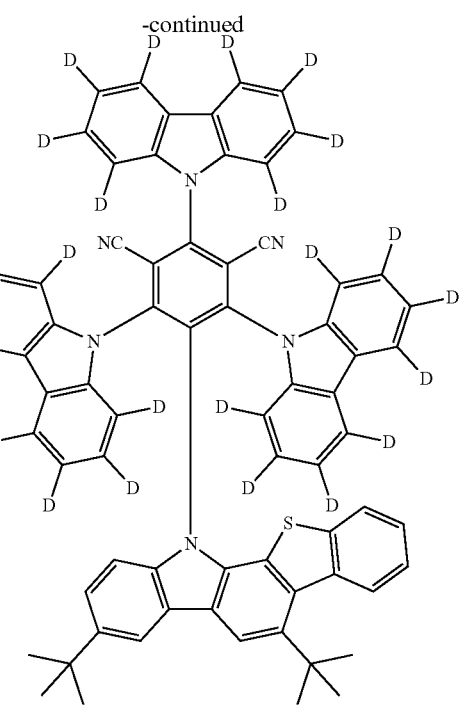
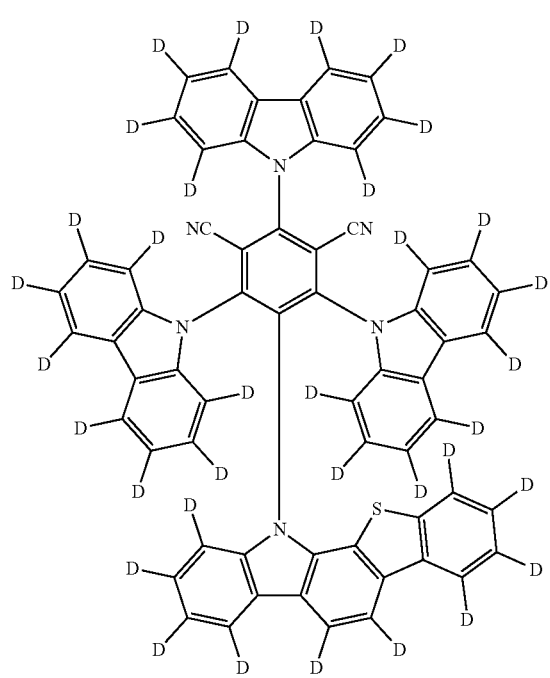
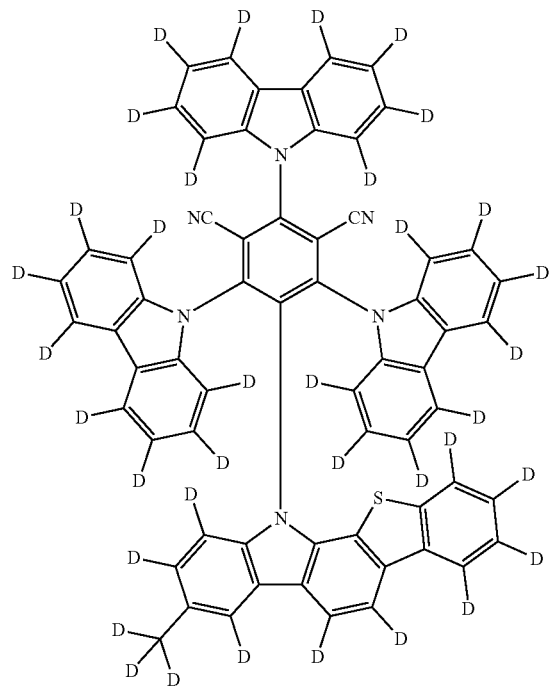

311
-continued
[Formula 86]
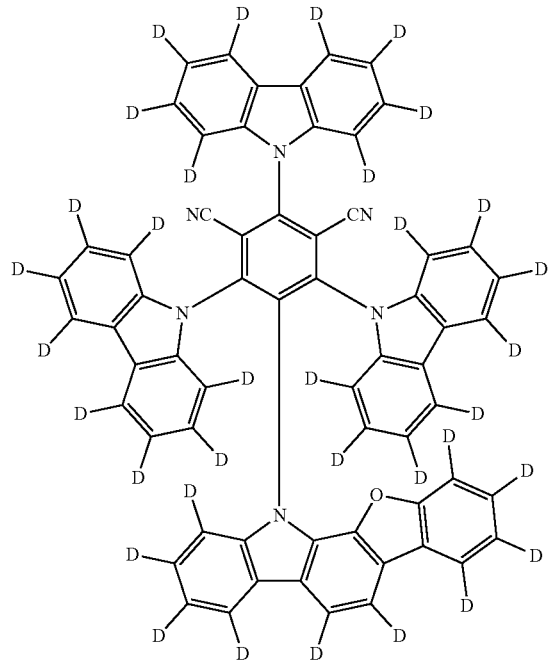
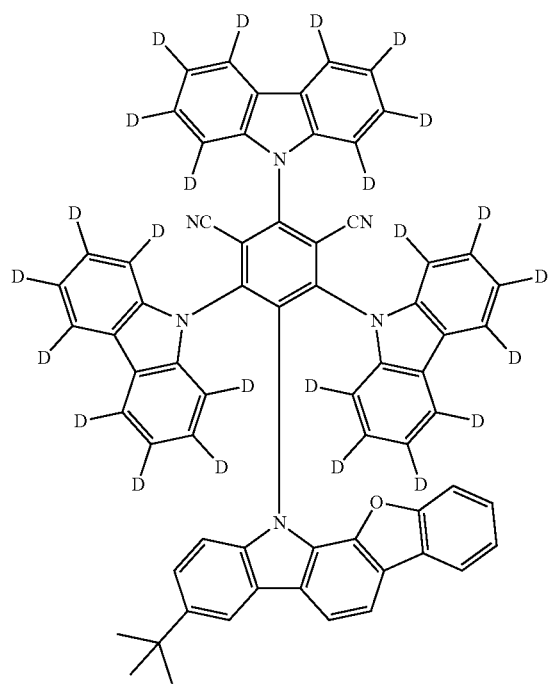
312
-continued
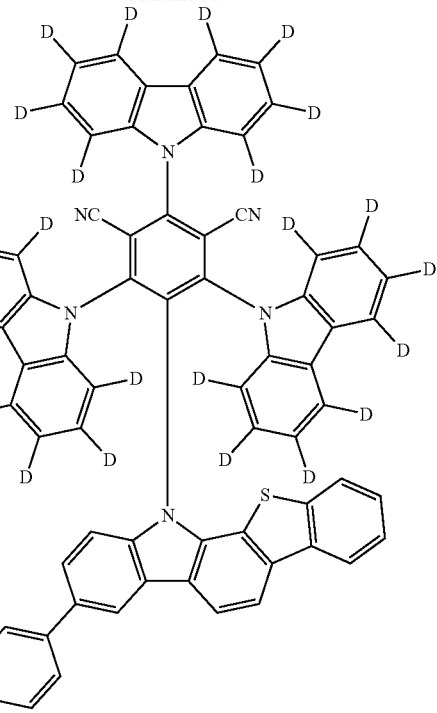
[Formula 87]
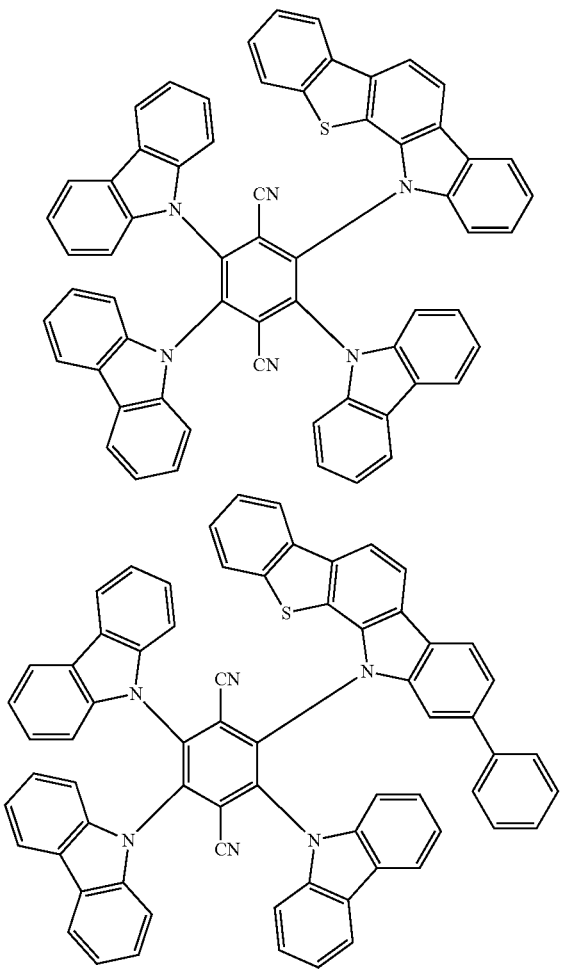

-continued
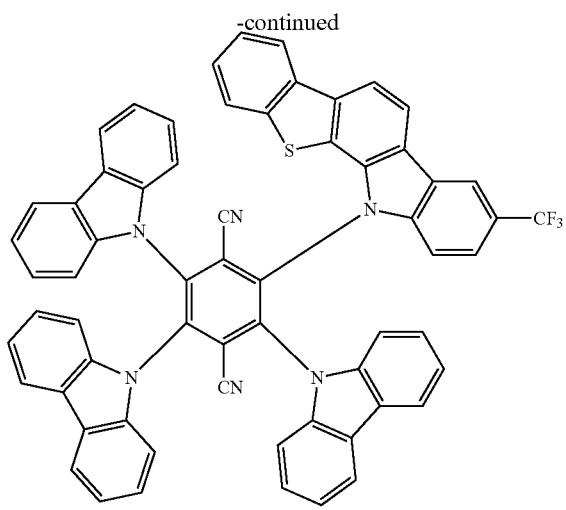 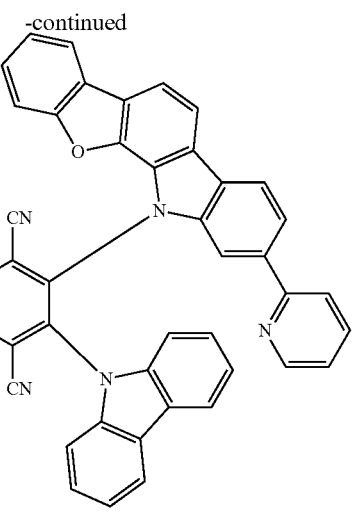
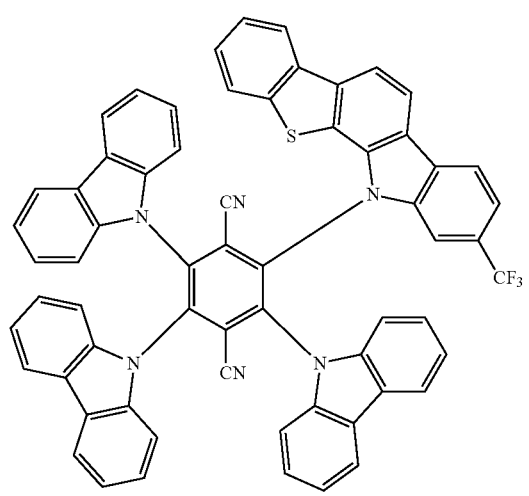 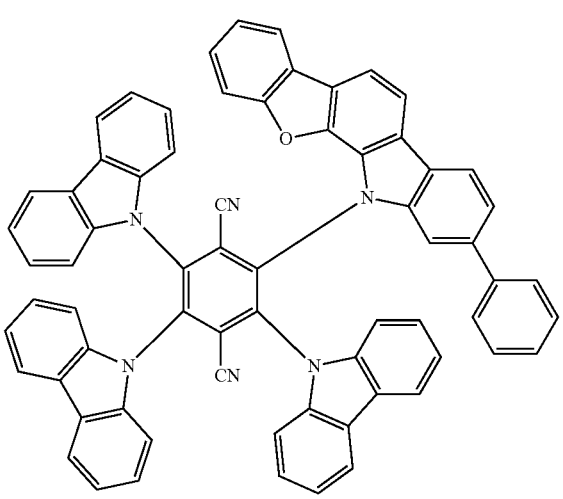
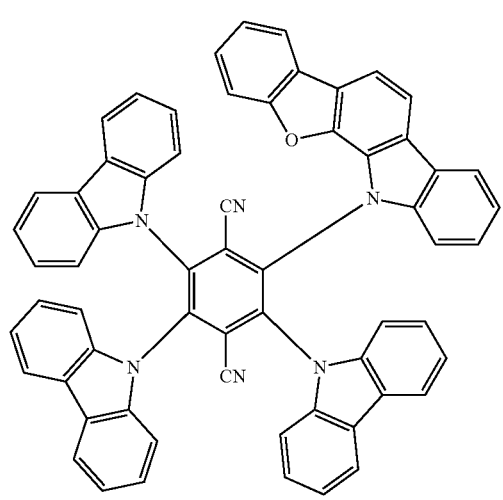 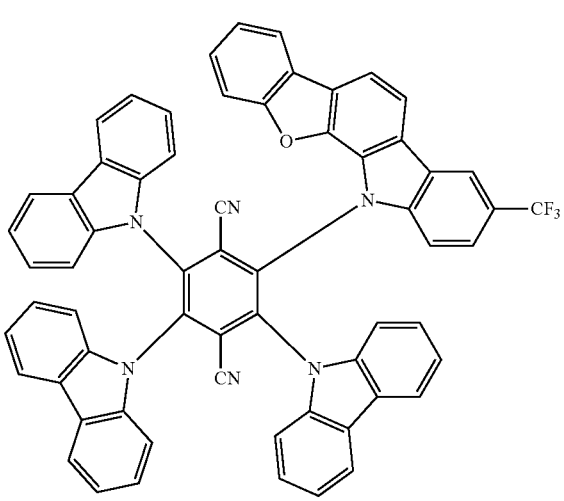

315
-continued
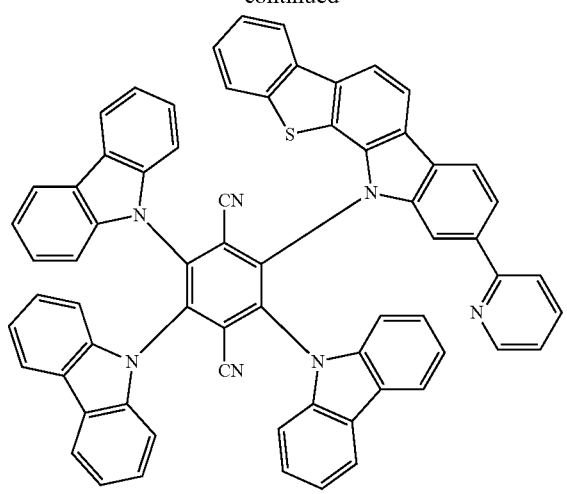
316
-continued
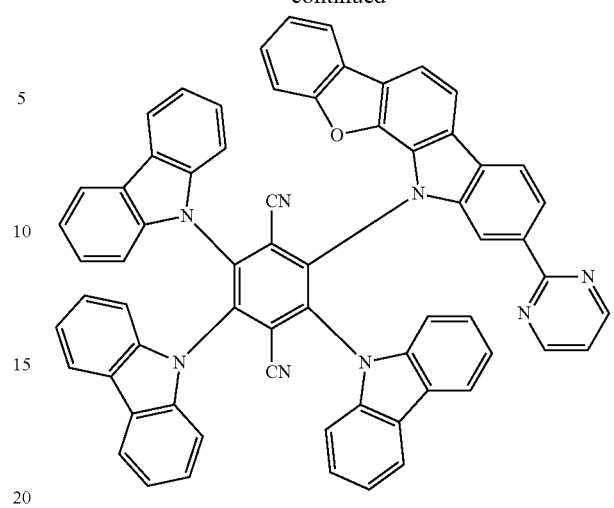
[Formula 88]
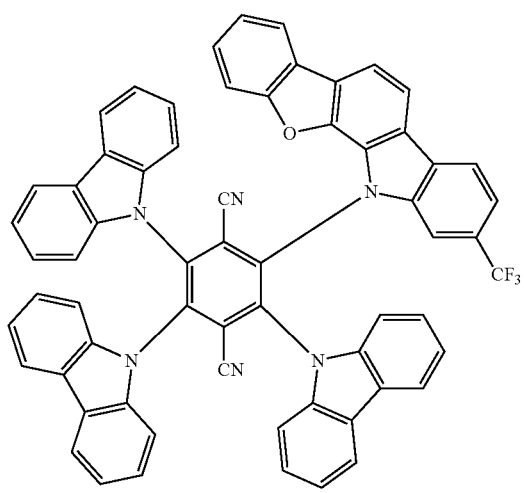
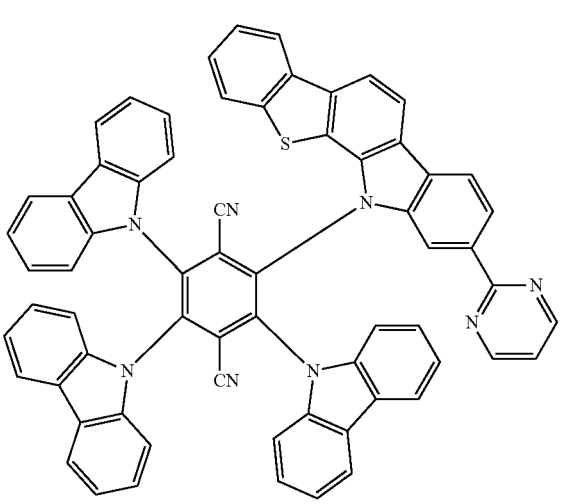
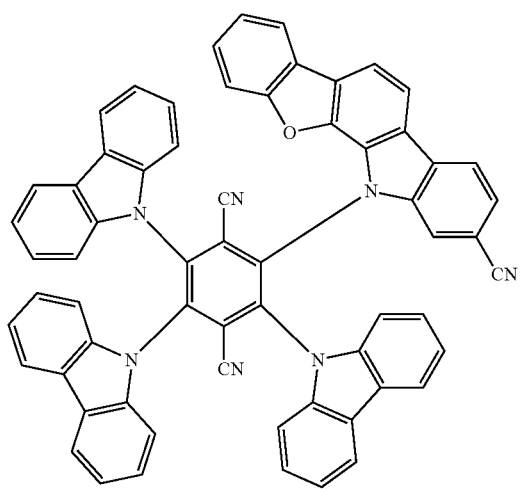
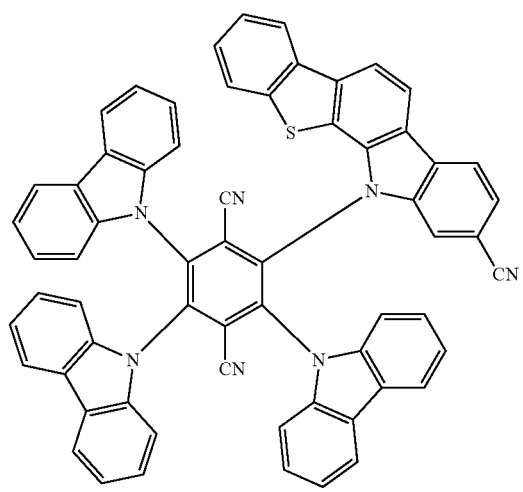

317
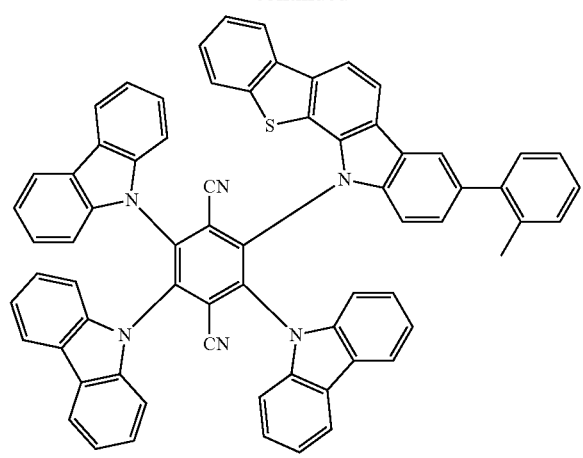
318
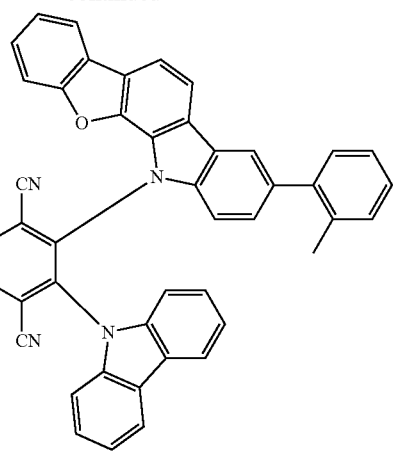
[Formula 89]
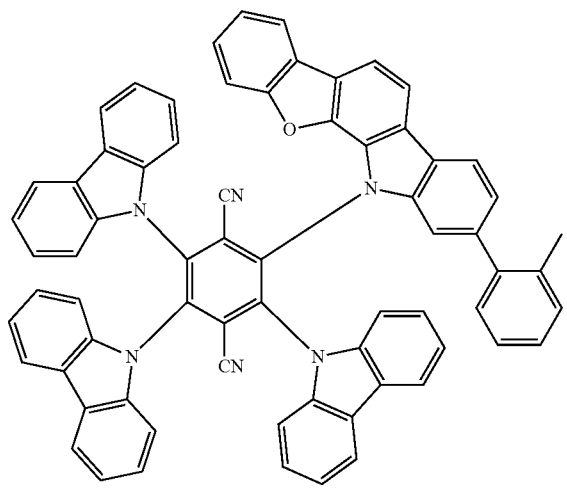
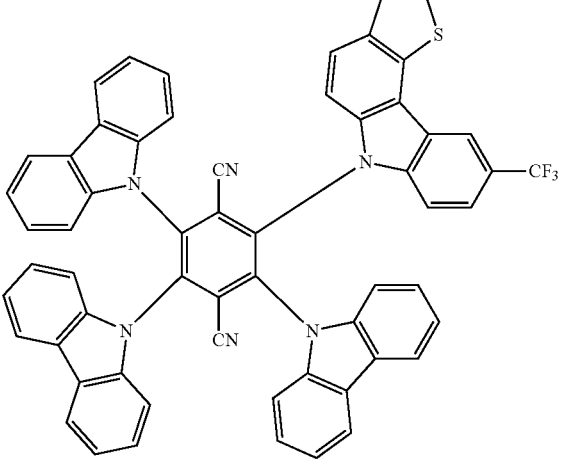
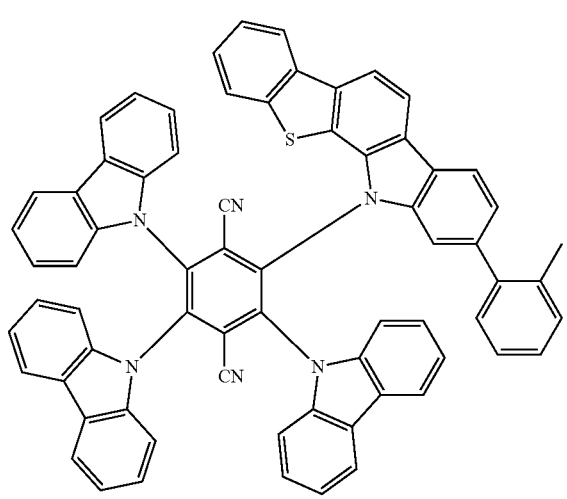
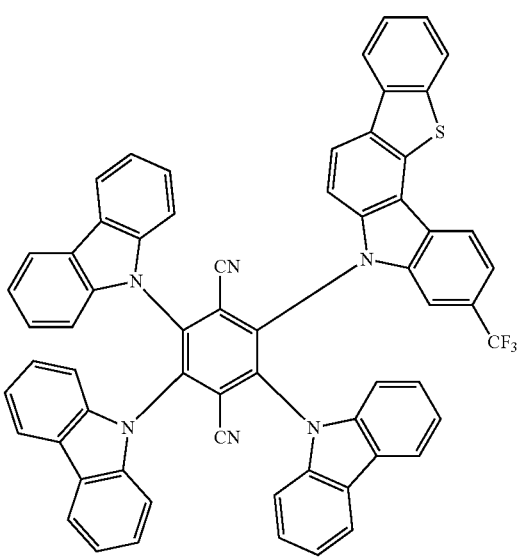

319
-continued
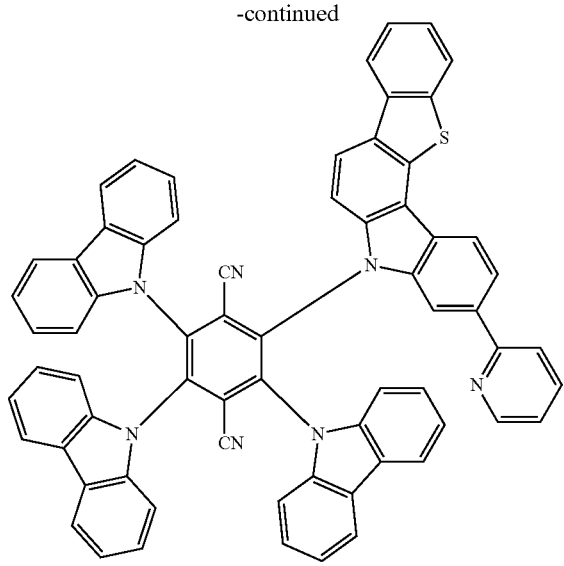
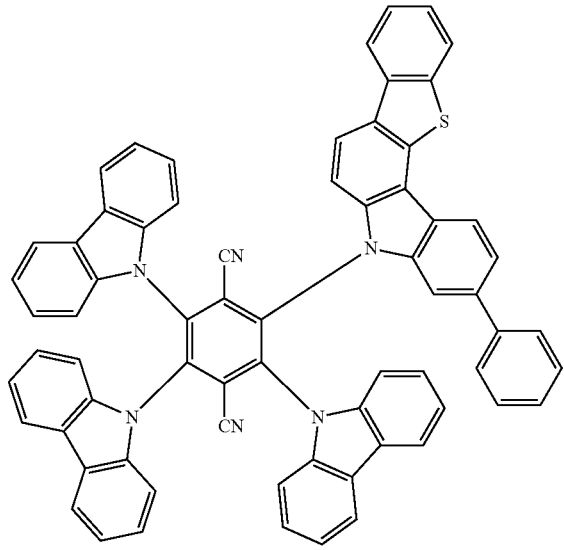
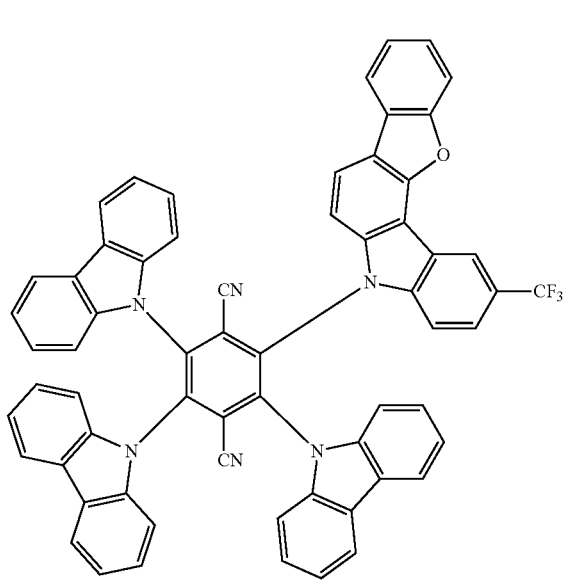
320
-continued
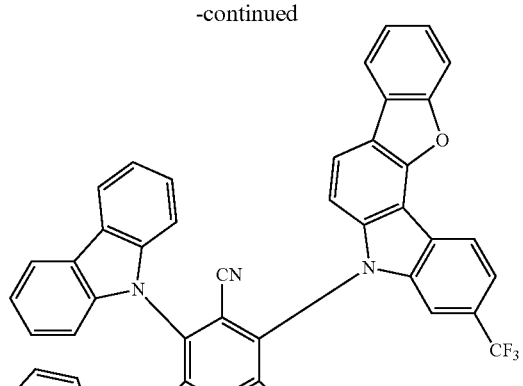
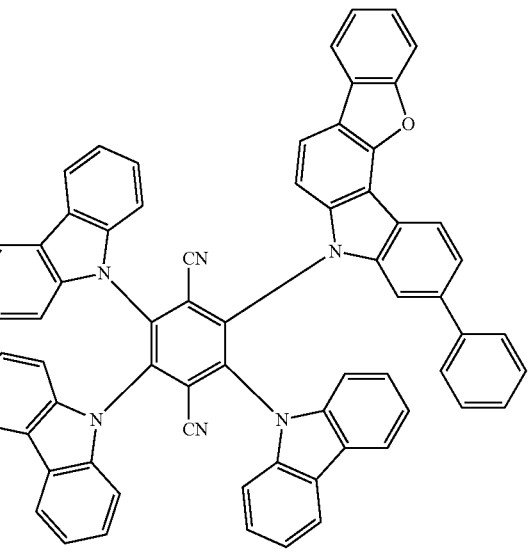
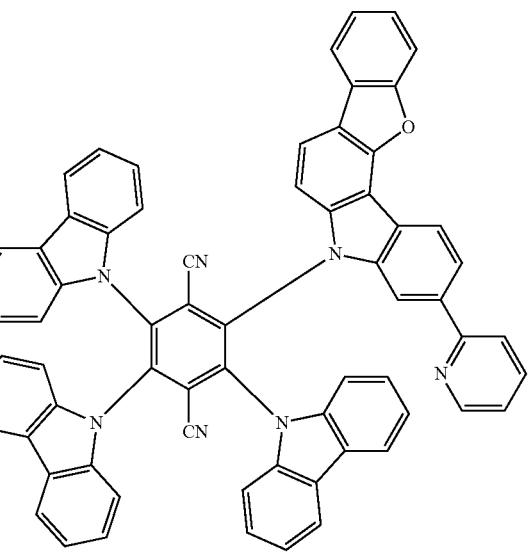

321
-continued
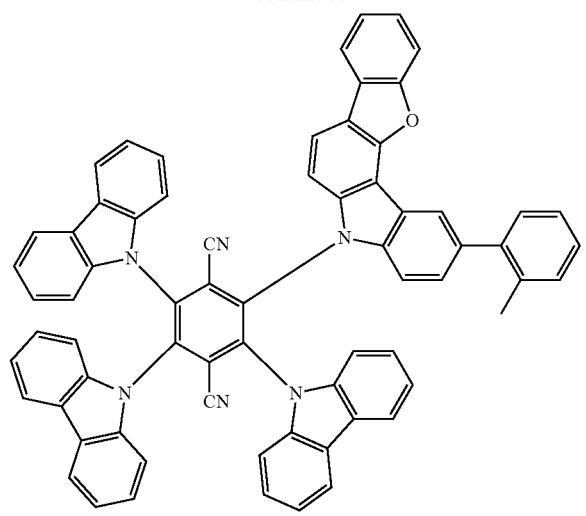
[Formula 90]
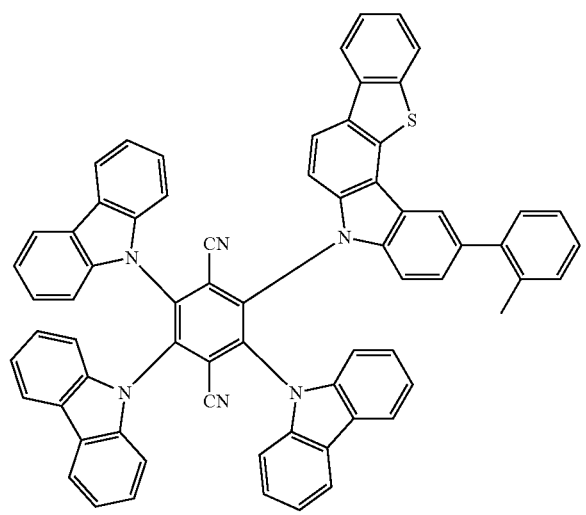
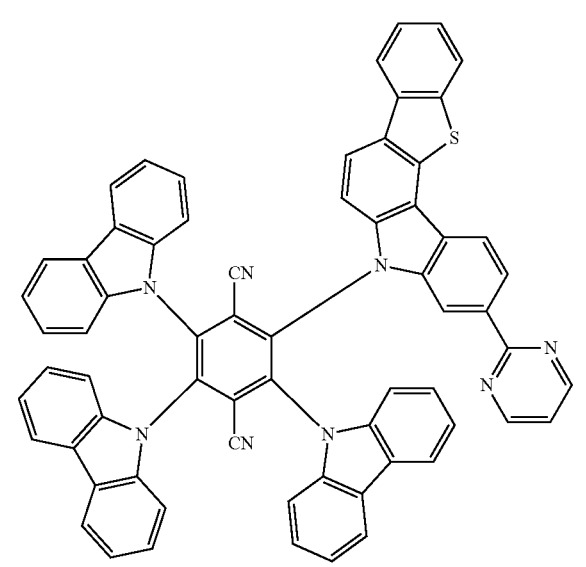
322
-continued
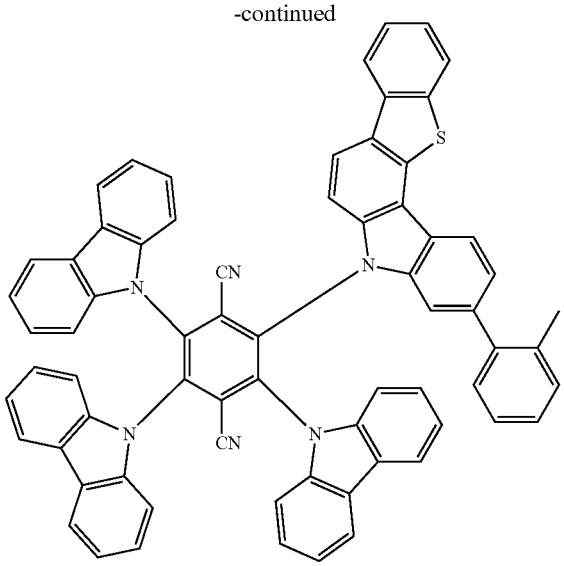
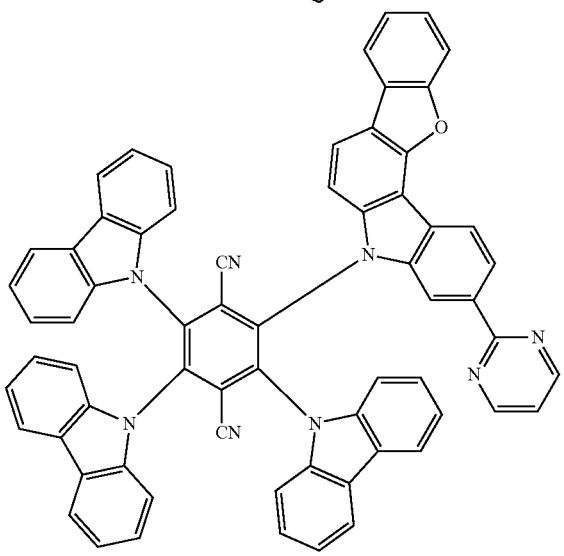
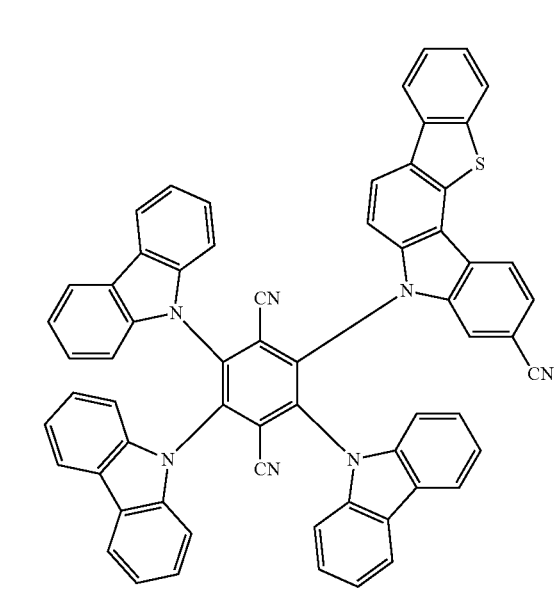 [SMILES: N#Cc1ccc2c3c4oc5ccccc5c4ccc3n(-c3c(C#N)c(-n4c5ccccc5c5ccccc54)c(-n4c5ccccc5c5ccccc54)c(C#N)c3-n3c4ccccc4c4ccccc43)c2c1]

-continued

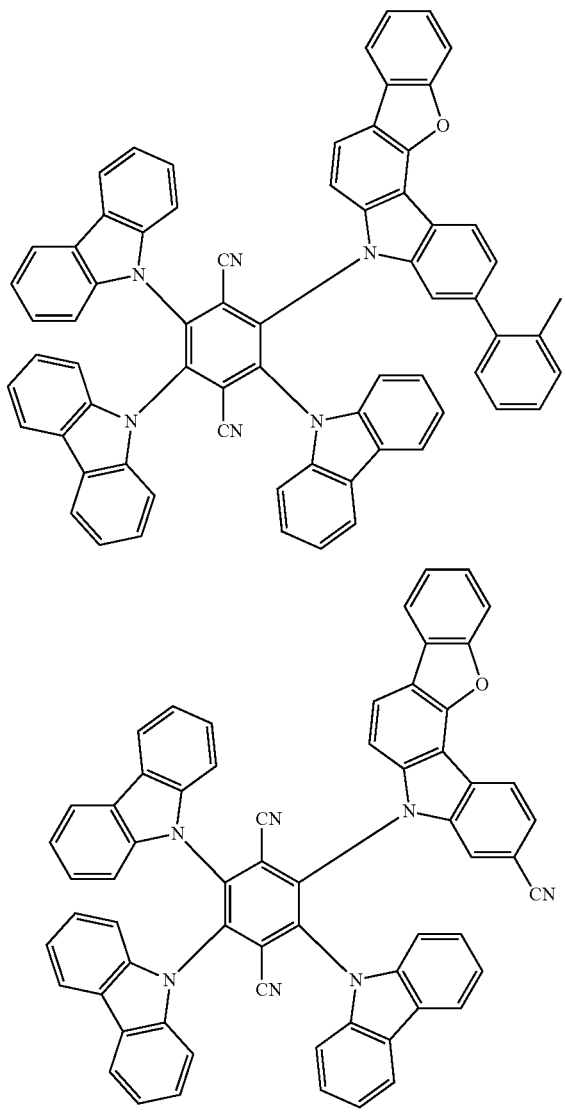

Second Exemplary Embodiment

Organic-EL-Device Material

An organic-EL-device material according to a second exemplary embodiment contains the compound according to the first exemplary embodiment (at least one of the compounds represented by the formulae (11) to (13).)

According to the second exemplary embodiment, the organic-EL-device material capable of decreasing a sublimation temperature when being sublimated and purified while maintaining TADF properties can be obtained.

The organic-EL-device material according to the second exemplary embodiment may further contain a compound other than the compound according to the first exemplary embodiment. When organic-EL-device material according to the second exemplary embodiment contains the compound other than the compound according to the first exemplary embodiment, the compound in the second exemplary embodiment may be solid or liquid.

Third Exemplary Embodiment

Organic EL Device

An arrangement of an organic EL device according to a third exemplary embodiment will be described below.

The organic EL device includes an anode, a cathode, and an at least one organic layer between the anode and the cathode. The organic layer typically includes a plurality of laminated layers formed of an organic compound. The organic layer may further include an inorganic compound. The organic EL device according to the exemplary embodiment includes a first organic layer between the anode and the cathode. The first organic layer contains at least one of the compounds represented by the formulae (11) to (13).

The first organic layer is, for instance, at least one layer selected from the group consisting of a hole injecting layer, a hole transporting layer, an emitting layer, an electron injecting layer, an electron transporting layer, a hole blocking layer and an electron blocking layer.

The first organic layer is preferably the emitting layer.

In the organic EL device of the exemplary embodiment, the first organic layer is the emitting layer.

In the exemplary embodiment, the organic layer may consist of the emitting layer as the first organic layer. Alternatively, the organic layer may further include, for instance, at least one layer selected from the group consisting of the hole injecting layer, the hole transporting layer, the electron injecting layer, the electron transporting layer, the hole blocking layer, and the electron blocking layer.

FIG. 1 schematically shows an exemplary structure of the organic EL device of the exemplary embodiment.

The organic EL device 1 includes a light-transmissive substrate 2, an anode 3, a cathode 4, and an organic layer 10 provided between the anode 3 and the cathode 4. The organic layer 10 includes a hole injecting layer 6, a hole transporting layer 7, an emitting layer 5 (the first organic layer), an electron transporting layer 8, and an electron injecting layer 9, which are sequentially layered on the anode 3.

In the organic EL device 1 according to the exemplary embodiment, the emitting layer 5 contains the first compound.

The first compound is the compound according to the first exemplary embodiment (at least one of the compounds represented by the formulae (11) to (13)).

It is preferable that the emitting layer 5 does not contain a phosphorescent material (dopant material).

It is preferable that the emitting layer 5 does not contain a heavy metal complex and a phosphorescent rare-metal complex. Examples of the heavy metal complex herein include iridium complex, osmium complex, and platinum complex.

It is also preferable that the emitting layer 5 does not contain a metal complex.

In the organic EL device 1 according to the exemplary embodiment, the emitting layer 5 contains the first compound and further a second compound.

In this arrangement, the first compound is preferably a host material (sometimes referred to as a matrix material hereinafter), and the second compound is preferably a dopant material (sometimes referred to as a guest material, an emitter, or a luminescent material hereinafter).

First Compound

The first compound is according to the first exemplary embodiment.

The first compound is preferably a delayed fluorescent compound.

Delayed Fluorescence

Delayed fluorescence is explained in "Yuki Hando-tai no Debaisu Bussei (Device Physics of Organic Semiconductors)" (edited by ADACHI, Chihaya, published by Kodansha, on pages 261-268). This document describes that, if an energy gap $\Delta E_{13}$ of a fluorescent material between a singlet state and a triplet state is reducible, a reverse energy transfer from the triplet state to the singlet state, which usually occurs at a low transition probability, would occur at a high efficiency to express thermally activated delayed fluorescence (TADF). Further, a mechanism of generating delayed fluorescence is explained in FIG. 10.38 in the document. The first compound in the exemplary embodiment is preferably a compound exhibiting thermally activated delayed fluorescence generated by such a mechanism.

In general, emission of delayed fluorescence can be confirmed by measuring the transient PL (Photo Luminescence).

The behavior of delayed fluorescence can also be analyzed based on the decay curve obtained from the transient PL measurement. The transient PL measurement is a method of irradiating a sample with a pulse laser to excite the sample, and measuring the decay behavior (transient characteristics) of PL emission after the irradiation is stopped. PL emission in TADF materials is classified into a light emission component from a singlet exciton generated by the first PL excitation and a light emission component from a singlet exciton generated via a triplet exciton. The lifetime of the singlet exciton generated by the first PL excitation is on the order of nanoseconds and is very short. Therefore, light emission from the singlet exciton rapidly attenuates after irradiation with the pulse laser.

On the other hand, the delayed fluorescence is gradually attenuated due to light emission from a singlet exciton generated via a triplet exciton having a long lifetime. As described above, there is a large temporal difference between the light emission from the singlet exciton generated by the first PL excitation and the light emission from the singlet exciton generated via the triplet exciton. Therefore, the luminous intensity derived from delayed fluorescence can be determined.

Figure 2:
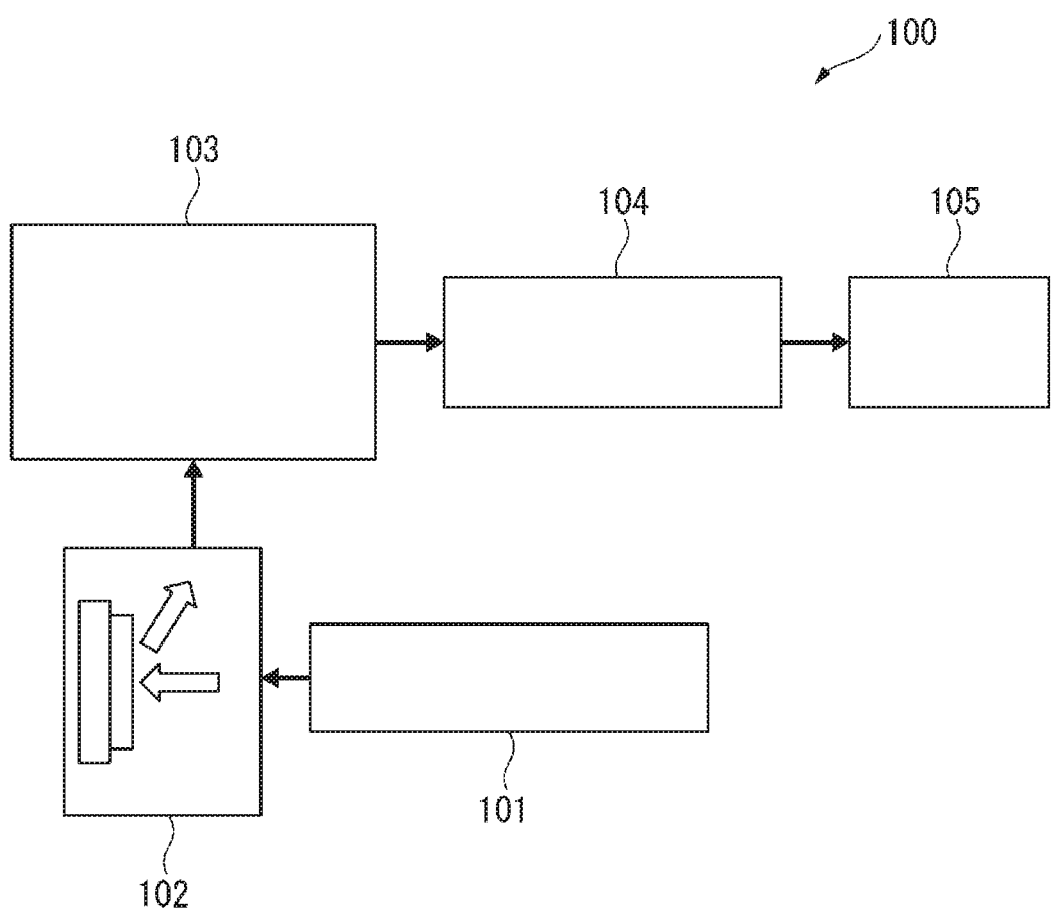

FIG. 2 shows a schematic diagram of an exemplary device for measuring the transient PL. An example of a method of measuring a transient PL using FIG. 2 and an example of behavior analysis of delayed fluorescence will be described.

A transient PL measuring device 100 in FIG. 2 includes: a pulse laser 101 capable of radiating a light having a predetermined wavelength; a sample chamber 102 configured to house a measurement sample; a spectrometer 103 configured to divide a light radiated from the measurement sample; a streak camera 104 configured to provide a two-dimensional image; and a personal computer 105 configured to import and analyze the two-dimensional image. A device for measuring the transient PL is not limited to the device described in the exemplary embodiment.

The sample to be housed in the sample chamber 102 is obtained by doping a matrix material with a doping material at a concentration of 12 mass % and forming a thin film on a quartz substrate.

The thin film sample housed in the sample chamber 102 is radiated with a pulse laser from the pulse laser 101 to excite the doping material. Emission is extracted in a direction of 90 degrees with respect to a radiation direction of the excited light. The extracted emission is divided by the spectrometer 103 to form a two-dimensional image in the streak camera 104. As a result, the two-dimensional image is obtainable in which the ordinate axis represents a time, the abscissa axis represents a wavelength, and a bright spot represents a luminous intensity. When this two-dimensional image is taken out at a predetermined time axis, an emission spectrum in which the ordinate axis represents the luminous intensity and the abscissa axis represents the wavelength is obtainable. Moreover, when this two-dimensional image is taken out at the wavelength axis, a decay curve (transient PL) in which the ordinate axis represents a logarithm of the luminous intensity and the abscissa axis represents the time is obtainable.

For instance, a thin film sample A was manufactured as described above from a reference compound H1 as the matrix material and a reference compound D1 as the doping material and was measured in terms of the transient PL.

[Formula 91]

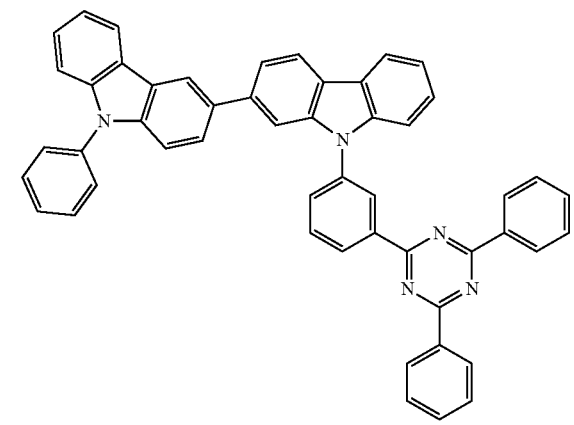

Reference Compound H1

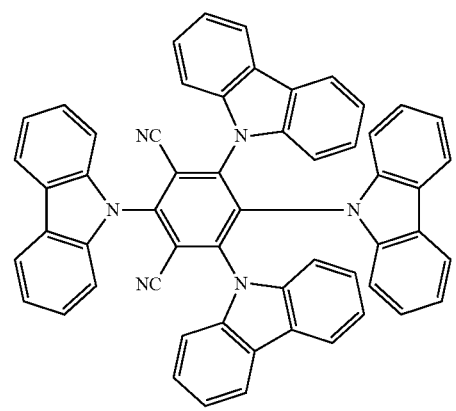

Reference Compound D1

The decay curve was analyzed with respect to the above thin film sample A and a thin film sample B. The thin film sample B was manufactured in the same manner as described above from a reference compound H2 as the matrix material and the reference compound D1 as the doping material.

Figure 3:
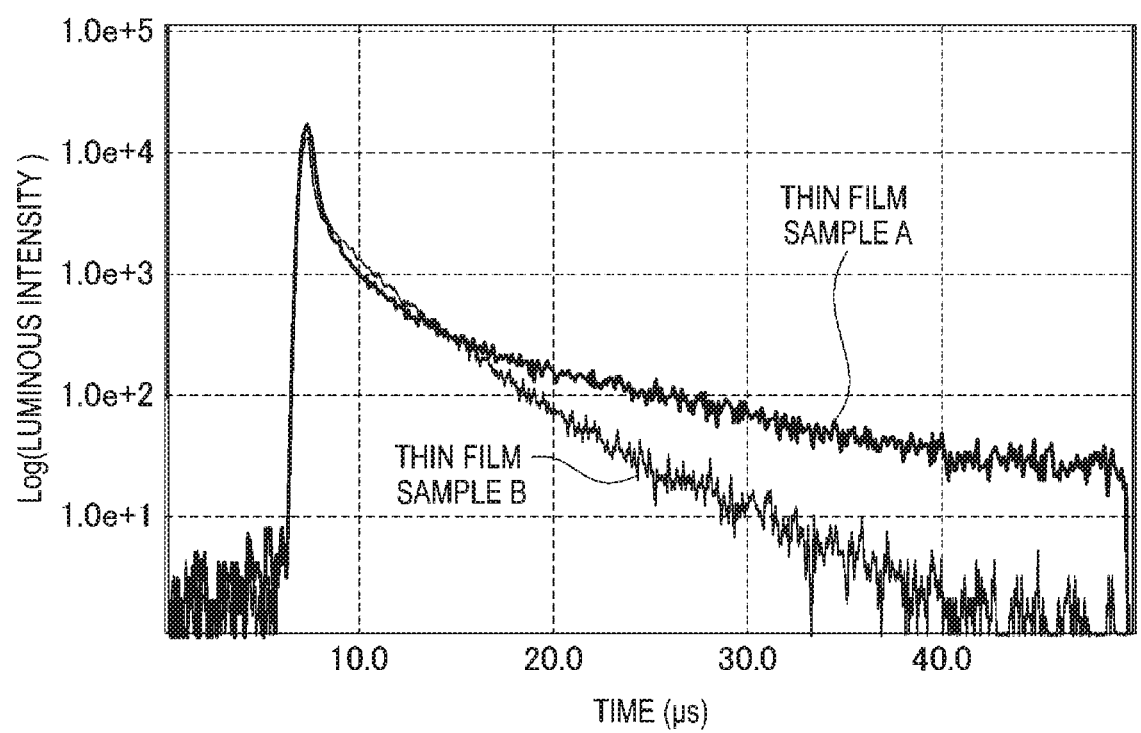
FIG. 3 shows an example of a decay curve of the transient PL.

FIG. 3 shows decay curves obtained from transient PL obtained by measuring the thin film samples A and B.

[Formula 92]

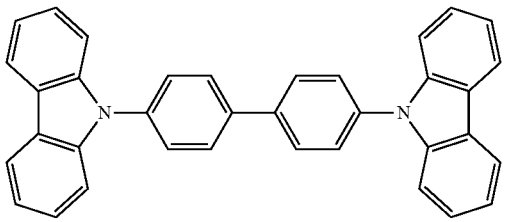

Reference Compound H2

As described above, an emission decay curve in which the ordinate axis represents the luminous intensity and the abscissa axis represents the time can be obtained by the transient PL measurement. Based on the emission decay curve, a fluorescence intensity ratio between fluorescence emitted from a singlet state generated by photo-excitation and delayed fluorescence emitted from a singlet state generated by inverse energy transfer via a triplet state can be estimated. In a delayed fluorescent material, a ratio of the intensity of the slowly decaying delayed fluorescence to the intensity of the promptly decaying fluorescence is relatively large.

Specifically, Prompt emission and Delay emission are present as emission from the delayed fluorescent material. Prompt emission is observed promptly when the excited state is achieved by exciting the compound of the exemplary embodiment with a pulse beam (i.e., a beam emitted from a pulse laser) having a wavelength absorbable by the delayed fluorescent material. Delay emission is observed not promptly when the excited state is achieved but after the excited state is achieved.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 2.

In the exemplary embodiment, a sample manufactured by a method shown below is used for measuring delayed fluorescence of the first compound. For instance, the first compound is dissolved in toluene to prepare a dilute solution with an absorbance of 0.05 or less at the excitation wavelength to eliminate the contribution of self-absorption. In order to prevent quenching due to oxygen, the sample solution is frozen and degassed and then sealed in a cell with a lid under an argon atmosphere to obtain an oxygen-free sample solution saturated with argon.

The fluorescence spectrum of the sample solution is measured with a spectrofluorometer FP-8600 (manufactured by JASCO Corporation), and the fluorescence spectrum of a 9,10-diphenylanthracene ethanol solution is measured under the same conditions. Using the fluorescence area intensities of both spectra, the total fluorescence quantum yield is calculated by an equation (1) in Morris et al. J. Phys. Chem. 80 (1976) 969.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 2.

In the exemplary embodiment, a measurement target compound (the first compound) preferably has a value of $X_D/X_P$ is 0.05 or more, provided that the amount of Prompt emission is denoted by $X_P$ and the amount of Delay emission is denoted by $X_D$.

Amounts of Prompt emission and Delay emission and a ratio of the amounts thereof in compounds other than the first compound herein are measured in the same manner as those of the first compound.

Second Compound

The second compound is preferably a fluorescent compound. The second compound may be a thermally activated delayed fluorescent compound or a compound exhibiting no thermally activated delayed fluorescence.

A fluorescent material is usable as the second compound in the exemplary embodiment. Specific examples of the fluorescent material include a bisarylaminonaphthalene derivative, aryl-substituted naphthalene derivative, bisarylaminoanthracene derivative, aryl-substituted anthracene derivative, bisarylaminopyrene derivative, aryl-substituted pyrene derivative, and bisarylamino Chrysene derivative, aryl-substituted chrysene derivative, bisarylaminofluoranthene derivative, aryl-substituted fluoranthene derivative, indenoperylene derivative, acenaphthofluoranthene derivative, pyromethene boron complex compound, compound having a pyromethene skeleton, metal complex of the compound having a pyrromethene skeleton, diketopyrrolopyrrole derivative, perylene derivative, and naphthacene derivative.

The second compound in the exemplary embodiment is also preferably represented by a formula (20) below.

The second compound is represented by the formula (20) below.

The second compound is preferably a fluorescent compound.

[Formula 93]

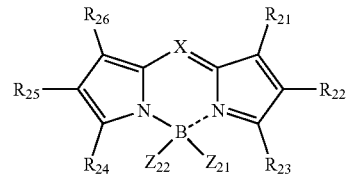

(20)

In the formula (20), X is a nitrogen atom, or a carbon atom bonded to Y.

Y is a hydrogen atom or a substituent.

$R_{21}$ to $R_{26}$ are each independently a hydrogen atom or a substituent, or at least one of a pair of $R_{21}$ and $R_{22}$, a pair of $R_{22}$ and $R_{23}$, a pair of $R_{24}$ and $R_{25}$, or a pair of $R_{25}$ and $R_{26}$ are mutually bonded to form a ring.

Y and $R_{21}$ to $R_{26}$ each being the substituent are each independently selected from the group consisting of a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, a substituted or unsubstituted alkylthio group having 6 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted alkenyl group having 2 to 30 carbon atoms, a substituted or unsubstituted aralkyl group having 7 to 30 carbon atoms, a substituted or unsubstituted heteroaryl group having 5 to 30 ring atoms, a halogen atom, a carboxy group, a substituted or unsubstituted ester group, a substituted or unsubstituted carbamoyl group, a substituted or unsubstituted amino group, a nitro group, a cyano group, a substituted or unsubstituted silyl group, and a substituted or unsubstituted siloxanyl group.

$Z_{21}$ and $Z_{22}$ are each independently a substituent, or are mutually bonded to form a ring, $Z_{21}$ and $Z_{22}$ as the substituent are each independently selected from the group consisting of a halogen atom, a substituted or unsubstituted alkyl group having 1 to 30 carbon atoms, a substituted or unsubstituted alkyl halide group having 1 to 30 carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, and a substituted or unsubstituted aryloxy group having 6 to 30 ring carbon atoms.

For instance, when a pair of $R_{25}$ and $R_{26}$ in the formula (20) is mutually bonded to form a ring, the second compound is represented by a formula (21) below.

[Formula 94]

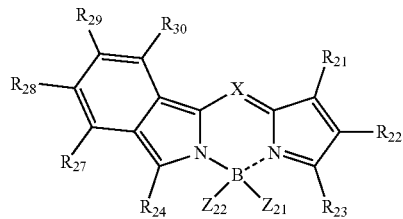

(21)

In the formula (21), X, Y, $R_{21}$ to $R_{24}$, $Z_{21}$ and $Z_{22}$ respectively represent the same as X, Y, $R_{21}$ to $R_{24}$, $Z_{21}$ and $Z_{22}$ in the formula (20). $R_{27}$ to $R_{30}$ each independently represent a hydrogen atom or a substituent. When $R_{27}$ to $R_{30}$ are each independently the substituent, the substituent represents the same as the substituents for $R_{21}$ to $R_{24}$.

When a pair of $R_{21}$ and $R_{22}$ in the formula (20) is mutually bonded to form a ring, the second compound is represented by a formula (20A) or (20B) below. However, a structure of the second compound is not limited to structures below.

[Formula 95]

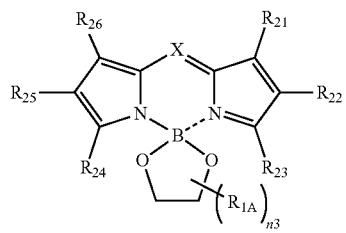

(20A)

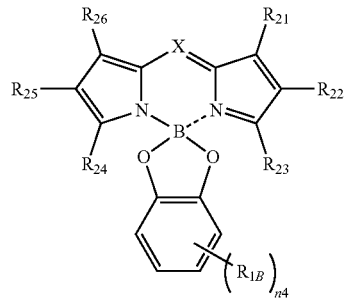

(20B)

In the formula (20A), X, Y and $R_{21}$ to $R_{26}$ respectively represent the same as X, Y and $R_{21}$ to $R_{26}$ in the formula (20). $R_{1A}$ each independently represent a hydrogen atom or a substituent. When $R_{1A}$ is the substituent, the substituent represents the same as the substituents for $R_{21}$ to $R_{26}$. n3 is 4.

In the formula (20B), X, Y and $R_{21}$ to $R_{26}$ respectively represent the same as X, Y and $R_{21}$ to $R_{26}$ in the formula (20). RIB each independently represent a hydrogen atom or a substituent. When $R_{1B}$ is the substituent, the substituent represents the same as the substituents for $R_{21}$ to $R_{26}$. n4 is 4.

It is preferable that at least one of $Z_{21}$ or $Z_{22}$ (preferably both of $Z_{21}$ and $Z_{22}$) is a group selected from the group consisting of a substituted or unsubstituted alkyl group having 1 to 30 carbon atoms, substituted or unsubstituted alkyl halide group having 1 to 30 carbon atoms, substituted or unsubstituted aryl group having 6 to 30 ring carbon atoms, substituted or unsubstituted alkoxy group having 1 to 30 carbon atoms, substituted or unsubstituted alkoxy halide group having 1 to 30 carbon atoms, and substituted or unsubstituted aryloxy group having 6 to 30 ring carbon atoms.

It is more preferable that at least one of $Z_{21}$ or $Z_{22}$ is a group selected from the group consisting of a fluorine-substituted alkoxy group having 1 to 30 carbon atoms, a fluorine-substituted aryloxy group having 6 to 30 ring carbon atoms, and an aryloxy group having 6 to 30 ring carbon atoms and substituted with a fluoroalkyl group having 1 to 30 carbon atoms.

Further preferably, at least one of $Z_{21}$ or $Z_{22}$ is a fluorine-substituted alkoxy group having 1 to 30 carbon atoms. Furthermore preferably, both of $Z_{21}$ and $Z_{22}$ are a fluorine-substituted alkoxy group having 1 to 30 carbon atoms.

It is also preferable that both of $Z_{21}$ and $Z_{22}$ are the same to each other.

Meanwhile, it is also preferable that at least one of $Z_{21}$ or $Z_{22}$ is a fluorine atom. It is also more preferable that both of $Z_{21}$ and $Z_{22}$ are fluorine atoms.

It is also preferable that at least one of $Z_{21}$ or $Z_{22}$ is a group represented by a formula (20a).

[Formula 96]

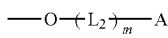
(20a)

In the formula (20a): A represents a substituted or unsubstituted alkyl group having 1 to 6 carbon atoms, substituted or unsubstituted alkyl halide group having 1 to 6 carbon atoms, or substituted or unsubstituted aryl group having 6 to 12 ring carbon atoms: L2 represents a substituted or unsubstituted alkylene group having 1 to 6 carbon atoms, or substituted or unsubstituted arylene group having 6 to 12 ring carbon atoms; and m is 0, 1, 2, 3, 4, 5, 6 or 7. When m is 2, 3, 4, 5, 6 or 7, a plurality of L2 are mutually the same or different. m is preferably 0, 1 or 2. When m is 0, A is directly bonded to O (oxygen atom).

When $Z_{21}$ and $Z_{22}$ of the formula (20) are each the group represented by the formula (20a), the second compound is represented by a formula (22).

The second compound is also preferably represented by the formula (22).

[Formula 97]

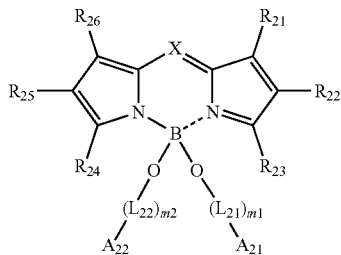
(22)

In the formula (22), X, Y bonded to a carbon atom as X, and $R_{21}$ to $R_{26}$ represent the same as X, Y and $R_{21}$ to $R_{26}$ in the formulae (20). $A_{21}$ and $A_{22}$ represent the same as A in the formula (20a) and may be mutually the same or different. $L_{21}$ and $L_{22}$ represent the same as $L_2$ in the formula (20a) and may be mutually the same or different. m1 and m2 are each independently 0, 1, 2, 3, 4, 5, 6 or 7, preferably 0, 1 or 2. When m1 is 2, 3, 4, 5, 6 or 7, a plurality of $L_{21}$ are mutually the same or different. When m2 is 2, 3, 4, 5, 6 or 7, a plurality of $L_{22}$ are mutually the same or different. When m1 is 0, $A_{21}$ is directly bonded to O (oxygen atom). When m2 is 0, $A_{22}$ is directly bonded to O (oxygen atom).

At least one of A or $L_2$ in the formula (20a) is preferably substituted with a halogen atom, more preferably substituted with a fluorine atom.

A in the formula (20a) is more preferably a perfluoroalkyl group having 1 to 6 carbon atoms or a perfluoroaryl group having 6 to 12 carbon atoms, further preferably a perfluoroalkyl group having 1 to 6 carbon atoms.

$L_2$ in the formula (20a) is more preferably a perfluoroalkylene group having 1 to 6 carbon atoms or a perfluoroarylene group having 6 to 12 carbon atoms, further preferably a perfluoroalkylene group having 1 to 6 carbon atoms.

Specifically, it is also preferable that the second compound is a compound represented by a formula (22a).

[Formula 98]

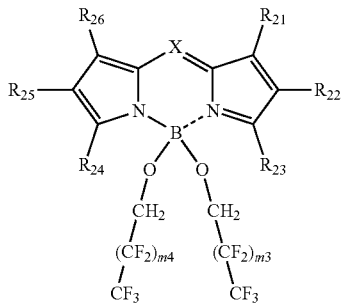
(22a)

In the formula (22a): X represents the same as X in the formula (20). Y bonded to a carbon atom as X represents the same as Y in the formula (20).

$R_{21}$ to $R_{26}$ each independently represent the same as $R_{21}$ to $R_{26}$ in the formula (20).

m3 is in a range from 0 to 4.

m4 is in a range from 0 to 4.

m3 and m4 are mutually the same or different.

In the formulae (20), (21), (22) and (22a): X is a carbon atom bonded to Y; and is a hydrogen atom or a substituent.

Y as the substituent is preferably a substituent selected from the group consisting of a substituted or unsubstituted alkyl group having 1 to 30 carbon atoms, substituted or unsubstituted alkyl halide group having 1 to 30 carbon atoms and substituted or unsubstituted aryl group having 6 to 30 ring carbon atoms, more preferably a substituted or unsubstituted aryl group having 6 to 30 ring carbon atoms.

In the formulae (20), (21), (22) and (22a), it is more preferable that X is a carbon atom bonded to Y; Y is a hydrogen atom or a substituent; Y as the substituent is a substituted or unsubstituted aryl group having 6 to 30 ring carbon atoms; when Y as the substituent is an aryl group having 6 to 30 ring carbon atoms having a substituent, the substituent is a substituted or unsubstituted alkyl group having 1 to 30 carbon atoms, a substituted or unsubstituted alkyl halide group having 1 to 30 carbon atoms, a substituted or unsubstituted alkoxy group having 1 to 30 carbon atoms, a substituted or unsubstituted alkoxy halide group having 1 to 30 carbon atoms, or an aryl group having 6 to 30 ring carbon atoms and substituted by an alkyl group having 1 to 30 carbon atoms.

In the second compound, $Z_{21}$ and $Z_{22}$ may be mutually bonded to form a ring. However, it is preferable that $Z_{21}$ and $Z_{22}$ are not mutually bonded.

In the formulae (20), (22) and (22a), at least one of $R_{21}$, $R_{23}$, $R_{24}$ or $R_{26}$ is preferably a substituted or unsubstituted alkyl group having 1 to 30 carbon atoms or a substituted or unsubstituted alkyl halide group having 1 to 30 carbon atoms.

In the formulae (20), (22) and (22a), $R_{21}$, $R_{23}$, $R_{24}$ and $R_{26}$ are more preferably each a substituted or unsubstituted alkyl group having 1 to 30 carbon atoms or a substituted or unsubstituted alkyl halide group having 1 to 30 carbon atoms. In this case, $R_{22}$ and $R_{25}$ are preferably hydrogen atoms.

In the formulae (20), (22) and (22a), at least one of $R_{21}$, $R_{23}$, $R_{24}$ or $R_{26}$ is preferably a substituted or unsubstituted aryl group having 6 to 30 ring carbon atoms.

In the formulae (20), (22) and (22a), $R_{21}$, $R_{23}$, $R_{24}$ and $R_{26}$ are more preferably each a substituted or unsubstituted aryl group having 6 to 30 ring carbon atoms. In this case, $R_{22}$ and $R_{25}$ are preferably hydrogen atoms.

In the formulae (20), (22) and (22a), it is more preferable that $R_{21}$, $R_{23}$, $R_{24}$ and $R_{26}$ are each independently a substituted or unsubstituted alkyl group having 1 to 30 carbon atoms (preferably 1 to 6 carbon atoms), a substituted or unsubstituted alkyl halide group having 1 to 30 carbon atoms (preferably 1 to 6 carbon atoms), or an aryl group having 6 to 30 ring carbon atoms (preferably 6 to 12 ring carbon atoms) and substituted with an alkyl group having 1 to 30 carbon atoms; and $R_{22}$ and $R_{25}$ are hydrogen atoms.

In the formula (21), at least one of $R_{21}$, $R_{23}$ or $R_{24}$ is preferably a substituted or unsubstituted alkyl group having 1 to 30 carbon atoms or a substituted or unsubstituted alkyl halide group having 1 to 30 carbon atoms.

In the formula (21), $R_{21}$, $R_{23}$ and $R_{24}$ are more preferably a substituted or unsubstituted alkyl group having 1 to 30 carbon atoms or a substituted or unsubstituted alkyl halide group having 1 to 30 carbon atoms. In this case, $R_{22}$ is preferably a hydrogen atom.

In the formula (21), at least one of $R_{21}$, $R_{23}$ or $R_{24}$ is preferably a substituted or unsubstituted aryl group having 6 to 30 ring carbon atoms.

In the formula (21), $R_{21}$, $R_{23}$ and $R_{24}$ are more preferably a substituted or unsubstituted aryl group having 6 to 30 ring carbon atoms. In this case, $R_{22}$ is preferably a hydrogen atom.

In the formula (21): it is more preferable that $R_{21}$, $R_{23}$, and $R_{24}$ are each independently a substituted or unsubstituted alkyl group having 1 to 30 carbon atoms (preferably 1 to 6 carbon atoms), a substituted or unsubstituted alkyl halide group having 1 to 30 carbon atoms (preferably 1 to 6 carbon atoms), or an aryl group having 6 to 30 ring carbon atoms (preferably 6 to 12 ring carbon atoms) and substituted with an alkyl group having 1 to 30 carbon atoms; and $R_{22}$ is a hydrogen atom.

In the second compound, examples of the fluorine-substituted alkoxy group include 2,2,2-trifluoroethoxy group, 2,2-difluoroethoxy group, 2,2,3,3,3-pentafluoro-1-propoxy group, 2,2,3,3-tetrafluoro-1-propoxy group, 1,1,1,3,3,3-hexafluoro-2-propoxy group, 2,2,3,3,4,4,4-heptafluoro-1-butyloxy group, 2,2,3,3,4,4-hexafluoro-1-butyloxy group, nonafluoro-tertiary-butyloxy group, 2,2,3,3,4,4,5,5,5-nonafluoropentanoxy group, 2,2,3,3,4,4,5,5,6,6,6-undecafluorohexanoxy group, 2,3-bis(trifluoromethyl)-2,3-butanedioxy group, 1,1,2,2-tetra(trifluoromethyl)ethylene glycoxy group, 4,4,5,5,6,6,6-heptafluorohexane-1,2-dioxy group, and 4,4,5,5,6,6,7,7,8,8,9,9,9-tridecafluorononane-1,2-dioxy group.

In the second compound, examples of the fluorine-substituted aryloxy group or the aryloxy group substituted with a fluoroalkyl group include a pentafluorophenoxy group, 3,4,5-trifluorophenoxy group, 4-trifluoromethylphenoxy group, 3,5-bistrifluoromethylphenoxy group, 3-fluoro-4-trifluoromethylphenoxy group, 2,3,5,6-tetrafluoro-4-trifluoromethylphenoxy group, 4-fluorocatecholato group, 4-trifluoromethylcatecholato group, and 3,5-bistrifluoromethylcatecholato group.

A substituent of the second compound that is "substituted or unsubstituted" is preferably a substituent selected from the group consisting of a substituted or unsubstituted aryl group having 6 to 30 ring carbon atoms, substituted or unsubstituted heteroaryl group having 5 to 30 ring atoms, alkyl group having 1 to 30 carbon atoms, alkyl halide group having 1 to 30 carbon atoms, cycloalkyl group having 3 to 30 ring carbon atoms, cyano group, amino group, substituted amino group, halogen atom, alkoxy group having 1 to 30 carbon atoms, aryloxy group having 6 to 30 ring carbon atoms, arylthio group having 6 to 30 carbon atoms, aralkyl group having 7 to 30 carbon atoms, substituted phosphoryl group, substituted silyl group, nitro group, carboxy group, alkenyl group having 2 to 30 carbon atoms, alkynyl group 2 to 30 carbon atoms, alkylthio group 1 to 30 carbon atoms, alkylsilyl group 3 to 30 carbon atoms, arylsilyl group having 6 to 30 ring carbon atoms, and hydroxy group.

The substituent of the second compound that is "substituted or unsubstituted" is more preferably a substituent selected from the group consisting of a substituted or unsubstituted aryl group having 6 to 30 ring carbon atoms, substituted or unsubstituted heteroaryl group having 5 to 30 ring atoms, alkyl group having 1 to 30 carbon atoms, alkyl halide group having 1 to 30 carbon atoms, and cycloalkyl group having 3 to 30 ring carbon atoms.

The substituent of the second compound that is "substituted or unsubstituted" is further preferably a substituent selected from the group consisting of a substituted or unsubstituted aryl group having 6 to 12 ring carbon atoms, substituted or unsubstituted heteroaryl group having 5 to 12 ring atoms, alkyl group having 1 to 6 carbon atoms, alkyl halide group having 1 to 6 carbon atoms, and cycloalkyl group having 3 to 12 ring carbon atoms.

When the second compound is a fluorescent compound, the second compound preferably emits light having a main peak wavelength in a range from 400 nm to 700 nm.

Herein, the main peak wavelength means a peak wavelength of an emission spectrum exhibiting a maximum luminous intensity among fluorescence spectra measured in a toluene solution in which a measurement target compound is dissolved at a concentration ranging from $10^{-6}$ mol/l to $10^{-5}$ mol/l. A spectrophotofluorometer (F-7000 manufactured by Hitachi High-Tech Science Corporation) is used as a measurement device.

The second compound preferably exhibits red or green light emission.

Herein, the red light emissions refers to a light emission in which a main peak wavelength of fluorescence spectrum is in a range from 600 nm to 660 nm.

When the second compound is a red fluorescent compound, the main peak wavelength of the second compound is preferably in a range from 600 nm to 660 nm, more preferably in a range from 600 nm to 640 nm, further preferably in a range from 610 nm to 630 nm.

Herein, the green light emissions refers to a light emission in which a main peak wavelength of fluorescence spectrum is in a range from 500 nm to 560 nm.

When the second compound is a green fluorescent compound, the main peak wavelength of the second compound is preferably in a range from 500 nm to 560 nm, more preferably in a range from 500 nm to 540 nm, further preferably in a range from 510 nm to 530 nm.

Herein, the blue light emissions refers to a light emission in which a main peak wavelength of fluorescence spectrum is in a range from 430 nm to 480 nm.

When the second compound is a blue fluorescent compound, the main peak wavelength of the second compound is preferably in a range from 430 nm to 480 nm, more preferably in a range from 445 nm to 480 nm.

Manufacturing Method of Second Compound

The second compound can be manufactured by a known method.

Examples of the second compound according to the exemplary embodiment are shown below. The second compound of the invention is by no means limited to the Examples.

A coordinate bond between a boron atom and a nitrogen atom in a pyrromethene ekeleton is shown by various means such as a solid line, a broken line, an arrow, and omission. Herein, the coordinate bond is shown by a solid line or a broken line, or the description of the coordinate bond is omitted.
[Formula 99]
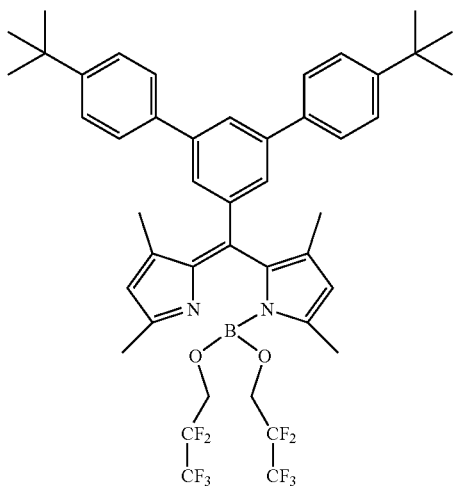
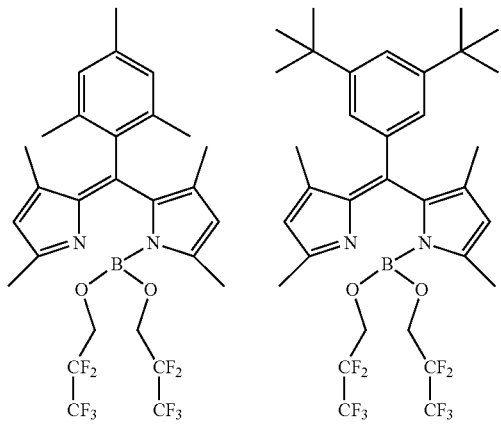
[Formula 100]
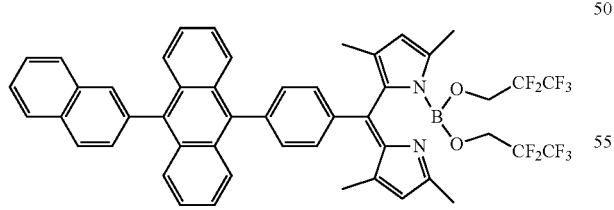
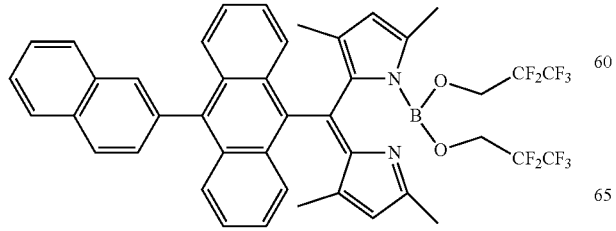
[Formula 101]
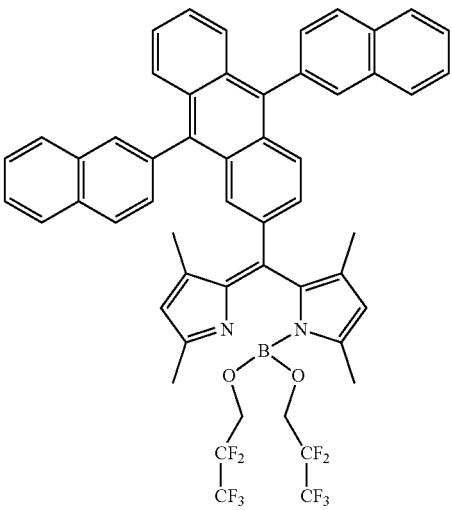
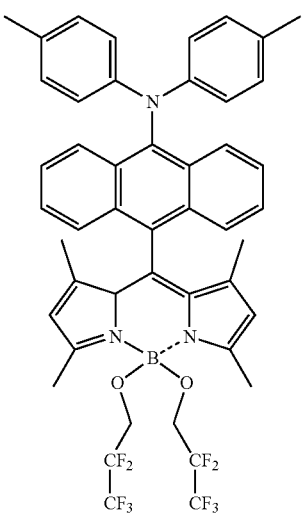
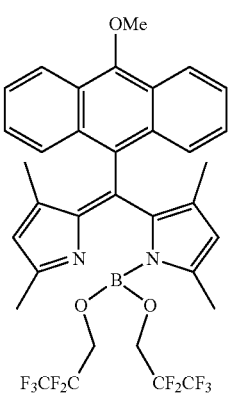

-continued
[Formula 102]
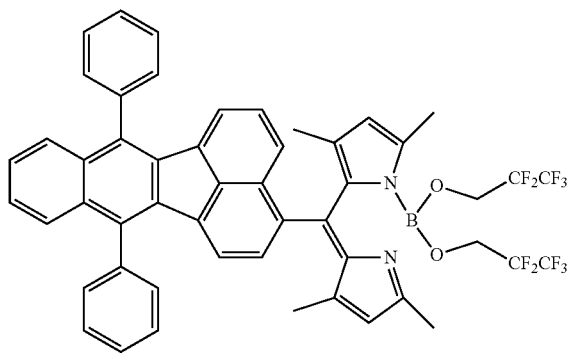
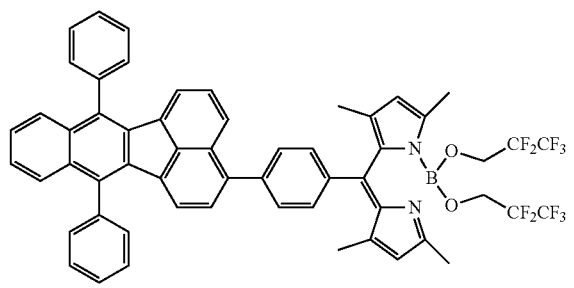
[Formula 103]
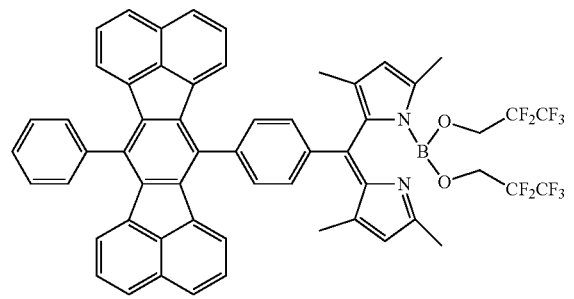
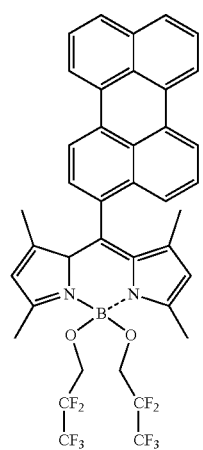
-continued
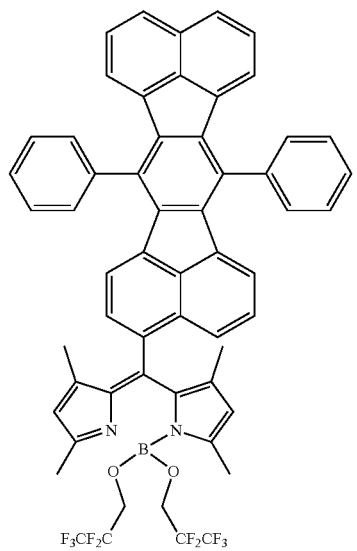
[Formula 104]
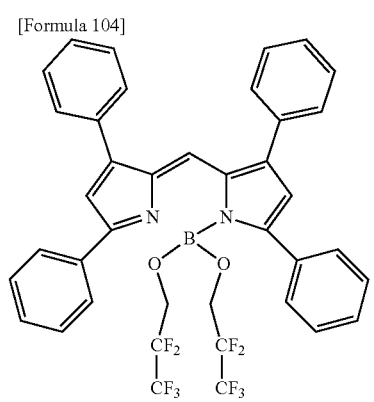
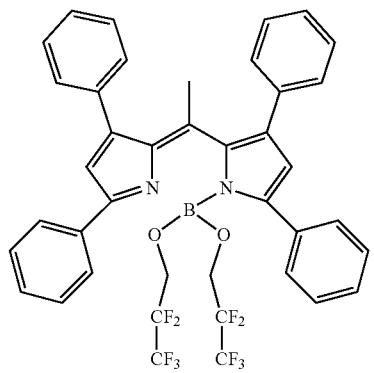
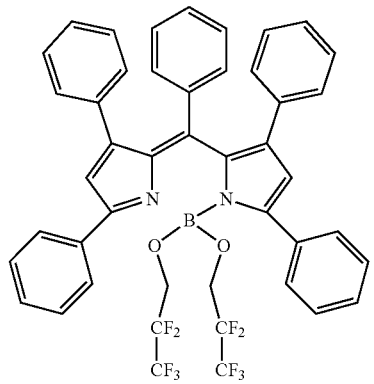

-continued
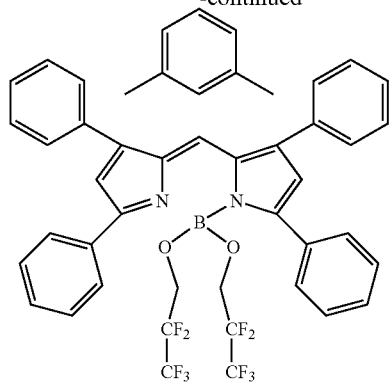
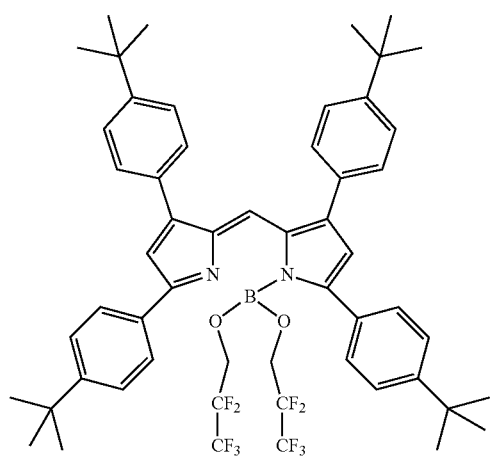
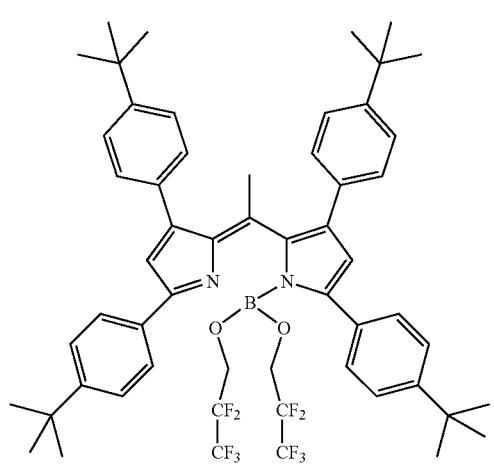
-continued
[Formula 105]
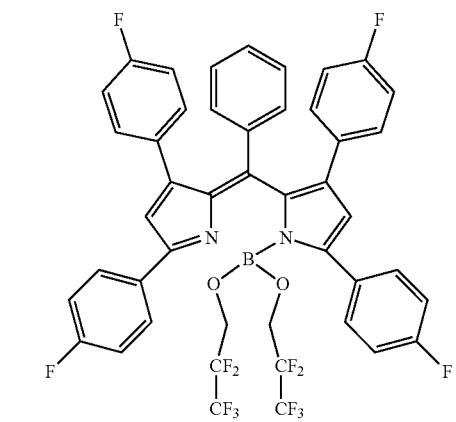
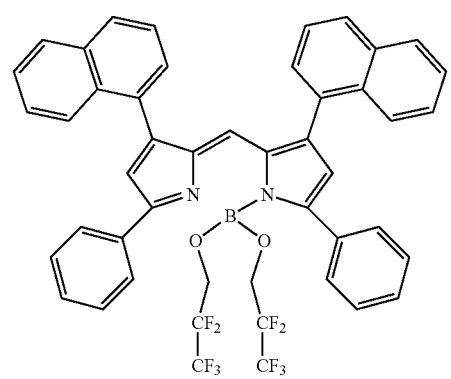
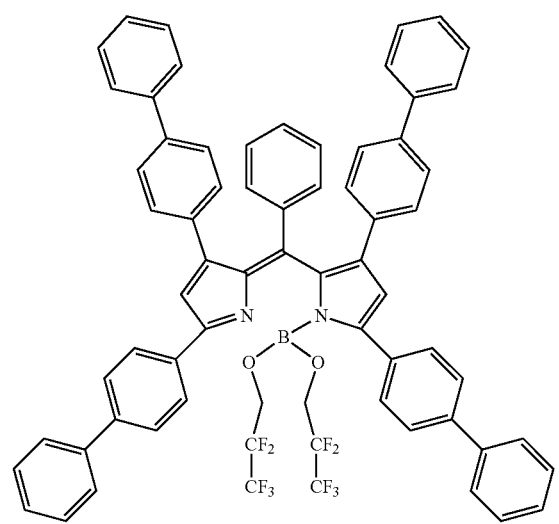

341
-continued
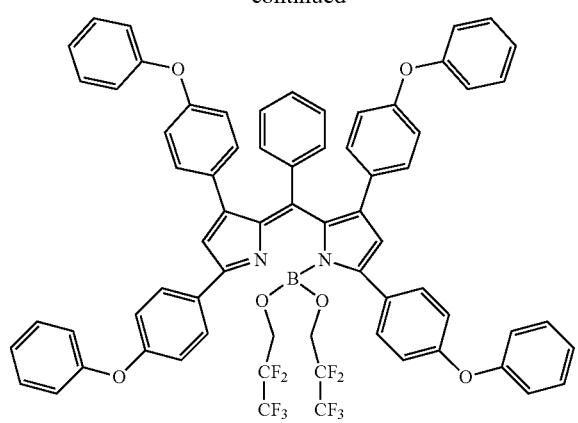
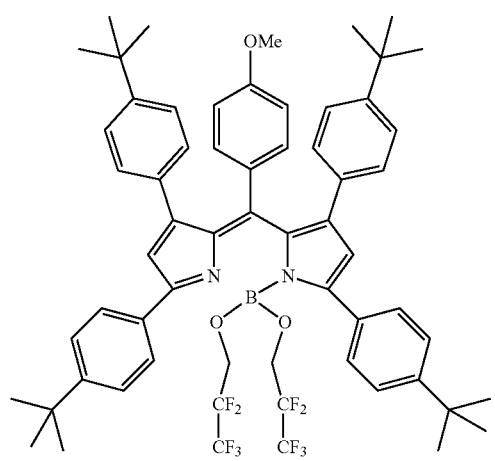
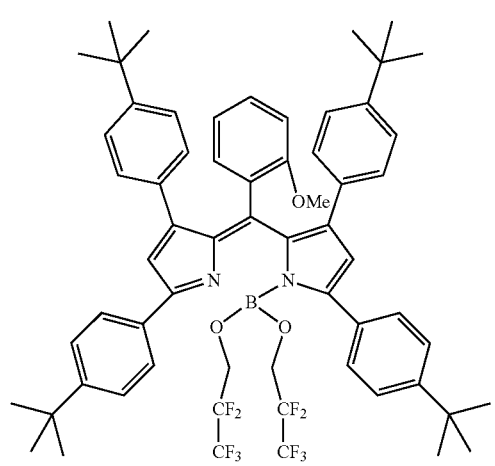
342
-continued
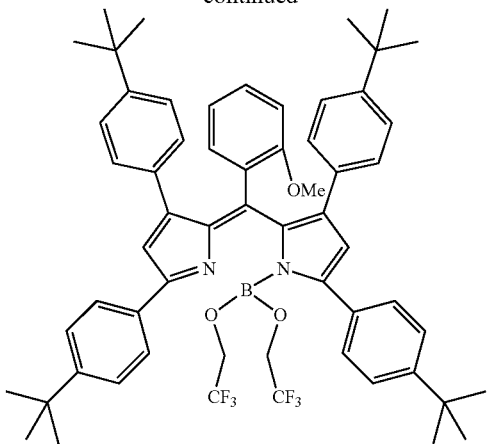
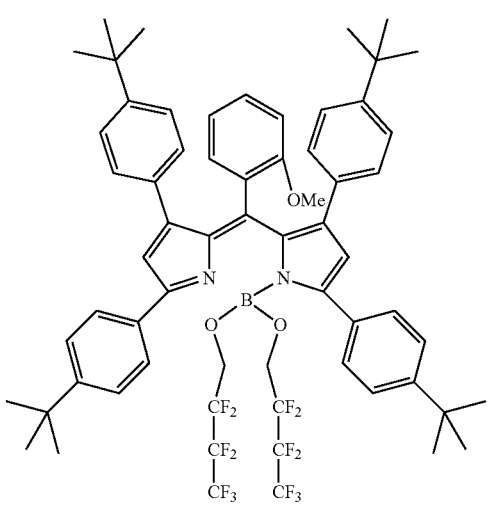
[Formula 106]
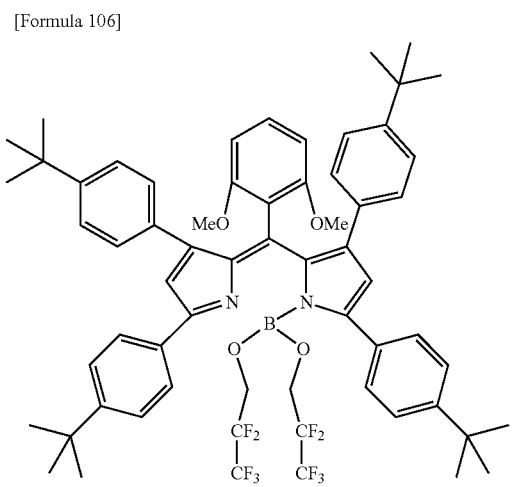

343
-continued
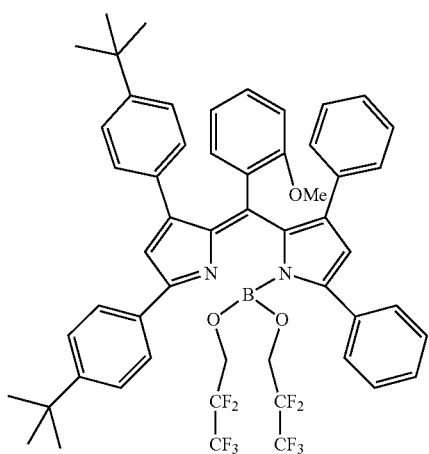
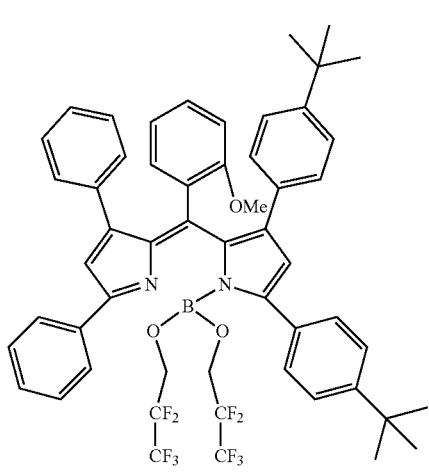
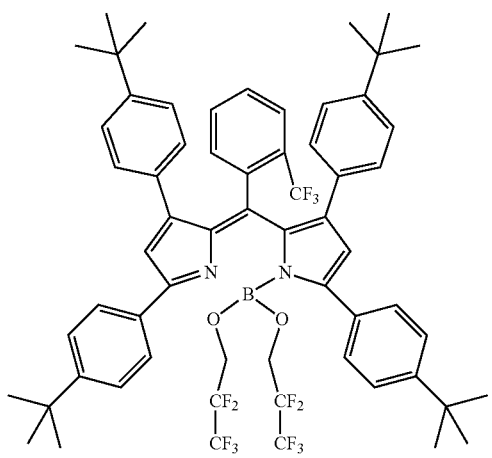
344
-continued
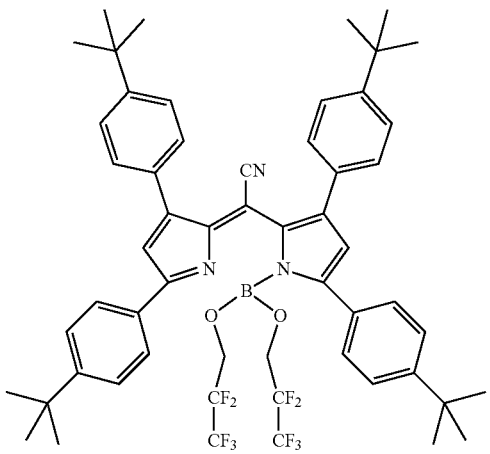
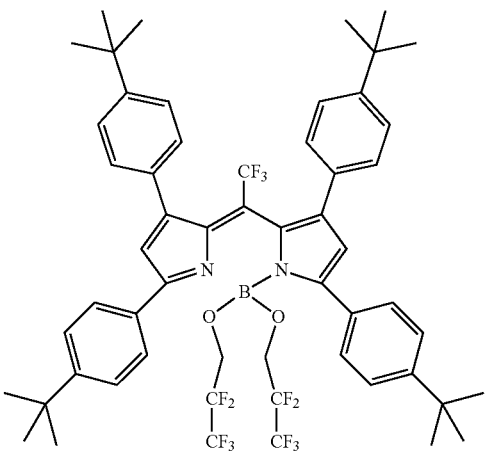
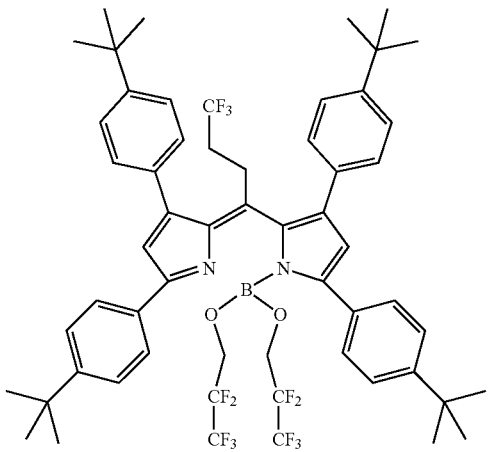

345
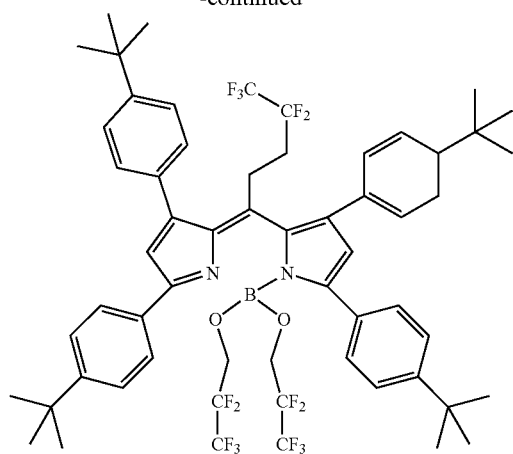
[Formula 107]
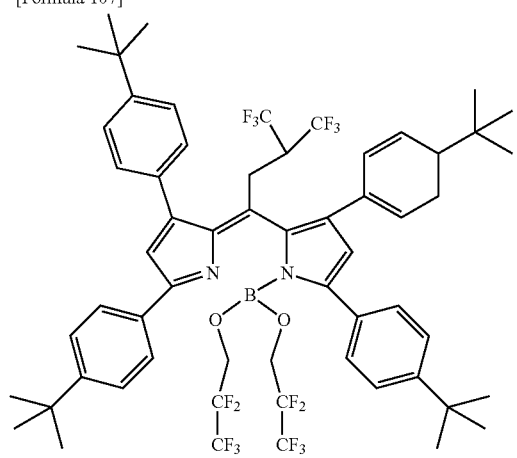
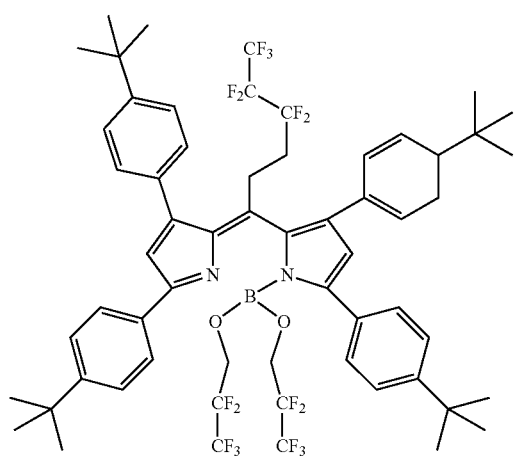
346
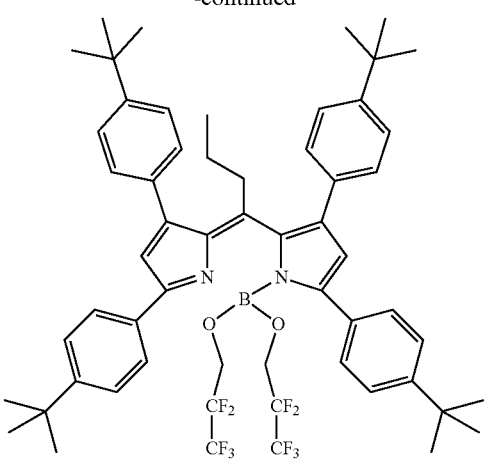
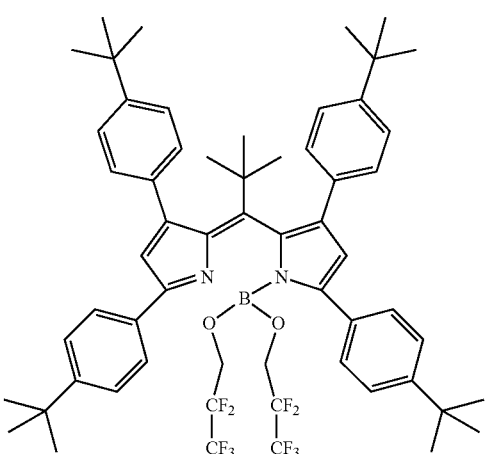
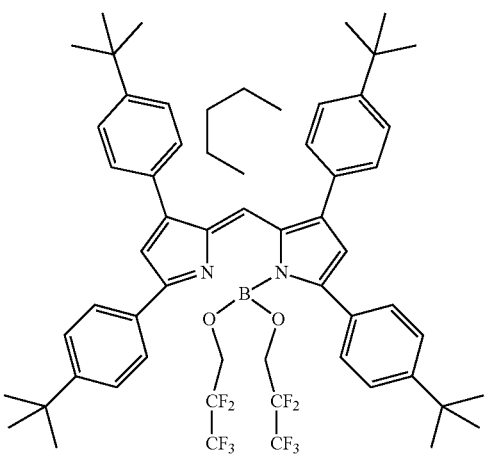

347
-continued
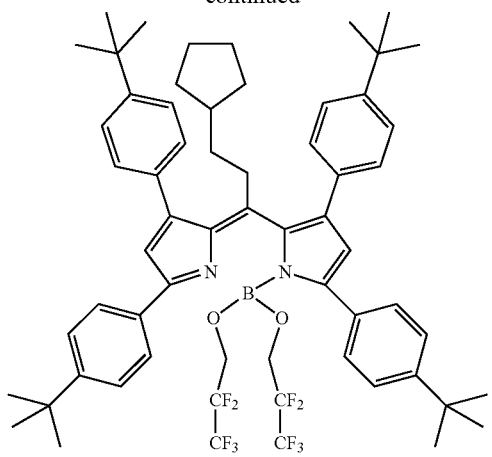
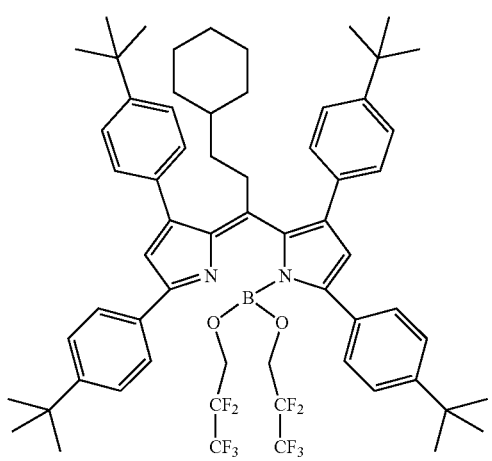
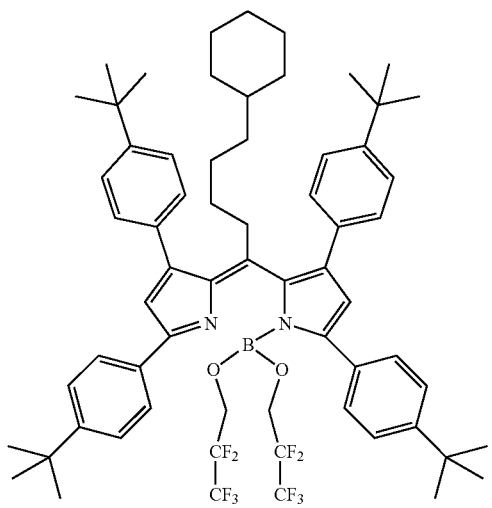
348
-continued
[Formula 108]
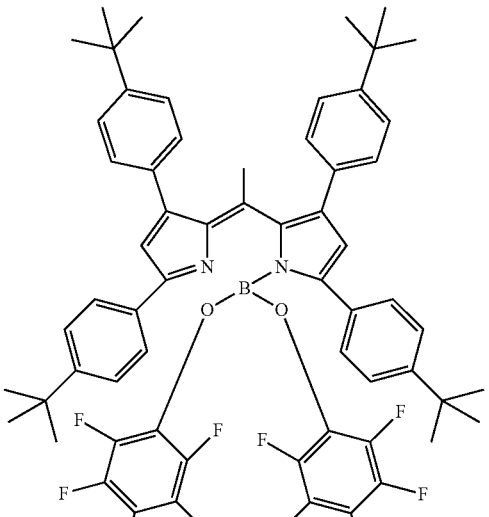
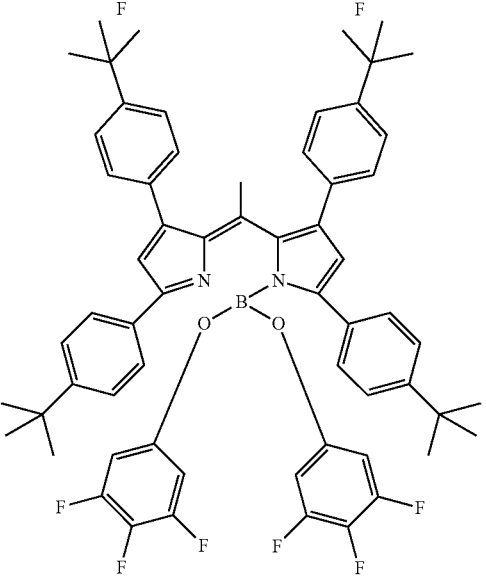
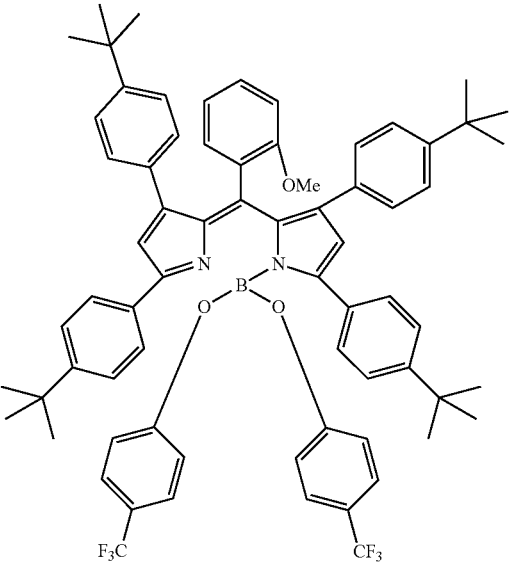

349
-continued
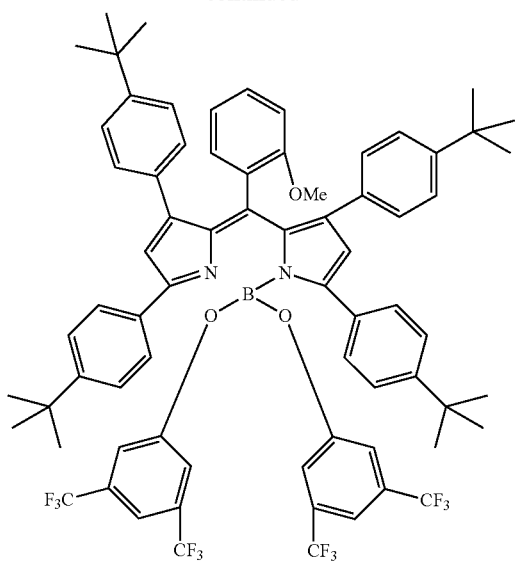
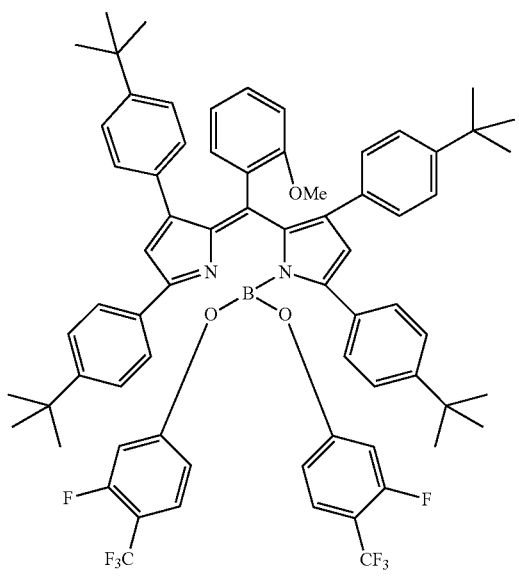
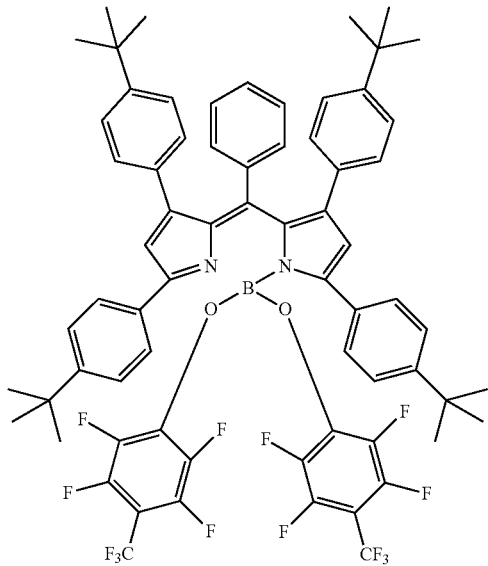
350
-continued
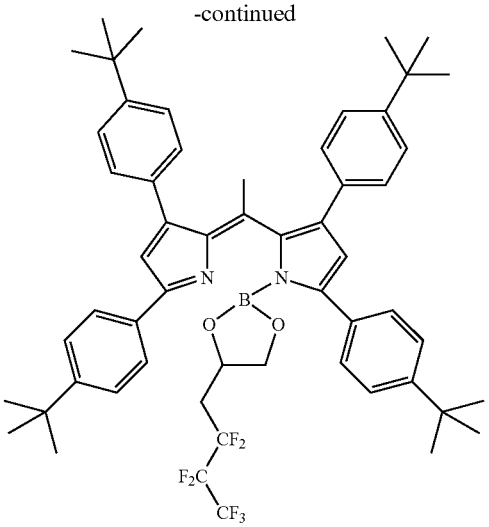
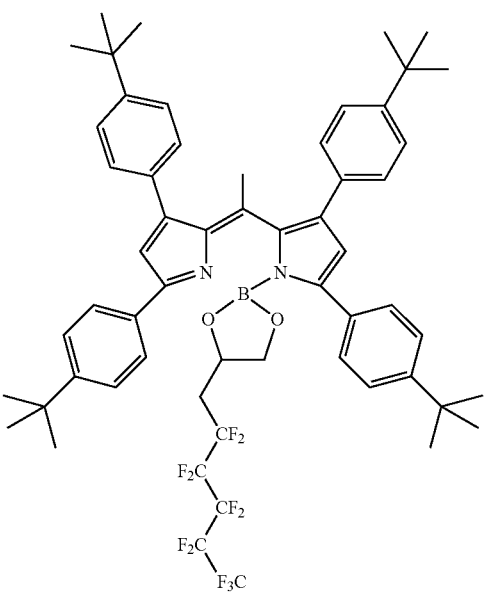
[Formula 109]
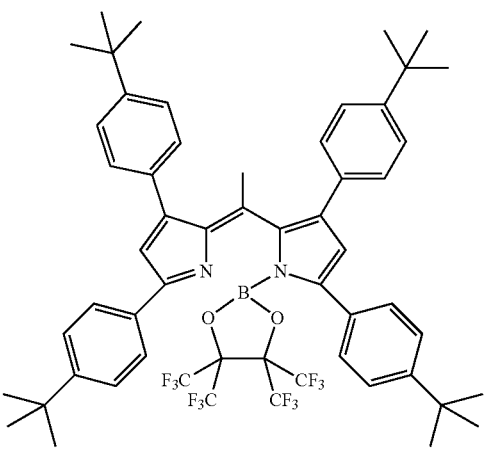

| 351 -continued | 352 -continued |
|---|---|
| 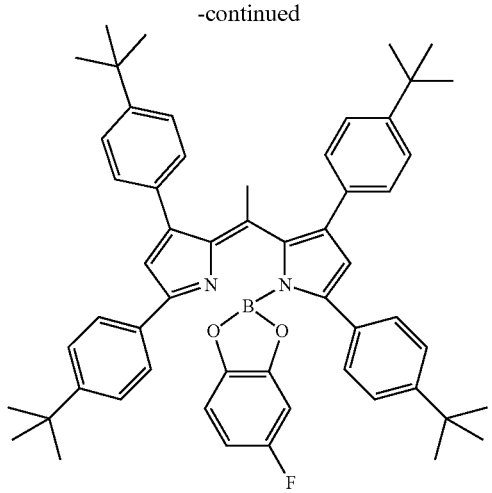 | 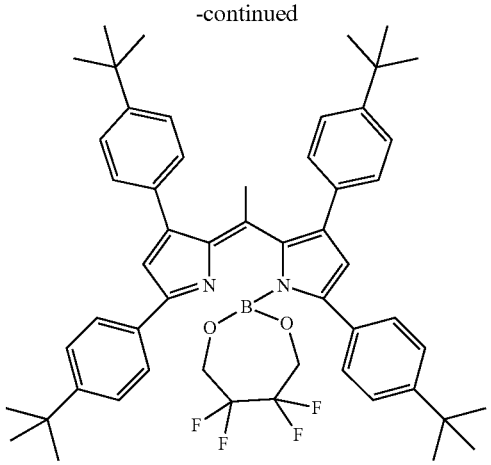 |
| 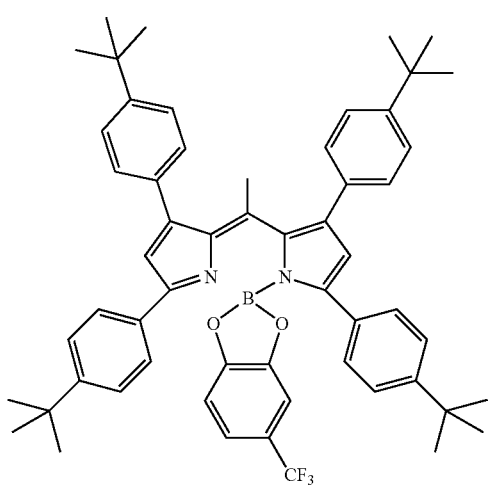 | 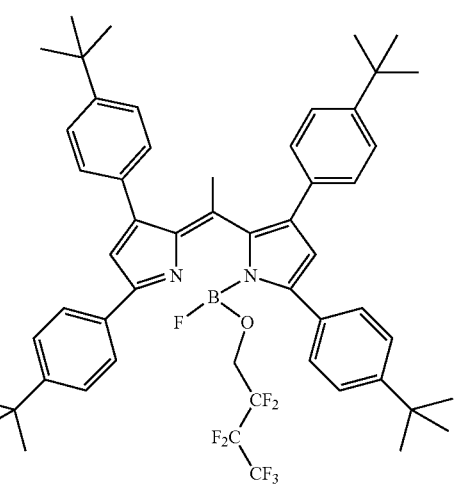 |
| 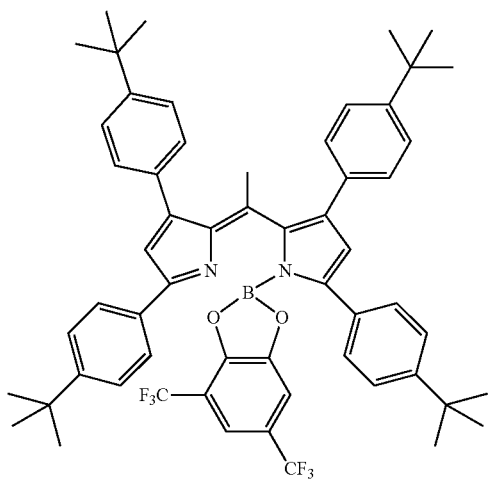 | 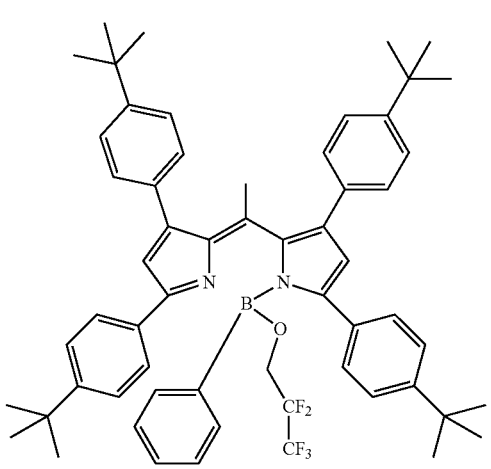 |

353
-continued
354
-continued
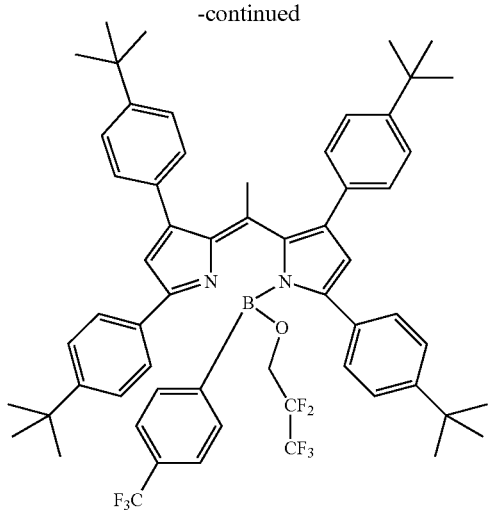
[Formula 110]
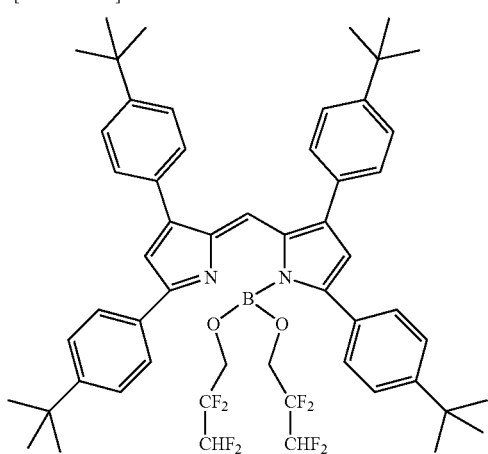
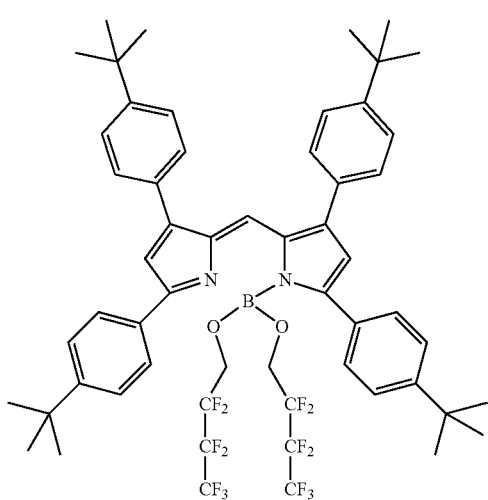
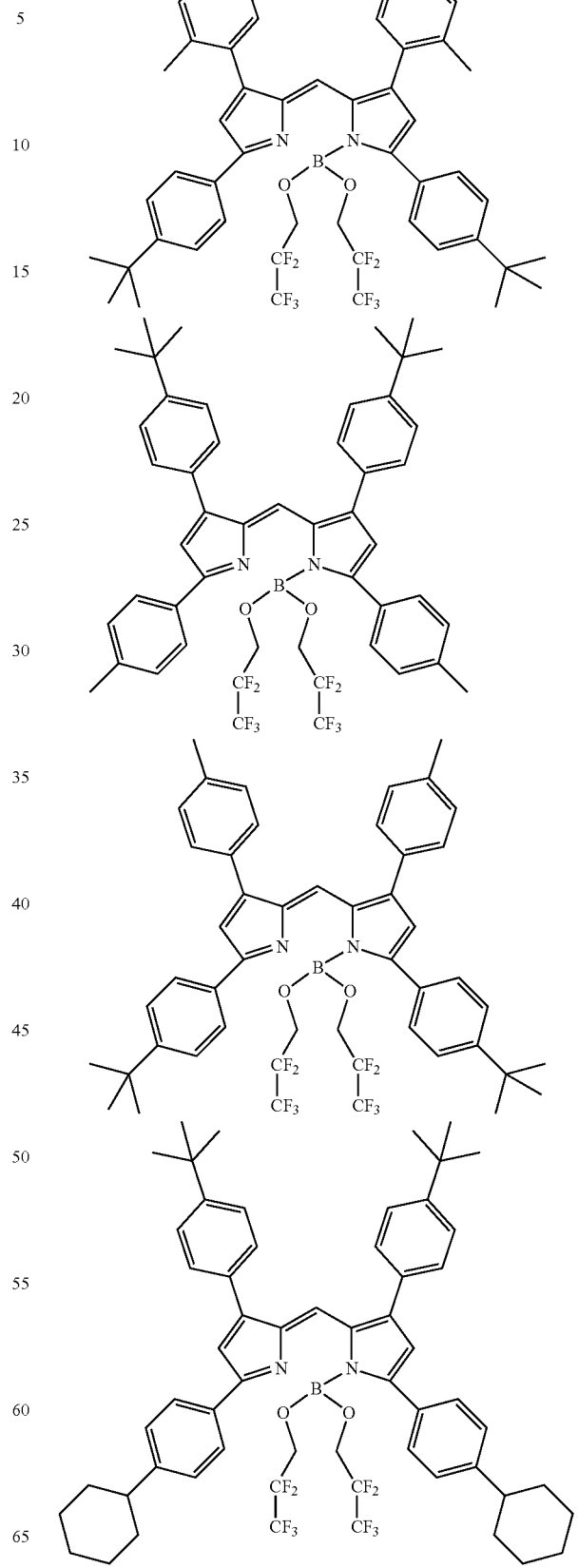

355
-continued
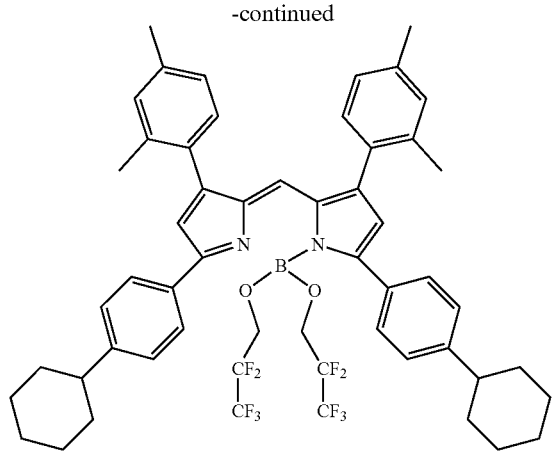
[Formula 111]
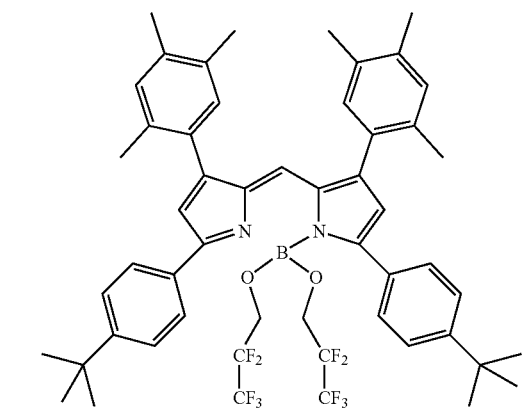
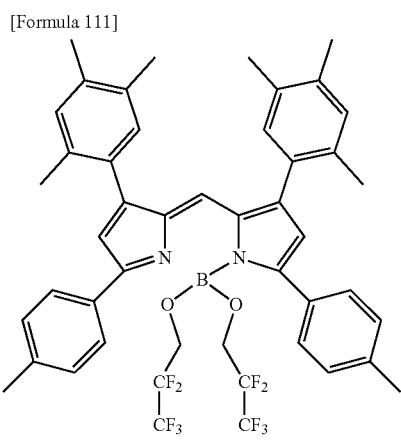
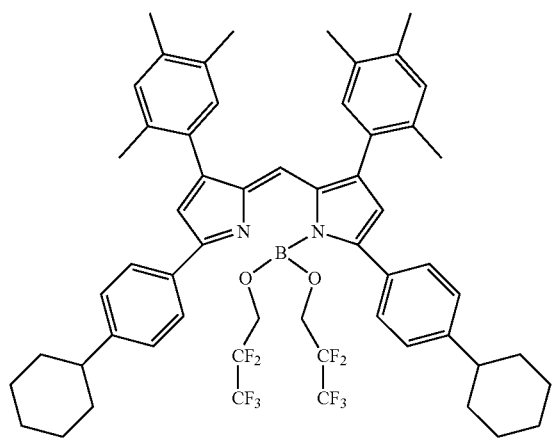
356
-continued
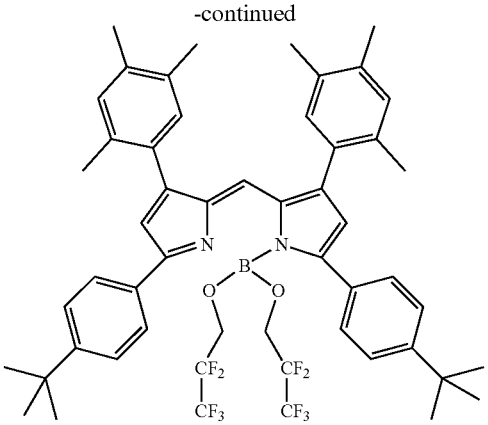
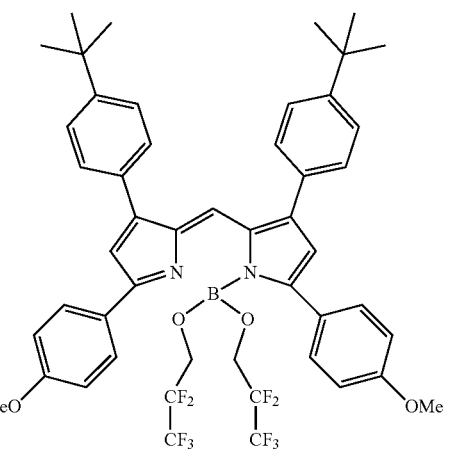
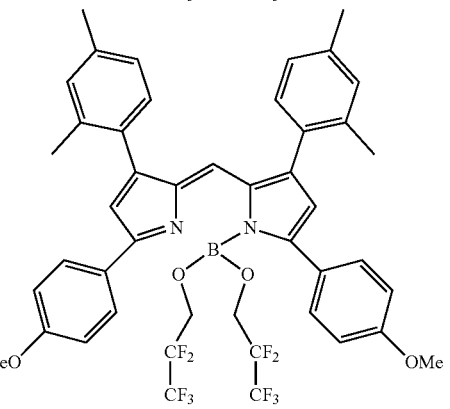
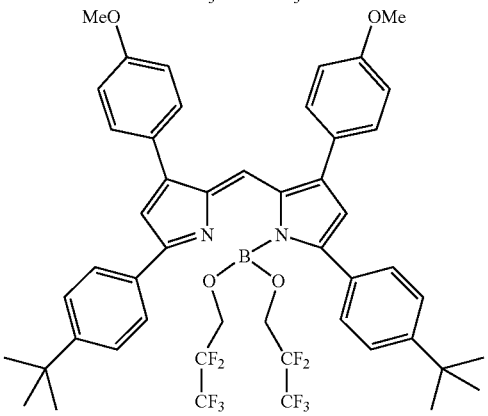

357
-continued
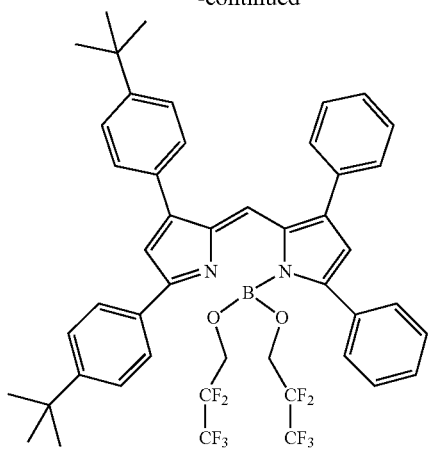
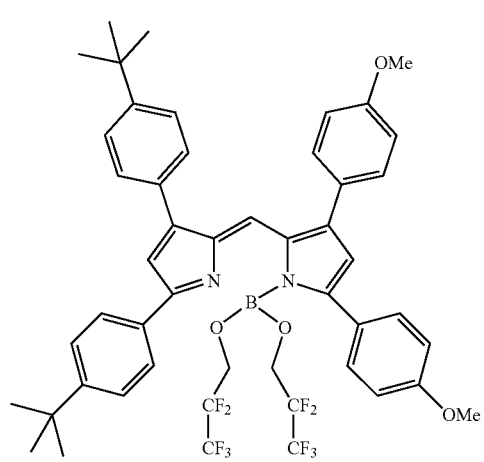
[Formula 112]
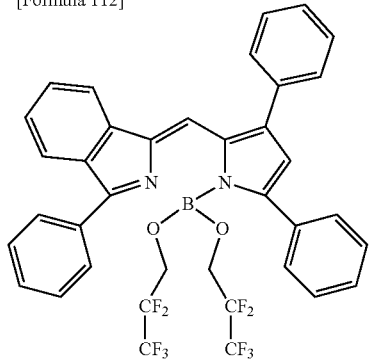
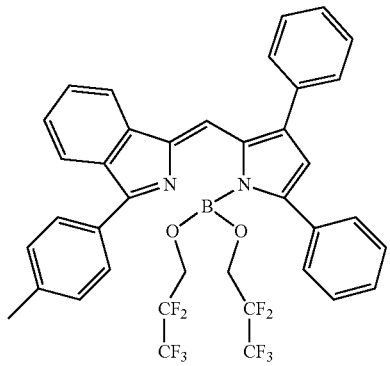
358
-continued
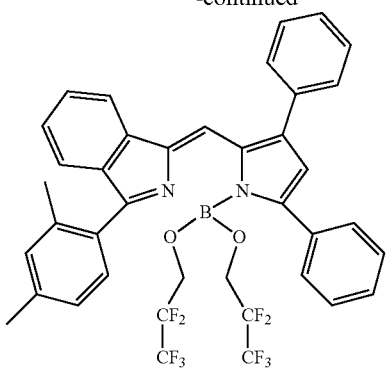
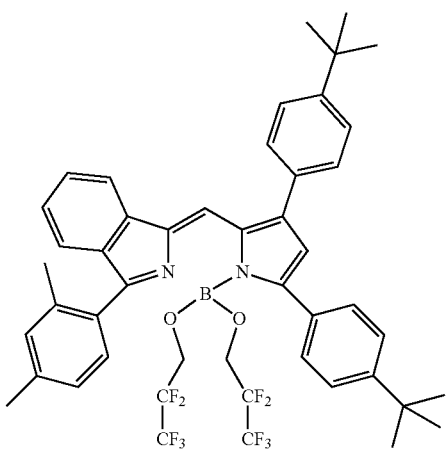
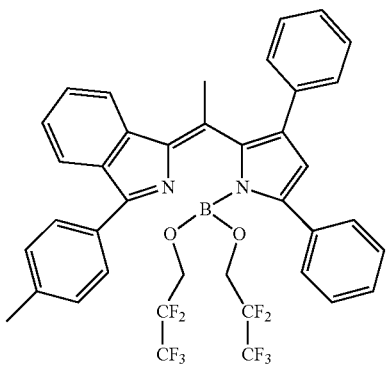
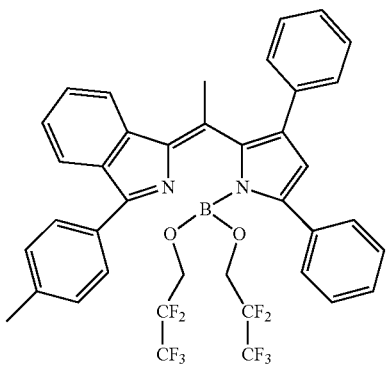

359
-continued

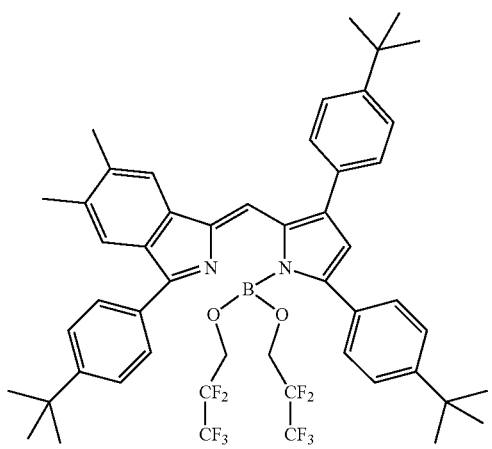
[Formula 113]
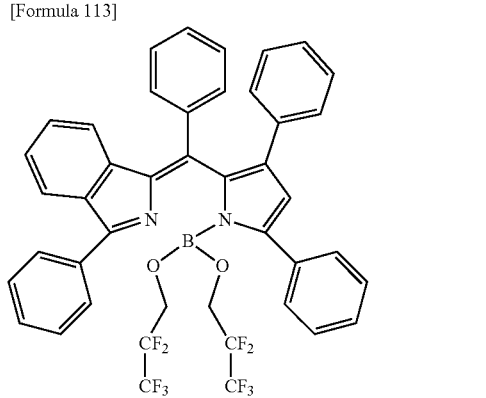
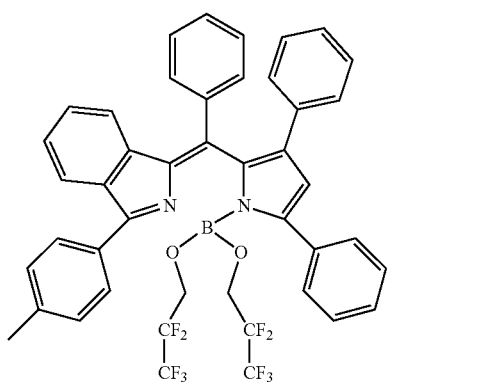
360
-continued
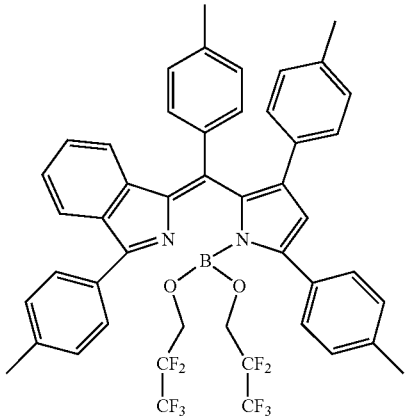
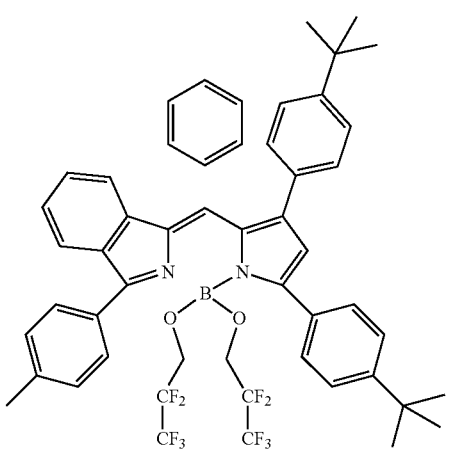
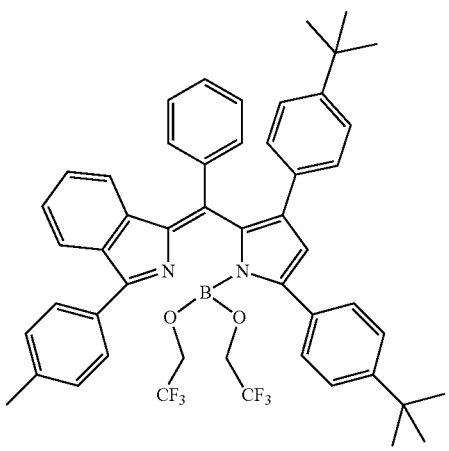

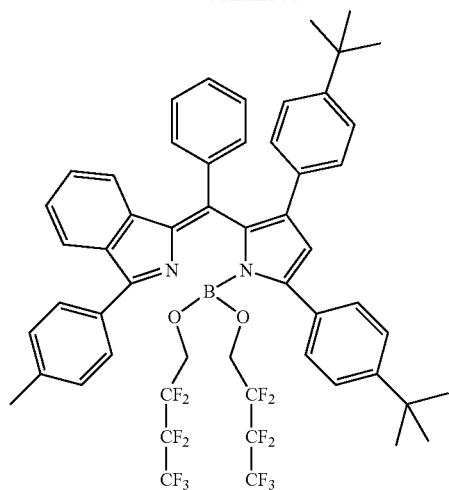
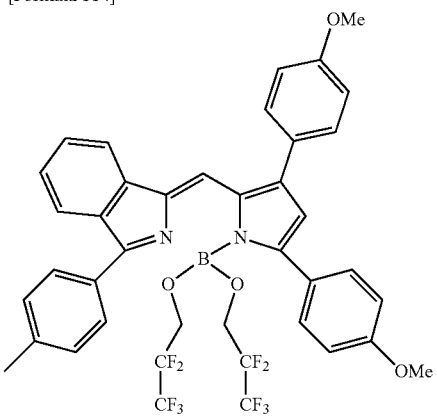
[Formula 114]
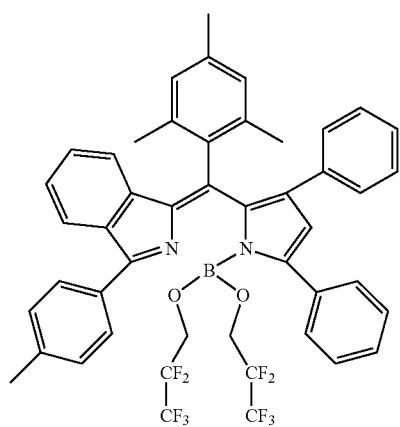
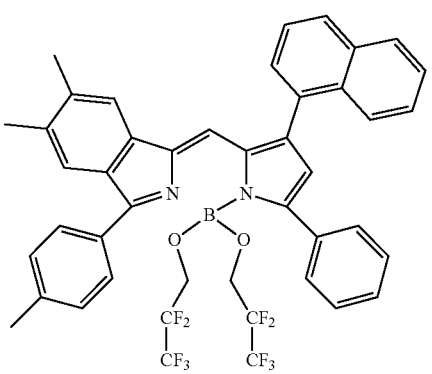
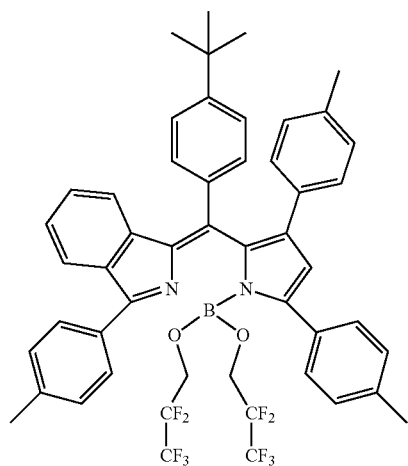
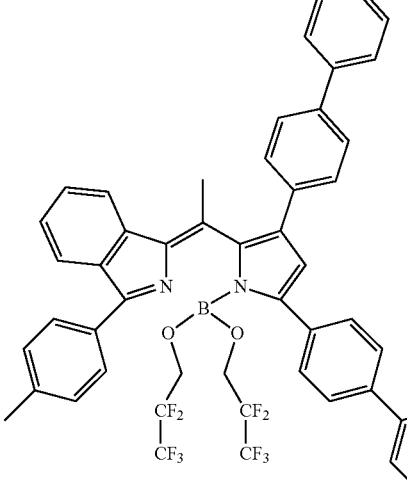

363
-continued
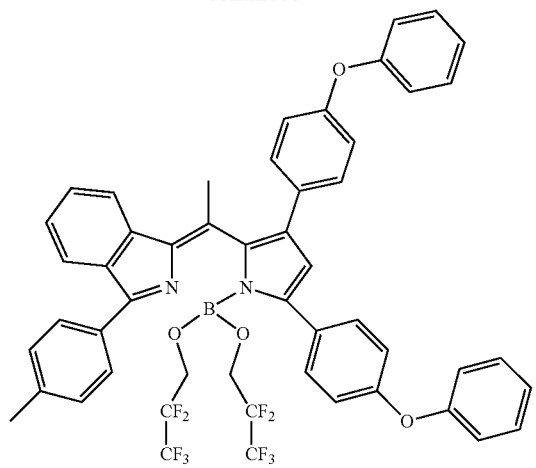
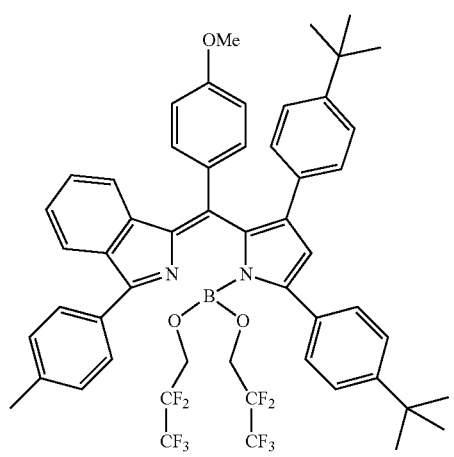
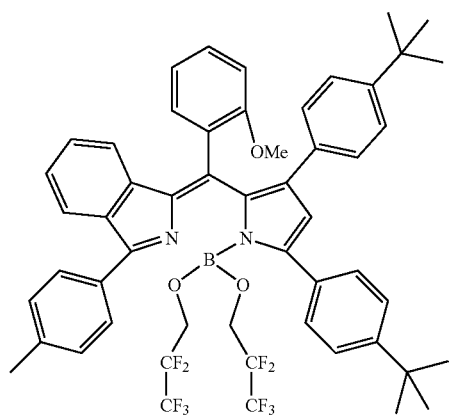
364
-continued
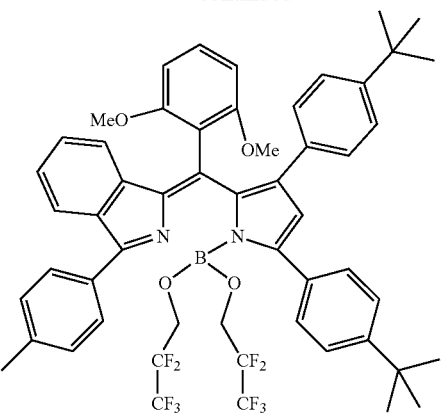
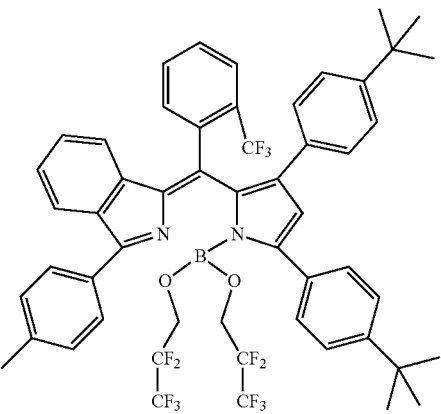
[Formula 115]
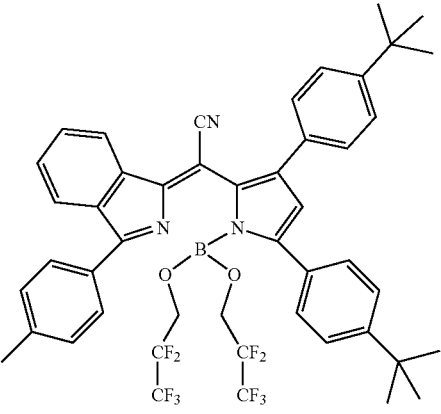
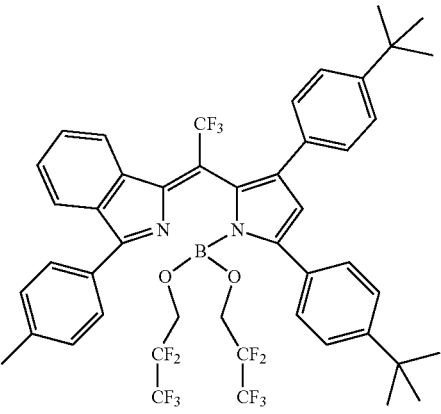

365
-continued
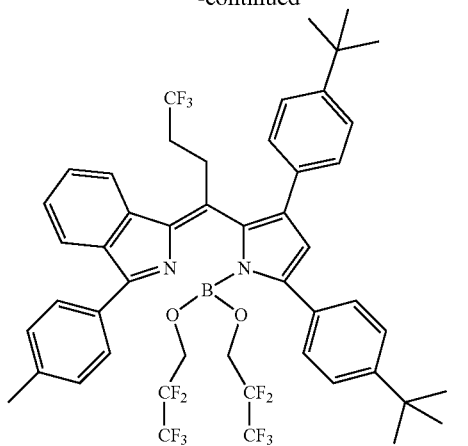
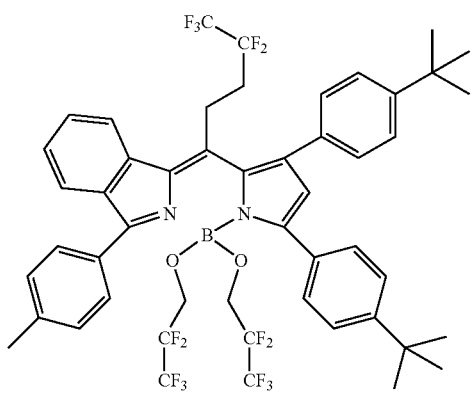
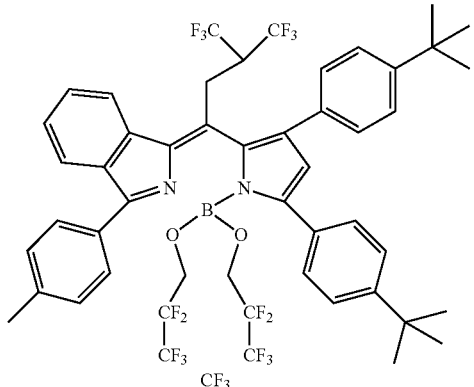
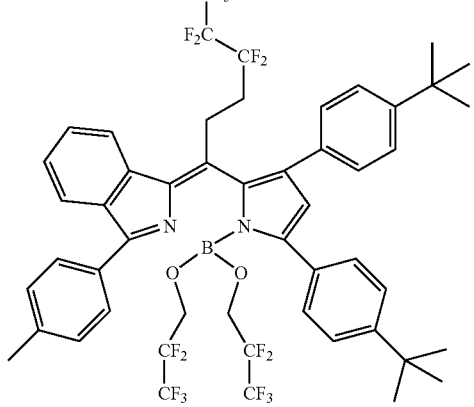
366
-continued
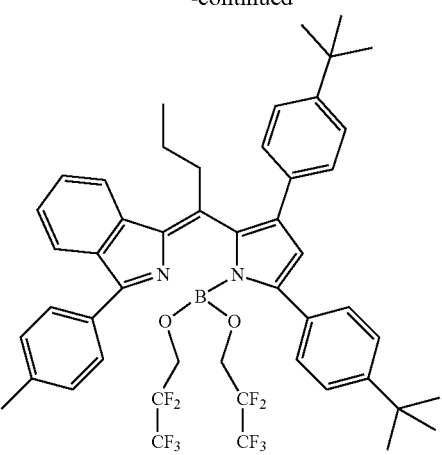
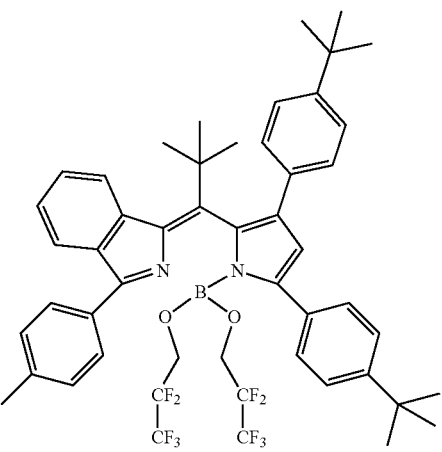
[Formula 116]
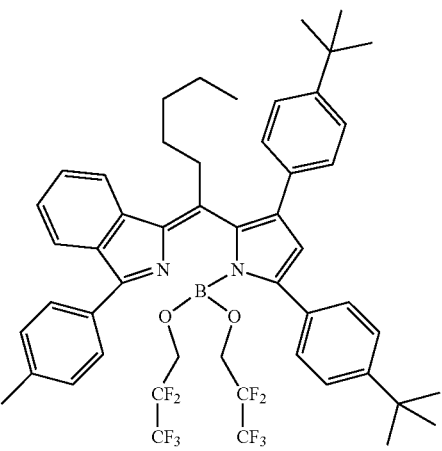

367
-continued
368
-continued
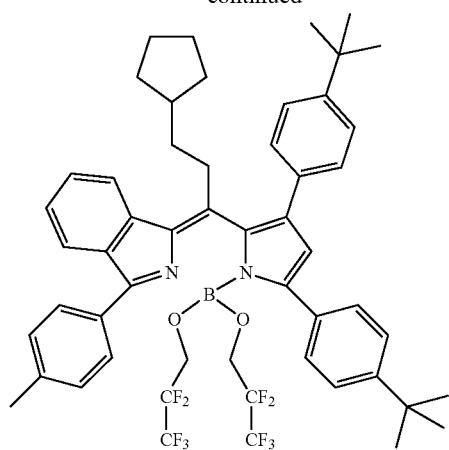
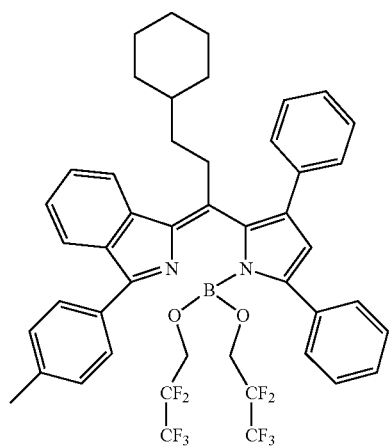
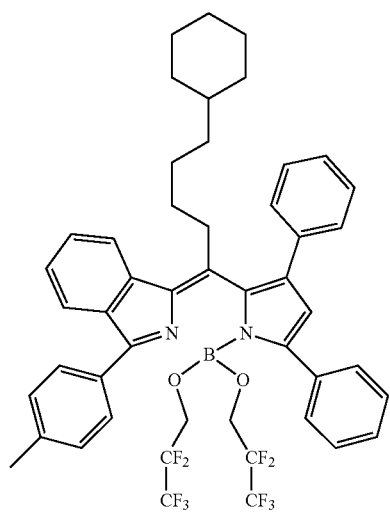
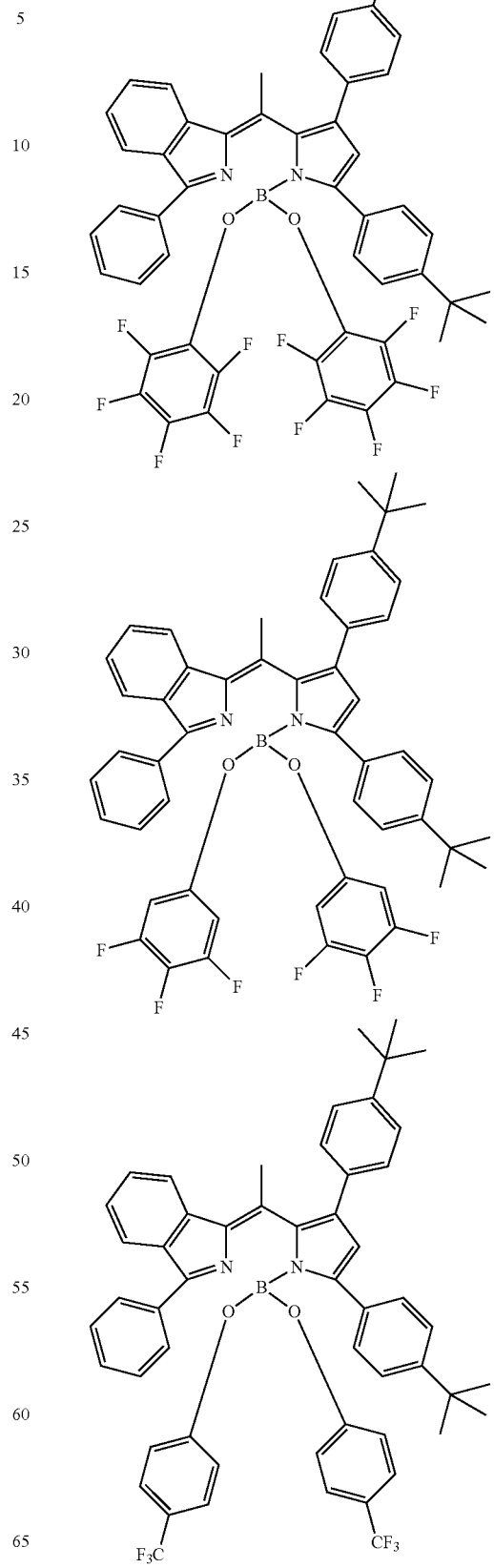

369
-continued
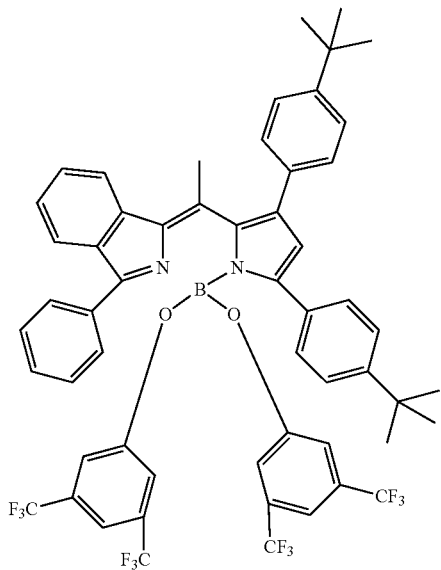
[Formula 117]
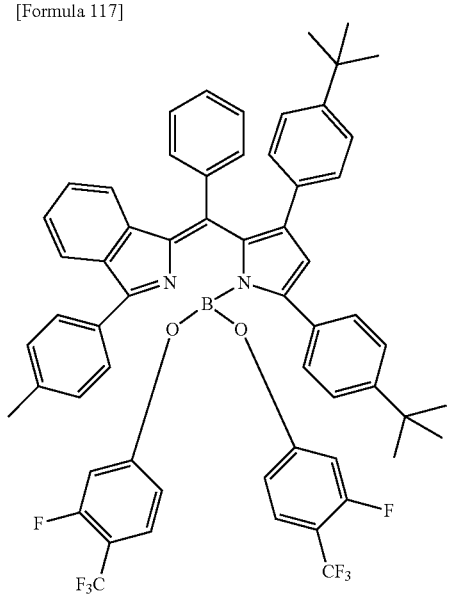
370
-continued
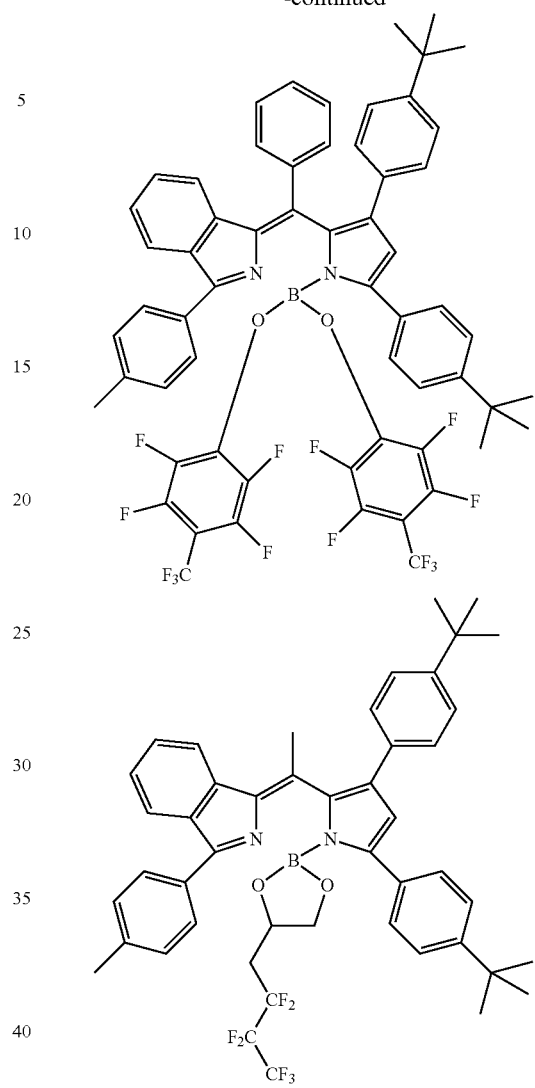
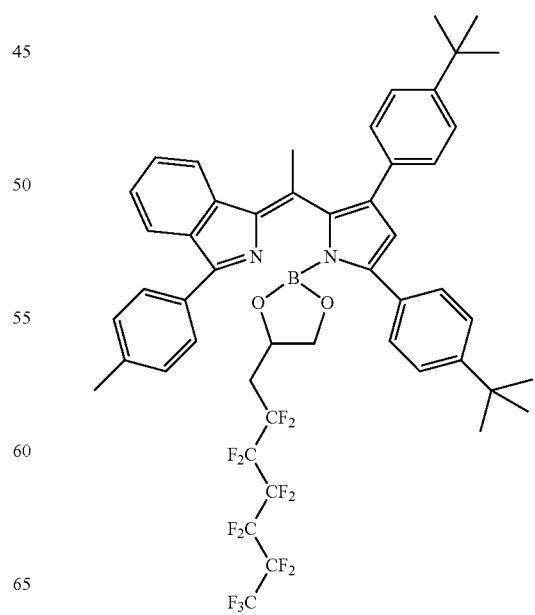

371
-continued
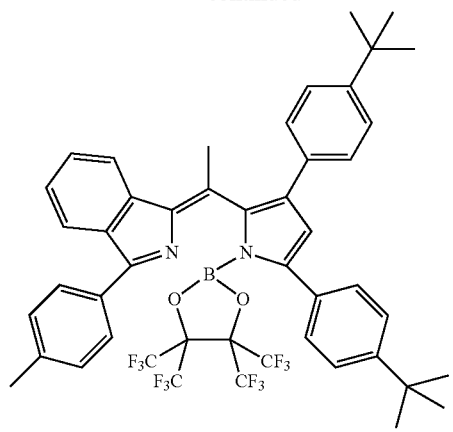
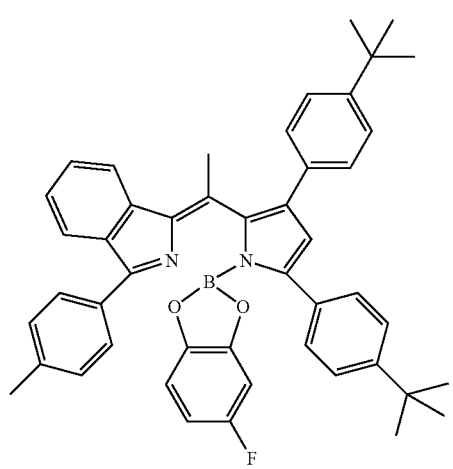
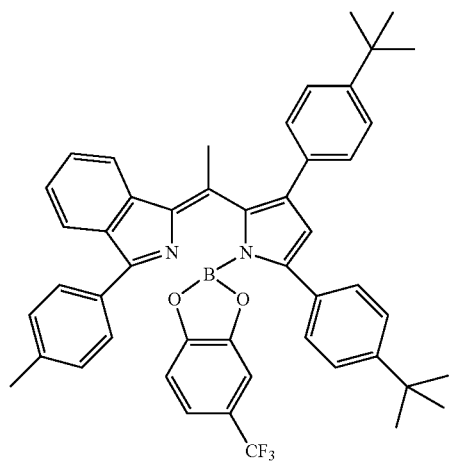
372
-continued
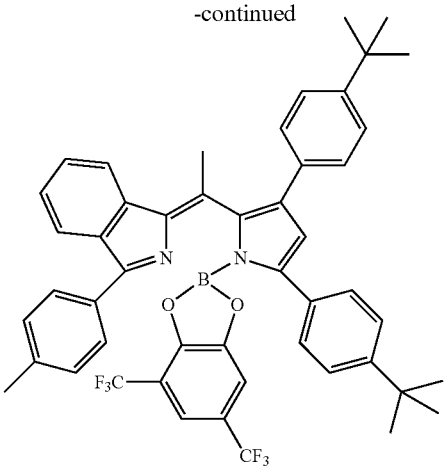
[Formula 118]
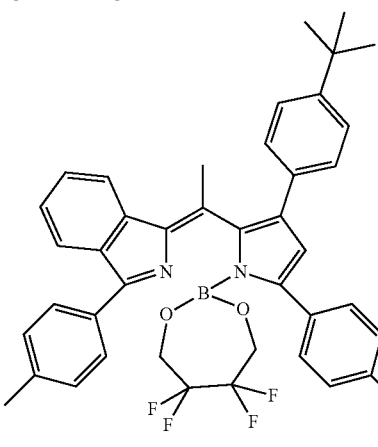
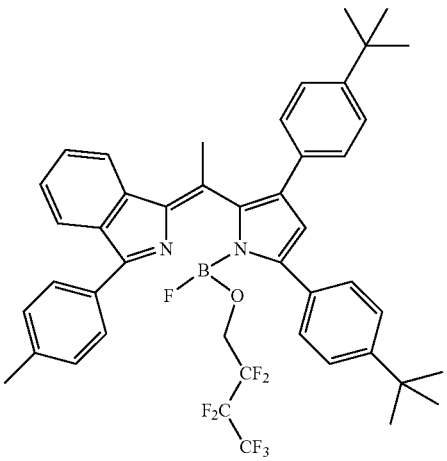

-continued
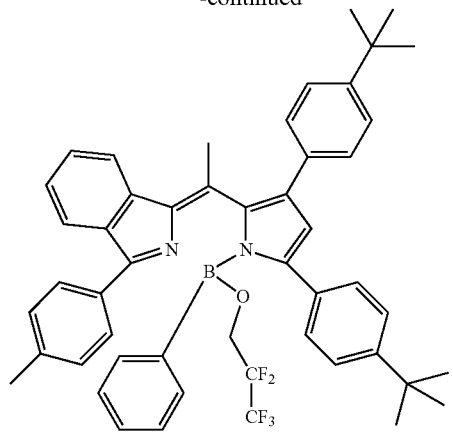
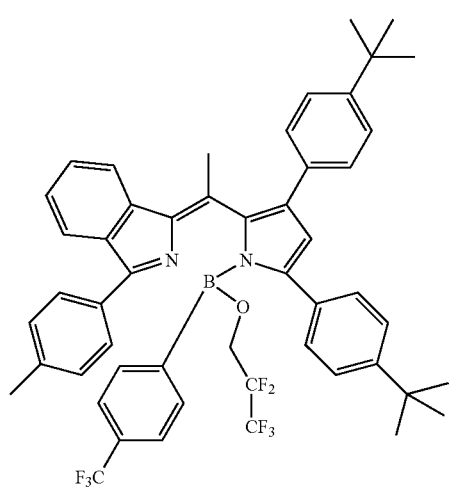
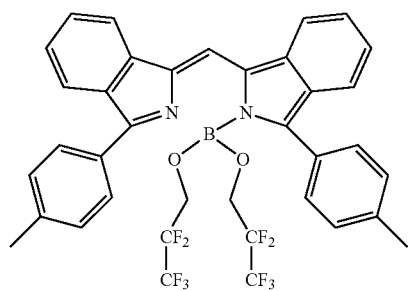
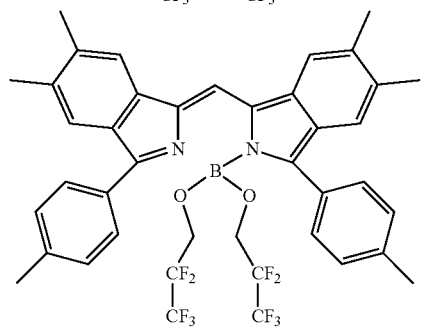
-continued
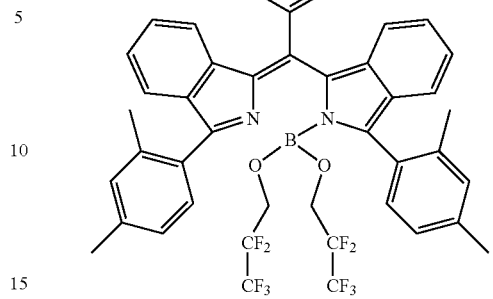
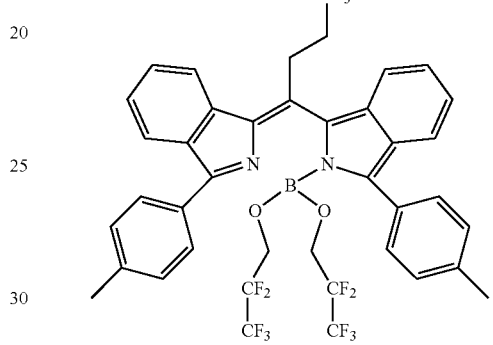
[Formula 119]
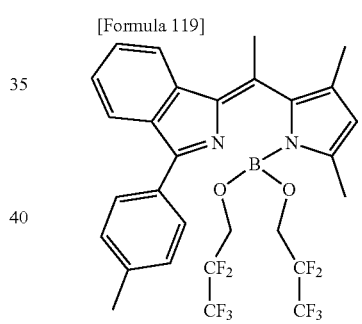
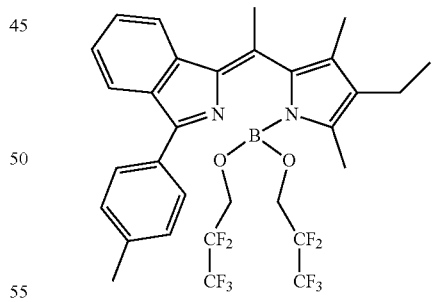
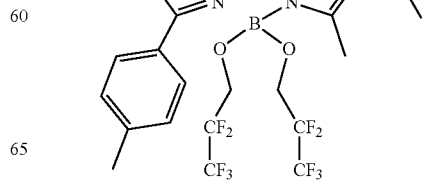

375
-continued
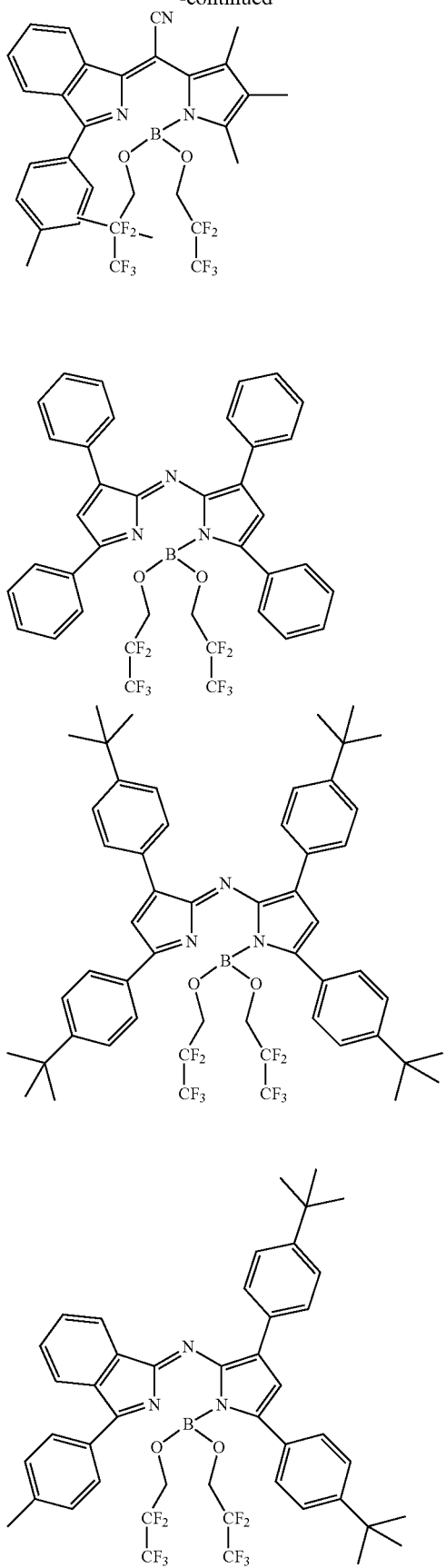
376
-continued
[Formula 120]
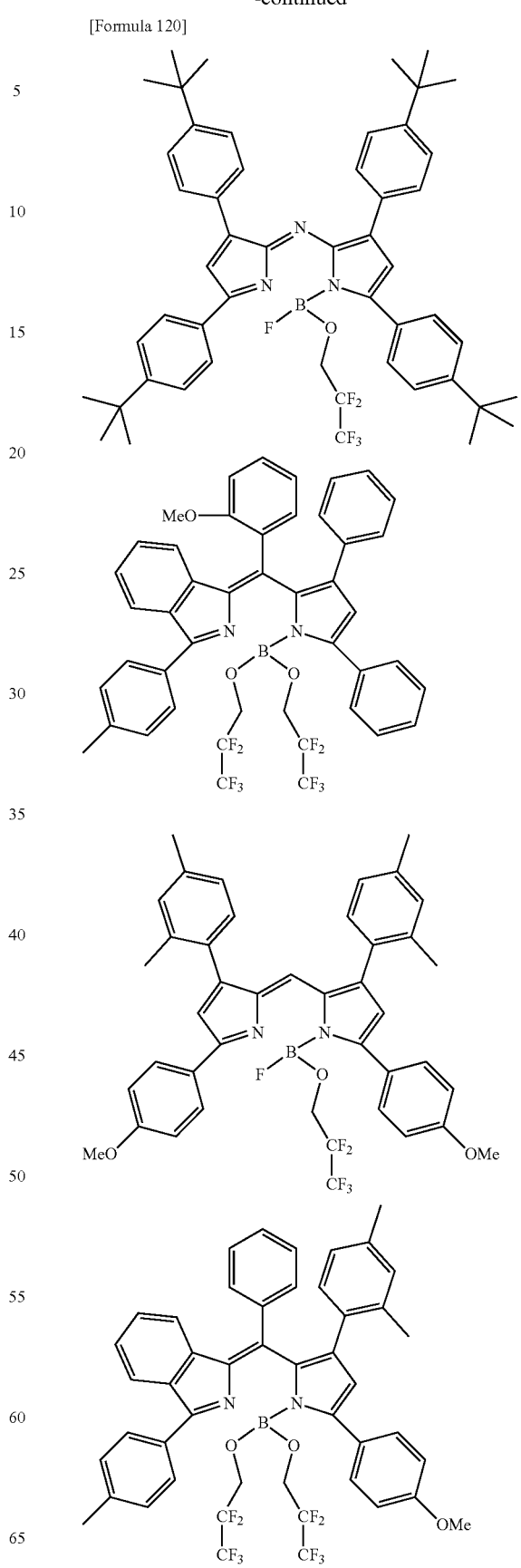

377
-continued
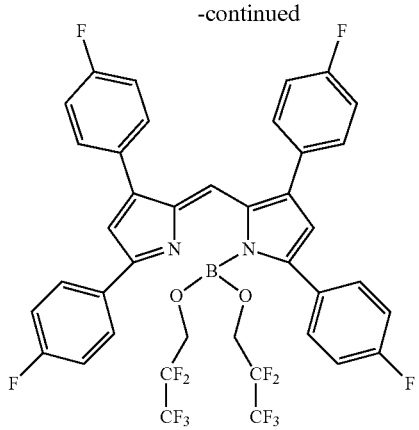
[Formula 121]
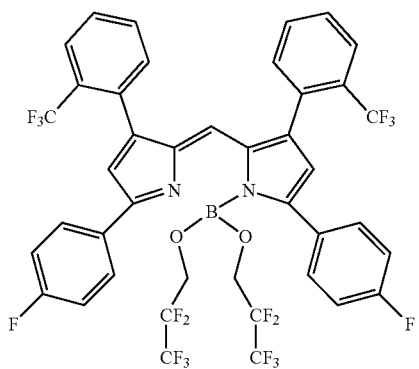
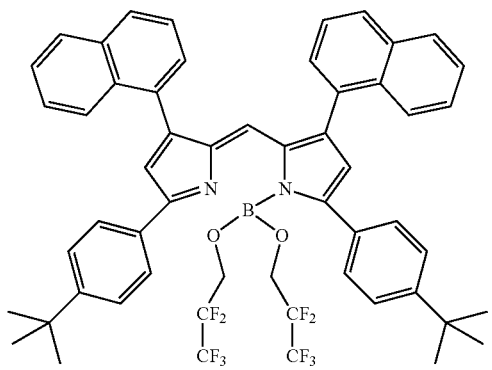
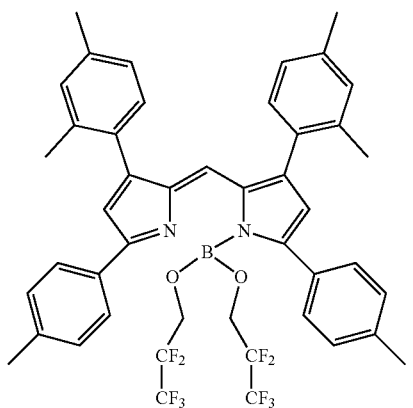
378
-continued
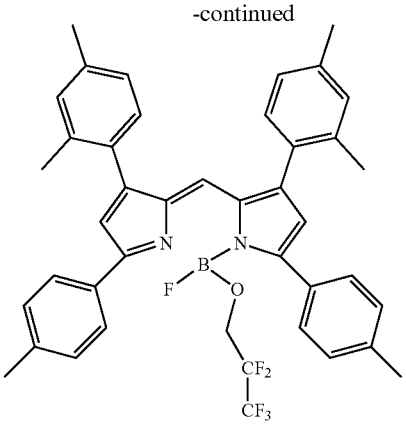
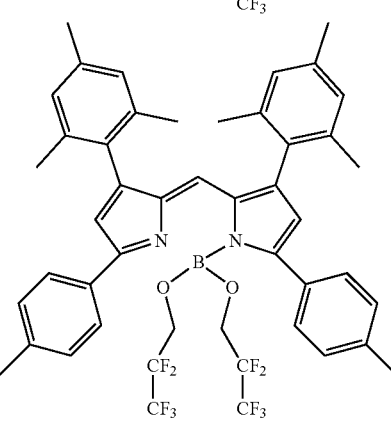
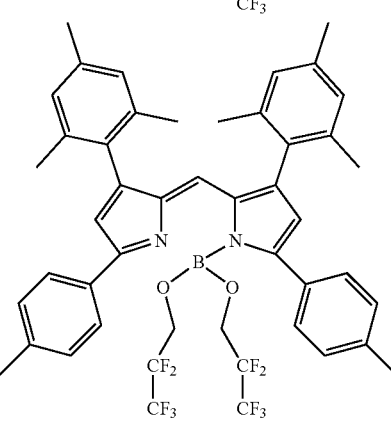
[Formula 122]

379
-continued
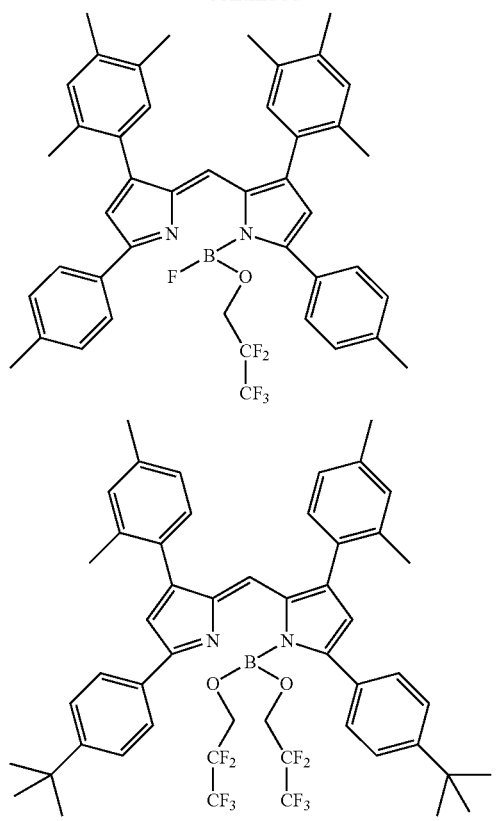
[Formula 123]
380
-continued
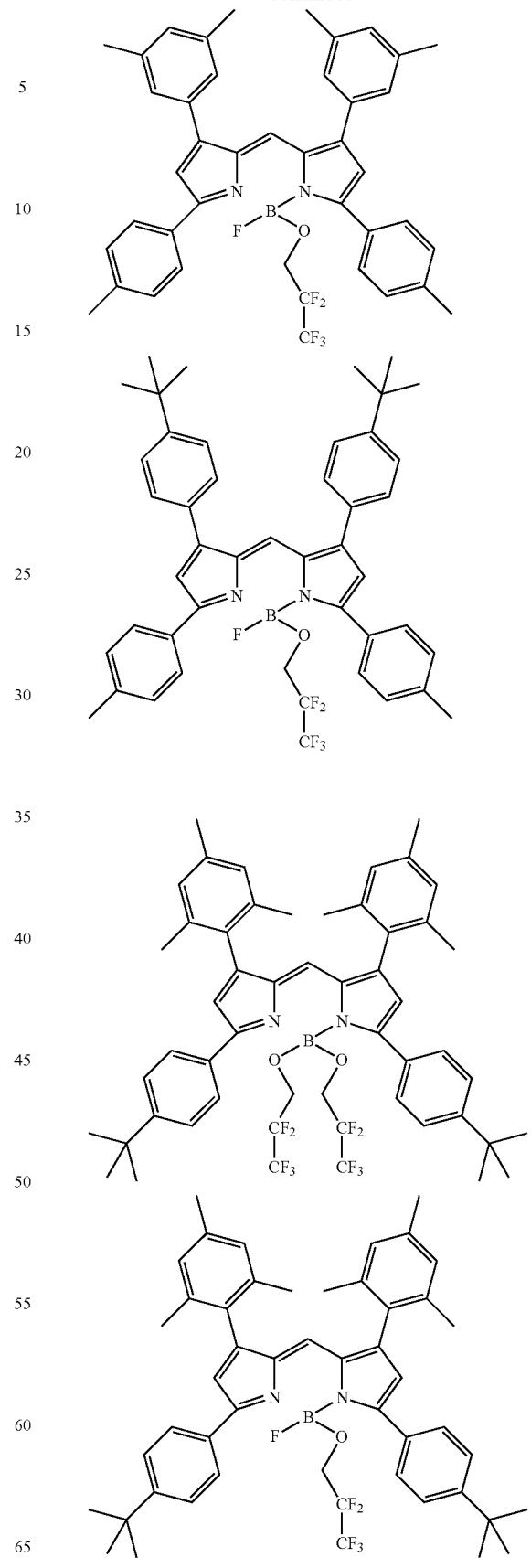

-continued
[Formula 124]
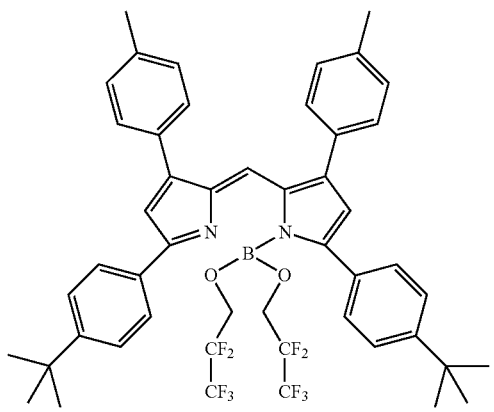
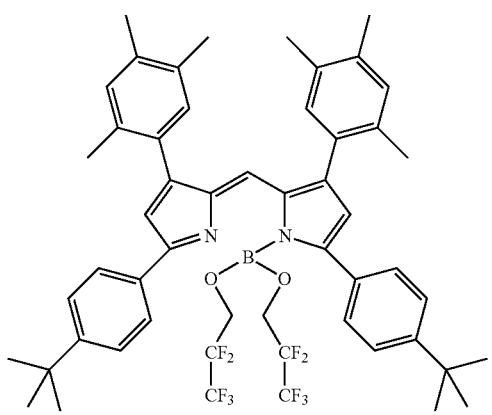
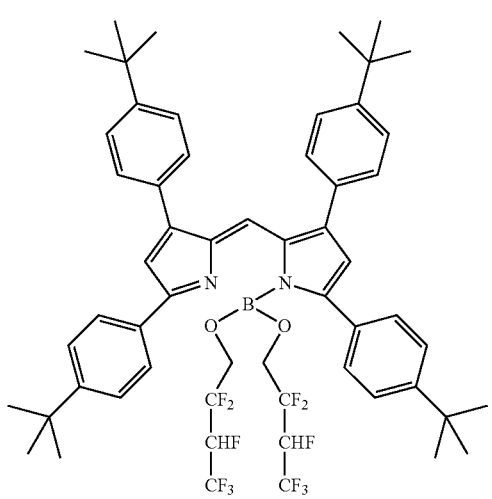
-continued
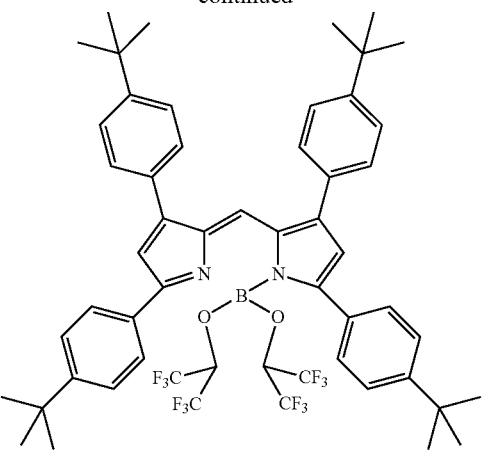
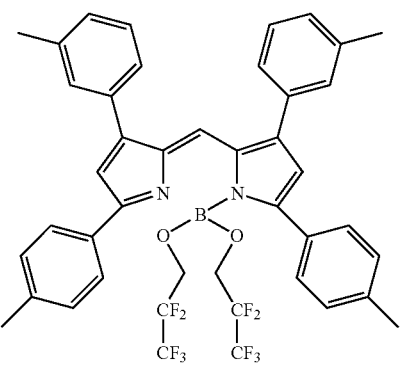
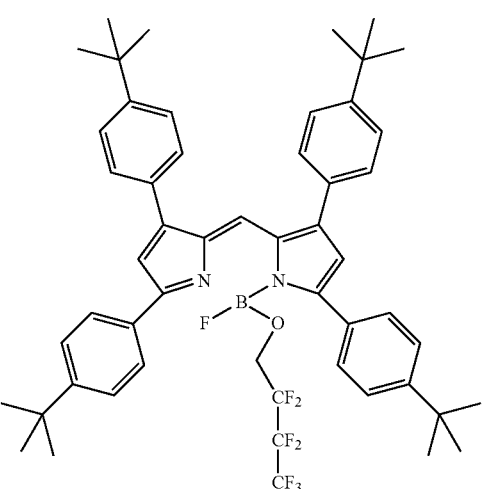

[Formula 125]
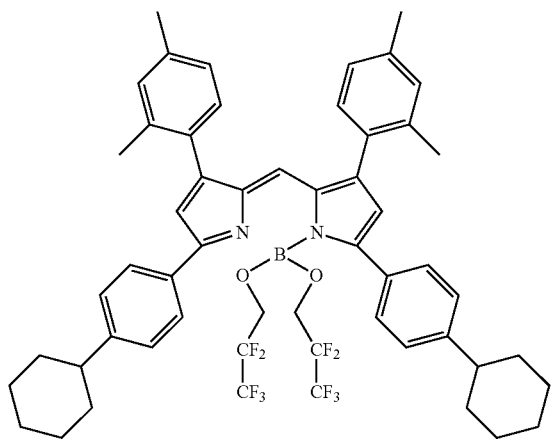
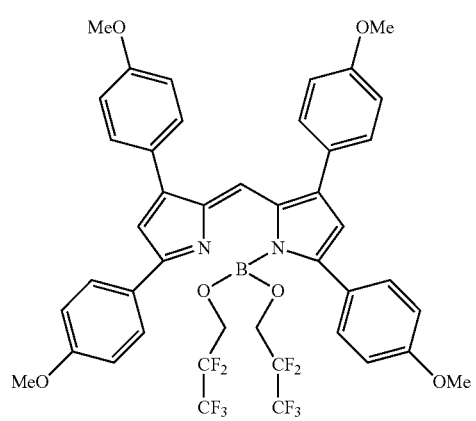
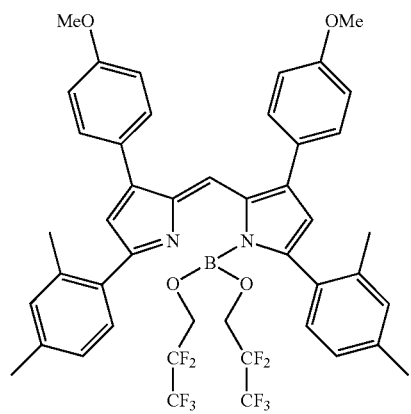
[Formula 126]
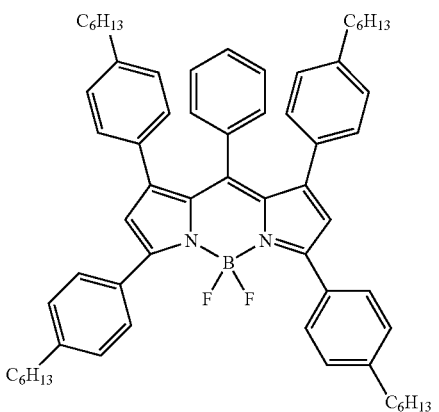
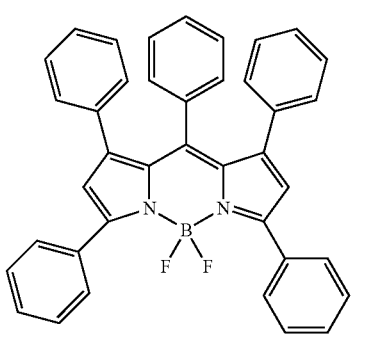
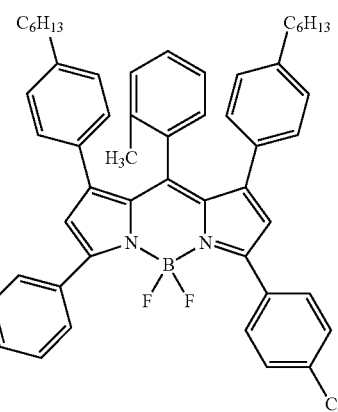
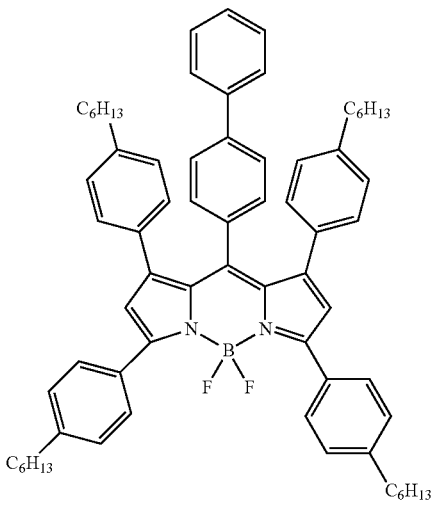

385
-continued
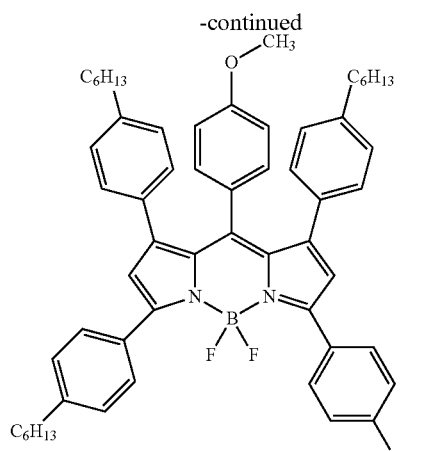
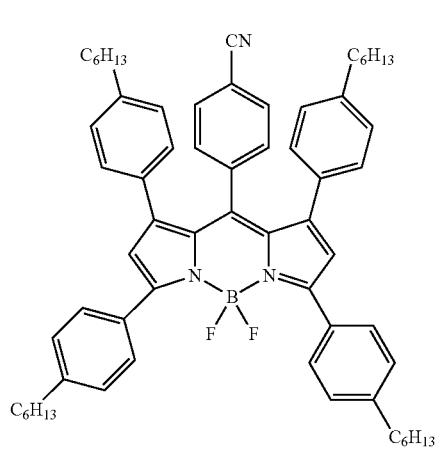
[Formula 127]
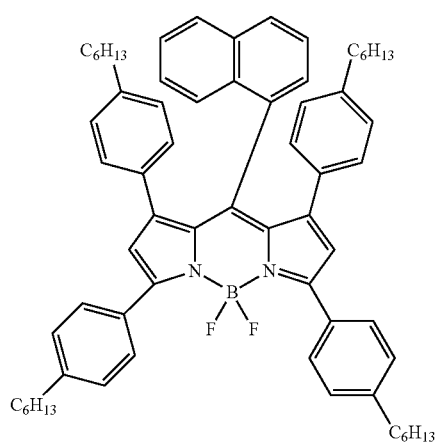
386
-continued
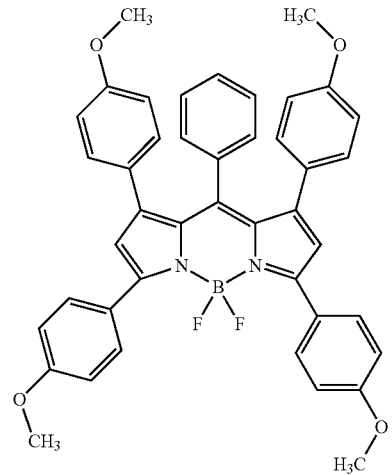
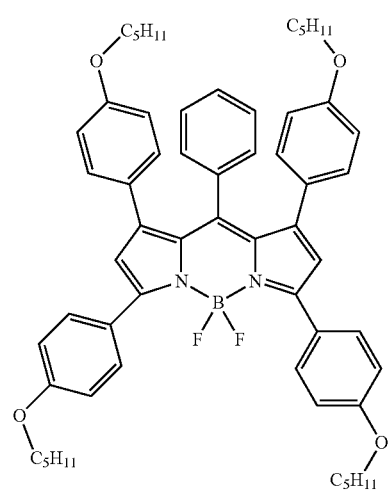
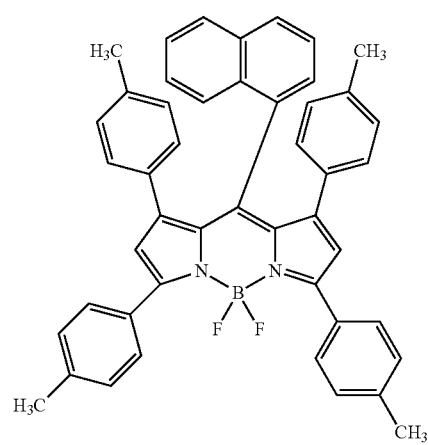

387
-continued
388
-continued
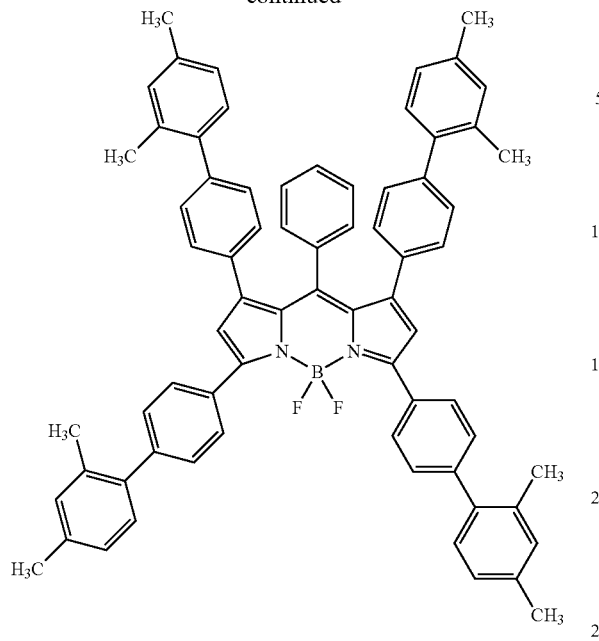
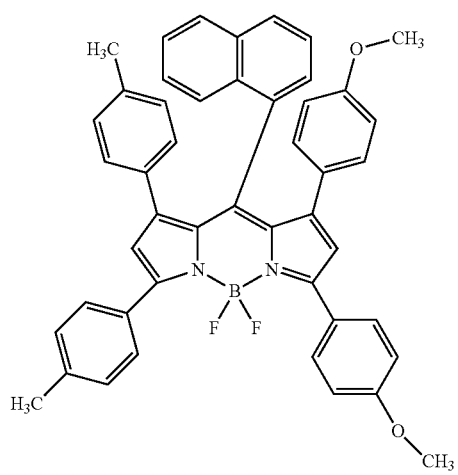
[Formula 128]
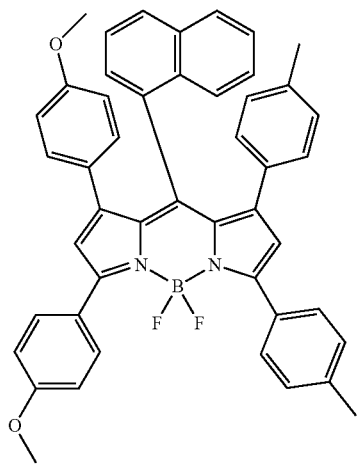
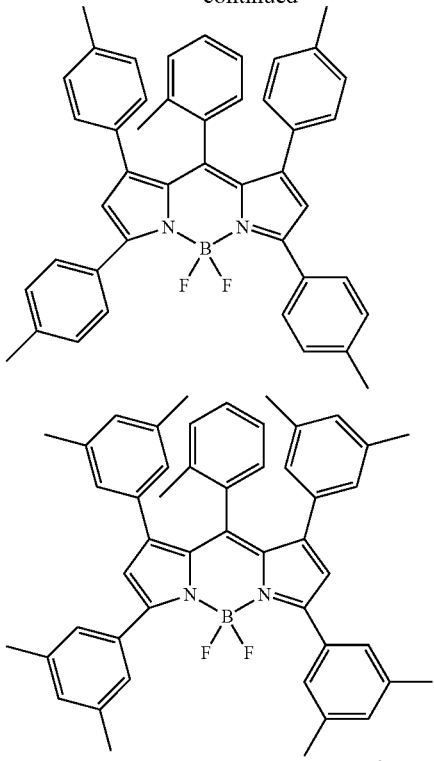

389
-continued
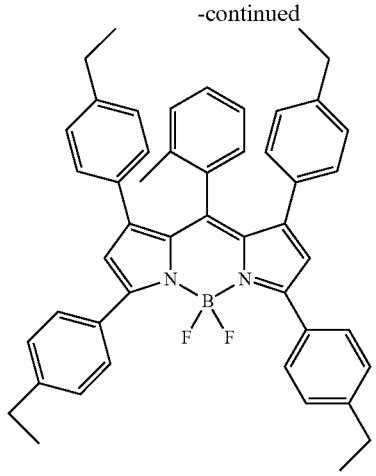
[Formula 129]
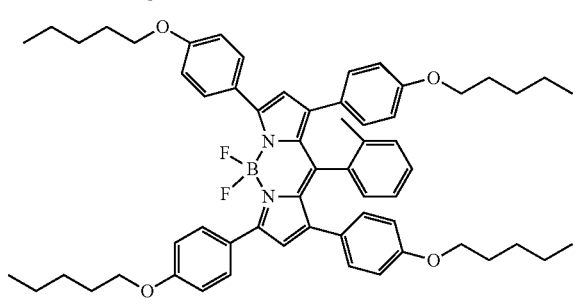
[Formula 130]
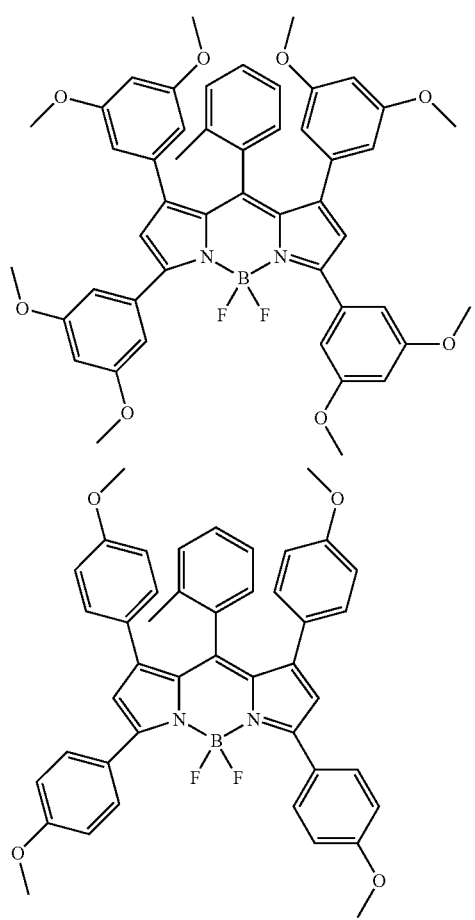
390
-continued
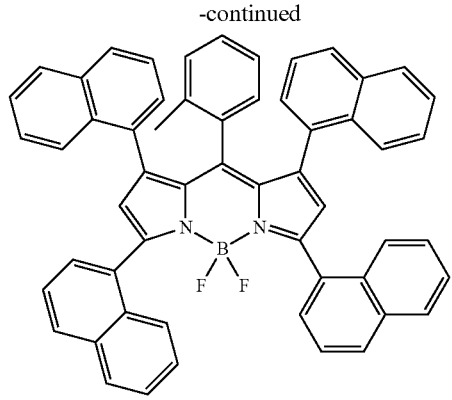
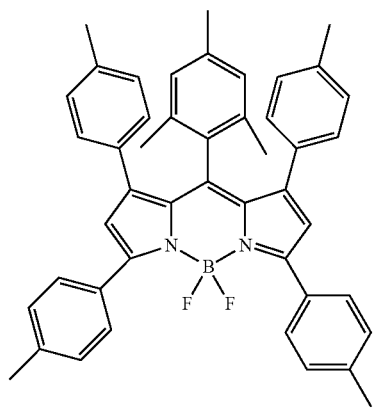
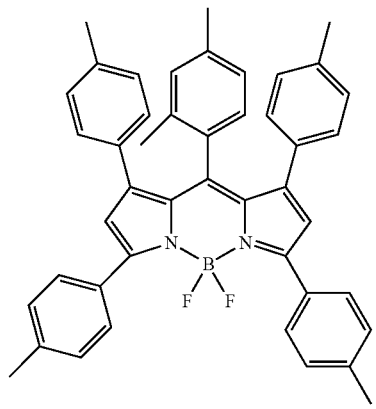

391
-continued
[Formula 131]
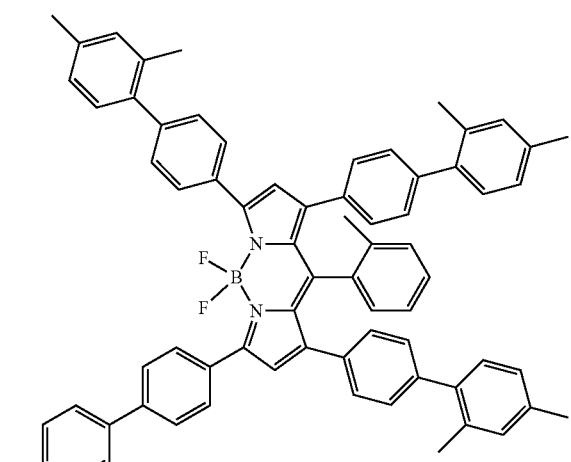
[Formula 132]
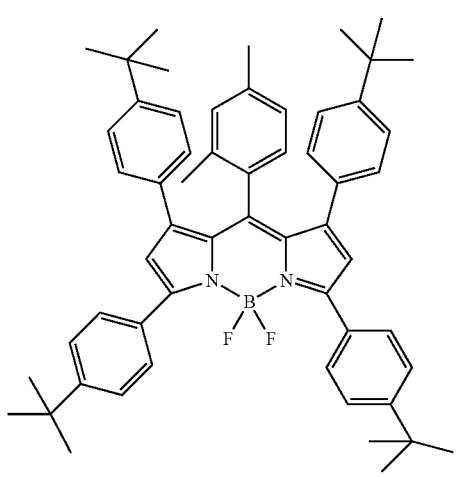
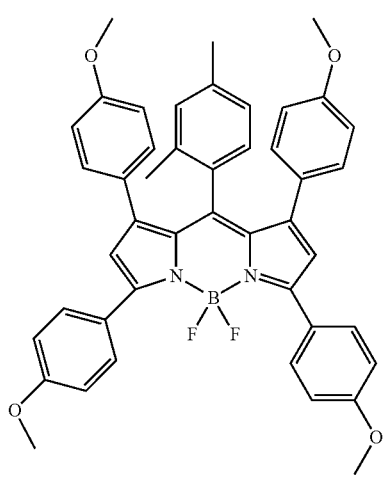
392
-continued
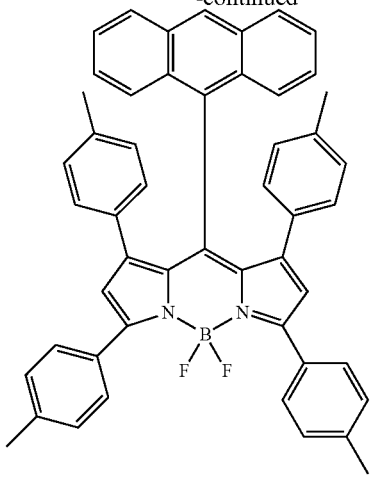
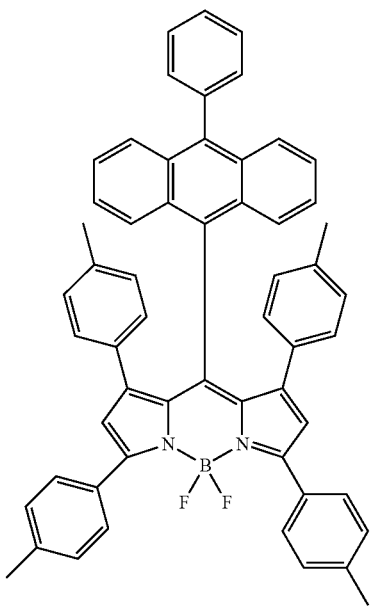
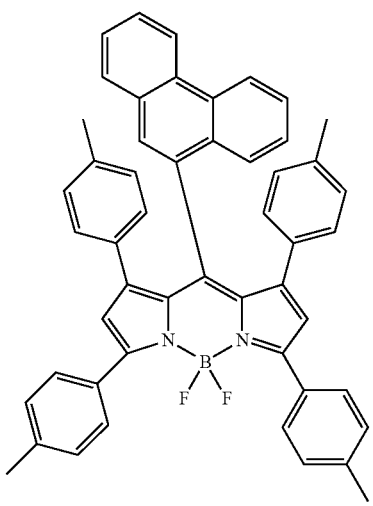

393
-continued
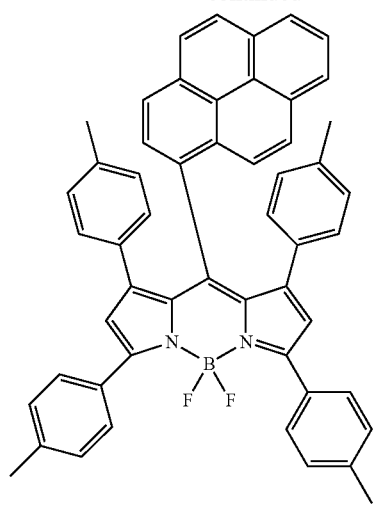
[Formula 133]
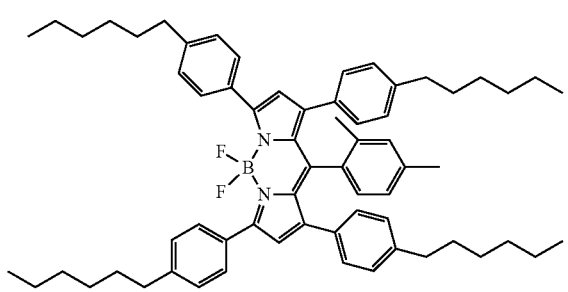
[Formula 134]
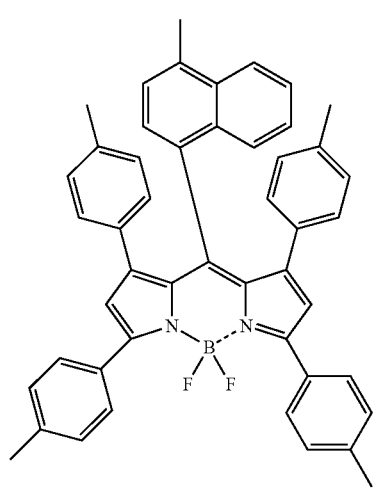
394
-continued
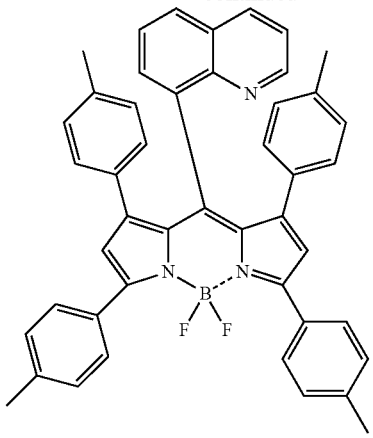
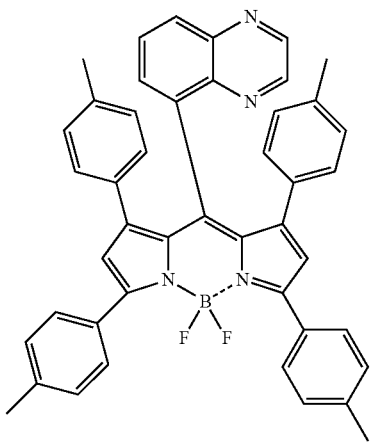
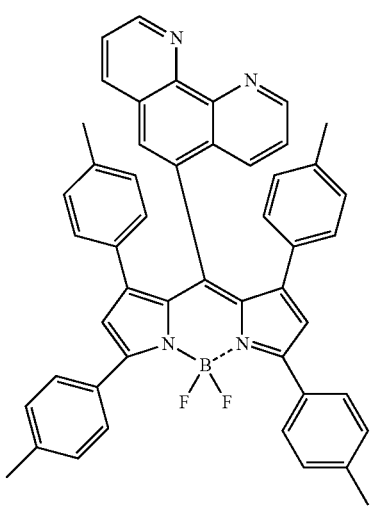

395
-continued
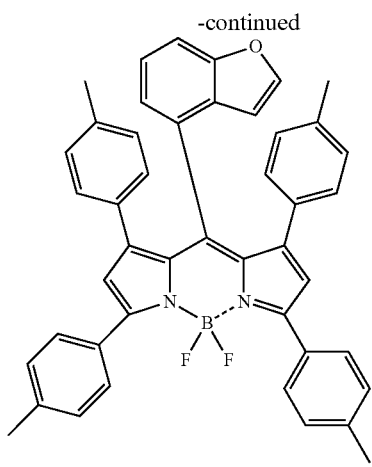
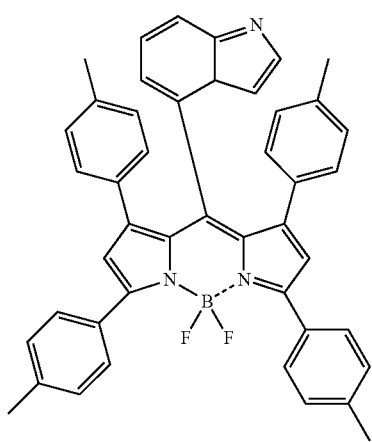
[Formula 135]
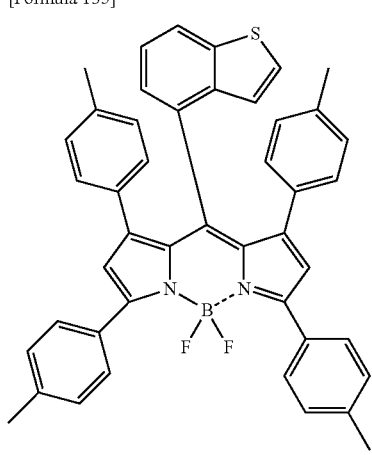
396
-continued
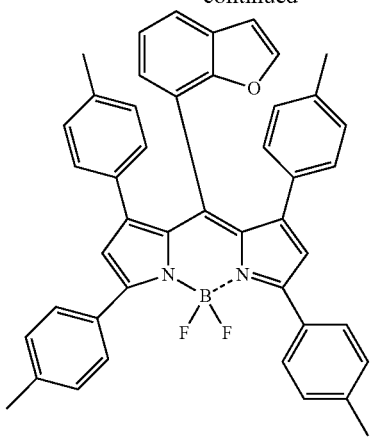
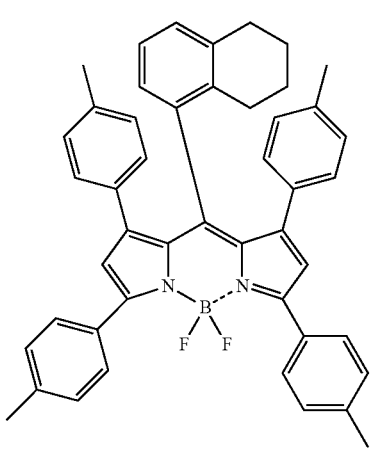
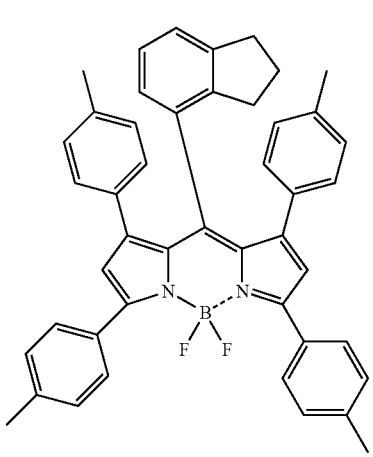

397
-continued
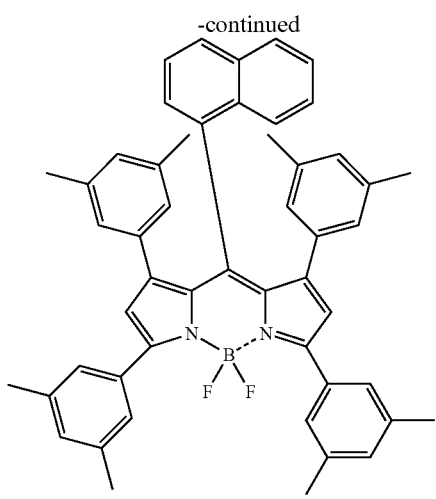
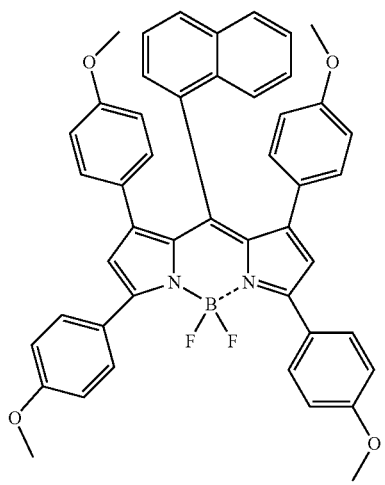
[Formula 136]
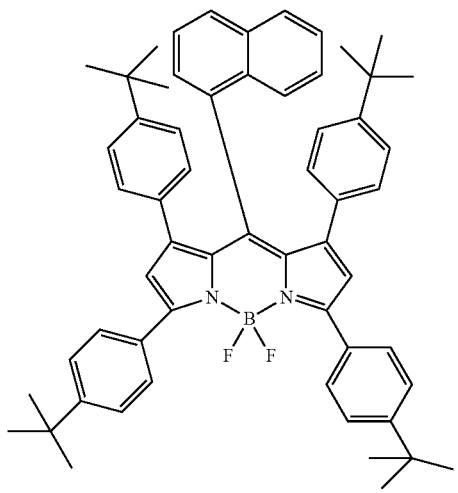
398
-continued
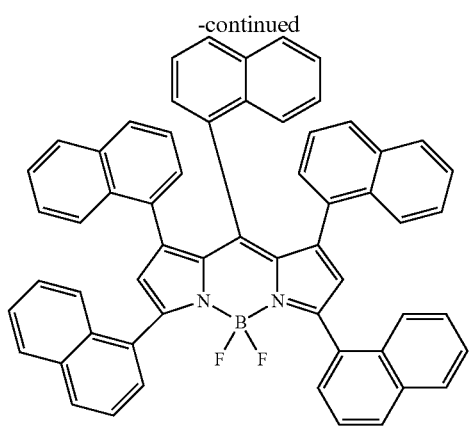
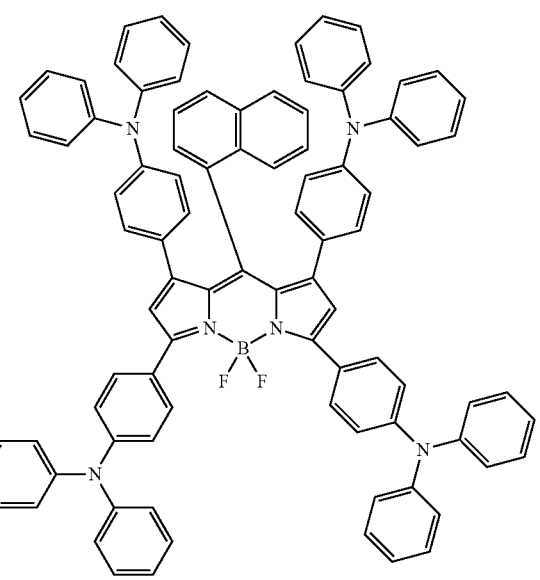
[Formula 137]
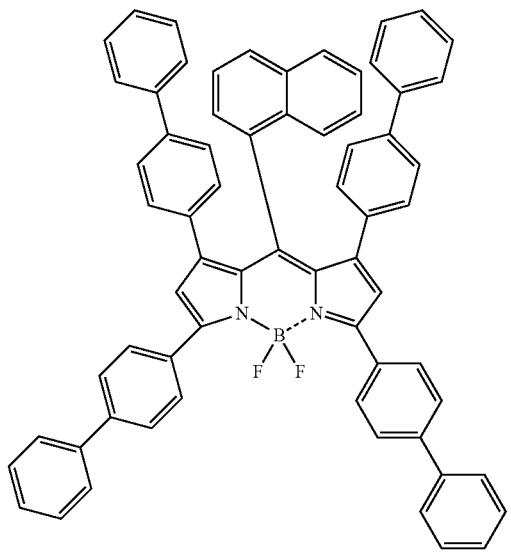

399
-continued
400
-continued
[Formula 138]
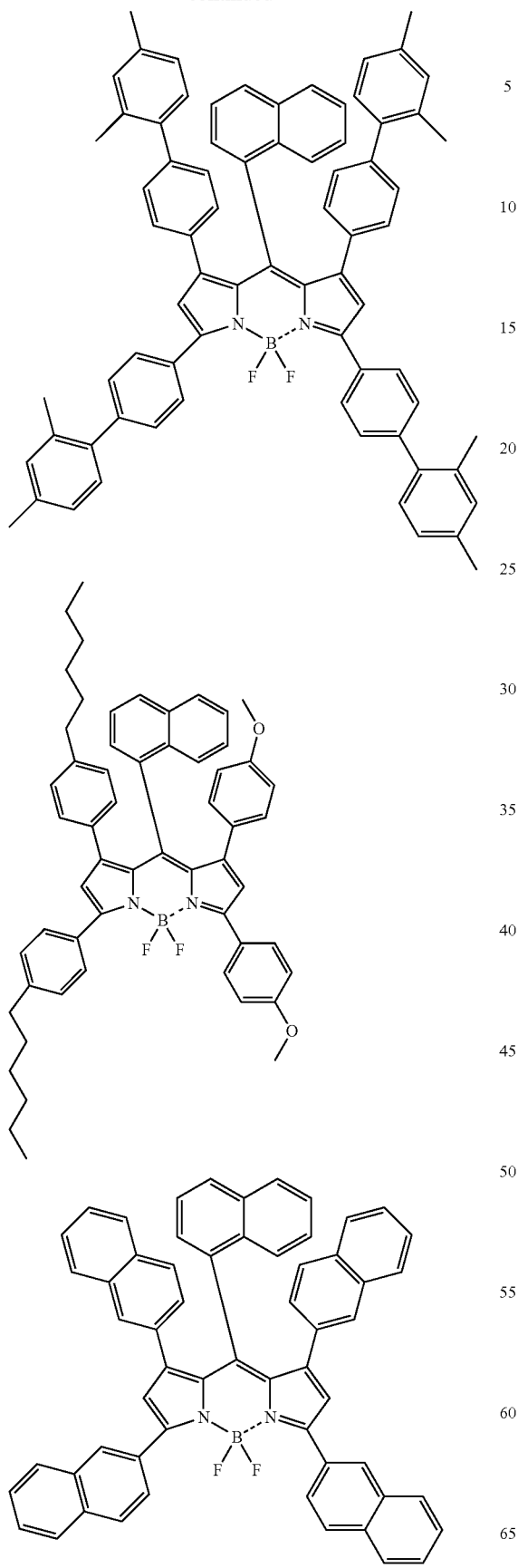
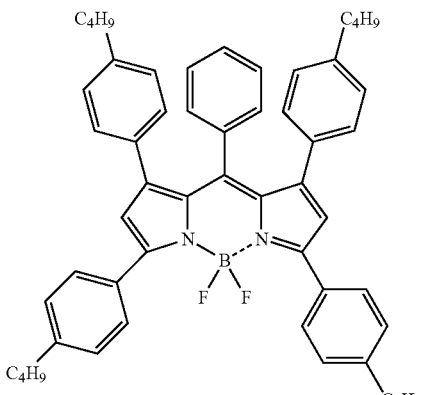
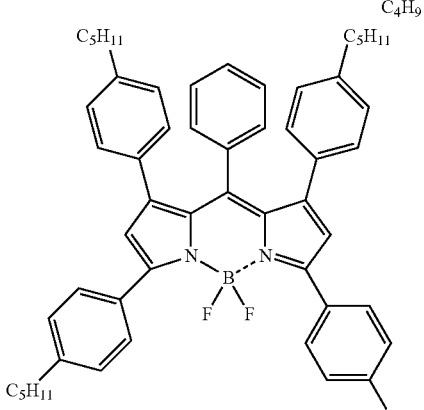
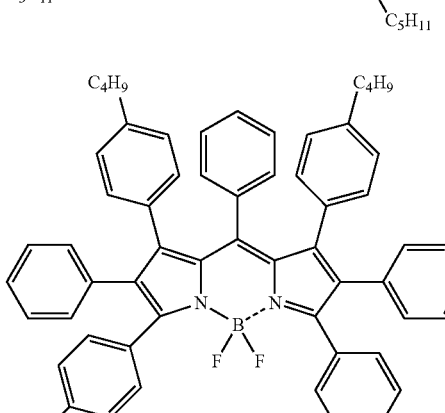
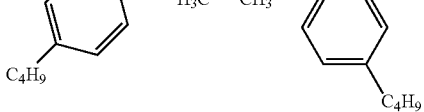

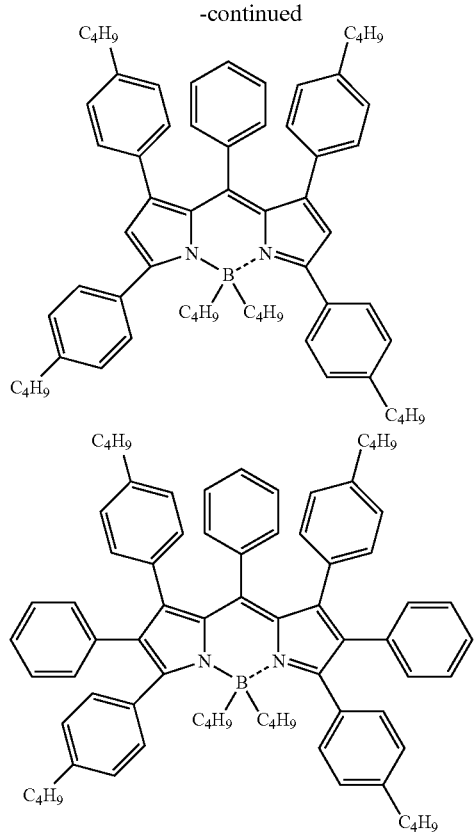
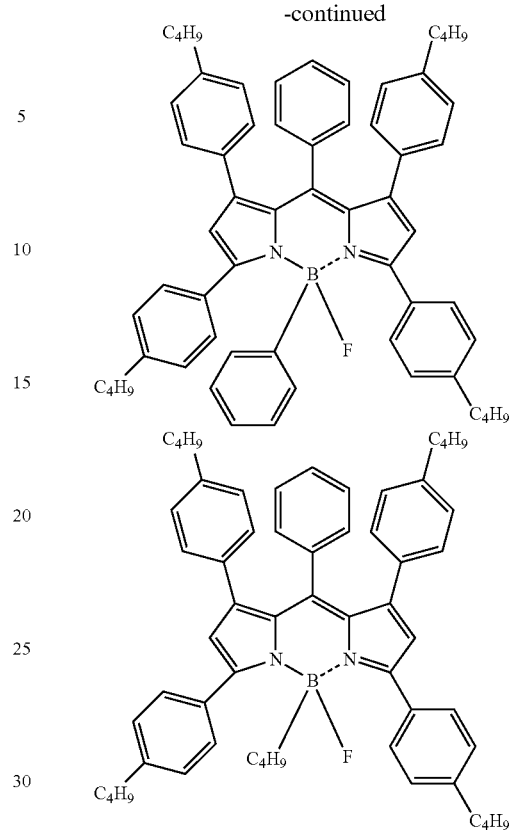
[Formula 139]
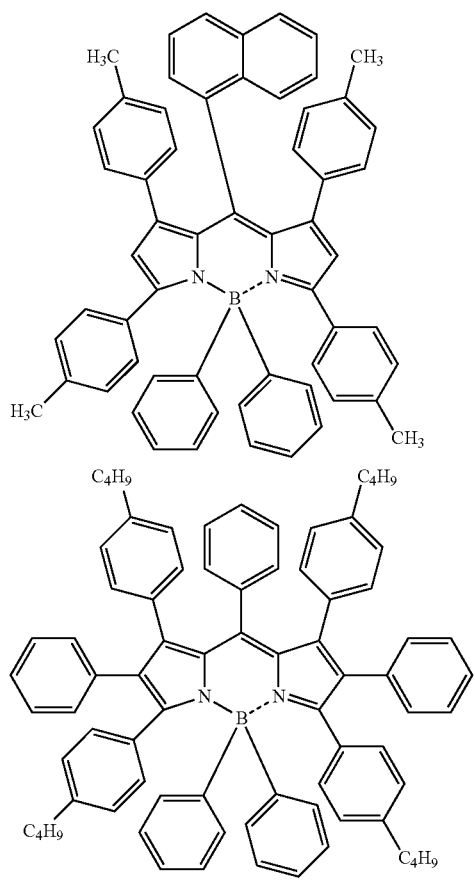
[Formula 140]
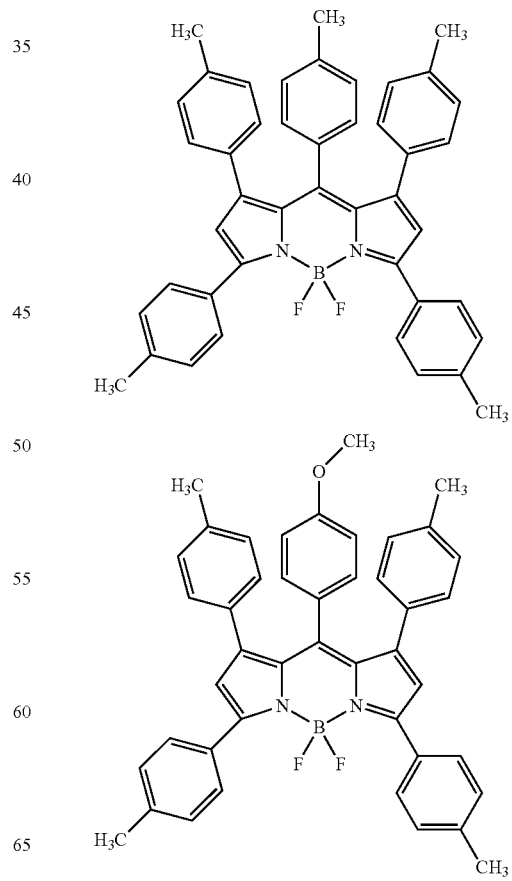

403
-continued
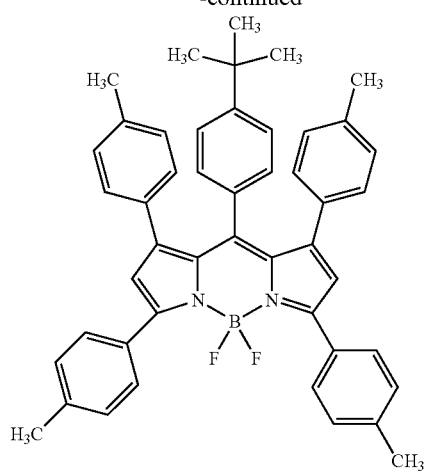
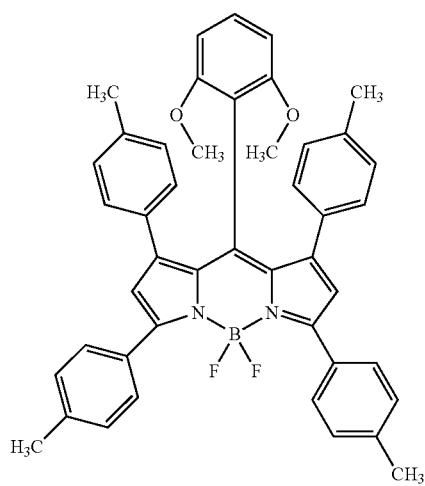
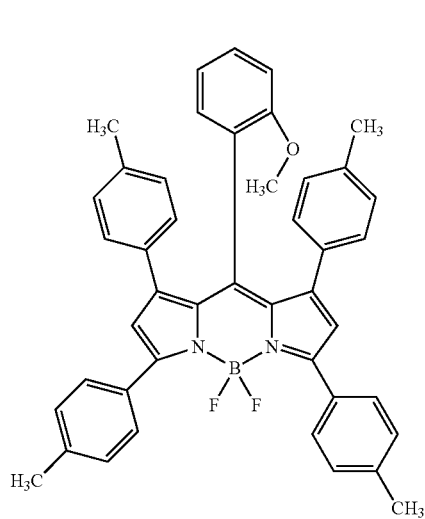
404
-continued
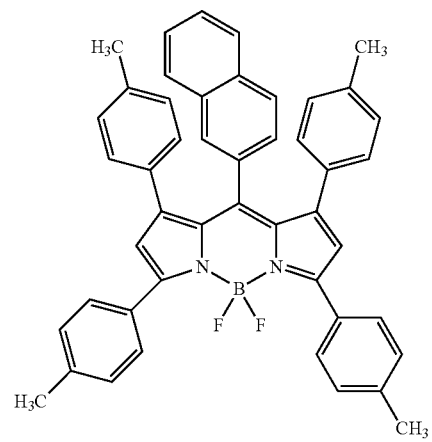
[Formula 141]
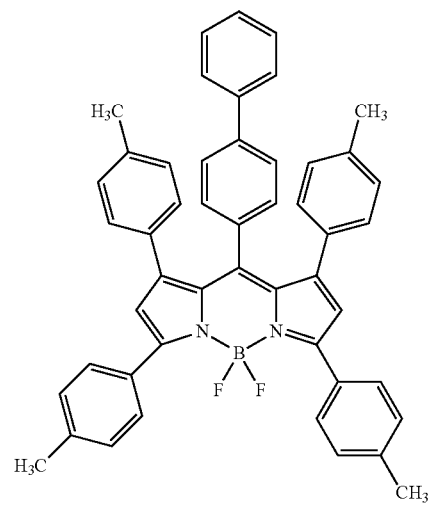

405
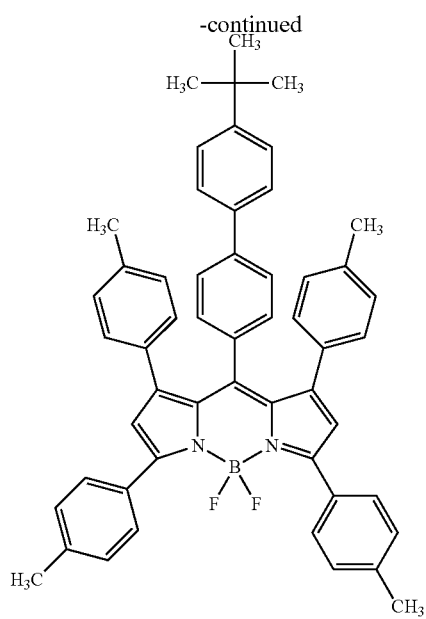
[Formula 142]
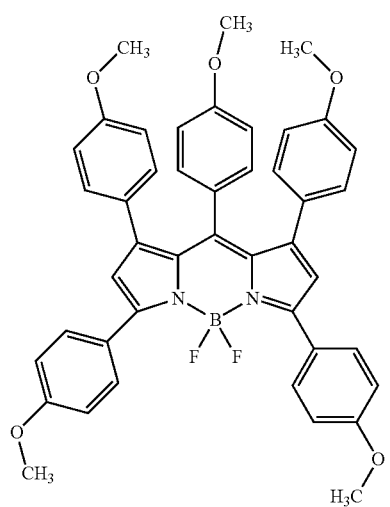
406
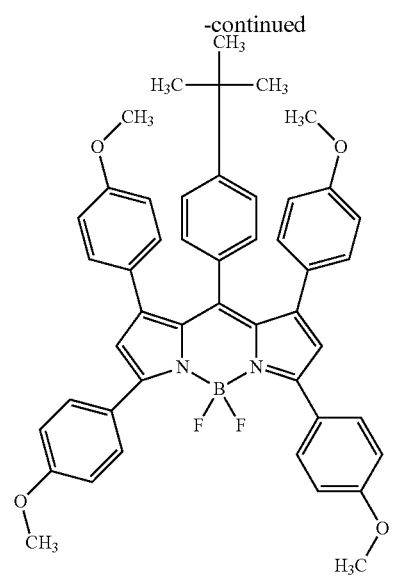
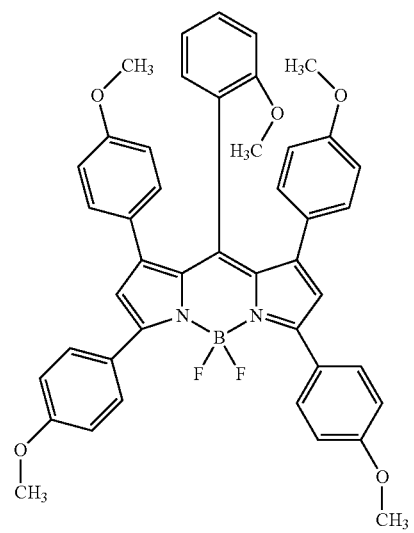

407
-continued
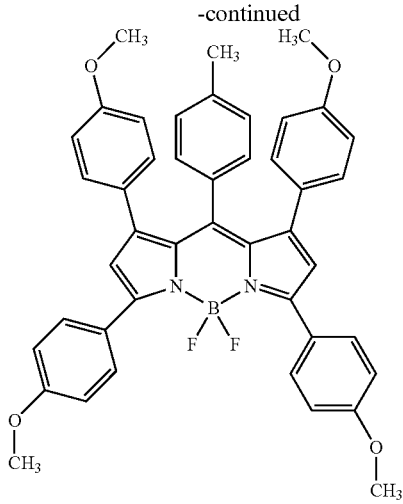
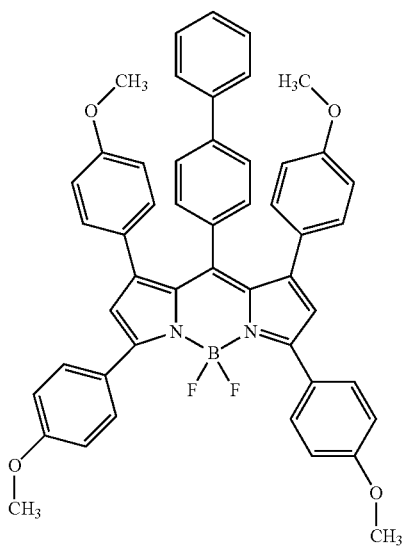
[Formula 143]
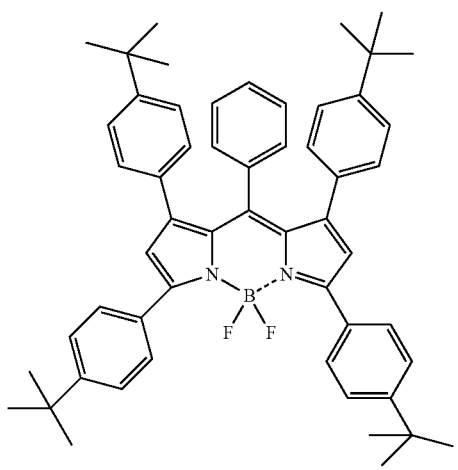
408
-continued
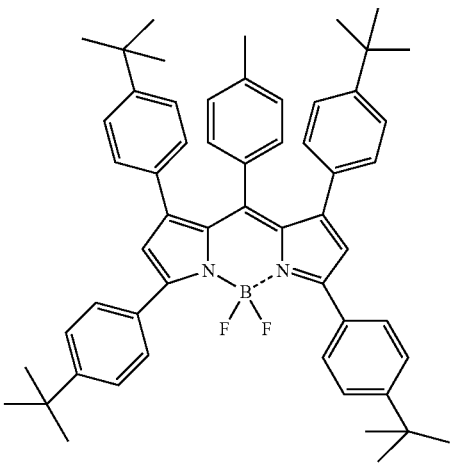
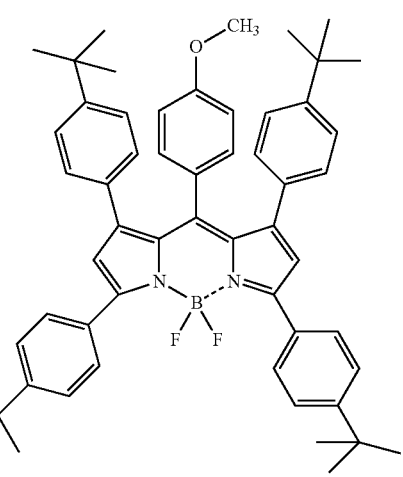
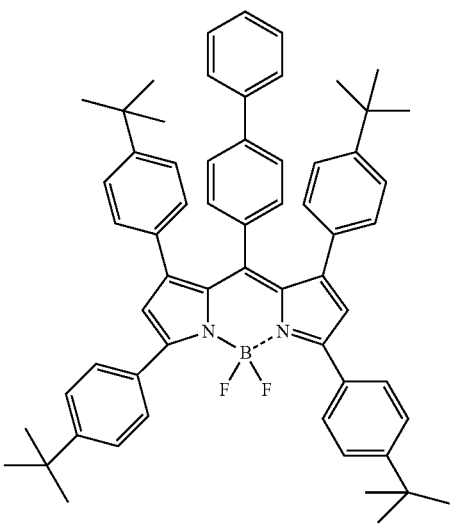

409
-continued
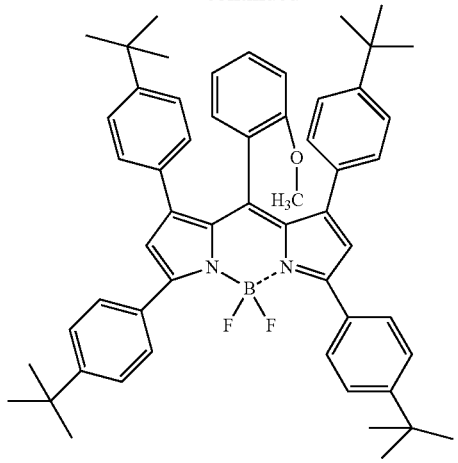
[Formula 144]
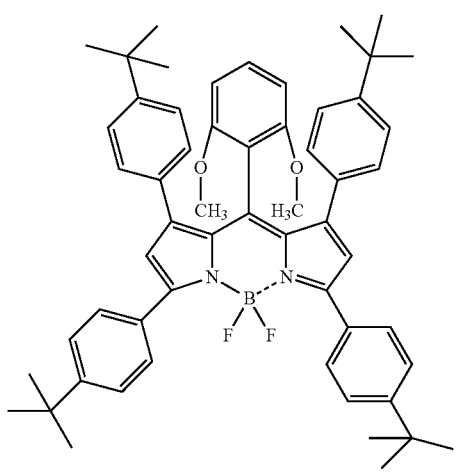
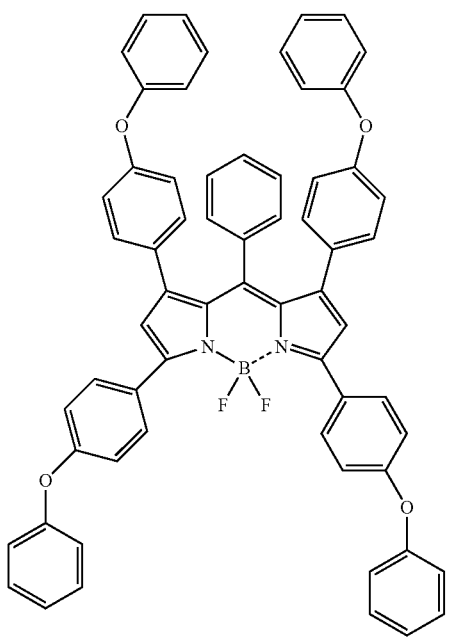
410
-continued
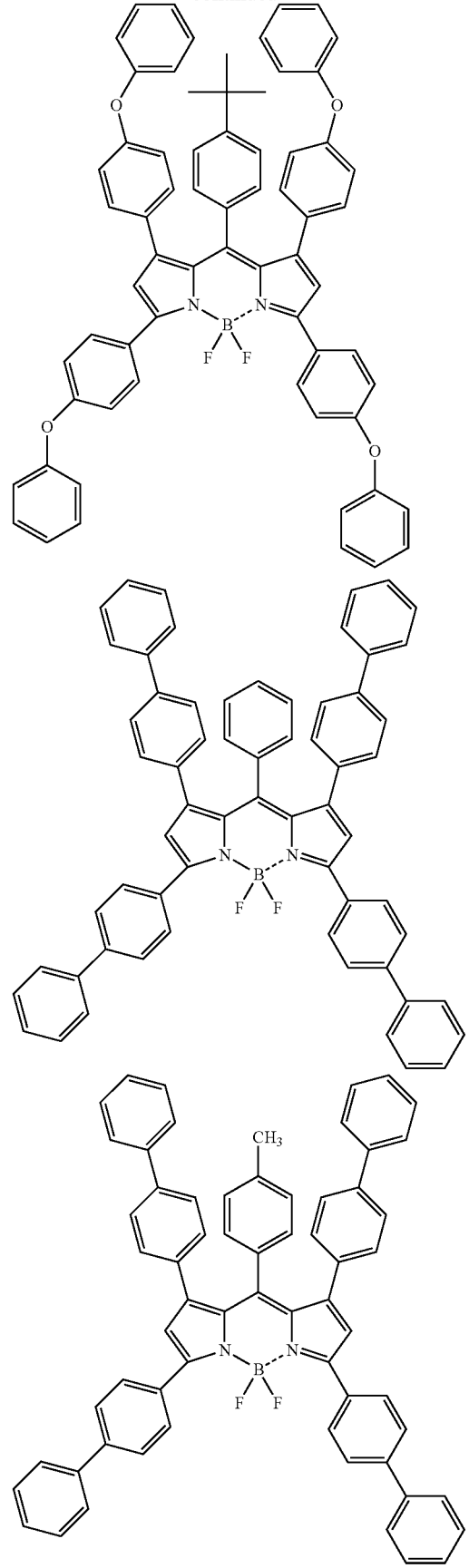

411
-continued
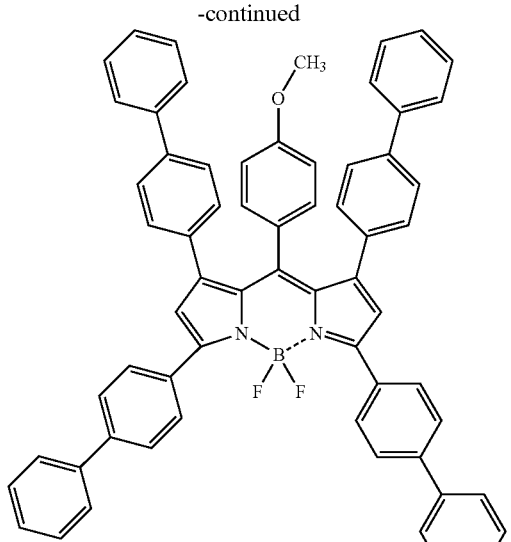
[Formula 145]
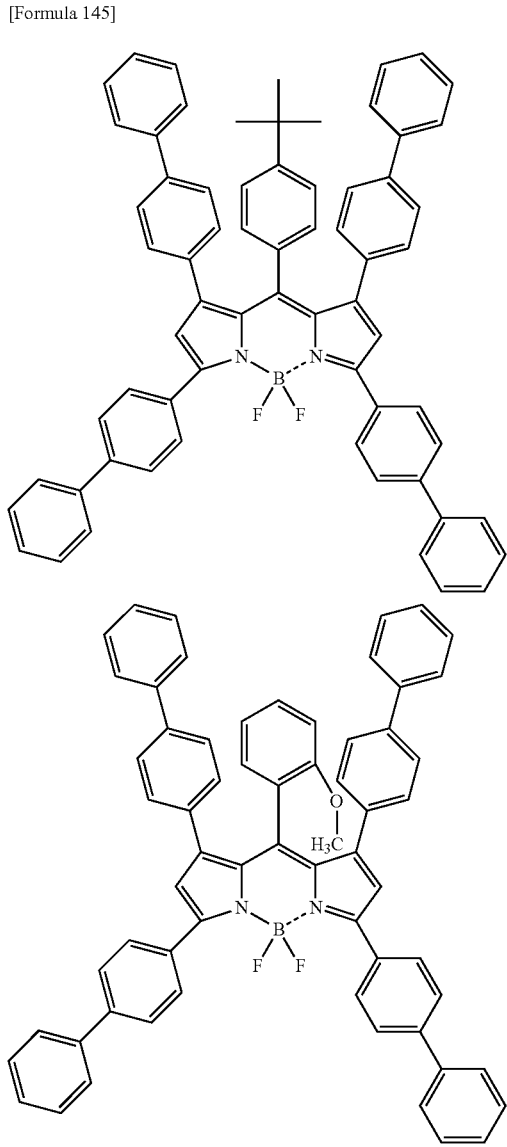
412
-continued
[Formula 146]
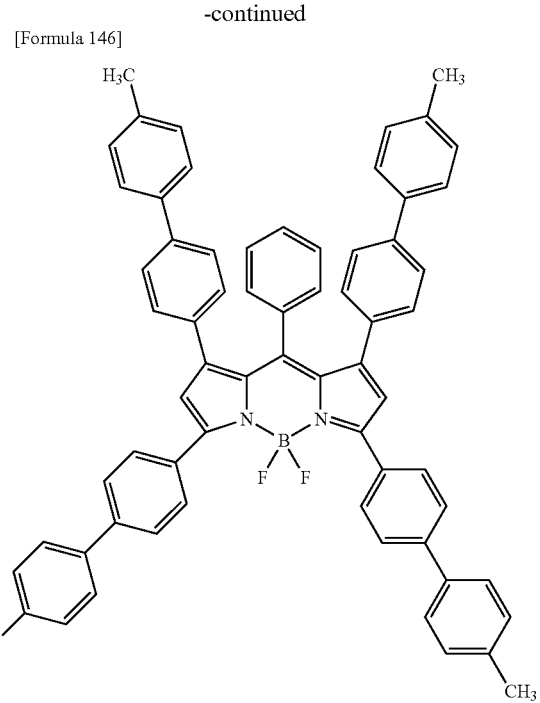
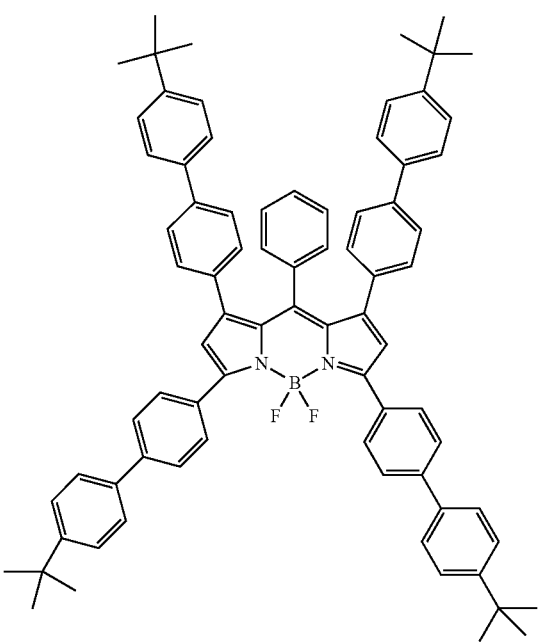

413
-continued
[Formula 147]
414
-continued
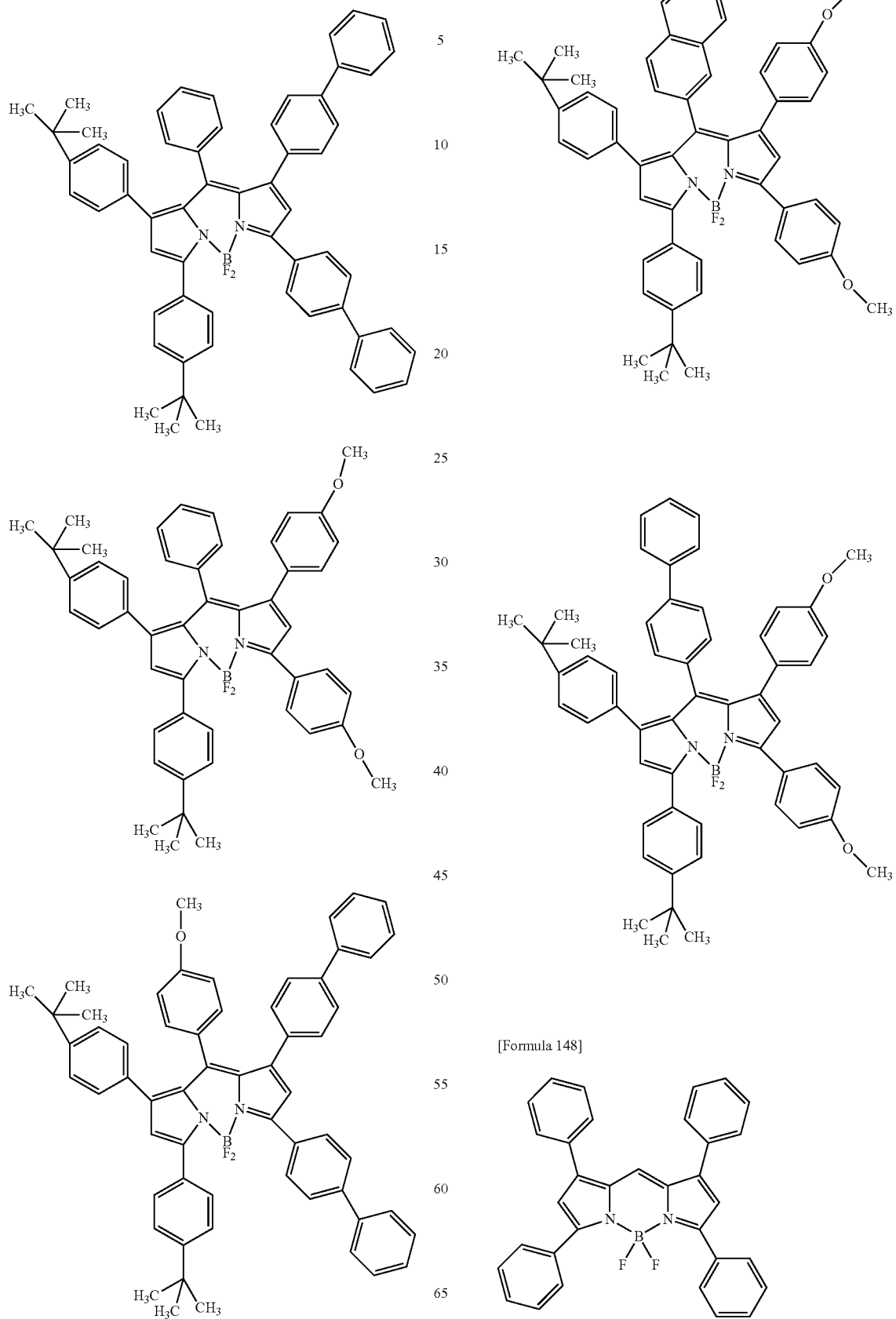
[Formula 148]

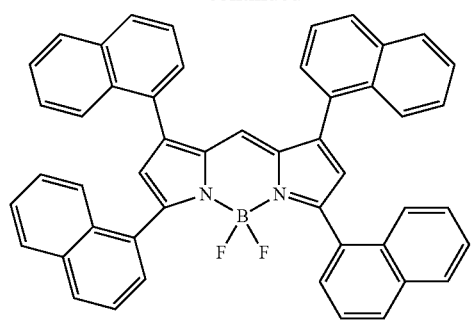
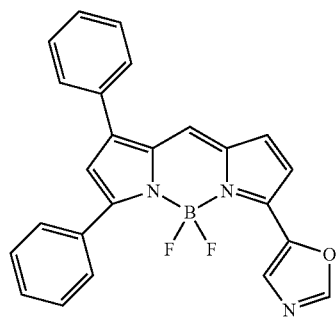
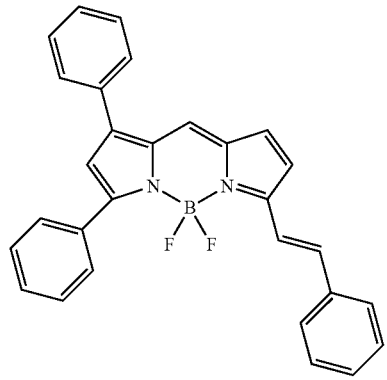
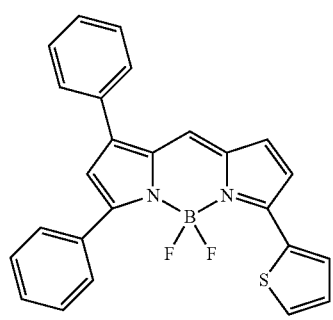
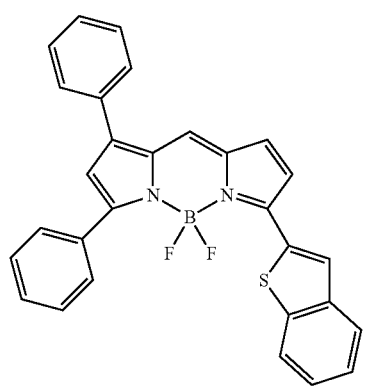
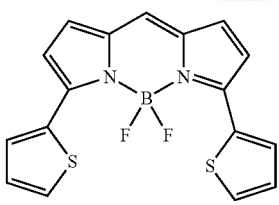
[Formula 149]
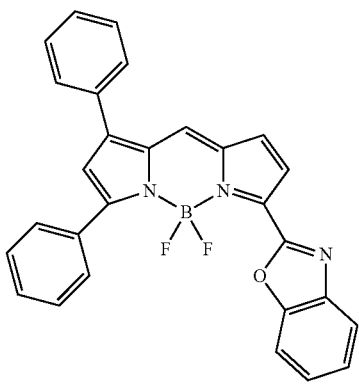
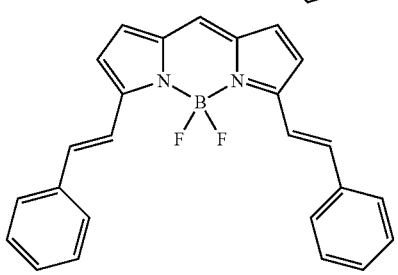
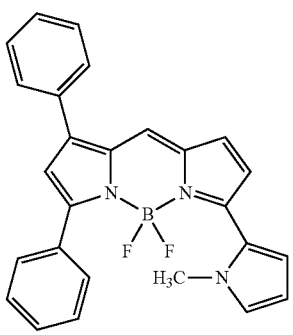
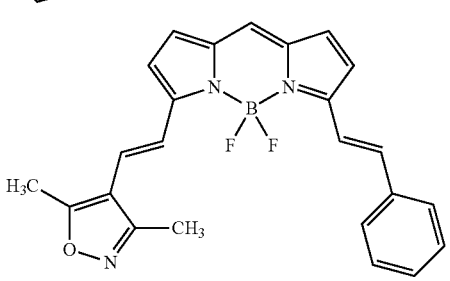
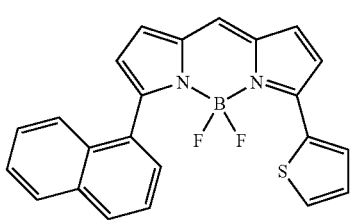

417
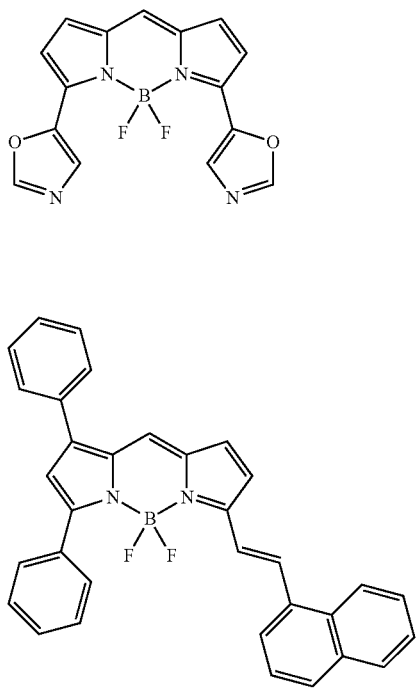
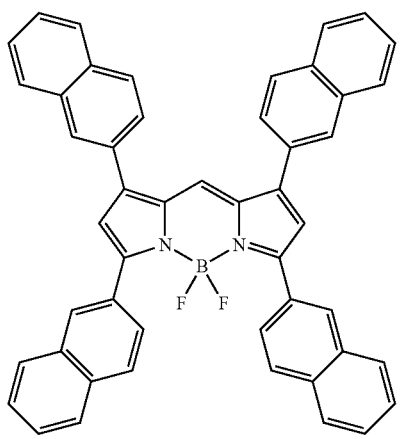
[Formula 150]
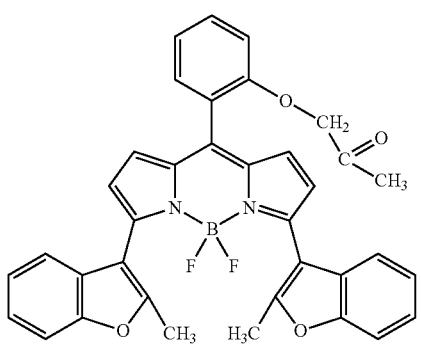
418
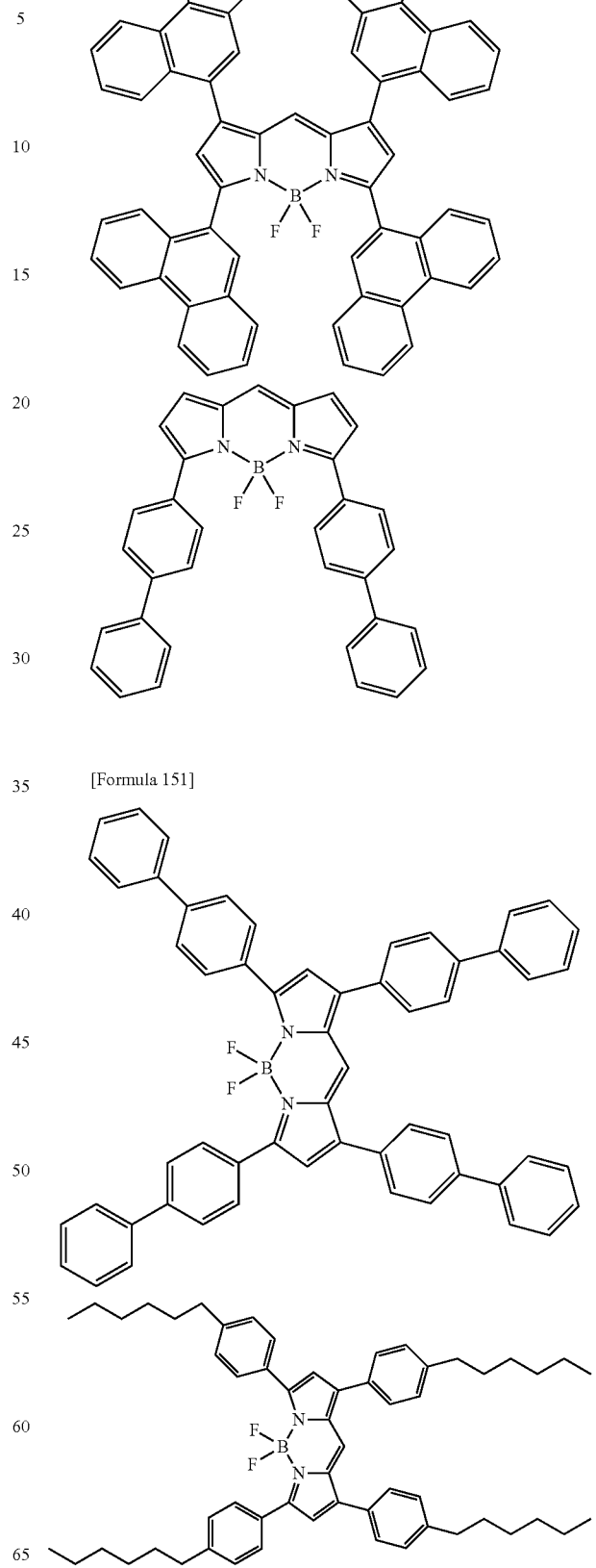
[Formula 151]

419
-continued
[Formula 152]
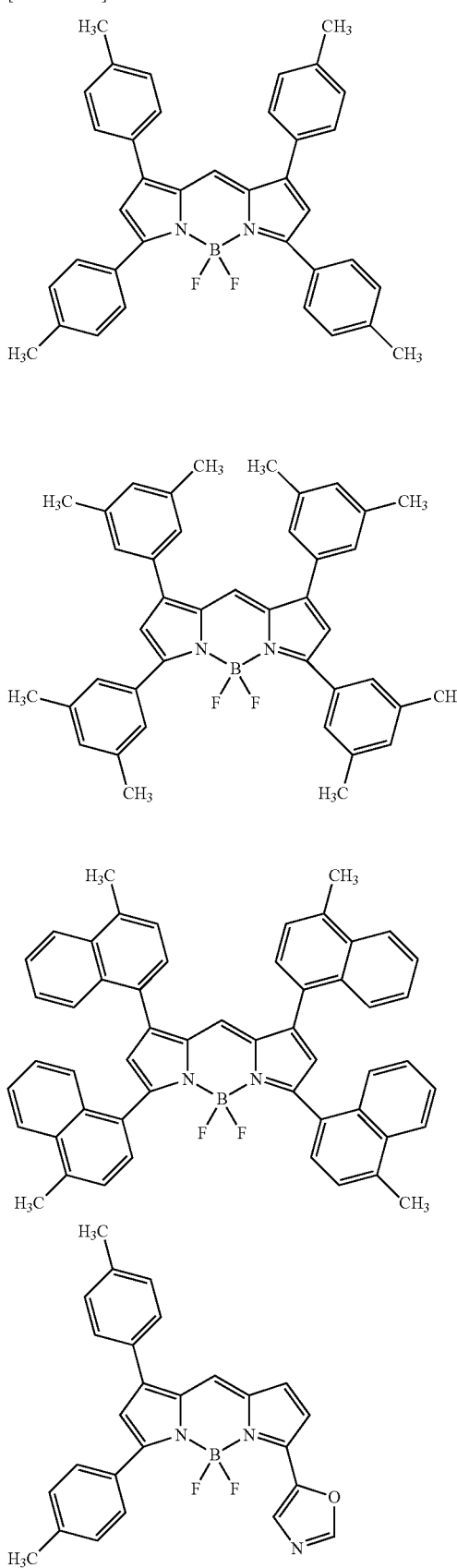
420
-continued
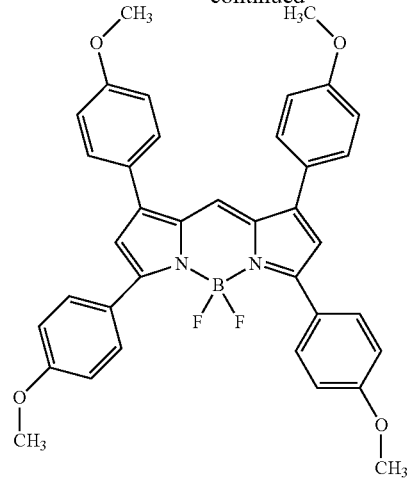
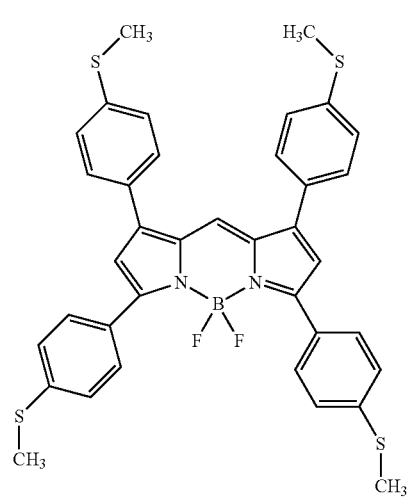
[Formula 153]
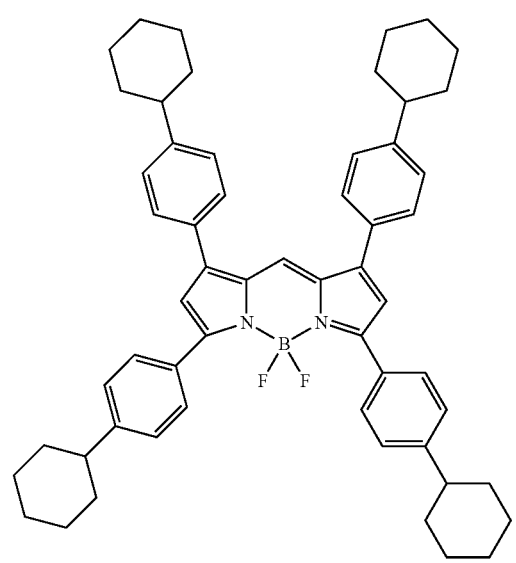

421
-continued
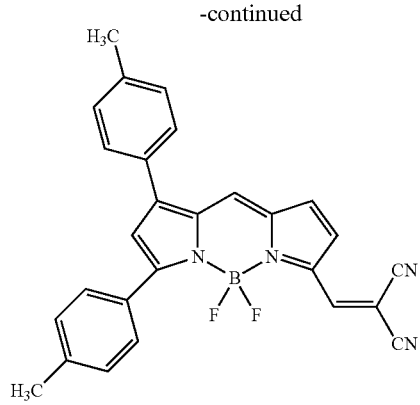
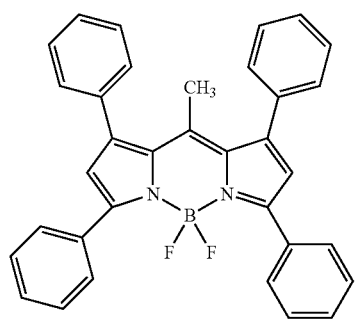
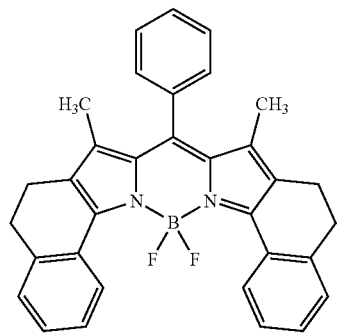
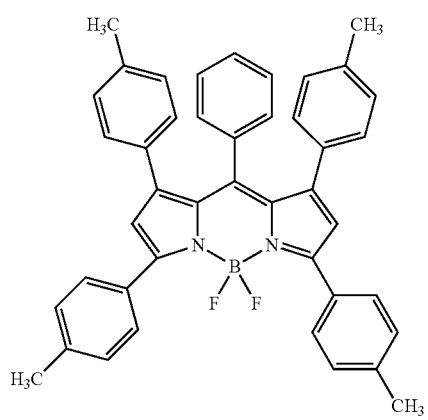
422
-continued
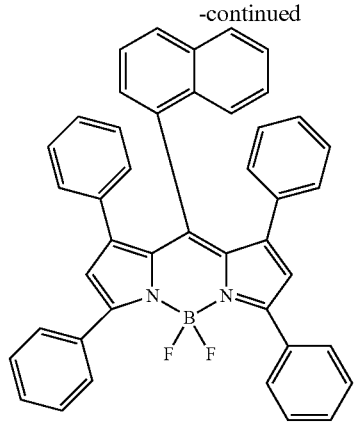
[Formula 154]
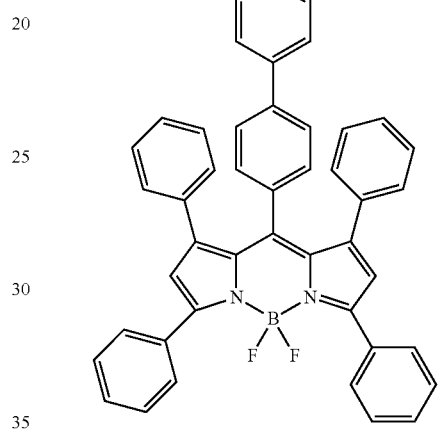
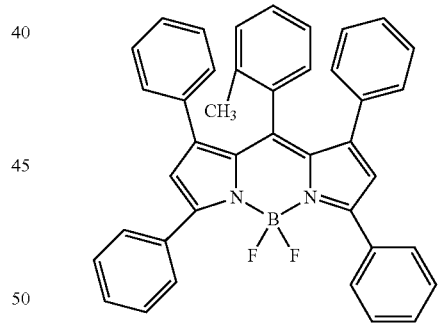
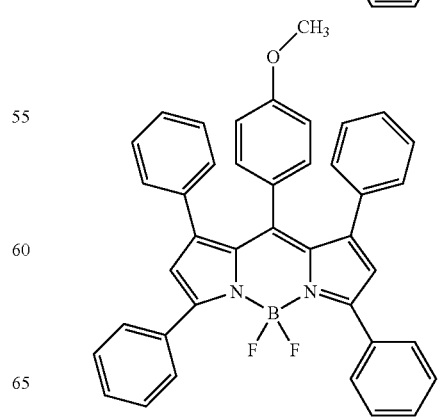

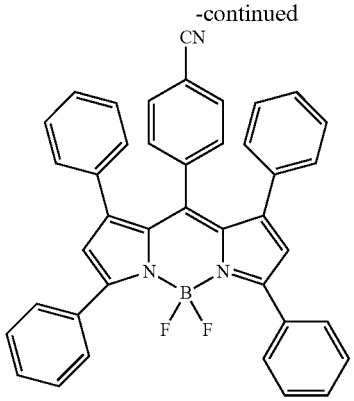
[Formula 155]
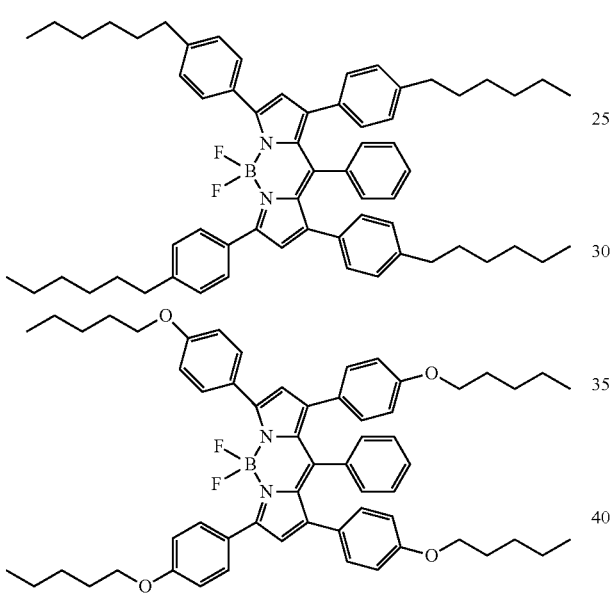
[Formula 156]
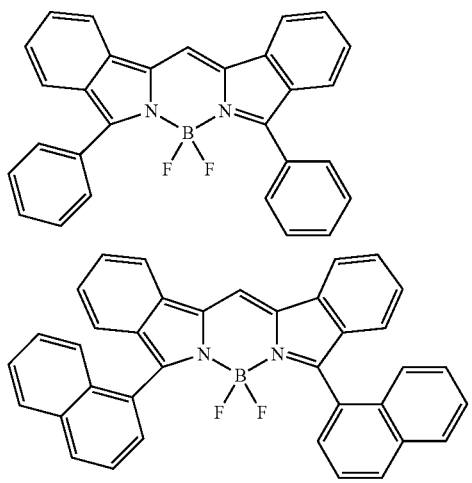
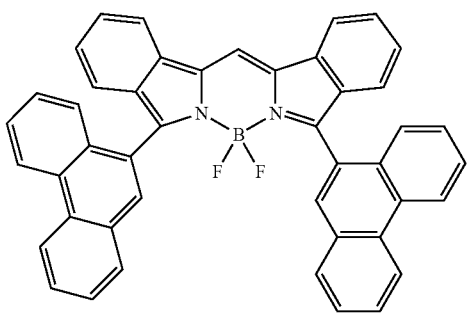
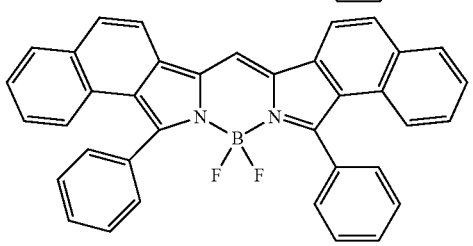
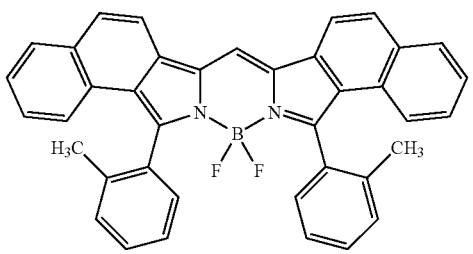
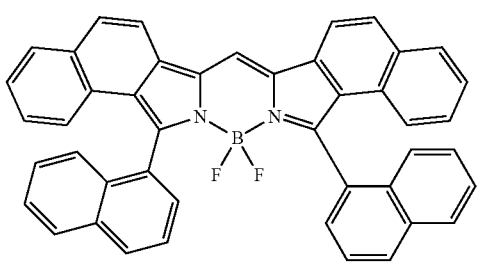
[Formula 157]
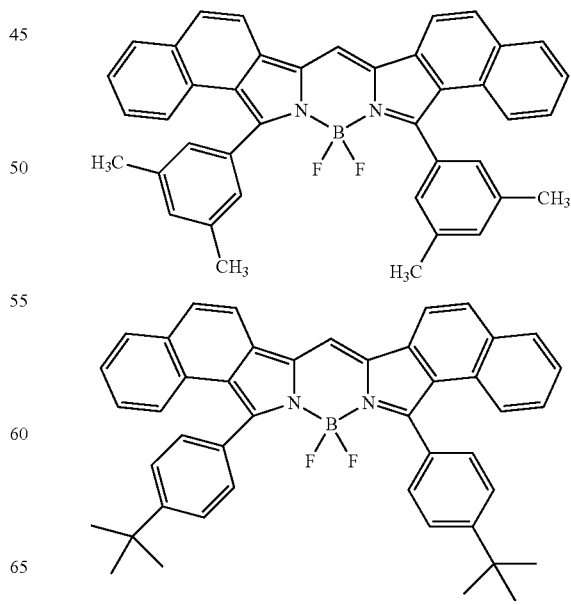

425
-continued
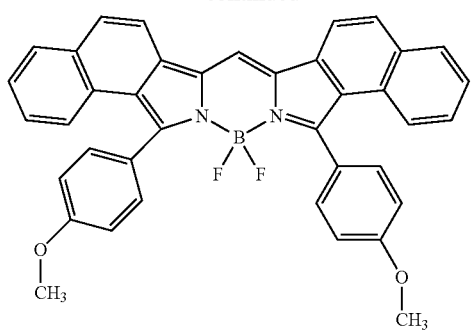
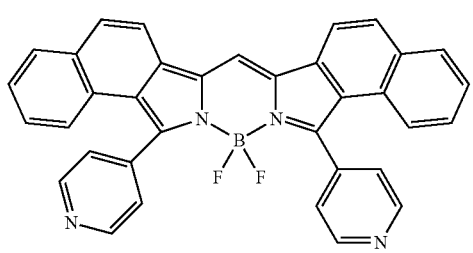
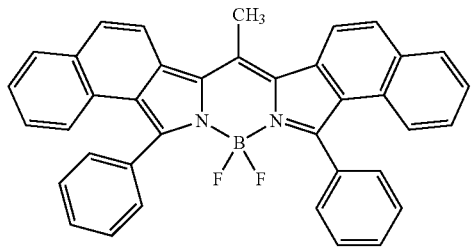
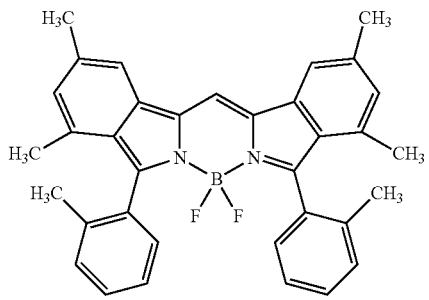
[Formula 158]
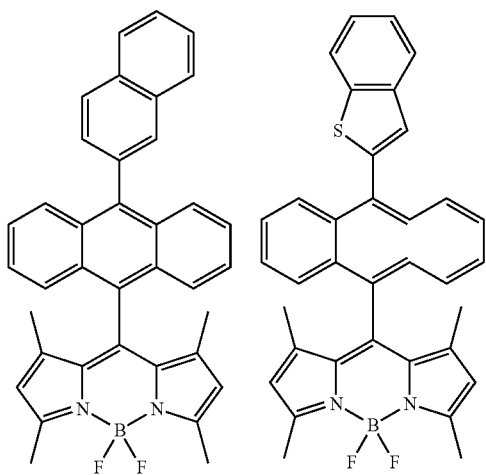
426
-continued
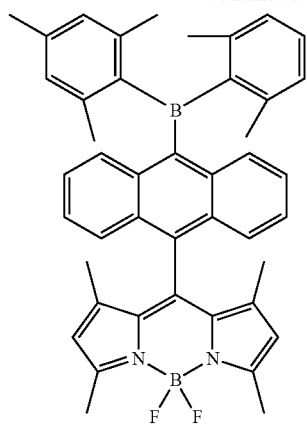
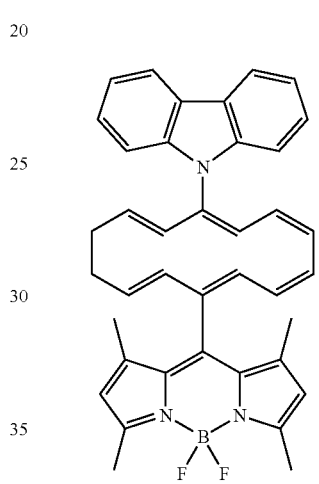
[Formula 159]
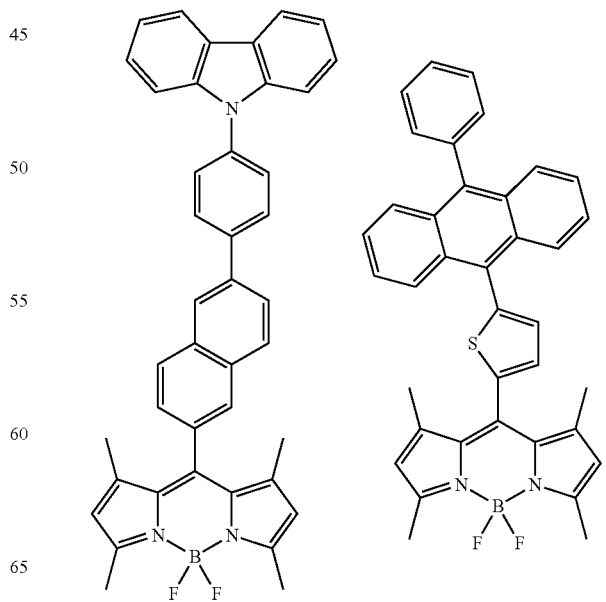

427
-continued
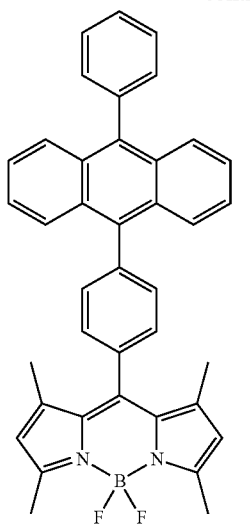
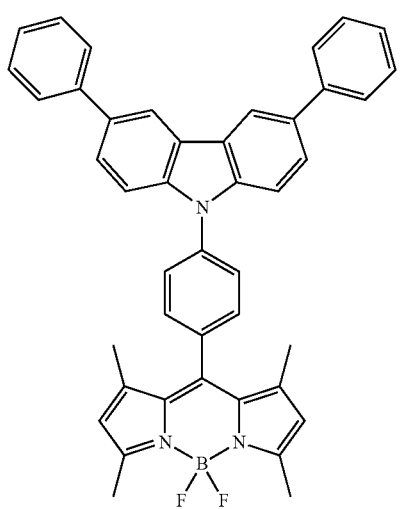
[Formula 160]
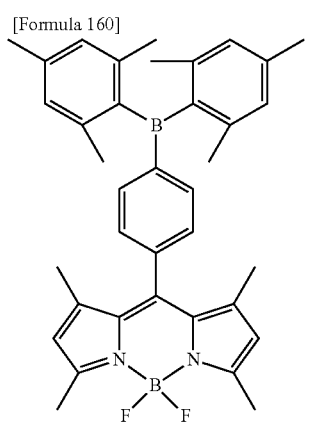
428
-continued
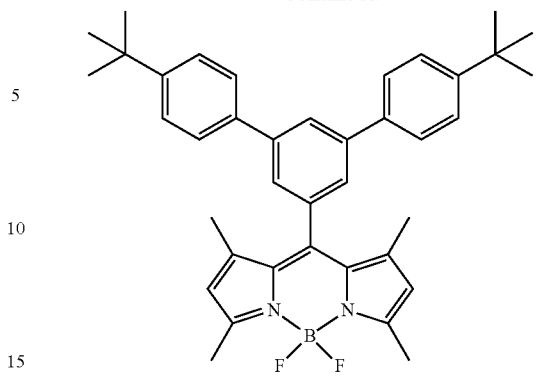
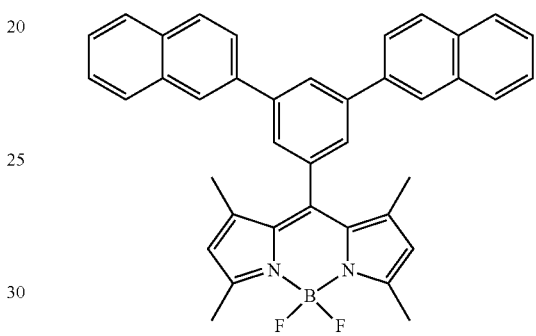
[Formula 161]
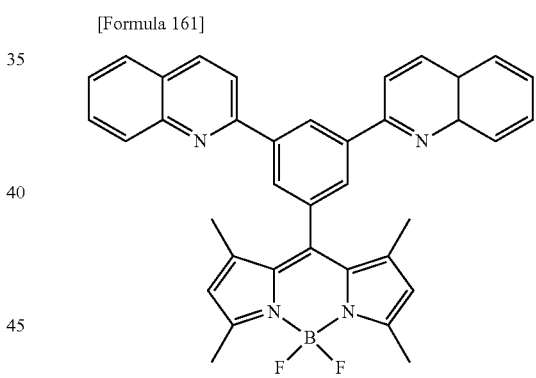
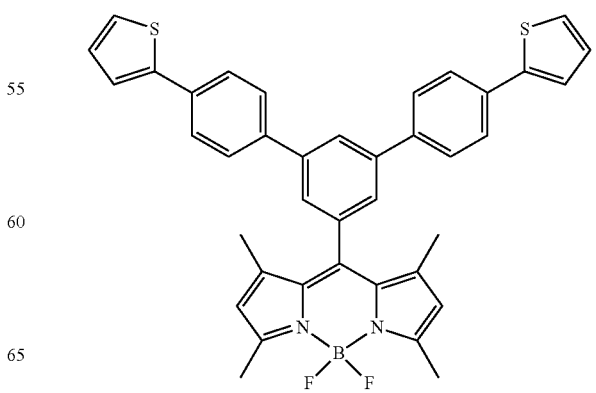

429
-continued
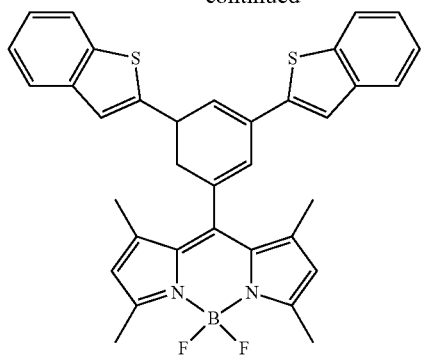
[Formula 162]
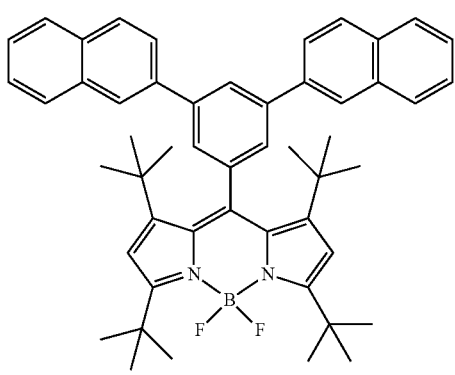
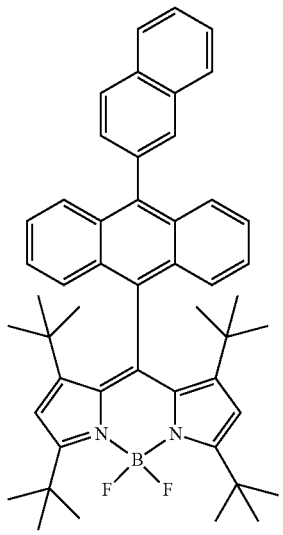
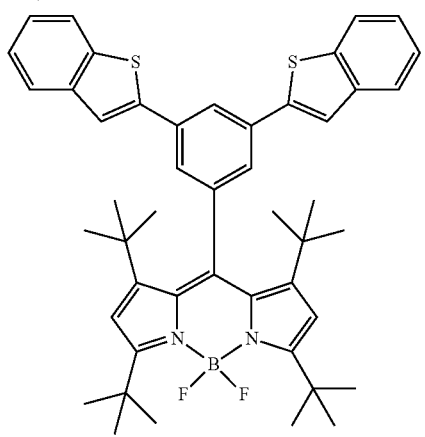
430
-continued
[Formula 163]
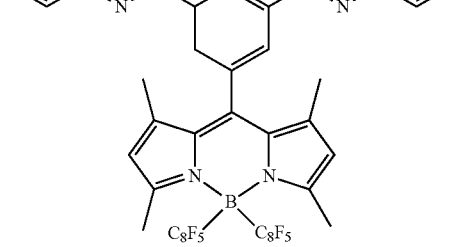
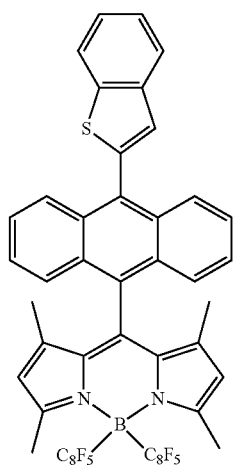
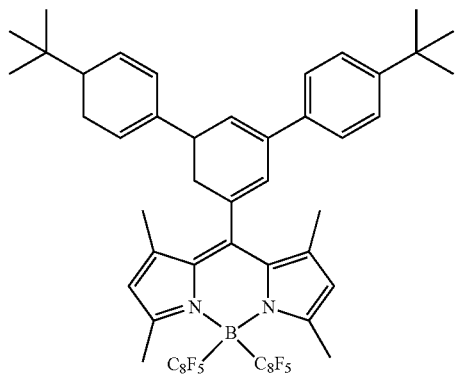

431
-continued
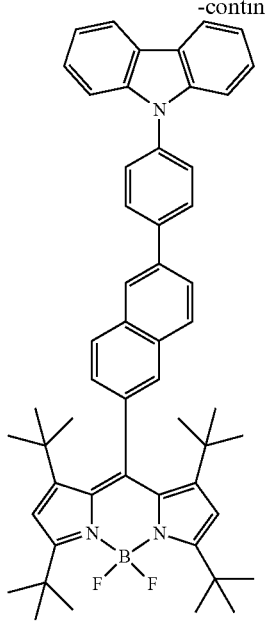
[Formula 164]
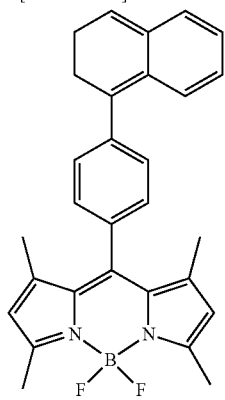
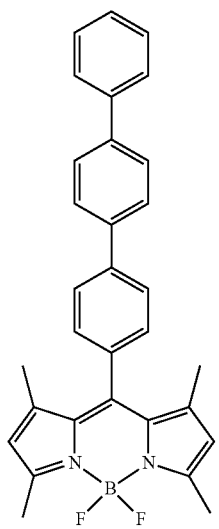
432
-continued
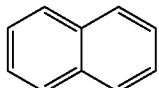
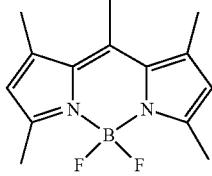
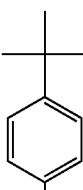
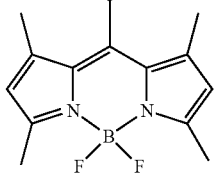
[Formula 165]
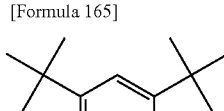
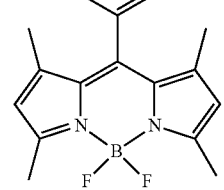

433
-continued
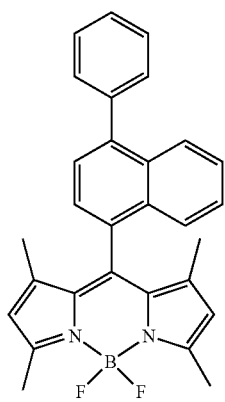
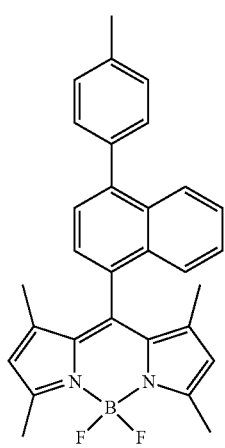
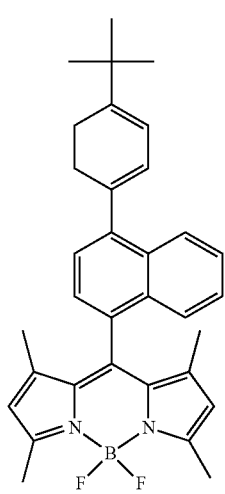
434
-continued
[Formula 166]
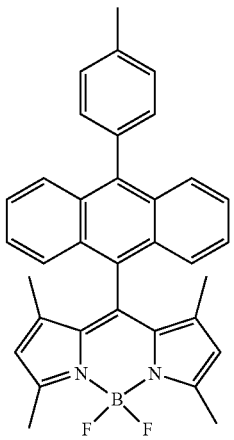
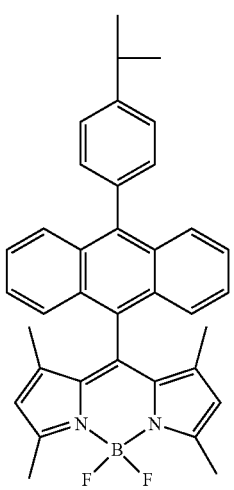
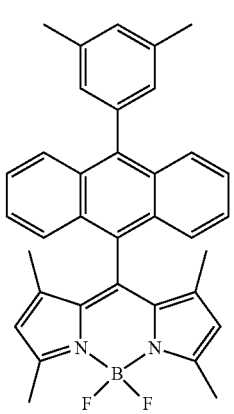

435
-continued
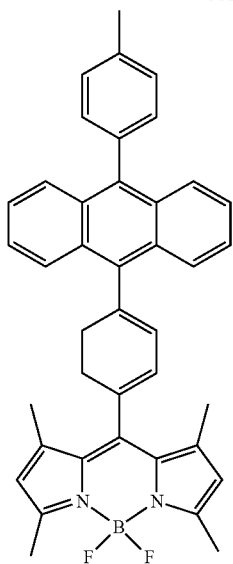
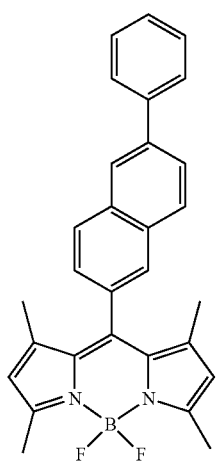
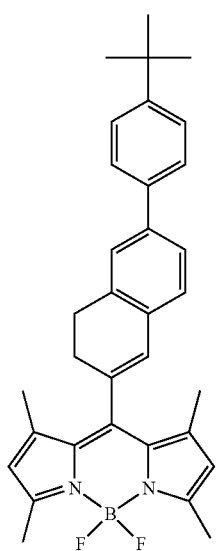
436
-continued
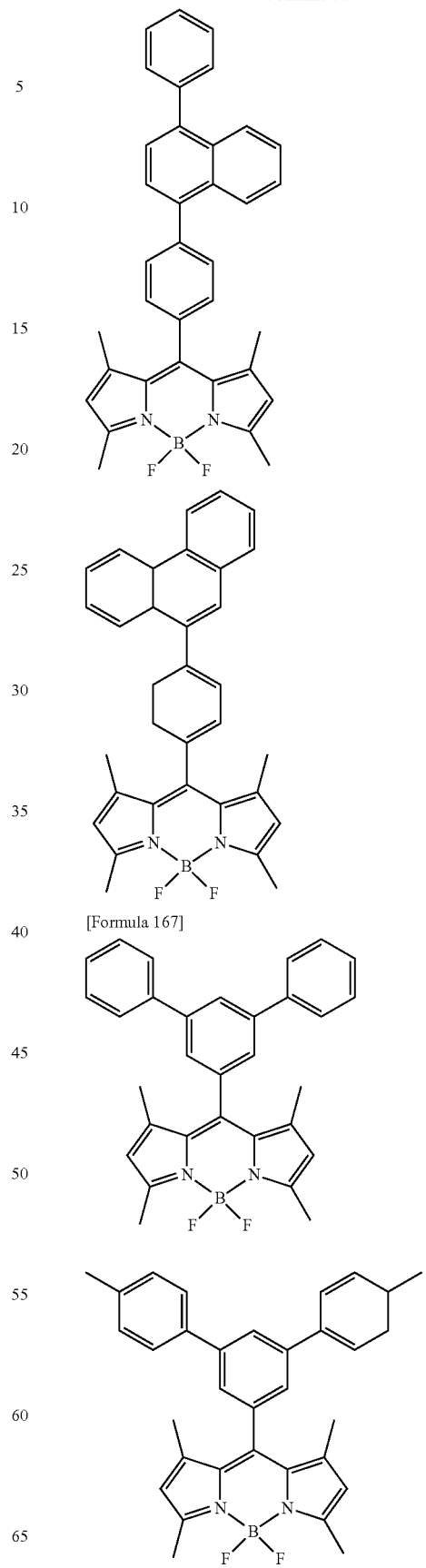
[Formula 167]

437
-continued
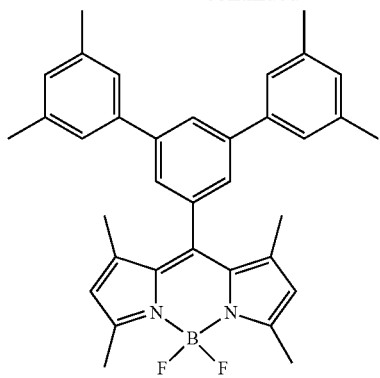
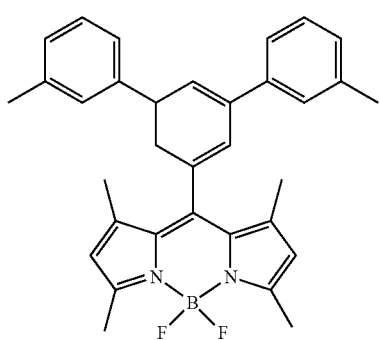
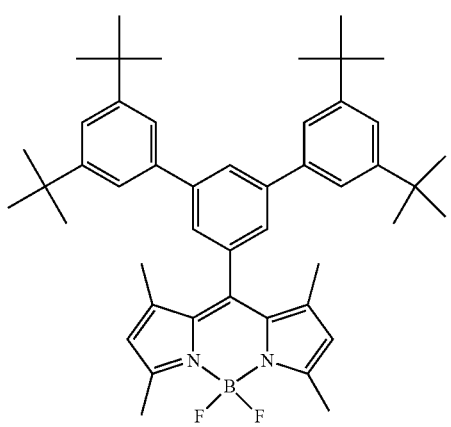
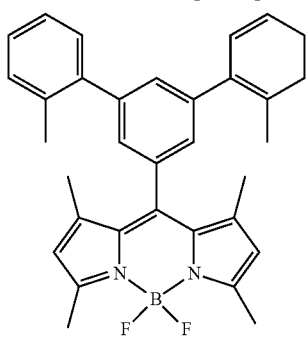
438
-continued
[Formula 168]
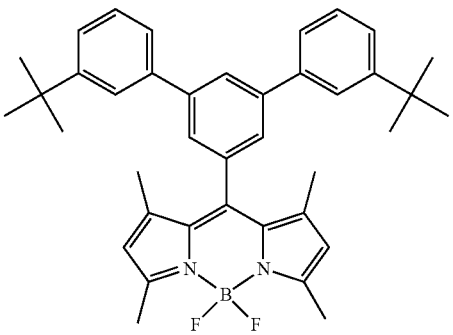
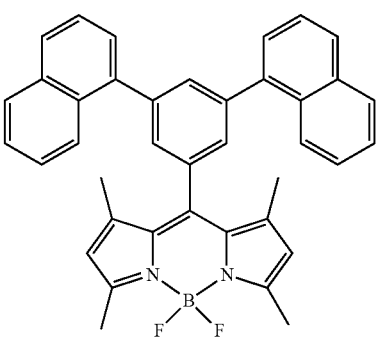
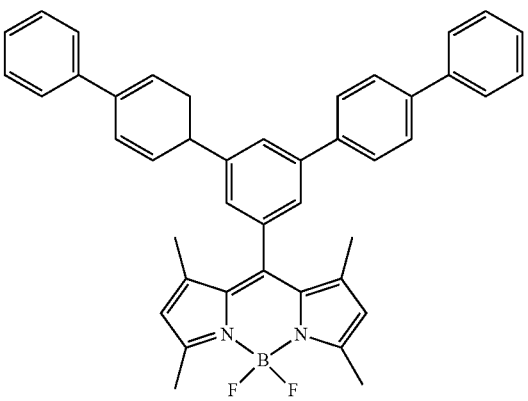
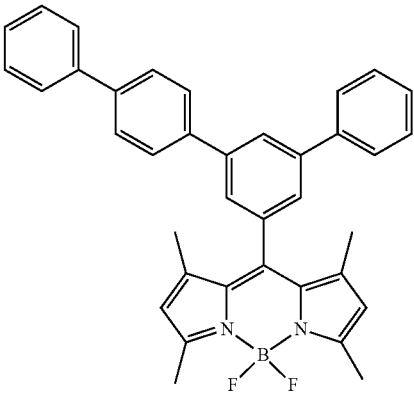

439
-continued
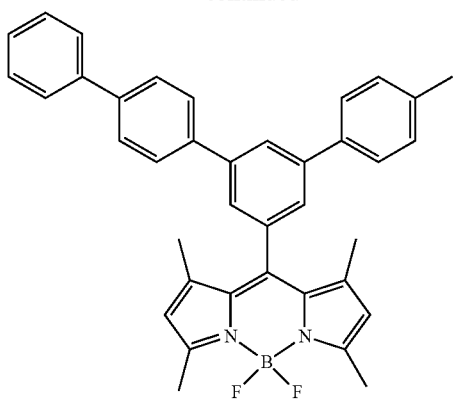
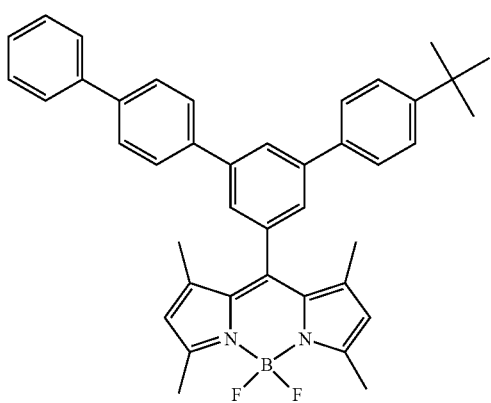
[Formula 169]
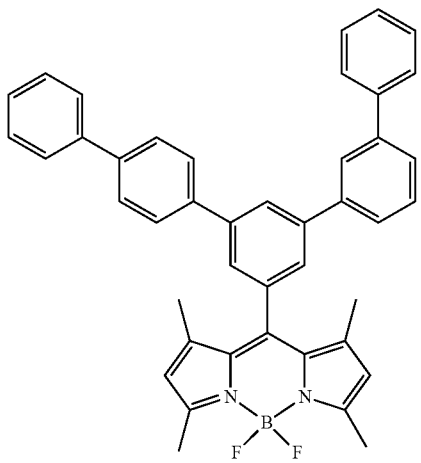
440
-continued
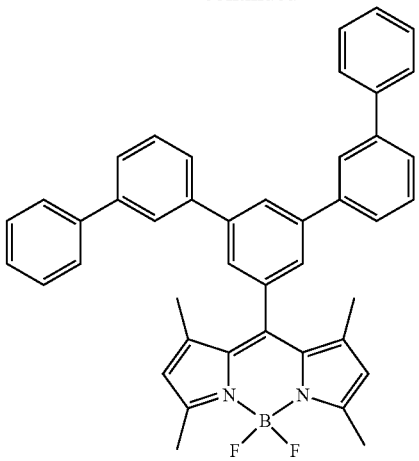
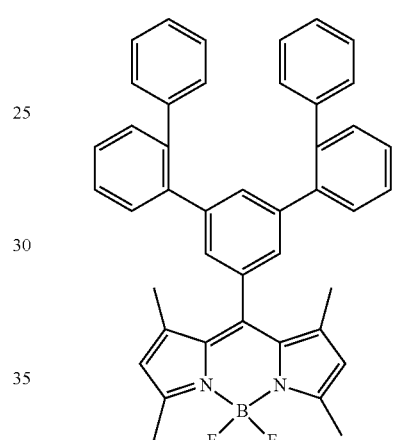
[Formula 170]
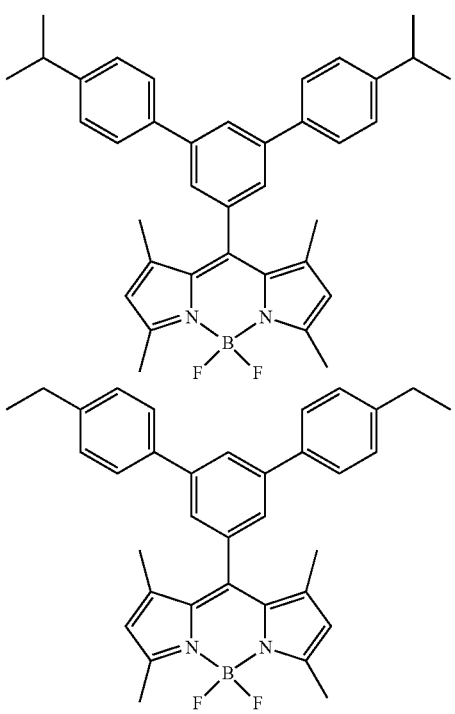

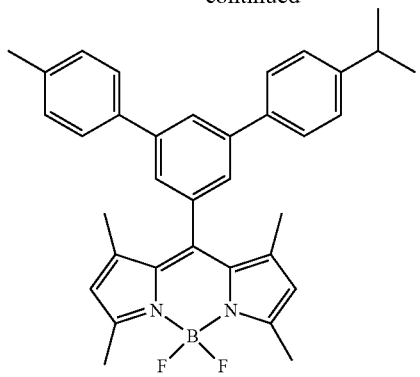
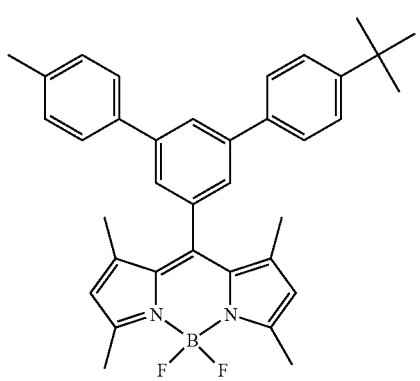
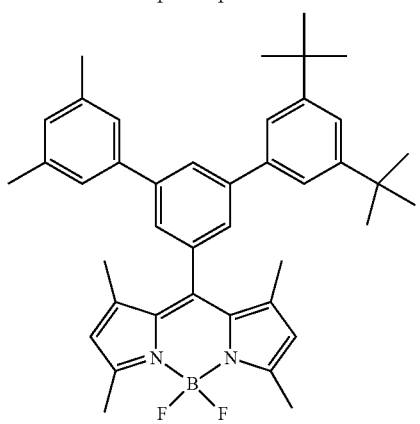
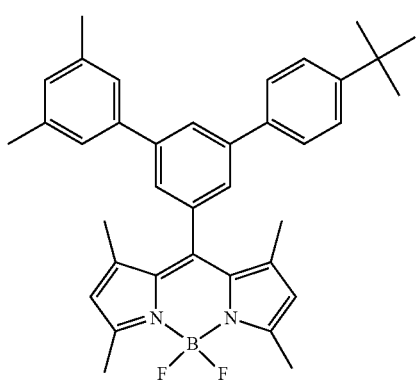
[Formula 171]
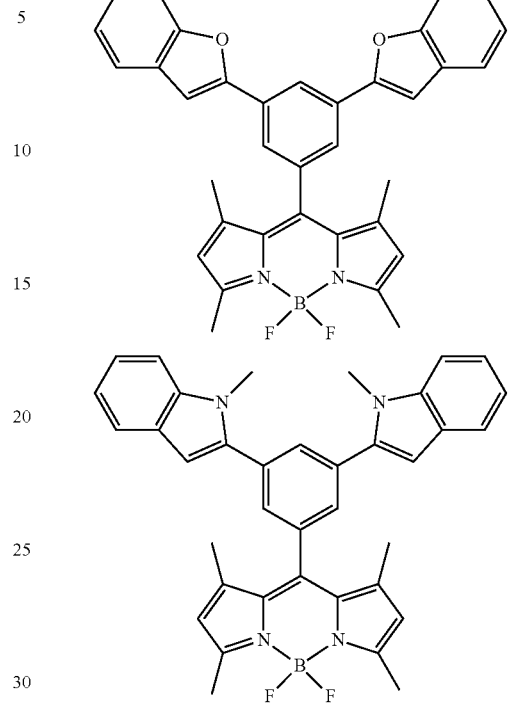
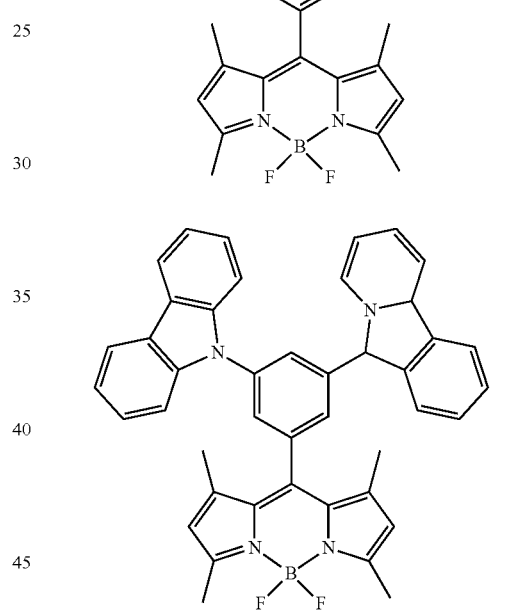
[Formula 172]
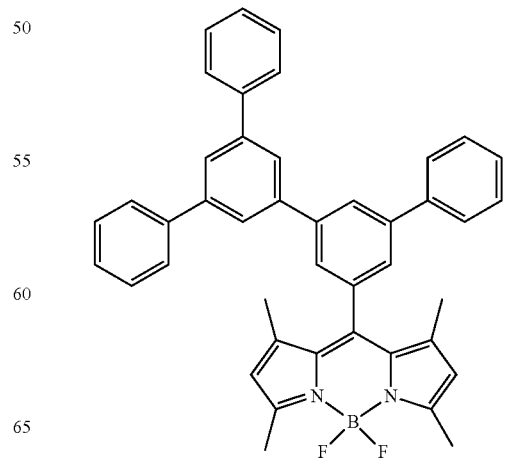

443
-continued
444
-continued
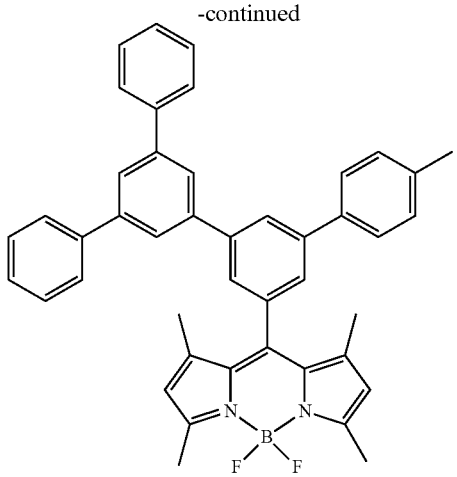
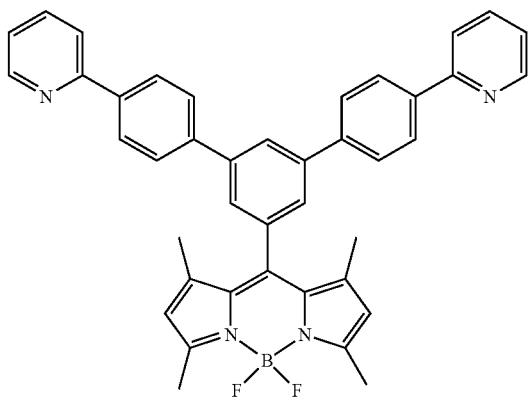
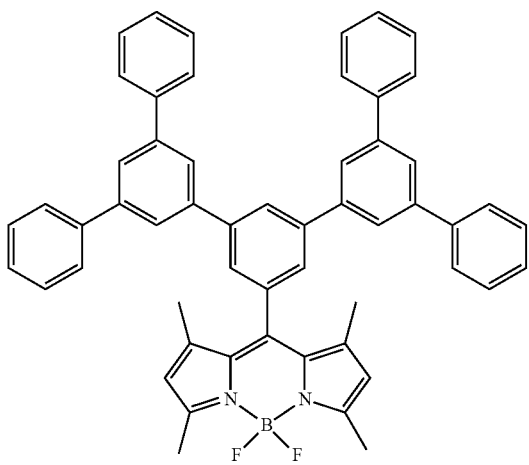
[Formula 173]
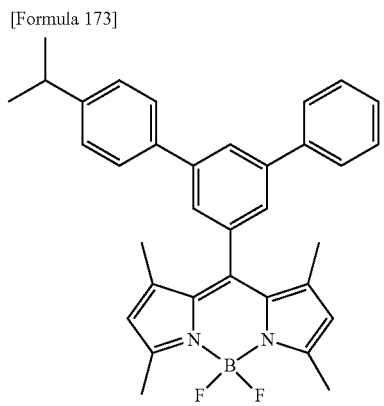
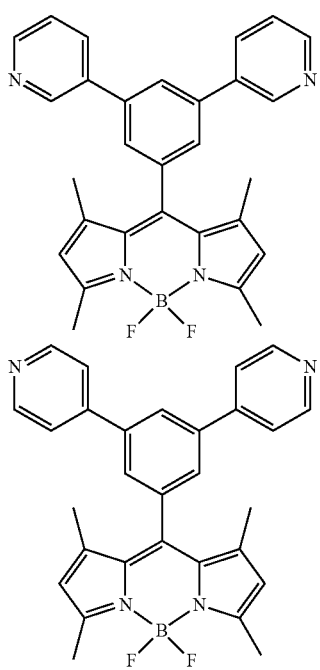
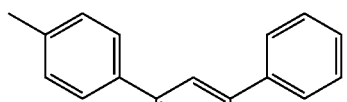
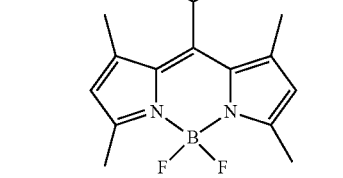
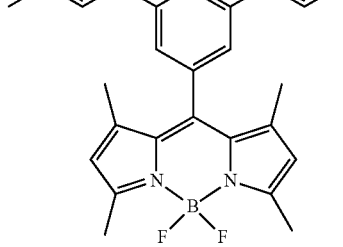

445
-continued
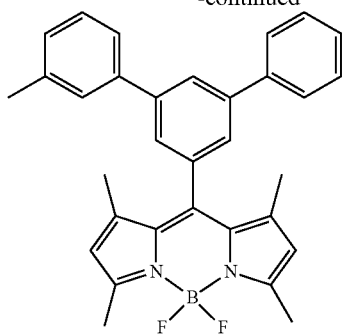
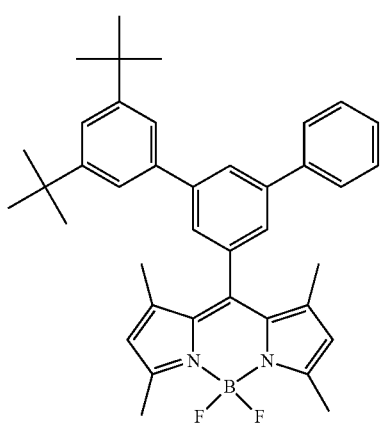
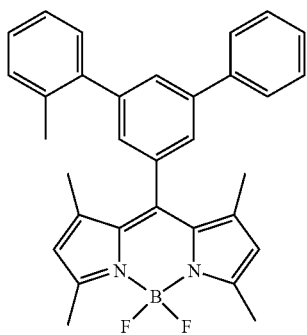
[Formula 174]
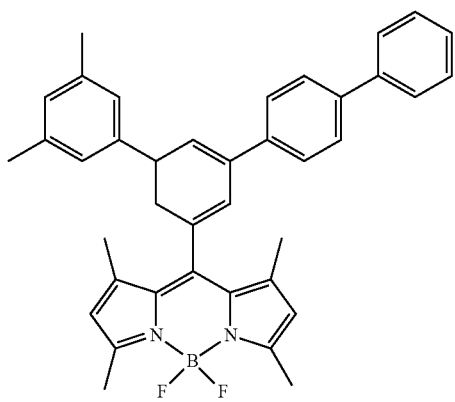
446
-continued
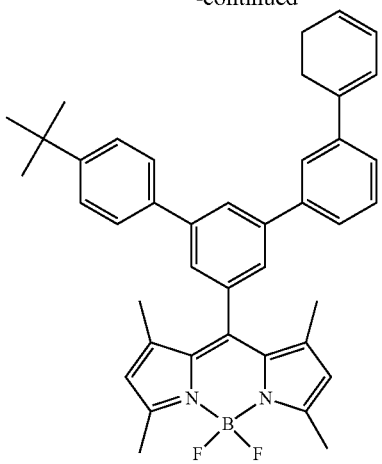
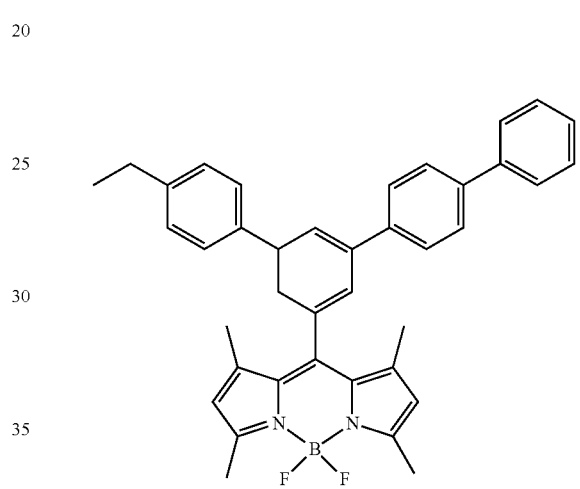
[Formula 175]

447
-continued
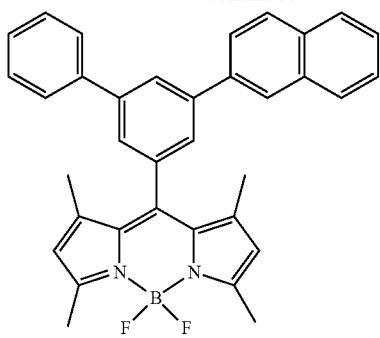
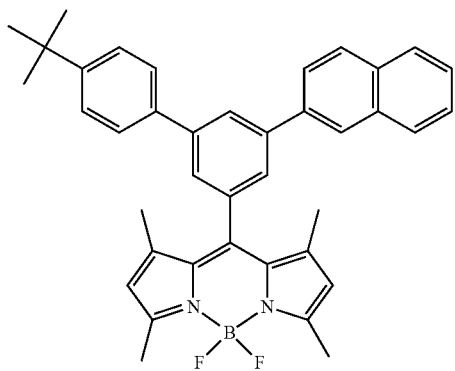
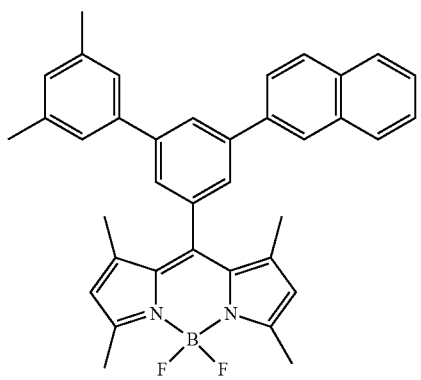
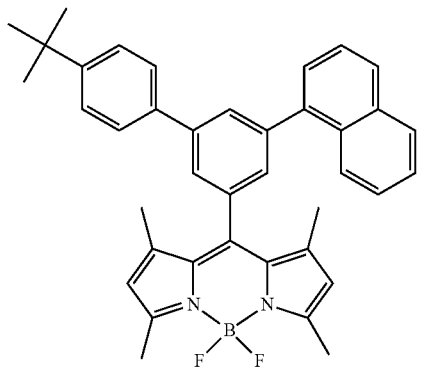
448
-continued
[Formula 176]
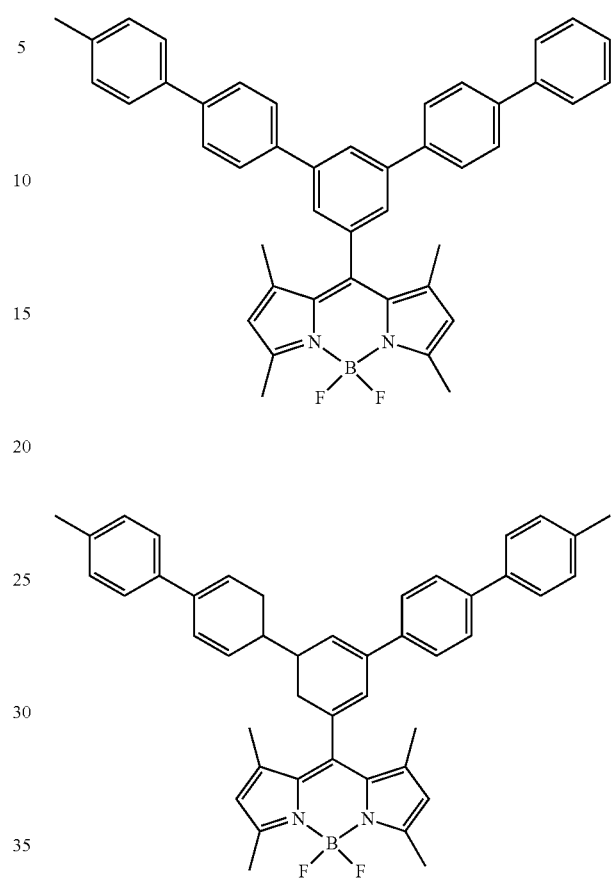
[Formula 177]
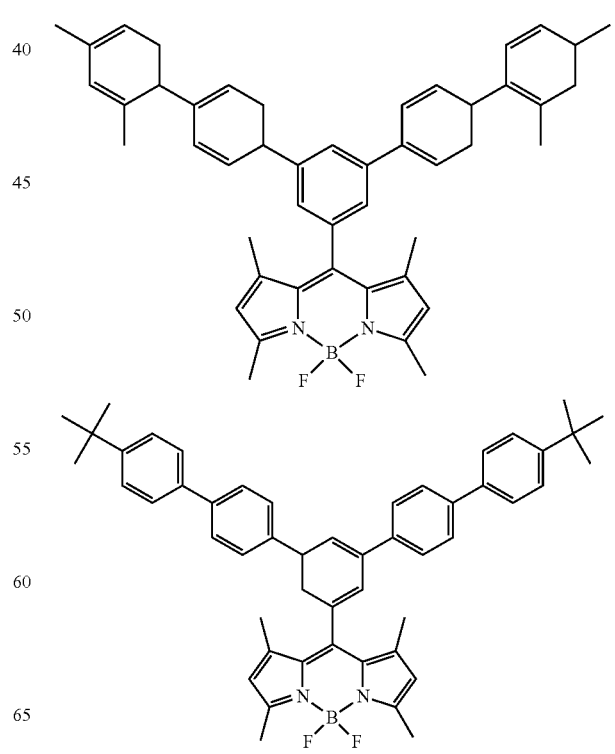

[Formula 178]

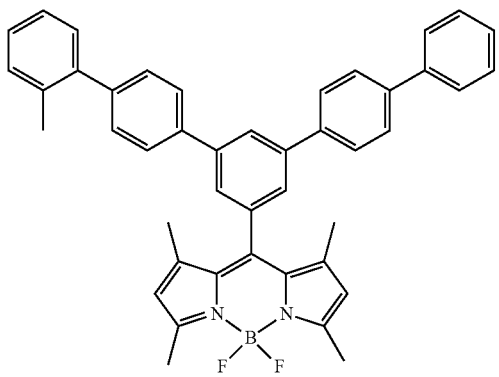

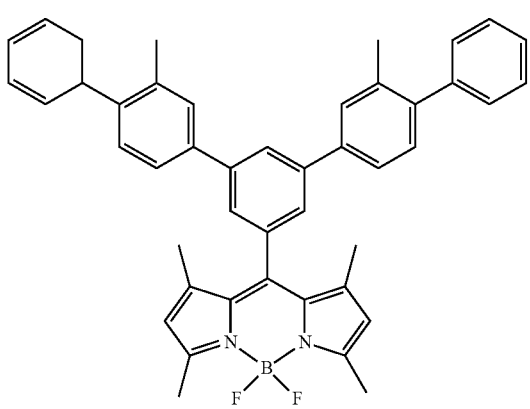

[Formula 179]

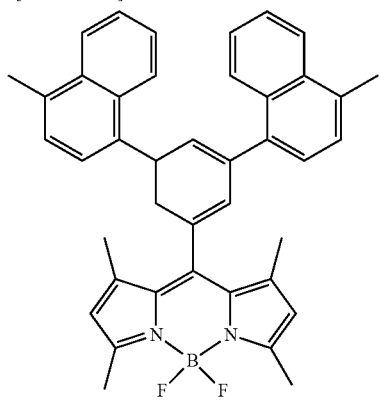

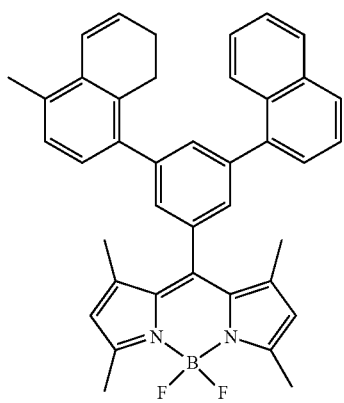

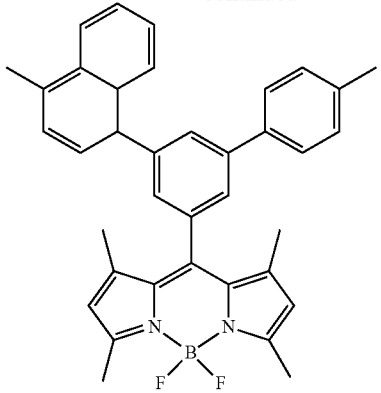

[Formula 180]

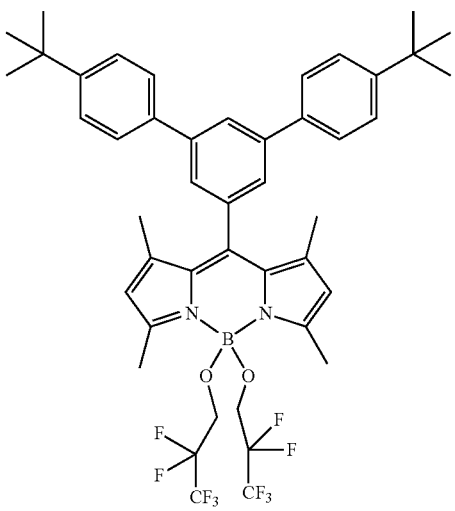

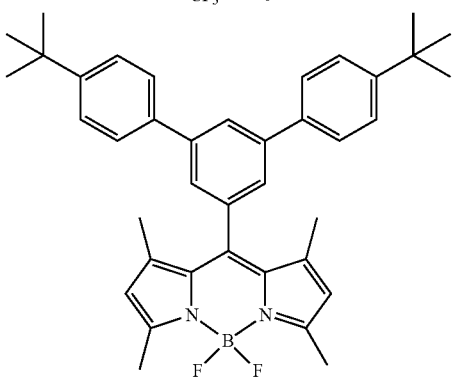

Relationship Between First Compound and Second Compound in Emitting Layer

In the organic EL device 1 of the exemplary embodiment, a singlet energy $S_1(Mat1)$ of the first compound and a singlet energy $S_1(Mat2)$ of the second compound preferably satisfy a relationship of a numerical formula (Numerical Formula 3).

$S_1(Mat1) > S_1(Mat2)$ (Numerical Formula 3)

An energy gap $T_{77K}(Mat1)$ at 77 [K] of the first compound is preferably larger than an energy gap $T_{77K}(Mat2)$ at 77 [K] of the second compound. In other words, a relationship of the following numerical formula (Numerical Formula 5) is preferably satisfied.

$T_{77K}(Mat1) > T_{77K}(Mat2)$ (Numerical Formula 5)

When the organic EL device 1 of the exemplary embodiment emits light, it is preferable that the second compound in the emitting layer 5 mainly emits light.

Relationship Between Triplet Energy and Energy Gap at 77K

Here, a relationship between a triplet energy and an energy gap at 77K will be described. In the exemplary embodiment, the energy gap at 77 [K] is different from a typical triplet energy in some aspects.

Triplet energy is measured as follows. Firstly, a solution in which a compound (measurement target) is dissolved in an appropriate solvent is encapsulated in a quartz glass tube to prepare a sample. A phosphorescent spectrum (ordinate axis: phosphorescent luminous intensity, abscissa axis: wavelength) of the sample is measured at a low temperature (77K). A tangent is drawn to the rise of the phosphorescent spectrum close to the short-wavelength region. The triplet energy is calculated by a predetermined conversion equation based on a wavelength value at an intersection of the tangent and the abscissa axis.

Here, the thermally activated delayed fluorescent compound among the compounds of the exemplary embodiment is preferably a compound having a small $\Delta ST$. When $\Delta ST$ is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the exemplary embodiment, the triplet energy is measured by the same method as a typical triplet energy T, but a value measured in the following manner is referred to as an energy gap $T_{77K}$ in order to differentiate the measured energy from the typical triplet energy in a strict meaning. The measurement target compound is dissolved in EPA (diethylether:isopentane:ethanol=5:5:2 in volume ratio) at a concentration of 10 μmol/L, and the obtained solution is encapsulated in a quartz cell to provide a measurement sample. A phosphorescent spectrum (ordinate axis: phosphorescent luminous intensity, abscissa axis: wavelength) of the sample is measured at a low temperature (77K). A tangent is drawn to the rise of the phosphorescent spectrum close to the short-wavelength region. An energy amount is calculated by a conversion equation below based on a wavelength value $\lambda_{edge}$ [nm] at an intersection of the tangent and the abscissa axis and is defined as an energy gap $T_{77K}$ at 77 [K].

$T_{77K}[eV]=1239.8/\lambda_{edge}$      Conversion Equation (F1):

The tangent to the rise of the phosphorescence spectrum close to the short-wavelength region is drawn as follows. While moving on a curve of the phosphorescence spectrum from the short-wavelength region to the maximum spectral value closest to the short-wavelength region among the maximum spectral values, a tangent is checked at each point on the curve toward the long-wavelength of the phosphorescence spectrum. An inclination of the tangent is increased along the rise of the curve (i.e., a value of the ordinate axis is increased). A tangent drawn at a point of the maximum inclination (i.e., a tangent at an inflection point) is defined as the tangent to the rise of the phosphorescence spectrum close to the short-wavelength region.

The maximum with peak intensity being 15% or less of the maximum peak intensity of the spectrum is not included in the above-mentioned maximum closest to the short-wavelength region. The tangent drawn at a point of the maximum spectral value being closest to the short-wavelength region and having the maximum inclination is defined as a tangent to the rise of the phosphorescence spectrum close to the short-wavelength region.

For phosphorescence measurement, a spectrophotofluorometer body F-4500 (manufactured by Hitachi High-Technologies Corporation) is usable. Any device for phosphorescence measurement is usable. A combination of a cooling unit, a low temperature container, an excitation light source and a light-receiving unit may be used for phosphorescence measurement.

Singlet Energy $S_1$

A method of measuring a singlet energy $S_1$ with use of a solution (occasionally referred to as a solution method) is exemplified by a method below.

A toluene solution in which a measurement target compound is dissolved at a concentration of 10 μmol/L is prepared and is encapsulated in a quartz cell to provide a measurement sample. Absorption spectrum (ordinate axis: absorption intensity, abscissa axis: wavelength) of the sample is measured at the normal temperature (300K). A tangent is drawn to the fall of the absorption spectrum close to the long-wavelength region, and a wavelength value $\lambda edge$ (nm) at an intersection of the tangent and the abscissa axis is obtained. The wavelength value $\lambda edge$ (nm) is substituted in a conversion equation (F2) below to calculate a singlent energy.

$S_1[eV]=1239.85/\lambda edge$      Conversion Equation (F2):

Any device for measuring absorption spectrum is usable. For instance, a spectrophotometer (U3310 manufactured by Hitachi, Ltd.) is usable.

The tangent to the fall of the absorption spectrum close to the long-wavelength region is drawn as follows. While moving on a curve of the absorption spectrum from the maximum spectral value closest to the long-wavelength region in a long-wavelength direction, a tangent at each point on the curve is checked. An inclination of the tangent is decreased and increased in a repeated manner as the curve falls (i.e., a value of the ordinate axis is decreased). A tangent drawn at a point of the minimum inclination closest to the long-wavelength region (except when absorbance is 0.1 or less) is defined as the tangent to the fall of the absorption spectrum close to the long-wavelength region.

The maximum absorbance of 0.2 or less is not included in the above-mentioned maximum absorbance close to the long-wavelength region.

In the exemplary embodiment, a difference $(S_1-T_{77K})$ between the singlet energy $S_1$ and the energy gap $T_{77K}$ at 77[K] is defined as $\Delta ST$.

In the exemplary embodiment, a difference $\Delta ST(Mat1)$ between the singlet energy $S_1(Mat1)$ of the first compound and the energy gap $T_{77K}(Mat1)$ at 77[K] of the the first compound is preferably less than 0.3 eV, more preferably less than 0.2 eV, further preferably less than 0.1 eV. In other words, $\Delta ST(Mat1)$ preferably satisfies a numerical formula ((Numerical Formula 1A), (Numerical Formula 1B) or (Numerical Formula 1C)) below.

$\Delta ST(Mat1)=S_1(Mat1)-T_{77K}(Mat1)<0.3$ eV      (Numerical Formula 1A)

$\Delta ST(Mat1)=S_1(Mat1)-T_{77K}(Mat1)<0.2$ eV      (Numerical Formula 1B)

$\Delta ST(Mat1)=S_1(Mat1)-T_{77K}(Mat1)<0.1$ eV      (Numerical Formula 10)

The organic EL device 1 in the exemplary embodiment preferably emits red light or green light.

When the organic EL device 1 in the exemplary embodiment emits green light, a main peak wavelength of the light from the organic EL device 1 is preferably in a range from 500 nm to 560 nm.

When the organic EL device 1 in the exemplary embodiment emits red light, a main peak wavelength of the light from the organic EL device 1 is preferably in a range from 600 nm to 660 nm.

When the organic EL device 1 in the exemplary embodiment emits blue light, a main peak wavelength of the light from the organic EL device 1 is preferably in a range from 430 nm to 480 nm.

A main peak wavelength of light from an organic EL device is measured as follows.

Voltage is applied on the organic EL device such that a current density was 10 mA/cm$^2$, where spectral radiance spectrum is measured by a spectroradiometer (CS-2000 manufactured by Konica Minolta, Inc.).

In the obtained spectral radiance spectrum, the peak wavelength of the emission spectrum at which the luminous intensity is maximized is measured, and this is taken as the main peak wavelength (unit: nm).

Film Thickness of Emitting Layer

A film thickness of the emitting layer of the organic EL device 1 in the exemplary embodiment is preferably in a range of 5 nm to 50 nm, more preferably in a range of 7 nm to 50 nm, further preferably in a range of 10 nm to 50 nm. When the film thickness of the emitting layer is 5 nm or more, the formation of the emitting layer and the adjustment of the chromaticity are easy. When the film thickness of the emitting layer is 50 nm or less, an increase in the drive voltage is likely to be reducible.

Content Ratio of Compounds in Emitting Layer

Content ratios of the first and second compounds in the emitting layer 5 are, for instance, preferably determined as follows.

The content ratio of the first compound is preferably in a range from 10 mass % to 80 mass %, more preferably in a range from 10 mass % to 60 mass %, further preferably in a range from 20 mass % to 60 mass %.

The content ratio of the second compound is preferably in a range from 0.01 mass % to 10 mass %, more preferably in a range from 0.01 mass % to 5 mass %, further preferably in a range from 0.01 mass % to 1 mass %.

It should be noted that the emitting layer 5 of the exemplary embodiment may further contain material(s) other than the first and second compounds.

The emitting layer 5 may include a single type of the first compound or may include two or more types of the first compound. The emitting layer 5 may include a single type of the second compound or may include two or more types of the second compound.

TADF Mechanism

Figure 4:
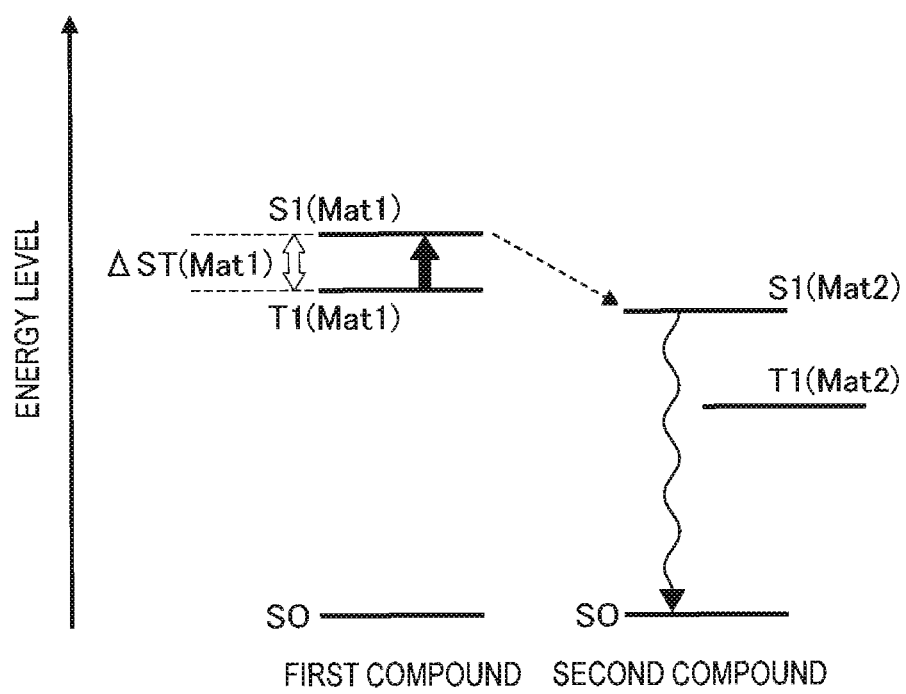
FIG. 4 shows a relationship in energy level and energy transfer between a first compound and a second compound in an emitting layer of an exemplary organic electroluminescence device according to a third exemplary embodiment of the invention.

FIG. 4 shows an example of a relationship between energy levels of the first compound and the second compound in the emitting layer. In FIG. 4, S0 represents a ground state. S1(Mat1) represents the lowest singlet state of the first compound. T1(Mat1) represents the lowest triplet state of the first compound. S1(Mat2) represents the lowest triplet state of the second compound. T1(Mat2) represents the lowest triplet state of the second compound.

A dashed arrow directed from S1(Mat1) to S1(Mat2) in FIG. 4 represents Förster energy transfer from the lowest singlet state of the first compound to the lowest singlet state of the second compound.

As shown in FIG. 4, when a compound having a small ΔST(Mat1) is used as the first compound, inverse intersystem crossing from the lowest triplet state T1(Mat1) to the lowest singlet state S1(Mat1) can be caused by a heat energy. Subsequently, Förster energy transfer from the lowest singlet state S1(Mat1) of the first compound the second compound occurs to generate the lowest singlet state S1(Mat2). Consequently, fluorescence from the lowest singlet state S1(Mat2) of the second compound can be observed. It is inferred that the internal quantum efficiency can be theoretically raised up to 100% also by using delayed fluorescence by the TADF mechanism.

The organic EL device 1 according to the third exemplary embodiment contains the first compound that is the compound according to the first exemplary embodiment (at least one of the compounds represented by the formulae (11) to (13)), and the second compound having the singlet energy smaller than that of the first compound in the emitting layer 5.

The organic EL device according to the third exemplary embodiment is applicable to an electronic device such as a display device and a light-emitting device.

An arrangement of an organic EL device 1 will be further described. The description of the reference signs may be omitted.

Substrate

A substrate is used as a support for the organic EL device. For instance, glass, quartz, plastics and the like are usable as the substrate. A flexible substrate is also usable. The flexible substrate is a bendable substrate, which is exemplified by a plastic substrate. Examples of the material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal having a large work function (specifically, 4.0 eV or more), an alloy, an electrically conductive compound and a mixture thereof are preferably used as the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The material is typically formed into a film by a sputtering method. For instance, the indium oxide-zinc oxide can be formed into a film by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode may be formed by a vacuum deposition method, a coating method, an inkjet method, a spin coating method or the like.

Among the EL layers formed on the anode, since the hole injecting layer adjacent to the anode is formed of a composite material into which holes are easily injectable irrespective of the work function of the anode, a material usable as an electrode material (e.g., metal, an alloy, an electroconductive compound, a mixture thereof, and the elements belonging to the group 1 or 2 of the periodic table) is also usable for the anode.

A material having a small work function such as elements belonging to Groups 1 and 2 in the periodic table of the elements, specifically, an alkali metal such as lithium (Li) and cesium (Cs), an alkaline earth metal such as magnesium (Mg), calcium (Ca) and strontium (Sr), alloys (e.g., MgAg and AlLi) including the alkali metal or the alkaline earth metal, a rare earth metal such as europium (Eu) and ytterbium (Yb), alloys including the rare earth metal are also usable for the anode. It should be noted that the vacuum deposition method and the sputtering method are usable for forming the anode using the alkali metal, alkaline earth metal and the alloy thereof. Further, when a silver paste is used for the anode, the coating method and the inkjet method are usable.

Cathode

It is preferable to use metal, an alloy, an electroconductive compound, and a mixture thereof, which have a small work function (specifically, 3.8 eV or less) for the cathode. Examples of the material for the cathode include elements belonging to Groups 1 and 2 in the periodic table of the elements, specifically, the alkali metal such as lithium (Li) and cesium (Cs), the alkaline earth metal such as magnesium (Mg), calcium (Ca) and strontium (Sr), alloys (e.g., MgAg and AlLi) including the alkali metal or the alkaline earth metal, the rare earth metal such as europium (Eu) and ytterbium (Yb), and alloys including the rare earth metal.

It should be noted that the vacuum deposition method and the sputtering method are usable for forming the cathode using the alkali metal, alkaline earth metal and the alloy thereof. Further, when a silver paste is used for the cathode, the coating method and the inkjet method are usable.

By providing the electron injecting layer, various conductive materials such as Al, Ag, ITO, graphene, and indium oxide-tin oxide containing silicon or silicon oxide may be used for forming the cathode regardless of the work function. The conductive materials can be formed into a film using the sputtering method, inkjet method, spin coating method and the like.

Hole Injecting Layer

The hole injecting layer is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule compound, such that 4,4',4"-tris (N,N-diphenylamino)triphenylamine (abbreviation: TDATA), 4,4',4"-tris[N-(3-methylphenyl)-N-phenylamino] triphenylamine (abbreviation: MTDATA), 4,4'-bis[N-(4-diphenylaminophenyl)-N-phenylamino]biphenyl(abbreviation: DRAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,34:20,30-h]quinoxaline-2,3,6,7,10,11-hexacarbonitrile (HAT-CN).

In addition, a high polymer compound (e.g., oligomer, dendrimer and polymer) is usable as the substance exhibiting a high hole injectability. Examples of the high polymer compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamido] (abbreviation: PTPDMA), and poly[N,N'-bis(4-butylphenyl)-N,N'-bis (phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly (styrene sulfonic acid)(PAni/PSS) are also usable.

Hole Transporting Layer

The hole transporting layer is a layer containing a highly hole-transporting substance. An aromatic amine compound, carbazole derivative, anthracene derivative and the like are usable for the hole transporting layer. Specific examples of a material for the hole transporting layer include an aromatic amine compound such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl) triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino) triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(V·s) or more.

For the hole transporting layer, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance.

When the hole transporting layer includes two or more layers, one of the layers with a larger energy gap is preferably provided closer to the emitting layer. An example of the material with a larger energy gap is HT-2 used in later-described Examples.

Electron Transporting Layer

The electron transporting layer is a layer containing a highly electron-transporting substance. For the electron transporting layer, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low-molecule organic compound, a metal complex such as Alq, tris(4-methyl-8-quinolinato)aluminum (abbreviation: Almq3), bis(10-hydroxybenzo[h]quinolinato)beryllium (abbreviation: BeEq2), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-Et- TAZ), bathophenanthroline (abbreviation: BPhen), bathocuproine (abbreviation: BCP), and 4,4'-bis(5-methylbenzoxazole-2-yl)stilbene (abbreviation: BzOs) is usable. In the exemplary embodiment, a benzimidazole compound is preferably usable. The above-described substances mostly have an electron mobility of $10^{-6}$ cm$^2$/(V·s) or more. It should be noted that any substance other than the above substance may be used for the electron transporting layer as long as the substance exhibits a higher electron transportability than the hole transportability. The electron transporting layer may be provided in the form of a single layer or a laminate of two or more layers of the above substance(s).

Moreover, a high polymer compound is usable for the electron transporting layer. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy) and the like are usable.

Electron Injecting Layer

The electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride (CaF2), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected form the anode.

Alternatively, the electron injecting layer may be provided by a composite material in a form of a mixture of the organic compound and the electron donor. Such a composite material exhibits excellent electron injectability and electron transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer are usable. As the electron donor, any substance exhibiting electron donating property to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Layer Formation Method

A method for forming each layer of the organic EL device in the third exemplary embodiment is subject to no limitation except for the above particular description. However, known methods of dry film-forming such as vacuum deposition, sputtering, plasma or ion plating and wet film-forming such as spin coating, dipping, flow coating or ink jet printing are applicable.

Film Thickness

A thickness of each of the organic layers in the organic EL device according to the third exemplary embodiment is not limited except for the above particular description. In general, the thickness preferably ranges from several nanometers to 1 μm in order to avoid defects such as a pin hole and to prevent efficiency from being deteriorated since a high voltage needs to be applied.

Fourth Exemplary Embodiment

An arrangement of an organic EL device according to a fourth exemplary embodiment will be described below. In the description of the fourth exemplary embodiment, the same components as those in the third exemplary embodiment are denoted by the same reference signs and names to simplify or omit an explanation of the components. In the fourth exemplary embodiment, any materials and compounds that are not specified may be the same as those in the third exemplary embodiment.

The organic EL device according to the fourth exemplary embodiment is different from the organic EL device according to the third exemplary embodiment in that the emitting layer further includes a third compound. The rest of the arrangement of the organic EL device according to the fourth exemplary embodiment is the same as in the third exemplary embodiment.

Specifically, in the fourth exemplary embodiment, the emitting layer as a first organic layer contains the first compound, the second compound and the third compound.

In the fourth exemplary embodiment, the first compound is preferably a host material, the second compound is preferably a dopant material, and the third compound is preferably a material that disperses the dopant material in the emitting layer.

Third Compound

The third compound may be a thermally activated delayed fluorescent compound or a compound exhibiting no thermally activated delayed fluorescence.

The third compound is not particularly limited, but is preferably a compound other than an amine compound. Although the third compound may be a carbazole derivative, dibenzofuran derivative, or dibenzothiophene derivative, the third compound is not limited thereto.

It is also preferable that the third compound has at least one of a partial structure represented by a formula (31), a partial structure represented by a formula (32), a partial structure represented by a formula (33) and a partial structure represented by a formula (34) in one molecule.

[Formula 181]

(31)

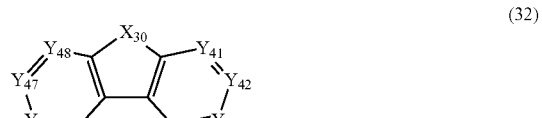

(32)

(33)

(34)

In the formula (31), $Y_{31}$ to $Y_{36}$ each independently represent a nitrogen atom or a carbon atom bonded to another atom in the molecule of the third compound.

At least one of $Y_{31}$ to $Y_{36}$ is a carbon atom bonded to another atom in the molecule of the third compound.

In the formula (32), $Y_{41}$ to $Y_{48}$ each independently represent a nitrogen atom or a carbon atom bonded to another atom in the molecule of the third compound.

At least one of $Y_{41}$ to $Y_{48}$ is a carbon atom bonded to another atom in the molecule of the third compound.

$X_{30}$ represents a nitrogen atom bonded to another atom in the molecule of the third compound, an oxygen atom, or a sulfur atom.

The mark * in the formulae (33) to (34) each independently shows a bonding position with another atom or another structure in the molecule of the third compound.

In the formula (32), it is also preferable that at least two of $Y_{41}$ to $Y_{48}$ are carbon atoms bonded to other atoms in the molecule of the third compound to form a cyclic structure including the carbon atoms.

For instance, the partial structure represented by formula (32) is preferably any one selected from the group consisting of partial structures represented by formulae (321), (322), (323), (324), (325) and (326).

[Formula 182]

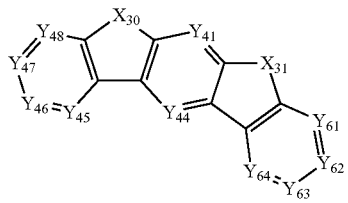
(321)

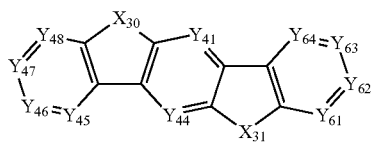
(322)

[Formula 183]

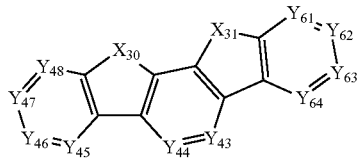
(323)

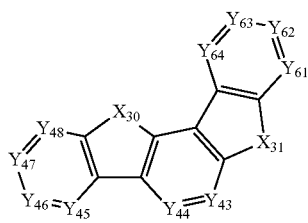
(324)

[Formula 184]

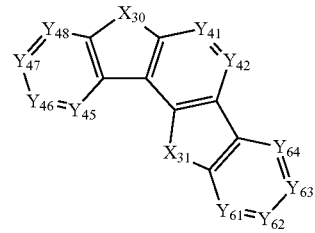
(325)

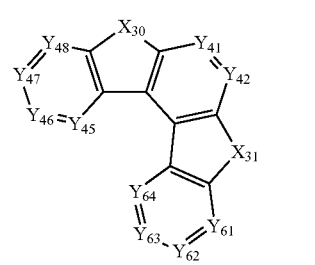
(326)

In the formulae (321) to (326), $X_{30}$ each independently represents a nitrogen atom bonded to another atom in the molecule of the third compound, an oxygen atom, or a sulfur atom.

$Y_{41}$ to $Y_{48}$ each independently represent a nitrogen atom or a carbon atom bonded to another atom in the molecule of the third compound.

$X_{31}$ each independently represents a nitrogen atom bonded to another atom in the molecule of the third compound, an oxygen atom, a sulfur atom, or a carbon atom bonded to another atom in the molecule of the third compound.

$Y_6$ to $Y_{64}$ each independently represent a nitrogen atom or a carbon atom bonded to another atom in the molecule of the third compound.

In the exemplary embodiments, the third compound preferably has the partial structure represented by the formula (323) among those represented by the formulae (323) to (326).

The partial structure represented by the formula (31) is preferably included in the third compound as at least one group selected from the group consisting of a group represented by a formula (33) and a group represented by a formula (34) below.

It is also preferable that the third compound has at least one of the partial structures represented by the formulae (33) and (34). Since bonding positions are situated in meta positions as shown in the partial structures represented by the formulae (33) and (34), an energy gap $T_{77K}$(Mat3) at 77 [K] of the second compound can be kept high.

[Formula 185]

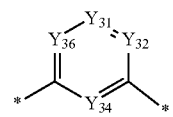
(33)

-continued (34)

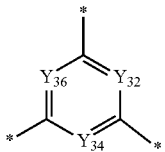

In the formula (33), $Y_{31}$, $Y_{32}$, $Y_{34}$ and $Y_{36}$ are each independently a nitrogen atom or $CR_{31}$.

In the formula (34), $Y_{32}$, $Y_{34}$ and $Y_{36}$ are each independently a nitrogen atom or $CR_{31}$.

In the formulae (33) and (34), $R_{31}$ each independently represents a hydrogen atom or a substituent.

$R_{31}$ as the substituent is each independently selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a halogen atom, a cyano group, a nitro group, and a substituted or unsubstituted carboxy group.

The substituted or unsubstituted aryl group having 6 to 30 ring carbon atoms for $R_{31}$ is preferably a non-fused ring.

The mark * in the formulae (33) and (34) each independently shows a bonding position with another atom or another structure in the molecule of the third compound.

In the formula (33), $Y_{31}$, $Y_{32}$, $Y_{34}$ and $Y_{36}$ are each independently preferably $CR_{31}$, in which a plurality of $R_{31}$ are the same or different.

In the formula (34), $Y_{32}$, $Y_{34}$ and $Y_{36}$ are each independently preferably $CR_{31}$, in which a plurality of $R_{31}$ are the same or different.

The substituted germanium group is preferably represented by $-Ge(R_{301})_3$. $R_{301}$ is each independently a substituent. The substituent $R_{301}$ is preferably a substituted or unsubstituted alkyl group having 1 to 30 carbon atoms or a substituted or unsubstituted aryl group having 6 to 30 ring carbon atoms. A plurality of $R_{301}$ are mutually the same or different.

The partial structure represented by the formula (32) is preferably included in the third compound as at least one group selected from the group consisting of groups represented by formulae (35) to (39) and a group represented by a formula (30a).

[Formula 186]

(35)

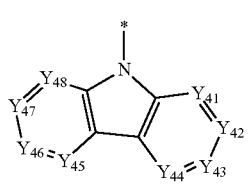

[Formula 187]

(36)

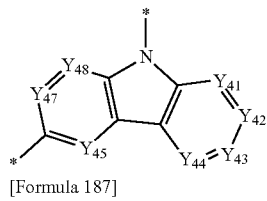

(37)

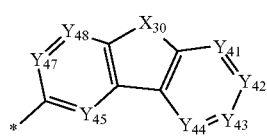

(38)

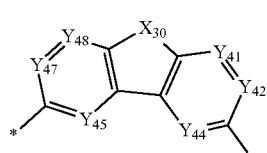

[Formula 188]

(39)

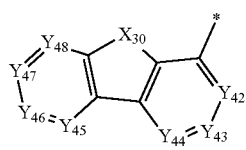

(30a)

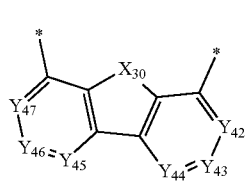

In the formula (35), $Y_{41}$ to $Y_{48}$ are each independently a nitrogen atom or $CR_{32}$.

In the formulae (36) and (37), $Y_{41}$ to $Y_{45}$, $Y_{47}$ and $Y_{48}$ are each independently a nitrogen atom or $CR_{32}$.

In the formula (38), $Y_{41}$, $Y_{42}$, $Y_{44}$, $Y_{45}$, $Y_{47}$ and $Y_{48}$ are each independently a nitrogen atom or $CR_{32}$.

In the formula (39), $Y_{42}$ to $Y_{48}$ are each independently a nitrogen atom or $CR_{32}$.

In the formula (30a), $Y_{42}$ to $Y_{47}$ are each independently a nitrogen atom or $CR_{32}$.

In the formulae (35) to (39) and (30a), $R_{32}$ each independently represents a hydrogen atom or a substituent.

$R_{32}$ as the substituent is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a halogen atom, a cyano group, a nitro group, and a substituted or unsubstituted carboxy group.

A plurality of $R_{32}$ are the same or different.

In the formulae (37) to (39) and (30a), $X_{30}$ is $NR_{33}$, an oxygen atom or a sulfur atom.

$R_{33}$ is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a fluorine atom, a cyano group, a nitro group, and a substituted or unsubstituted carboxy group.

A plurality of $R_{33}$ are the same or different.

The substituted or unsubstituted aryl group having 6 to 30 ring carbon atoms for $R_{33}$ is preferably a non-fused ring.

The mark * in the formulae (35) to (39) and (30a) each independently shows a bonding position with another atom or another structure in the molecule of the third compound.

In the formula (35), $Y_{41}$ to $Y_{48}$ are each independently preferably $CR_{32}$. In the formulae (36) and (37), $Y_{41}$ to $Y_{45}$, $Y_{47}$ and $Y_{48}$ are each independently preferably $CR_{32}$. In the formula (38), $Y_{41}$, $Y_{42}$, $Y_{44}$, $Y_{45}$, $Y_{47}$ and $Y_{48}$ are each independently preferably $CR_{32}$. In the formula (39), $Y_{42}$ to $Y_{48}$ are each independently preferably $CR_{32}$. In the formula (30a), $Y_{42}$ to $Y_{47}$ are each independently preferably $CR_{32}$. A plurality of $R_{32}$ are the same or different.

In the third compound, $X_{30}$ is preferably an oxygen atom or a sulfur atom, more preferably an oxygen atom.

In the third compound, $R_{31}$ and $R_{32}$ each independently represent a hydrogen atom or a substituent. $R_{31}$ and $R_{32}$ as the substituents are preferably each independently a group selected from the group consisting of a fluorine atom, a cyano group, a substituted or unsubstituted alkyl group having 1 to 30 carbon atoms, a substituted or unsubstituted aryl group having 6 to 30 ring carbon atoms, and a substituted or unsubstituted heteroaryl group having 5 to 30 ring atoms. $R_{31}$ and $R_{32}$ are more preferably a hydrogen atom, a cyano group, a substituted or unsubstituted aryl group having 6 to 30 ring carbon atoms, or a substituted or unsubstituted heteroaryl group having 5 to 30 ring atoms. When $R_{31}$ and $R_{32}$ as the substituents are each a substituted or unsubstituted aryl group having 6 to 30 ring carbon atoms, the aryl group is preferably a non-fused ring.

It is also preferable that the third compound is an aromatic hydrocarbon compound or an aromatic heterocyclic compound.

Manufacturing Method of Third Compound

The third compound can be manufactured by methods disclosed in International Publication No. WO2012/153780, International Publication No. WO2013/038650, and the like. Furthermore, the second compound can be manufactured, for instance, by application of known substitution reactions and/or materials depending on a target compound.

Examples of the substituent in the third compound are shown below, but the invention is not limited thereto.

Specific examples of the aryl group (occasionally referred to as an aromatic hydrocarbon) group) include a phenyl group, tolyl group, xylyl group, naphthyl group, phenanthryl group, pyrenyl group, chrysenyl group, benzo[c]phenanthryl group, benzo[g]chrysenyl group, benzoanthryl group, triphenylenyl group, fluorenyl group, 9,9-dimethylfluorenyl group, benzofluorenyl group, dibenzofluorenyl group, biphenyl group, terphenyl group, quarterphenyl group and fluoranthenyl group, among which a phenyl group, biphenyl group, terphenyl group, quarterphenyl group, naphthyl group, triphenylenyl group and fluorenyl group may be preferable.

Specific examples of the aryl group having a substituent include a tolyl group, xylyl group and 9,9-dimethylfluorenyl group.

As is understood from the specific examples, the aryl group includes both fused aryl group and non-fused aryl group.

Preferable examples of the aryl group include a phenyl group, biphenyl group, terphenyl group, quarterphenyl group, naphthyl group, triphenylenyl group and fluorenyl group.

Specific examples of the heteroaryl group (occasionally referred to as a heterocyclic group, heteroaromatic ring group or aromatic heterocyclic group) include a pyrrolyl group, pyrazolyl group, pyrazinyl group, pyrimidinyl group, pyridazynyl group, pyridyl group, triazinyl group, indolyl group, isoindolyl group, imidazolyl group, benzimidazolyl group, indazolyl group, imidazo[1,2-a]pyridinyl group, furyl group, benzofuranyl group, isobenzofuranyl group, dibenzofuranyl group, azadibenzofuranyl group, thiophenyl group, benzothienyl group, dibenzothienyl group, azadibenzothienyl group, quinolyl group, isoquinolyl group, quinoxalinyl group, quinazolinyl group, naphthyridinyl group, carbazolyl group, azacarbazolyl group, phenanthridinyl group, acridinyl group, phenanthrolinyl group, phenazinyl group, phenothiazinyl group, phenoxazinyl group, oxazolyl group, oxadiazolyl group, furazanyl group, benzoxazolyl group, thienyl group, thiazolyl group, thiadiazolyl group, benzothiazolyl group, triazolyl group and tetrazolyl group, among which a dibenzofuranyl group, dibenzothienyl group, carbazolyl group, pyridyl group, pyrimidinyl group, triazinyl group, azadibenzofuranyl group and azadibenzothienyl group may be preferable.

The heteroaryl group is preferably a dibenzofuranyl group, dibenzothienyl group, carbazolyl group, pyridyl group, pyrimidinyl group, triazinyl group, azadibenzofuranyl group or azadibenzothienyl group, and more preferably a dibenzofuranyl group, dibenzothienyl group, azadibenzofuranyl group and azadibenzothienyl group.

In the third compound, it is also preferable that the substituted silyl group is selected from the group consisting of a substituted or unsubstituted trialkylsilyl group, a substituted or unsubstituted arylalkylsilyl group, or a substituted or unsubstituted triarylsilyl group.

Specific examples of the substituted or unsubstituted trialkylsilyl group include trimethylsilyl group and triethylsilyl group.

Specific examples of the substituted or unsubstituted arylalkylsilyl group include diphenylmethylsilyl group, ditolylmethylsilyl group, and phenyldimethylsilyl group.

Specific examples of the substituted or unsubstituted triarylsilyl group include triphenylsilyl group and tritolylsilyl group.

In the third compound, it is also preferable that the substituted phosphine oxide group is a substituted or unsubstituted diaryl phosphine oxide group.

Specific examples of the substituted or unsubstituted diaryl phosphine oxide group include a diphenyl phosphine oxide group and ditolyl phosphine oxide group.

In the third compound, the substituted carboxy group is exemplified by a benzoyloxy group.

Specific examples of the third compound in the exemplary embodiment are shown below. It should be noted that the third compound of the invention is not limited to the specific examples.

[Formula 189]
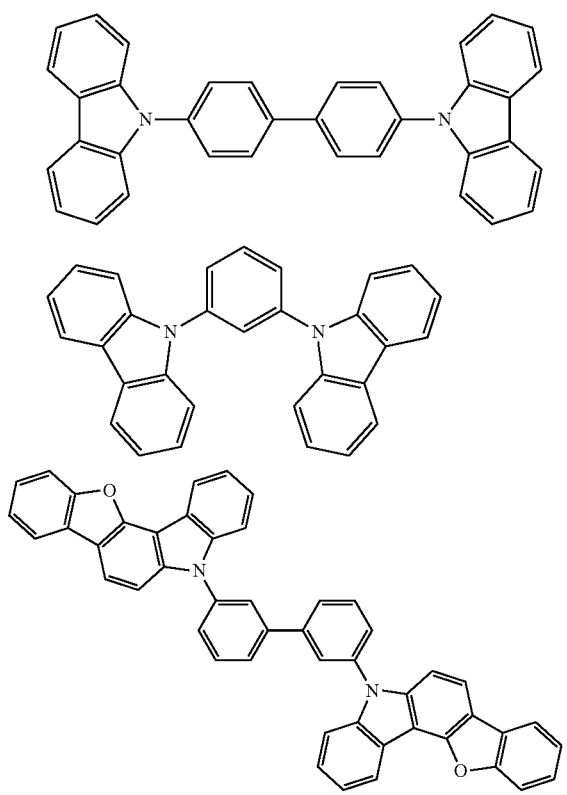
[Formula 190]
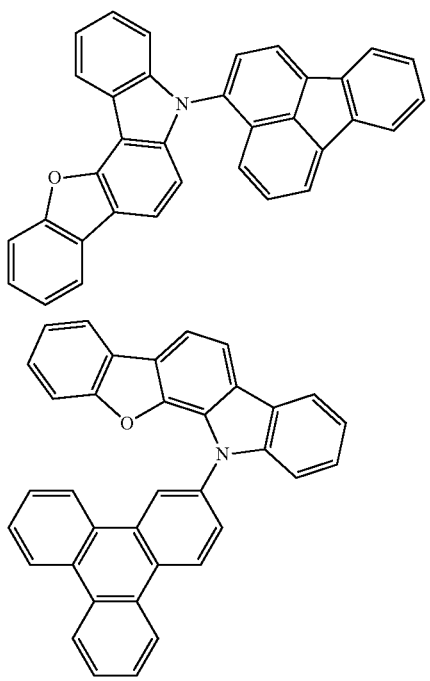
[Formula 191]
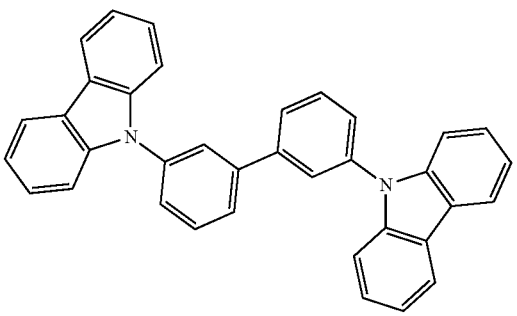
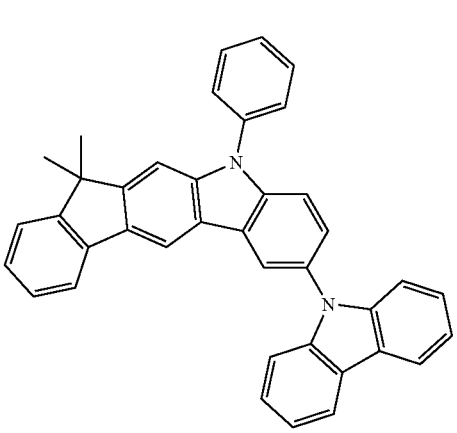
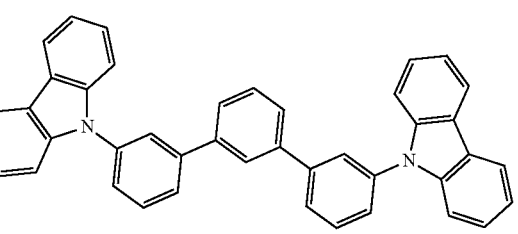

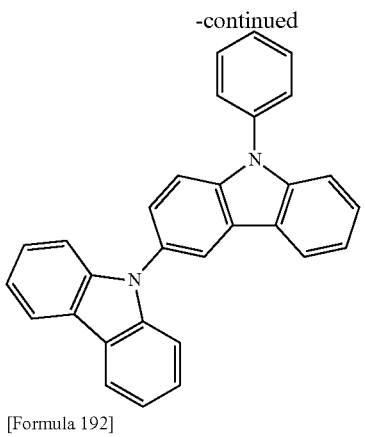

[Formula 192]

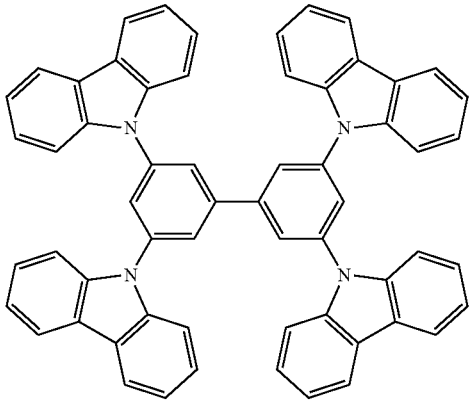 [SMILES: c1ccc2c(c1)c1ccccc1n2-c1cc(-c2cc(-n3c4ccccc4c4ccccc43)cc(-n3c4ccccc4c4ccccc43)c2)cc(-n2c3ccccc3c3ccccc32)c1]

Relationship Between First Compound, Second Compound and Third Compound in Emitting Layer In the organic EL device of the exemplary embodiment, the singlet energy S1(Mat1) of the first compound and a singlet energy S1(Mat3) of the third compound preferably satisfies a relationship of Numerical Formula 2 below.

$S_1(Mat3) > S_1(Mat1)$ (Numerical Formula 2)

The energy gap $T_{77K}(Mat3)$ at 77 [K] of the third compound is preferably larger than an energy gap $T_{77K}(Mat1)$ at 77 [K] of the first compound.

The energy gap $T_{77K}(Mat3)$ at 77 [K] of the third compound is preferably larger than the energy gap $T_{77K}(Mat2)$ at 77 [K] of the second compound The singlet energy $S_1(Mat1)$ of the first compound, the singlet energy $S_1(Mat2)$ of the second compound, the singlet energy $S_1(Mat3)$ of the third compound preferably satisfy a relationship of Numerical Formula 2A.

$S_1(Mat3) > S_1(Mat1) > S_1(Mat2)$ (Numerical Formula 2A)

The energy gap $T_{77K}(Mat1)$ at 77[K] of the first compound, the energy gap $T_{77K}(Mat2)$ at 77[K] of the second compound, and the energy gap $T_{77K}(Mat3)$ at 77[K] of the third compound preferably satisfy a relationship of Numerical Formula 2B.

$T_{77K}(Mat3) > T_{77K}(Mat1) > T_{77K}(Mat2)$ (Numerical Formula 2B)

When the organic EL device of the exemplary embodiment emits light, it is preferable that the fluorescent compound in the emitting layer mainly emits light.

The organic EL device of the fourth exemplary embodiment preferably emits red light or green light in the same manner as the organic EL device of the third exemplary embodiment.

A main peak wavelength of the organic EL device can be measured by the same method as that for the organic EL device of the third exemplary embodiment.

Content Ratio of Compounds in Emitting Layer

Content ratios of the first, second and third compounds in the emitting layer are, for instance, preferably determined as follows.

The content ratio of the first compound is preferably in a range from 10 mass % to 80 mass %, more preferably in a range from 10 mass % to 60 mass %, further preferably in a range from 20 mass % to 60 mass %.

The content ratio of the second compound is preferably in a range from 0.01 mass % to 10 mass %, more preferably in a range from 0.01 mass % to 5 mass %, further preferably in a range from 0.01 mass % to 1 mass %.

The content ratio of the third compound is preferably in a range from 10 mass % to 80 mass %.

An upper limit of the total of the respective content ratios of the first, second and third compounds in the emitting layer is 100 mass %. It should be noted that the emitting layer of the exemplary embodiment may further contain material(s) other than the first, second and third compounds.

The emitting layer may include a single type of the first compound or may include two or more types of the first compound. The emitting layer may include a single of the second compound or may include two or more types of the second compound. The emitting layer may include a single of the third compound or may include two or more types of the third compound.

Figure 5:
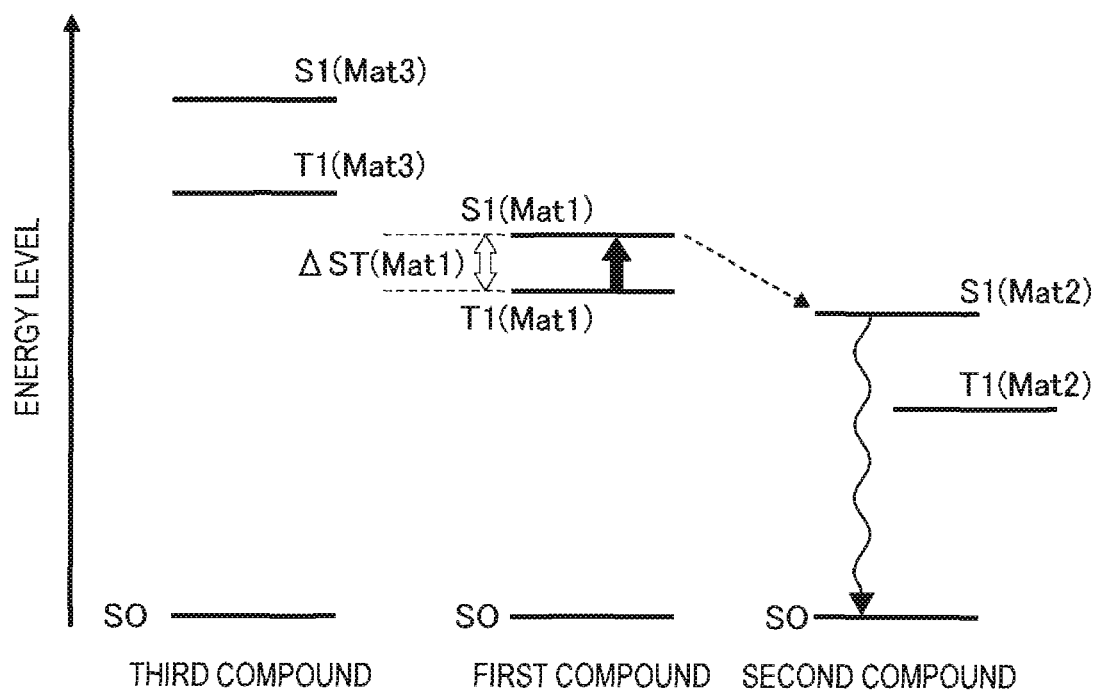
FIG. 5 shows a relationship in energy level and energy transfer between a first compound, a second compound and a third compound in an emitting layer of an exemplary organic electroluminescence device according to a fourth exemplary embodiment of the invention.

FIG. 5 shows an example of a relationship between energy levels of the first, second and third compounds in the emitting layer. In FIG. 5, S0 represents a ground state. S1(Mat1) represents the lowest singlet state of the first compound. T1(Mat1) represents the lowest triplet state of the first compound. S1(Mat2) represents the lowest singlet state of the second compound. T1(Mat2) represents the lowest triplet state of the second compound. S1(Mat3) represents the lowest singlet state of the third compound. T1(Mat3) represents the lowest triplet state of the third compound. A dashed arrow directed from S1(Mat1) to S1(Mat2) in FIG. 5 represents Förster energy transfer from the lowest singlet state of the first compound to the lowest singlet state of the fluorescent compound.

As shown in FIG. 5, when a compound having a small ΔST(Mat1) is used as the first compound, inverse intersystem crossing from the lowest triplet state T1(Mat1) to the lowest singlet state S1(Mat1) can be caused by a heat energy. Subsequently, Förster energy transfer from the lowest singlet state S1(Mat1) of the first compound the second compound occurs to generate the lowest singlet state S1(Mat2). Consequently, fluorescence from the lowest singlet state S1(Mat2) of the second compound can be observed. It is inferred that the internal quantum efficiency can be theoretically raised up to 100% also by using delayed fluorescence by the TADF mechanism.

The organic EL device 1 according to the fourth exemplary embodiment contains the first compound that is the compound according to the first exemplary embodiment (at least one of the compounds represented by the formulae (11) to (13)), the second compound having the singlet energy smaller than that of the first compound in the emitting layer 5, and the third compound having the singlet energy larger than that of the first compound.

The organic EL device according to the fourth exemplary embodiment is applicable to an electronic device such as a display device and a light-emitting device.

Fifth Exemplary Embodiment

An arrangement of an organic EL device according to a fifth exemplary embodiment will be described below. In the description of the fifth exemplary embodiment, the same components as those in the third and fourth exemplary embodiments are denoted by the same reference signs and names to simplify or omit an explanation of the components. In the fifth exemplary embodiment, any materials and compounds that are not specified may be the same as those in the third and fourth exemplary embodiments.

The organic EL device according to the fifth exemplary embodiment is different from the organic EL device according to the third exemplary embodiment in that the emitting layer further includes a fourth compound in place of the second compound. The rest of the arrangement of the organic EL device according to the fifth exemplary embodiment is the same as in the third exemplary embodiment.

In the fifth exemplary embodiment, the emitting layer contains the first compound and the fourth compound.

In the fifth exemplary embodiment, the first compound is preferably a dopant material (occasionally referred to as a guest material, emitter or luminescent material) and the fourth compound is preferably a host material (occasionally referred to as a matrix material).

The fourth compound may be a thermally activated delayed fluorescent compound or a compound exhibiting no thermally activated delayed fluorescence.

Although the fourth compound is not particularly limited, for instance, the third compound described in the fourth exemplary embodiment is usable as the fourth compound.
Relationship between First Compound and Fourth Compound in Emitting Layer In the organic EL device of the exemplary embodiment, the singlet energy $S_1(Mat1)$ of the first compound and a singlet energy $S_1(Mat4)$ of the fourth compound preferably satisfies a relationship of Numerical Formula 4 below.

$$S_1(Mat4) > S_1(Mat1) \quad \text{(Numerical Formula 4)}$$

An energy gap $T_{77K}(Mat4)$ at 77 [K] of the fourth compound is preferably larger than the energy gap $T_{77K}(Mat1)$ at 77 [K] of the first compound. In other words, a relationship of Numerical Formula 4A is preferably satisfied.

$$T_{77K}(Mat4) > T_{77K}(Mat1) \quad \text{(Numerical Formula 4A)}$$

When the organic EL device of the exemplary embodiment emits light, it is preferable that the first compound in the emitting layer mainly emits light.
Content Ratios of Compounds in Emitting Layer Content ratios of the first and fourth compounds in the emitting layer are, for instance, preferably determined as follows.

The content ratio of the first compound is preferably in a range from 10 mass % to 80 mass %, more preferably in a range from 10 mass % to 60 mass %, further preferably in a range from 20 mass % to 60 mass %.

The content ratio of the fourth compound is preferably in a range from 20 mass % to 90 mass %, more preferably in a range from 40 mass % to 90 mass %, further preferably in a range from 40 mass % to 80 mass %.

It should be noted that the emitting layer of the exemplary embodiment may further contain material(s) other than the first and fourth compounds.

The emitting layer may include a single type of the first compound or may include two or more types of the first compound. The emitting layer may include a single type of the fourth compound or may include two or more types of the fourth compound.

Figure 6:
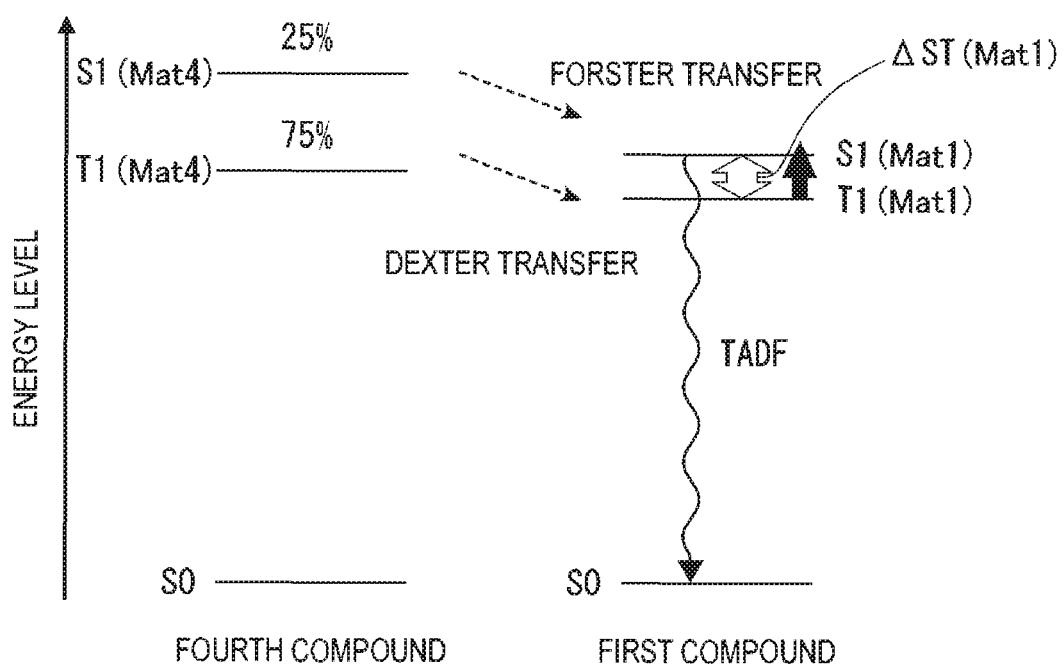
FIG. 6 shows a relationship in energy level and energy transfer between the first compound and a fourth compound in an emitting layer of an exemplary organic electroluminescence device according to a fifth exemplary embodiment of the invention.

FIG. 6 shows an example of a relationship between energy levels of the first and fourth compounds in the emitting layer. In FIG. 6, S0 represents a ground state. $S_1(Mat1)$ represents the lowest singlet state of the first compound. T1(Mat1) represents the lowest triplet state of the first compound. $S_1(Mat4)$ represents the lowest singlet state of the fourth compound. T1(Mat4) represents the lowest triplet state of the fourth compound. Dashed arrows in FIG. 6 represent energy transfer from the fourth compound to the first compound in the lowest singlet state and in the lowest triplet state, respectively. An energy transfer occurs by Förster transfer from the lowest singlet state $S_1$ of the fourth compound to the lowest singlet state $S_1$ of the first compound or an energy transfer occurs by Dexter transfer from the lowest triplet state T1 of the fourth compound to the lowest triplet state T1 of the first compound. Further, when a material having a small $\Delta ST(Mat1)$ is used as the first compound, inverse intersystem crossing can be caused by a heat energy from the lowest triplet state T1 to the lowest singlet state $S_1$ in the first compound. Consequently, fluorescence from the lowest singlet state $S_1$ of the first compound can be observed. It is inferred that the internal quantum efficiency can be theoretically raised up to 100% also by using delayed fluorescence by the TADF mechanism.

The organic EL device according to the fifth exemplary embodiment contains the first compound that is the compound according to the first exemplary embodiment (at least one of the compounds represented by the formulae (11) to (13)), and the fourth compound having the singlet energy larger than that of the first compound in the emitting layer.

The organic EL device according to the fifth exemplary embodiment is applicable to an electronic device such as a display device and a light-emitting device.

Sixth Exemplary Embodiment

Electronic Device

An electronic device according to a sixth exemplary embodiment is installed with one of the organic EL devices according to the above exemplary embodiments. Examples of the electronic device include a display device and a light-emitting unit. Examples of the display device include a display component (e.g., an organic EL panel module), TV, mobile phone, tablet and personal computer. Examples of the light-emitting unit include an illuminator and a vehicle light.

Modification of Embodiment(s)

It should be noted that the invention is not limited to the above exemplary embodiments but may include any modification and improvement as long as such modification and improvement are compatible with the invention.

For instance, the emitting layer is not limited to a single layer, but may be provided by laminating a plurality of emitting layers. When the organic EL device has a plurality of emitting layers, it is only required that at least one of the emitting layers satisfies the conditions described in the above exemplary embodiments. For instance, in some embodiments, the rest of the emitting layers is a fluorescent emitting layer or a phosphorescent emitting layer with use of emission caused by electron transfer from the triplet excited state directly to the ground state.

When the organic EL device includes the plurality of emitting layers, in some embodiments, the plurality of emitting layers are adjacent to each other, or provide a so-called tandem-type organic EL device in which a plurality of emitting units are layered through an intermediate layer.

For instance, in some embodiments, a blocking layer is provided adjacent to at least one side of a side near the anode and a side near the cathode of the emitting layer. The blocking layer is preferably provided in contact with the emitting layer to at least block holes, electrons or excitons.

For instance, when the blocking layer is provided in contact with the cathode-side of the emitting layer, the blocking layer permits transport of electrons, but blocks holes from reaching a layer provided near the cathode (e.g., the electron transporting layer) beyond the blocking layer. When the organic EL device includes the electron transporting layer, the organic EL device preferably includes the blocking layer between the emitting layer and the electron transporting layer.

When the blocking layer is provided in contact with the anode-side of the emitting layer, the blocking layer permits transport of holes, but blocks electrons from reaching a layer provided near the anode (e.g., the hole transporting layer) beyond the blocking layer. When the organic EL device includes the hole transporting layer, the organic EL device preferably includes the blocking layer between the emitting layer and the hole transporting layer.

Moreover, for instance, in some embodiments, the blocking layer abuts on the emitting layer so that excited energy does not leak out from the emitting layer toward neighboring layer(s). The blocking layer blocks excitons generated in the emitting layer from transferring to a layer(s) (e.g., the electron transporting layer and the hole transporting layer) closer to the electrode(s) beyond the blocking layer.

The emitting layer and the blocking layer are preferably bonded with each other.

Specific structure and shape of the components in the invention may be designed in any manner as long as the object of the invention can be achieved.

Herein, numerical ranges represented by "x to y" represents a range whose lower limit is the value (x) recited before "to" and whose upper limit is the value (y) recited after "to."

Rx and Ry are mutually bonded to form a ring, which means herein, for instance, that Rx and Ry contain a carbon atom, a nitrogen atom, an oxygen atom, a sulfur atom or a silicon atom, the atom (a carbon atom, a nitrogen atom, an oxygen atom, a sulfur atom or a silicon atom) contained in Rx and the atom (a carbon atom, a nitrogen atom, an oxygen atom, a sulfur atom or a silicon atom) contained in Ry are mutually bonded via a single bond, a double bond, a triple bond or a divalent linking group to form a ring having 5 or more ring atoms (specifically, a heterocyclic ring or an aromatic hydrocarbon ring). x represents a number, a character or a combination of a number and a character. y represents a number, a character or a combination of a number and a character.

The divalent linking group is not particularly limited and is exemplified by —O—, —CO—, —CO$_2$—, —S—, —SO—, —SO$_2$—, —NH—, —NRa—, and a group obtained by combining two or more linking groups of those.

Specific examples of the heterocyclic ring include a cyclic structure (heterocyclic ring) obtained by removing a bond from a "heteroaryl group" exemplarily shown in the later-described "Description of Each Substituent in Formula." The heterocyclic ring may have a substituent.

Specific examples of the aromatic hydrocarbon ring include a cyclic structure (aromatic hydrocarbon ring) obtained by removing a bond from an "aryl group" exemplarily shown in the later-described "Description of Each Substituent in Formula." The aromatic hydrocarbon ring may have a substituent.

Examples of Ra include a substituted or unsubstituted alkyl group having 1 to 30 carbon atoms, a substituted or unsubstituted aryl group having 6 to 30 ring carbon atoms, and a substituted or unsubstituted heteroaryl group having 5 to 30 ring atoms.

Rx and Ry are mutually bonded to form a ring, which means, for instance, that an atom contained in $Rx_1$ and an atom contained in $Ry_1$ in a molecular structure represented by a formula (E1) below form a ring (cyclic structure) E represented by a formula (E2); that an atom contained in $Rx_1$ and an atom contained in $Ry_1$ in a molecular structure represented by a formula (F1) below form a ring (cyclic structure) F represented by a formula (F2); that an atom contained in $Rx_1$ and an atom contained in $Ry_1$ in a molecular structure represented by a formula (G1) below form a ring (cyclic structure) G represented by a formula (G2); that an atom contained in $Rx_1$ and an atom contained in $Ry_1$ in a molecular structure represented by a formula (H1) below form a ring (cyclic structure) H represented by a formula (H2); and that an atom contained in $Rx_1$ and an atom contained in $Ry_1$ in a molecular structure represented by a formula (I1) below form a ring (cyclic structure) I represented by a formula (I2).

In the formulae (E1) to (I1), * each independently represents a bonding position to another atom in a molecule. Two * in the formula (E1) correspond one-to-one to two * in the formula (E2). Two * in the formula (F1) correspond one-to-one to two in the formula (F2). Two * in the formula (G1) correspond one-to-one to two in the formula (G2). Two * in the formula (H1) correspond one-to-one to two * in the formula (H2). Two * in the formula (I1) correspond one-to-one to two * in the formula (I2).

[Formula 193]

(E1)

(F1)

(G1)

(H1)

(I1)

[Formula 194]

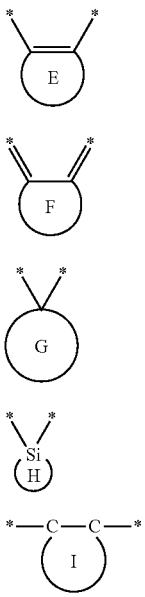

(E2)

(F2)

(G2)

(H2)

(I2)

In the molecular structures represented by the respective formulae (E2) to (I2), E to I each represent a cyclic structure (the ring having 5 or more ring atoms). In the formulae (E2) to (I2), * each independently represents a bonding position to another atom in a molecule. Two * in the formula (E2) correspond one-to-one to two * in the formula (E1). Similarly, two * in each of the formulae (F2) to (I2) correspond one-to-one to two * in in each of the formulae (F1) to (I1).

For instance, in the formula (E1), $Rx_1$ and $Ry_1$ are mutually bonded to for the ring E in the formula (E2) and the ring E is an unsubstituted benzene ring, the molecular structure represented by the formula (E1) is a molecular structure represented by a formula (E3) below. Herein, two * in the formula (E3) each independently correspond to two * in the formula (E2) and the formula (E1).

For instance, in the formula (E1), $Rx_1$ and $Ry_1$ are mutually bonded to for the ring E in the formula (E2) and the ring E is an unsubstituted pyrrole ring, the molecular structure represented by the formula (E1) is a molecular structure represented by a formula (E4) below. Herein, two * in the formula (E4) each independently correspond to two * in the formula (E2) and the formula (E1). In the formulae (E3) and (E4), * each independently represents a bonding position to another atom in a molecule.

[Formula 195]

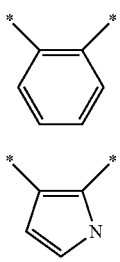

(E3)

(E4)

Herein, the ring carbon atoms refer to the number of carbon atoms among atoms forming a ring of a compound (e.g., a monocyclic compound, fused-ring compound, cross-linking compound, carbon ring compound, and heterocyclic compound) in which the atoms are bonded to each other to form the ring. When the ring is substituted by a substituent(s), carbon atom(s) contained in the substituent(s) is not counted in the ring carbon atoms. Unless specifically described, the same applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring and/or a naphthalene ring is substituted by a substituent (e.g., an alkyl group), the number of carbon atoms of the alkyl group is not counted in the number of the ring carbon atoms. When a fluorene ring is substituted by a substituent (e.g., a fluorene ring) (i.e., a spirofluorene ring is included), the number of carbon atoms of the fluorene ring as the substituent is not counted in the number of the ring carbon atoms of the fluorene ring.

Herein, the ring atoms refer to the number of atoms forming a ring of a compound (e.g., a monocyclic compound, fused-ring compound, crosslinking compound, carbon ring compound, and heterocyclic compound) in which the atoms are bonded to each other to form the ring (e.g., monocyclic ring, fused ring, ring assembly). Atom(s) not forming a ring and atom(s) included in a substituent when the ring is substituted by the substituent are not counted in the number of the ring atoms. Unless specifically described, the same applies to the "ring atoms" described later. For instance, a pyridine ring has six ring atoms, a quinazoline ring has ten ring atoms, and a furan ring has five ring atoms. A hydrogen atom(s) and/or an atom(s) of a substituent which are bonded to carbon atoms of a pyridine ring and/or quinazoline ring are not counted in the ring atoms. When a fluorene ring is substituted by a substituent (e.g., a fluorene ring) (i.e., a spirofluorene ring is included), the number of atoms of the fluorene ring as the substituent is not counted in the number of the ring atoms of the fluorene ring.

Description of Each Substituent in Formula Herein

Examples of the aryl group (occasionally referred to as an aromatic hydrocarbon group) herein include a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

Herein, the aryl group preferably has 6 to 20 ring carbon atoms, more preferably 6 to 14 ring carbon atoms, further preferably 6 to 12 ring carbon atoms. Among the aryl group, a phenyl group, biphenyl group, naphthyl group, phenanthryl group, terphenyl group and fluorenyl group are preferable. A carbon atom in a position 9 of each of 1-fluorenyl group, 2-fluorenyl group, 3-fluorenyl group and 4-fluorenyl group is preferably substituted by a substituted or unsubstituted alkyl group or a substituted or unsubstituted aryl group described later herein.

The heteroaryl group (occasionally referred to as heterocyclic group, heteroaromatic ring group or aromatic heterocyclic group) herein preferably contains as a hetero atom, at least one atom selected from the group consisting of nitrogen, sulfur, oxygen, silicon, selenium atom and germanium atom, and more preferably contains at least one atom selected from the group consisting of nitrogen, sulfur and oxygen.

Examples of the heterocyclic group hereint are a pyridyl group, pyrimidinyl group, pyrazinyl group, pyridazinyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothienyl group, benzoxazolyl group, benzothiazolyl group, benzisoxazolyl group, benzisothiazolyl group, benzoxadiazolyl group, benzothiadiazolyl group, dibenzofuranyl group, dibenzothienyl group, piperidinyl group, pyrrolidinyl group, piperazinyl group, morpholyl group, phenazinyl group, phenothiazinyl group, and phenoxazinyl group.

Herein, the heterocyclic group preferably has 5 to 20 ring carbon atoms, more preferably 5 to 14 ring carbon atoms. Among the above heterocyclic group, a 1-dibenzofuranyl group, 2-dibenzofuranyl group, 3-dibenzofuranyl group, 4-dibenzofuranyl group, 1-dibenzothienyl group, 2-dibenzothienyl group, 3-dibenzothienyl group, 4-dibenzothienyl group, 1-carbazolyl group, 2-carbazolyl group, 3-carbazolyl group, 4-carbazolyl group, and 9-carbazolyl group are further preferable. A nitrogen atom in position 9 of 1-carbazolyl group, 2-carbazolyl group, 3-carbazolyl group and 4-carbazolyl group is preferably substituted by the substituted or unsubstituted aryl group or the substituted or unsubstituted heterocyclic group described herein.

Herein, the heterocyclic group may be a group derived from any one of moieties represented by formulae (XY-1) to (XY-18) below.

[Formula 196]

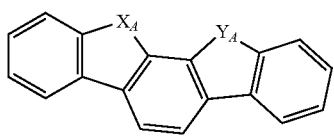
(XY-1)

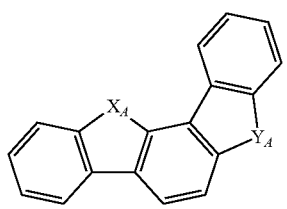
(XY-2)

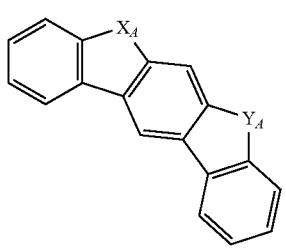
(XY-3)

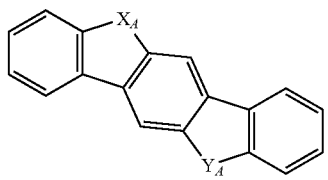
(XY-4)

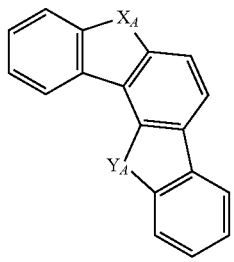
(XY-5)

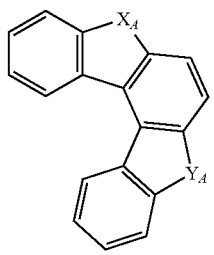
(XY-6)

[Formula 197]

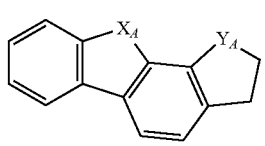
(XY-7)

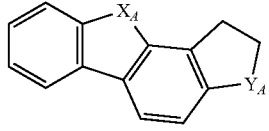
(XY-8)

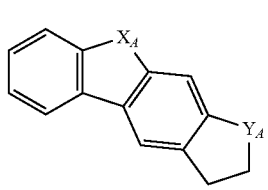
(XY-9)

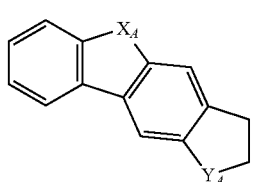
(XY-10)

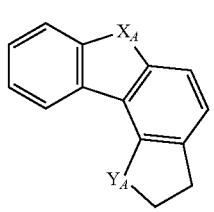
(XY-11)

-continued (XY-12)
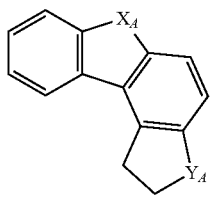

[Formula 198]

(XY-13)
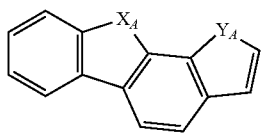

(XY-14)
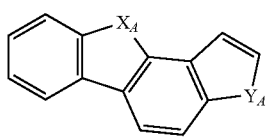

(XY-15)
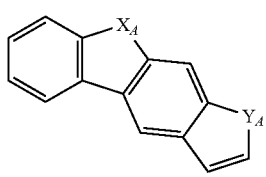

(XY-16)
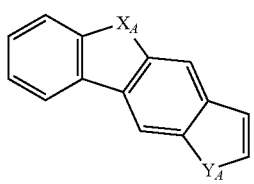

(XY-17)
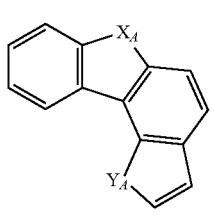

(XY-18)
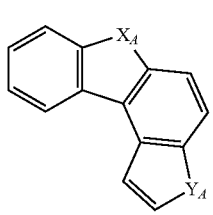

In the formulae (XY-1) to (XY-18), XA and YA each independently represent a hetero atom, and preferably represent an oxygen atom, sulfur atom, selenium atom, silicon atom or germanium atom. Each of the moieties represented by the respective formulae (XY-1) to (XY-18) has a bond at any position to provide a heterocyclic group. The heterocyclic group may be substituted.

Examples of a substituted or unsubstituted carbazolyl group herein may contain groups represented by formulae (XY-19) to (XY-22) in which a further group is fused to a carbazole ring. The groups each may have a substituent. Moreover, the position of the bond may be changed as needed

[Formula 199]

(XY-19)
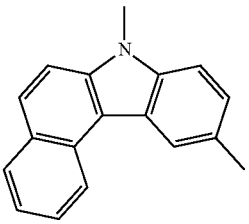

(XY-20)
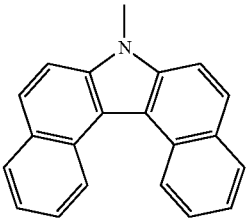

(XY-21)
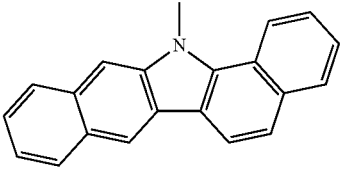

(XY-22)
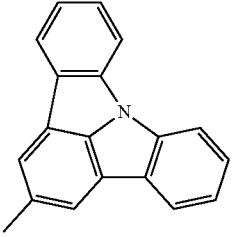

The alkyl group herein may be linear, branched or cyclic. Also, the alkyl group may be an alkyl halide group.

Examples of the linear or branched alkyl group include: a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

Herein, the linear or branched alkyl group preferably has 1 to 10 carbon atoms, more preferably 1 to 6 carbon atoms. As the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group and neopentyl group are further more preferable.

Herein, examples of the cyclic alkyl group include a cycloalkyl group.

Examples of the cycloalkyl group herein are a cyclopropyl group, cyclobutyl group, cyclopentyl group, cyclohexyl group, 4-metylcyclohexyl group, adamantyl group and norbornyl group. The cycloalkyl group preferably has 3 to 10 ring carbon atoms, more preferably 5 to 8 ring carbon atoms.

Among the cycloalkyl group, a cyclopentyl group and a cyclohexyl group are further more preferable.

Herein, the alkyl halide group provided by substituting the alkyl group with a halogen atom is exemplified by an alkyl halide group provided by substituting the alkyl group with at least one halogen atom, preferably at least one fluorine atom.

Herein, examples of the alkyl halide group include a fluoromethyl group, difluoromethyl group, trifluoromethyl group, fluoroethyl group, trifluoromethylmethyl group, trifluoroethyl group, and pentafluoroethyl group.

Herein, examples of a substituted silyl group include an alkylsilyl group and an arylsilyl group.

Herein, the alkylsilyl group is exemplified by a trialkylsilyl group having the above examples of the alkyl group. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups in the trialkylsilyl group may be mutually the same or different.

Herein, examples of the arylsilyl group include a dialkylarylsilyl group, alkyldiarylsilyl group and triarylsilyl group.

The dialkylarylsilyl group is exemplified by a dialkylarylsilyl group including two of the alkyl groups listed as the examples of the alkyl group and one of the aryl groups listed as the examples of the aryl group. The dialkylarylsilyl group preferably has 8 to 30 carbon atoms.

The alkyldiarylsilyl group is exemplified by an alkyldiarylsilyl group including one of the alkyl groups listed as the examples of the alkyl group and two of the aryl groups listed as the examples of the aryl group. The alkyldiarylsilyl group preferably has 13 to 30 carbon atoms.

The triarylsilyl group is exemplified by a triarylsilyl group including three of the aryl group listed as the above examples of the aryl group. The triarylsilyl group preferably has 18 to 30 carbon atoms.

Herein, the alkyl sulfonyl group is represented by —SO$_2$R$_w$, where R$_w$ represents a substituted or unsubstituted alkyl group.

Examples of the substituted or unsubstituted alkylsulfonyl group herein include a group represented by the above —SO$_2$R$_w$, where R$_w$ is substituted or unsubstituted alkyl group.

Herein, an aryl group in an aralkyl group (occasionally referred to as an arylalkyl group) is an aromatic hydrocarbon group or a heterocyclic group.

The aralkyl group herein is preferably a group having an aryl group and is represented by —Z$_3$-Z$_4$. Z$_3$ is exemplified by an alkylene group corresponding to the above alkyl group. Z$_4$ is exemplified by the above aryl group. In this aralkyl group, an aryl moiety has 6 to 30 carbon atoms, preferably 6 to 20 carbon atoms, more preferably 6 to 12 carbon atoms and an alkyl moiety has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

The alkoxy group herein is represented by —OZ$_1$. Z$_1$ is exemplified by the above alkyl group. Examples of the alkoxy group include a methoxy group, ethoxy group, propoxy group, butoxy group, pentyloxy group and hexyloxy group. Thealkoxy group preferably has 1 to 20 carbon atoms.

A halogenated alkoxy group provided by substituting an alkoxy group with a halogen atom is exemplified by one provided by substituting an alkoxy group with one or more fluorine atoms.

Herein, an aryl group in an aryloxy group (sometime referred to as an arylalkoxy group) also includes a heteroaryl group.

The arylalkoxy group herein is represented by —OZ$_2$. Z$_2$ is exemplified by the above aryl group. The arylalkoxy group preferably has 6 to 20 ring carbon atoms. The arylalkoxy group is exemplified by a phenoxy group.

Herein, the substituted amino group is represented by —NHRV or —N(RV)2. R$_V$ is exemplified by the above alkyl group and aryl group.

Herein, the alkenyl group is linear or branched. Examples of the alkenyl group include a vinyl group, propenyl group, butenyl group, oleyl group, eicosapentaenyl group, docosahexaenyl group, styryl group, 2,2-diphenylvinyl group, 1,2,2-triphenylvinyl group, and 2-phenyl-2-propenyl group.

The alkynyl group herein may be linear or branched. Examples of the alkynyl group are an ethynyl group, a propynyl group and a 2-phenylethynyl group.

Herein, the alkylthio group and the arylthio group are represented by —SR$_V$. R$_V$ is exemplified by the above alkyl group and aryl group. The alkylthio group preferably has 1 to 20 carbon atoms. The arylthio group preferably has 6 to 20 ring carbon atoms.

Herein, examples of the halogen atom include a fluorine atom, a chlorine atom, a bromine atom and an iodine atom, among which a fluorine atom is preferable.

Herein, examples of a substituted phosphino group include a phenyl phosphanyl group.

The arylcarbonyl group herein is represented by —COY'. Y' is exemplified by the above aryl group. Examples of the arylcarbonyl group herein include a phenyl carbonyl group, diphenyl carbonyl group, naphthyl carbonyl group, and triphenyl carbonyl group.

The acyl group herein is represented by —COR'. R' is exemplified by the above alkyl group. Herein, examples of the acyl group include an acetyl group and a propionyl group.

A substituted phosphoryl group herein is represented by a formula (P).

[Formula 200]

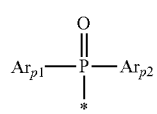

(P)

In the formula (P), Ar$_{P1}$ and Ar$_{P2}$ are each a substituent selected from the group consisting of the above alkyl group and the above aryl group.

Herein, examples of an ester group include an alkyl ester group. The alkyl ester group is represented by —C(=O)

OR$^E$. R$^E$ is exemplified by a substituted or unsubstituted alkyl group. The alkyl group is exemplified by the above "alkyl group herein."

A siloxanyl group herein is a silicon compound group via an ether bond, examples of which include a trimethylsiloxanyl group.

Herein, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a ring including a saturated ring, unsaturated ring, or aromatic ring.

Herein, a hydrogen atom includes isotope having different numbers of neutrons, specifically, protium, deuterium and tritium.

Herein, the substituent meant by "substituted or unsubstituted" is at least one group selected from the group consisting of an aryl group, heteroaryl group, linear alkyl group, branched alkyl group, cycloalkyl group, alkyl halide group, substituted or unsubstituted silyl group (e.g., alkylsilyl group, arylsilyl group), alkoxy group, alkoxy halide group, aryloxy group, substituted or unsubstituted amino group, alkylthio group, arylthio group, aralkyl group, alkenyl group, halogen atom, alkynyl group, cyano group, hydroxy group, nitro group, carboxy group and substituted phosphoryl group.

Herein, the substituent meant by "substituted or unsubstituted" is also exemplified by a diaryl boron group (Ar$_{B1}$Ar$_{B2}$B—). Ar$_{B1}$ and Ar$_{B2}$ are exemplified by the above aryl group.

Examples of the substituent meant by "substituted or unsubstituted" and preferable ones of the examples thereof are the same as the examples of the substituent and the preferable ones of the examples thereof in "Description of Each Substituent."

The substituent meant by "substituted or unsubstituted" may be further substituted by at least one group selected from the group consisting of an aryl group, heteroaryl group, linear alkyl group, branched alkyl group, cycloalkyl group, alkyl halide group, alkylsilyl group, arylsilyl group, alkoxy group, alkoxy halide group, aryloxy group, substituted or unsubstituted amino group, alkylthio group, arylthio group, aralkyl group, alkenyl group, alkynyl group, halogen atom, cyano group, hydroxy group, nitro group, and carboxy group. In addition, adjacent two or more of the substituents may be bonded to each other to form a ring.

The substituent meant by "substituted or unsubstituted" may be further substituted by an acyl group.

"Unsubstituted" in "substituted or unsubstituted" means that a group is not substituted by the above-described substituents but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group.

Herein, "XX to YY atoms" in the description of "substituted or unsubstituted ZZ group having XX to YY atoms" represent atoms of an unsubstituted ZZ group and does not include atoms of a substituent(s) of the substituted ZZ group.

The same description as the above applies to "substituted or unsubstituted" in compounds or moieties thereof described herein.

Herein, when the substituents are bonded to each other to form a ring, the ring is structured to be a saturated ring, an unsaturated ring, an aromatic hydrocarbon ring or a hetero ring.

Herein, examples of the aromatic hydrocarbon group and the heterocyclic group in the linking group include a divalent or multivalent group obtained by eliminating one or more atoms from the above monovalent groups.

EXAMPLES

Example(s) of the invention will be described below. However, the invention is not limited to Example(s).

Compounds used in Examples and Comparatives will be shown below.

[Formula 201]

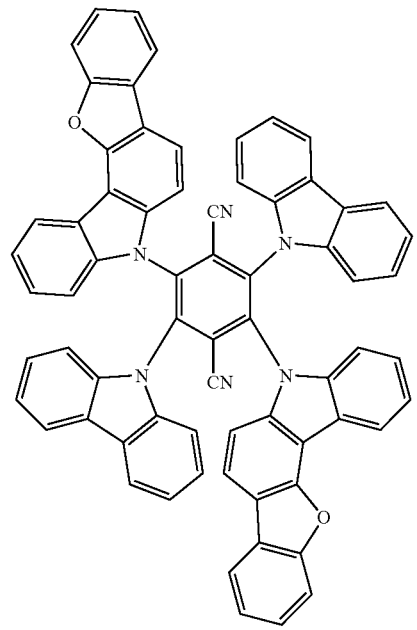

TADF1

TADF2

483
-continued
[Formula 202]
TADF3
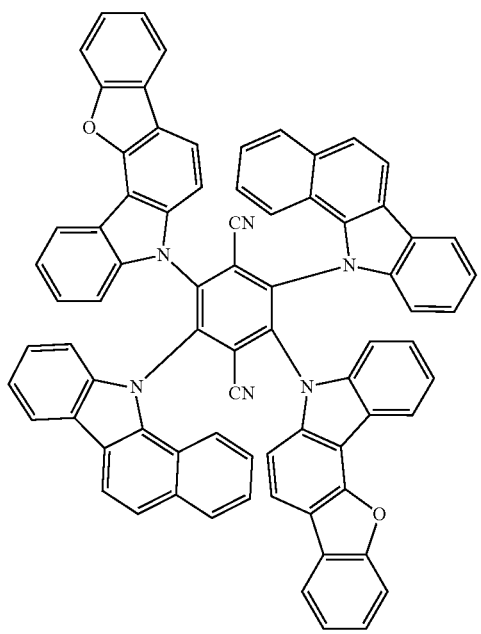
TADF4
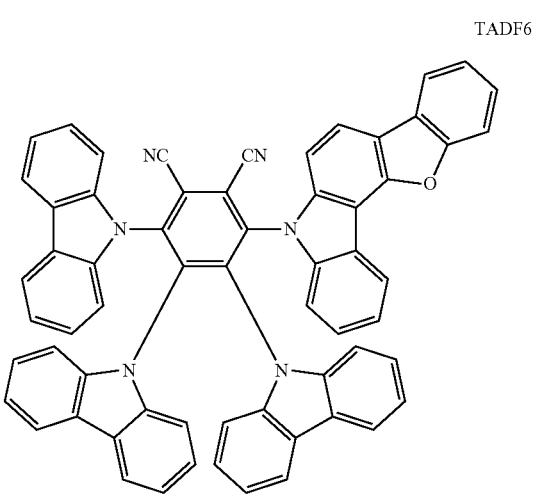
484
-continued
[Formula 203]
TADF5
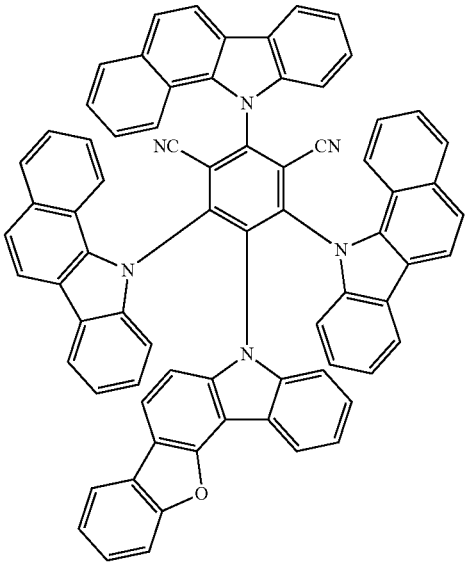
TADF6
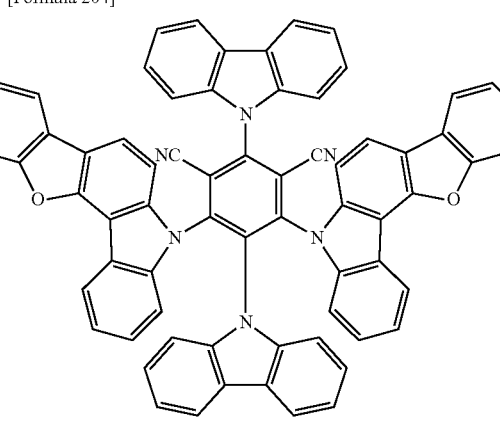
[Formula 204] TADF7

TADF8
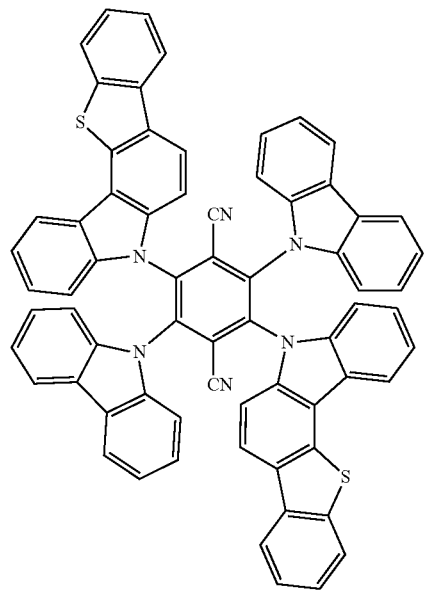
[Formula 205]
TADF9
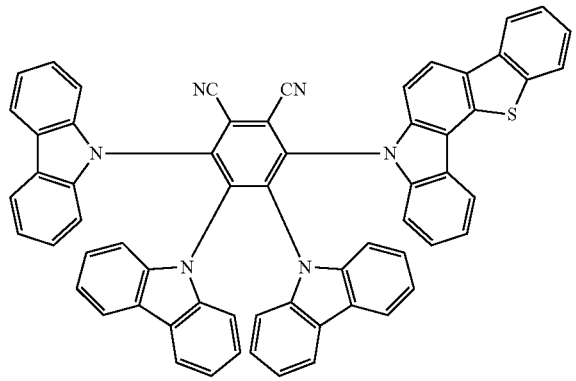
TADF10
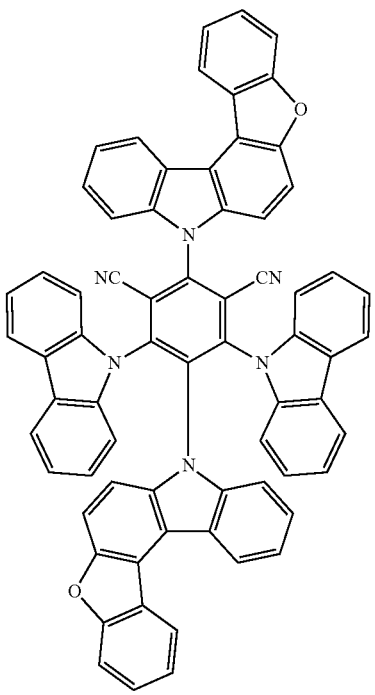
[Formula 206]
TADF11
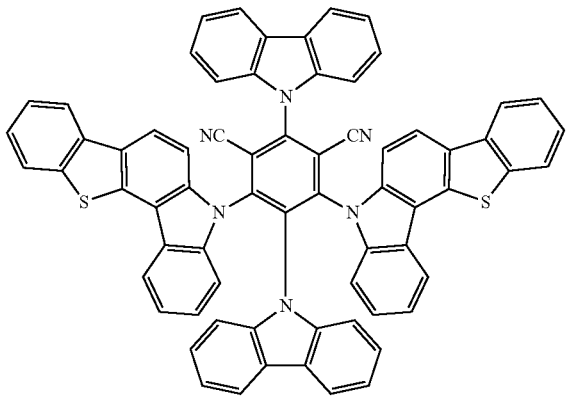
[Formula 207]
TADF12
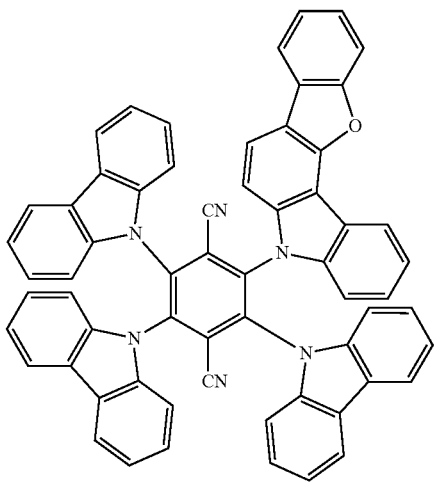

TADF13
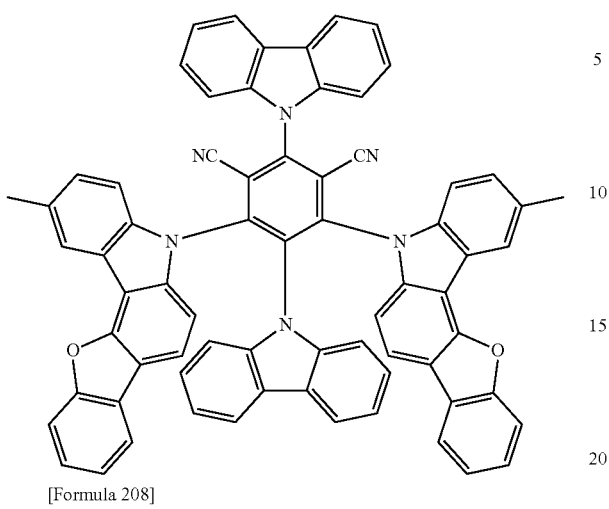
[Formula 208]
TADF14
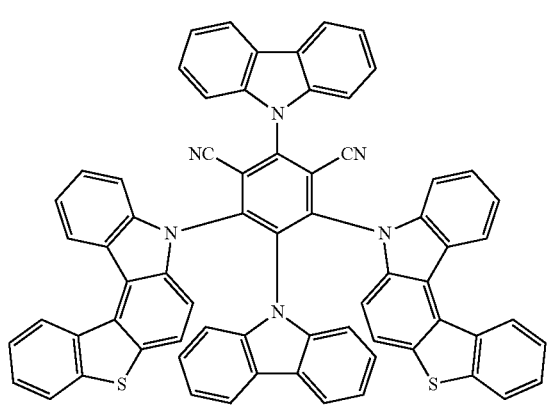
TADF15
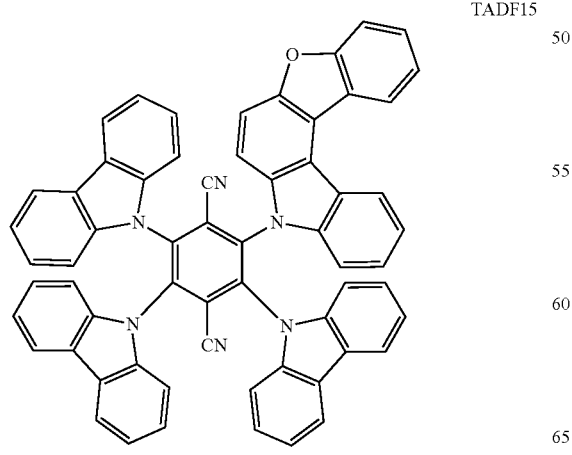
[Formula 209]
TADF16
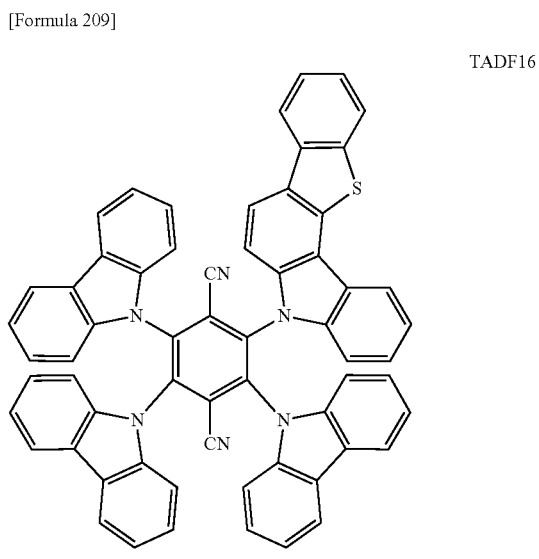
TADF17
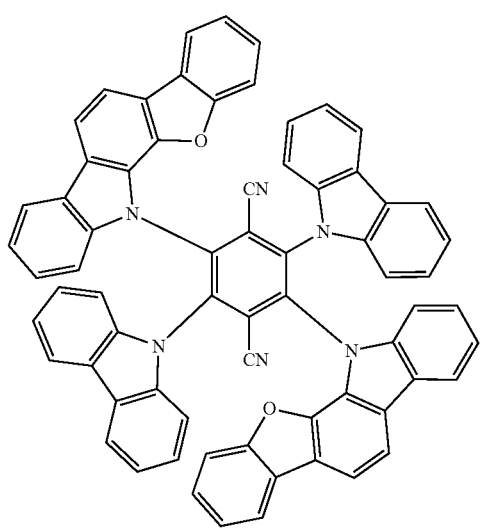
[Formula 210]
TADF18
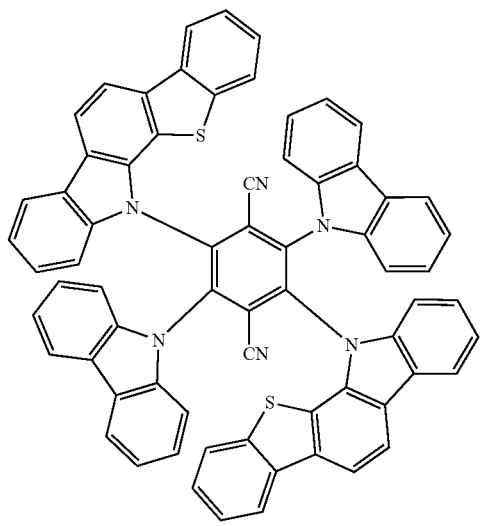

-continued
TADF19
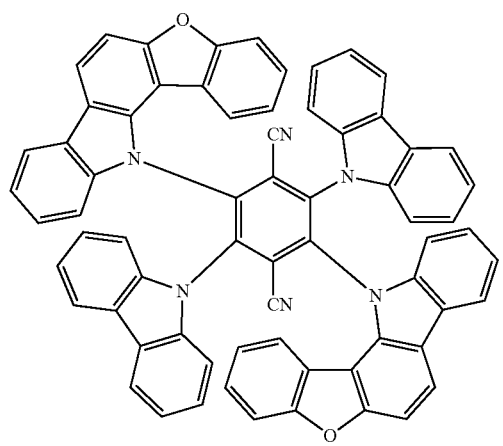
[Formula 211]
TADF20
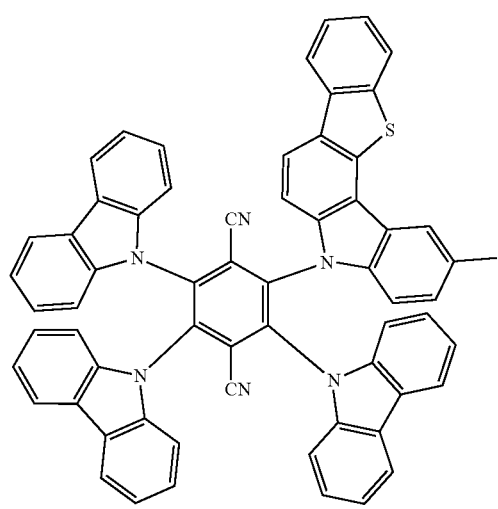
TADF21
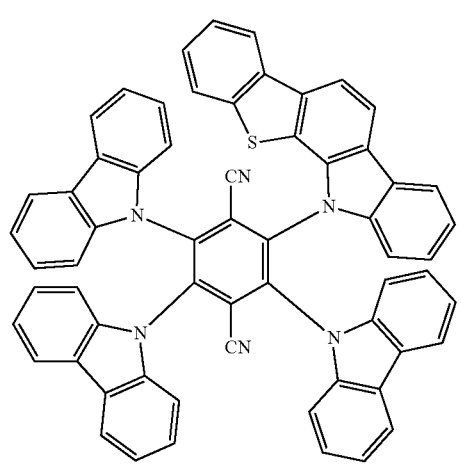
[Formula 212]
TADF22
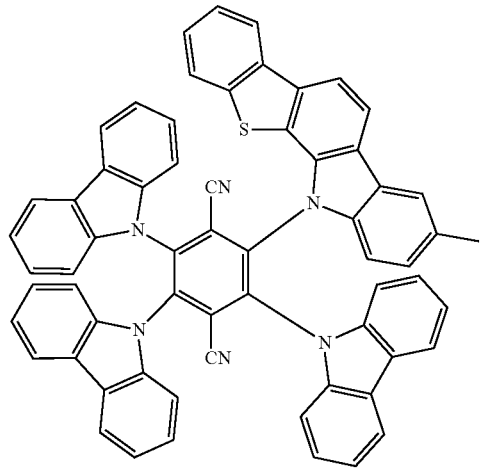
TADF23
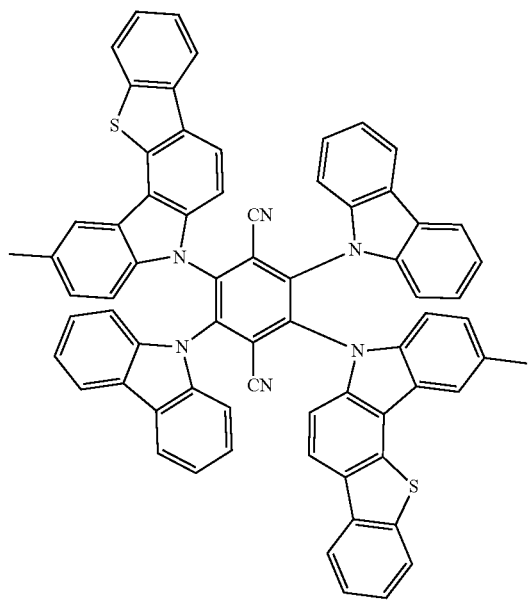
[Formula 213]
TADF24
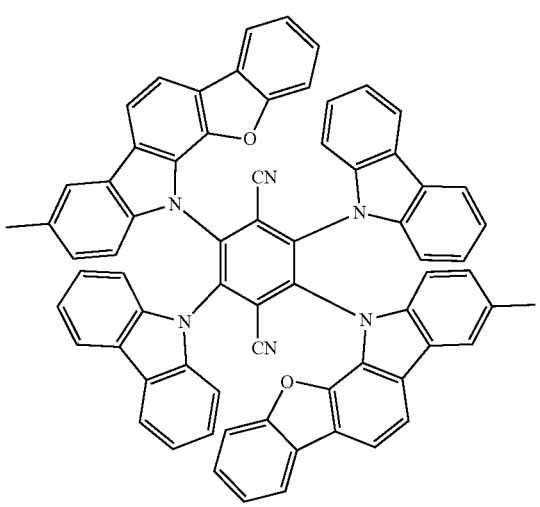

-continued
TADF25
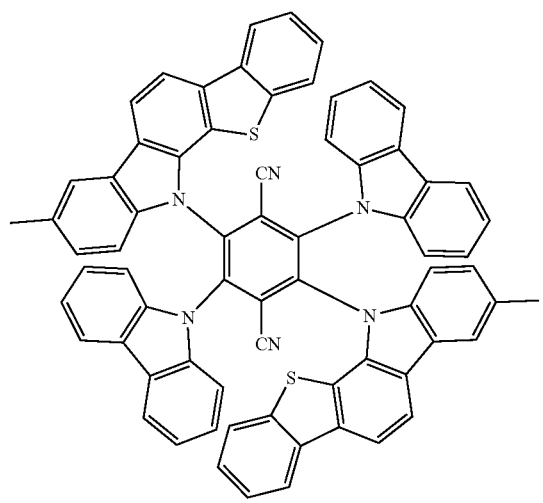
[Formula 214]
TADF26
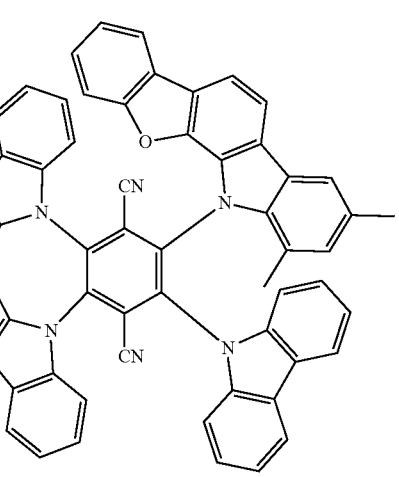
TADF27
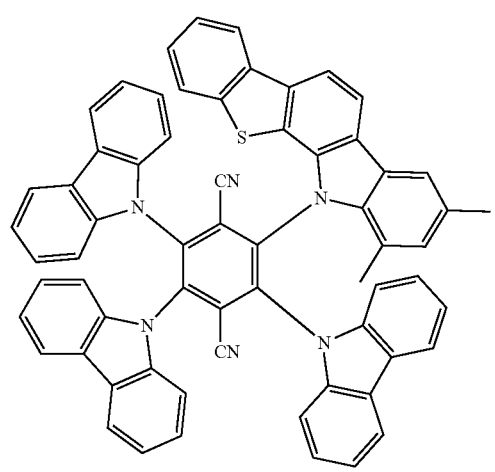
-continued
[Formula 215]
TADF28
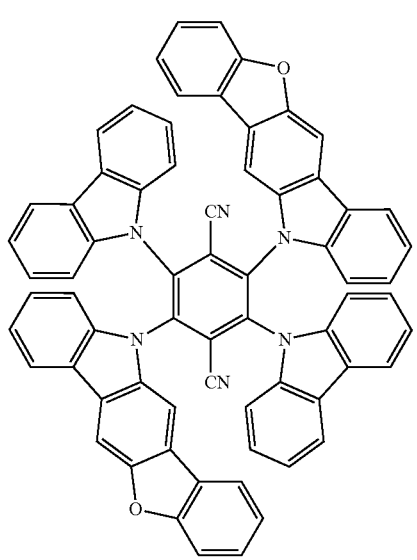
[Formula 216]
TADF29
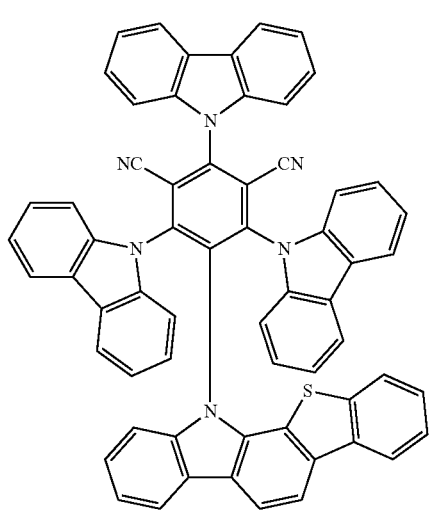
TADF30
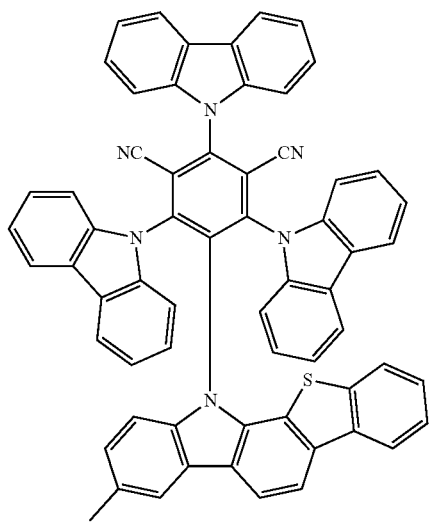

493
-continued
[Formula 217]
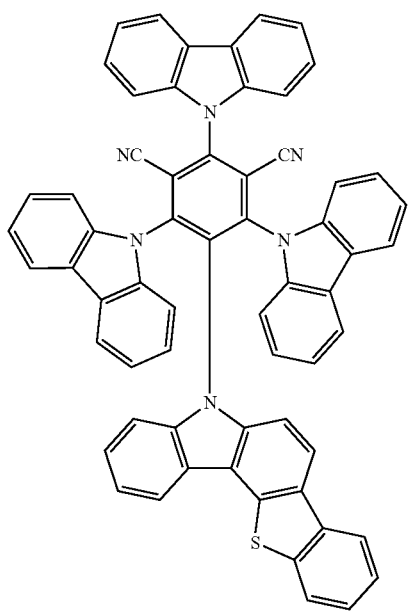
TADF31
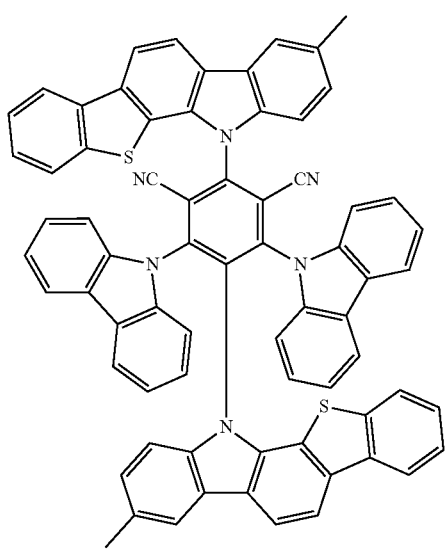
TADF32
494
-continued
[Formula 218]
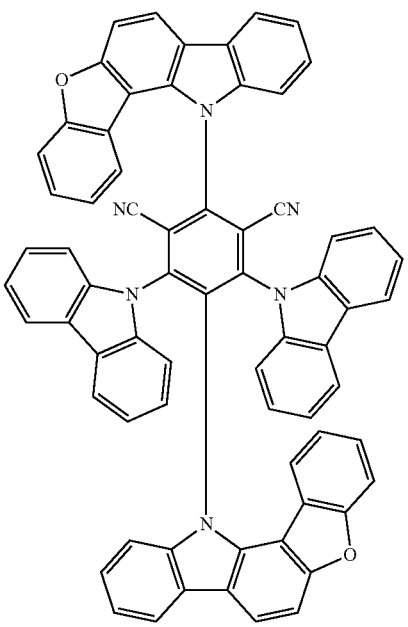
TADF33
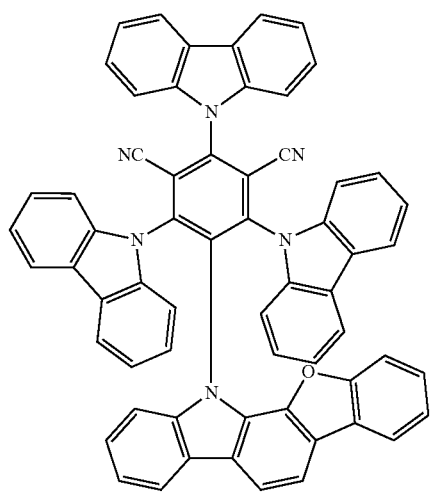
TADF34

-continued
[Formula 219]
TADF35
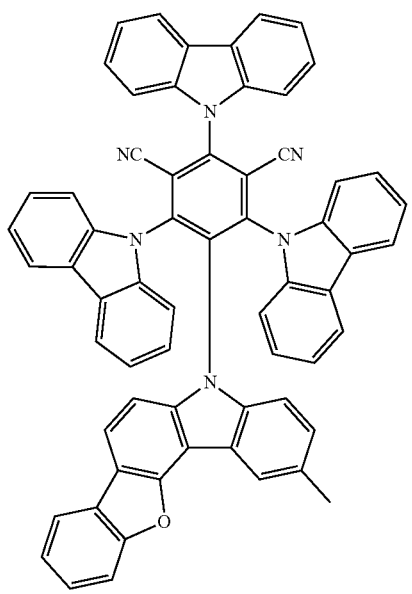
[Formula 220]
TADF37
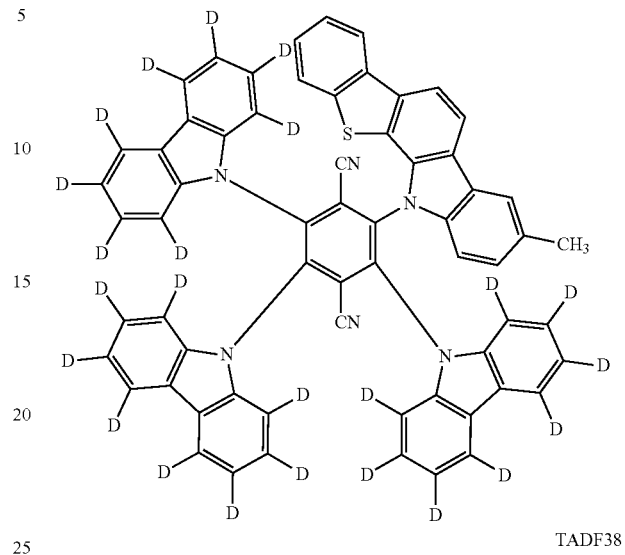
TADF38
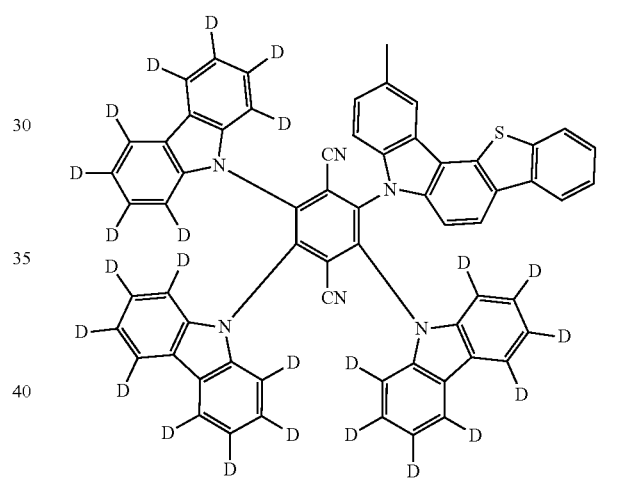
TADF36
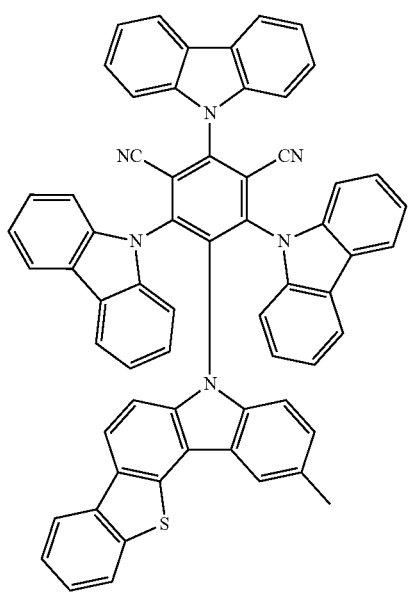
[Formula 221]
TADF39
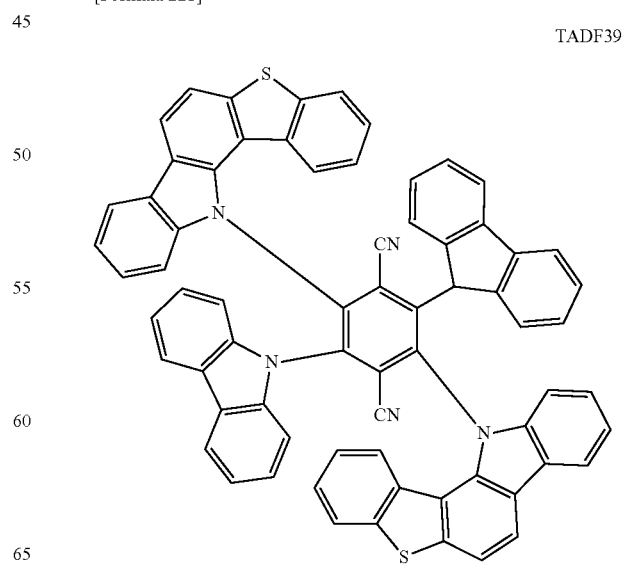

[Formula 222]
HA
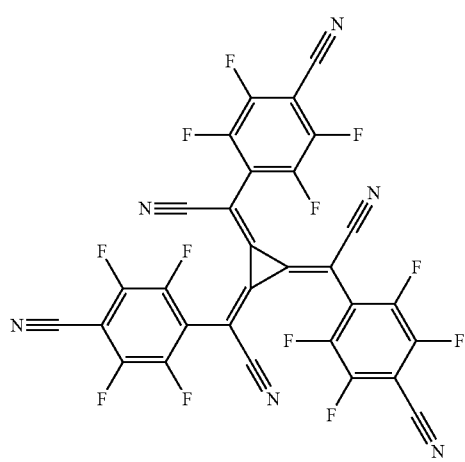
[Formula 223]
HT-1
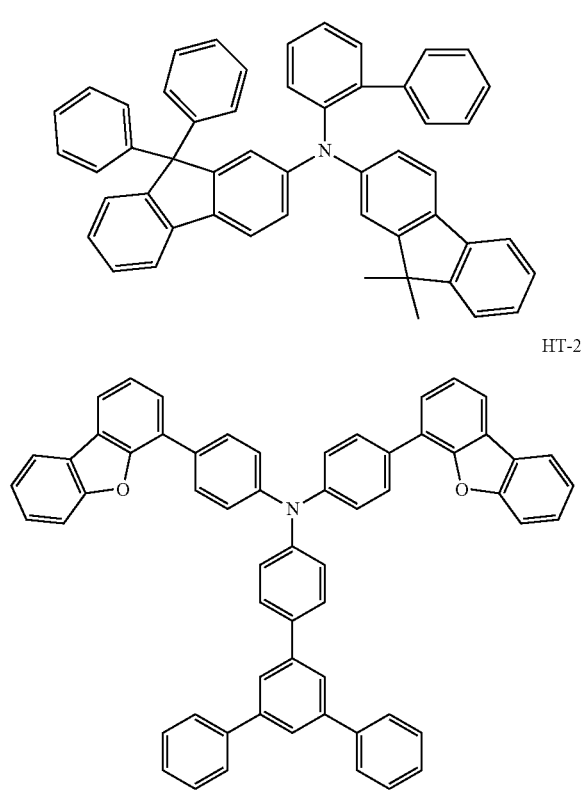
HT-2
[Formula 224]
CBP
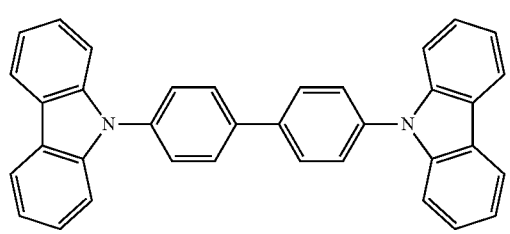
RD-1
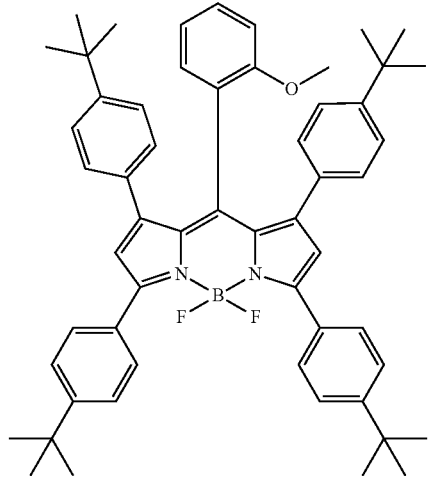
[Formula 225]
ET-1
ET-2

-continued
[Formula 226]
HT-3
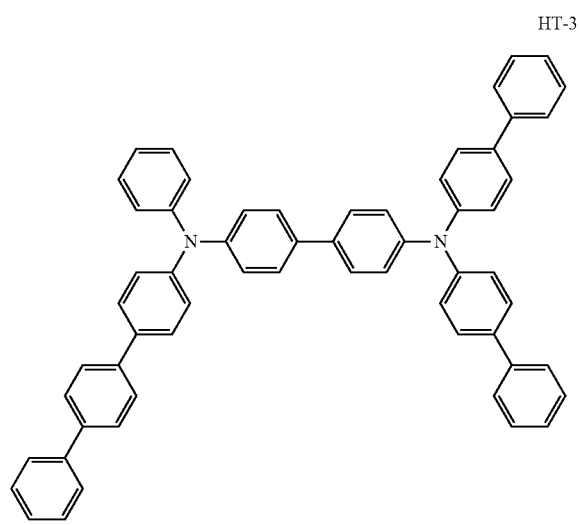
RD-4
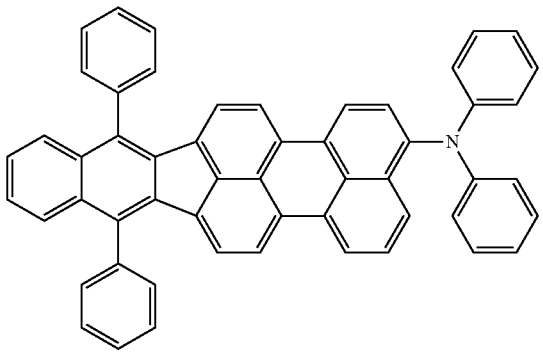
[Formula 228]
RD-2
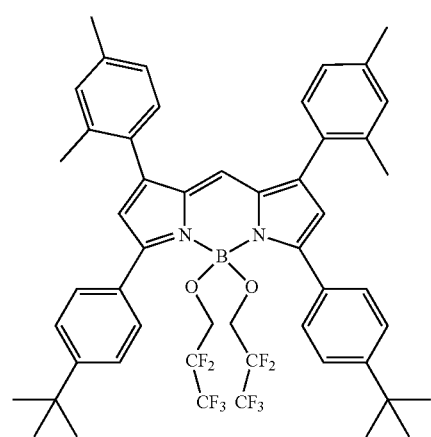
Comparative Compound 1
[Formula 227]
RD-3
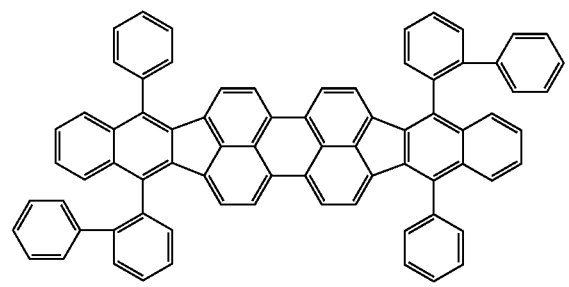
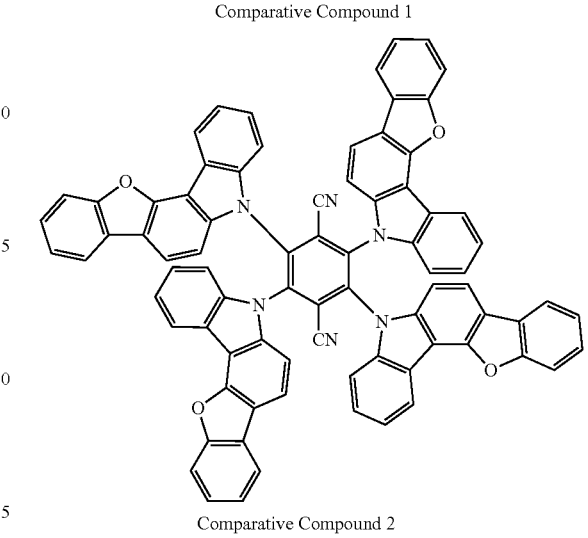
Comparative Compound 2

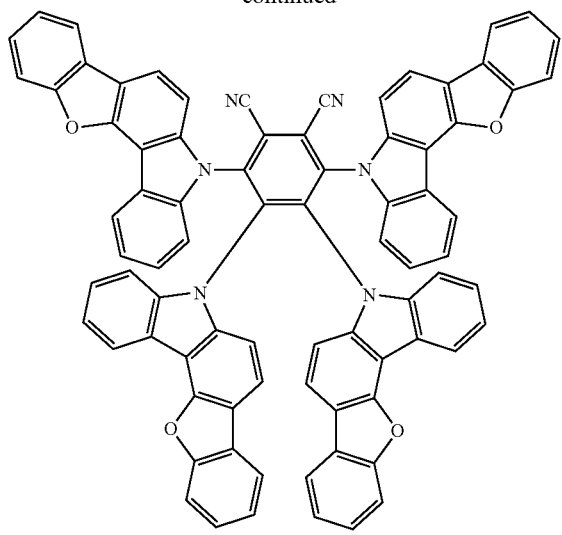

Comparative Compound 3

(1) Synthesis Example 1: Synthesis of Compound TADF1

(1-1) Synthesis of Intermediate A

[Formula 230]

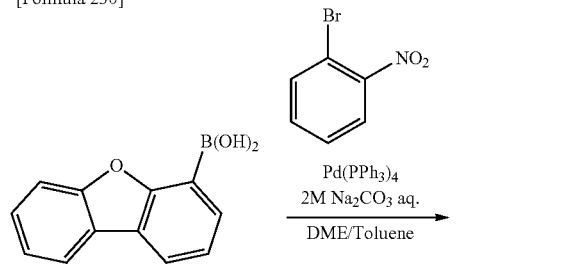

Under nitrogen atmosphere, 2M sodium carbonate aqueous solution (124 mL, 248 mmol), 1,2-dimethoxyethane (DME) (250 mL), toluene (250 mL), and tetrakis(triphenylphosphine)palladium(0) (Pd[PPh$_3$]$_4$) (7.2 g, 6.2 mmol) were added to 2-bromonitrobenzene (25.0 g, 123.8 mmol) and 4-dibenzofuran boronic acid (31.5 g, 148.5 mmol) and the obtained mixture was heated to reflux with stirring for 12 hours. After the reaction, the mixture was cooled to the room temperature (25 degrees C.). A sample was transferred to a separating funnel, added with water (500 mL), and extracted with dichloromethane. The extracted sample was dried over MgSO$_4$, filtered and condensed. The obtained sample was purified by silica-gel column chromatography to obtain a white solid (24.0 g). The solid was identified as an intermediate A by analysis according to FD-MS (Field Desorption Mass Spectrometry) (a yield rate: 67%).

(1-2) Synthesis of Intermediate B

[Formula 231]

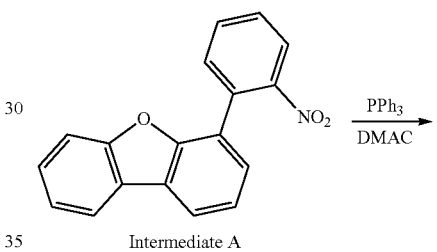

Intermediate A

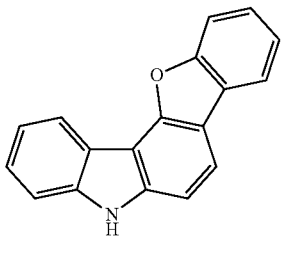

Intermediate B

Under argon atmosphere, dimethylacetamide (DMAC) (166 mL) was added to the intermediate A (24.0 g, 83.0 mmol) and triphenylphosphine (PPh$_3$) (54.4 g, 207.4 mmol) and the obtained mixture was heated to reflux with stirring for 20 hours. After the reaction, the mixture was cooled to the room temperature (25 degrees C.). A sample was transferred to a separating funnel, added with water (400 mL), and extracted with dichloromethane. The extracted sample was dried over MgSO$_4$, filtered and condensed. The obtained sample was purified by silica-gel column chromatography to obtain a white solid (14.5 g). The solid was identified as an intermediate B by analysis according to FD-MS (a yield rate: 68%).

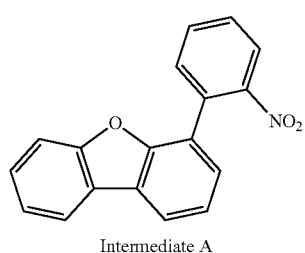

Intermediate A

(1-3) Synthesis of Intermediate C

[Formula 232]

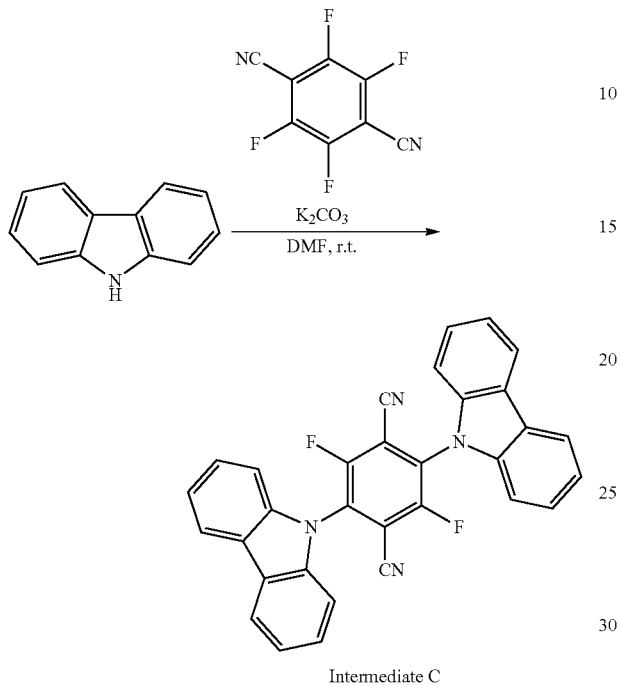

Intermediate C

Under nitrogen atmosphere, to a 50-mL Schlenk tube, carbazole (2.0 g, 12 mmol), potassium carbonate (3.3 g, 24 mmol), tetrafluoroterephthalonitrile (4.8 g, 24 mmol), and N,N-dimethyl formamide (DMF) (20 mL) were added and stirred at the room temperature (25 degrees C.). After eight hours, water (200 mL) was added to the mixture. The deposited solid was purified by silica-gel column chromatography to obtain an orange solid (1.95 g). The solid was identified as an intermediate C by analysis according to ASAP-MS (Atmospheric Pressure Solid Analysis Probe Mass Spectrometry) and $^1$H-NMR (a yield rate: 66%). In the scheme, "r.t," represents the room temperature.

(1-4) Synthesis of TADF1

[Formula 233]

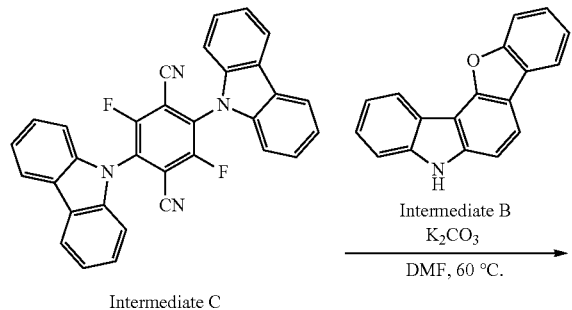

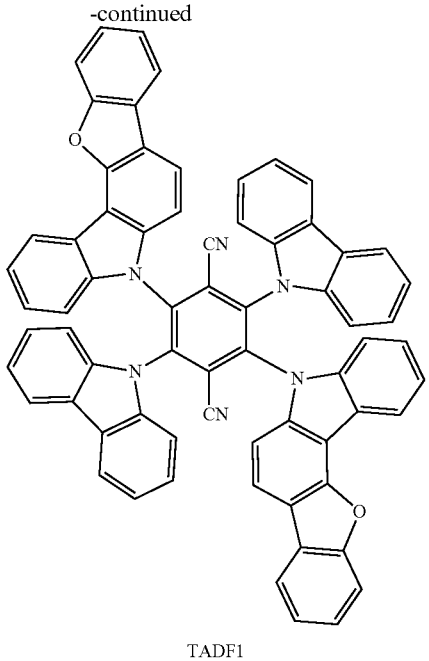

TADF1

Under nitrogen atmosphere, to a 50-mL Schlenk tube, the intermediate C (0.57 g, 2.2 mmol), potassium carbonate (0.62 g, 4.4 mmol), the intermediate B (0.5 g, 1.0 mmol), and DMF (10 mL) were added and stirred at 60 degrees C. for six hours. After the reaction, the mixture was cooled to the room temperature (25 degrees C.). Water (200 mL) was added to the mixture. The deposited solid was purified by silica-gel column chromatography to obtain a red solid (0.75 g). The solid was identified as TADF1 by analysis according to ASAP-MS and $^1$H-NMR (a yield rate: 77%).

Example 1a

The same compound TADF1 as that in Example 1 was prepared according to the following method. The compound TADF1 prepared in Example 1 was used for Evaluation of Compounds described later.

Synthesis of Intermediate a

[Formula 234]

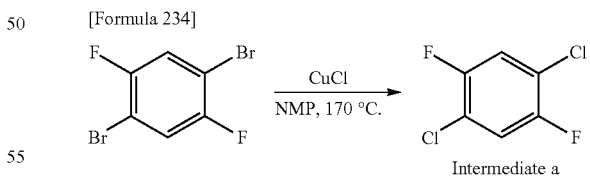

Intermediate a

Under nitrogen atmosphere, into a 500-mL eggplant flask, 1,4-dibromo-2,5-difluorobenzene (15.2 g, 55.9 mmol), copper chloride(I) (13.8 g, 139 mmol), and NMP (200 mL) were put and heated at 170 degrees C. with stirring. After four hours, the mixture was heated to 175 degrees C., further stirred for 1 hour, and then cooled to the room temperature (25 degrees C.). Water (200 mL) was added to the mixture. The deposited solid was removed by filtration through cerite. The filtrate was extracted with ethyl acetate. Subsequently, the obtained organic layer was washed with water and a saturated saline solution. After being dried over magnesium sulfate, the solvent was removed by a rotary evaporator under reduced pressure. The obtained compound was isolated and purified by silica-gel column chromatography to obtain 1,4-dichloro-2,5-difluorobenzene (intermediate a) (4.11 g, 22.5 mmol, a yield rate of 40%).

Synthesis of Intermediate b

[Formula 235]

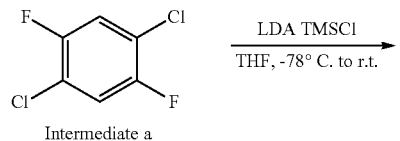

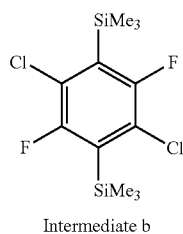

Intermediate b

Under nitrogen atmosphere, into a 200-mL three-necked flask, 1,4-dichloro-2,5-difluorobenzene (intermediate a) (4.11 g, 22.5 mmol), chlorotrimethylsilane (TMSCl) (6.3 mL, 50 mmol), and THF (25 mL) were put. The mixture was cooled to −78 degrees C. in a dry ice/aceton bath. Subsequently, lithium diisopropylamide (LDA), which was prepared, was all dropped into the mixture. The obtained solution was stirred for two hours at the room temperature (25 degrees C.). After added with water (10 mL), the solution was extracted with ethyl acetate. Subsequently, the obtained organic layer was washed with water and a saturated saline solution. After being dried over magnesium sulfate, the solvent was removed by a rotary evaporator under reduced pressure. The obtained 2,5-dichloro-3,6-difluoro-1,4-phenylenebistrimethylsilane (intermediate b) (6.61 g, 20.2 mmol) was not puried and used in a next reaction.

Synthesis of Intermediate c

[Formula 236]

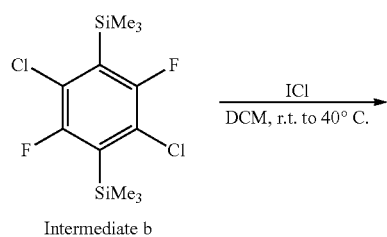

Intermediate b

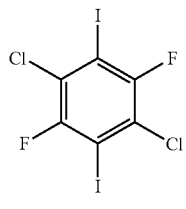

Intermediate c

Under nitrogen atmosphere, into a 500-mL eggplant flask, 2,5-dichloro-3,6-difluoro-1,4-phenylenebistrimethylsilane (intermediate b)(6.61 g, 20.2 mmol), and dichloromethane (DCM) (100 mL) were put. Iodine monochloride (2.5 mL) was dropped into the mixture at the room temperature (25 degrees C.) and subsequently stirred at 40 degrees C. Iodine monochloride (2.5 mL) was dropped into a reaction system every two hours, resulting in addition of the total amount of 4.5 mL of iodine monochoride. After all of iodine monochoride was dropped into the reactant mixture, the reactant mixture was further stirred for 1 hour and 30 minutes and returned to the room temperature (25 degrees C.). The reactant mixture was added with a saturated acueous solution of sodium thiosulfate (20 mL) and extracted with dichloromethane. Subsequently, the obtained organic layer was washed with water and a saturated saline solution. After being dried over magnesium sulfate, the solvent was removed by a rotary evaporator under reduced pressure. The obtained solution was purified by silica-gel column chromatography (eluent:hexane) to obtain 1,4-dichloro-2,5-difluoro-3,6-diiodobenzene (intermediate c) (6.20 g, 14.3 mmol, a yield rate of 71%).

Synthesis of Intermediate d

[Formula 237]

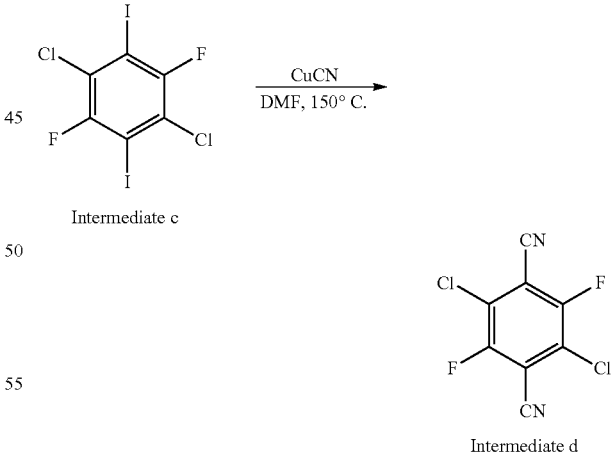

Intermediate d

Into a 5-mL vial, 1,4-dichloro-2,5-difluoro-3,6-diiodobenzene (intermediate c) (435 mg, 1.0 mmol), copper cyanide (360 mg, 4.0 mmol), and DMF (5 mL) were put and heated at 150 degrees C. with stirring. After 1 hour and 30 minutes, the reaction solution was cooled to the room temperature (25 degrees C.) and poured into 10-mL ammonia water. After the reaction solution was extracted with methylene chloride, the obtained organic layer was washed

Synthesis of Intermediate e

[Formula 238]

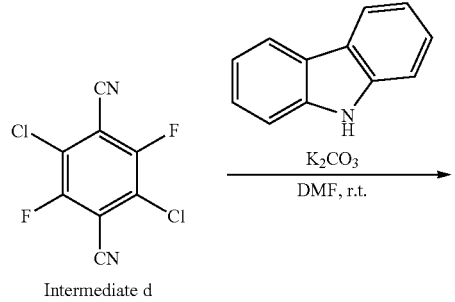

Intermediate d

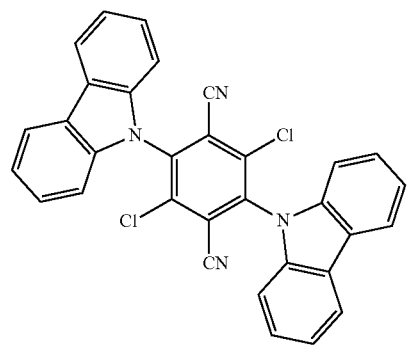

Intermediate e

Under nitrogen atmosphere; into a 50-mL eggplant flask, 1,4-dicyano-2,5-dichloro-3,6-difluorobenzene (intermediate d)(348 mg; 1.5 mmol), 9H-carbazole (501 mg, 3.0 mmol), potassium carbonate (415 mg, 3.0 mmol), and DMF (10 mL) were put and stirred at the room temperature (25 degrees C.). After 1 hour, water and methanol were each added at 3 mL to the mixture. The obtained mixture was extracted with methylene chloride. Subsequently, the obtained organic layer was washed with water and a saline solution; and dried over magnesium sulfate. The solvent was removed by a rotary evaporator under reduced pressure. The obtained compound was purified by silica-gel column chromatography to obtain 1,4-dicyano-25-di(9H-carbazolyl)-3,6-dichlorobenzene (intermediate e) (345 mg, 0.65 mmol, a yield rate of 44%). The obtained product (intermediate e) was identified in terms of a structure according to $^1$H-NMR and LCMS (Liquid chromatography mass spectrometry).

with water and a saturated saline solution. After being dried over magnesium sulfate, the solvent was removed by a rotary evaporator under reduced pressure. The obtained solution was purified by silica-gel column chromatography (eluent:hexane/ethyl acetate=5/1 (volume ratio) to obtain 1,4-dicyano-2,5-dichloro-3,6-difluorobenzene (intermediate d) (0.16 g).

Synthesis of TADF1

[Formula 239]

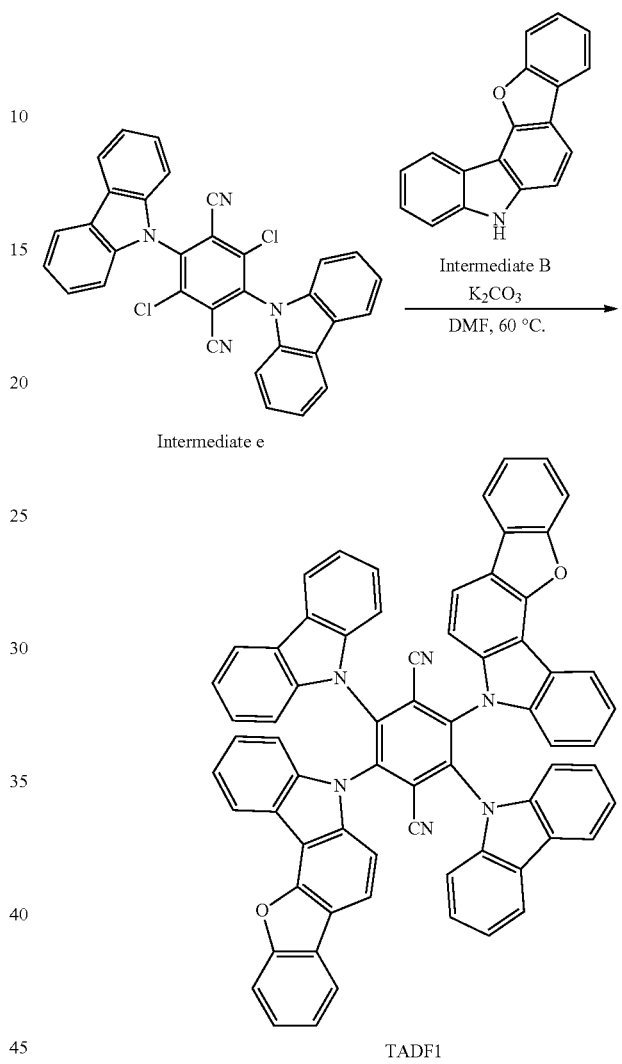

Into a 5-mL vial, 1,4-dicyano-2,5-di(9H-carbazolyl)-3,6-dichlorobenzene (intermediate e) (52 mg, 0.1 mmol), 5H-benzofuro[3,2-c]carbazole (intermediate B) (62 mg, 0.24 mmol), potassium carbonate (34 mg, 0.25 mmol), and DMF (2 mL) were put and heated with stirring at 60 degrees C. for 10 hours. After cooled to the room temperature (25 degrees C.), the reaction solution was purified by silica-gel column chromatography to obtain 1,4-dicyano-2,5-bis(5H-benzofuro[3,2-c]carbazole-5-yl)-3,6-di(9H-carbazolyl)benzene (TADF1) (27 mg, 0.028 mmol, a yield rate of 30%). The obtained product (TADF1) was identified in terms of a structure according to $^1$H-NMR and LCMS.

Moreover, it was confirmed that the measurement result according to $^1$H-NMR of the compound obtained by the method of Example 1a was in line with the measurement result according to $^1$H-NMR of the compound TADF1 obtained by the method of Example 1.

It should be noted that the intermediate B used in Example 1a was prepared by the same method as the synthesis method of the intermediate B in Example 1, Example 2
(2) Synthesis Example 2: Synthesis of Compound TADF2
(2-1) Synthesis of TADF2
[Formula 240]
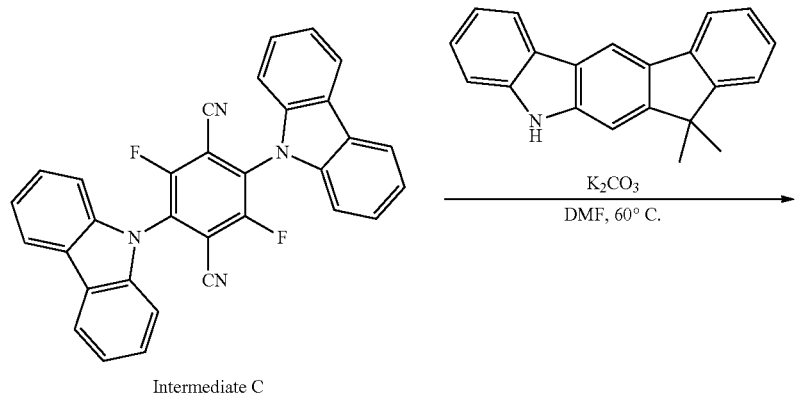
Intermediate C
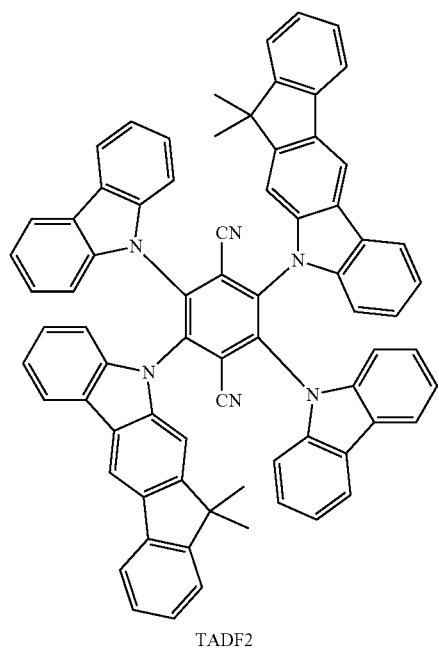
TADF2

Under nitrogen atmosphere, to a 50-mL Schlenk tube, 7,7-dimethyl-5H-indeno[2,1-b]carbazole (0.63 g, 2.2 mmol), potassium carbonate (0.62 g, 4.4 mmol), the intermediate C (0.5 g, 1.0 mmol), and DMF (10 mL) were added and stirred at 60 degrees C. for six hours. After the reaction, the mixture was cooled to the room temperature (25 degrees C.). Water (30 mL) was added to the mixture. The deposited solid was purified by silica-gel column chromatography to obtain a red solid (0.82 g). The solid was identified as TADF2 by analysis according to ASAP-MS (a yield rate: 79%).

Example 3

(3) Synthesis Example 3: Synthesis of Compound TADF3

(3-1) Synthesis of Intermediate D

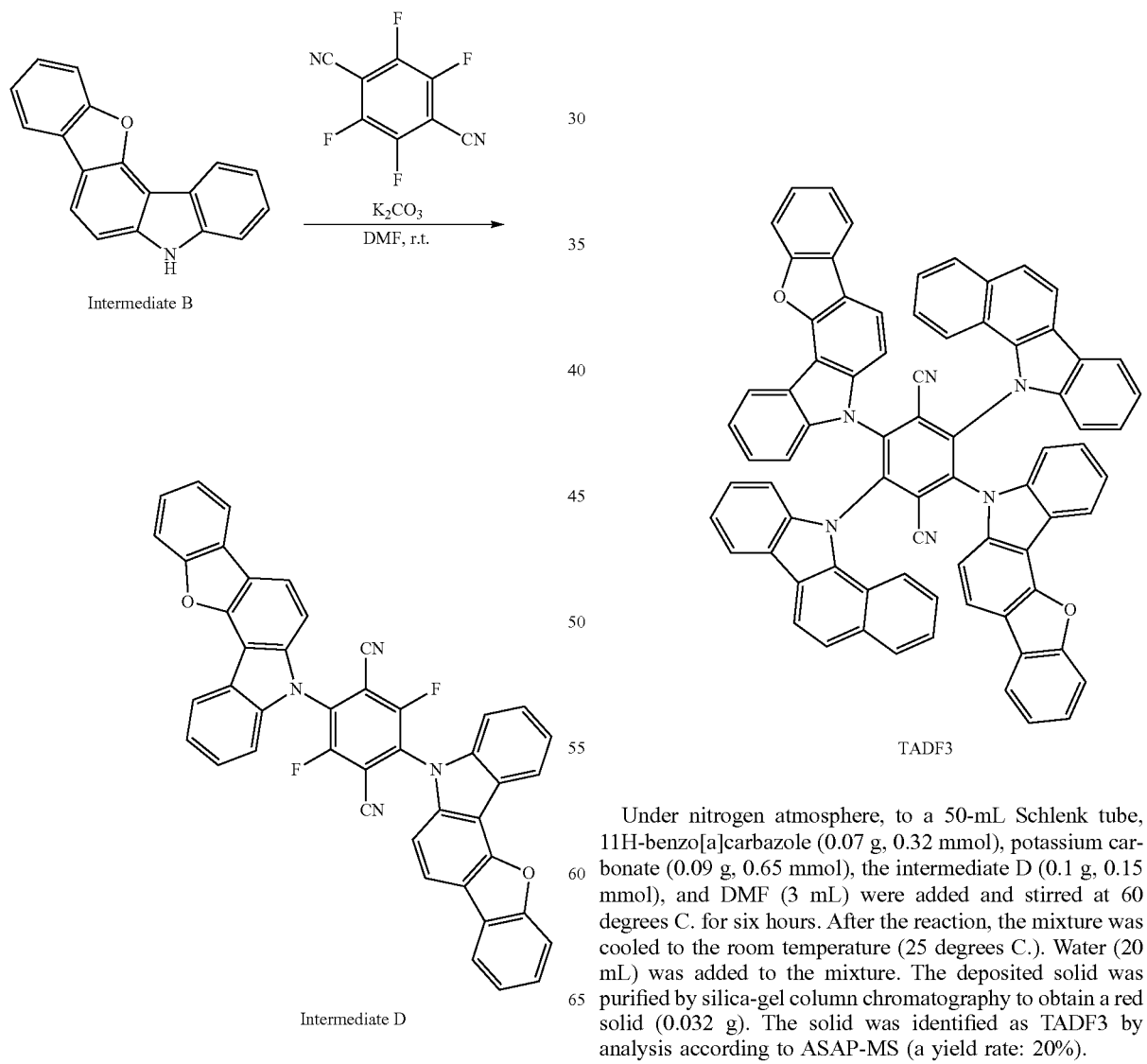

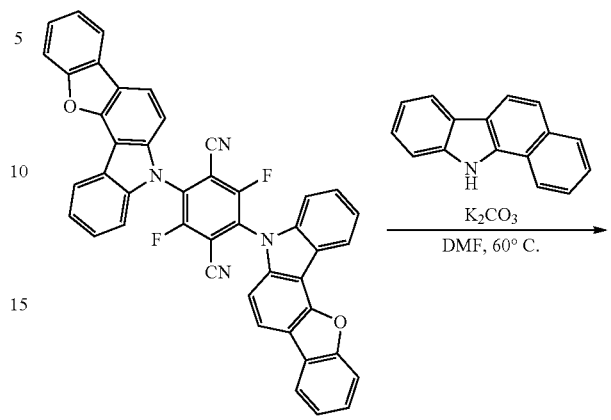

TADF3

Under nitrogen atmosphere, to a 50-mL Schlenk tube, 11H-benzo[a]carbazole (0.07 g, 0.32 mmol), potassium carbonate (0.09 g, 0.65 mmol), the intermediate D (0.1 g, 0.15 mmol), and DMF (3 mL) were added and stirred at 60 degrees C. for six hours. After the reaction, the mixture was cooled to the room temperature (25 degrees C.). Water (20 mL) was added to the mixture. The deposited solid was purified by silica-gel column chromatography to obtain a red solid (0.032 g). The solid was identified as TADF3 by analysis according to ASAP-MS (a yield rate: 20%).

Example 4

(4) Synthesis Example 4: Synthesis of Compound TADF4

(4-1) Synthesis of Intermediate E

[Formula 243]

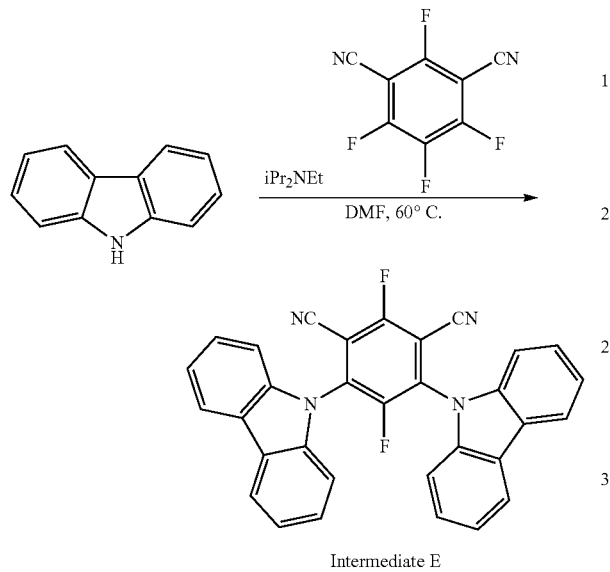

Intermediate E

Under nitrogen atmosphere, into a 500-mL three-necked flask, carbazole (17 g, 100 mmol), N,N-diisopropylethylamine (iPr$_2$NEt) (21 g, 150 mmol), tetrafluoroisophthalonitrile (8 g, 40 mmol), and N,N-dimethyl formamide (DMF) (200 mL) were put and heated at 60 degrees C. with stirring. After hour hours, water (1000 mL) was added to the reactant mixture. The deposited solid was purified by silica-gel column chromatography to obtain a yellow solid (7.5 g). The solid was identified as an intermediate E by analysis according to ASAP-MS and $^1$H-NMR (a yield rate: 38%).

(4-2) Synthesis of TADF4

[Formula 244]

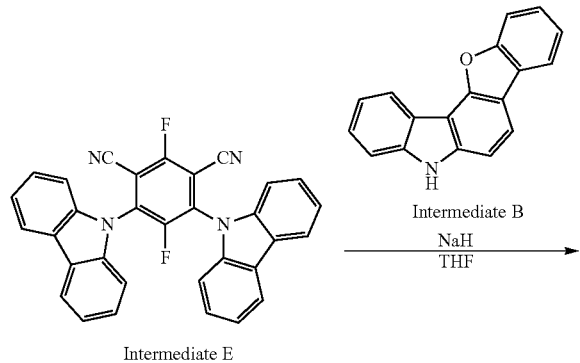

Intermediate E

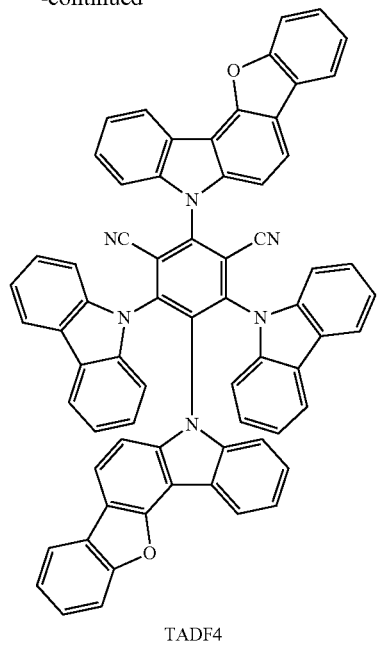

TADF4

Under nitrogen atmosphere, into a 100-mL three-necked flask, the intermediate B (1.9 g, 7.5 mmol), sodium hydride (containing oil at 40 mass %)(0.3 g, 7.5 mmol), and tetrahydrofuran (THF) (38 mL) were put, and stirred at the room temperature (25 degrees C.) for 30 minutes. Next, the intermediate E (1.5 g, 3 mmol) was put into the reactant mixture. After two hours, the reactant mixture was added to water (200 mL). The deposited solid was purified by silica-gel column chromatography to obtain an orange solid (2.47 g). The solid was identified as TADF4 by analysis according to ASAP-MS (a yield rate: 85%).

Example 5

(5) Synthesis Example 5: Synthesis of Compound TADF5

(5-1) Synthesis of Intermediate F

[Formula 245]

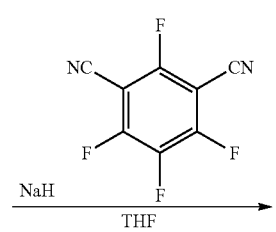

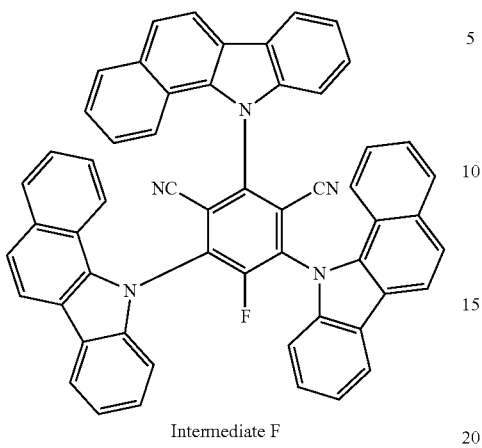

Intermediate F

Under nitrogen atmosphere, into a 300-mL three-necked flask, 11H-benzo[a]carbazole (10 g, 50 mmol), sodium hydride (containing oil at 40 mass %)(2 g, 50 mmol), and tetrahydrofuran (THF) (200 mL) were put, and stirred at the room temperature (25 degrees C.) for 30 minutes. Next, tetrafluoroisophthalonitrile (2.5 g, 12.5 mmol) was put into the reactant mixture. After two hours, the reactant mixture was added to water (200 mL). The deposited solid was purified by silica-gel column chromatography to obtain an orange solid (7.2 g). The solid was identified as an intermediate F by analysis according to ASAP-MS and $^1$H-NMR (a yield rate: 73%).

(5-2) Synthesis of TADF5

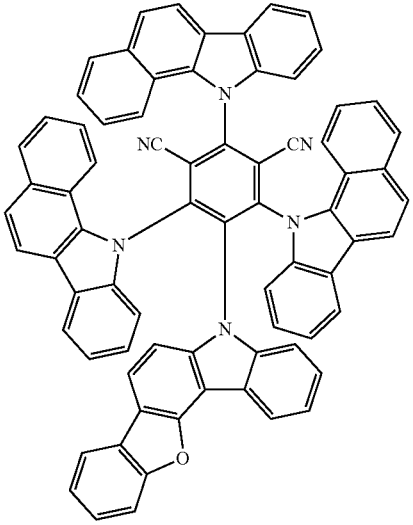

TADF5

Under nitrogen atmosphere, into a 100-mL three-necked flask, the intermediate B (0.77 g, 3.0 mmol), sodium hydride (containing oil at 40 mass %) (0.12 g, 3.0 mmol), and tetrahydrofuran (THF) (20 mL) were put, and stirred at the room temperature (25 degrees C.) for 30 minutes. Next, the intermediate F (2.0 g, 2.5 mmol) was put into the reactant mixture. After two hours, the reactant mixture was added to water (100 mL). The deposited solid was purified by silica-gel column chromatography to obtain a red solid (1.57 g). The solid was identified as TADF5 by analysis according to ASAP-MS (a yield rate: 61%).

Example 6

(6) Synthesis Example 6: Synthesis of Compound TADF6

(6-1) Synthesis of Intermediate G

[Formula 246]

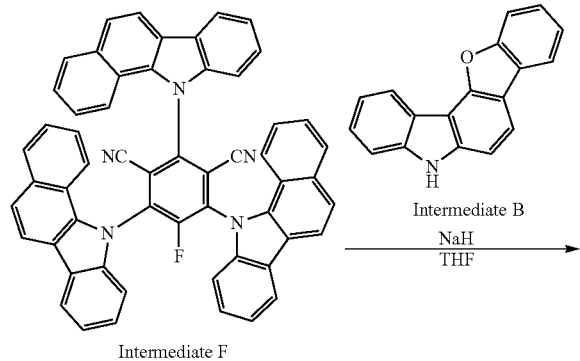

[Formula 247]

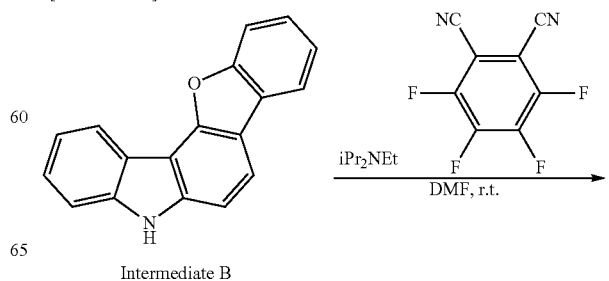

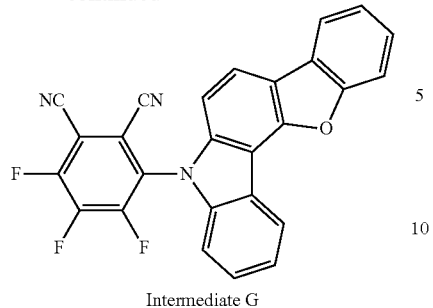

Intermediate G

Under nitrogen atmosphere, into a 500-mL three-necked flask, the intermediate B (13 g, 50 mmol), N,N-diisopropylethylamine (iPr$_2$NEt) (10 g, 75 mmol), tetrafluorophthalonitrile (20 g, 100 mmol), and N,N-dimethyl formamide (DMF) (250 mL) were put and stirred at the room temperature (25 degrees C.). After 12 hours, water (200 mL) was added to the mixture. The deposited solid was purified by silica-gel column chromatography to obtain an orange solid (9.8 g). The solid was identified as an intermediate F by analysis according to ASAP-MS (a yield rate: 45%).

(6-2) Synthesis of TADF6

[Formula 248]

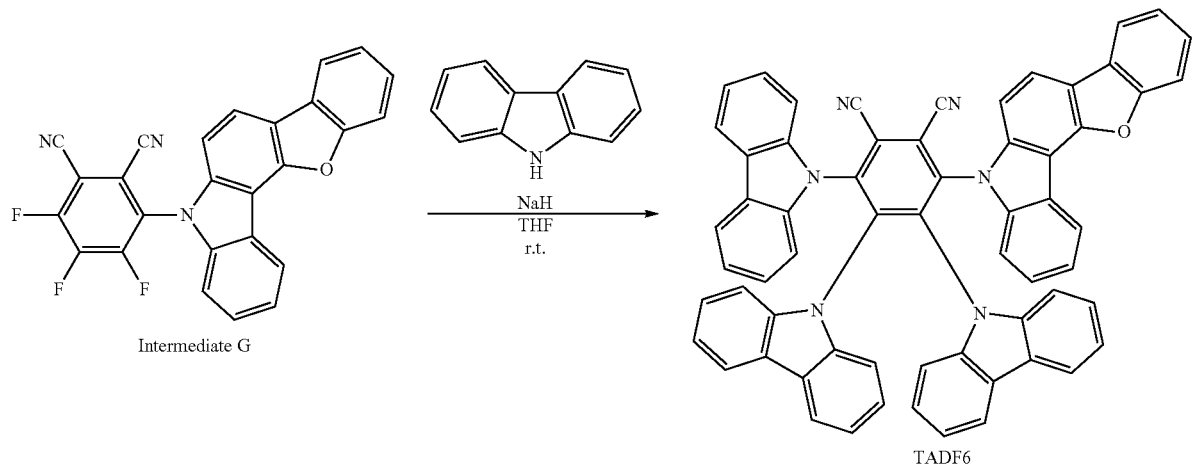

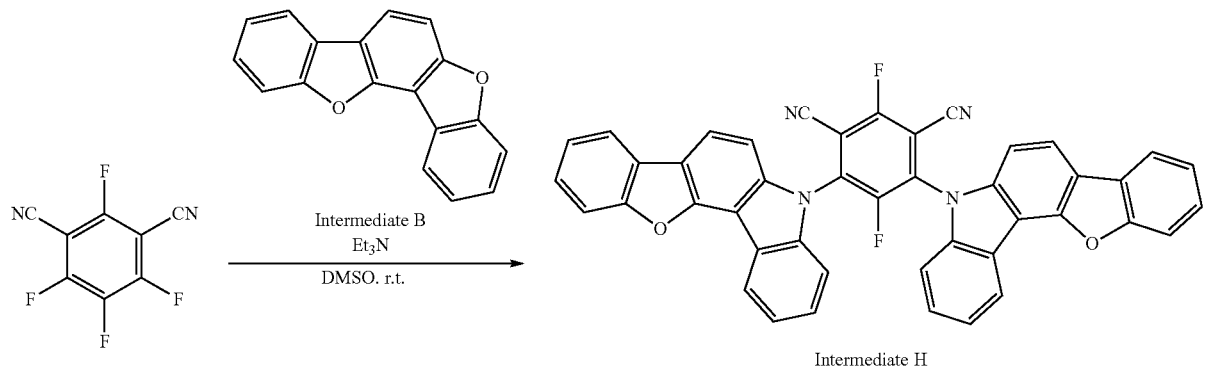

-continued
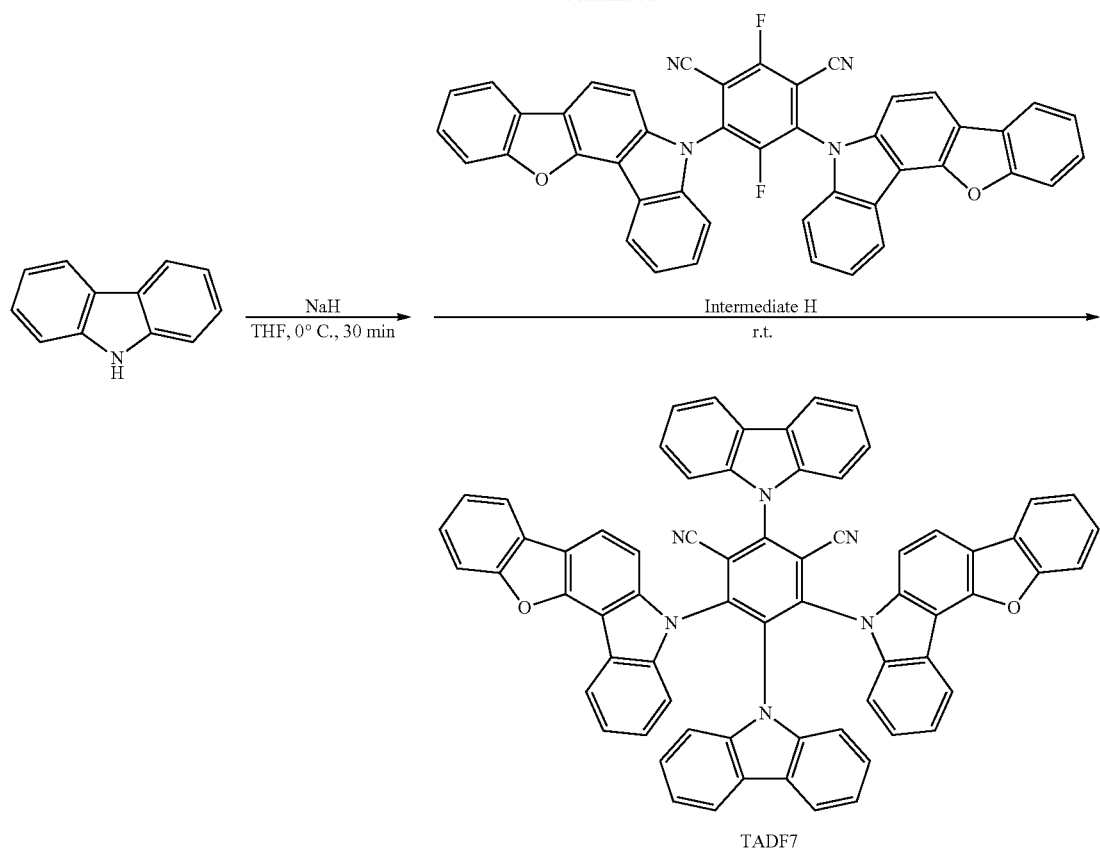
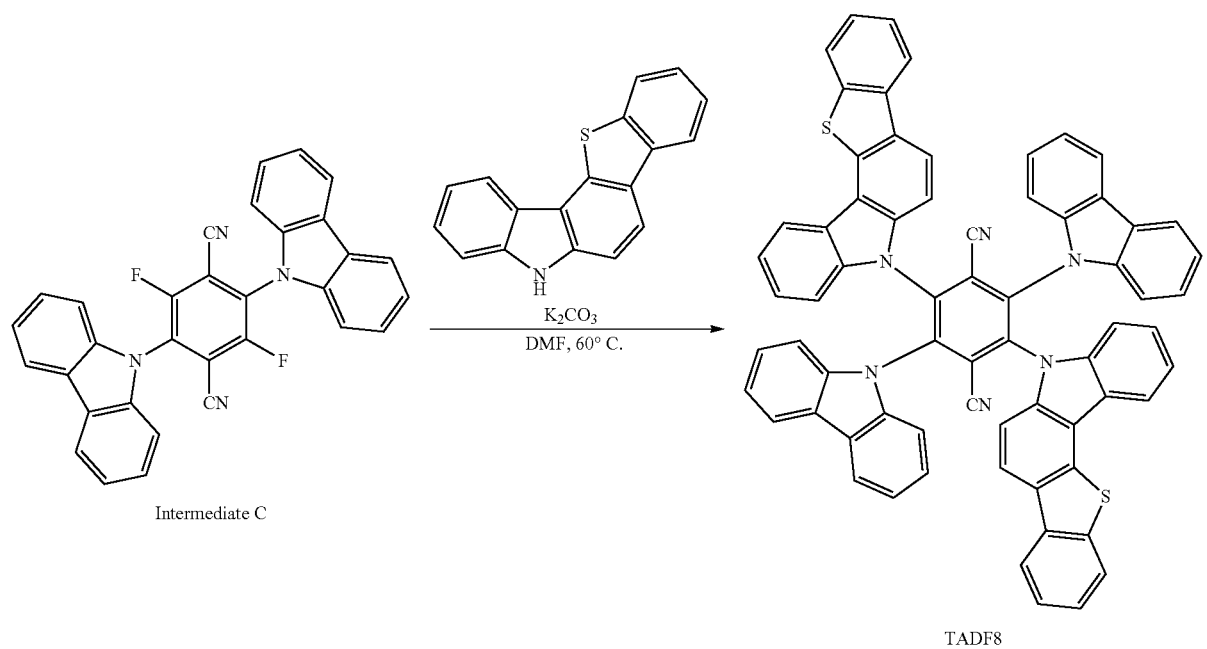

Under nitrogen atmosphere, to a 50-mL Schlenk tube, the intermediate C (1.0 g, 2.0 mmol), potassium carbonate (1.4 g, 10.0 mmol), 5H-Benzo[4,5]thieno[3,2-c]carbazole (1.4 g, 5.0 mmol), and DMF (20 mL) were added and stirred at 60 degrees C. for six hours. After the reaction, the mixture was cooled to the room temperature (25 degrees C.). Water (30 mL) was added to the mixture. The deposited solid was purified by silica-gel column chromatography to obtain a red solid (1.60 g). The solid was identified as TADF8 by analysis according to ASAP-MS (a yield rate: 80%).

Example 9

(9) Synthesis Example 9: Synthesis of Compound TADF9

(9-1) Synthesis of Intermediate K

[Formula 252]

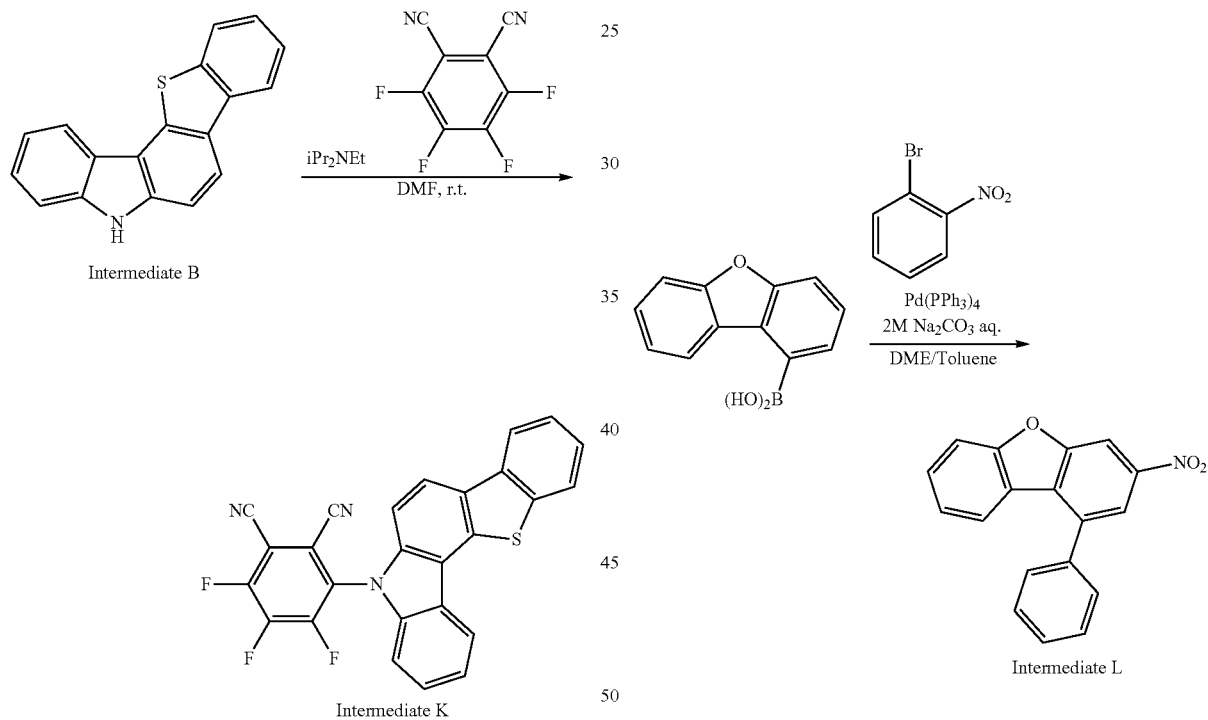

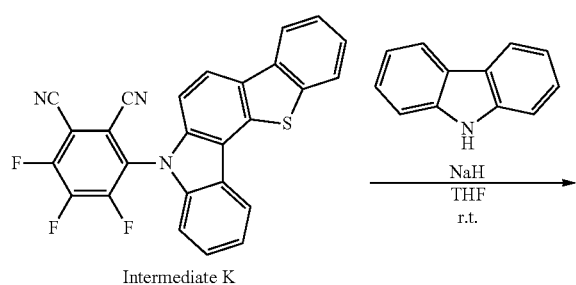

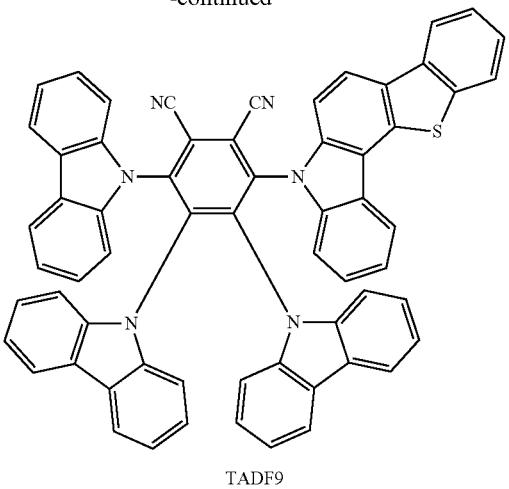

TADF9

Under nitrogen atmosphere, 2M sodium carbonate aqueous solution (100 mL, 200 mmol), 1,2-dimethoxyethane (DME) (200 mL), toluene (200 mL), and tetrakis(triphenylphosphine)palladium(0) (Pd[PPh₃]₄) (5.7 g, 5.0 mmol) were added to 2-bromonitrobenzene (20.0 g, 99.0 mmol) and 1-dibenzofuran boronic acid (25.2 g, 118.8 mmol) and the obtained mixture was heated to reflux with stirring for 12 hours.

After the reaction, the mixture was cooled to the room temperature (25 degrees C.). A sample was transferred to a separating funnel, added with water (500 mL), and extracted with dichloromethane. The extracted sample was dried over MgSO₄, filtered and condensed. The sample was purified by silica-gel column chromatography to obtain a white solid (20.0 g). The solid was identified as an intermediate L by analysis according to FD-MS (a yield rate: 70%).

(10-2) Synthesis of Intermediate M

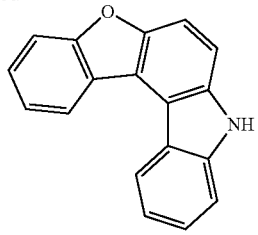

Intermediate M

[Formula 255]

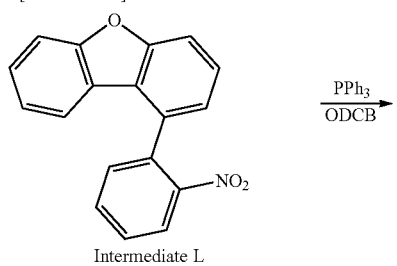

Intermediate L

Under argon atmosphere, orthodichlorobenzen (ODCB) (150 mL) was added to the intermediate L (20.0 g, 69.0 mmol) and triphenylphosphine (45.2 g, 172.5 mmol), and the obtained mixture was heated to reflux with stirring for 24 hours. After the reaction, the mixture was cooled to the room temperature (25 degrees C.). A sample was transferred to a separating funnel, added with water (400 mL), and extracted with dichloromethane. The extracted sample was dried over $MgSO_4$, filtered and condensed. The sample was purified by silica-gel column chromatography to obtain a white solid (9.0 g). The solid was identified as an intermediate M by analysis according to FD-MS (a yield rate: 51%).

(10-3) Synthesis of TADF10

[Formula 256]

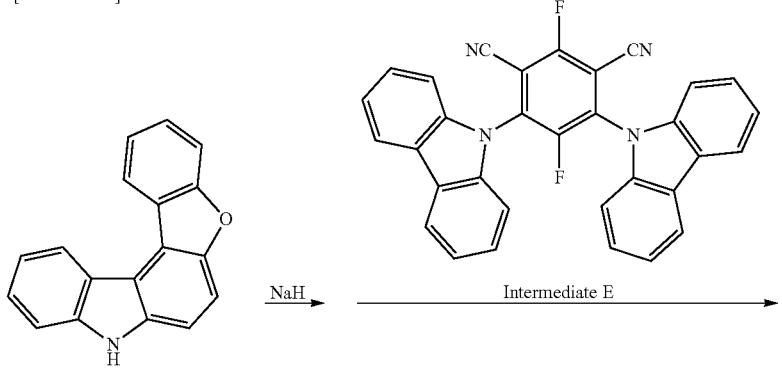

Intermediate M

-continued
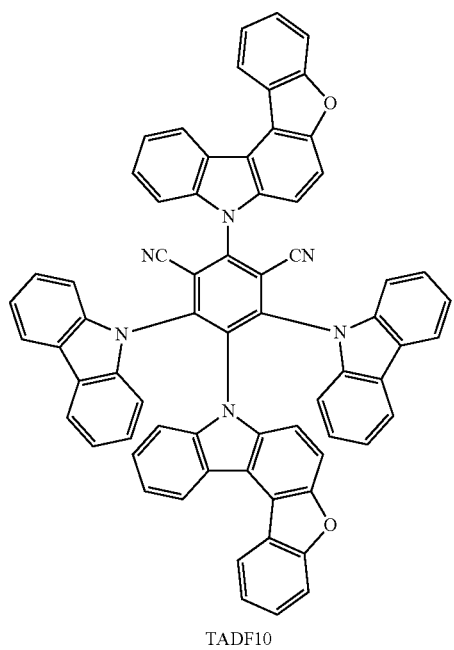
TADF10
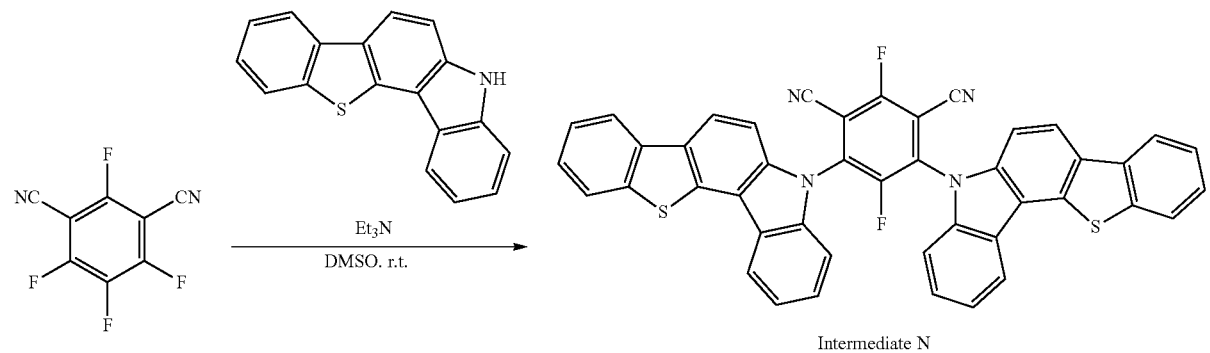
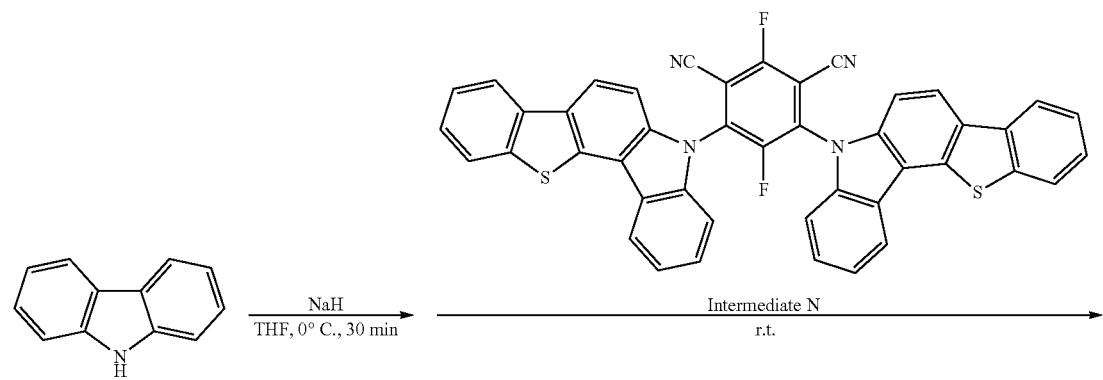

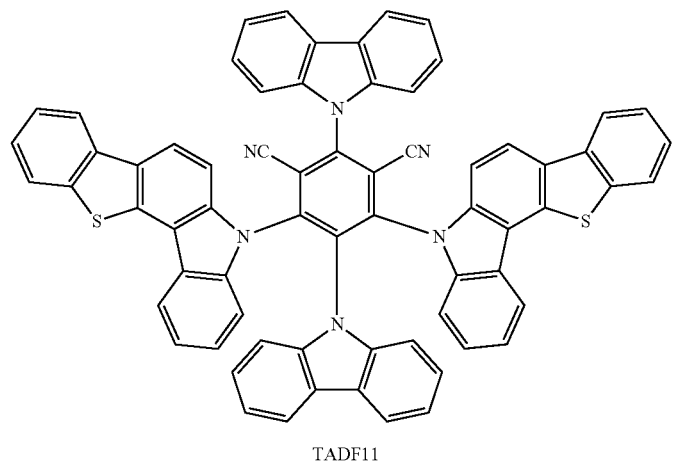
TADF11
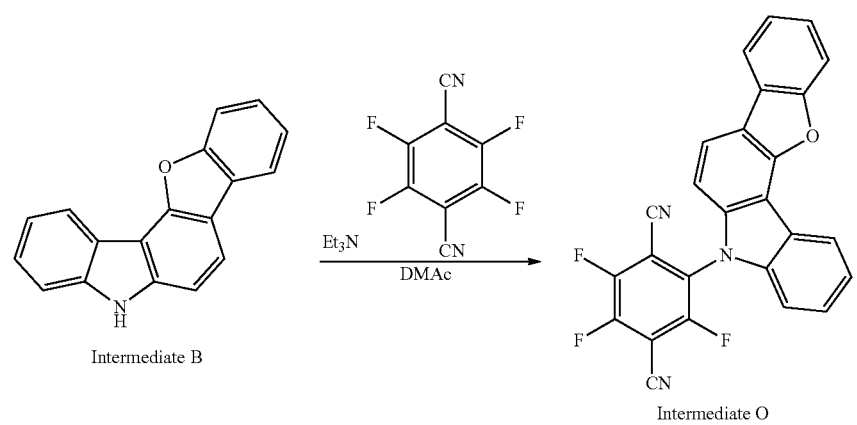
Intermediate B → Intermediate O

Under nitrogen atmosphere, into a 500-mL three-necked flask, the intermediate B (6.5 g, 25 mmol), triethylamine (Et₃N) (5.1 g, 50 mmol), tetrafluoroterephthalonitrile (20 g, 100 mmol), and N,N-dimethylacetamide (DMAc) (250 mL) were put. After heated with stirring for ten hours at 60 degrees C., the mixture was returned to the room temperature (25 degrees C.) and added with water (500 mL). The deposited solid was purified by silica-gel column chromatography to obtain a yellow solid (0.66 g). The solid was identified as an intermediate 0 by analysis according to ASAP-MS (a yield rate: 6%).

(12-2) Synthesis of TADF12

[Formula 260]

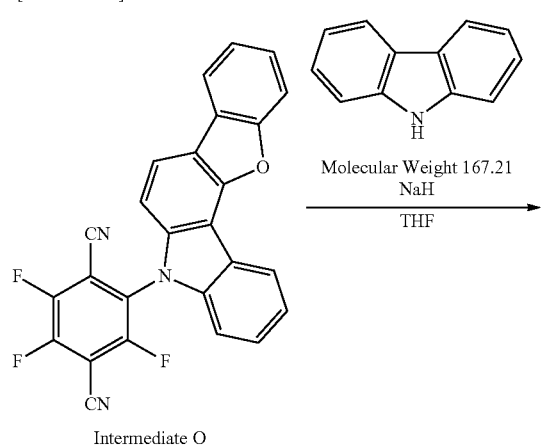

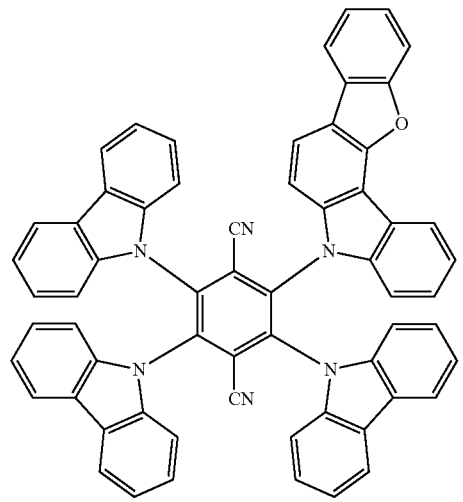

TADF12

Under nitrogen atmosphere, into a 100-mL three-necked flask, carbazole (0.77 g, 4.62 mmol), sodium hydride (0.18 g (60 mass %, dispersed in liquid paraffin), 4.62 mmol), and tetrahydrofuran (THF) (20 mL) were put, and the obtained mixture was stirred at the room temperature (25 degrees C.) for 30 minutes. Next, the intermediate 0 (0.5 g, 1.1 mmol) was put into the reactant mixture. After two hours, the reactant mixture was added with water (100 mL). The deposited solid was purified by silica-gel column chromatography to obtain a red solid (0.87 g). The solid was identified as TADF12 by analysis according to ASAP-MS (a yield rate: 90%).

Example 13

(13) Synthesis Example 13: Synthesis of Compound TADF13

(13-1) Synthesis of Intermediate V1

[Formula 261]

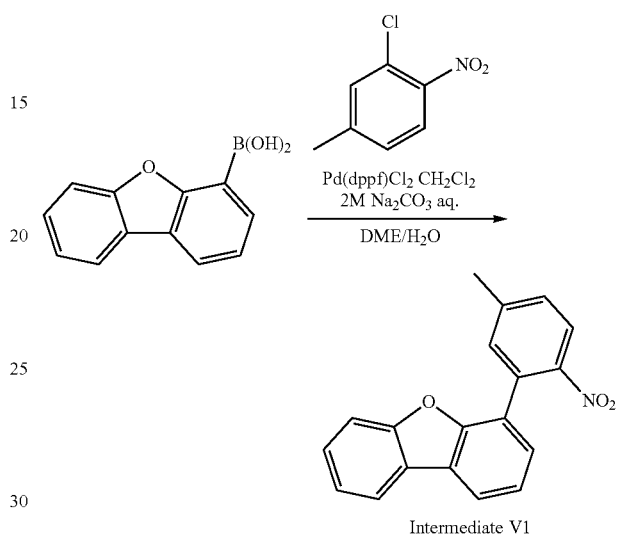

Intermediate V1

Under nitrogen atmosphere, 2M sodium carbonate aqueous solution (220 mL, 435 mmol), 1,2-dimethoxyethane (DME) (440 mL), and [1,1'-bis(diphenylphosphino)ferrocene]palladium(II)dichloride-dichloromethane adduct (Pd(dppf)Cl₂·CH₂Cl₂) (2.4 g, 2.9 mmol) were added to 3-chloro-4-nitrotoluene (25.0 g, 145 mmol) and 4-dibenzofuran boronic acid (30.7 g, 145 mmol). The obtained mixture was heated to reflux with stirring for four hours.

After the reaction, the mixture was cooled to the room temperature (25 degrees 0). A sample was transferred to a separating funnel, added with water (500 mL), and extracted with ethyl acetate. The extracted sample was dried over MgSO₄, filtered and condensed. The sample was purified by silica-gel column chromatography to obtain a yellow solid (35 g). The solid was identified as an intermediate V1 by analysis according to GC-MS (GasChromatograph Mass Spectrometry) (a yield rate: 80%).

(13-2) Synthesis of Intermediate V2

[Formula 262]

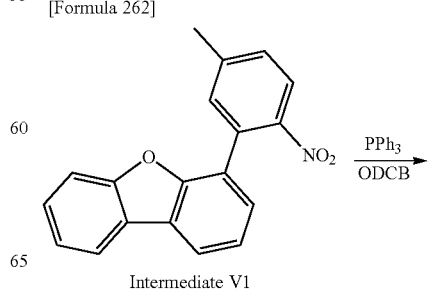

Intermediate V1

531
-continued

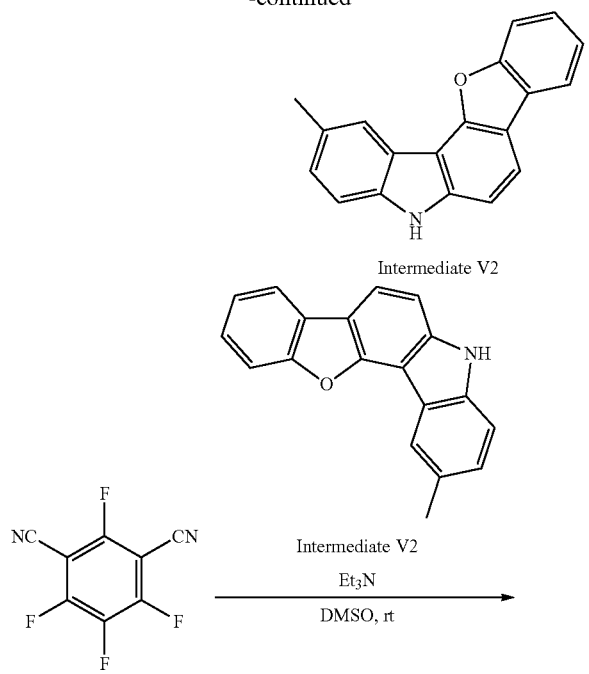

Intermediate V2

[Formula 264]

532
-continued

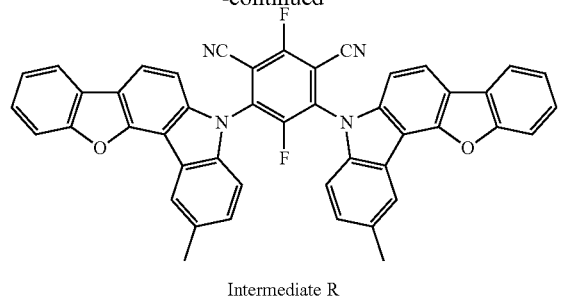

Intermediate R 25 mmol), the intermediate V2 (10.2 g, 37.5 mmol), triethylamine (Et₃N) (5.3 mL, 37.5 mmol), and DMSO (150 mL) were put, and the obtained mixture was stirred at the room temperature (25 degrees C.). After ten hours, water (200 mL) was added to the mixture. The deposited solid was collected by filtration using a Kiriyama funnel. The obtained solid was purified by silica-gel column chromatography to obtain a yellow solid (5.0 g). The solid was identified as an intermediate R by analysis according to ASAP-MS (a yield rate: 38%).

(13-4) Synthesis of TADF13

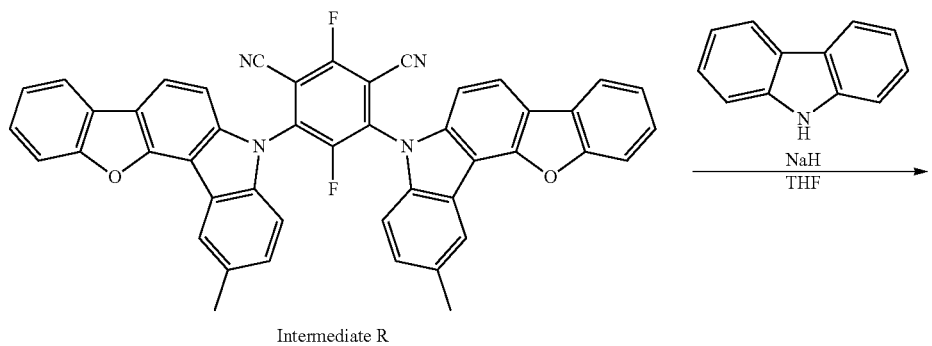

Intermediate R

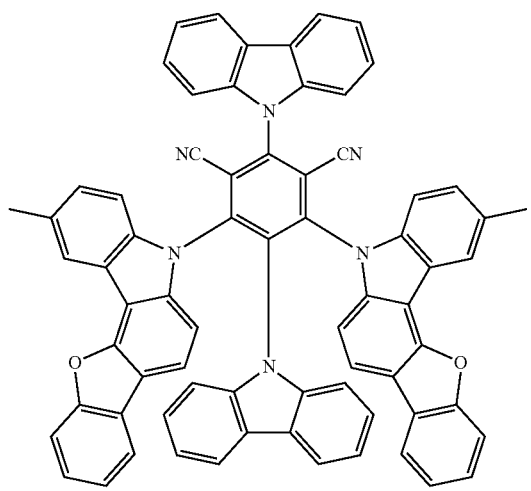

TADF13

Under nitrogen atmosphere, into a 100-mL three-necked flask, carbazole (3 g, 18 mmol), sodium hydride (0.72 g (60 mass %, dispersed in liquid paraffin), 18 mmol), and tetrahydrofuran (THF) (100 mL) were put, and the obtained mixture was stirred at the room temperature (25 degrees C.) for 30 minutes. Next, the intermediate R (1.5 g, 8.2 mmol) was put into the reactant mixture. After two hours, the reactant mixture was added with water (100 mL). The deposited solid was purified by silica-gel column chromatography to obtain an orange solid (4.5 g). The solid was identified as TADF13 by analysis according to ASAP-MS (a yield rate: 78%).

Example 14

(14) Synthesis Example 14: Synthesis of Compound TADF14

(14-1) Synthesis of Intermediate S

[Formula 265]

(14-2) Synthesis of TADF14

[Formula 266]

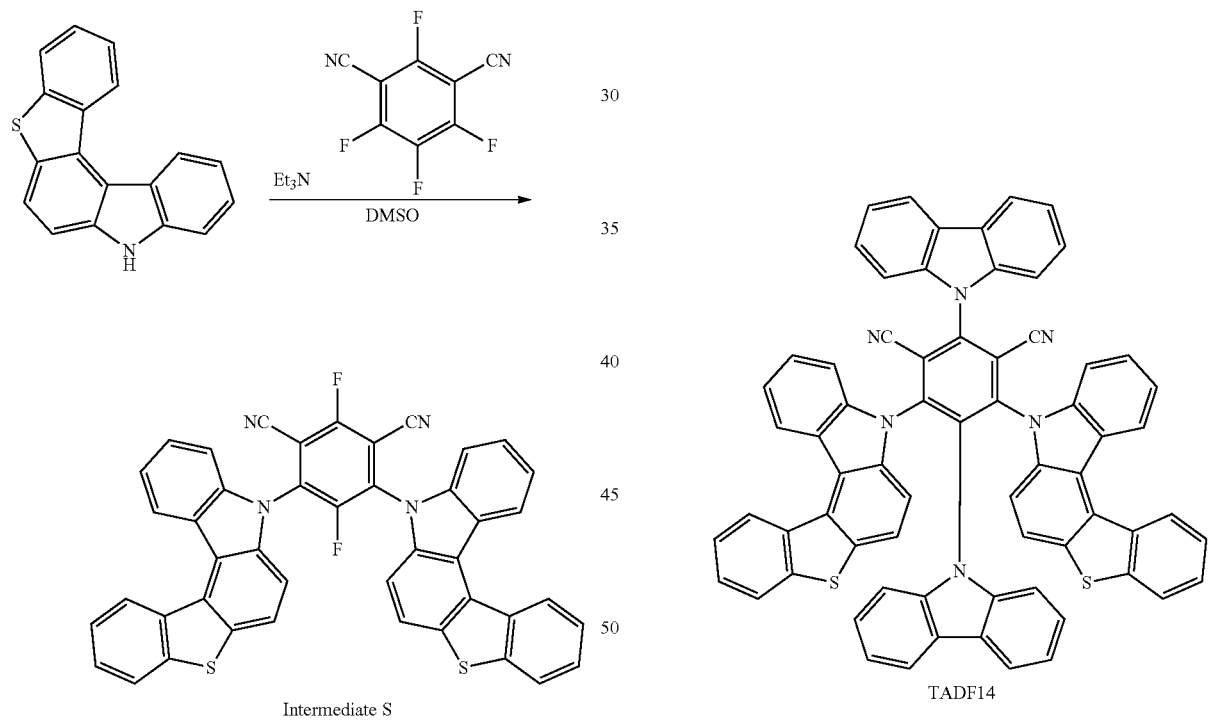

Under nitrogen atmosphere, into a 500-mL three-necked eggplant flask, tetrafluoroisophthalonitrile (5.0 g, 25 mmol), 8H-benzo[4,5]thieno[2,3-c]carbazole (10.2 g, 37.5 mmol), triethylamine (Et$_3$N) (5.3 mL, 37.5 mmol), and DMSO (150 mL) were put, and the obtained mixture was stirred at the room temperature (25 degrees C.). After eight hours, water (200 mL) was added to the mixture. The deposited solid was collected by filtration using a Kiriyama funnel. The obtained solid was purified by silica-gel column chromatography to obtain a yellow solid (8.5 g). The solid was identified as an intermediate S by analysis according to ASAP-MS (a yield rate: 64%).

Under nitrogen atmosphere, into a 100-mL three-necked flask, carbazole (3 g, 18 mmol), sodium hydride (0.72 g (60 mass %, dispersed in liquid paraffin), 18 mmol), and tetrahydrofuran (THF) (100 mL) were put, and the obtained mixture was stirred at the room temperature (25 degrees C.) for 30 minutes. Next, the intermediate S (1.5 g, 8.2 mmol) was put into the reactant mixture. After two hours, the reactant mixture was added with water (100 mL). The deposited solid was purified by silica-gel column chromatography to obtain an orange solid (2.8 g). The solid was identified as TADF14 by analysis according to ASAP-MS (a yield rate: 34%).

Example 15

(15) Synthesis Example 15: Synthesis of Compound TADF15

(15-1) Synthesis of Intermediate T

[Formula 267]

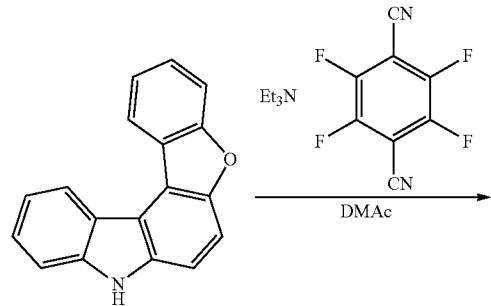

Intermediate M

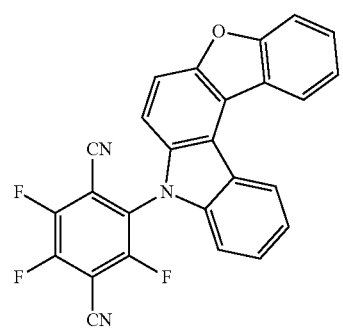

Intermediate T

Under nitrogen atmosphere, into a 500-mL three-necked flask, the intermediate B (6.5 g, 25 mmol), triethylamine (5.1 g, 50 mmol), tetrafluoroterephthalonitrile (20 g, 100 mmol), and N,N-dimethylacetamide (DMAc) (250 mL) were put. After heated with stirring for ten hours at 40 degrees C., the mixture was returned to the room temperature (25 degrees C.) and added with water (500 mL). The deposited solid was purified by silica-gel column chromatography to obtain a yellow solid (0.98 g). The solid was identified as an intermediate T by analysis according to ASAP-MS (a yield rate: 9%).

(15-2) Synthesis of TADF15

[Formula 268]

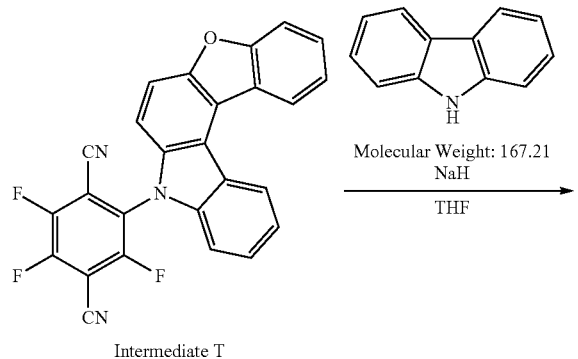

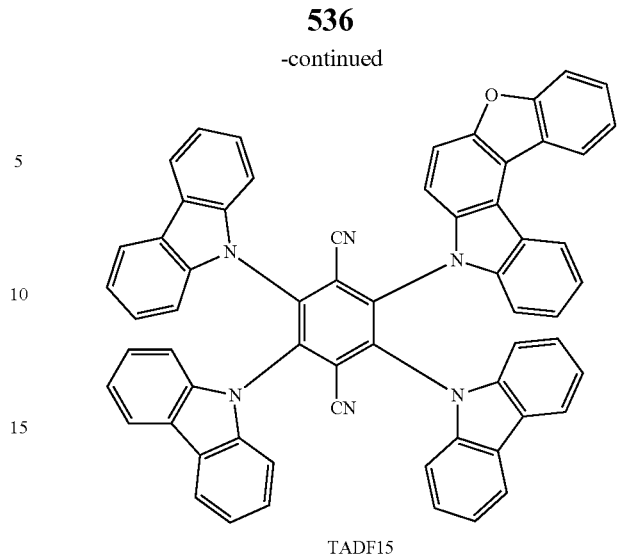

TADF15

Under nitrogen atmosphere, into a 100-mL three-necked flask, carbazole (0.61 g, 3.63 mmol), sodium hydride (0.15 g (60 mass %, dispersed in liquid paraffin), 3.63 mmol), and tetrahydrofuran (THF) (20 mL) were put, and the obtained mixture was stirred at the room temperature (25 degrees C.) for 30 minutes. Next, the intermediate 0 (0.8 g, 1.1 mmol) was put into the reactant mixture. After two hours, the reactant mixture was added with water (100 mL). The deposited solid was purified by silica-gel column chromatography to obtain a red solid (1.3 g). The solid was identified as TADF15 by analysis according to ASAP-MS (a yield rate: 81%).

Example 16

(16) Synthesis Example 16: Synthesis of Compound TADF16

(16-1) Synthesis of Intermediate U

[Formula 269]

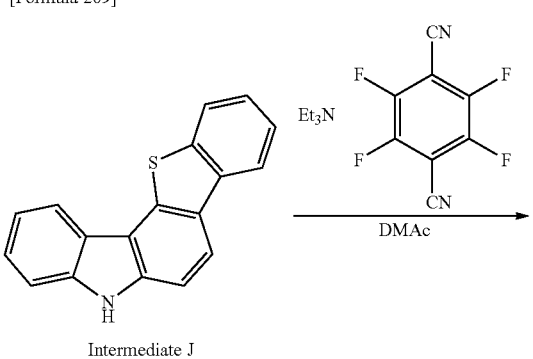

Intermediate J

537

-continued

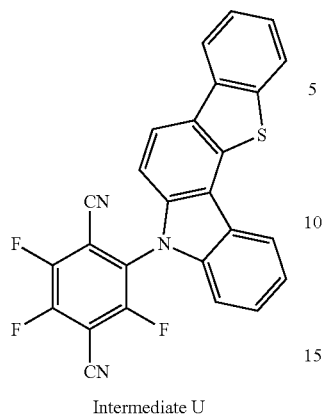

Intermediate U

Under nitrogen atmosphere, into a 500-mL three-necked flask, the intermediate B (6.8 g, 25 mmol), triethylamine (Et₃N)(5.1 g, 50 mmol), tetrafluoroterephthalonitrile (25 g, 125 mmol), and N,N-dimethylacetamide (DMAc) (250 mL) were put. After heated with stirring for ten hours at 40 degrees C., the mixture was returned to the room temperature (25 degrees C.) and added with water (500 mL). The deposited solid was purified by silica-gel column chromatography to obtain a yellow solid (1.5 g). The solid was identified as an intermediate U by analysis according to ASAP-MS (a yield rate: 13%).

(16-2) Synthesis of TADF16

[Formula 270]

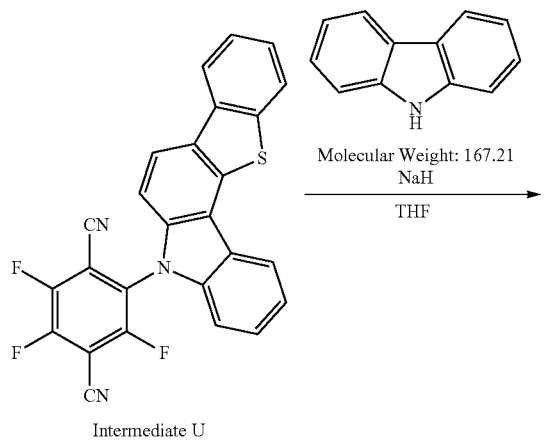

Intermediate U

538

-continued

TADF16

Under nitrogen atmosphere, into a 100-mL three-necked flask, carbazole (1.20 g, 7.26 mmol), sodium hydride (0.17 g (60 mass %, dispersed in liquid paraffin), 7.26 mmol), and tetrahydrofuran (THF) (20 mL) were put, and the obtained mixture was stirred at the room temperature (25 degrees C.) for 30 minutes. Next, the intermediate U (1.0 g, 2.2 mmol) was put into the reactant mixture. After two hours, the reactant mixture was added with water (100 mL). The deposited solid was purified by silica-gel column chromatography to obtain a red solid (1.7 g). The solid was identified as TADF16 by analysis according to ASAP-MS (a yield rate: 85%).

Example 17

(17) Synthesis Example 17: Synthesis of Compound TADF17

(17-1) Synthesis of TADF17

[Formula 271]

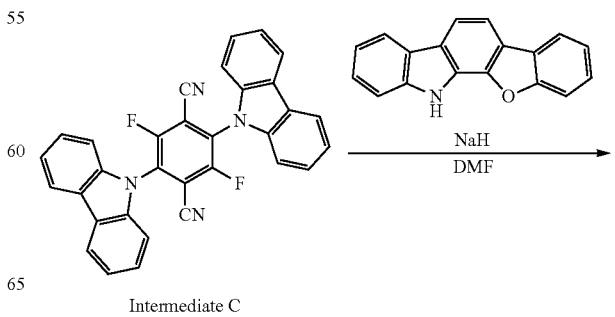

Intermediate C

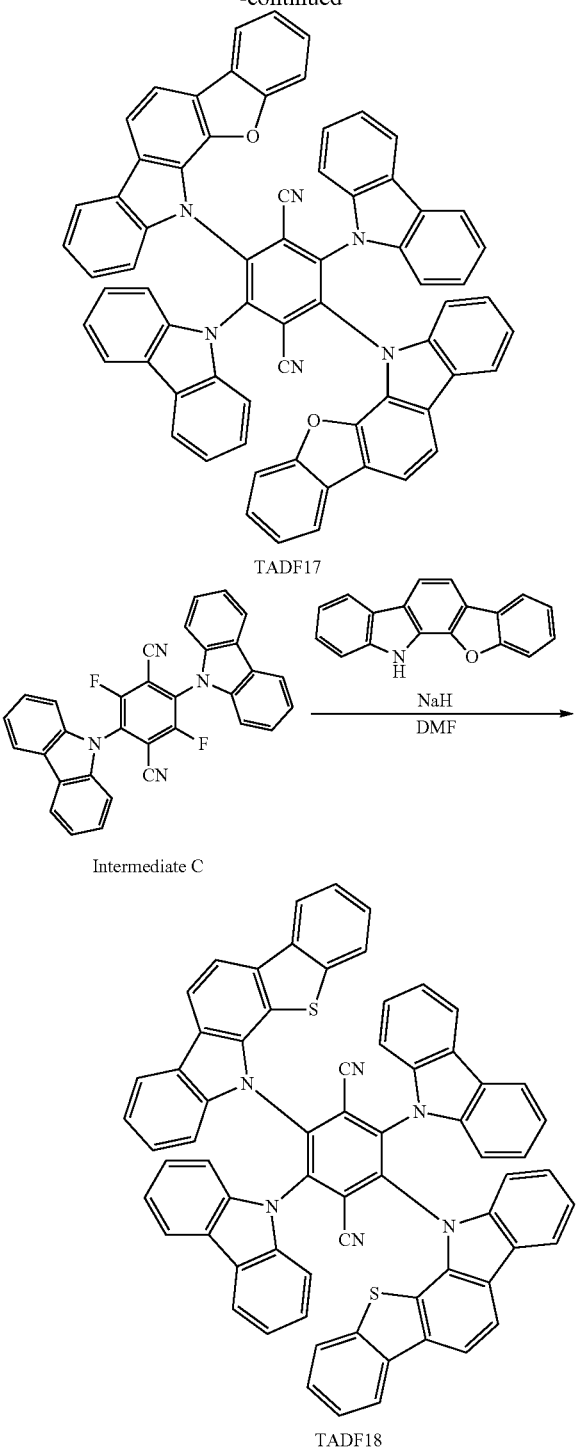

TADF17

Intermediate C

TADF18

Under nitrogen atmosphere, into a 100-mL three-necked flask, 12H-[1]Benzothieno[2,3-a]carbazole (1.98 g, 7.27 mmol), sodium hydride (0.29 g (60 mass %, dispersed in liquid paraffin), 7.27 mmol), and DMF (30 mL) were put, and the obtained mixture was stirred at the room temperature (25 degrees C.) for 30 minutes. Next, the intermediate C (1.5 g, 3.0 mmol) was put into the reactant mixture. After two hours, the reactant mixture was added with a saturated aqueous solution of ammonium chloride (100 mL). The deposited solid was purified by silica-gel column chroma- tography to obtain a red solid (2.0 g). The solid was identified as TADF18 by analysis according to ASAP-MS (a yield rate: 66%).

Example 19

(19) Synthesis Example 19: Synthesis of Compound TADF19

(19-1) Synthesis of TADF19

[Formula 273]

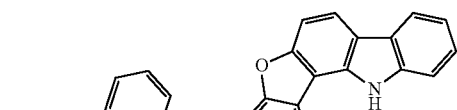

Intermediate C

TADF19

Under nitrogen atmosphere, into a 100-mL three-necked flask, 12H-Benzofuro[3,2-a]carbazole (1.20 g, 7.26 mmol), sodium hydride (0.29 g (60 mass %, dispersed in liquid paraffin), 7.26 mmol), and DMF (40 mL) were put, and the obtained mixture was stirred at the room temperature (25 degrees 0) for 30 minutes. Next, the intermediate C (1.0 g, 2.2 mmol) was put into the reactant mixture, After two hours, the reactant mixture was added with a saturated aqueous solution of ammonium chloride (100 mL). The deposited solid was purified by silica-gel column chroma- tography to obtain a red solid (1.1 g). The solid was identified as TADF19 by analysis according to ASAP-MS (a yield rate: 52%).

Compounds in Examples 20 to 27 were synthesized using at least one of intermediates P, Q, $A_1$ to $A_4$ and C2 to J2 below. The intermediates P, Q, $A_1$ to $A_4$ and C2 to J2 were synthesized by the following method.

541
Synthesis of Intermediate P and Intermediate Q

[Formula 274]

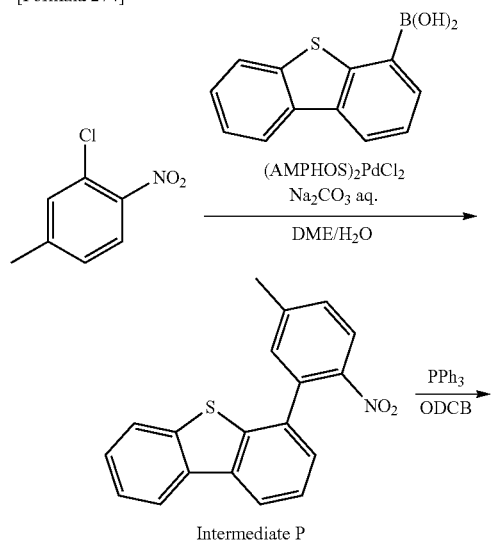

Intermediate P

Intermediate Q

Under nitrogen atmosphere, 2M sodium carbonate aqueous solution (220 mL, 435 mmol), 1,2-dimethoxyethane (DME) (440 mL), and dichlorobis[di-tert-butyl(4-dimethylaminophenyl)phosphine]palladium (II) ((AMPHOS)$_2$PdCl$_2$) (2.1 g, 2.9 mmol) were added to 3-chloro-4-nitrotoluene (25.0 g, 146 mmol) and 4-dibenzothiophene boronic acid (34 g, 146 mmol). The obtained mixture was heated to reflux with stirring for four hours.

After the reaction, the mixture was cooled to the room temperature (25 degrees C.). A sample was transferred to a separating funnel, added with water (500 mL), and extracted with ethyl acetate. The extracted sample was dried over MgSO$_4$, filtered and condensed. The sample was purified by silica-gel column chromatography to obtain a yellow solid (40 g). The solid was identified as an intermediate P by analysis according to GC-MS (a yield rate: 86%).

Under argon atmosphere, orthodichlorobenzene (ODCB) (240 mL) was added to the intermediate P (15.0 g, 47 mmol) and triphenylphosphine (31 g, 117 mmol), and the obtained mixture was heated to reflux with stirring for 20 hours. After the reaction, the mixture was cooled to the room temperature (25 degrees C.). The reactant solution was condensed using an evaporator. The obtained solid was purified by silica-gel column chromatography to obtain a white solid (8.4 g). The solid was identified as an intermediate Q by analysis according to GC-MS (a yield rate: 62%).

542
Synthesis of Intermediate A$_1$ and Intermediate A$_2$

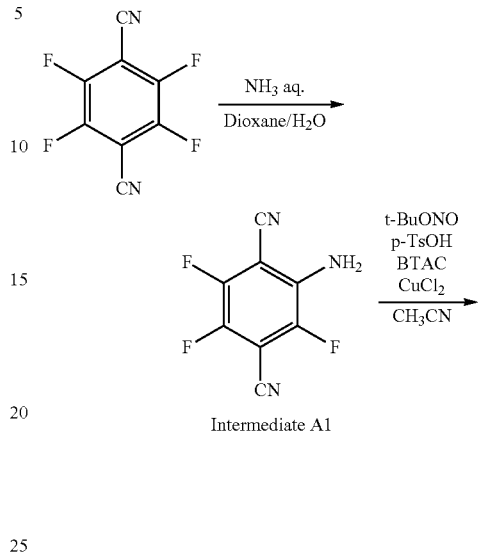

Intermediate A1

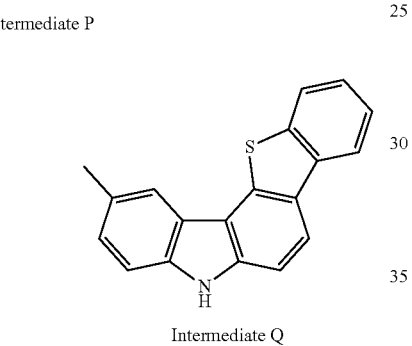

Intermediate A2

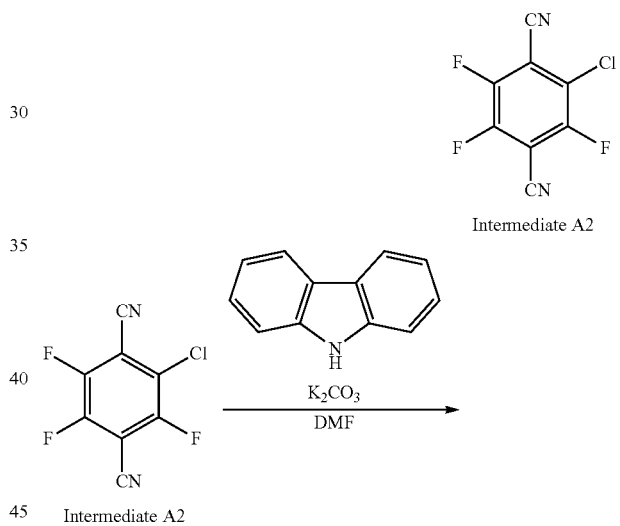

Intermediate A2

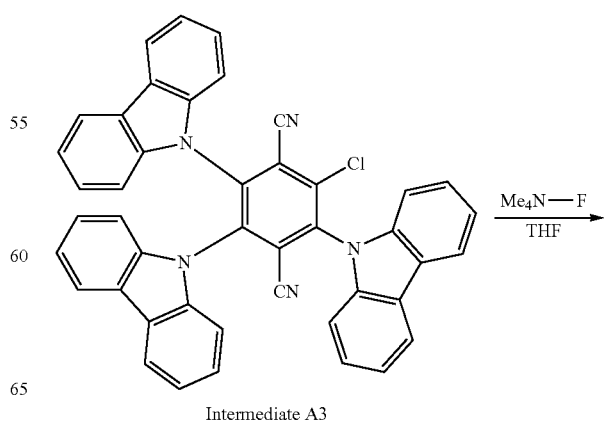

Intermediate A3

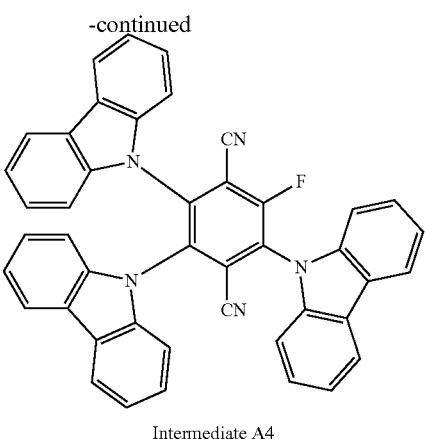

Intermediate A4

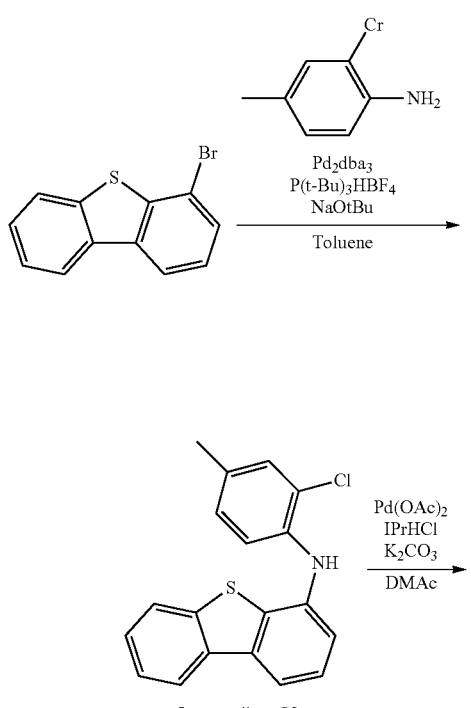

Intermediate C2

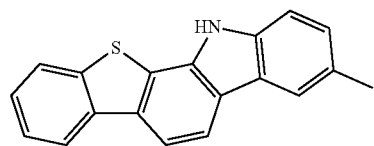

Intermediate D2

Under nitrogen atmosphere, to a three-necked flask, 4-bromodibenzothiophene (26.0 g, 100 mmol), 2-chloro-4-methylaniline (17 g, 120 mmol), tris(dibenzylidene acetone)dipalladium(0) (Pd₂dba₃) (0.9 g, 1 mmol), tri-tert-butylphosphonium tetrafluoroborate (P(t-Bu)₃HBF₄) (2.3 g, 8 mmol), sodium tert-butoxide (NaOtBu) (11.5 g, 120 mmol) and toluene (350 mL) were added. The obtained mixture was heated with stirring at 60 degrees C. for seven hours, and then cooled to the room temperature (25 degrees C.). The reactant solution was purified by silica-gel column chromatography to obtain a white solid (26 g). The solid was identified as an intermediate C₂ by analysis according to GC-MS (a yield rate: 80%).

Under nitrogen atmosphere, to a 1-L three-necked flask, the intermediate C (26.0 g, 80 mmol), 1,3-bis(2,6-diisopropylphenyl)imidazorium chloride(IPrHCl)(1.4 g, 3.2 mmol), palladium acetate(II)(Pd(OAc)₂) (0.36 g, 1.6 mmol), potassium carbonate (22.0 g, 160 mmol) and N,N-dimethylacetamide (DMAc) (400 mL) were added. The obtained mixture was stirred at 130 degrees C. for seven hours and then cooled to the room temperature (25 degrees C.). The reactant solution was purified by silica-gel column chromatography to obtain a white solid (21 g). The solid was identified as an intermediate D₂ by analysis according to GC-MS (a yield rate: 91%).

Synthesis of Intermediate E2 and Intermediate F2

[Formula 278]

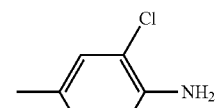

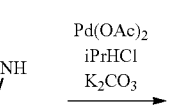

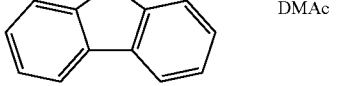

Intermediate E2

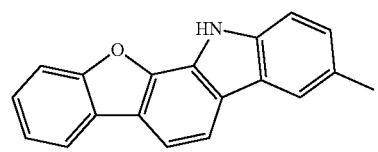

Intermediate F2

Synthesis of Intermediate I2 and Intermediate J2

[Formula 280]

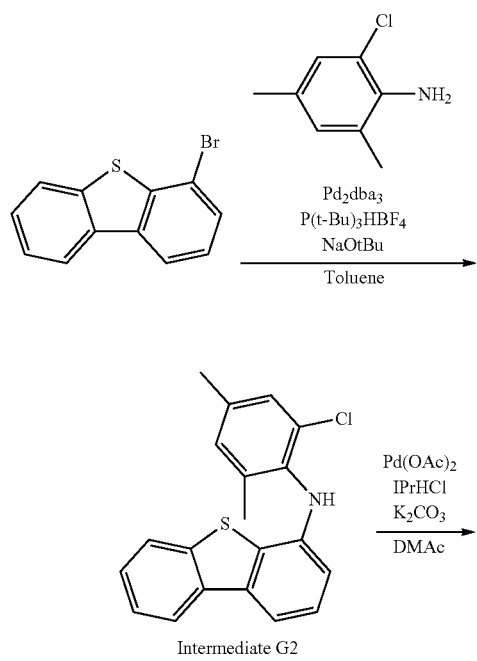

Intermediate G2

Intermediate H2

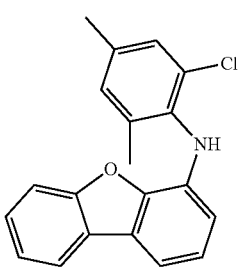

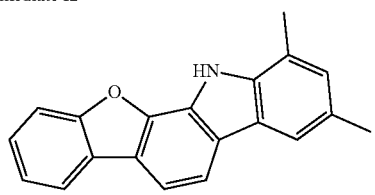

Intermediate I2

Intermediate J2

Under nitrogen atmosphere, to a 1-L three-necked flask, 4-bromodibenzothiophene (26.0 g, 100 mmol), 2-chloro-4,6-dimethylaniline (18.7 g, 120 mmol), tris(dibenzylideneacetone)dipalladium(0) (0.9 g, 1 mmol), tri-tert-butylphosphonium tetrafluoroborate (2.3 g, 8 mmol), sodium tert-butoxide (11.5 g, 120 mmol) and toluene (350 mL) were added. The obtained mixture was heated with stirring at 60 degrees C. for seven hours, and then cooled to the room temperature (25 degrees C.). The reactant solution was purified by silica-gel column chromatography to obtain a white solid (23.7 g). The solid was identified as an intermediate G2 by analysis according to GC-MS (a yield rate: 70%).

Under nitrogen atmosphere, to a 1-L three-necked flask, the intermediate C (23.0 g, 68 mmol), 1,3-bis(2,6-diisopropylphenyl)imidazorium chloride(IPrHCl)(1.2 g, 2.71 mmol), palladium acetate(II) (0.31 g, 1.36 mmol), potassium carbonate (18.8 g, 136 mmol) and N,N-dimethylacetamide (DMAc) (400 mL) were added. The obtained mixture was stirred at 130 degrees C. for seven hours and then cooled to the room temperature (25 degrees C.). The reactant solution was purified by silica-gel column chromatography to obtain a white solid (19.5 g). The solid was identified as an intermediate H2 by analysis according to GC-MS (a yield rate: 95%).

Under nitrogen atmosphere, to a 1-L three-necked flask, 4-bromodibenzofuran (26.0 g, 100 mmol), 2-chloro-4,6-dimethylaniline (17 g, 120 mmol), tris(dibenzylideneacetone)dipalladium(0) (0.9 g, 1 mmol), tri-tert-butylphosphonium tetrafluoroborate (2.3 g, 8 mmol), sodium tert-butoxide (11.5 g, 120 mmol) and toluene (350 mL) were added. The obtained mixture was heated with stirring at 60 degrees C. for seven hours, and then cooled to the room temperature (25 degrees C.). The reactant solution was purified by silica-gel column chromatography to obtain a white solid (28 g). The solid was identified as an intermediate I2 by analysis according to GC-MS (a yield rate: 88%).

Under nitrogen atmosphere, to a 1-L three-necked flask, the intermediate C (28 g, 88 mmol), 1,3-bis(2,6-diisopropylphenyl)imidazorium chloride (IPrHCl) (1.5 g, 3.5 mmol), palladium acetate(II) (0.4 g, 1.76 mmol), potassium carbonate (24.3 g, 176 mmol) and N,N-dimethylacetamide (DMAc) (450 mL) were added. The obtained mixture was stirred at 130 degrees C. for seven hours and then cooled to the room temperature (25 degrees C.). The reactant solution was purified by silica-gel column chromatography to obtain a white solid (21 g). The solid was identified as an intermediate J2 by analysis according to GC-MS (a yield rate: 85%).

Example 20
(20) Synthesis Example 20: Synthesis of Compound TADF20
(20-1) Synthesis of TADF20
[Formula 281]
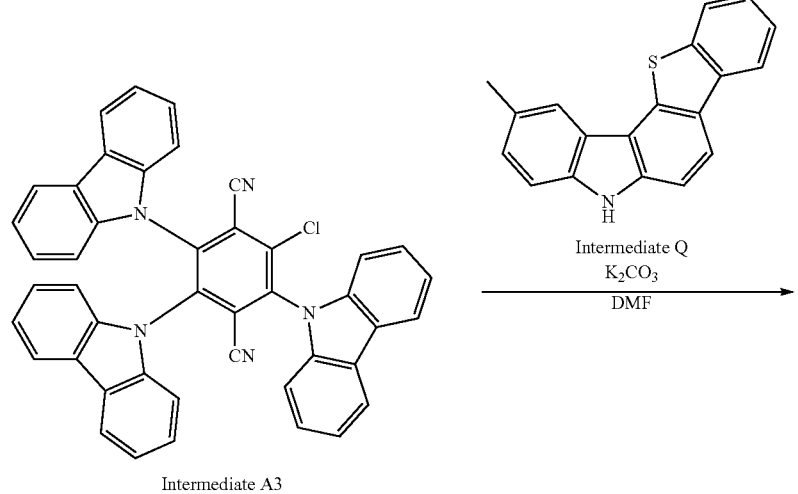
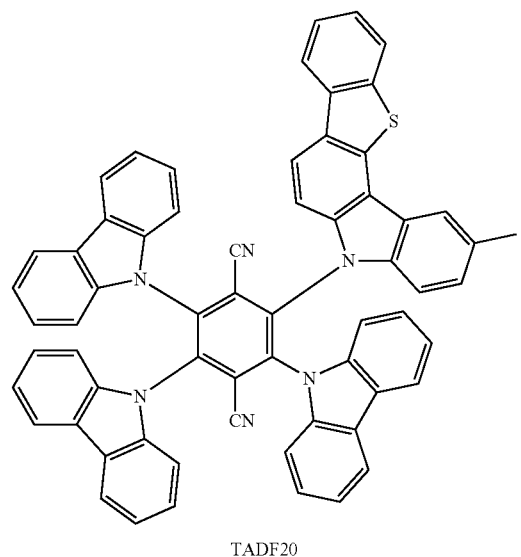

Under nitrogen atmosphere, into a 100-mL three-necked flask, the intermediate $A_3$ (2 g, 3.0 mmol), the intermediate Q (1.0 g, 3.6 mmol), potassium carbonate (0.6 g, 4.5 mmol) and DMF (30 mL) were put. The obtained mixture was stirred at 70 degrees C. for eight hours. A saturated aqueous solution of ammonium chloride (50 mL) was added to the reactant mixture. The deposited solid was purified by silica-gel column chromatography to obtain a red solid (1.6 g). The solid was identified as TADF20 by analysis according to ASAP-MS (a yield rate: 59%).

Example 21

(21) Synthesis Example 21: Synthesis of Compound TADF21

(21-1) Synthesis of TADF21

[Formula 282]

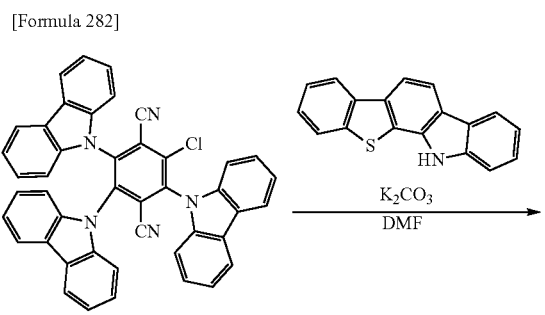

Example 22

(22) Synthesis Example 22: Synthesis of Compound TADF22

(22-1) Synthesis of TADF22

[Formula 283]

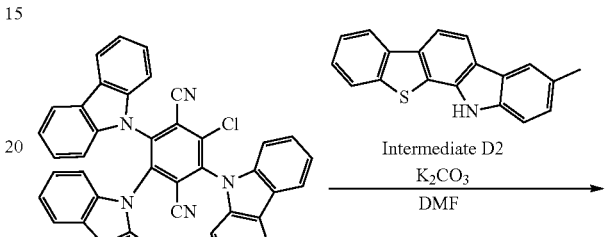

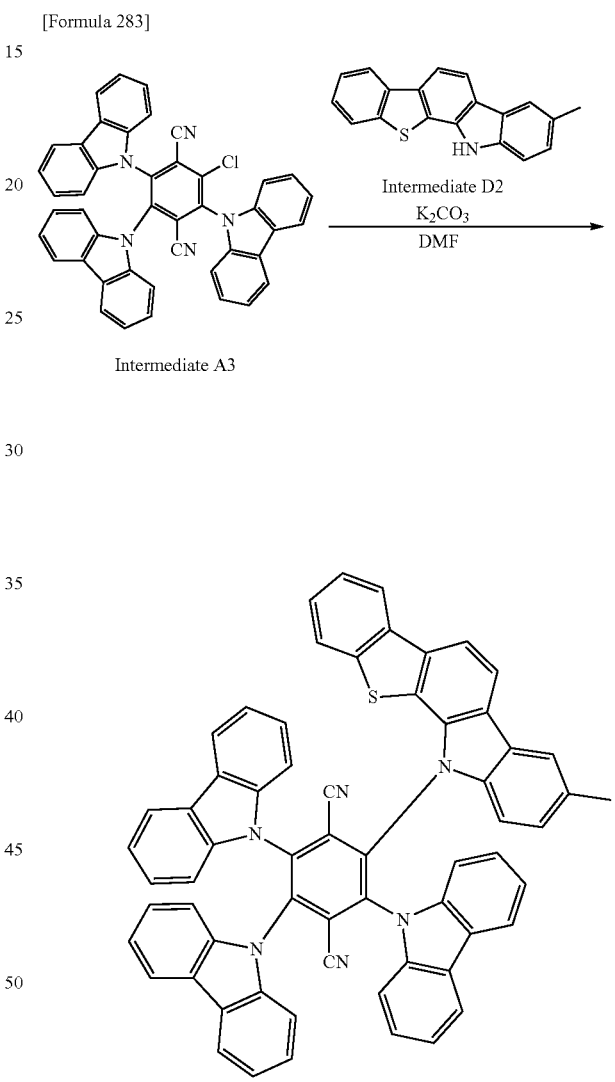

Under nitrogen atmosphere, to a 100-mL three-necked flask, the intermediate $A_3$ (2 g, 3.0 mmol), 12H-[1]Benzothieno[2,3-a]carbazole (0.98 g, 3.6 mmol), potassium carbonate (0.6 g, 4.5 mmol) and DMF (30 mL) were put. The obtained mixture was stirred at 70 degrees C. for eight hours. A saturated aqueous solution of ammonium chloride (50 mL) was added to the reactant mixture. The deposited solid was purified by silica-gel column chromatography to obtain a red solid (1.5 g). The solid was identified as TADF21 by analysis according to ASAP-MS (a yield rate: 56%).

Under nitrogen atmosphere, to a 100-mL three-necked flask, the intermediate $A_3$ (2 g, 3.0 mmol), the intermediate $D_2$ (1.0 g, 3.6 mmol), potassium carbonate (0.6 g, 4.5 mmol) and DMF (30 mL) were put. The obtained mixture was stirred at 70 degrees C. for eight hours. A saturated aqueous solution of ammonium chloride (50 mL) was added to the reactant mixture. The deposited solid was purified by silica-gel column chromatography to obtain a red solid (1.8 g). The solid was identified as TADF22 by analysis according to ASAP-MS (a yield rate: 66%).

551
Example 23

(23) Synthesis Example 23: Synthesis of Compound TADF23

(23-1) Synthesis of TADF23

552
Example 24

(24) Synthesis Example 24: Synthesis of Compound TADF24

(24-1) Synthesis of TADF24

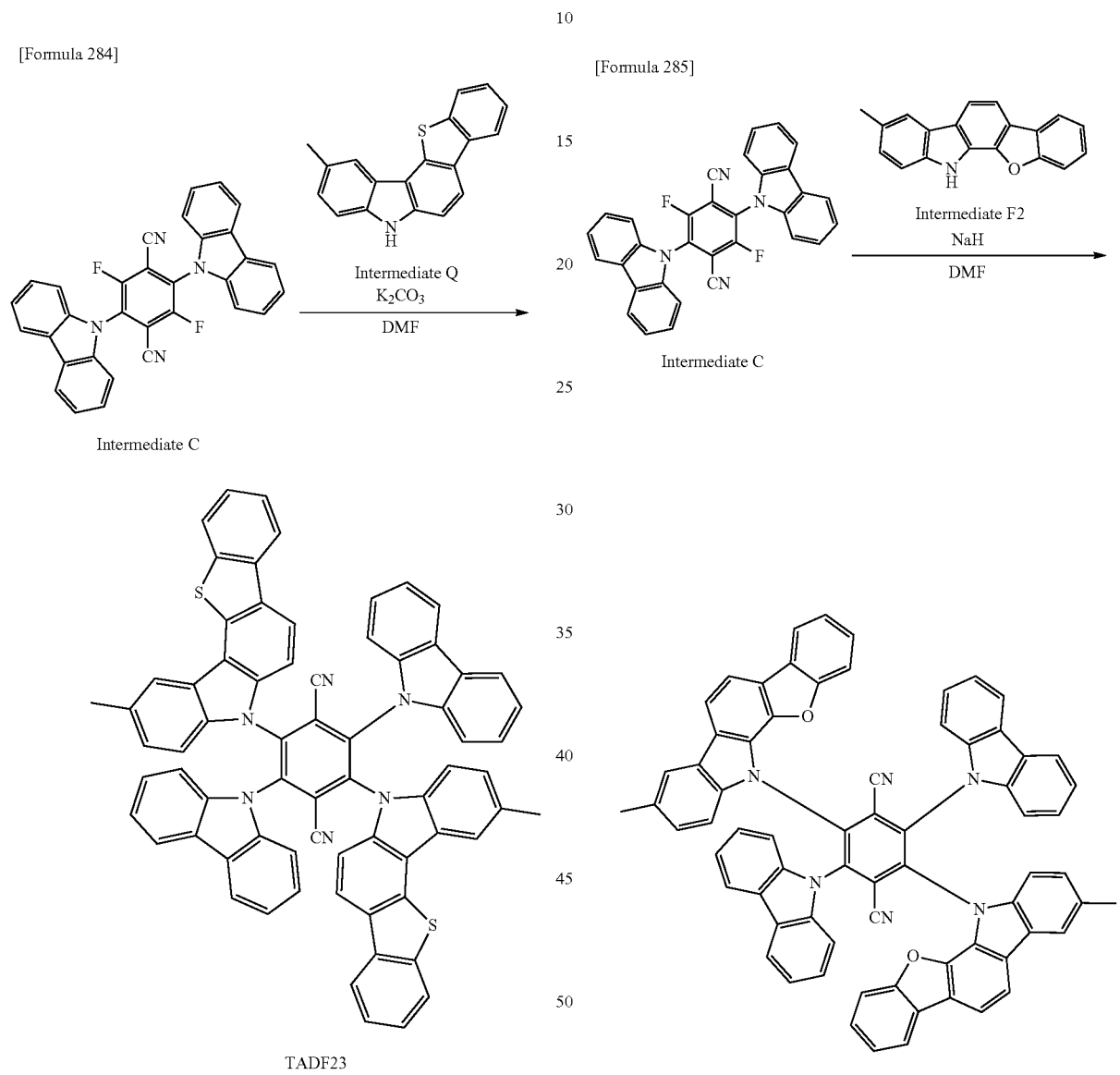

TADF23

TADF24

Under nitrogen atmosphere, to a 100-ml three-necked flask, the intermediate C (1.0 g, 2.0 mmol), potassium carbonate (0.28 g, 5.0 mmol) and the intermediate Q (1.4 g, 5.0 mmol), and DMF (30 ml) were added. The obtained mixture was stirred at 70 degrees C. for six hours.

After the reaction, the mixture was cooled to the room temperature (25 degrees C.) A saturated aqueous solution of ammonium chloride (50 mL) was added to the reactant mixture. The deposited solid was purified by silica-gel column chromatography to obtain a red solid (1.8 g). The solid was identified as TADF23 by analysis according to ASAP-MS (a yield rate: 88%).

Under nitrogen atmosphere, into a 100-mL three-necked flask, the intermediate F2 (2.00 g, 7.38 mmol), sodium hydride (0.30 g (60 mass %, dispersed in liquid paraffin), 7.38 mmol), and DMF (30 mL) were put, and the obtained mixture was stirred at the room temperature (25 degrees C.) for 30 minutes. Next, the intermediate C (1.68 g, 3.4 mmol) was put into the reactant mixture. After two hours, the reactant mixture was added with a saturated aqueous solution of ammonium chloride (50 mL). The deposited solid was purified by silica-gel column chromatography to obtain an orange solid (2.8 g). The solid was identified as TADF24 by analysis according to ASAP-MS (a yield rate: 83%).

Example 25

(25) Synthesis Example 25: Synthesis of Compound TADF25

(25-1) Synthesis of TADF25

[Formula 286]

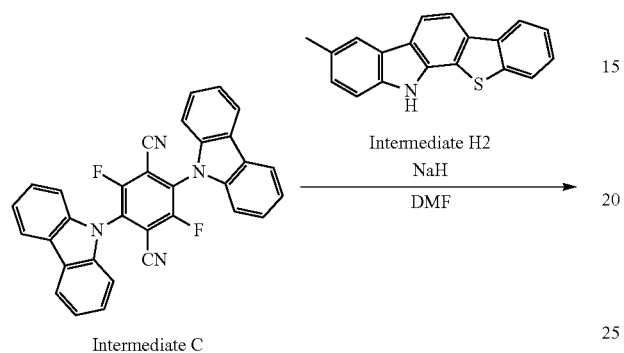

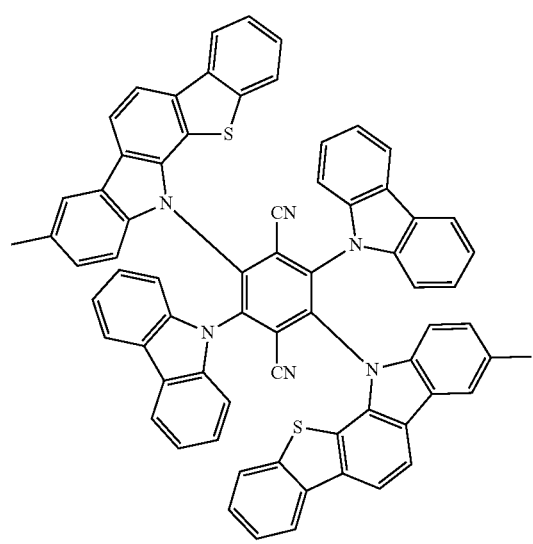

TADF25

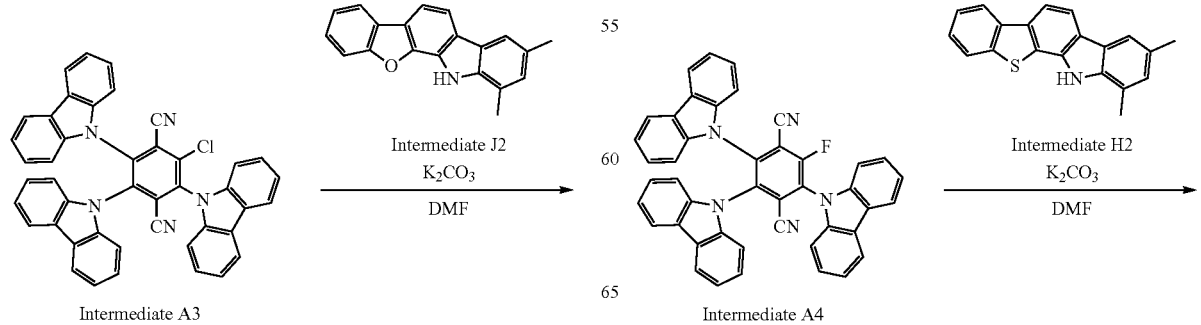

TADF26

Under nitrogen atmosphere, to a 100-mL three-necked flask, the intermediate $A_3$ (2 g, 3.0 mmol), the intermediate J2 (1.0 g, 3.6 mmol), potassium carbonate (0.6 g, 4.5 mmol) and DMF (30 mL) were put. The obtained mixture was stirred at 70 degrees C. for eight hours. A saturated aqueous solution of ammonium chloride (50 mL) was added to the reactant mixture. The deposited solid was purified by silica-gel column chromatography to obtain a red solid (1.2 g). The solid was identified as TADF26 by analysis according to ASAP-MS (a yield rate: 44%).

Example 27

(27) Synthesis Example 27: Synthesis of Compound TADF27

(27-1) Synthesis of TADF27

[Formula 288]

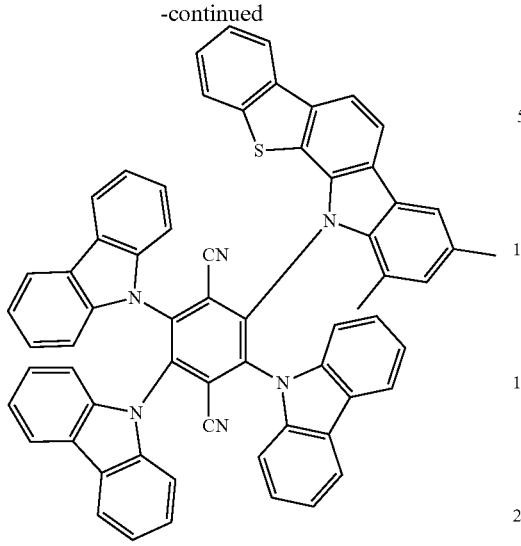

TADF27

Under nitrogen atmosphere, to a 100-mL three-necked flask, the intermediate $A_4$ (1.9 g, 3.0 mmol), the intermediate $H_2$ (1.1 g, 3.6 mmol), potassium carbonate (0.6 g, 4.5 mmol) and DMF (30 mL) were put. The obtained mixture was stirred at 70 degrees C. for eight hours. A saturated aqueous solution of ammonium chloride (50 mL) was added to the reactant mixture. The deposited solid was purified by silica-gel column chromatography to obtain a red solid (1.4 g). The solid was identified as TADF27 by analysis according to ASAP-MS (a yield rate: 51%).

Example 28

(28) Synthesis Example 28: Synthesis of Compound TADF28

(28-1) Synthesis of Intermediate M2 and Intermediate N2

[Formula 289]

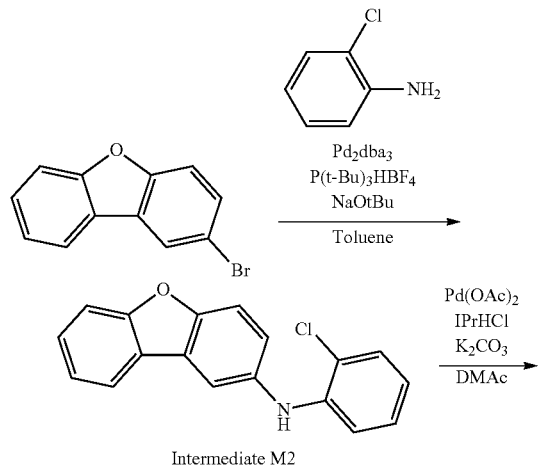

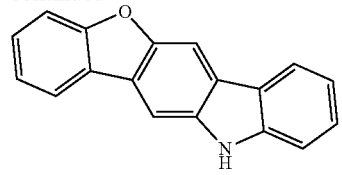

Intermediate N2

Under nitrogen atmosphere, to a 1-L three-necked flask, 2-bromodibenzofuran (12.4 g, 50 mmol), 2-chloroaniline (7.5 g, 60 mmol), tris(dibenzylidene acetone)dipalladium(0) (0.45 g, 0.5 mmol), tri-tert-butylphosphonium tetrafluoroborate (1.2 g, 4 mmol), sodium tert-butoxide (5.8 g, 60 mmol) and toluene (200 mL) were added. The obtained mixture was heated with stirring at 80 degrees C. for six hours, and then cooled to the room temperature (25 degrees C.). The reactant solution was purified by silica-gel column chromatography to obtain a white solid (13.5 g). The solid was identified as an intermediate M2 by analysis according to GC-MS (a yield rate: 92%).

Under nitrogen atmosphere, to a 1-L three-necked flask, the intermediate M2 (13.5 g, 46 mmol), 1,3-bis(2,6-diisopropylphenyl)imidazorium chloride (IPrHCl) (0.81 g, 3.6 mmol), palladium acetate(II) (0.21 g, 0.92 mmol), potassium carbonate (12.7 g, 92 mmol) and N,N-dimethylacetamide (DMAc) (400 mL) were added. The obtained mixture was stirred at 130 degrees C. for four hours and then cooled to the room temperature (25 degrees C.). The reactant solution was purified by silica-gel column chromatography to obtain a white solid (6.0 g). The solid was identified as an intermediate N2 by analysis according to GC-MS (a yield rate: 51%).

(28-2) Synthesis of TADF28

[Formula 290]

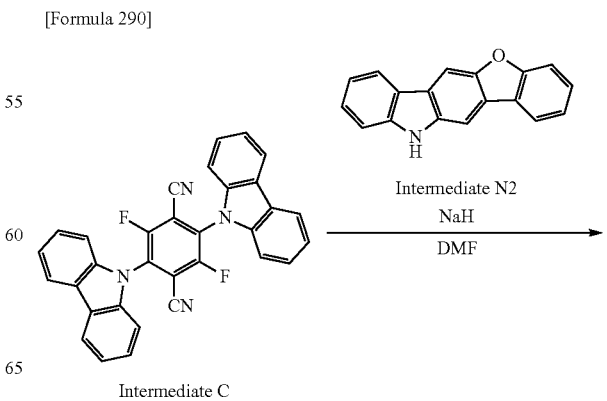

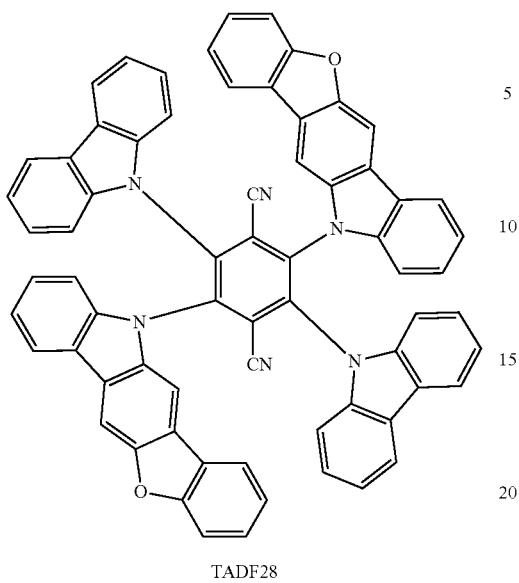

TADF28

Under nitrogen atmosphere, into a 100-mL three-necked flask, the intermediate N2 (2.16 g, 8.4 mmol), sodium hydride (0.34 g (60 mass %, dispersed in liquid paraffin), 3.4 mmol), and DMF (50 mL) were put, and the obtained mixture was stirred at the room temperature (25 degrees C.) for 30 minutes. Next, the intermediate C (2.00 g, 4.0 mmol) was put into the reactant mixture. After two hours, the reactant mixture was added with a saturated aqueous solution of ammonium chloride (30 mL). The deposited solid was purified by silica-gel column chromatography to obtain an orange solid (3.00 g). The solid was identified as TADF28 by analysis according to ASAP-MS (a yield rate: 78%).

Example 29

(29) Synthesis Example 29: Synthesis of Compound TADF29

(29-1) Synthesis of Intermediate 02

[Formula 291]

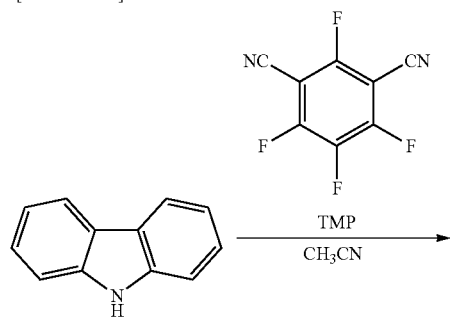

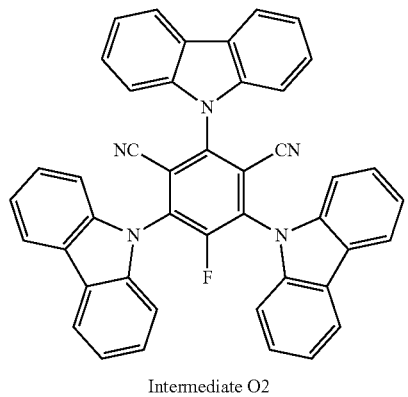

Intermediate O2

Under nitrogen atmosphere, to a 500-mL three-necked flask, carbazole (17 g, 100 mmol), tetramethylpiperidine (TMP) (22 g, 150 mmol), tetrafluoroisophthalonitrile (6.6 g, 33 mmol), and acetonitrilel (CH$_3$CN) (200 mL) were put. The obtained mixture was heated with stirring at 80 degrees C. for four hours. A solvent was distilled away from the reactant solution using an evaporator. The obtained solid was purified by silica-gel column chromatography to obtain a yellow solid (13 g). The solid was identified as an intermediate O2 by analysis according to ASAP-MS (a yield rate: 65%).

(29-2) Synthesis of TADF29

[Formula 292]

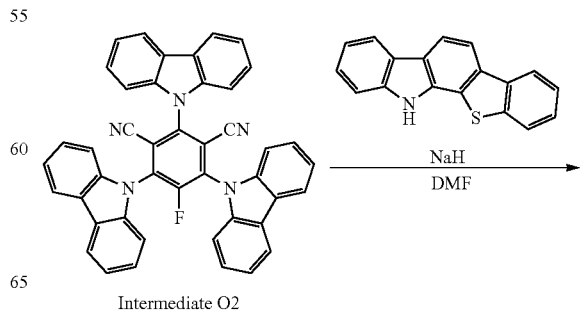

Intermediate O2

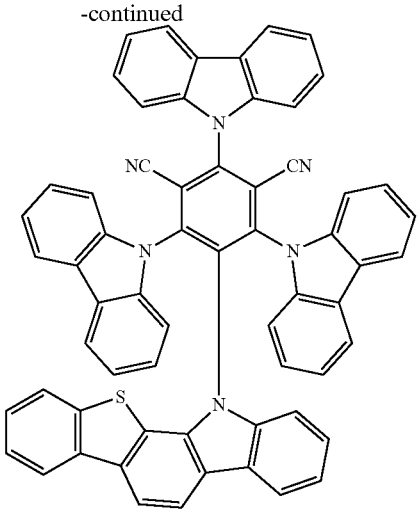

TADF29

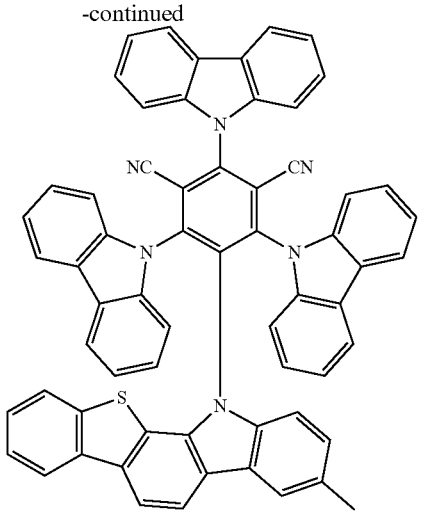

TADF30

Under nitrogen atmosphere, into a 100-mL three-necked flask, 12H-[1]Benzothieno[2,3-a]carbazole (2.02 g, 7.27 mmol), sodium hydride (0.29 g (60 mass %; dispersed in liquid paraffin), 7.27 mmol), and DMF (30 mL) were put, and the obtained mixture was stirred at the room temperature (25 degrees C.) for 30 minutes. Next, the intermediate O2 (3.9 g, 5.59 mmol) was put into the reactant mixture. After two hours, the reactant mixture was added with a saturated aqueous solution of ammonium chloride (100 mL). The deposited solid was purified by silica-gel column chromatography to obtain a red solid (2.9 g). The solid was identified as TADF29 by analysis according to ASAP-MS (a yield rate: 58%).

Example 30

(30) Synthesis Example 30: Synthesis of Compound TADF30

(30-1) Synthesis of TADF30

Under nitrogen atmosphere, into a 100-mL three-necked flask, the intermediate $D_2$ (2.30 g, 8.00 mmol), sodium hydride (0.32 g (60 mass %, dispersed in liquid paraffin), 8.00 mmol), and DMF (40 mL) were put, and the obtained mixture was stirred at the room temperature (25 degrees C.) for 30 minutes. Next, the intermediate O2 (3.4 g, 5.33 mmol) was put into the reactant mixture. After two hours, the reactant mixture was added with a saturated aqueous solution of ammonium chloride (100 mL). The deposited solid was purified by silica-gel column chromatography to obtain a yellow solid (3.0 g). The solid was identified as TADF30 by analysis according to ASAP-MS (a yield rate: 61%).

Example 31

(31) Synthesis Example 31: Synthesis of Compound TADF31

(31-1) Synthesis of TADF31

[Formula 293]

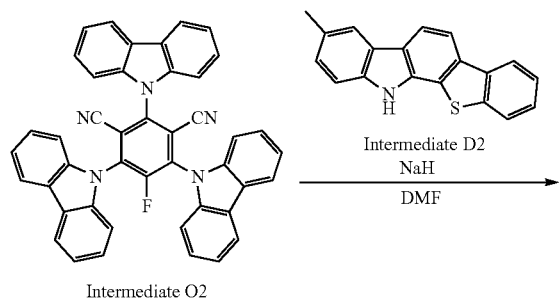

[Formula 294]

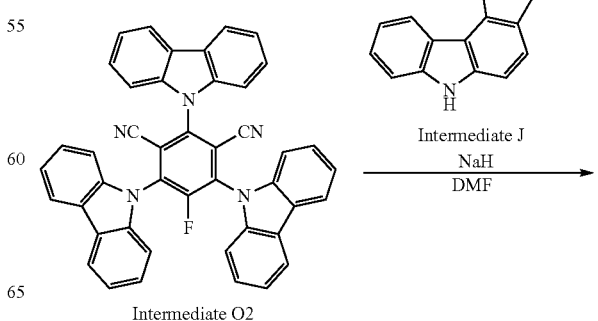

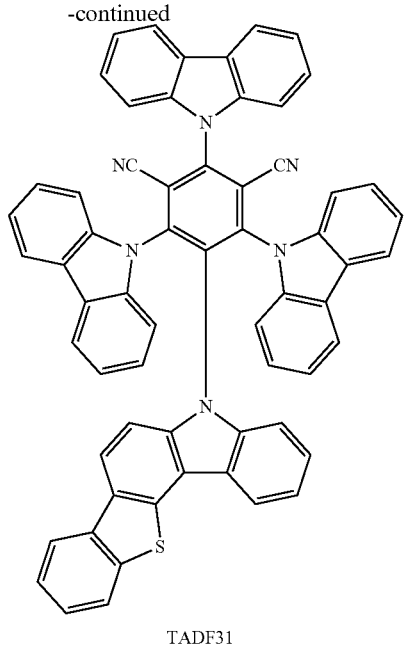

TADF31

Under nitrogen atmosphere, into a 100-mL three-necked flask, the intermediate J (2.00 g, 7.19 mmol), sodium hydride (0.29 g (60 mass %, dispersed in liquid paraffin), 7.19 mmol), and DMF (30 were put, and the obtained mixture was stirred at the room temperature (25 degrees C.) for 30 minutes. Next, the intermediate O2 (3.9 g, 5.59 mmol) was put into the reactant mixture. After two hours, the reactant mixture was added to a saturated aqueous solution of ammonium chloride (100 mL). The deposited solid was purified by silica-gel column chromatography to obtain a yellow solid (3.3 g). The solid was identified as TADF31 by analysis according to ASAP-MS (a yield rate: 66%).

Example 32

(32) Synthesis Example 32: Synthesis of Compound TADF32

(32-1) Synthesis of TADF32

[Formula 295]

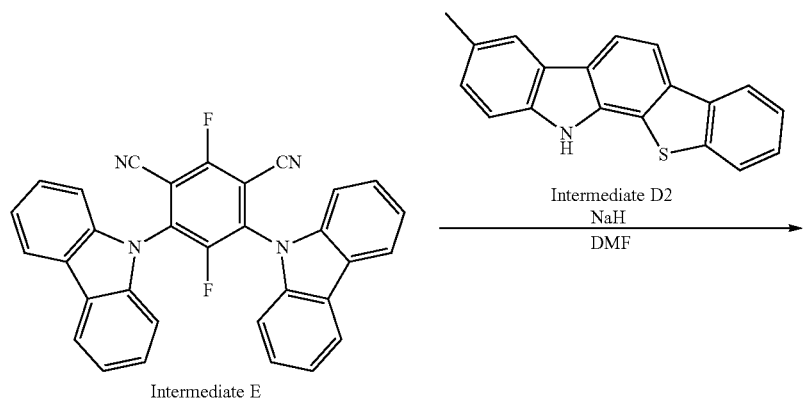

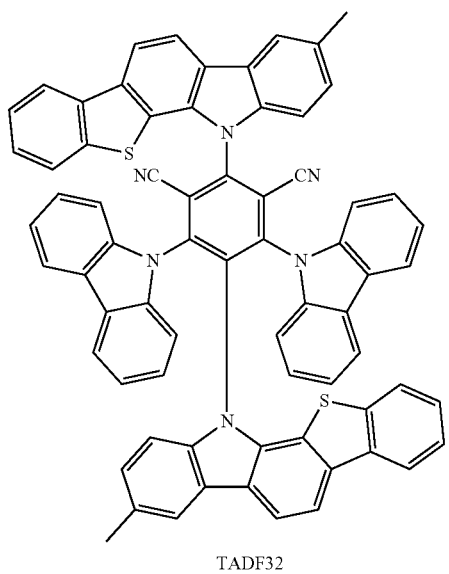

TADF32

Under nitrogen atmosphere, into a 100-mL three-necked flask, the intermediate $D_2$ (1.4 g, 5.0 mmol), sodium hydride (containing oil at 40 mass %) (0.2 g, 5.0 mmol), and DMF (40 mL) were put, and the obtained mixture was stirred at the room temperature (25 degrees C.) for 30 minutes. Next, the intermediate E (1.0 g, 2 mmol) was put into the reactant mixture. The obtained mixture was stirred for two hours. Subsequently, the obtained reactant mixture was added to water (50 mL). The deposited solid was purified by silica-gel column chromatography to obtain an orange solid (1.85 g). The solid was identified as TADF32 by analysis according to ASAP-MS (a yield rate: 90%).

Example 33

(33) Synthesis Example 33: Synthesis of Compound TADF33

(33-1) Synthesis of TADF33

[Formula 296]

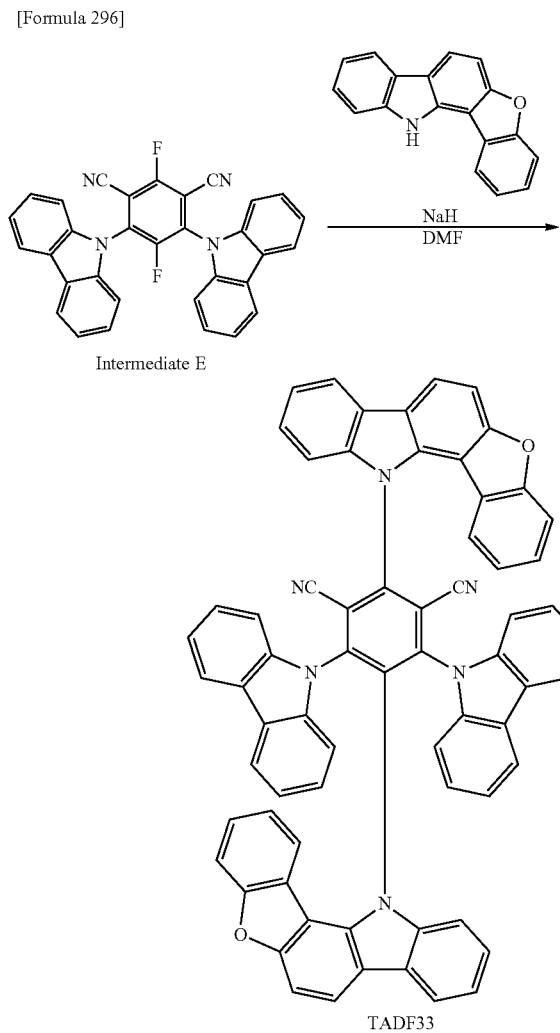

TADF33

Under nitrogen atmosphere, into a 100-mL three-necked flask, 12H-Benzofuro[3,2-a]carbazole (1.3 g, 5.0 mmol), sodium hydride (containing oil at 40 mass %) (0.2 g, 5.0 mmol), and DMF (40 mL) were put, and the obtained mixture was stirred at the room temperature (25 degrees C.) for 30 minutes. Next, the intermediate E (1.0 g, 2 mmol) was put into the reactant mixture. The obtained mixture was stirred for two hours. Subsequently, the obtained reactant mixture was added to water (50 mL). The deposited solid was purified by silica-gel column chromatography to obtain an orange solid (1.70 g). The solid was identified as TADF33 by analysis according to ASAP-MS (a yield rate: 88%).

Example 34

(34) Synthesis Example 34: Synthesis of Compound TADF34

(34-1) Synthesis of TADF34

[Formula 297]

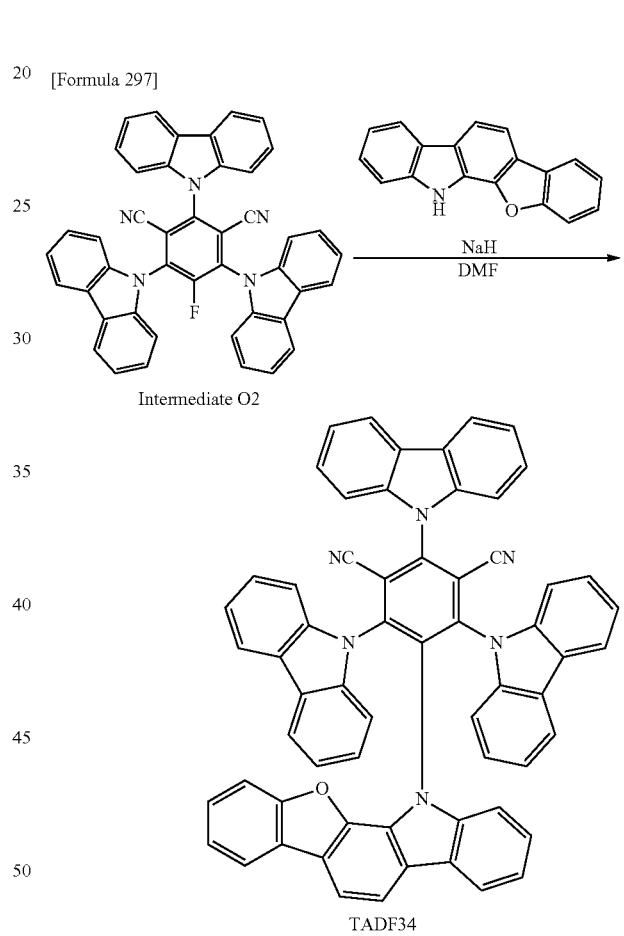

TADF34

Under nitrogen atmosphere, into a 100-mL three-necked flask, 12H-Benzofuro[2,3-a]carbazole (1.87 g, 7.27 mmol), sodium hydride (0.29 g (60 mass %, dispersed in liquid paraffin), 7.27 mmol), and DMF (30 mL) were put, and the obtained mixture was stirred at the room temperature (25 degrees C.) for 30 minutes. Next, the intermediate O2 (3.9 g, 5.59 mmol) was put into the reactant mixture. After two hours, the reactant mixture was added to a saturated aqueous solution of ammonium chloride (100 mL). The deposited solid was purified by silica-gel column chromatography to obtain a yellow solid (3.5 g). The solid was identified as TADF34 by analysis according to ASAP-MS (a yield rate: 71%).

Example 35

(35) Synthesis Example 35: Synthesis of Compound TADF35

(35-1) Synthesis of TADF35

[Formula 298]

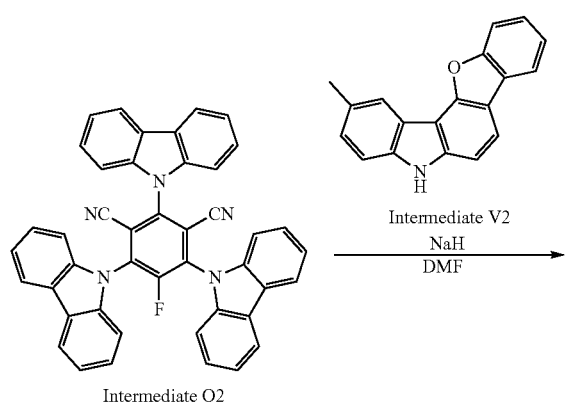

Example 36

(36) Synthesis Example 36: Synthesis of Compound TADF36

(36-1) Synthesis of TADF36

[Formula 299]

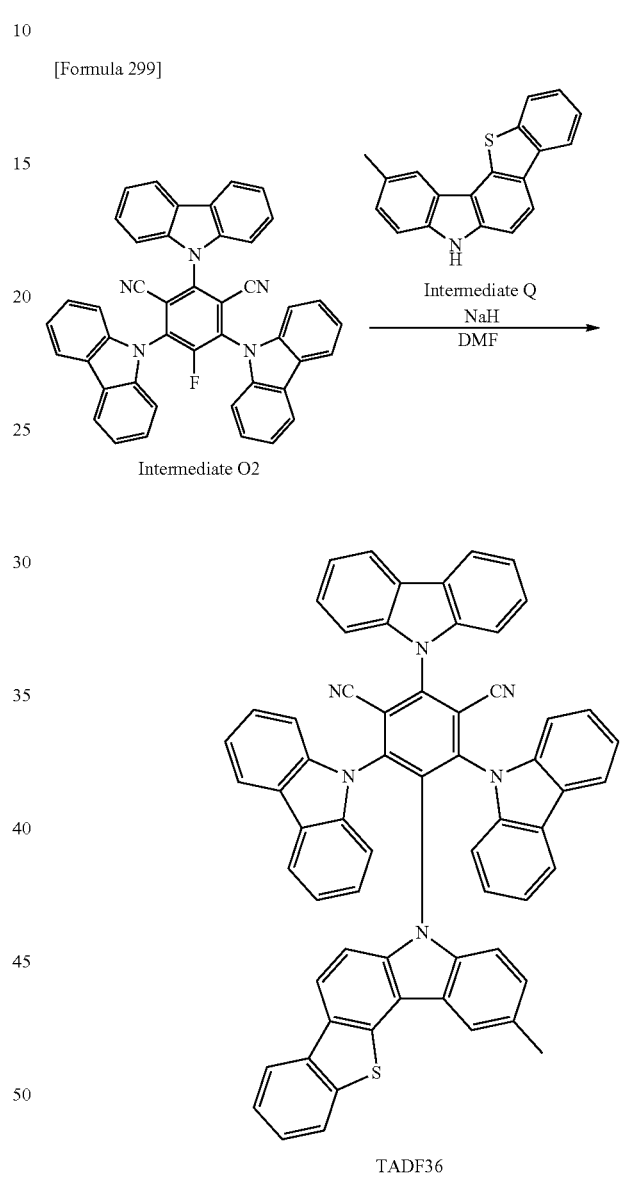

Under nitrogen atmosphere, into a 100-mL three-necked flask, the intermediate V2 (2.00 g, 7.38 mmol), sodium hydride (0.30 g (60 mass %, dispersed in liquid paraffin), 7.38 mmol), and DMF (40 mL) were put, and the obtained mixture was stirred at the room temperature (25 degrees C.) for 30 minutes. Next, the intermediate O2 (4.0 g, 5.68 mmol) was put into the reactant mixture. After two hours, the reactant mixture was added to a saturated aqueous solution of ammonium chloride (100 mL). The deposited solid was purified by silica-gel column chromatography to obtain a yellow solid (4.0 g). The solid was identified as TADF35 by analysis according to ASAP-MS (a yield rate: 79%).

Under nitrogen atmosphere, into a 100-mL three-necked flask, the intermediate Q (2.00 g, 7.00 mmol), sodium hydride (0.28 g (60 mass %, dispersed in liquid paraffin), 7.00 mmol), and DMF (40 mL) were put, and the obtained mixture was stirred at the room temperature (25 degrees C.) for 30 minutes. Next, the intermediate O2 (3.6 g, 5.38 mmol) was put into the reactant mixture. After two hours, the reactant mixture was added to a saturated aqueous solution of ammonium chloride (100 mL). The deposited solid was purified by silica-gel column chromatography to obtain a yellow solid (2.6 g). The solid was identified as TADF36 by analysis according to ASAP-MS (a yield rate: 61%).

Example 37

(37) Synthesis Example 37: Synthesis of Compound TADF37

(37-1) Synthesis of Intermediate P2

[Formula 300]

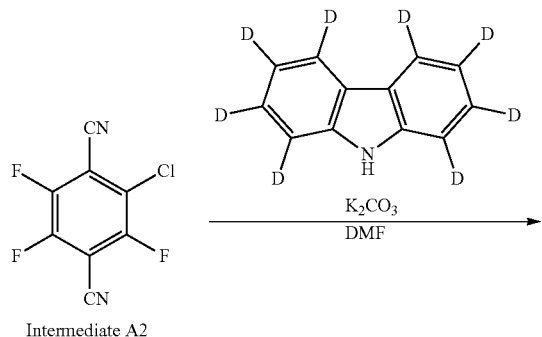

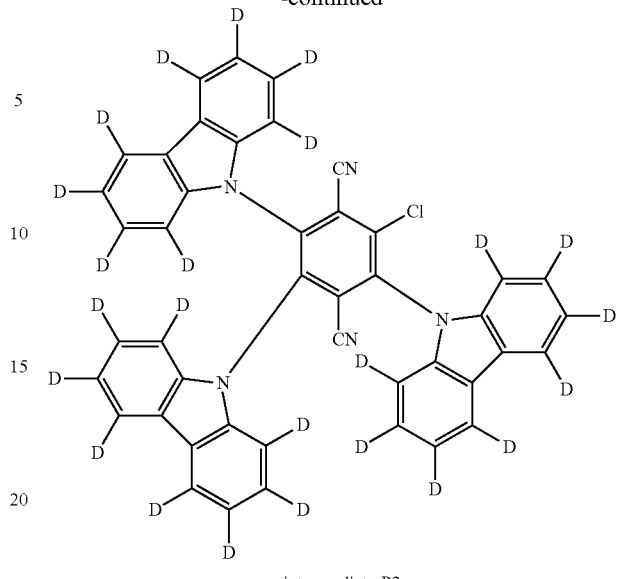

intermediate P2

Under nitrogen atmosphere, into a 1000-mL three-necked flask, the intermediate A2 (1.16 g, 5.35 mmol), carbazole-1,2,3,4,5,6,7,8-d8 (whose deuterium ratio of 98% was used)(3 g, 17.1 mmol), potassium carbonate (3.5 g, 25.7 mmol) and DMF (30 mL) were put. The obtained mixture was stirred at 0 degrees C. for nine hours. The reactant mixture was added to a saturated aqueous solution of ammonium chloride (30 mL). The deposited solid was purified by silica-gel column chromatography to obtain a yellow solid (3.0 g). The solid was identified as an intermediate P2 by analysis according to ASAP-MS (a yield rate: 82%).

(37-2) Synthesis of TADF37

[Formula 301]

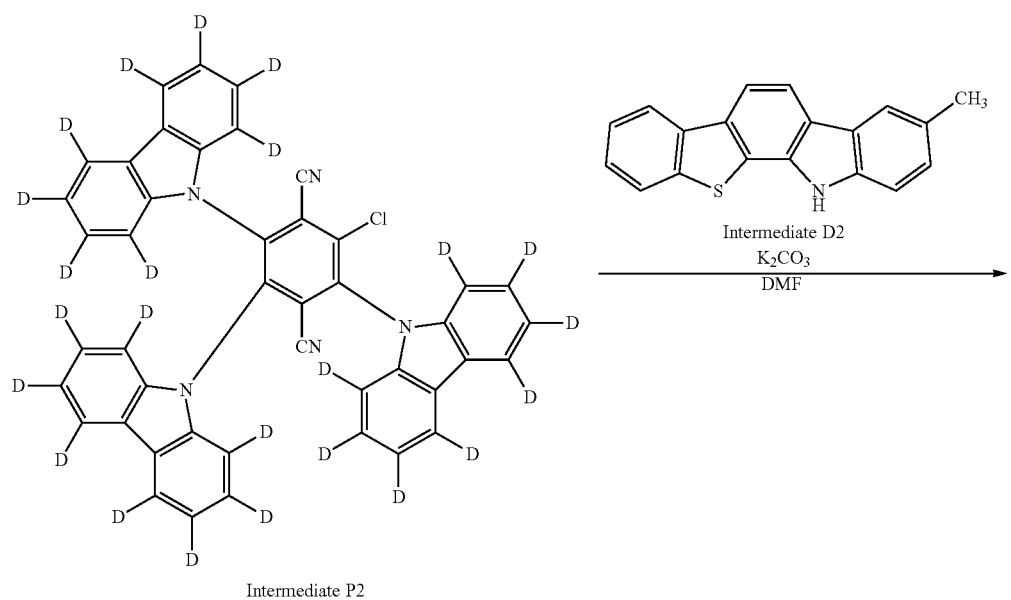

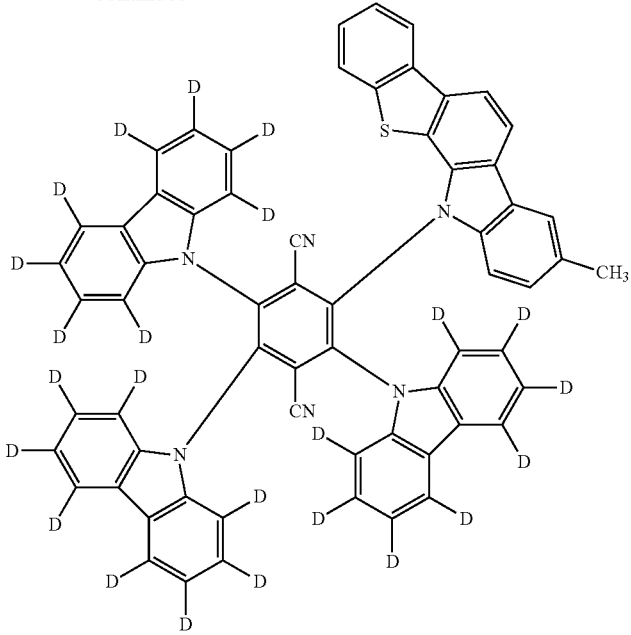

TADF37

Under nitrogen atmosphere, 1 into a 100-mL three-necked flask, the intermediate P2 (2.6 g, 3.8 mmol), the intermediate D₂ (1.6 g, 5.7 mmol), potassium carbonate (1.2 g, 8.9 mmol) and DMF (30 mL) were put. The obtained mixture was stirred at 115 degrees C. for six hours. A saturated aqueous solution of ammonium chloride (50 mL) was added to the reactant mixture. The deposited solid was purified by silica-gel column chromatography to obtain a red solid (2.5 g). The solid was identified as TADF37 by analysis according to ASAP-MS (a yield rate: 70%).

Example 38

(38) Synthesis Example 38: Synthesis of Compound TADF38

(38-1) Synthesis of TADF38

[Formula 302]

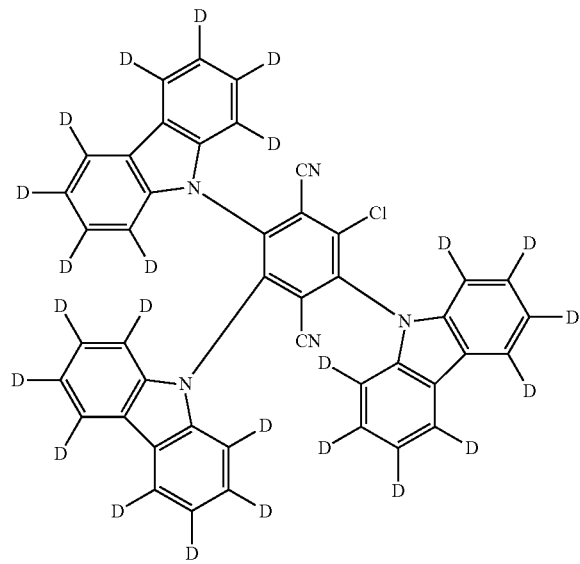

Intermediate P2

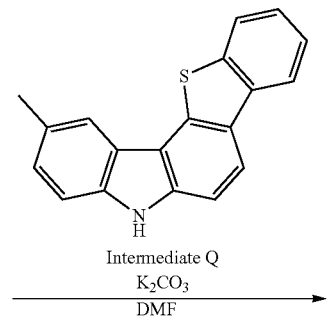

Intermediate Q
K₂CO₃
DMF

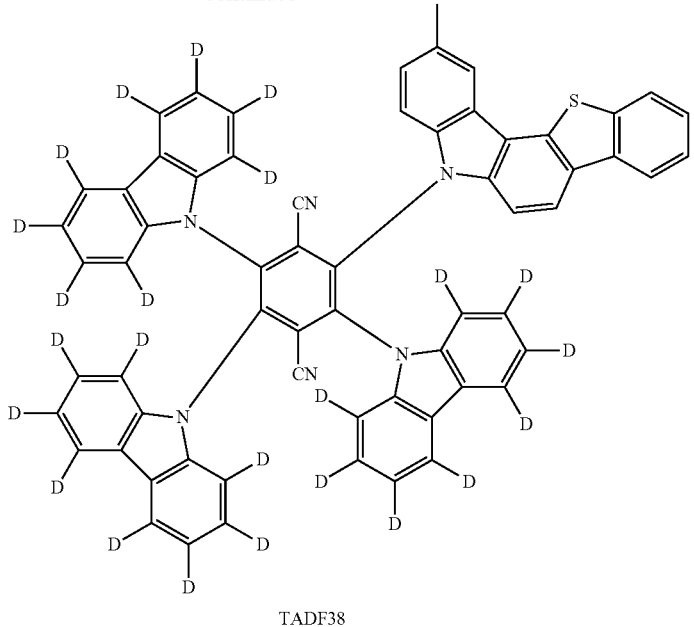

TADF38

Under nitrogen atmosphere, into a 100-mL three-necked flask, the intermediate P2 (3.0 g, 4.4 mmol), the intermediate Q (1.6 g, 5.7 mmol), potassium carbonate (1.2 g, 8.6 mmol) and DMF (30 mL) were put. The obtained mixture was stirred at 115 degrees C. for six hours. A saturated aqueous solution of ammonium chloride (50 mL) was added to the reactant mixture. The deposited solid was purified by silica-gel column chromatography to obtain a red solid (3.3 g). The solid was identified as TADF38 by analysis according to ASAP-MS (a yield rate: 80%).

Example 39

(39) Synthesis Example 39: Synthesis of Compound TADF39

(39-1) Synthesis of Intermediate K2 and Intermediate L$_2$

[Formula 303]

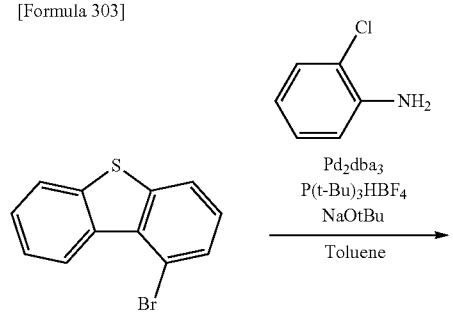

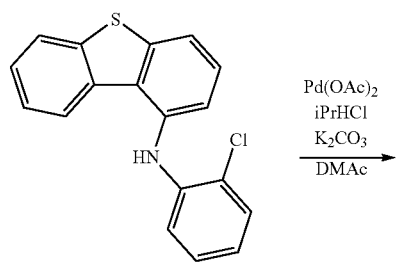

Intermediate K2

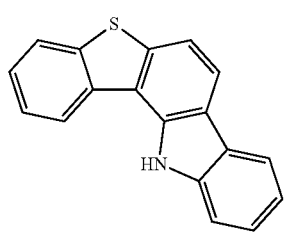

Intermediate L2

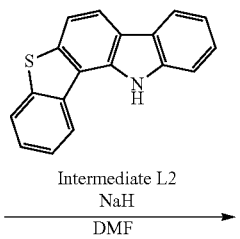

Intermediate C

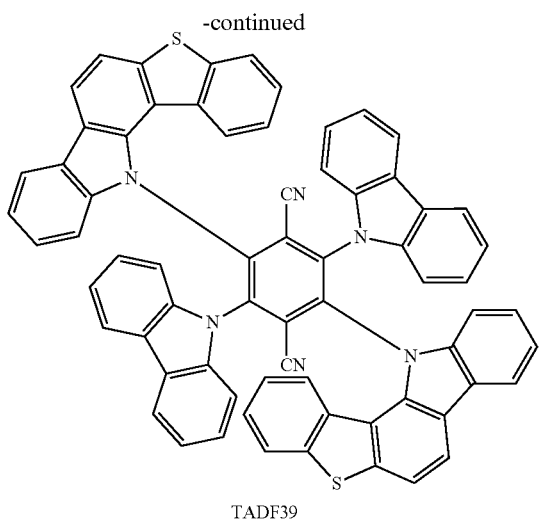

TADF39

Under nitrogen atmosphere, into a 200-mL three-necked flask, the intermediate $L_2$ (1.82 g, 6.67 mmol), sodium hydride (0.26 g (60 mass %, dispersed in liquid paraffin), 6.67 mmol), and DMF (60 mL) were put, and the obtained mixture was stirred at the room temperature (25 degrees C.) for 30 minutes. Next, the intermediate C (1.5 g, 3.0 mmol) was put into the reactant mixture. After two hours, the reactant mixture was added to a saturated aqueous solution of ammonium chloride (100 mL). The deposited solid was purified by silica-gel column chromatography to obtain a red solid (1.8 g). The solid was identified as TADF39 by analysis according to ASAP-MS (a yield rate: 61%).

Comparatives 1 to 3

Comparative compounds 1 to 3 were synthesized by a method in conformity with the method of synthesizing the compound TADF1.

Evaluation of Compounds

Methods of measuring properties of the compounds are shown below.

Weight Reduction Temperature

A 1%-weight loss temperature and a 5%-weight loss temperature were measured under the following conditions using a differential thermogravimetric simultaneous measurement device.

Results are shown in Table 59.

Thermogravimetric differential calorimetry (TG-DTA), which is a method of continuously measuring a change in mass of a sample when the sample is heated, is used for detecting a physical change accompanied by the change in mass such as sublimation and evaporation.

Accordingly, in this evaluation, the "high" weight loss temperature obtained by TG-DTA is regarded as a "high" sublimation temperature under high vacuum while the "low" weight loss temperature obtained by TG-DTA is regarded as a "low" sublimation temperature under high vacuum. Herein, "under high vacuum" refers to a range from $1.0 \times 10^{-6}$ Pa to $1.0 \times 10^{-3}$ Pa.

Measurement Conditions

Device: differential thermogravimetric simultaneous measurement device (STA7200RV manufactured by Hitachi High Technologies)

Container: aluminum pan

Mass of Sample: 3.0 mg

Measurement atmosphere: nitrogen gas atmosphere

Temperature Increase Rate: 10 degrees C. per minute

Measurement Range: from 35 to 600 degrees C.

Sublimation Temperature

A sublimation temperature of each of the compounds was measured under the following conditions using a vacuum evaporation apparatus.

Results are shown in Table 59.

Measurement Conditions Pressure: $10^{-5}$ Pa

Temperature: from 300 to 400 degrees C.

Heating Time: from 5 to 10 minutes

Delayed Fluorescence

Delayed Fluorescence of Compound TADF1

Delayed fluorescence was checked by measuring a transient PL using an apparatus shown in FIG. 2. A dilute solution was prepared by dissolving the compound TADF1 in toluene, the dilute solution (sample solution) having an absorbance of 0.05 or less at an excitation wavelength in order to remove contribution of self-absorption. Moreover, in order to prevent quenching due to oxygen, the sample solution was frozen and degassed, and then sealed in a cell with a lid under an argon atmosphere to obtain an oxygen-free sample solution saturated with argon.

Fluorescence spectrum of the sample solution was measured with a spectrophotofluorometer FP-8600 (manufactured by JASCO Corporation). Moreover, fluorescence spectrum of an ethanol solution of 9,10-diphenylanthracene was measured under the same conditions. Using fluorescence area intensities of both the spectra, a total fluorescence quantum yield was calculated according to the equation (1) in Morris et al. J. Phys. Chem. $80(1976)_{969}$.

Prompt emission was observed immediately when the excited state was achieved by exciting the compound TADF1 with a pulse beam (i.e., a beam emitted from a pulse laser) having a wavelength to be absorbed by the compound TADF1, and Delay emission was observed not immediately when the excited state was achieved but after the excited state was achieved. Delayed fluorescence in Examples means that an amount of Delay emission is 5% or more relative to an amount of Prompt emission. Specifically, the delayed fluorescence means that a value of $X_D/X_P$ is 0.05 or more, provided that the amount of Prompt emission is denoted by $X_P$ and the amount of Delay emission is denoted by $X_D$.

The amount of Prompt emission, the amount of Delay emission, and a ratio thereof can be obtained according to the method as described in "Nature 492, 234-238, 2012" (Reference Literature 1). A device used for calculating the amount of Prompt emission and the amount of Delay emission is not limited to the device described in Reference Literature 1 or FIG. 2.

It was confirmed that the amount of Delay emission was 5% or more relative to the amount of Prompt emission in the compound TADF1. Specifically, it was confirmed that the value of $X_D/X_P$ was 0.05 or more in the compound TADF1.

Delayed Fluorescence of Compounds TADF 2 to 39 and Comparative Compounds 1 to 3

Compounds TADF 2 to 39 and comparative compounds 1 to 3 were checked in terms of delayed fluorescence in the same manner as above except that the compound TADF1 was replaced by compounds TADF 2 to 39 and comparative compounds 1 to 3.

It was confirmed that the value of $X_D/X_P$ was 0.05 or more in the compound compounds TADF 2 to 39 and comparative compounds 1 to 3.

Singlet Energy $S_1$

The compounds TADF1 to 39, the comparative compounds 1 to 3, and compounds RD-1 to RD-4 and CBP were measured in terms of singlet energy $S_1$ by the above solution method. Results are shown in Table 59.

Measurement results of the compounds RD-1 to RD-4 and CBP are as follows.

A singlet energy $S_1$ of the compound RD-1 was 2.02 eV.
A singlet energy $S_1$ of the compound RD-2 was 2.00 eV.
A singlet energy $S_1$ of the compound RD-3 was 2.04 eV.
A singlet energy $S_1$ of the compound RD-4 was 2.12 eV.
A singlet energy $S_1$ of the compound CBP was 3.41 eV.

ΔST $T_{77K}$ of each of the compounds TADF1 to TADF39 and the comparative compounds 1 to 3 was measured. ΔST was checked from the measurement results of $T_{77K}$ and the values of the singlet energy $S_1$ described above.

$T_{77K}$ of each of the compounds TADF1 to TADF39 and the comparative compounds 1 to 3 was measured by the measurement method described above in "Relationship between Triplet Energy and Energy Gap at 77K."

ΔST of each of each of the compounds TADF1 to TADF39 and the comparative compounds 1 to 3 was less than 0.01 eV.

Main Peak Wavelength of Compounds

A 5-μmol/L toluene solution of each of the compounds (measurement target) was prepared and put in a quartz cell. An emission spectrum (ordinate axis: fluorescence intensity, abscissa axis: wavelength) of each of the samples was measured at a normal temperature (300K). In Examples, the emission spectrum was measured using a spectrophotometer manufactured by Hitachi, Ltd. (device name: F-7000). It should be noted that a fluorescence spectrum measuring device may be different from the above device. A peak wavelength of the fluorescence spectrum exhibiting the maximum luminous intensity was defined as a main peak wavelength.

Results are shown in Table 59.

Measurement results of the compounds RD-1 to RD-4 are as follows.

A main peak wavelength of the compound RD-1 was 609 nm.
A main peak wavelength of the compound RD-2 was 613 nm.
A main peak wavelength of the compound RD-3 was 647 nm.
A main peak wavelength of the compound RD-4 was 585 nm.

TABLE 59

| | compound | molecular weight | main peak wavelength [nm] | singlet energy $S_1$ [eV] | weight loss temperature (° C.) TG1 % | weight loss temperature (° C.) TG5 % | sublimation temperature (° C.) |
|---|---|---|---|---|---|---|---|
| Example 1 | TADF1 | 969 | 550 | 2.29 | 441.1 | 485.9 | 380 |
| Example 2 | TADF2 | 1021 | 566 | 2.24 | 429.4 | 491.9 | — |
| Example 3 | TADF3 | 1069 | 577 | 2.21 | 420.0 | 496.0 | — |
| Example 4 | TADF4 | 969 | 518 | 2.54 | 432.3 | 479.0 | 358 |
| Example 5 | TADF5 | 1029 | 553 | 2.40 | 419.4 | 477.3 | — |
| Example 6 | TADF6 | 879 | 535 | 2.52 | 397.7 | 437.6 | 321 |
| Example 7 | TADF7 | 969 | 526 | 2.49 | — | — | 358 |
| Example 8 | TADF8 | 1001 | 548 | 2.27 | 459.7 | 509.7 | — |
| Example 9 | TADF9 | 895 | 531 | 2.53 | 398.5 | 444.0 | — |
| Example 10 | TADF10 | 969 | 517 | 2.54 | 430.4 | 481.1 | — |
| Example 11 | TADF11 | 1001 | 521 | 2.51 | 448.0 | 501.3 | — |
| Example 12 | TADF12 | 879 | 545 | 2.34 | 403.4 | 447.8 | 317 |
| Example 13 | TADF13 | 997 | 531 | 2.46 | 415.2 | 472.2 | 260 |
| Example 14 | TADF14 | 1001 | 539 | 2.45 | 456.6 | 502.2 | 356 |
| Example 15 | TADF15 | 879 | 546 | 2.34 | 376.6 | 439.0 | 273 |
| Example 16 | TADF16 | 895 | 543 | 2.34 | — | — | 283 |
| Example 17 | TADF17 | 969 | 521 | 2.38 | 414.4 | 505.6 | 339 |
| Example 18 | TADF18 | 1001 | 548 | 2.31 | 439.9 | 488.7 | 356 |
| Example 19 | TADF19 | 969 | 551 | 2.31 | 460.4 | 512.4 | 364 |
| Example 20 | TADF20 | 909 | 550 | 2.32 | — | — | 302 |
| Example 21 | TADF21 | 895 | 539 | 2.34 | — | — | 316 |
| Example 22 | TADF22 | 909 | 545 | 2.32 | 399.3 | 449.3 | 310 |
| Example 23 | TADF23 | 1029 | 554 | 2.27 | 451.6 | 496.1 | — |
| Example 24 | TADF24 | 997 | 552 | 2.34 | — | — | — |
| Example 25 | TADF25 | 1029 | 544 | 2.28 | 425.7 | 482.6 | 316 |
| Example 26 | TADF26 | 907 | 544 | 2.38 | — | — | — |
| Example 27 | TADF27 | 923 | 559 | 2.34 | — | — | — |
| Example 28 | TADF28 | 969 | 546 | 2.31 | 434.9 | 475.5 | — |
| Example 29 | TADF29 | 895 | 506 | 2.58 | 359.8 | 445.4 | — |
| Example 31 | TADF31 | 895 | 512 | 2.53 | 410.1 | 460.0 | — |
| Example 32 | TADF32 | 1029 | — | — | 433.6 | 480.4 | — |
| Example 34 | TADF34 | 879 | 494 | 2.64 | 392.1 | 439.1 | — |
| Example 37 | TADF37 | 933 | 545 | 2.32 | 406.1 | 455.3 | 313 |
| Example 38 | TADF38 | 933 | 550 | 2.32 | — | — | 306 |
| Comparative 1 | comparative compound 1 | 1149 | 536 | 2.44 | 493.1 | 539.9 | 390 |
| Comparative 2 | camperative compound 2 | 1149 | 563 | 2.22 | 475.1 | 527.5 | 400 |
| Comparative 3 | comparative compound 3 | 1149 | 550 | 2.41 | 465.2 | 522.7 | 385 |

Description about Table
"TG1%" represents a 1%-weight loss temperature.
"TG5%" represents a 5%-weight loss temperature.
"–" represents no measurement.

As shown in Table 59, the compounds in Examples where the 1%-weight loss temperature and the 5%-weight loss temperature were measured exhibited lower 1%-weight loss temperature and 5%-weight loss temperature than the comparative compounds 1 to 3 in Comparatives 1 to 3.

In addition, as shown in Table 59, the compounds in Examples where the sublimation temperature was measured exhibited the lower sublimation temperature under high vacuum ($10^{-5}$ Pa) than the comparative compounds 1 to 3 in Comparatives 1 to 3.

It was also confirmed that the compounds TADF1 to 6 in Examples 1 to 6 exhibited the lower sublimation temperature under high vacuum (from $1.0 \times 10^{-6}$ Pa to $1.0 \times 10^{-3}$ Pa) than the comparative compounds 1 to 3 in Comparatives 1 to 3.

Manufacturing of Organic EL Device 1

In Example 12A below, an organic EL device was manufactured using the compound (TADF1), as the first compound, in which two groups each represented by the formula (1-1) and two groups each represented by the formula (2-1) were bonded to para-dicyanobenzene.

In Examples 12A-1 and 12A-2, organic EL devices were manufactured using the respective compounds (TADF12, TADF16), as the first compound, in which a single group represented by the formula (1-1) and three groups each represented by the formula (2-1) were bonded to para-dicyanobenzene.

In Comparative 12B, an organic EL device was manufactured using a compound (comparative compound 2) in which four groups each represented by the formula (1-1) were bonded to para-dicyanobenzene.

Example 12A

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for one minute. A film of ITO was set to be 130-nm thick.

After the glass substrate having the transparent electrode line was cleaned, the glass substrate was mounted on a substrate holder of a vacuum evaporation apparatus. Initially, a compound HT-1 and a compound HA were co-deposited on a surface of the glass substrate where the transparent electrode line was provided in a manner to cover the transparent electrode, thereby forming a 10-nm-thick hole injecting layer. In the hole injecting layer, a concentration of the compound HT-1 was set at 97 mass % and a concentration of the compound HA was set at 3 mass %.

Next, the compound HT-1 was vapor-deposited on the hole injecting layer to form a 200-nm-thick first hole transporting layer on the hole injecting layer.

Next, a compound HT-2 was vapor-deposited on the first hole transporting layer to form a 10-nm-thick second hole transporting layer.

Subsequently, the compound TADF1 (first compound), the compound RD-1 (second compound) and the compound CBP (third compound) were co-deposited on the second hole transporting layer to form a 25-nm-thick emitting layer (first organic layer). A concentration of the compound TADF1 was set at 25 mass %, a concentration of the compound RD-1 was set at 1 mass %, and a concentration of the compound CBP was set at 74 mass % in the emitting layer.

Next, a compound ET-1 was vapor-deposited on the emitting layer to form a 10-nm-thick first electron transporting layer.

Next, a compound ET-2 was vapor-deposited on the first electron transporting layer to form a 30-nm-thick second electron transporting layer.

Next, lithium fluoride (LiF) was vapor-deposited on the second electron transporting layer to form a 1-nm-thick electron injecting electrode (cathode).

A metal aluminum (Al) was then vapor-deposited on the electron injecting electrode to form an 80-nm-thick metal Al cathode.

A device arrangement of the organic EL device of Example 12A is roughly shown as follows.

ITO(130)/HT-1:HA(10.97%:3%)/HT-1(200)/HT-2(10)/CBP:TADF1:RD-1(25.74%:25%:1%)/ET-1(10)/ET-2(30)/LiF(1)/Al(80)

Numerals in parentheses represent a film thickness (unit: nm).

The numerals (97%:3%) represented by percentage in the same parentheses indicate a ratio (mass %) of the compound HT-1 and the compound HA in the hole injecting layer. The numerals (74%:25%:1%) represented by percentage in the same parentheses indicate a ratio (mass %) of the third compound, the first compound and the second compound in the emitting layer. Hereinafter, the same notation is applied.

Example 12A-1

The organic EL device in Example 12A-1 was manufactured in the same manner as in Example 12A except that the compound TADF12 was used in place of the compound TADF1 in the emitting layer of Example 12A.

A device arrangement of the organic EL device in Example 12A-1 is roughly shown as follows.

ITO(130)/HT-1:HA(10.97%:3%)/HT-1(200)/HT-2(10)/CBP:TADF12:RD-1(25.74%:25%:1%)/ET-1(10)/ET-2(30)/LiF(1)/Al(80)

Example 12A-2

The organic EL device in Example 12A-2 was manufactured in the same manner as in Example 12A except that the compound TADF16 was used in place of the compound TADF1 in the emitting layer of Example 12A.

A device arrangement of the organic EL device in Example 12A-2 is roughly shown as follows.

ITO(130)/HT-1:HA(10.97%:3%)/HT-1(200)/HT-2(10)/CBP:TADF16:RD-1(25.74%:25%:1%)/ET-1(10)/ET-2(30)/LiF(1)/Al(80)

Comparative 12B

The organic EL device in Comparative 12B was manufactured in the same manner as in Example 12A except that the comparative compound 2 was used in place of the compound TADF1 in the emitting layer of Example 12A.

A device arrangement of the organic EL device in Comparative 12B is roughly shown as follows.

ITO(130)/HT-1:HA(10.97%:3%)/HT-1(200)/HT-2(10)/CBP: Comparative Compound 2:RD-1(25.74%:25%:1%)/ET-1(10)/ET-2(30)/LiF(1)/Al(80)

Evaluation 1-1

The organic EL devices manufactured in Example 12A and Comparative 12B were evaluated as follows. Evaluation results are shown in Table 60.

External Quantum Efficiency EQE Voltage was applied on each of the organic EL devices such that a current density was 0.1 mA/cm$^2$ or 10 mA/cm$^2$ where spectral radiance spectra were measured using a spectroradiometer (CS-2000 manufactured by Konica Minolta, Inc.). The external quantum efficiency EQE (unit: %) was calculated based on the obtained spectral-radiance spectra, assuming that the spectra were provided under a Lambertian radiation.

Hereinafter, the external quantum efficiency EQE (%) at 0.1 mA/cm$^2$ of the current density will be referred to as "EQE (%) at a low current." The external quantum efficiency EQE (%) at 10 mA/cm$^2$ of the current density will be referred to as "EQE (%) at a high current."

Provided that "EQE (%) at a low current" in Comparative 12B was 100%, "EQE (%) at a low current" in Example 12A was calculated as "EQE (relative value: %) at a low current" using the following numerical formula (Numerical Formula 100).

EQE (relative value: %) at a low current in Example 12A=(EQE (%) at a low current in Example 12A/EQE (%) at a low current in Comparative 12B)×100    (Numerical Formula 100)

Provided that "EQE (%) at a high current" in Comparative 12B was 100%, "EQE (%) at a high current" in Example 12A was calculated as "EQE (relative value: %) at a high current" using the following numerical formula (Numerical Formula 101).

EQE (relative value: %) at a high current in Example 12A=(EQE (%) at a high current in Example 12A/EQE (%) at a high current in Comparative 12B)×100    (Numerical Formula 101)

Chromaticity CIEx, CIEy, and Main Peak Wavelength $\lambda_p$

Voltage was applied on each of the organic EL devices such that a current density was 10 mA/cm$^2$, where spectral radiance spectra were measured using a spectroradiometer (CS-2000 manufactured by Konica Minolta, Inc.). Chromaticity CIEx, CIEy, and a main peak wavelength $\lambda_p$ (unit: nm) were calculated from the obtained spectral radiance spectra.

TABLE 60

| | Emitting layer | | | Evaluation | | | | |
|---|---|---|---|---|---|---|---|---|
| | first compound | second compound | third compound | EQE at low current (relative value: %) | EQE at high current (relative value: %) | CIEx | CIEy | $\lambda_p$ [nm] |
| Example 12A | TADF1 | RD-1 | CBP | 189 | 196 | 0.66 | 0.34 | 620 |
| Comparative 12B | comparative compound 2 | RD-1 | CBP | 100 | 100 | 0.66 | 0.34 | 621 |

Description about Table

The "at a low current" refers to a current whose current density is 1 mA/cm$^2$. The "at a high current" refers to a current whose current density is 10 mA/cm$^2$. The same is applied to Tables below.

As compared with the organic EL device in Comparative 12B, the organic EL device in Example 12A improved the external quantum efficiency EQE both at the low current (at the current density being 0.1 mA/cm$^2$) and at the high current (at the current density being 10 mA/cm$^2$).

Evaluation 1-2

The organic EL devices manufactured in Examples 12A-1 and 12A-2 and Comparative 12B were evaluated as follows. Evaluation results are shown in Table 61.

External Quantum Efficiency EQE

Provided that "EQE (%) at a low current" in Comparative 12B was 100%, "EQE (%) at a low current" in Example 12A-1 was calculated as "EQE (relative value: %) at a low current" using the same method as that of the organic EL device manufactured in Example 12A. Also with respect to the organic EL device in Example 12A-2, "EQE (relative value: %) at a low current" was obtained using the same method.

Drive Voltage

Voltage (unit: V) when current was applied between the anode and the cathode such that a current density was 10 mA/cm$^2$ was measured.

Provided that a "drive voltage (V)" in Comparative 12B was 100%, a "drive voltage (V)" in Example 12A-1 was calculated as a "drive voltage (relative value: %)" using the following numerical formula (Numerical Formula 100A). Also with respect to the organic EL device in Example 12A-2, a "drive voltage (relative value: %)" was obtained using the same method.

drive voltage (relative value: %) in Example 12A-1=(drive voltage (V) in Example 12A-1/drive voltage (V) in Comparative 12B)×100    (Numerical Formula 100A)

Values of Chromaticity CIEx, CIEy, and Main Peak Wavelength $\lambda_p$

Chromaticity CIEx, CIEy, and a main peak wavelength $\lambda_p$ (unit: nm) were calculated using the same method as that for the organic EL device manufactured in Example 12A.

TABLE 61

| | Emitting layer | | | Evaluation | | | | |
|---|---|---|---|---|---|---|---|---|
| | first compound | second compound | third compound | drive voltage (relative value: %) | EQE at low current (relative value: %) | CIEx | CIEy | λp [nm] |
| Example 12A-1 | TADF12 | RD-1 | CBP | 98 | 226 | 0.66 | 0.34 | 620 |
| Example 12A-2 | TADF16 | RD-1 | CBP | 97 | 231 | 0.65 | 0.35 | 619 |
| Comparative 12B | comparative compound 2 | RD-1 | CBP | 100 | 100 | 0.66 | 0.34 | 621 |

The organic EL devices in Examples 12A-1 and 12A-2 exhibited a lower drive voltage and a higher external quantum efficiency EQE at a low current (at a current density being 0.1 mA/cm²) than those of the organic EL device in Comparative 12B.

Manufacturing 2 of Organic EL Device 2

In Examples 13A and 13A-1, organic EL devices were manufactured using the respective compounds (TADF7, TADF13), as the first compound, in which two groups each represented by the formula (1-1) and two groups each represented by the formula (2-1) were bonded to meta-dicyanobenzene.

In Comparative 13B, an organic EL device was manufactured using a compound (comparative compound 1) in which four groups each represented by the formula (1-1) were bonded to meta-dicyanobenzene.

Example 13A

The organic EL device in Example 13A was manufactured in the same manner as in Example 12A except that the compound TADF7 was used in place of the compound TADF1 in the emitting layer of Example 12A.

A device arrangement of the organic EL device in Example 13A is roughly shown as follows.

ITO(130)/HT-1:HA(10.97%:3%)/HT-1(200)/HT-2(10)/ CBP:TADF7:RD-1(25.74%:25%:1%)/ET-1(10)/ET-2(30)/ LiF(1)/Al(80)

Example 13A-1

The organic EL device in Example 13A-1 was manufactured in the same manner as in Example 12A except that the compound TADF13 was used in place of the compound TADF1 in the emitting layer of Example 12A.

A device arrangement of the organic EL device in Example 13A-1 is roughly shown as follows.

ITO(130)/HT-1:HA(10.97%:3%)/HT-1(200)/HT-2(10)/ CBP:TADF13:RD-1(25.74%:25%:1%)/ET-1(10)/ET-2(30)/ LiF(1)/Al(80)

Comparative 13B

The organic EL device in Comparative 13B was manufactured in the same manner as in Example 12A except that the comparative compound 1 was used in place of the compound TADF1 in the emitting layer of Example 12A.

A device arrangement of the organic EL device in Comparative 13B is roughly shown as follows.

ITO(130)/HT-1:HA(10.97%:3%)/HT-1(200)/HT-2(10)/ CBP: comparative compound 1:RD-1(25.74%:25%:1%)/ ET-1 (10)/ET-2(30)/LiF(1)/Al(80)

Evaluation 2-1

The organic EL devices manufactured in Example 13A and Comparative 13B were evaluated as follows. Evaluation results are shown in Table 62.

Drive Voltage

Voltage (unit: V) when current was applied between the anode and the cathode such that a current density was 10 mA/cm² was measured.

Provided that a "drive voltage (V)" in Comparative 13B was 100%, a "drive voltage (V)" in Example 13A was calculated as a "drive voltage (relative value: %)" using the following numerical formula (Numerical Formula 103).

drive voltage (relative value: %) in Example 13*A*= (drive voltage (*V*) in Example 13*A*/drive voltage (*V*) in Comparative 13*B*)×100   (Numerical Formula 103)

Values of Chromaticity CIEx, CIEy, and Main Peak Wavelength $\lambda_p$

Chromaticity CIEx, CIEy, and a main peak wavelength $\lambda_p$ (unit: nm) were calculated using the same method as that for the organic EL device manufactured in Example 12A.

TABLE 62

| | Emitting layer | | | Evaluation | | | |
|---|---|---|---|---|---|---|---|
| | first compound | second compound | third compound | drive voltage (relative value: %) | CIEx | CIEy | λp [nm] |
| Example 13A | TADF7 | RD-1 | CBP | 96 | 0.64 | 0.36 | 619 |
| Comparative 13B | comparative compound 1 | RD-1 | CBP | 100 | 0.64 | 0.36 | 619 |

The organic EL device in Example 13A exhibited a lower drive voltage than that of organic EL device in Comparative 13B.

Evaluation 2-2

The organic EL devices manufactured in Example 13A-1 and Comparative 13B were evaluated as follows. Evaluation results are shown in Table 63.

Drive Voltage

Provided that a "drive voltage (unit: V)" in Comparative 13B was 100%, a "drive voltage (unit: V)" in Example 13A-1 was calculated as a "drive voltage (relative value: %)" using the same method as that of the organic EL device manufactured in Example 12A-1.

Values of Chromaticity CIEx, CIEy, and Main Peak Wavelength $\lambda_p$

Chromaticity CIEx, CIEy, and a main peak wavelength $\lambda_p$ (unit: nm) were calculated using the same method as that for the organic EL device manufactured in Example 12A.

TABLE 63

|  | Emitting layer | | | Evaluation | | | |
| --- | --- | --- | --- | --- | --- | --- | --- |
|  | first compound | second compound | third compound | drive voltage (relative value:%) | CIEx | CIEy | $\lambda p$ [nm] |
| Example 13A-1 | TADF13 | RD-1 | CBP | 93 | 0.64 | 0.36 | 620 |
| Comparative 13B | comparative compound 1 | RD-1 | CBP | 100 | 0.64 | 0.36 | 619 |

The organic EL device in Example 13A-1 exhibited a lower drive voltage than that of organic EL device in Comparative 13B.

Manufacturing 3 of Organic EL Device 3

In Example 14A, an organic EL device was manufactured using the compound (TADF6), as the first compound, in which a single group represented by the formula (1-1) and three groups each represented by the formula (2-1) were bonded to ortho-dicyanobenzene.

In Comparative 14B, an organic EL device was manufactured using a compound (comparative compound 3) in which four groups each represented by the formula (1-1) were bonded to ortho-dicyanobenzene.

Example 14A

The organic EL device in Example 14A was manufactured in the same manner as in Example 12A except that the compound TADF6 was used in place of the compound TADF1 in the emitting layer of Example 12A.

A device arrangement of the organic EL device in Example 14A is roughly shown as follows.

ITO(130)/HT-1:HA(10.97%:3%)/HT-1(200)/HT-2(10)/ CBP:TADF6:RD-1(25.74%:25%:1%)/ET-1(10)/ET-2(30)/ LiF(1)/Al(80)

Comparative 14B

The organic EL device in Comparative 14B was manufactured in the same manner as in Example 12A except that the comparative compound 3 was used in place of the compound TADF1 in the emitting layer of Example 12A.

A device arrangement of the organic EL device in Comparative 14B is roughly shown as follows.

ITO(130)/HT-1:HA(10.97%:3%)/HT-1(200)/HT-2(10)/ CBP: Comparative Compound 3:RD-1(25.74%:25%:1%)/ ET-1(1%)/ET-2(30)/LiF(1)/Al(80)

Evaluation 3

The organic EL devices manufactured in Example 14A and Comparative 14B were evaluated as follows. Evaluation results are shown in Table 64.

Drive Voltage

Provided that a "drive voltage (unit: V)" in Comparative 14B was 100%, a "drive voltage (unit: V)" in Example 14A was calculated as a "drive voltage (relative value: %)" using the same method as that of the organic EL device manufactured in Example 13A.

External Quantum Efficiency EQE

Provided that "EQE (%) at a low current" in Comparative 14B was 100%, "EQE (%) at a low current" in Example 14A was calculated as "EQE (relative value: %) at a low current" using the same method as that of the organic EL device manufactured in Example 12A.

Chromaticity CIEx, CIEy, and Main Peak Wavelength $\lambda_p$

Chromaticity CIEx, CIEy, and a main peak wavelength $\lambda_p$ (unit: nm) were calculated using the same method as that for the organic EL device manufactured in Example 12A.

TABLE 64

|  | Emitting layer | | | Evaluation | | | | |
| --- | --- | --- | --- | --- | --- | --- | --- | --- |
|  | | | | | EQE | | | |
|  | first compound | second compound | third compound | drive voltage (relative value: %) | at low current (relative value: %) | CIEx | CIEy | $\lambda p$ [nm] |
| Example 14A | TADF6 | RD-1 | CBP | 98 | 116 | 0.65 | 0.35 | 620 |
| Comparative 14B | comparative compound 3 | RD-1 | CBP | 100 | 100 | 0.66 | 0.34 | 620 |

The organic EL device in Example 14A exhibited a lower drive voltage and a higher external quantum efficiency EQE at a low current (at a current density being 0.1 mA/cm$^2$) than those of the organic EL device in Comparative 14B.

Manufacturing 4 of Organic EL Device 4

In Example 15A, an organic EL device was manufactured using the compound (TADF18), as the first compound, in which two groups each represented by the formula (1-4) and two groups each represented by the formula (2-1) were bonded to para-dicyanobenzene.

In Examples 15A-1 and 15A-5, organic EL devices were manufactured using the compounds (TADF20, TADF38), as the first compound, in which a single group represented by the formula (1-1) and three groups each represented by the formula (2-1) were bonded to para-dicyanobenzene.

In Examples 15A-2 and 15A-4, organic EL devices were manufactured using the compounds (TADF22, TADF37), as the first compound, in which a single group represented by the formula (1-4) and three groups each represented by the formula (2-1) were bonded to para-dicyanobenzene.

In Example 15A-3, an organic EL device was manufactured using the compounds (TADF28), as the first compound, in which two groups each represented by the formula (1-2) and two groups each represented by the formula (2-1) were bonded to para-dicyanobenzene.

Example 15A

The organic EL device in Example 15A was manufactured in the same manner as in Example 12A except that the compound TADF18 was used in place of the compound TADF1 in the emitting layer of Example 12A.

A device arrangement of the organic EL device in Example 15A is roughly shown as follows.
ITO(130)/HT-1:HA(10.97%:3%)/HT-1(200)/HT-2(10)/CBP:TADF18:RD-1(25.74%:25%:1%)/ET-1(10)/ET-2(30)/LiF(1)/Al(80)

Numerals in parentheses represent a film thickness (unit: nm).

Example 15A-1

The organic EL device in Example 15A-1 was manufactured in the same manner as in Example 12A except that the compound TADF20 was used in place of the compound TADF1 in the emitting layer of Example 12A.

A device arrangement of the organic EL device in Example 15A-1 is roughly shown as follows.
ITO(130)/HT-1:HA(10.97%:3%)/HT-1(200)/HT-2(10)/CBP:TADF20:RD-1(25.74%:25%:1%)/ET-1(10)/ET-2(30)/LiF(1)/Al(80)

Example 15A-2

The organic EL device in Example 15A-2 was manufactured in the same manner as in Example 12A except that the compound TADF22 was used in place of the compound TADF1 in the emitting layer of Example 12A.

A device arrangement of the organic EL device in Example 15A-2 is roughly shown as follows.
ITO(130)/HT-1:HA(10.97%:3%)/HT-1(200)/HT-2(10)/CBP:TADF22:RD-1(25.74%:25%:1%)/ET-1(10)/ET-2(30)/LiF(1)/Al(80)

Example 15A-3

The organic EL device in Example 15A-3 was manufactured in the same manner as in Example 12A except that the compound TADF28 was used in place of the compound TADF1 in the emitting layer of Example 12A.

A device arrangement of the organic EL device in Example 15A-3 is roughly shown as follows.
ITO(130)/HT-1:HA(10.97%:3%)/HT-1(200)/HT-2(10)/CBP:TADF28:RD-1(25.74%:25%:1%)/ET-1(10)/ET-2(30)/LiF(1)/Al(80)

Example 15A-4

The organic EL device in Example 15A-4 was manufactured in the same manner as in Example 12A except that the compound TADF37 was used in place of the compound TADF1 in the emitting layer of Example 12A.

A device arrangement of the organic EL device in Example 15A-4 is roughly shown as follows.
ITO(130)/HT-1:HA(10.97%:3%)/HT-1(200)/HT-2(10)/CBP:TADF37:RD-1(25.74%:25%:1%)/ET-1(10)/ET-2(30)/LiF(1)/Al(80)

Example 15A-5

The organic EL device in Comparative 15A-5 was manufactured in the same manner as in Example 12A except that the compound TADF38 was used in place of the compound TADF1 in the emitting layer of Example 12A.

A device arrangement of the organic EL device in Example 15A-5 is roughly shown as follows.
ITO(130)/HT-1:HA(10.97%:3%)/HT-1(200)/HT-2(10)/CBP:TADF38:RD-1(25.74%:25%: 1%)/ET-1(10)/ET-2(30)/LiF(1)/Al(80)

Evaluation 4

The organic EL devices manufactured in Examples 15A and 15A-1 to 15A-5 were evaluated as follows. Evaluation results are shown in Table 65. Evaluation results of Comparative 12B are also shown in Table 65.

External Quantum Efficiency EQE

Provided that "EQE (%) at a low current" in Comparative 12B was 100%, "EQE (%) at a low current" in each of Examples 15A and 15A-1 to 15A-5 was calculated as "EQE (relative value: %) at a low current" using the same method as that of the organic EL device manufactured in Example 12A. Provided that "EQE (%) at a high current" in Comparative 12B was 100%, "EQE (%) at a high current" in each of Examples 15A and 15A-1 to 15A-5 was calculated as "EQE (relative value: %) at a high current."

Drive Voltage

Provided that a "drive voltage (unit: V)" in Comparative 12B was 100%, a "drive voltage (unit: V)" in each of Examples 15A and 15A-1 to 15A-5 was calculated as a "drive voltage (relative value: %)" using the same method as that of the organic EL device manufactured in Example 13A.

Chromaticity CIEx, CIEy, and Main Peak Wavelength $\lambda_p$

Chromaticity CIEx, CIEy, and a main peak wavelength $\lambda_p$ (unit: nm) were calculated using the same method as that for the organic EL device manufactured in Example 12A.

TABLE 65

| | Emitting layer | | | | Evaluation | | | | |
| | | | | | EQE | | | | |
| | first compound | second compound | third compound | drive voltage (relative value: %) | at low current (relative value: %) | at high current (relative value: %) | CIEx | CIEy | $\lambda p$ [nm] |
|---|---|---|---|---|---|---|---|---|---|
| Example 15A | TADF18 | RD-1 | CBP | 95 | 186 | 250 | 0.66 | 0.34 | 620 |
| Example 15A-1 | TADF20 | RD-1 | CBP | 98 | 252 | 260 | 0.66 | 0.34 | 620 |
| Example 15A-2 | TADF22 | RD-1 | CBP | 97 | 256 | 288 | 0.66 | 0.34 | 620 |

TABLE 65-continued

|  | Emitting layer | | | Evaluation | | | | | |
|---|---|---|---|---|---|---|---|---|---|
|  | | | | | EQE | | | | |
|  | first compound | second compound | third compound | drive voltage (relative value: %) | at low current (relative value: %) | at high current (relative value: %) | CIEx | CIEy | λp [nm] |
| Example 15A-3 | TADF28 | RD-1 | CBP | 100 | 215 | 228 | 0.66 | 0.34 | 620 |
| Example 15A-4 | TADF37 | RD-1 | CBP | 98 | 250 | 270 | 0.66 | 0.34 | 620 |
| Example 15A-5 | TADF38 | RD-1 | CBP | 100 | 213 | 220 | 0.66 | 0.34 | 620 |
| Comparative 12B | comparative compound 2 | RD-1 | CBP | 100 | 100 | 100 | 0.66 | 0.34 | 621 |

As compared with the organic EL device in Comparative 12B, the organic EL devices in Examples 15A-1 to 15A-5 improved the external quantum efficiency EQE both at the low current (at the current density being 0.1 mA/cm$^2$) and at the high current (at the current density being 10 mA/cm$^2$). Further, the organic EL devices of Examples 15A, 15A-1 to 15A-2 and 15A-4 exhibited a lower drive voltage than that of the organic EL device of Comparative 12B.

Manufacturing of Organic EL Device 5

In Examples 16A, 6A-1 and 16A-2, organic EL devices were manufactured using the compound (TADF22), as the first compound, in which a single group represented by the formula (1-4) and three groups each represented by the formula (2-1) were bonded to para-dicyanobenzene.

In Comparatives 16B, 16B-1 and 16B-2, organic EL devices were manufactured using a compound (comparative compound 2) in which four groups each represented by the formula (1-1) were bonded to para-dicyanobenzene.

Example 16A

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for one minute. A film of ITO was set to be 130-nm thick.

After the glass substrate having the transparent electrode line was cleaned, the glass substrate was mounted on a substrate holder of a vacuum evaporation apparatus. Initially, a compound HT-1 and a compound HA were co-deposited on a surface of the glass substrate where the transparent electrode line was provided in a manner to cover the transparent electrode, thereby forming a 10-nm-thick hole injecting layer. In the hole injecting layer, a concentration of the compound HT-1 was set at 97 mass % and a concentration of the compound HA was set at 3 mass %.

Next, the compound HT-1 was vapor-deposited on the hole injecting layer to form a 200-nm-thick first hole transporting layer on the hole injecting layer.

Next, a compound HT-2 was vapor-deposited on the first hole transporting layer to form a 10-nm-thick second hole transporting layer.

Subsequently, the compound TADF22 (first compound), the compound RD-2 (second compound) and the compound CBP (third compound) were co-deposited on the second hole transporting layer to form a 25-nm-thick emitting layer (first organic layer). A concentration of the compound TADF22 was set at 25 mass %, a concentration of the compound RD-2 was set at 1 mass %, and a concentration of the compound CBP was set at 74 mass % in the emitting layer.

Next, a compound ET-1 was vapor-deposited on the emitting layer to form a 10-nm-thick first electron transporting layer.

Next, a compound ET-2 was vapor-deposited on the first electron transporting layer to form a 30-nm-thick second electron transporting layer.

Next, lithium fluoride (LiF) was vapor-deposited on the second electron transporting layer to form a 1-nm-thick electron injecting electrode (cathode).

A metal aluminum (Al) was then vapor-deposited on the electron injecting electrode to form an 80-nm-thick metal Al cathode.

A device arrangement of the organic EL device in Example 16A is roughly shown as follows.

ITO(130)/HT-1:HA(10.97%:3%)/HT-1(200)/HT-2(10)/CBP:TADF22:RD-2(25.74%:25%:1%)/ET-1(10)/ET-2(30)/LiF(1)/Al(80)

Numerals in parentheses represent a film thickness (unit: nm).

Example 16A-1

The organic EL device in Example 16A-1 was manufactured in the same manner as in Example 16A except that the compound RD-3 was used in place of the compound RD-2 in the emitting layer of Example 16A.

A device arrangement of the organic EL device in Example 16A-1 is roughly shown as follows.

ITO(130)/HT-1:HA(10.97%:3%)/HT-1(200)/HT-2(10)/CBP: TADF22:RD-3(25.74%:25%:1%)/ET-1(10)/ET-2(30)/LiF(1)/Al(80)

Example 16A-2

The organic EL device in Example 16A-2 was manufactured in the same manner as in Example 16A except that the compound RD-4 was used in place of the compound RD-2 in the emitting layer of Example 16A.

A device arrangement of the organic EL device in Example 16A-2 is roughly shown as follows.

ITO(130)/HT-1:HA(10.97%:3%)/HT-1(200)/HT-2(10)/CBP: TADF22:RD-4(25.74%:25%:1%)/ET-1(10)/ET-2(30)/LiF(1)/Al(80)

Comparative 16B

The organic EL device in Comparative 16B was manufactured in the same manner as in Example 16A except that the comparative compound 2 was used in place of the compound TADF22 in the emitting layer of Example 16A.

A device arrangement of the organic EL device in Example 16B is roughly shown as follows.

ITO(130)/HT-1:HA(10.97%:3%)/HT-1(200)/HT-2(10)/CBP: comparative compound 2:RD-2(25.74%:25%:1%)/ET-1(10)/ET-2(30)/LiF(1)/Al(80)

Comparative 16B-1

The organic EL device in Comparative 16B-1 was manufactured in the same manner as in Example 16A-1 except that the comparative compound 2 was used in place of the compound TADF22 in the emitting layer of Example 16A-1.

A device arrangement of the organic EL device in Example 16B-1 is roughly shown as follows.

ITO(130)/HT-1:HA(10.97%:3%)/HT-1(200)/HT-2(10)/ CBP: comparative compound 2: RD-3(25.74%:25%:1%)/ ET-1(10)/ET-2(30)/LiF(1)/Al(80)

Comparative 16B-2

The organic EL device in Comparative 16B-2 was manufactured in the same manner as in Example 16A-2 except that the comparative compound 2 was used in place of the compound TADF22 in the emitting layer of Example 16A-2.

A device arrangement of the organic EL device in Example 16B-2 is roughly shown as follows.

ITO(130)/HT-1:HA(10.97%:3%)/HT-1(200)/HT-2(10)/ CBP:Comparative Compound 2:RD-4(25.74%:25%:1%)/ ET-1(10)/ET-2(30)/LiF(1)/Al(80)

Evaluation 5

The organic EL devices manufactured in Examples 16A, 16A-1 and 16A-2 and Comparatives 16B, 16B-1 and 16B-2 were evaluated as follows. Evaluation results are shown in Table 66.

External Quantum Efficiency EQE

Provided that "EQE (%) at a low current" in each of Comparatives 16B, 16B-1 and 16B-2 was 100%, "EQE (%) at a low current" in each of Examples 16A, 16A-1 and 16-2 was calculated as "EQE (relative value: %) at a low current" using the same method as that of the organic EL device manufactured in Example 12A. Provided that "EQE (%) at a high current" in each of Comparatives 16B, 16B-1 and 16B-2 was 100%, "EQE (%) at a high current" in each of Examples in each of Examples 16A, 16A-1 and 16-2 was calculated as "EQE (relative value: %) at a high current."

Drive Voltage

Provided that a "drive voltage (unit: V)" in each of Comparatives 16B, 16B-1 and 16B-2 was 100%, a "drive voltage (unit: V)" in each of Examples 16A, 16A-1 and 16-2 was calculated as a "drive voltage (relative value: %)" using the same method as that of the organic EL device manufactured in Example 13A.

Chromaticity CIEx, CIEy, and Main Peak Wavelength $\lambda_p$

Chromaticity CIEx, CIEy, and a main peak wavelength $\lambda_p$ (unit: nm) were calculated using the same method as that for the organic EL device manufactured in Example 12A.

current (at the current density being 10 mA/cm$^2$) and exhibited a lower drive voltage.

As compared with the organic EL device in Comparative 16B-1, the organic EL device in Example 16A-1 improved the external quantum efficiency EQE both at the low current (at the current density being 0.1 mA/cm$^2$) and at the high current (at the current density being 10 mA/cm$^2$) and exhibited a lower drive voltage.

As compared with the organic EL device in Comparative 16B-2, the organic EL device in Example 16A-2 improved the external quantum efficiency EQE both at the low current (at the current density being 0.1 mA/cm$^2$) and at the high current (at the current density being 10 mA/cm$^2$) and exhibited a lower drive voltage.

The invention claimed is:
1. A compound represented by one of formulae (11) to (13):

(11)

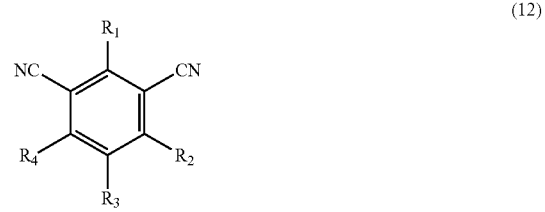

(12)

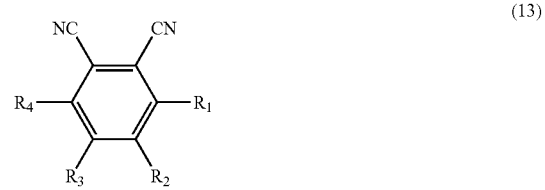

(13)

TABLE 66

| | Emitting layer | | | Evaluation | | | | | |
|---|---|---|---|---|---|---|---|---|---|
| | | | | | EQE | | | | |
| | first compound | second compound | third compound | drive voltage (relative value: %) | at low current (relative value: %) | at high current (relative value: %) | CIEx | CIEy | λp [nm] |
| Example 16A | TADF22 | RD-2 | CBP | 96 | 226 | 194 | 0.67 | 0.33 | 621 |
| Comparatiw 16B | comparative compound 2 | RD-2 | CBP | 100 | 100 | 100 | 0.67 | 0.33 | 621 |
| Example 16A-1 | TADF22 | RD-3 | CBP | 96 | 224 | 180 | 0.66 | 0.34 | 611 |
| Comparative 16B-1 | comparative compound 2 | RD-3 | CBP | 100 | 100 | 100 | 0.66 | 0.34 | 611 |
| Example 16A-2 | TADF22 | RD-4 | CBP | 94 | 356 | 334 | 0.58 | 0.42 | 597 |
| Comparative 16B-2 | comparative compound 2 | RD-4 | CBP | 100 | 100 | 100 | 0.61 | 0.39 | 604 |

As compared with the organic EL device in Comparative 16B, the organic EL device in Example 16A improved the external quantum efficiency EQE both at the low current (at the current density being 0.1 mA/cm$^2$) and at the high wherein $R_1$ to $R_4$ are each independently a group represented by one of formulae (1-1) to (1-6) or a group represented by one of formulae (2-1) to (2-4); at least one of $R_1$ to $R_4$ is the group represented by one of formulae (1-1) to (1-6) while at least one of $R_1$ to $R_4$ is the group represented by one of formulae (2-1) to (2-4):

(1-1)
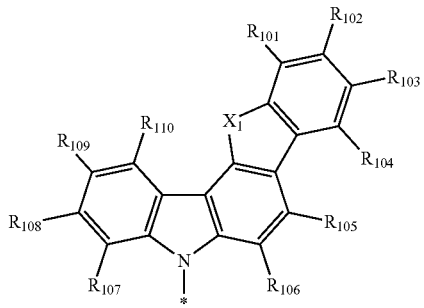

(1-2)
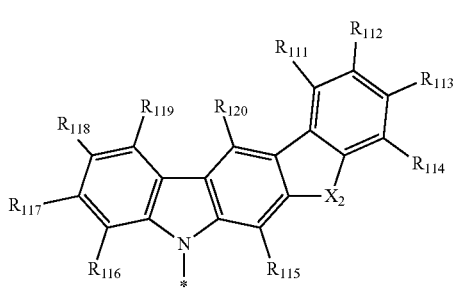

(1-3)
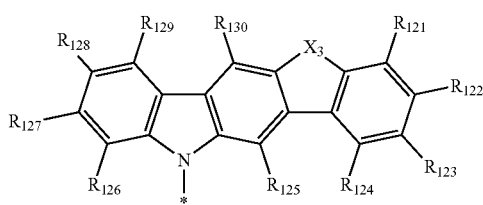

(1-4)
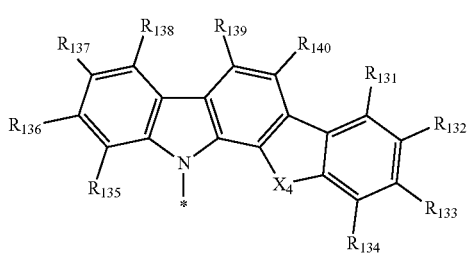

(1-5)
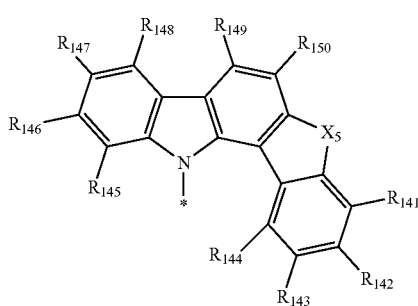

(1-6)
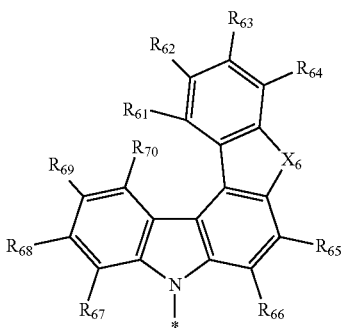

wherein in the formula (1-1): $X_1$ is an oxygen atom, a sulfur atom, or $CR_{151}R_{152}$; $R_{101}$ to $R_{110}$ are each independently a hydrogen atom or a substituent; $R_{151}$ and $R_{152}$ are each independently a hydrogen atom or a substituent, or $R_{151}$ and $R_{152}$ are mutually bonded to form a ring;

$R_{101}$ to $R_{110}$, $R_{151}$ and $R_{152}$ as the substituent each independently represent a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkysilyl group having 3 to 6 carbon atoms, a substituted or unsubstituted alkoxy group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms;

in the formula (1-2): $X_2$ and $R_{111}$ to $R_{120}$ respectively represent the same as $X_1$ and $R_{101}$ to $R_{110}$ in the formula (1-1);

in the formula (1-3): $X_3$ and $R_{121}$ to $R_{130}$ respectively represent the same as $X_1$ and $R_{101}$ to $R_{110}$ in the formula (1-1);

in the formula (1-4): $X_4$ and $R_{131}$ to $R_{140}$ respectively represent the same as $X_1$ and $R_{101}$ to $R_{110}$ in the formula (1-1);

in the formula (1-5): $X_5$ and $R_{141}$ to $R_{150}$ respectively represent the same as $X_1$ and $R_{101}$ to $R_{110}$ in the formula (1-1); and in the formula (1-6): $X_6$ and $R_{61}$ to $R_{70}$ respectively represent the same as $X_1$ and $R_{101}$ to $R_{110}$ in the formula (1-1), and * each independently represents a bonding position to a carbon atom in a benzene ring in each of the formulae (11) to (13);

(2-1)
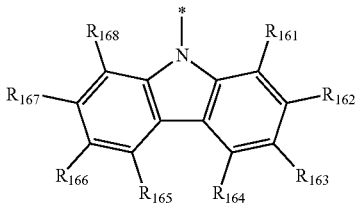

(2-2)

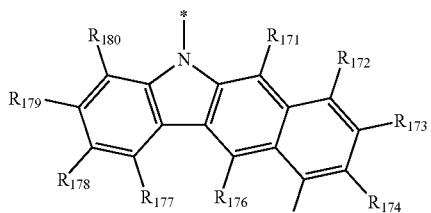

(2-3)

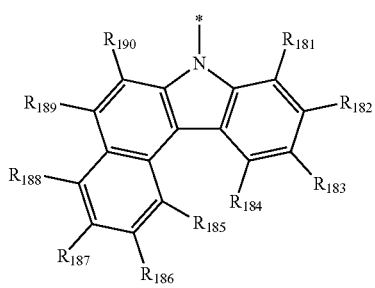

(2-4)

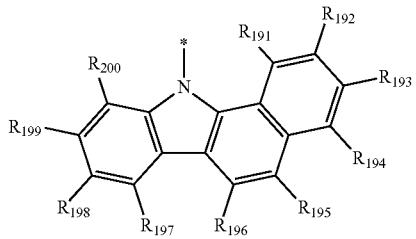

wherein in the formula (2-1): $R_{161}$ to $R_{168}$ each independently represent a hydrogen atom or a substituent;

$R_{161}$ to $R_{168}$ as the substituent each independently represent; a halogen atom, substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 30 carbon atoms, a substituted or unsubstituted alkysilyl group having 3 to 6 carbon atoms, a substituted or unsubstituted alkoxy group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms;

in the formula (2-2), $R_{171}$ to $R_{180}$ each independently represent a hydrogen atom or a substituent, and $R_{171}$ to $R_{180}$ as the substituent each independently represent the same examples of the substituent for $R_{161}$ to $R_{168}$ in the formula (2-1);

in the formula (2-3), $R_{181}$ to $R_{190}$ each independently represent a hydrogen atom or a substituent, and $R_{181}$ to $R_{190}$ as the substituent each independently represent the same examples of the substituent for $R_{161}$ to $R_{168}$ in the formula (2-1); and in the formula (2-4), $R_{191}$ to $R_{200}$ each independently represent a hydrogen atom or a substituent, and $R_{19}$, to $R_{200}$ as the substituent each independently represent the same examples of the substituent for $R_{161}$ to $R_{168}$ in the formula (2-1); and * each independently represents a bonding position to a carbon atom in a benzene ring in each of the formulae (11) to (13).

2. The compound according to claim 1, wherein
when three of the groups for $R_1$ to $R_4$ are selected from the groups represented by the formulae (1-1) to (1-6), all of the three groups are the same group represented by one of the formulae (1-1) to (1-6) and having the same substituent, and when two of the groups for $R_1$ to $R_4$ are selected from the groups represented by the formulae (1-1) to (1-6), all of the two groups are the same group represented by one of the formulae (1-1) to (1-6) and having the same substituent.

3. The compound according to claim 1, wherein
when three of the groups for $R_1$ to $R_4$ are selected from the groups represented by the formulae (2-1) to (2-4), all of the three groups are the same group represented by one of the formulae (2-1) to (2-4) and having the same substituent, and when two of the groups for $R_1$ to $R_4$ are selected from the groups represented by the formulae (2-1) to (2-4), all of the two groups are the same group represented by one of the formulae (2-1) to (2-4) and having the same substituent.

4. The compound according to claim 1, wherein
the compound is one of compounds respectively represented by formulae (101) to (123):

(101)

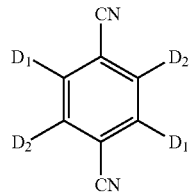

(102)

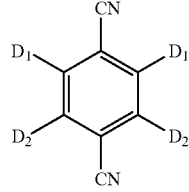

(103)

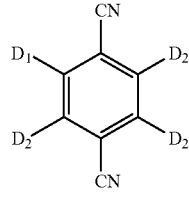

(104)

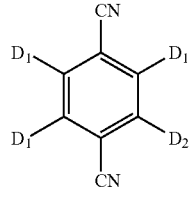

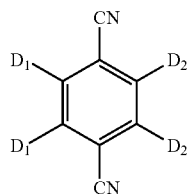
(105)
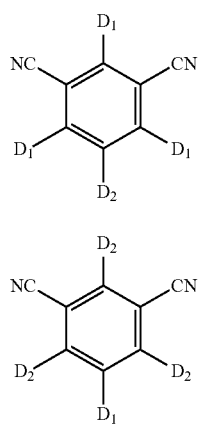
(106)
(107)
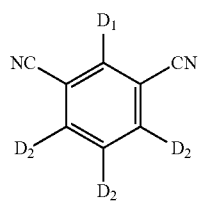
(108)
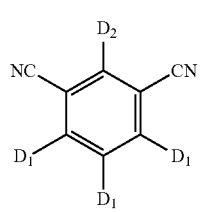
(109)
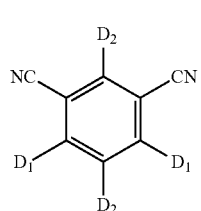
(110)
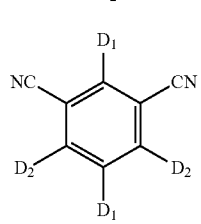
(111)
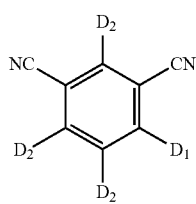
(112)
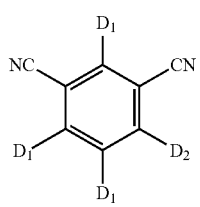
(113)
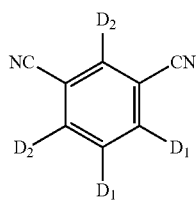
(114)
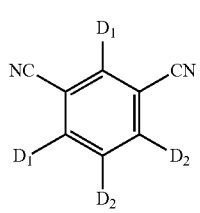
(115)
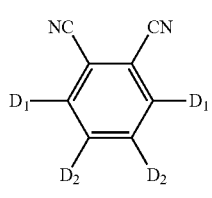
(116)
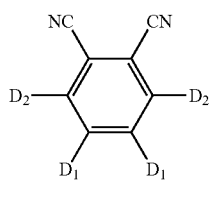
(117)
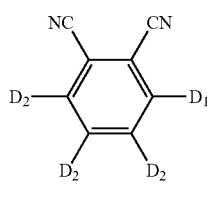
(118)
(119)

(120)
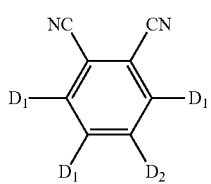

(121)
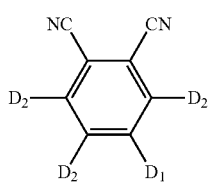

(122)
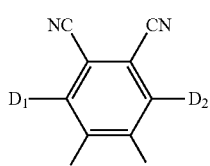

(123)
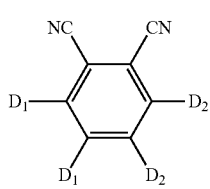

wherein D₁ each independently represents one of the groups respectively represented by the formulae (1-1) to (1-6);
  D₂ each independently represents one of the groups respectively represented by the formulae (2-1) to (2-4);
  a plurality of D₁ are mutually the same or different; and
  a plurality of D₂ are mutually the same or different.

5. The compound according to claim 4, wherein
  D₁ in the formulae (101) to (123) are mutually the same group.

6. The compound according to claim 4, wherein
  D₂ in the formulae (101) to (123) are mutually the same group.

7. The compound according to claim 4, wherein
  D₁ are mutually the same group and
  D₂ are mutually the same group in the formulae (101) to (123).

8. The compound according to claim 4, wherein
  the compound is one of the compounds respectively represented by the formulae (101), (106), (107), (110), (111), and (116) to (119).

9. The compound according to claim 1, wherein
  the groups represented by the formulae (2-1) to (2-4) each are one of groups represented by formulae (2-5) to (2-17):

(2-5)
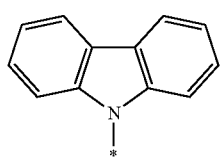

(2-6)
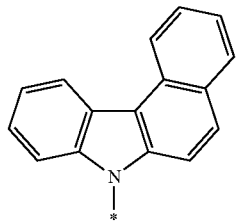

(2-7)
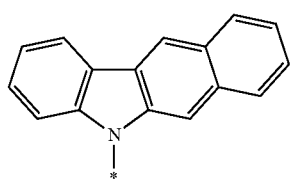

(2-8)
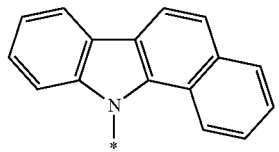

(2-9)
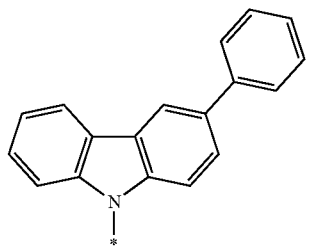

(2-10)
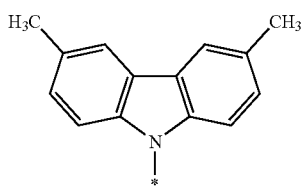

(2-11)
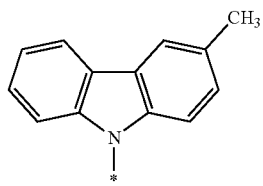

(2-12)
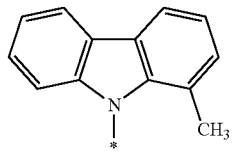

(2-13)
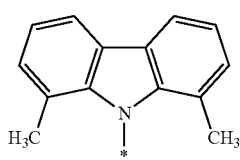

-continued

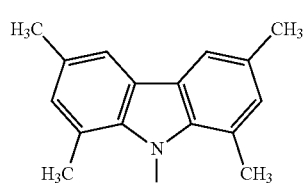
(2-14)

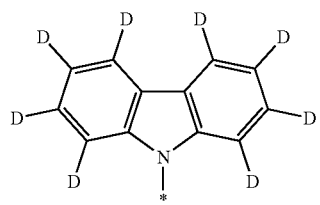
(2-15)

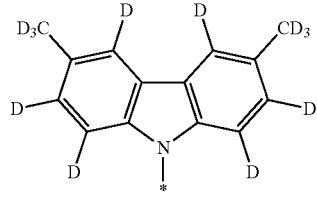
(2-16)

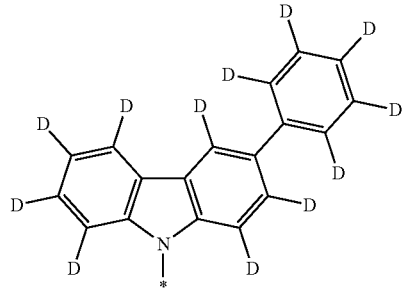
(2-17)

wherein * each independently represents a bonding position to a carbon atom in a benzene ring in the formulae (11) to (13), and D represents deuterium.

10. The compound according to claim 9, wherein
the group represented by the formula (2-1) is the group represented by the formula (2-5) or the group represented by the formula (2-15).

11. The compound according to claim 1, wherein
$X_1$ to $X_6$ are oxygen atoms in the formulae (1-1) to (1-6).

12. The compound according to claim 1, wherein
$X_1$ to $X_6$ are sulfur atoms in the formulae (1-1) to (1-6).

13. The compound according to claim 1, wherein
each of the groups which are to be represented by the formulae (1-1) to (1-6) is the group represented by the formula (1-1), the group represented by the formula (1-2), or the group represented by the formula (1-4).

14. The compound according to claim 1, wherein
each of the groups which are to be represented by the formulae (2-1) to (2-4) is the group represented by the formula (2-1).

15. The compound according to claim 4, wherein
the compound is one of the compounds respectively represented by formulae (101), (106), (107), (110), (111), and (116) to (119) below:

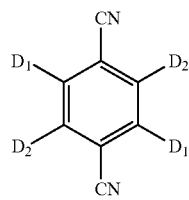
(101)

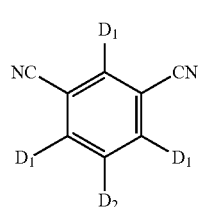
(106)

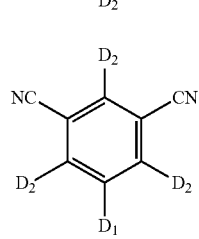
(107)

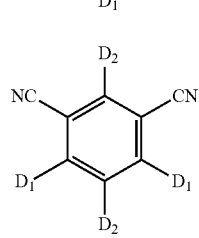
(110)

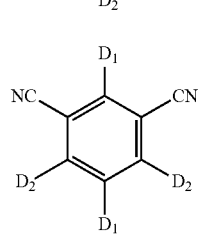
(111)

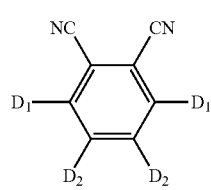
(116)

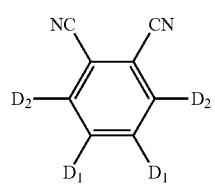
(117)

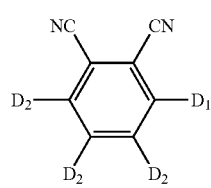
(118)

-continued (119)

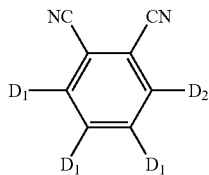

wherein $D_1$ is each independently the group represented by the formula (1-1), the group represented by the formula (1-2), or the group represented by the formula (1-4);
$D_2$ is each independently one of the groups represented by the formulae (2-5) to (2-14);
a plurality of $D_1$ are mutually the same or different; and
a plurality of $D_2$ are mutually the same or different.

16. The compound according to claim 4, wherein the compound is represented by the formula (11).
17. The compound according to claim 4, wherein the compound is represented by the formula (12).
18. The compound according to claim 4, wherein the compound is represented by the formula (13).
19. The compound according to claim 1, wherein $R_{101}$ to $R_{150}$, $R_{151}$, $R_{152}$, $R_{161}$ to $R_{168}$, $R_{171}$ to $R_{200}$, $R_{171}$ to $R_{180}$ and $R_{61}$ to $R_{70}$ as the substituent are each independently a halogen atom, an unsubstituted aryl group having 6 to 14 ring carbon atoms, an unsubstituted heterocyclic group having 5 to 14 ring atoms, an unsubstituted alkyl group having 1 to 6 carbon atoms, an unsubstituted alkyl halide group having 1 to 6 carbon atoms, an unsubstituted alkylsilyl group having 3 to 6 carbon atoms, an unsubstituted alkoxy group having 1 to 6 carbon atoms, an unsubstituted aryloxy group having 6 to 14 ring carbon atoms, an unsubstituted alkylamino group having 2 to 12 carbon atoms, an unsubstituted alkylthio group having 1 to 6 carbon atoms, or an unsubstituted arylthio group having 6 to 14 ring carbon atoms.
20. The compound according to claim 19, wherein $R_{101}$ to $R_{150}$, $R_{151}$, $R_{152}$, $R_{161}$ to $R_{168}$, $R_{171}$ to $R_{200}$ and $R_{61}$ to $R_{70}$ as the substituent are each independently an unsubstituted aryl group having 6 to 14 ring carbon atoms or an unsubstituted alkyl group having 1 to 6 carbon atoms.
21. The compound according to claim 1, wherein in the formulae (1-1) to (1-6), $R_{101}$ to $R_{150}$ and $R_{61}$ to $R_{70}$ are each a hydrogen atom and $R_{151}$ and $R_{152}$ are an unsubstituted aryl group having 6 to 14 ring carbon atoms or an unsubstituted alkyl group having 1 to 6 carbon atoms, and
in the formulae (2-1) to (2-4), $R_{161}$ to $R_{168}$ and $R_{171}$ to $R_{200}$ are each a hydrogen atom.
22. The compound according to claim 1, wherein on a basis of a calculation of a sum of atomic weights of atoms forming each of $R_1$ to $R_4$,
a minimum sum M1(min) among the sums of the groups corresponding to the groups represented by the formulae (1-1) to (1-6) and a maximum sum M2(max) among the sums of the groups corresponding to the groups represented by the formulae (2-1) to (2-4) satisfy a relationship represented by a numerical formula (Numerical Formula 1);

$M1(min) > M2(max)$ (Numerical Formula 1).

23. An organic-electroluminescence-device material comprising the compound according to claim 1.

24. An organic electroluminescence device comprising:
an anode;
a cathode; and
a first organic layer provided between the anode and the cathode, wherein
the first organic layer comprises a first compound, and
the first compound is the compound according to claim 1.
25. The organic electroluminescence device according to claim 24, wherein
the first organic layer is an emitting layer.
26. The organic electroluminescence device according to claim 24, wherein
the first organic layer comprises a second compound in addition to the first compound, and
the second compound is a fluorescent compound.
27. The organic electroluminescence device according to claim 26, wherein
the first organic layer comprises a third compound in addition to the first compound and the second compound, and
a singlet energy $S_1(Mat1)$ of the first compound and a singlet energy $S_1(Mat3)$ of the third compound satisfy a relationship of a numerical formula (Numerical Formula 2);

$S_1(Mat3) > S_1(Mat1)$ (Numerical Formula 2).

28. The organic electroluminescence device according to claim 26, wherein
the second compound is a compound represented by a formula (20), and
a singlet energy $S_1(Mat1)$ of the first compound and a singlet energy $S_1(Mat2)$ of the second compound satisfy a relationship of a numerical formula (Numerical Formula 3);

$S_1(Mat1) > S_1(Mat2)$ (Numerical Formula 3)

(20)

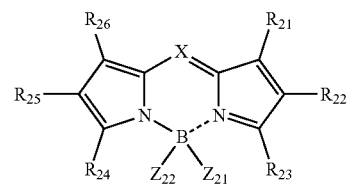

wherein X is a nitrogen atom, or a carbon atom bonded to Y;
Y is a hydrogen atom or a substituent;
$R_{21}$ to $R_{26}$ are each independently a hydrogen atom or a substituent, or at least one of a pair of $R_{21}$ and $R_{22}$, a pair of $R_{22}$ and $R_{23}$, a pair of $R_{24}$ and $R_{25}$, or a pair of $R_{25}$ and $R_{26}$ are mutually bonded to form a ring;
Y and $R_{21}$ to $R_{26}$ as the substituent are each independently selected from the group consisting of a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, a substituted or unsubstituted alkylthio group having 6 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted alkenyl group having 2 to 30 carbon atoms, a substituted or unsubstituted aralkyl group having 7 to 30 carbon atoms, a substituted or unsubstituted heteroaryl group having 5 to 30 ring atoms, a halogen atom, a carboxy group, a substituted or unsubstituted ester group, a substituted or unsubstituted carbamoyl group, a substituted or unsubstituted amino group, a nitro group, a cyano group, a substituted or unsubstituted silyl group, and a substituted or unsubstituted siloxanyl group;

$Z_{21}$ and $Z_{22}$ are each independently a substituent, or are mutually bonded to form a ring; and $Z_{21}$ and $Z_{22}$ as the substituent are each independently selected from the group consisting of a halogen atom, a substituted or unsubstituted alkyl group having 1 to 30 carbon atoms, a substituted or unsubstituted alkyl halide group having 1 to 30 carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, and a substituted or unsubstituted aryloxy group having 6 to 30 ring carbon atoms.

29. The organic electroluminescence device according to claim 26, wherein the second compound has a main peak wavelength in a range from 600 nm to 660 nm.

30. The organic electroluminescence device according to claim 29, wherein the organic electroluminescence device emits light having a main peak wavelength in a range from 600 nm to 660 nm.

31. The organic electroluminescence device according to claim 26, wherein the second compound has a main peak wavelength in a range from 500 nm to 560 nm.

32. The organic electroluminescence device according to claim 31, wherein the organic electroluminescence device emits light having a main peak wavelength in a range from 500 nm to 560 nm.

33. The organic electroluminescence device according to claim 24, wherein the first organic layer comprises a fourth compound in addition to the first compound, and a singlet energy $S_1(Mat1)$ of the first compound and a singlet energy $S_1(Mat4)$ of the fourth compound satisfy a relationship of a numerical formula(Numerical Formula 4):

$$S_1(Mat4) > S_1(Mat1) \quad \text{(Numerical Formula 4)}.$$

34. The organic electroluminescence device according to claim 24, wherein the first organic layer does not comprise a metal complex.

35. The organic electroluminescence device according to claim 24, wherein the first compound is a delayed fluorescent compound.

36. An electronic device comprising the organic electroluminescence device according to claim 24.

* * * * *